United States Patent
Poma et al.

(10) Patent No.: US 11,918,649 B2
(45) Date of Patent: *Mar. 5, 2024

(54) PD-L1-BINDING MOLECULES COMPRISING SHIGA TOXIN A SUBUNIT SCAFFOLDS

(71) Applicant: Molecular Templates, Inc., Austin, TX (US)

(72) Inventors: Eric Poma, New York, NY (US); Hilario Ramos, Austin, TX (US); Erin Willert, Round Rock, TX (US); Richard Shimkets, Commerce, GA (US); Crystal Jackson, Jefferson, GA (US); Thomas Vincent, Athens, GA (US)

(73) Assignee: Molecular Templates, Inc., Austin, TX (US)

(*) Notice: Subject to any disclaimer, the term of this patent is extended or adjusted under 35 U.S.C. 154(b) by 515 days.

This patent is subject to a terminal disclaimer.

(21) Appl. No.: 17/025,729

(22) Filed: Sep. 18, 2020

(65) Prior Publication Data

US 2021/0079097 A1     Mar. 18, 2021

Related U.S. Application Data

(60) Provisional application No. 63/041,288, filed on Jun. 19, 2020, provisional application No. 62/970,610, filed on Feb. 5, 2020, provisional application No. 62/933,197, filed on Nov. 8, 2019, provisional application No. 62/902,243, filed on Sep. 18, 2019.

(51) Int. Cl.
| | |
|---|---|
| A61K 39/395 | (2006.01) |
| A61P 35/00 | (2006.01) |
| C07K 14/25 | (2006.01) |
| C07K 16/28 | (2006.01) |
| C07K 16/30 | (2006.01) |
| A61K 39/00 | (2006.01) |

(52) U.S. Cl.
CPC ........ *A61K 39/39558* (2013.01); *A61P 35/00* (2018.01); *C07K 14/25* (2013.01); *C07K 16/2827* (2013.01); *A61K 2039/505* (2013.01); *C07K 2317/56* (2013.01); *C07K 2317/565* (2013.01); *C07K 2317/622* (2013.01); *C07K 2317/73* (2013.01); *C07K 2317/76* (2013.01); *C07K 2319/55* (2013.01)

(58) Field of Classification Search
None
See application file for complete search history.

(56) References Cited

U.S. PATENT DOCUMENTS

| | | |
|---|---|---|
| 4,342,566 A | 8/1982 | Theofilopoulos et al. |
| 4,704,692 A | 11/1987 | Ladner |
| 4,816,567 A | 3/1989 | Cabilly et al. |
| 7,635,757 B2 | 12/2009 | Freeman et al. |
| 7,887,801 B2 | 2/2011 | Wels et al. |
| 7,892,540 B2 | 2/2011 | Chen et al. |
| 7,943,743 B2 | 5/2011 | Korman et al. |
| 8,217,149 B2 | 7/2012 | Irving et al. |
| 8,460,927 B2 | 6/2013 | Chen |
| 8,530,637 B2 | 9/2013 | Wels et al. |
| 8,552,154 B2 | 10/2013 | Freeman et al. |
| 8,779,108 B2 | 7/2014 | Queva et al. |
| 8,981,063 B2 | 3/2015 | Chen |
| 9,102,727 B2 | 4/2015 | Freeman et al. |
| 9,493,565 B2 | 11/2016 | Queva et al. |
| 9,580,507 B2 | 2/2017 | Korman et al. |
| 9,624,298 B2 | 4/2017 | Nastri et al. |
| 9,920,123 B2 | 3/2018 | Irving et al. |
| 10,501,538 B2 | 12/2019 | Zhang et al. |
| 10,815,469 B2 | 10/2020 | Poma et al. |
| 11,078,298 B2 | 8/2021 | Catania et al. |
| 11,136,395 B2 | 10/2021 | Poma et al. |
| 2002/0197695 A1 | 12/2002 | Glucksmann et al. |
| 2004/0028685 A1 | 2/2004 | Kinch et al. |

(Continued)

FOREIGN PATENT DOCUMENTS

| | | |
|---|---|---|
| WO | WO 94/04679 A1 | 3/1994 |
| WO | WO 94/29348 A2 | 12/1994 |

(Continued)

OTHER PUBLICATIONS

Baxevanis (Expert Opinion: Drug Discovery, vol. 3, No. 4, p. 441-452, 2008) (Year: 2008).*
Ribas (The Journal of Experimental Medicine, vol. 213, No. 13, p. 2835-2840, 2016) (Year: 2016).*
Polyak et al. (Blood, vol. 99, No. 9, p. 3256-3262, 2002) (Year: 2002).*
Komenaka et al., Clinics in Dermatology, 2004, vol. 22, p. 251-265 (Year: 2004).*
Evans et al. (Q. J. Med 1999: 92: 299-307) (Year: 1999).*
Schiffman et al. (The New England Journal of Medicine, Vo. 353, No. 20, p. 2101-2104, 2005) (Year: 2005).*

(Continued)

*Primary Examiner* — Michael Allen
(74) *Attorney, Agent, or Firm* — COOLEY LLP; Ivor Elrifi

(57) ABSTRACT

Provided herein are PD-L1 binding molecules comprising or conjugated to a toxin, e.g. a Shiga toxin A Subunit derived polypeptide. In some embodiments, the PD-L1 binding molecules are cytotoxic. In some embodiments, the PD-L1 binding molecules are capable of delivering a CD8+ T-cell epitope to an MHC class molecule inside a PD-L1 positive cell. The PD-L1 binding molecules described herein have uses for selectively killing specific cells (e.g., PD-L1 positive tumor cells and/or immune cells); for selectively delivering cargos to specific cells (e.g., PD-L1 positive tumor cells or immune cells), and as therapeutic and/or diagnostic molecules for treating and diagnosing a variety of conditions, including cancers and tumors involving PD-L1 expressing cells (e.g., PD-L1 positive tumor cells or immune cells).

43 Claims, 58 Drawing Sheets

Specification includes a Sequence Listing.

(56) References Cited

U.S. PATENT DOCUMENTS

| | | | |
|---|---|---|---|
| 2006/0115832 A1* | 6/2006 | Hoon | C12Q 1/6886 435/6.16 |
| 2007/0298434 A1 | 12/2007 | Gariepy et al. | |
| 2009/0156417 A1 | 6/2009 | Gariepy et al. | |
| 2010/0041074 A1 | 2/2010 | Kimura | |
| 2012/0178111 A1* | 7/2012 | Diamandis | G01N 33/57423 435/7.1 |
| 2013/0196928 A1 | 8/2013 | Gariepy et al. | |
| 2015/0259428 A1 | 9/2015 | Poma et al. | |
| 2016/0017784 A1 | 1/2016 | Kumar | |
| 2016/0069900 A1 | 3/2016 | Ayanoglu et al. | |
| 2016/0177284 A1 | 6/2016 | Poma et al. | |
| 2016/0376328 A1 | 12/2016 | Poma et al. | |
| 2017/0002016 A1 | 1/2017 | Shishido et al. | |
| 2017/0143814 A1 | 5/2017 | Poma et al. | |
| 2017/0275382 A1 | 9/2017 | Poma et al. | |
| 2017/0281764 A1 | 10/2017 | Tso et al. | |
| 2017/0283497 A1 | 10/2017 | Schiffer-Mannioui | |
| 2018/0243432 A1 | 8/2018 | Poma et al. | |
| 2018/0258143 A1 | 9/2018 | Poma et al. | |
| 2018/0291359 A1 | 10/2018 | Poma et al. | |
| 2019/0083644 A1 | 3/2019 | Yoo et al. | |
| 2019/0153044 A1 | 5/2019 | Poma et al. | |
| 2021/0017284 A1* | 1/2021 | Shimkets | C07K 16/2827 |
| 2021/0079098 A1 | 3/2021 | Poma et al. | |
| 2021/0324082 A1 | 10/2021 | Poma et al. | |
| 2022/0195050 A1 | 6/2022 | Poma et al. | |

FOREIGN PATENT DOCUMENTS

| | | |
|---|---|---|
| WO | WO 2007/005874 A2 | 1/2007 |
| WO | WO 2018/080812 A1 | 1/2007 |
| WO | WO 2008/097866 | 8/2008 |
| WO | WO 2011/000054 | 1/2011 |
| WO | WO 2014/164680 | 10/2014 |
| WO | WO 2014/164693 | 10/2014 |
| WO | WO 2015/113005 | 7/2015 |
| WO | WO 2015/113007 | 7/2015 |
| WO | WO 2015/138435 | 9/2015 |
| WO | WO 2015/138452 | 9/2015 |
| WO | WO 2015/191764 | 12/2015 |
| WO | WO 2016/196344 | 12/2016 |
| WO | WO 2017/019623 | 2/2017 |
| WO | WO 2018/106895 | 6/2018 |
| WO | WO 2018/140427 | 8/2018 |
| WO | WO 2018/159615 A1 | 9/2018 |
| WO | WO 2018/162749 A1 | 9/2018 |
| WO | WO 2019/059400 A1 | 3/2019 |
| WO | WO 2019/183093 | 9/2019 |
| WO | WO 2020/081493 | 4/2020 |
| WO | WO 2020/154475 | 7/2020 |
| WO | WO 2020/154475 A1 | 7/2020 |
| WO | WO 2021/055816 A1 | 3/2021 |

OTHER PUBLICATIONS

Cuzick et al. (The Lancet, vol. 361, p. 296-300, 2003) (Year: 2003).*

Hernandez-Ledesma (Peptides, vol. 30, p. 426-430, 2009) (Year: 2009).*

Paul (Fundamental Immunology, 3rd Edition, 1993, pp. 292-295) (Year: 1993).*

Bendig M. M. (Methods: A Companion to Methods in Enzymology, 1995; 8:83-93) (Year: 1995).*

Rudikoff et al. (Proceedings of the National Academy of Sciences USA, vol. 79, p. 1979-1983, 1982) (Year: 1982).*

Dubel (Handbook of Therapeutic Antibodies, 2007, p. 100-101) (Year: 2007).*

Johnson and Wu (Methods in Molecular Biology, Antibody Engineering: Methods and Protocols, vol. 248, p. 11-25, 2004) (Year: 2004).*

Burgess et al. (J of Cell Bio. 111:2129-2138, 1990) (Year: 1990).*

Lazar et al. (Molecular and Cellular Biology 8:1247-1252, 1988) (Year: 1988).*

Cheung, M. C. et al., "An evolved ribosome-inactivating protein targets and kills human melanoma cells in vitro and in vivo," Molecular Cancer 9:28 (2010), 14 pages.

Al-Jaufy, A. Y. et al., "Cytotoxicity of a Shiga Toxin A Subunit-CD4 Fusion Protein to Human Immunodeficiency Virus-Infected Cells," Infection and Immunity, vol. 62, No. 3, pp. 956-960 (Mar. 1994).

LaPointe, P. et al., "A Role for the Protease-sensitive Loop Region of Shiga-like Toxin 1 in the Retrotranslocation of Its A1 Domain from the Endoplasmic Reticulum Lumen," The Journal of Biological Chemistry, vol. 280, No. 24, pp. 23310-23318 (Jun. 2005).

Di, R. et al., "Identification of amino acids critical for the cytotoxicity of Shiga toxin 1 and 2 in *Saccharomyces cerevisiae*," Toxicon, 57:525-539 (2011).

Hovde, C. J. et al., "Evidence that glutamic acid 167 is an active-site residue of Shiga-like toxin I," Proc. Natl. Acad. Sci. USA, vol. 85, pp. 2568-2572 (Apr. 1988).

Deresiewicz, R. L. et al., "Mutations Affecting the Activity of the Shiga-like Toxin I A-Chain," Biochemistry, 31:3272-3280 (1992).

Deresiewicz, R. L. et al., "The role of tyrosine-114 in the enzymatic activity of the Shiga-like toxin I A-chain," Mol. Gen. Genet., 241:467-473 (1993).

Ohmura, M. et al., "Characterization of non-toxic mutant toxins of Vero toxin 1 that were constructed by replacing amino acids in the A subunit," Microbial Pathogenesis, vol. 15, Issue 3, pp. 169-176 (Sep. 1993).

Cao, C. et al., "Construction of Mutant Genes for a Non-Toxic Verotoxin 2 Variant (VT2vp1) of *Escherichia coli* and Characterization of Purified Mutant Toxins," Microbiol. Immunol., vol. 38, No. 6, pp. 441-447 (1994).

Suhan, M. L. et al., "Disruption of an Internal Membrane-Spanning Region in Shiga Toxin 1 Reduces Cytotoxicity," Infection and Immunity, vol. 66, No. 11, pp. 5252-5259 (Nov. 1998).

Haddad, J. E. et al., "Minimum Domain of the Shiga Toxin A Subunit Required for Enzymatic Activity," Journal of Bacteriology, vol. 175, No. 16, pp. 4970-4978 (Aug. 1993).

McCluskey, A. J. et al., "Charged and Hydrophobic Surfaces on the A Chain of Shiga-Like Toxin 1 Recognize the C-Terminal Domain of Ribosomal Stalk Proteins," PLoS ONE, 7(2):e31191 (2012).

Tang, F. et al., "Tumor cells versus host immune cells: whose PD-L1 contributes to PD-1/PD-L1 blockade mediated cancer immunotherapy?," Cell & Bioscience, 8:34 (2018), 8 pages.

Ribas, A. et al., "Cancer immunotherapy using checkpoint blockade," Science 359:1350-1355 (Mar. 2018).

Das, S. et al., "Immune-related adverse events and antitumor efficacy of immune checkpoint inhibitors," Journal for Immuno Therapy of Cancer, 7:306 (2019).

Nakamura, Y., "Biomarkers for Immune Checkpoint Inhibitor-Mediated Tumor Response and Adverse Events," Frontiers in Medicine, vol. 6, Article 119 (May 2019), 18 pages.

Ji, C. et al., "Myocarditis in Cynomolgus Monkeys Following Treatment with Immune Checkpoint Inhibitors," Clin Cancer Res., May 2019;25:4735-4748.

Kowanetz, M. et al., "Differential regulation of PD-L1 expression by immune and tumor cells in NSCLC and the response to treatment with atezolizumab (anti-PD-L1)," PNAS, vol. 115, No. 43, pp. e10119-e10126 (Oct. 2018).

Molecular Templates, Molecular Templates Provides Corporate Update and Outlines 2020 Milestones, Jan. 8, 2020, 2 pages.

Brieschke, B. et al., Abstract 4912, "Antigen Seeding Technology by Engineered Toxin Bodies Provides a Targeted Immuno-Oncology Approach for Treatment of Cancers," Molecular Templates, AACR Annual Meeting 2018; Apr. 14-18, 2018; Chicago, IL, 2018, 2 pages.

Ramos, H. J. et al., Abstract 3900, "The safety and efficacy profile of a PD-L1 directed, Engineered Toxin Body, as a novel targeted direct-cell kill approach for the treatment of PD-L1 expressing cancers," Molecular Templates, AACR Annual Meeting 2019; Mar. 29-Apr. 3, 2019; Atlanta, GA, AACR 2019, 2 pages.

Dekker, J. D. et al., Abstract 1791, "Engineered toxin bodies delivering immunogenic MHC class I peptides to tumor cells

(56) References Cited

OTHER PUBLICATIONS summon polyfunctional and relevant CTL responses against cancers," Molecular Templates, AAI 2019, 2 pages.
Brieschke, B. et al., Abstract No. 12, "PD-L1 targeted engineered toxin body provides direct cytotoxicity and T-cell mediated tumor targeting," 2020 ASCO-SITC Clinical Immuno-Oncology Symposium, 1 page.
Brieschke, B. et al., P9, "Identification and Functional Profiling of PD-L1 Targeted Engineered Toxin Bodies for Antigen Seeding Technology and Redirection of T Cell Response to Tumors," Journal for Immuno Therapy of Cancer 2018, 6(Suppl 1):114, p. 5.
Brieschke, B. et al., Abstract 11078, "Identification and Functional Profiling of PD-L1 Targeted Engineered Toxin Bodies for Antigen Seeding Technology (AST) and Redirection of T cell Response to Tumors," Molecular Templates, SITC 2018, 1 page.
Brieschke, B. et al., Abstract P804, "In vivo efficacy of a PD-L1 targeted Engineered Toxin Body (ETB) comprised of direct cytotoxicity and T-cell mediated tumor targeting," Molecular Templates, SITC 2019, 1 page.
Molecular Templates, "New Data on Molecular Templates' Engineered Toxin Bodies to be Presented at the American Association of Cancer Research (AACR) Annual Meeting 2019," Feb. 27, 2019, 2 pages.
Molecular Templates, "Study on Molecular Templates' PD-L1 Etb with Antigen Seeding Technology Presented at SITC Annual Meeting," Nov. 9, 2018, 1 page.
Ramos, H. J. et al., Abstract No. 3366, "In vivo efficacy of a PD-L1 targeted, antigen seeding engineered toxin body," AACR Annual Meeting 2020, 1 page.
Quayle, S. et al., P803, "CUE-101, a novel HPV16 E7:pMHC:IL-2:Fc fusion protein, enhances tumor antigen specific T cell activation for the treatment of HPV16-driven malignancies," Journal for Immuno Therapy of Cancer 2019, 7(Suppl 1):283, pp. 159-160.
Burgess, B. J. et al., "Proteolytic cleavage at arginine residues within the hydrophilic disulphide loop of the *Escherichia coli* Shiga-like toxin I A subunit is not essential for cytotoxicity," Molecular Microbiology, 10(1):171-179 (1993).
Glockshuber, R. et al., "A comparison of strategies to stabilize immunoglobulin Fv-fragments," Biochemistry, 29(6):1362-1367 (1990); doi: 10.1021/bi00458a002.
Lea, N. et al., "Proteolytic cleavage of the A subunit is essential for maximal cytotoxicity of *Escherichia coli* O157:h7 Shiga-like toxin-1," Microbiology, 145(5):999-1004 (1999).
Nilson, B. H. K. et al., "Protein L from *Peptostreptococcus magnus* binds to the kappa light chain variable domain," Journal of Biological Chemistry, 267(4):2234-2239 (1992).
Nilson, B. H. K. et al., "Purification of antibodies using protein L-binding framework structures in the light chain variable domain," Journal of Immunological Methods, 164(1):33-40 (1993).
Press Release Molecular Templates Provides Corporate Update and Outlines 2022 Milestones, Austin, Texas, Nov. 30, 2021, 6 pages.
Romaniuk, D. S. et al., "Rapid Multiplex Genotyping of 20 HLA-A*02:01 Restricted Minor Histocompatibility Antigens," Front. Immunol., vol. 10, Article 1226 (2019), 10 pages; https://doi.org/10.3389/fimmu.2019.01226.
Rozanov, D. V. et al., "MHC class I loaded ligands from breast cancer cell lines: A potential HLA-I-typed antigen collection," J Proteomics, 176:13-23 (2018); doi:10.1016/j.jprot.2018.01.004.
Song, S. et al., "Full screening and accurate subtyping of HLA-A*02 alleles through group-specific amplification and mono-allelic sequencing," Cellular & Molecular Immunology, 10:490-496 (2013).
Stone, J. D. et al., "T-cell receptor binding affinities and kinetics: impact on T-cell activity and specificity," Immunology, 126:165-176 (2009).
Vannitamby, A. et al., "A Novel Approach to Detect Programed Death Ligand 1 (PD-L1) Status and Multiple Tumor Mutations Using a Single Non-Small-Cell Lung Cancer (NSCLC) Bronchoscopy Specimen," The Journal of Molecular Diagnostics, 21(2):186-197 (2019).

Xu, S.. et al., "PD-L1 monoclonal antibody-conjugated nanoparticles enhance drug delivery level and chemotherapy efficacy in gastric cancer cells," Int J Nanomedicine, 14:17-32 (2019).
U.S. Appl. No. 62/746,153, filed Oct. 16, 2018, Willert.
Abelson, A. K. et al., "No evidence of association between genetic variants of the PDCD1 ligands and SLE," Genes and Immunity, 8:69-74 (2007).
Akula, Y. T. et al., "TAM Receptor Tyrosine Kinases as Emerging Targets of Innate Immune Checkpoint Blockade for Cancer Therapy," Immunol Rev., 276(1):165-177 (2017); doi:doi:10.1111/imr.12522.
Alpdogan, O. & Van Den Brink, M. R. M., "Immune Tolerance and Transplantation," Semin Oncol, 39:629-642 (2012).
Andorsky, D. J. et al., "Programmed Death Ligand 1 Is Expressed by Non-Hodgkin Lymphomas and Inhibits the Activity of Tumor-Associated T Cells," Clin Cancer Res, 17(13):4232-4244 (2011).
Antignani, A. & Fitzgerald, D., Immunotoxins: The Role of the Toxin, Toxins, 5:1486-1505 (2013).
Arrieta, O. et al., "Expression of PD-1/PD-L1 and PD-L2 in peripheral T-cells from non-small cell lung cancer patients," Oncotarget, 8(60):101994-102005 (2017).
Au, T. K. et al., "The plant ribosome inactivating proteins luffin and saporin are potent inhibitors of HIV-1 integrase," FEBS Letters, 471:169-172 (2000).
Bagga, S. et al., "The Cytotoxic Activity of Ribosome-inactivating Protein Saporin-6 Is Attributed to Its rRNA N-Glycosidase and Internucleosomal DNA Fragmentation Activities," The Journal of Biological Chemistry, 278(7):4813-4820 (2003).
Ballbach, M. et al., "Expression of checkpoint molecules on myeloid-derived suppressor cells," Immunology Letters, 192:1-6 (2017).
Barbieri, L. et al., "Polynucleotide: adenosine glycosidase activity of ribosome-inactivating proteins: effect on DNA, RNA and poly(A)," Nucleic Acids Research, 25(3):518-522 (1997).
Barbieri, L. et al., "Polynucleotide: adenosine glycosidase activity of saporin-L1: effect on various forms of mammalian DNA," Biochimica et Biophysica Acta, 1480:258-266 (2000).
Barbieri, L. et al., "Polynucleotide: Adenosine Glycosidase Is the Sole Activity of Ribosome-Inactivating Proteins on DNA," J. Biochem, 128:883-889 (2000).
Barbieri, L. et al., "Polynucleotide :adenosine glycosidase activity of saporin-L1: effect on DNA, RNA and poly(A)," Biochem. J., 319:507-513 (1996).
Barbieri, L. et al., "Some ribosome-inactivating proteins depurinate ribosomal RNA at multiple sites," Biochem. J., 286:1-4 (1992).
Barbieri, L. et al., "Unexpected activity of saporins," Nature, 372:624 (1994).
Bielaszewska, M. et al., "Shiga Toxin Gene Loss and Transfer In Vitro and In Vivo during Enterohemorrhagic *Escherichia coli* O26 Infection in Humans," Applied and Environmental Microbiology, 73(10):3144-3150 (2007).
Bocanegra, A. et al., "PD-L1 Expression in Systemic Immune Cell Populations as a Potential Predictive Biomarker of Responses to PD-L1/PD-1 Blockade Therapy in Lung Cancer," Int. J. Mol. Sci., 20:1631 (2019); doi.10.3390/http://dx.doi.org/10.3390/ijms20071631, 13 pages.
Bräunlein, E. & Krackhardt, A. M., "Identification and Characterization of Neoantigens As Well As Respective Immune Responses in Cancer Patients," Frontiers in Immunology, 8:1702 (2017), 8 pages.
Brieschke, B. et al., "In vivo efficacy of a PD-L1 targeted Engineered Toxin Body (ETB) comprised of direct cytotoxicity and T-cell mediated tumor targeting," Journal for ImmunoTherapy of Cancer, 7(Suppl 1):P804 (2019), 2 pages.
Brigotti, M. et al., "Damage to nuclear DNA induced by Shiga toxin 1 and ricin in human endothelial cells," The FASEB Journal, 16:365-372 (2002).
Brigotti, M. et al., "Shiga toxin 1: damage to DNA in vitro," Toxicon, 39:341-348 (2001).
Brigotti, M. et al., "The RNA-N-Glycosidase Activity of Shiga-like Toxin 1: Kinetic Parameters of the Native and Activated Toxin," Toxicon, 35(9):1431-1437 (1997).
Brown, J. A. et al., "Blockade of Programmed Death-1 Ligands on Dendritic Cells Enhances T Cell Activation and Cytokine Production," The Journal of Immunology, 170:1257-1266 (2003).

(56) References Cited

OTHER PUBLICATIONS

Butte, M. J. et al., "Programmed Death-1 Ligand 1 Interacts Specifically with the B7-1 Costimulatory Molecule to Inhibit T Cell Responses," Immunity, 27:111-122 (2007).
Cao, C. et al., "Construction of Mutant Genes for a Non-Toxic Verotoxin 2 Variant (VT2vp1 of *Escherichia coli* and Characterization of Purified Mutant Toxins," Microbiol. Immunol., 38(6):441-447 (1994).
Carreras-Sangrà, N. et al., "Production and characterization of a colon cancer-specific immunotoxin based on the fungal ribotoxin α-sarcin," Protein Engineering, Design & Selection, 25(8):425-435 (2012).
Chatterjee, S. et al., "Noninvasive Imaging of Immune Checkpoint Ligand PD-L1 in Tumors and Metastases for Guiding Immunotherapy," Molecular Imaging, 16:1-5 (2017).
Chen, L. & Han, X., "Anti-PD-1/PD-L1 therapy of human cancer: past, present, and future," J Clin Invest., 125(9):3384-3391 (2015); https://doi.org/10.1172/JCI80011.
Chen, L., "Co-Inhibitory Molecules of the B7-CD28 Family in the Control of T-cell Immunity," Nature, Nature Reviews Immunology, 4:336-347 (2004).
Chen, J. et al., "Interferonγ-induced PD-L1 surface expression on human oral squamous carcinoma via PKD2 signal pathway," Immunobiology, 217:385-393 (2012).
Chen, B. J. et al., "PD-L1 Expression Is Characteristic of a Subset of Aggressive B-cell Lymphomas and Virus-Associated Malignancies," Clin Cancer Res, 19(13):3462-3473 (2013).
Chen, L. et al., "PD-L1 Expression Promotes Epithelial to Mesenchymal Transition in Human Esophageal Cancer," Cell Physiol biochem, 42:2267-2280 (2017); doi:10.1159/000480000 Published online: Aug. 17, 2017.
Chen, M. -F. et al., "The role of PD-L1 in the radiation response and prognosis for esophageal squamous cell carcinoma related to IL-6 and T-cell immunosuppression," Oncotarget, 7(7):7913-7924 (2016).
Darvin, P. et al., "Immune checkpoint inhibitors: recent progress and potential biomarkers," Experimental & Molecular Medicine, 50:165 (2018), https://doi.org/10.1038/s12276-018-0191-1, 11 pages.
De Lorenzo, C. & D'Alessio, G., "From ImmunoToxins to ImmunoRNases," Current Pharmaceutical Biotechnology, 9:210-214 (2008).
De Lorenzo, C. et al., "Intracellular route and mechanism of action of ERB-hRNase, a human anti-Erb2 anticancer immunoagent," FEBS Letters, 581:296-300 (2007).
De Sousa Linhares, A. et al., "Therapeutic PD-L1 antibodies are more effective than PD-1 antibodies in blocking PD-1/PD-L1 signaling," Scientific Reports, 9:11472 (2019), 9 pages; https://doi.org/10.1038/s41598-019-47910-1.
De Virgilio, M. et al., "Ribosome-Inactivating Proteins: From Plant Defense to Tumor Attack," Toxins, 2:2699-2737 (2010); doi:10.3390/toxins2112699.
Deng, R. et al., "B7H1/CD80 Interaction Augments PD-1-Dependent T Cell Apoptosis and Ameliorates Graft-versus-Host Disease," The Journal of Immunology, 194:560-574 (2015).
Déret, S. et al., "SUBIM: a program for analysing the Kabat database and determining the variability subgroup of a new immunoglobulin sequence," CABIOS, 11(4):435-439 (1995).
Dhanda, S. K. et al., "IEDB-AR: Immune epitope database—analysis resource in 2019," Nucleic Acids Research, 47:W502-W506 (2019).
Dong, H. et al., "B7-H1, a third member of the B7 family, co-stimulates T-cell proliferation and interleukin-10 secretion," Nature Medicine, 5(12):1365-1369 (1999).
Dong, H. et al., "Tumor-associated B7-H1 promotes T-cell apoptosis: A potential mechanism of immune evasion," Nature Medicine, 8(8):793-800 (2002).
Engedal, N. et al., "Shiga toxin and its use in targeted cancer therapy and imaging," Microbial Biotechnology, 4(1):32-46 (2011).
Erice, A. et al., "Anti-Human Immunodeficiency Virus Type 1 Activity of an Anti-CD4 Immunoconjugate Containing Pokeweed Antiviral Protein," Antimicrobial Agents and Chemotherapy, 37(4):835-838 (1993).
Flies, D. B. et al., "Blockade of the B7-H1/DP-1 Pathway for Cancer Immunotherapy," Yale Journal of Biology and Medicine, 84:409-421 (2011).
Foss, F. M. et al., "Diphtheria Toxin Fusion Proteins," Clinical Applications of Immunotoxins, 234:63-81 (1998).
Fracasso, G. et al., "Ribosome-Inactivating Protein-Containing Conjugates for Therapeutic Use," Toxic Plant Proteins, Plant Cell Monographs, 18:225-263, J. M. Lord and M. R. Hartley (eds.) (2010).
Freeman, G. J. et al., "Engagement of the PD-1 Immunoinhibitory Receptor by a Novel B7 Family Member Leads to Negative Regulation of Lymphocyte Activation," J. Exp. Med., 192(7):1027-1034 (2000).
Fuenmayor, J. & Montaño, R. F., "Novel Antibody-Based Proteins for Cancer Immunotherapy," Cancers, 3:33370-3393 (2011); doi:10.3390/cancers3033370.
Gabrilovich, D. I., "Myeloid-derived suppressor cells," Cancer Immunol Res, 5(1):3-8 (2017); doi:10.1158/2326-6066.CIR-16-0297.
Gato-Cañas, M. et al., "PDL1 Signals through Conserved Sequence Motifs to Overcome Interferon-Mediated Cytotoxicity," Cell Reports, 20:1818-1829 (2017).
Ge, X. et al., "Cancer Immunotherapies Targeting Tumor-Associated Regulatory T Cells," Oncotargets and Therapy, 12:11033-11044 (2019).
GenBank Accession No. AAI13735.1, CD274 molecule [*Homo sapiens*], Jun. 29, 2006, 2 pages.
Gielis, S. et al., "Detection of Enriched T Cell Epitope Specificity in Full T Cell Receptor Sequence Repertoires," Frontiers in Immunology, vol. 10, Article 2820, pp. 1-2 (2019).
González-Escalona, N. & Kase, J. A., "Virulence gene profiles and phylogeny of Shiga toxin-positive *Escherichia coli* strains isolated from FDA regulated foods during 2010-2017," PLoS ONE, 14(4):e0214620 (2019), https://doi.org/10.1371/journal.pone.0214620, 26 pages.
Grotiuz, G. et al., "Shiga Toxin-2 Producing *Acinetobacter haemolyticus* Associated with a Case of Bloody Diarrhea," Journal of Clinical Microbiology, 44(10):3838-3841 (2006).
Grotzke, J. E. et al., "The ongoing saga of the mechanism(s) of MHC class I-restricted cross-presentation," Current Opinion in Immunology, 46:89-96 (2017).
Haeryfar, S. M. M. & Schell, T. D., "PD-1/PD-L1 co-inhibition shapes anticancer T cell immunodominance: facing the consequences of an immunological ménage à trois," Cancer Immunology, Immunotherapy, 67:1669-1672 (2018).
Hartley, G. P. et al., "Programmed Cell Death Ligand 1 (PD-L1) Signaling Regulates Macrophage Proliferation and Activation," Cancer Immunol Res, 6(10):1260-1273 (2018).
Hayashi, M. et al., "Association of an A/C single nucleotide polymorphism in programmed cell death-ligand 1 gene with Graves' disease in Japanese patients," European Journal of Endocrinology, 158:817-822 (2008).
Head, S. C. et al., "Preparation of VT1 and VT2 Hybrid Toxins from Their Purified Dissociated Subunits," The Journal of Biological Chemistry, 266(6):3617-3621 (1991).
Henson, S. M. & Akbar, A. N., KLRG1—more than a marker for T cell senescence, Age, 31:285-291 (2009).
Hegde, N. R. et al., "The use of databases, data mining and immunoinformatics in vaccinology: where are we?" Expert Opinion on Drug Discovery, 13(2):117-130 (2018).
Hirano, F. et al., "Blockade of B7-H1 and PD-1 by Monoclonal Antibodies Potentiates Cancer Therapeutic Immunity," Cancer Res, 65(3):1089-1096 (2005).
Ilié, M. et al., "Detection of PD-L1 in circulating tumor cells and white blood cells from patients with advanced non-small-cell lung cancer," Annals of Oncology, 29:193-199 (2018).
Ishida, Y. et al., "Induced expression of PD-1, a novel member of the immunoglobulin gene superfamily, upon programmed cell death," The EMBO Journal, 11(11):3887-3895 (1992).

(56) References Cited

OTHER PUBLICATIONS

Jalali, S. et al., "Reverse signaling via PD-L1 supports malignant cell growth and survival in classical Hodgkin lymphoma," Blood Cancer Journal, 9:22 (2019), https://doi.org/10.1038/s41408-019-0185-9, 9 pages.

Johannes, L. & Römer, W., "Shiga Toxins—from cell biology to biomedical applications," Nature Reviews Microbiology, 8:105-116 (2010).

Khalil, R. K. S. et al., "Phage-mediated Shiga toxin (Stx) horizontal gene transfer and expression in non-Shiga toxigenic *Enterobacter* and *Escherichia coli* strains," Pathogens and Disease, 74(5):ftw037 (2016); doi:10.1093/femspd/ftw037, 11 pages.

Kar, P. et al., "Current methods for the prediction of T-cell epitopes," Peptide Science, 110:e24046 (2018); https://doi.org/10.1002/pep2.24046, 17 pages.

Karwacz, K. et al., "PD-L1 co-stimulation contributes to ligand-induced T cell receptor down-modulation on CD8+T cells," EMBO Mol Med, 3:581-592 (2011).

Kehry, M. et al., "W. 73—Discovery of Checkpoint Agonist Antibodies for Autoimmune/ Inflammatory Disease," General Autoimmunity Poster, W. 73 FOCiS Annual Meeting, Jun. 19, 2019, 3 pages.

Lacadena, J. et al., "Fungal ribotoxins: molecular dissection of a family of natural killers," FEMS, 31:212-237 (2007).

Lakhrif, Z. et al., "A method to confer protein L binding ability to any antibody fragment," MAbs, 8(2):379-388 (2016).

Latchman, Y. et al., "PD-L2 is a second ligand for PD-1 and inhibits T cell activation," Nature Immunology, 2(3):261-268 (2001).

Lau, J. et al., "Tumour and host cell PD-L1 is required to mediate suppression of anti-tumour immunity in mice," Nature Communications, 8:14572 (2017); doi:10.1038/ncomms14572, 11 pages.

Lecis, D. et al., "Immune Checkpoint Ligand Reverse Signaling: Looking Back to Go Forward in Cancer Therapy," Cancers, 11:624 (2019); doi:10.3390/cancers11050624, 13 pages.

Lee, H. T. et al., "Molecular mechanism of PD-1/PD-L1 blockade via anti-PD-L1 antibodies atezolizumab and durvalumab," Scientific Reports, 7(1):5532 (2017), 12 pages; doi:10.1038/s41598-017-06002-8.

Lee, H. T. et al., "Molecular Interactions of Antibody Drugs Targeting PD-1, PD-L1, and CTLA-4 in Immuno-Oncology," Molecules, 24:1190 (2019); http://dx.doi.org/10.3390/molecules24061190, 16 pages.

Li, Y. et al., "Correction to: Discovery and preclinical characterization of the antagonist anti-PD-L1 monoclonal antibody LY3300054," Journal for Immuno Therapy of Cancer, vol. 6, No. 1, Jun. 2018, p. 1.

Lin, H. et al., "Selection and Characterization of Human Anti-MAGE-A1 scFv and Immunotoxin," Anti-Cancer Agents in Medicinal Chemistry, 13:1259-1266 (2013).

Ling, J. et al., "Cleavage of supercoiled double-stranded DNA by several ribosome-inactivating proteins in vitro," FEBS Letters, 345:143-146 (1994).

Lu, C. et al., "The expression profiles and regulation of PD-L1 in tumor-induced myeloid-derived suppressor cells," Oncoimmunology, 5(12):e1247135 (2016), 13 pages; http://dx.doi.org/10.1080/2162402X.2016.1247135.

Lu, C. et al., "Current perspectives on the immunosuppressive tumor microenvironment in hepatocellular carcinoma: challenges and opportunities," Molecular Cancer, 18:130 (2019); https://doi.org/10.1186/s12943-019-1047-6, 12 pages.

Lyu, M.-A. et al., "Cell Targeting Fusion Constructs Containing Recombinant Gelonin," Chapter 8: Methods in Immunology, 502:167-214 (2012).

Ma, W. et al., "Current status and perspectives in translational biomarker research for PD-1/PD-L1 immune checkpoint blockade therapy," Journal of Hematology & Oncology, 9:47 (2016); doi:10.1186/s13045-016-0277-y.

Ma, Y. et al., "Polymorphisms of co-inhibitory molecules (CTLA-4/PD-1/PD-L1) and the risk of non-small cell lung cancer in a Chinese population," Int J Clin Exp Med, 8(9):16585-16591 (2015).

Meeting Abstracts, "33rd Annual Meeting & Pre-Conference Programs of the Society for Immunotherapy of Cancer (SITC 2018)," Washington, D.C., USA, Nov. 7-11, 2018, Journal for ImmunoTherapy of Cancer, vol. 6, Supplement No. 1, Nov. 2018, pp. 1-205.

Meeting Abstracts, "34th Annual Meeting & Pre-Conference Programs of the Society for Immunotherapy of Cancer (SITC 2019): Part 2: National Harbor, MD, USA, Nov. 10, 2019," Journal for ImmunoTherapy of Cancer, vol. 7, Supplement No. 1, Nov. 2019, pp. 1-237, Abstract P804.

Memarnejadian, A. et al., "PD-1 Blockade Promotes Epitope Spreading in Anticancer CD8+ T Cell Responses by Preventing Fratricidal Death of Subdominant Clones to Relieve Immunodomination," The Journal of Immunology, 199:3348-3359 (2017).

Menzel, C. et al., "Human antibody RNase fusion protein targeting CD30+ lymphomas," Blood, 111:3830-3837 (2008).

Mitchell, A. L. et al., "Programmed Death Ligand 1 (PD-L1) Gene Variants Contribute to Autoimmune Addison's Disease and Graves' Disease Susceptibility," J Clin Endocrinol Metab, 94:5139-5145 (2009).

Moise, L. et al., "T cell epitope engineering: an avian H7N9 influenza vaccine strategy for pandemic preparedness and response," Human Vaccines & Immunotherapeutics, 14(9):2203-2207 (2018).

Molecular Templates Inc.: R&D Day, Conference Call Transcript (Nov. 15, 2019) Fair Disclosure Wire, pp. 1-17; retrieved on Jan. 15, 2021 from https://dialog.proquest.com/professional/docview/2320577373, 17 pages.

Molecular Templates Corporate Presentation, Nov. 2019, 26 pages.

Muzard, J. et al., "Grafting of protein L-binding activity onto recombinant antibody fragments," Analytical Biochemistry, 388:331-338 (2009).

Myers, K. V. et al., "Targeting Tyro3, Axl and MerTK (TAM receptors): implications for macrophages in the tumor microenvironment," Molecular Cancer, 18:94 (2019); https://doi.org/10.1186/s12943-019-1022-2, 14 pages.

Newton, D. L. et al., "Potent and specific antitumor effects of an anti-CD22-targeted cytotoxic ribonuclease: potential for the treatment of non-Hodgkin lymphoma," Blood, 97:528-535 (2001).

Nilson, B. H. K. et al., "Protein L from *Peptostreptococcus magnus* Binds to the K Light Chain Variable Domain," The Journal of Biological Chemistry, 267(4):2234-2239 (1992).

Nilson, B. H. K. et al., "Purification of antibodies using protein L-binding framework structures in the light chain variable domain," Journal of Immunological Methods, 164:33-40 (1993).

Nomi, T. et al., "Clinical Significance and Therapeutic Potential of the Programmed Death-1 Ligand/programmed Death-1 Pathway in Human Pancreatic Cancer," Clin Cancer Res, 13(7):2151-2157 (2007).

O'Brien, A. D. et al., "Shiga Toxin: Biochemistry, Genetics, Mode of Action, and Role in Pathogenesis," Current Topics in Microbiology and Immunology, 180:65-94 (1992).

Olsnes, S., "The history of ricin, abrin and related toxins," Toxicon, 44:361-370 (2004).

Park, J.-J. et al., "B7-H1/CD80 interaction is required for the induction and maintenance of peripheral T-cell tolerance," Blood, 116(8):1291-1298 (2010).

Parikh, B. A. & Tumer, N. E., "Antiviral Activity Of Ribosome Inactivating Proteins In Medicine," Mini-Reviews in Medicinal Chemistry, 4:523-543 (2004).

Pastan, I. et al., "Immunotoxin therapy of cancer," Nature Reviews Cancer, 6:559-565 (2006).

Pastan, I. et al., "Recombinant toxins as novel therapeutic agents," Annu. Rev. Biochem., 61:331-354 (1992).

Picard, D. et al., "Pokeweed Antiviral Protein Inhibits Brome Mosaic Virus Replication in Plant Cells," The Journal of Biological Chemistry, 280(20):20069-20075 (2005).

Pillai, R. N. et al., "Comparison of the Toxicity Profile of PD-1 Versus PD-L1 Inhibitors in Non-Small Cell Lung Cancer: A Systematic Analysis of the Literature," Cancer, 124:271-277 (2018).

Polito, L. et al., "Saporin-S6: A Useful Tool in Cancer Therapy," Toxins, 5:1698-1722 (2013).

Press Release Molecular Templates' Presentations at the American Association of Cancer Research (AACR) Annual Meeting 2019 Highlight Evolution of ETB Platform, Apr. 2, 2019, 3 pages.

(56) References Cited

OTHER PUBLICATIONS

Press Release New Data on Molecular Templates' Engineered Toxin Bodies to be Presented at the American Association of Cancer Research (AACR) Annual Meeting 2019, Feb. 27, 2019, 4 pages.
Press Release Molecular Templates Announces FDA Acceptance of IND Application for MT-5111, An Engineered Toxin Body Targeting HER2, Austin Texas, Apr. 22, 2019, 2 pages.
Prima, V. et al., "COX2/mPGES1/PGE2 pathway regulates PD-L1 expression in tumor-associated macrophages and myeloid-derived suppressor cells," PNAS, 114(5):1117-1122 (2017).
Probert, W. S. et al., "Isolation and Identification of an *Enterobacter cloacae* Strain Producing a Novel Subtype of Shiga Toxin Type 1," Journal of Clinical Microbiology, 52(7):2346-2351 (2014).
Puri, M. et al., "Ribosome-inactivating proteins: current status and biomedical applications," Drug Discovery Today, 17(13-14):774-783 (2012).
Rajagopalan, S. et al., "Abstract 595: Next-generation engineered toxin bodies:CD38, PD-L1 and HER2 targeted ETBs," In: Proceedings of the 107th Annual Meeting of the American Association for Cancer Research; Apr. 16-20, 2016; New Orleans, LA. Philadelphia (PA): AACR; Cancer Res 2016;76(14 Suppl):Abstract nr 595, 2 pages.
Ribas, A. & Wolchok, J. D., "Cancer immunotherapy using checkpoint blockade," Science, 359:1350-1355 (2018).
Roncuzzi, L. & Gasperi-Campani, A., "DNA-nuclease activity of the single-chain ribosome-inactivating proteins dianthin 30, saporin 6 and gelonin," FEBS Letters, 392:16-20 (1996).
Saha, A. et al., "Host programmed death ligand 1 is dominant over programmed death ligand 2 expression in regulating graft-versus-host disease lethality," Blood, 122(17):3062-3073 (2013).
Scheutz, F. et al., "Multicenter Evaluation of a Sequence-Based Protocol for Subtyping Shiga Toxins and Standardizing Stx Nomenclature," Journal of Clinical Microbiology, 50(9):2951-2963 (2012).
Shapira, A. & Benhar, I., "Toxin-Based Therapeutic Approaches," Toxins, 2:2519-2583 (2010); doi:10.3390/toxins2112519.
Sharma, N. et al., "Isolation and Characterization of an RIP (Ribosome-Inactivating Protein)-Like Protein from Tobacco with Dual Enzymatic Activity," Plant Physiology, 134:171-181 (2004).
Singh, N. K. et al., "Emerging Concepts in TCR Sp[Specificity: Rationalizing and (Maybe) Predicting Outcomes," The Journal of Immunology, 199:2203-2213 (2017).
Spranger, S. et al., "Up-Regulation of PD-L1, IDO, and Tregs in the Melanoma Tumor Microenvironment Is Driven by CD8+ T Cells," Science Translational Medicine, 5(200):200ra116 (2013), 10 pages.
Stirpe, F. et al., "Activities associated with the presence of ribosome-inactivating proteins increase in senescent and stressed levels," FEBS Letters, 382:309-312 (1996).
Stirpe, F., "On the action of ribosome-inactivating proteins: are plant ribosomes species-specific," Biochemical Journal Letters, 202:279-280 (1982).
Strauch, E. et al., "Characterization of a Shiga Toxin-Encoding Temperate Bacteriophage of *Shigella sonnei*," Infection and Immunity, 69(12):7588-7595 (2001).
Strome, S. E. et al., "B7-H1 Blockade Augments Adoptive T-Cell Immunotherapy for Squamous Cell Carcinoma," Cancer Research, 63:6501-6505 (2003).
Tesh, V. L. et al., "Comparison of the Relative Toxicities of Shiga-Like Toxins Type I and Type II for Mice," Infection and Immunity, 61(8):3392-3402 (1993).
Thompson, R. H. et al., "PD-1 Is Expressed by Tumor-Infiltrating Immune Cells and Is Associated with Poor Outcome for Patients with Renal Cell Carcinoma," Clin Cancer Res, 13(6):1757-1761 (2007).
Thompson, R. H. et al., "Tumor B7-H1 Is Associated with Poor Prognosis in Renal Cell Carcinoma Patients with Long-term Follow-up," Cancer Res, 66(7):3381-3385 (2006).
Tkachev, V. et al., "Programmed Death-1 Controls T Cell Survival by Regulating Oxidative Metabolism," The Journal of Immunology, 194:5789-5800 (2015).

UnitProtKB Q9NZQ7 (PD1L1_Human), last modified Apr. 7, 2021, 10 pages.
Van Heeckeren, W. J. et al., "Randomised comparison of two B-cell purging protocols for patients with B-cell non-Hodgkin lymphoma: in vivo purging with rituximab versus ex vivo purging with CliniMACS CD34+ cell enrichment device," British Journal of Haematology, 132:42-55 (2005).
Von Minckwitz, G. et al., "Phase I clinical study of the recombinant antibody toxin scFv(FRP5)-ETA specific for the ErbB2/HER2 receptor in patients with advanced solid malignomas," Breast Cancer Research, 7(5):R617-R626 (2005).
Vouri, M. & Hafizi, S., "TAM Receptor Tyrosine Kinases in Cancer Drug Resistance," Cancer Res, 77(11):2775-2778 (2017).
Walsh, M. J. et al., "Ribosome-inactivating proteins. Potent poisons and molecular tools," Virulence, 4(8):774-784 (2013).
Wang, P. & Tumer, N. E., "Pokeweed antiviral protein cleaves double-stranded supercoiled DNA using the same active site required to depurinate rRNA," Nucleic Acids Research, 27(8):1900-1905 (1999).
Wang, S. -C. et al., "Polymorphisms of Genes for Programmed Cell Death 1 Ligands in Patients with Rheumatoid Arthritis," J Clin Immunol, 27:563-567 (2007).
Weldon, J. E. & Pastan, I., "A guide to taming a toxin—recombinant immunotoxins constructed from *Pseudomonas exotoxin* A for the treatment of cancer," FEBS Journal, 278:4683-4700 (2011).
Weidle, U. H. et al., "Prospects of Bacterial and Plant Protein-based Immunotoxins for Treatment of Cancer," Cancer Genomics & Proteomics, 11:25-38 (2014).
Wels, W. et al., "Selective Inhibition of Tumor Cell Growth by a Recombinant Single-Chain Antibody-Toxin Specific for the erbB-2 Receptor," Cancer Research, 52:6310-6317 (1992).
Wintterle, S. et al., "Expression of the B7-Related Molecule B7-H1 by Glioma Cells: A Potential Mechanism of Immune Paralysis," Cancer Research, 63:7462-7467 (2003).
Wu, C. -T. et al., "The role of PD-L1 in the radiation response and clinical outcome for bladder cancer," Scientific Reports, 6:19740 (2016), 9 pages; doi:10.1038/srep19740.
Xiao, W. et al., "IFNAR1 Controls Autocrine Type I IFN Regulation of PD-L1 Expression in Myeloid-Derived Suppressor Cells," The Journal of Immunology, 201:264-277 (2018).
Yang, Q. et al., "Association of polymorphisms in the programmed cell death of 1 (PD-1) and PD-1 ligand genes with ankylosing spondylitis in a Chinese population," Clinical and Experimental Rheumatology, 29:13-18 (2011).
Zhang, Y. et al., "Expression and clinical significance of programmed death-1 on lymphocytes and programmed death ligand-1 on monocytes in the peripheral blood of patients with cervical cancer," Oncology Letters, 14:7225-7231 (2017).
Zhaxybayeva, O. & Doolittle, W. F., "Lateral gene transfer," Current Biology, 21(7):R242-R246 (2011).
Zheng, P. & Zhou, Z., "Human Cancer Immunotherapy with PD-1/PD-L1 Blockade," Biomarkers in Cancer, 7(S2):15-18 (2015); doi:10.4137/BiC.s29325.
Zou, W. & Chen, L., "Inhibitory B7-family molecules in the tumour microenvironment," Nature Reviews Immunology, 8:467-477(2008).
Lapadula, W. J. et al., "Revising the Taxonomic Distribution, Origin and Evolution of Ribosome Inactivating Protein Genes," PLoS One, 8(9):e72825 (2013); doi:10.1371/journal.pone.0072825, 8 pages.
Ogishi, M. & Yotsuyanagi, H., "Quantitative Prediction of the Landscape of T Cell Epitope Immunogenicity in Sequence Space," Frontiers in Immunology, vol. 10, Article 827, 2019, pp. 1-20.
Schumacher, F. -R. et al., "Building proteomic tool boxes to monitor MHC class I and class II peptides," Proteomics, 17(1-2) (2017), 16 pages; doi:10.1002/pmic.201600061.
European Medicines Agency (EMA) Assessment Report, Jul. 26, 2018, Committee for Medicinal Products for Human Use (CHMP), 143 pages.
MedlinePlus, PDL1 (Immunotherapy) Tests, 2019, retrieved from the Internet https://medlineplus.gov/lab-tests/pdl1-immunotherapy-tests/#:~: text=A%20PD%2DL1%20test%20uses,of%20cancer%20treatment%20called%20immunotherapy, 7 pages.

(56) References Cited

OTHER PUBLICATIONS

Naucler, C. S. et al., "The emerging role of human cytomegalovirus infection in human carcinogenesis: a review of current evidence and potential therapeutic implications," Oncotarget, 10(42):4333-4347 (2019).
Vilabona, L., "HLA-A*02 and Its Prognostic Traits in Cancer," Department of Oncology-Pathology, Karolinska Institutet, Stockholm 2016, 58 pages.
Yan, W. et al., "Squamous cell carcinoma—similarities and differences among anatomical states," Am J Cancer Res, 1(3):275-300 (2011).

* cited by examiner

FIGURE 1 (continued)

| Cell-Targeting Molecule Function: | Potency (ng / mL) |
|---|---|
| Protein synthesis inhibition | 0.36 |
| Binding human PD-L1 | 1.8 |
| Binding cynomolgus PD-L1 | 1.7 |
| Cytotoxicity to PD-L1 positive tumor cells | 1 to 110 |
| Cytotoxicity to PD-L1 positive monocytes | 2 to 200 |
| Cytotoxicity to PD-L1 positive tumor cells in the presence of CTLs | 20

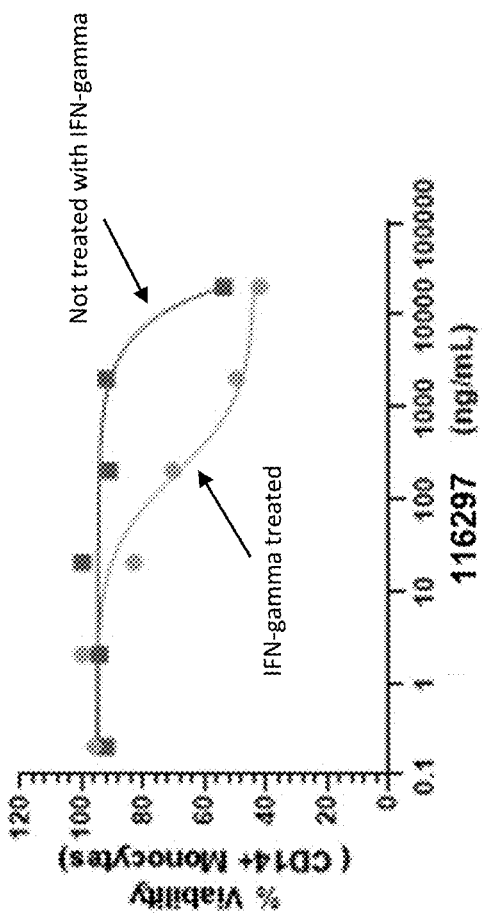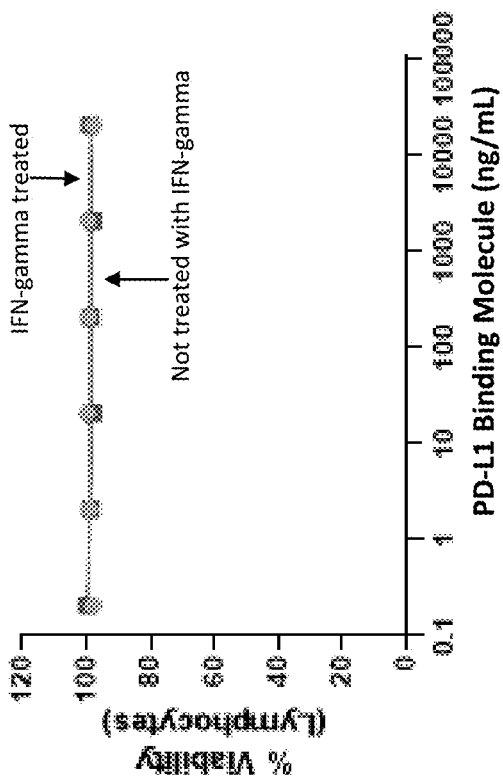
FIGURE 20A
FIGURE 20B

| Cell line tested | Cytotoxic potency of 116297: $CD_{50}$ (ng/mL) in the presence of CTLs | Fold induction of IFN-γ secretion by 116297-treated tumor cell / CTL co-culture over 116297-treated tumor cells alone |
|---|---|---|
| MDA-MB-231 | 18.4 | 55.0 |
| L1236 | 253.0 | 38.0 |
| MCF-7 | > 20,000 | 6.6 |

FIGURE 23

| Response | MDA-MB-231 | PDX2 | PDX2B |
|---|---|---|---|
| Dose | 6 mg/kg (dose 1) 2m/kg (3 x week) | 6 mg/kg (dose 1) 2m/kg (3 x week) | 2 mg/kg (3 x week) |
| T/C response | 60% | 21% | 43% |
| Mean to endpoint | Vehicle: 49 116279: > 50 | Vehicle: 52 116279: >60 | Vehicle: 59 116279: >65 |

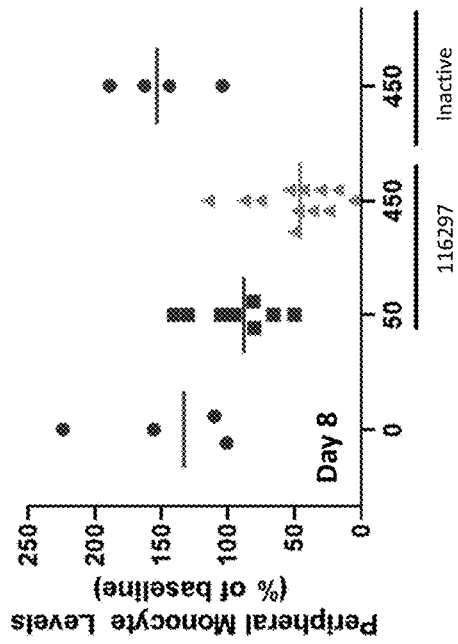
FIGURE 41B
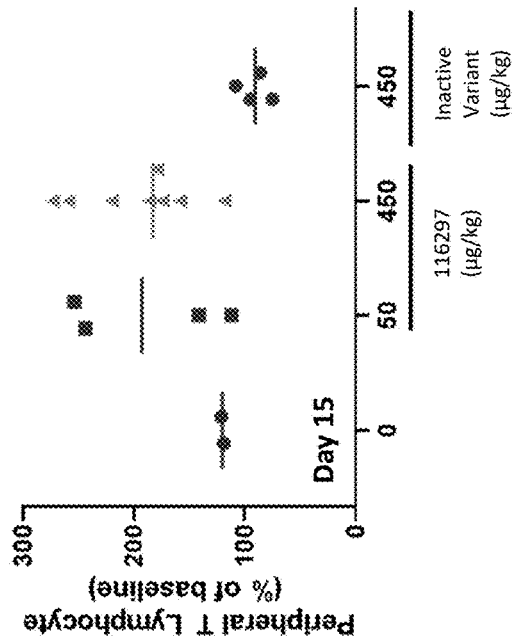
FIGURE 41C
FIGURE 41A

| Group | Dosing | Immune Effects | Pharmacodynamic Response |
|---|---|---|---|
| 116297 | 50 µg/kg | ↑Monocyte depletion<br>↑T cell, B cell, Eosinophil expansion increased with sequential dosing | Minimal Troponin-I release; no significant cardiac findings; evidence of skin inflammation |
| 116297 | 450 µg/kg | ↑↑T cell, B cell, NK, Eosinophil expansion; increased with sequential dosing<br>Cytokine induction<br>IL-2, IFN-γ, TNF-α, IL-6, IL-10 | Troponin-I release associated with CD3+ T cardiac infiltration minimal monocyte and B ell infiltration; resolving with dose cessation evidence of skin inflammation |
| SLTA-inactive | 450 µg/kg | No remarkable findings | No Remarkable findings |

FIGURE 42B

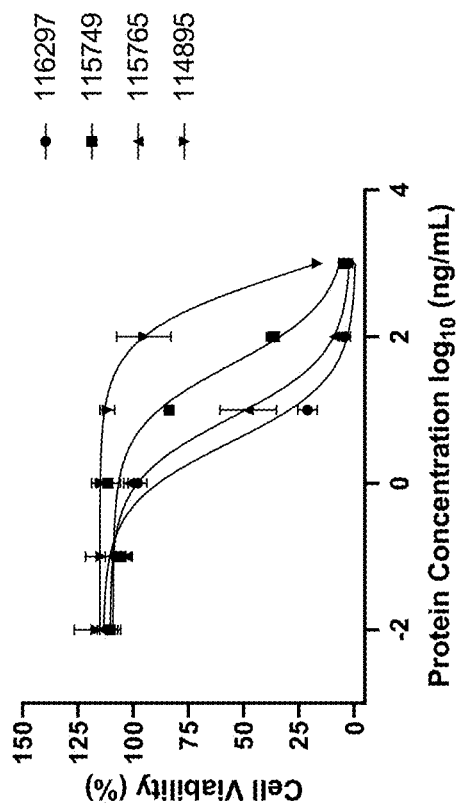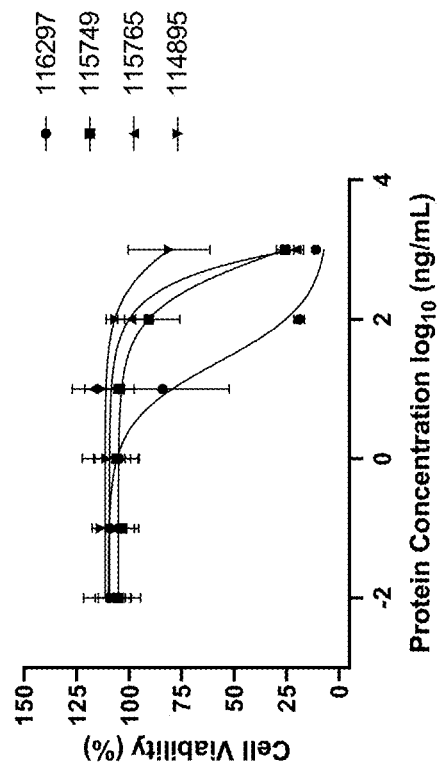
FIGURE 43A
FIGURE 43B

| Treatment Group | Dosing | Immune Effects | Pharmacodynamic Response |
|---|---|---|---|
| 116297 | 50 µg/kg<br>1 dose per week/4 weeks | ↑Monocyte depletion<br>↑T cell, B cell, Eosinophil expansion increased with sequential dosing | no significant cardiac findings<br>✓ Evidence of skin inflammation |
| 116297 | 450 µg/kg<br>1 dose per week/4 weeks | ↑↑Monocyte depletion<br>↑↑↑T cell, B cell, NK, Eosinophil expansion; increased with sequential dosing<br>Cytokine induction:<br>IL-2, IFN-γ, TNF-α, IL-6, IL-10 | ✓ CD3+ T cardiac infiltration, minimal monocyte and B cell infiltration; resolving with dose cessation<br>✓ Evidence of skin inflammation |
| 116555 | 450 µg/kg<br>1 dose per week/4 weeks | No remarkable findings | No Remarkable irAE findings |
| 115749 | 450 µg/kg<br>3 doses per week/2 weeks | No remarkable findings | ✓ Skin inflammation at >150 µg/kg |
| 115765 | 450 µg/kg<br>3 doses per week/2 weeks | No remarkable findings | No Remarkable irAE findings |
| 115695 | 450 µg/kg<br>3 doses per week/2 weeks | No remarkable findings | No Remarkable irAE findings |

FIGURE 44

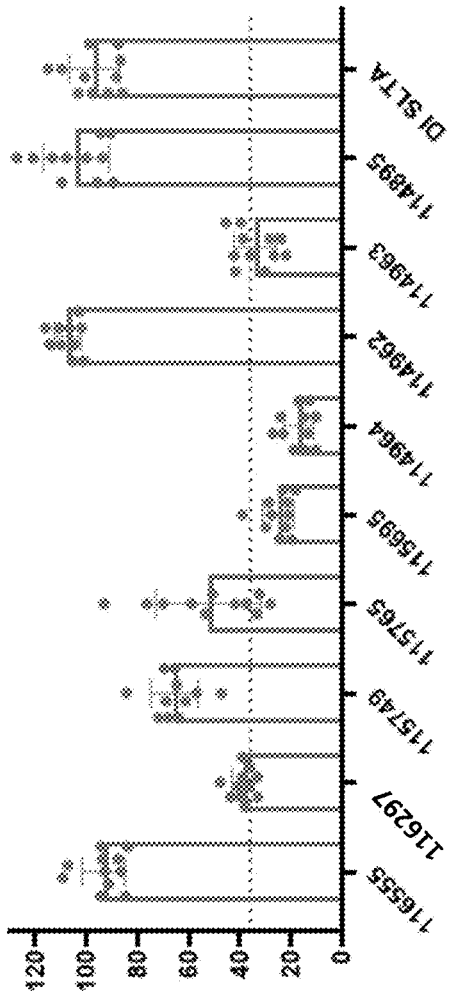
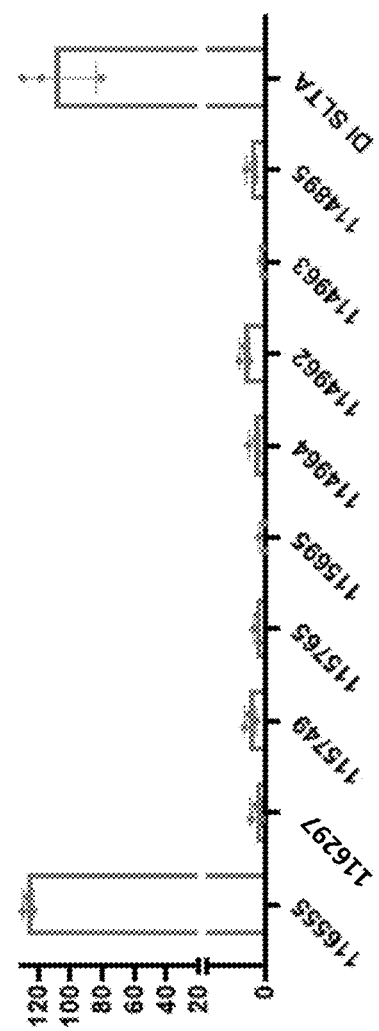
FIGURE 46A
FIGURE 46B

PD-L1-BINDING MOLECULES COMPRISING SHIGA TOXIN A SUBUNIT SCAFFOLDS

CROSS-REFERENCE TO RELATED APPLICATIONS

This application claims priority to U.S. Provisional Application No. 63/041,288, filed on Jun. 19, 2020, 62/970,610, filed on Feb. 5, 2020, 62/933,197, filed on Nov. 8, 2019, and 62/902,243, filed on Sep. 18, 2019, each which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is MTEM_016_04US_SubSeqList_ST25.txt. The file is 501,663 bytes, was created on Jun. 6, 2023, and is being submitted electronically.

TECHNICAL FIELD

The present application relates to PD-L1 binding molecules comprising toxins, such as, e.g., a catalytic active protein toxin or fragment thereof. In some embodiments, the PD-L1-targeting molecules described herein can kill a PD-L1-expressing cell due to the catalytic activity of a toxin component. In some embodiments, the PD-L1 binding molecules described herein can deliver a CD8+ T-cell epitope to the MHC class I system of a PD-L1-expressing cell. In some embodiments, the PD-L1-targeting molecules described herein comprise a Shiga toxin effector polypeptide derived from the A Subunit of a naturally occurring Shiga toxin. In some embodiments, the PD-L1-targeing molecules described herein comprise Shiga toxin effector polypeptides that comprise multiple amino acid substitution mutations relative to a wild-type Shiga toxin. The PD-L1 binding molecules described herein are useful (1) for selectively killing a specific PD-L1-expressing cell type(s) amongst other cells and (2) as therapeutic molecules for treating a variety of diseases, disorders, and conditions involving PD-L1-expressing cells, including cancers and tumors.

BACKGROUND

The following includes information that may be useful in understanding the invention(s) described herein. It is not an admission that any of the information provided herein is prior art or relevant to the presently described or claimed invention(s), or that any publication or document that is specifically or implicitly referenced herein is prior art.

PD-L1, programmed cell death ligand 1 (also known as CD274), is expressed on the cell surface of tumors from a variety of malignancies. PD-L1 can bind to the immune checkpoint receptor PD-1 on T-cells and inhibit T-cell activation signals leading to evasion of immune surveillance by the tumor cell, tumor, and/or other cells in the tumor microenvironment, i.e. T-cell suppression and/or T-cell anergy.

Blockade of the PD-L1/PD-1 signaling axis by therapeutic antibodies can have clinical efficacy for certain diverse indications and may allow for proliferation and/or activation of anti-tumor T-cells beyond normal physiologic conditions. Oncological indications which may benefit from a PD-L1 targeted agent include but are not limited to lung cancer, melanoma, bladder cancer, Hodgkin's lymphoma, breast cancer (including, but not limited to, triple negative breast cancer, i.e., breast cancer that is negative for HER2, estrogen receptor, and progesterone receptor), as well as other neoplasms involving cells which express PD-L1, such as tumor cells with high mutational burdens and/or frequencies of indels. Thus, PD-L1 is a target for delivery of anti-neoplastic agents, including immunotoxins for the alleviation and treatment of certain diseases, disorders, and conditions.

PD-L1 is also expressed on the surface of certain immune cell types. Thus, PD-L1 is a putative target for delivery of immunomodulatory agents (including immunotoxins, immunogens, and vaccines) to such immune cells for the prevention, alleviation, and treatment of certain diseases, disorders, and conditions, such as, e.g., certain immune disorders.

PD-L1 expression may serve a diagnostic marker for the characterization of a cell-type, tissue, disease, disorder, or condition. PD-L1 expression may serve a diagnostic marker for the selection or stratification of patients most likely to respond to certain therapies or therapeutic approaches or to monitor changes in patients during or after receipt of a therapeutic regimen or other intervention. Thus, PD-L1 is a target for diagnostic detection and characterization, such as, e.g., to detect or characterize cells capable of internalizing an immunotoxin-linked diagnostic agent for information-gathering regarding the status of certain diseases, disorders, and conditions, including the progression and effects of treatments thereof.

There is a need in the art to develop molecules comprising PD-L1-targeting immunoglobulin binding domains and toxin components for the creation of PD-L1-targeting molecules which deliver toxins to PD-L1-expressing cells for therapeutic or diagnostic purposes. For example, there is an urgent need for new therapeutics to supplement present day therapies aimed at killing PD-L1-bearing neoplasms.

Thus, it would be desirable to have cytotoxic molecules which bind PD-L1 for use as therapeutic and/or diagnostic molecules to treat and diagnose a variety of diseases, such as, e.g., cancers and tumors, that can be treated by selective killing of or selective delivery of a beneficial agent into a PD-L1 positive cell. In particular, it would be desirable to have PD-L1-binding, cytotoxic, binding molecules comprising toxins that exhibit low immunogenicity, low off-target toxicity, and potent on-target cytotoxicity. Furthermore, it would be desirable to have PD-L1-targeting therapeutic and/or diagnostic molecules exhibiting low immunogenicity, low off-target toxicity, high stability, and/or the ability to deliver peptide-epitope cargos for presentation by the MHC class I system of a target cell. For example, it would be desirable to have PD-L1 binding molecules comprising Shiga toxin A Subunit derived components that maintain potent cytotoxicity while 1) reducing the potential for unwanted antigenicities and/or immunogenicities, 2) reducing the potential for non-specific toxicities, and/or 3) having the ability to deliver peptide-epitope cargos for presentation by the MHC class I system of a target cell, and which also exhibit potent Shiga toxin A Subunit based cytotoxicity to target cells. Certain PD-L1 binding molecules targeting human PD-L1 may offer additional advantages if they do not compete for binding with an already approved anti-PD-L1 therapeutic(s) and/or diagnostic(s). PD-L1 binding molecules comprising toxins (e.g. an immunotoxin) may exhibit unique mechanisms of action if their binding to PD-L1 functions to modulate the PD-L1/PD-1 signaling axis.

BRIEF SUMMARY

Provided herein are various embodiments of PD-L1 binding molecules, and compositions thereof. For example, in some embodiments, a PD-L1 binding molecule comprises a Shiga toxin A subunit effector polypeptide and a binding region capable of specifically binding an extracellular part of PD-L1, wherein the binding region comprises (a) a heavy chain variable region (VH) comprising (i) a CDR1 comprising the amino acid sequence EYTMH (SEQ ID NO:27), (ii) a CDR2 comprising the amino acid sequence GINPNNGGTWYNQKFKG (SEQ ID NO:29), and (iii) a CDR3 comprising the amino acid sequence PYYYGSREDYFDY (SEQ ID NO:32); and (b) a light chain variable region (VL) comprising (i) a CDR1 comprising the amino acid sequence SASSSVSYMY (SEQ ID NO:19), (ii) a CDR2 comprising the amino acid sequence LTSNLAS (SEQ ID NO:20), and (iii) a CDR3 comprising the amino acid sequence QQWSSNPPT (SEQ ID NO:26).

Also provided herein are pharmaceutical compositions comprising the PD-L1 binding molecules described herein and at least one pharmaceutically acceptable excipient or carrier.

Also provided herein are polynucleotides encoding a PD-L1 binding molecules described herein, or complements thereof, and expression vectors or host cells comprising the same.

Also provided herein are methods for making the PD-L1 binding molecules described herein, the methods comprising expressing a PD-L1 binding molecule and recovering the PD-L1 binding molecule.

Also provided herein are methods for purifying the PD-L1 binding molecules described herein from an expression system composition comprising the PD-L1 binding molecule and at least one other biomolecule, the method comprising (i) contacting the expression system composition with a bacterial protein L to create a PD-L1 binding molecule-protein L complex, and (ii) recovering the PD-L1 binding molecule-protein L complex.

Also provided herein are methods for killing a PD-L1 expressing cell comprising a step of contacting the cell with a PD-L1 binding molecule or a pharmaceutical composition according as described herein.

Also provided herein are methods for treating a disease, disorder, or condition in a subject comprising a step of administering to a subject in need thereof a therapeutically effective amount of a PD-L1 binding molecule or a pharmaceutical composition described herein.

Also provided herein are methods of treating cancer in a patient using immunotherapy, the methods each comprising the step of administering to the patient in need thereof a PD-L1 binding molecule and/or pharmaceutical composition described herein.

Also provided herein are methods for treating cancer comprising administering to a subject in need thereof an effective amount of a PD-L1 binding molecule or a pharmaceutical composition described herein. In some embodiments, the cancer is any one of the following: bladder cancer (e.g., urothelial carcinoma), breast cancer (e.g., HER2 positive breast cancer, triple negative breast cancer), colon cancer (e.g., colorectal cancer such as metastatic microsatellite instability-high or mismatch repair deficient colorectal cancer), endometrial cancer, esophageal cancer, fallopian tube cancer, gastrointestinal cancer (e.g., gastric cancer, biliary tract neoplasm, gastroesophageal junction cancer), glioblastoma, glioma, head and neck cancer (e.g., squamous cell carcinoma of the head and neck), kidney cancer (e.g., renal cell carcinoma), liver cancer (e.g., hepatocellular carcinoma), lung cancer (e.g., non-small cell lung cancer, small-cell lung cancer), lymphoma (e.g., diffuse large B-cell lymphoma, Hodgkin lymphoma, non-Hodgkin lymphoma, primary mediastinal large B-cell lymphoma), Merkel cell carcinoma, mesothelioma (e.g., pleural mesothelioma), myeloma (e.g., multiple myeloma), nasopharyngeal neoplasm, ovarian cancer, pancreatic cancer, peritoneal neoplasm, prostate cancer, skin cancer (e.g., squamous cell cancer of the skin, melanoma, transitional cell carcinoma, or urothelial cancer.

These and other features, aspects and advantages of the present invention will become better understood with regard to the following description, appended claims, and accompanying figures. The aforementioned elements of the invention may be individually combined or removed freely in order to make other embodiments of the invention, without any statement to object to such synthesis or removal hereinafter.

BRIEF DESCRIPTION OF THE DRAWINGS

FIG. 1 depicts exemplary PD-L1 binding molecules comprising one or more toxins or toxin subsunits, such as Shiga toxin A Subunit effector polypeptides, and one or more PD-L1 binding regions. In one exemplary PD-L1 binding molecule, the PD-L1 binding region is a scFv, and the scFv is shown participating in intermolecular variable domain exchange with a neighboring scFv (bottom left). The depictions of exemplary molecules in FIG. 1 are for illustrative purposes of certain, general arrangements of the structural features of some embodiments of the PD-L1 binding molecules described herein. It is to be understood that these exemplary molecules do not intend, nor should any be construed, to be wholly definitive as to the arrangement of any structural features and/or components of a molecule as described herein. The relative size, location, or number of features shown in the schematics of FIG. 1 have been simplified. The schematics in FIG. 1 are not intended to accurately portray any information regarding the relative sizes of molecular structures in any embodiment as described herein.

FIG. 2 graphically shows PD-L1 binding characteristics of exemplary PD-L1 binding molecules using recombinant PD-L1 proteins from different mammalian species. The exemplary PD-L1 binding molecules 115749 (SEQ ID NO:113) and 115750 (SEQ ID NO:114) were tested for binding to recombinant PD-L1 proteins originating from human, cynomolgus macaque, or mouse using in an enzyme-linked immuno assay (ELISA) format. A control PD-L1 binding molecule consisting of a DI-SLT-A1 fusion protein (114964) (comprising immunoglobulin binding domains present in atezolizumab, which had previously been shown to bind to PD-L1 proteins from human, macaque, and mouse origins) was used as a positive control for PD-L1 binding. Background subtracted ELISA signals detected as absorbance values at 450 nanometer (nm) using a plate reader are shown on the Y-axis. In FIGS. 2-3, the term "bkg sub" refers to "background subtraction" used to adjust the measured values relative to a buffer-only control. Both PD-L1 binding molecules 115749 (SEQ ID NO:113) and 115750 (SEQ ID NO:114) bound to human PD-L1 and cynomolgus macaque PD-L1 but did not bind to murine PD-L1 in this assay.

FIG. 3 graphically shows PD-L1 binding characteristics of exemplary PD-L1 binding molecules using recombinant PD-L1 proteins of human or cynomolgus macaque origins. The exemplary PD-L1 binding molecules 115749 (SEQ ID NO:113), 116188 (SEQ ID NO:126), and 116297 (SEQ ID NO:128) were tested for binding to recombinant PD-L1 proteins using in an ELISA format. The background subtracted ELISA signal for 115749 (SEQ ID NO:113), 116188 (SEQ ID NO:126), and 116297 (SEQ ID NO:128) tested over a series of PD-L1 binding molecule concentrations as measured in absorbance at 450 nm was graphed on the Y-axis versus the logarithm to base 10 of the PD-L1 binding molecule concentration in ng/mL on the X-axis. The PD-L1 binding molecules 115749 (SEQ ID NO:113), 116188 (SEQ ID NO:126), and 116297 (SEQ ID NO:128) each bound both human PD-L1 protein and cynomolgus macaque PD-L1 protein with similar binding characteristics. The term "binding molecule" as used in FIGS. 3-5 and 10A-10B, 11, and 12 refers to a type of PD-L1-targeting immunotoxin described in the Examples, infra, as a PD-L1 binding molecule comprising a Shiga toxin a Subunit component and antibody immunoglobulin domains for PD-L1 targeting.

FIG. 4 graphically shows PD-L1 binding characteristics of an exemplary PD-L1 binding molecule 115749 (SEQ ID NO:113) to PD-L1 positive HCC1954 cells determined using a flow cytometry method. The fluorescence signal of FITC measured as mean fluorescent intensity (MFI) was plotted over the concentration of the PD-L1 binding molecule tested in microgram per milliliter (μg/mL) graphed on a logarithmic scale. In this assay, 115749 (SEQ ID NO:113) exhibited dose-dependent binding to PD-L1 expressing HCC1954 cells.

FIG. 5 graphically shows the in vitro protein synthesis inhibition activities of exemplary PD-L1 binding molecules over a range of concentrations. For each sample molecule, the luminescent intensity of luciferase expressed during the assay in relative luminescent units (RLU times $e^3$) was plotted over the logarithm to base 10 of the concentration of the PD-L1 binding molecule tested in nanogram per milliliter (ng/mL). These exemplary PD-L1 binding molecules 115749 (SEQ ID NO:113) and 115961 (SEQ ID NO:123) exhibited ribosome inhibition activities comparable to a positive "control" molecule, a Shiga toxin effector polypeptide (DI-SLTA) alone, not coupled with any targeting agent or binding region (i.e., a polypeptide comprising SEQ ID NO: 41), although 115961 (SEQ ID NO:123) exhibited slightly less inhibition of protein synthesis. The term "DI-SLTA" as used in FIGS. 5, 9, and 11 refers to a Shiga toxin component in exemplary PD-L1 binding molecules, wherein the Shiga toxin component was de-immunized (also referred to herein in the Examples, supra, as "DI-SLT-A1"). The "No binding molecule Positive Control" refers to samples tested which lacked any PD-L1 binding molecule (i.e., a polypeptide comprising SEQ ID NO: 41). The term "Neg. control" refers to samples which had no luciferase added but the luminescence signal was still measured.

FIG. 6A-6B graphically shows the results of a cell-kill assay investigating the cytotoxic activities of the exemplary PD-L1 binding molecules 115749 (SEQ ID NO:113) (FIG. 6A) and 115750 (SEQ ID NO:114) (FIG. 6B) to CHO-K1 cells expressing different PD-L1 proteins, from either human, cynomolgus macaque, or mouse origin. The percent viability of cells for each cell type was plotted over the logarithm to base 10 of the PD-L1 binding molecule concentrations administered to the respective cells. The PD-L1 binding molecules 115749 (SEQ ID NO:113) and 115750 (SEQ ID NO:114) killed cells expressing human or cynomolgus macaque PD-L1 targets but did not kill cells expressing a murine PD-L1 in this assay.

FIGS. 7-9 graphically show the results of a cell-kill assays investigating the activities of the exemplary PD-L1 binding molecules to PD-L1 positive and/or PD-L1 negative cell types. The percent viability of cells for each cell type was plotted over the logarithm to base 10 of the concentration of PD-L1 binding molecule administered to the respective cell samples. In certain experiments, the specificity of cell-targeting was shown by using the same assay with a cell line negative for cell-surface expression of PD-L1. In certain experiments, an untargeted, catalytically active DI-SLT-A1 fragment (114951) was used as a control (also referred to in the Examples as "DI-SLT-1A only").

FIG. 7 shows 115749 (SEQ ID NO:113) and 115750 (SEQ ID NO:114) exhibited cytotoxicity to four, different PD-L1-expressing cell-types: HCC-1954, HCC-827, JIMT-1, and MDA-MB-231, but not a control cell line, MDA-MB-486 which does not express PD-L1 on the cell surface. The untargeted DI SLT-1A alone ("114951") exhibited relatively low cytotoxicity at the concentrations tested and was cytotoxic only at high concentrations. The cytotoxicity observed when contacting the PD-L1 negative cell line MDA-MB-468 with 115749 (SEQ ID NO:113) and 115750 (SEQ ID NO:114) is consistent with untargeted cytotoxicity (see FIG. 9, infra, untargeted DI SLT-1A alone ("DI-SLT-1A only")).

FIG. 8 shows 115744 (SEQ ID NO:108), 115745 (SEQ ID NO:109), 115747 (SEQ ID NO:111), 115748 (SEQ ID NO:112), 115749 (SEQ ID NO:113), 115750 (SEQ ID NO:114), 115751 (SEQ ID NO:115), 115752 (SEQ ID NO:116), 115753 (SEQ ID NO:117), 115754 (SEQ ID NO:118), 115755 (SEQ ID NO:119), 115756 (SEQ ID NO:120), and 115757 (SEQ ID NO:121) exhibited cytotoxicity to two, different PD-L1-expressing cell-types: HCC-1954 and MDA-MB-231 (transfected to express human PD-L1).

FIG. 9 shows 116297 and 116299 exhibited cytotoxicity to four, different PD-L1-expressing cell-types: HCC 1954, JIMT-1, HCC 827, and MDA-MB-231. The untargeted DI SLT-1A alone ("DI-SLT-1A only") exhibited relatively low cytotoxicity at the concentrations tested (DI SLT-1A was cytotoxic only at high concentrations and only for certain cell lines). No measurable cytotoxicity was observed when contacting the PD-L1 negative cells SKBR3 and MCF-7 with either 116297 (SEQ ID NO:128) and 116299 (SEQ ID NO:129) at the concentrations tested.

FIGS. 10A and 10B show the results of experiments investigating the intercellular engagement of T-cell responses to viral antigen cargo delivery by exemplary, PD-L1 binding molecules. FIG. 10A shows results related to T-cell engagement resulting in increases in cytokine secretion. Pairs of exemplary, PD-L1 binding molecules were tested wherein the only difference between the pair is that one comprised a carboxy-terminal viral antigen cargo and the other did not. FIG. 10B shows results (CD50) related to cytotoxic T-cell engagement resulting in tumor cell killing.

FIG. 10A graphically shows induction of an immune response in the form of interferon gamma (IFN-γ) secretion as measured by ELISA of supernatants taken from the co-culture. Pairs of exemplary, PD-L1 binding molecules (115749 (SEQ ID NO:113) and 115961 (SEQ ID NO:123)) or (115750 (SEQ ID NO:114) and 115962 (SEQ ID NO:124)) were tested for induction of IFN-γ a series of PD-L1 binding molecule concentrations. The resulting IFN-γ levels as measured by absorbance at 450 nm was graphed on the Y-axis versus the PD-L1 binding molecule concentration in ng/mL on the X-axis using a logarithmic scale. The phrase "no antigen" refers to samples tested wherein the PD-L1-targeting immunotoxin molecule tested did not comprise any carboxy-terminal viral CD8+ T-cell epitope cargo (also referred to in the Examples, infra, as "no antigen control", "control PD-L1 binding molecule", or the control within a "match pair"). The "AST capable" DI-SLT-A1 fusion proteins 115749 (SEQ ID NO:113) and 115750 (SEQ ID NO:114) were able to stimulate the human cytotoxic T lymphocytes that recognize the CMV antigen (CMV-CTLs) to drive IFN-γ secretion, whereas the "no antigen control" proteins 115961 (SEQ ID NO:123) and 115962 (SEQ ID NO:124) did not induce any significant amount of IFN-γ secretion. Administration of the antigen-cargo carrying PD-L1 binding molecule 115749 (SEQ ID NO:113) or 115750 (SEQ ID NO:114) to PD-L1 expressing MDA-MB-231 cells was able to stimulate the CMV-CTL cells to increase cytokine IFN-γ secretion in a co-culture of cells at a ratio of 1:1 CMV-CTLs to target cells.

FIG. 10B graphically shows that the exemplary PD-L1 binding molecules 115749 (SEQ ID NO:113) and 115962 (SEQ ID NO:124) exhibited cytotoxicity to PD-L1 expressing MDA-MB-231 ("NR" indicates that the cells were transfected with a nuclear red dye) cells in co-culture with CMV-CTL cells. The percent viability of cells relative to control at the 80-hour timepoint was plotted against the concentration of administered PD-L1 binding molecule graphed on a logarithmic scale. Pairs of exemplary, PD-L1 binding molecules (115749 (SEQ ID NO:113) and 115961 (SEQ ID NO:123)) or (115750 (SEQ ID NO:114) and 115962 (SEQ ID NO:124)) were tested for cytotoxicity (CD50) in this co-culture cell-kill assay. The phrase "no antigen" refers to samples tested wherein the PD-L1-targeting immunotoxin molecule tested did not comprise any carboxy-terminal viral CD8+ T-cell cargo. "AST capable" PD-L1 binding molecules are those comprising a carboxy-terminal CMV antigen and able to stimulate human cytotoxic T lymphocytes by delivering the antigen to PD-L1 positive/HLA:A2 positive cells.

FIG. 11 graphically shows induction of an immune response in the form of IFN-γ secretion as measured by ELISA of supernatants taken from the co-culture of PD-L1 expressing MDA-MB-231(NR) cells with CMV-CTLs at a ratio of 1:1. Exemplary, PD-L1 binding molecules 115749 (SEQ ID NO:113), 116297 (SEQ ID NO:128), 116299 (SEQ ID NO:129), 115961 (SEQ ID NO:123), and 116187 (SEQ ID NO:125) were tested for induction of IFN-γ using a series of PD-L1 binding molecule concentrations. The resulting IFN-γ levels as measured by absorbance at 450 nm was graphed on the Y-axis versus the PD-L1 binding molecule concentration in ng/mL on the X-axis using a logarithmic scale. The phrase "no Ag control" refers to samples tested wherein the PD-L1-targeting immunotoxin molecule tested did not comprise any carboxy-terminal viral antigen cargo (also referred to in the Examples, infra, as "no antigen control", "no antigen", "control binding molecule", or the control within a "match pair"). The PD-L1 binding molecules 115749 (SEQ ID NO:113), 116297 (SEQ ID NO:128), and 116299 (SEQ ID NO:129) were able to stimulate the CMV-CTL cells to secrete IFN-γ, whereas the "no Ag control" proteins 115961 (SEQ ID NO:123) and 116187 (SEQ ID NO:125) and the "DI-SLT-1A only" administered at the same protein concentrations did not induce any significant amount of IFN-γ secretion in this assay.

FIG. 12 graphically shows the results of a Promega PD-1/PD-L1 Blockage Bioassay experiment. T-cell activation as measured in RLU was plotted on the Y-axis versus the PD-L1 binding molecule or antibody concentration in nanomolar (nM) graphed on a logarithmic scale. The exemplary, PD-L1 binding molecules 115749 (SEQ ID NO:113), 115750 (SEQ ID NO:114), and 115962 (SEQ ID NO:124) all showed the ability in this assay to block the PD-L1 interaction with PD-1 at some concentrations, but the activity was lower than in samples administered the positive control, monoclonal antibody anti-hPD-L1-hIgG1.

FIG. 13 is a table showing PD-L1 binding molecule function and activity/potency (e.g. IC50, CD50, and $K_D$ in ng/mL) associated therewith.

FIG. 14 graphically shows the in vitro protein synthesis inhibition activities of exemplary PD-L1 binding molecules over a range of concentrations. For each sample molecule, the luminescent intensity of luciferase expressed during the assay in relative luminescent units (RLU times $e^3$) was plotted over the logarithm to base 10 of the concentration of the PD-L1 binding molecule tested in nanogram per milliliter (ng/mL). These exemplary PD-L1 binding molecules 116297 (SEQ ID NO:128) and 115749 (SEQ ID NO:113) exhibited ribosome inhibition activities comparable to a positive "control" molecule, a Shiga toxin effector polypeptide (DI-SLTA) alone, not coupled with any targeting agent or binding region (i.e., a polypeptide comprising SEQ ID NO: 41).

FIG. 15 is a graph showing human or cynomolgus PD-L1 binding (absorbance at 450 nm) relative to binding molecule concentration.

FIG. 16 is a graph showing cell viability percent relative to binding molecule concentration (ng/mL) in a PD-L1+ cell line. FIG. 16 shows that 116297 (SEQ ID NO:128) can exhibit greater cytotoxicity than 115749 (SEQ ID NO:113).

FIG. 17A shows the results of a binding assay testing 116297 (SEQ ID NO:128) binding to human (Hu) and cynomolgus (Cyno) PD-L1 expressed by transgenic CHO-K1 cells. A control anti-human-PD-L1 antibody ("PD-L1 mAb") atezolizumab was used in the binding assay. FIG. 17B shows the results of a cell viability assay. Cell viability percent is plotted relative to binding molecule concentration.

FIGS. 18A and 18B report cell-surface PD-L1 expression levels and $CD_{50}$ values for 116297 (SEQ ID NO:128) for a variety of clinically relevant tumor cell lines.

FIG. 19 shows the results of a flow cytometry assay using human donor PBMC samples, which included monocytes and lymphocytes cultured in the presence or absence of IFN-γ. The monocytes were induced by interferon gamma treatment to elevate their expression of PD-L1.

FIG. 20A-20B shows percent viability of PD-L1 positive human immune cells ex vivo, including CD14 positive monocytes (top panel) and lymphocytes (bottom panel) after treatment of various concentrations of 116297 (SEQ ID NO:128), and optionally after treatment with IFN-γ.

FIG. 21A shows PD-L1 expression as determined using mean fluorescence intensity (MFI) in populations of monocytes or lymphocytes left untreated, or treated with IFN-γ. FIG. 21B shows PD-L1 expression relative to potency (IC50-ng/mL) in populations of monocytes or lymphocytes left untreated, or treated with IFN-γ.

FIG. 22 shows the results of a cytotoxicity assay wherein MDA-MB231 cells (HLA:A02 positive) previously incubated with 116297 (SEQ ID NO:128) or 116296 (SEQ ID NO:127) were contacted with antigen-specific cytotoxic T-lymphocytes (CTLs, co-culture).

FIG. 23 is a chart showing cytotoxic potency and fold induction of interferon-gamma secretion by 116297 in various cell lines.

FIG. 24A shows the results of a viability study in the presence or absence of cytotoxic T lymphocytes (CTLs), wherein percent viable cells (MDA-MB231) are plotted relative to concentration of 116297 (ng/mL). FIG. 24B shows interferon gamma secretion at various concentrations of 116297 (ng/mL).

Figure 28A:
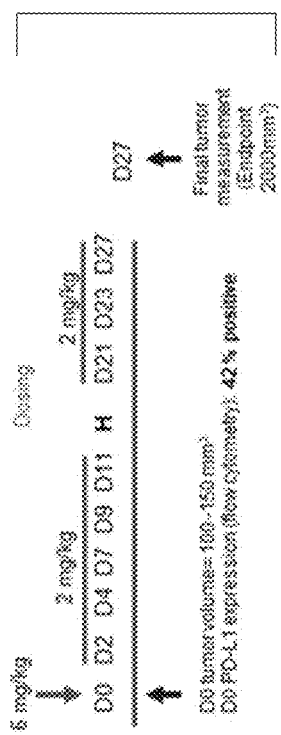

FIG. 28A is a schematic showing an experimental protocol for a xenograft (PDX) animal model using human patient derived tumors. Mice are injected with tumor cells. After the tumor volume reaches 100-150 mm 3, on day 0, the mice are dosed with 6 mg/kg of either 115749 or 116297. The mice are given subsequent doses of 2 mg/kg on days 2, 4, 7, 9, 11, 21, 23, and 27. Tumor volume is measured periodically, with the final tumor measurement occurring on day 27.

Figure 28B:
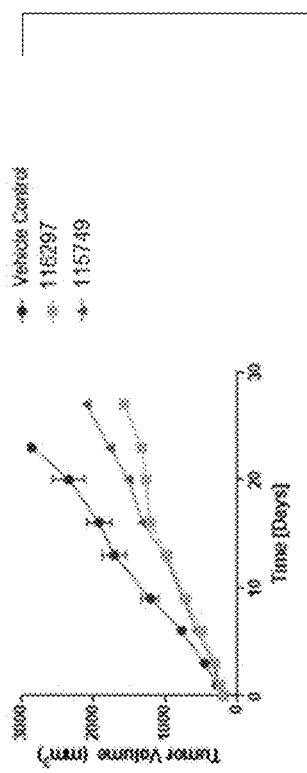
Figure 28C:
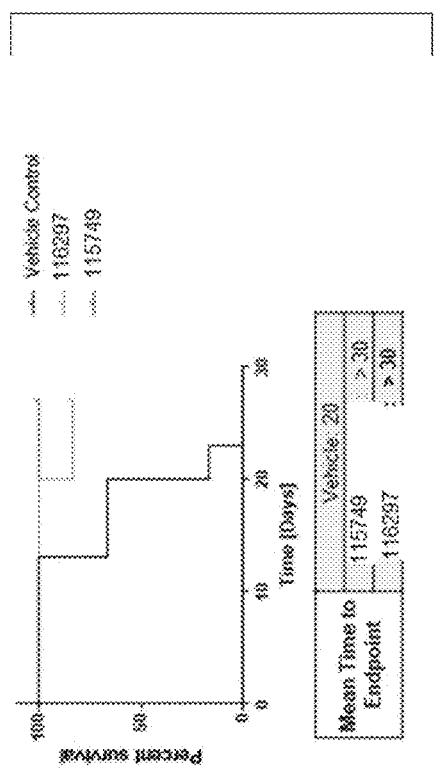

FIG. 28B is a graph showing tumor volume over time. FIG. 28C is a Kaplan-Meier survival curve.

Figure 29A:
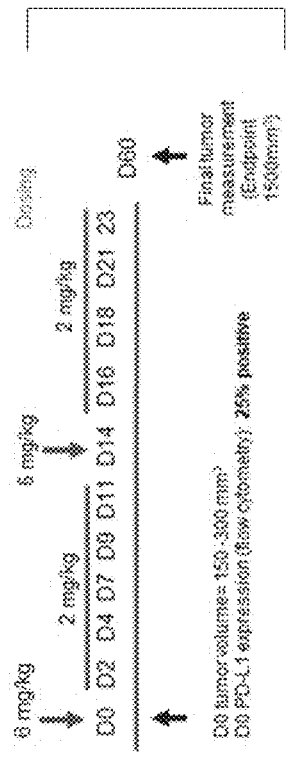
Figure 29B:
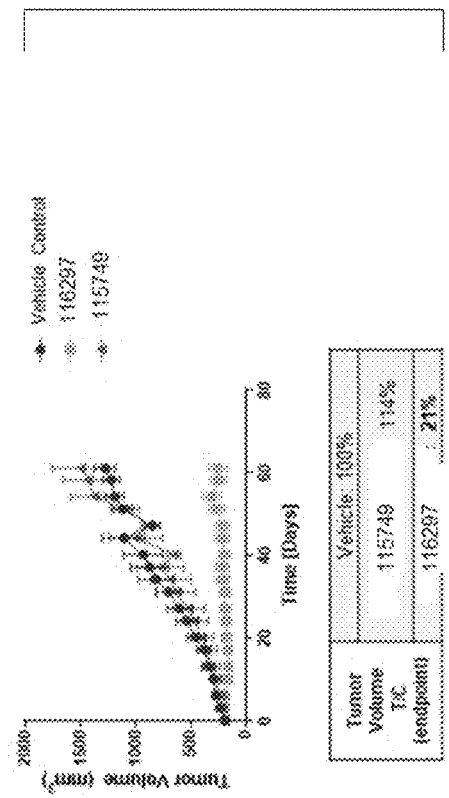
Figure 29C:
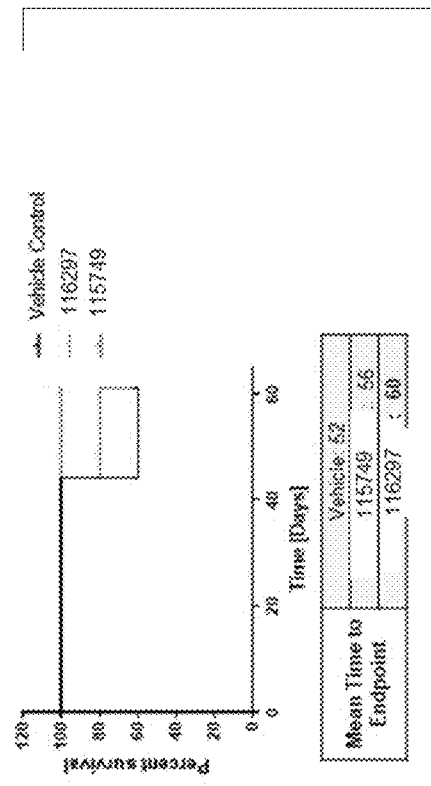

FIG. 29A is a schematic showing an experimental protocol for a xenograft (PDX) animal model using human patient derived tumors. Mice are injected with tumor cells. After the tumor volume reaches 100-150 mm 3, on day 0, the mice are dosed with 6 mg/kg of either 115749 or 116297. The mice are given subsequent doses of 2 mg/kg on days 2, 4, 7, 9, 11, 16, 18, 21, and 33, and a dose of 6 mg/kg on day 14. Tumor volume is measured periodically, with the final tumor measurement occurring on day 60. FIG. 29B is a graph showing tumor volume over time. FIG. 29C is a Kaplan-Meier survival curve.

Figure 30:
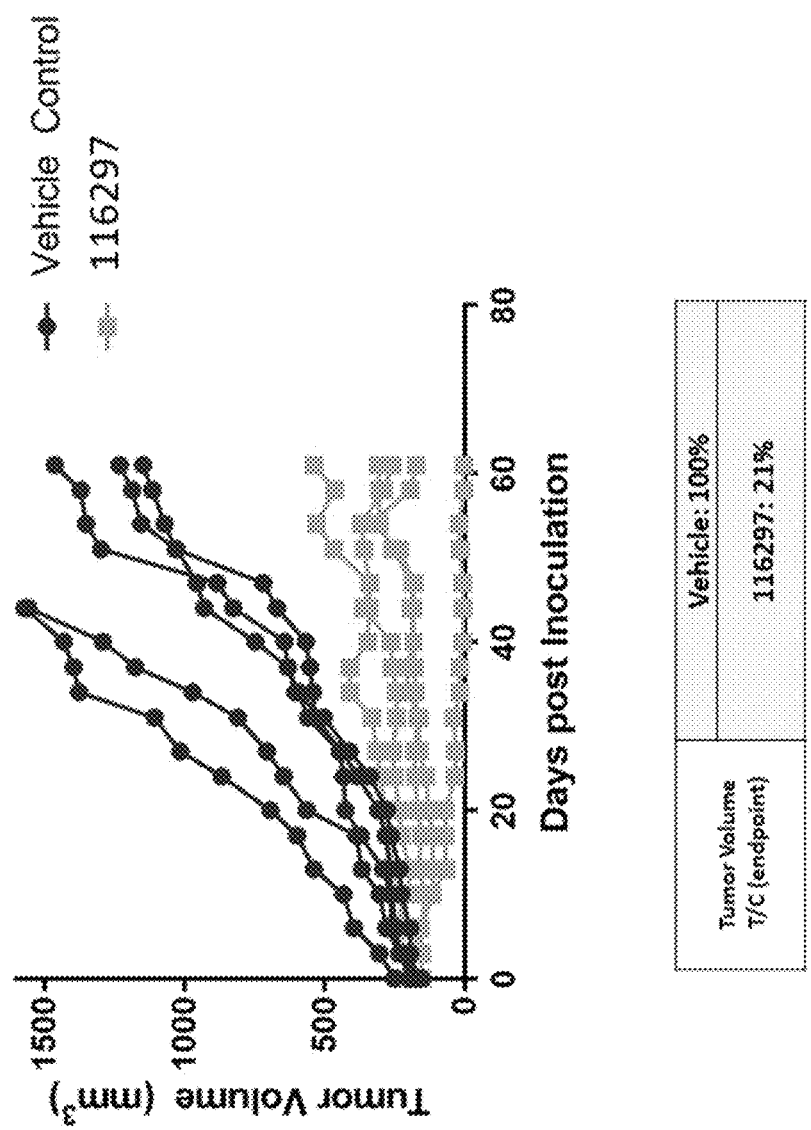

FIG. 30 is a graph showing tumor volume at various days post-inoculation in mice treated with vehicle control or 116297.

Figure 31:
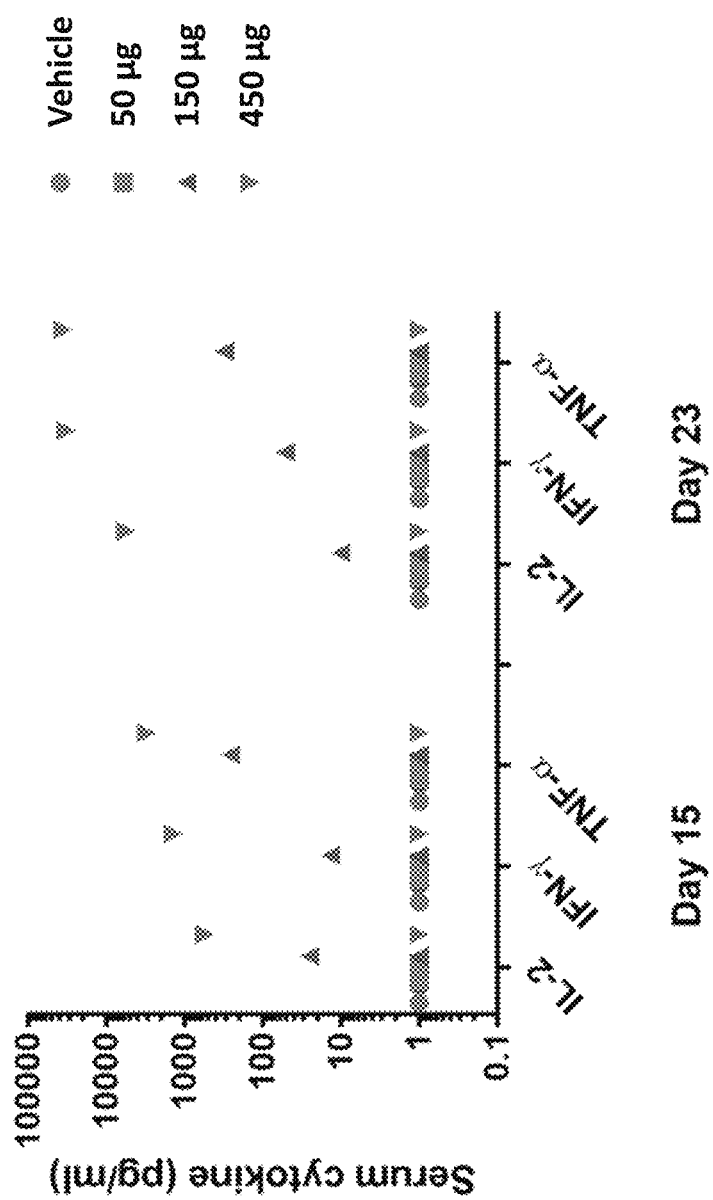

FIG. 31 is a graph showing serum Type I cytokine levels (interleukin-2 (IL-2), IFN-γ, tumor necrosis factor-alpha (TNF-α)) in primates at days 15 and 23 following administration of various doses of 116297 (SEQ ID NO:128).

Figure 32:
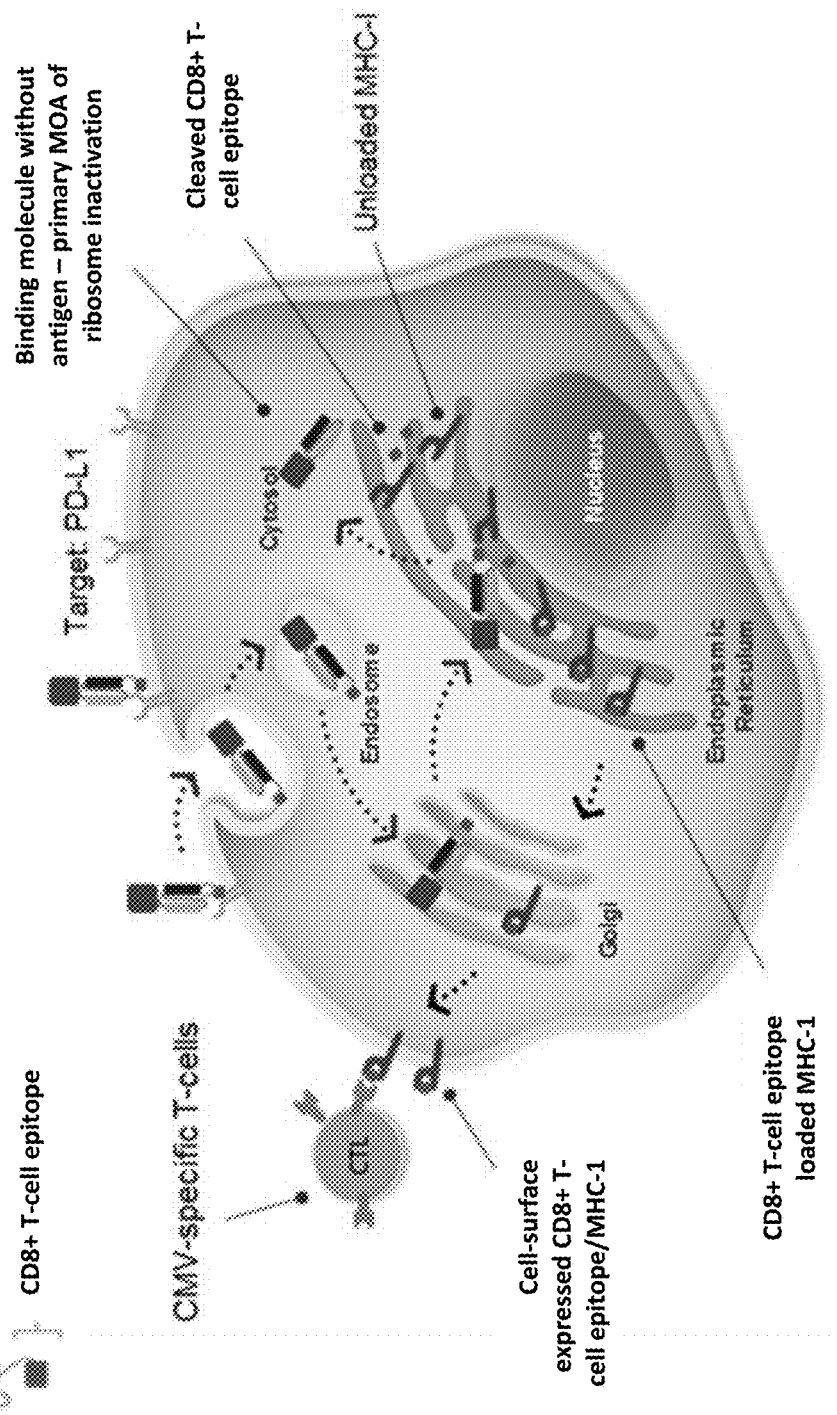

FIG. 32 is a schematic drawing showing potential mechanisms of action of exemplary PD-L1 binding molecules, such as, e.g., 116297 (SEQ ID NO:128).

Figure 33:
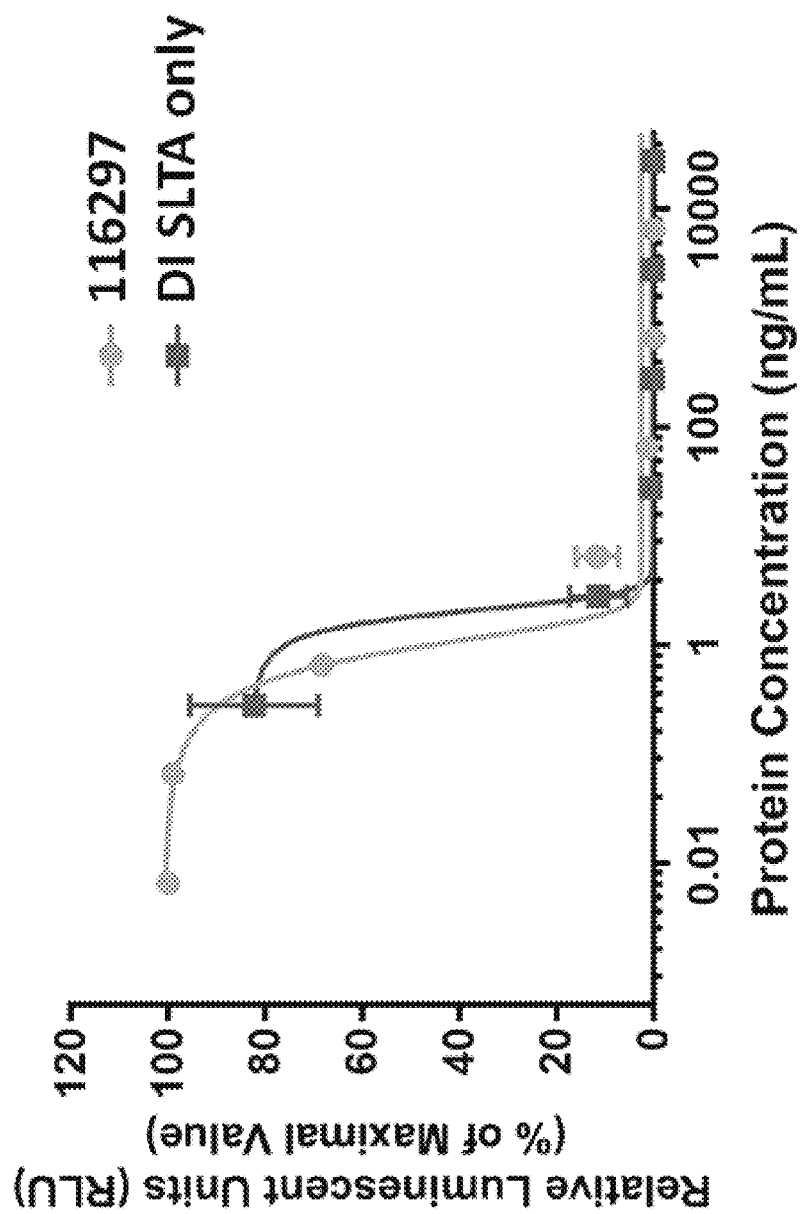

FIG. 33 shows the results of a ribosome inhibition assay for the exemplary PD-L1 binding molecule 116297 (SEQ ID NO:128).

Figure 34:
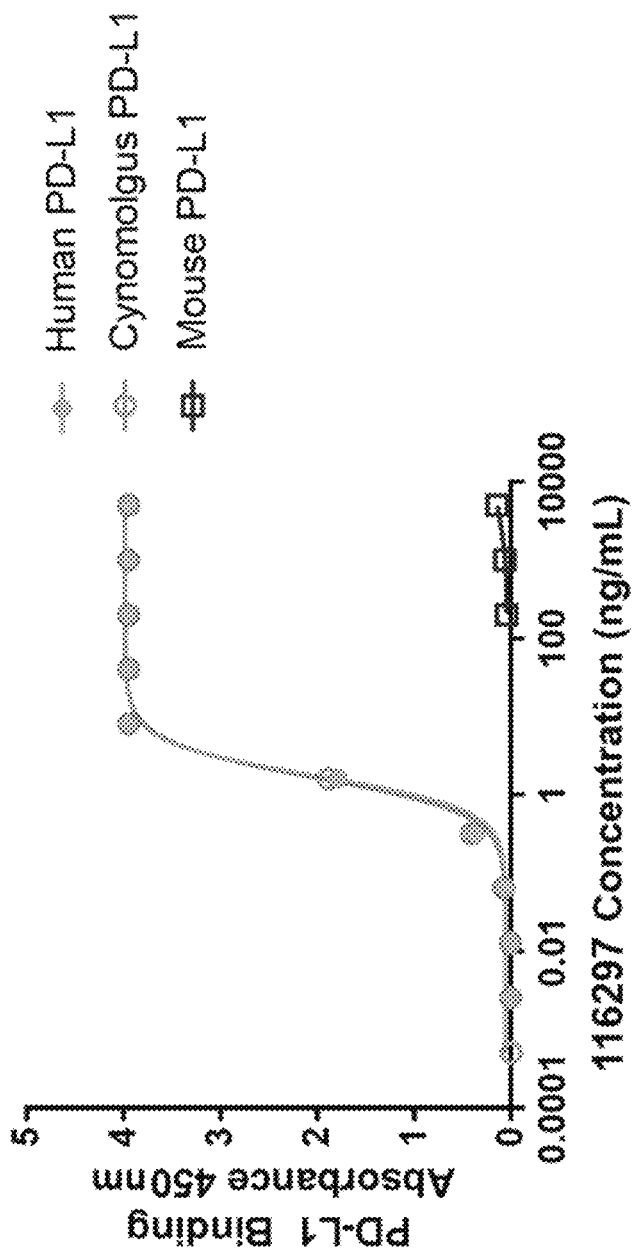

FIG. 34 shows results of a PD-L1 target binding assay for the exemplary PD-L1 binding molecule 116297 (SEQ ID NO:128).

Figure 41D:
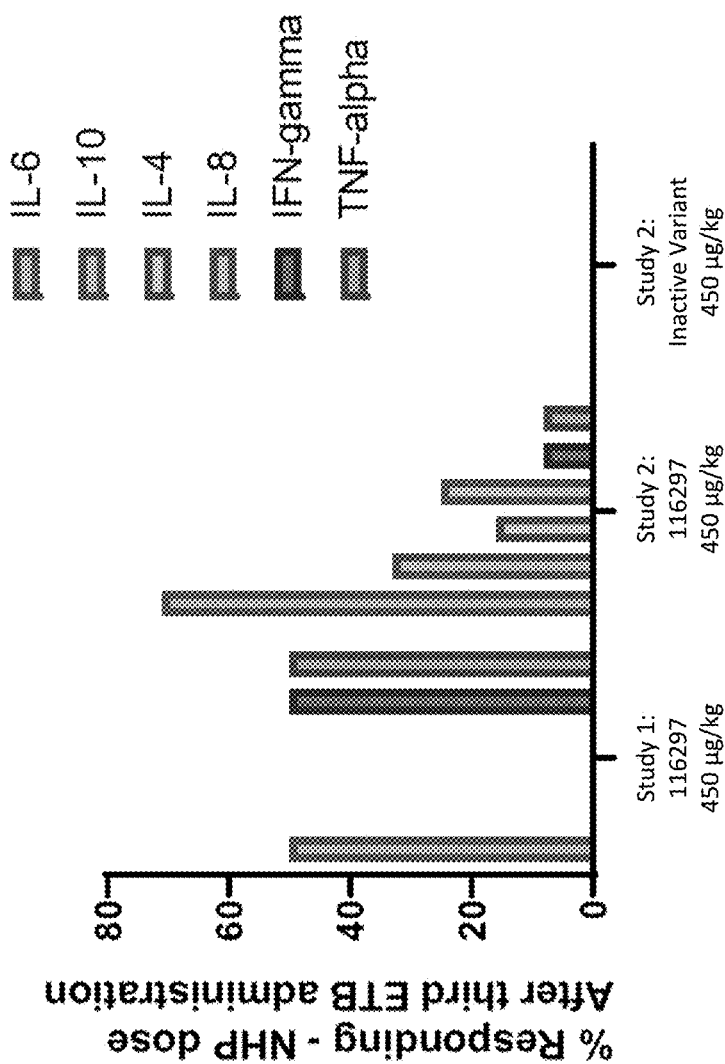

FIG. 35 is a schematic that shows how PD-L1 binding molecule treatment(s) may induce anti-tumor effects, such as, e.g., by directly killing PD-L1-expressing tumor cells and PD-L1 positive immune cells resulting in alterations of tumor immunophenotypes.

FIG. 36 is a schematic that shows the structure and activity of 116297, a cytotoxic fusion protein designed for depletion of PD-L1 Tumor (TC) and Immune cells (IC). 116297 delivers a deimmunized Shiga-like toxin A and CMV restricted peptide antigen to cells. 116297 comprises a specific targeting domain to PD-L1 on the surface of T-cells and immune cells. 116297 is routed to ribosomes in the cell, and mediates cell-kill via enzymatic and irreversible inactivation thereof, mediated by DI SLTA. By delivering a non-self antigenic peptide, 116297 can recruit CMV-reactive CD8+ T-cells response to tumors. 116297 has a unique dual mechanism of action, which cannot be achieved with current monoclonal antibody therapies: it depletes both T-cells and immune cells directly. PD-L1+TC refers to a PD-L1 expressing tumor cell, and PD-L1+IC refers to a PD-L1 expressing immune cell.

FIG. 37A-37D show that 116297 targets PD-L1 tumor cells (TC) for depletion via distinct modes of action. FIG. 37A is a graph showing a range of cytotoxic potencies (CD50) measured for 116297 to tumor lung, skin, breast, and ovary tumor cell lines across a range of PD-L1 expression levels. FIG. 37B shows surface PD-L1 expression as determined using immunohistochemistry (22C3), scored for intensity as TCO-3 (bottom panel). FIG. 37C shows percent cell viability in MDA-MB-231 cells expressing either PD-L1 or HLA:A02, co-cultured with cytotoxic T-lymphocytes (CTLs) and treated with 116297 or a control binding molecule. The phrase "no Ag binding molecule control" refers to samples tested wherein the PD-L 1-targeting immunotoxin molecule tested did not comprise any carboxy-terminal viral antigen cargo. "Inactive binding molecule control" refers to a PD-L1 binding molecule comprising an enzymatically inactive Shiga toxin subunit A effector. "No CTL" refers to samples in which no cytotoxic T lymphocytes were not added, and "CTL" refers to samples in which they were added.

FIG. 37D shows secretion of interferon gamma in MDA-MB-231 cells expressing either PD-L1 or HLA:A02, co-cultured with cytotoxic T-lymphocytes (CTLs).

FIG. 38A-38D show that 116297 controls PD-L1 positive tumors in vivo. Tumor volume growth is shown in immunodeficient mice implanted with various human tumor cell lines, including triple negative breast cancer line MDA-MB-231 (FIG. 38A) and PDX2 (FIG. 38B) after treatment with 116297. In FIG. 38A-38B, asterisks indicate statistical significance. FIG. 38C is a graph showing tumor volume (as a percent of Day 0) in immunodeficient mice implanted with non-small cell lung cancer cells (PDX2b) and treated with 116297. "Binding molecule comprising catalytically inactive SLTA inactive variant" refers to a PD-L1 binding molecule comprising an enzymatically inactive Shiga toxin subunit A effector. FIG. 38D is a table summarizing model and efficacy endpoints in various cell types.

FIG. 39A is a graph illustrating cell viability after treatment with various doses of 116297 in representative PD-L1 high (HCC1954) mid/hi (MDA-MB-231) and neg (MCF7) tumors and isolated human CD14 positive monocytes untreated or treated with IFN-γ to induce PD-L1 expression. FIG. 39B is a graph showing correlation between potency (CD50, ng/mL) and PD-L1 surface molecules on representative PD-L1 high (HCC1954) mid/hi (MDA-MB-231) and neg (MCF7) tumor cells.

FIG. 40A shows pharmacokinetics and serum half-life of 116297. FIG. 40B is a graph showing 116297 in vitro potency and receptor occupancy versus CMAX.

FIG. 41A is a schematic showing the dosing regimen for a non-human primate study. FIG. 41B shows peripheral monocyte levels in non-human primates, as a percent of baseline. Depletion of monocytes preceded an expansion of T cells, B cells, NK cells and Eosinophils which were expanded peripherally at day 15 and persistent through the endpoint of study. "Inactive variant" refers to a PD-L1 binding molecule comprising an enzymatically inactive Shiga toxin subunit A effector. FIG. 41C shows peripheral T-lymphocyte levels in non-human primates, as a percent of baseline. FIG. 41D an analysis of serum cytokine responses across two independent studies in non-human primates. Data is displayed as a percent of responder for study 1 (n=2 NHP) and study 2 (n=8 NHP for 116297 group and n=5 for inactive variant group). Data reflects induction of cytokines any time after dose 3 in the studies.

Figure 42A:
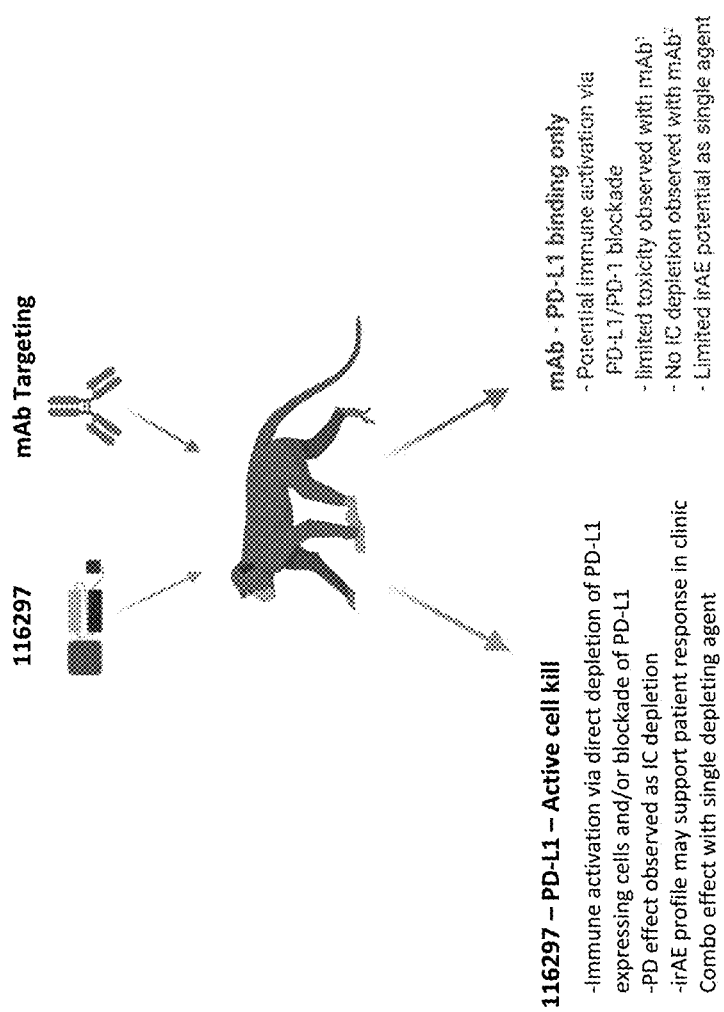

FIG. 42A is a schematic profiling direct cell kill of PD-L1 expressing cells and physical inhibition of PD-L1 signaling ("blockade") in NHPs with 116297. FIG. 42B is a chart summarizing immune effects and pharmacodynamics response observed in the NHP studies.

FIG. 43A-43B shows comparative in vitro data for different PD-L1 binding molecules (116297, 115749, 115765, and 114985) in HCC 1954 cells (FIG. 43A) and MDA-MB-231 cells (FIG. 43B).

FIG. 44 shows comparative in vivo data for different PD-L1 binding molecules (16297, 116555, 115749, 115765, and 115695).

Figure 45A:
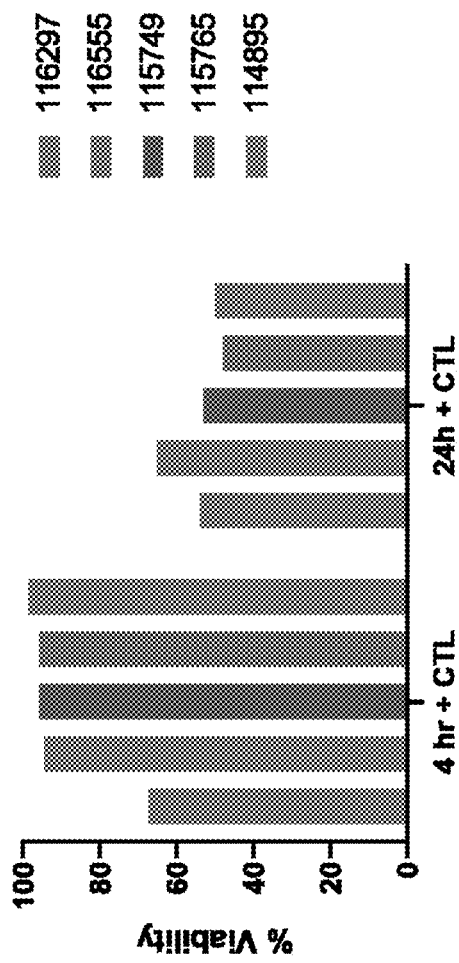
Figure 45B:
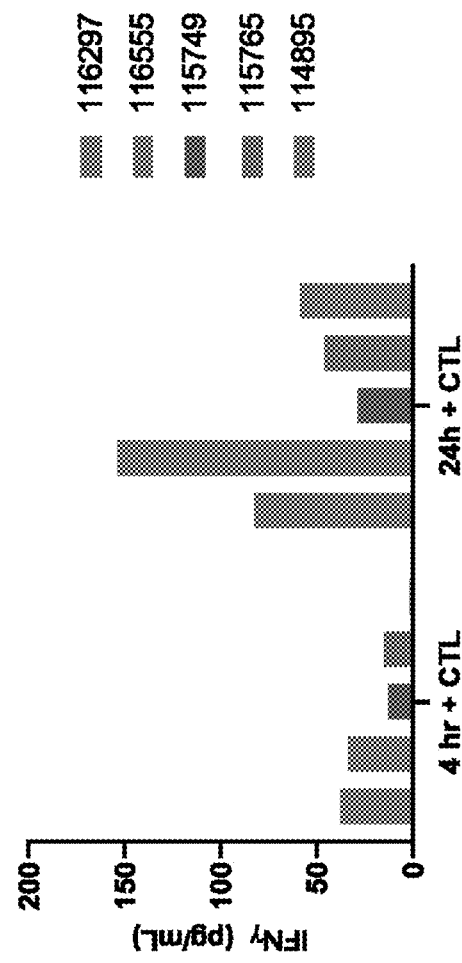

FIG. 45A-45B show the results of an experiment wherein target cells were treated with a PD-L1 binding molecule for 4 hours (acute) or 24 hours (sustained). After the PD-L1 binding molecule was washed out, the cells were contacted with CTLs, and IFN-γ production (FIG. 45A) and cytotoxicity (FIG. 45B) were measured.

FIG. 46A-46B show the results of an experiment wherein monocytes (IC) isolated from donor patients or tumor cells (HCC1954) were treated with either 20 µg/mL (FIG. 46A) or 2 µg/mL (FIG. 46B) various PD-L1 targeting molecules. Cell kill was measured using a standard CELLTITER GLO® (cell viability) assay.

DETAILED DESCRIPTION

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope of the invention to those skilled in the art.

In order that the present invention may be more readily understood, certain terms are defined below. Additional definitions may be found within the detailed description of the invention.

As used in the specification and the appended claims, the terms "a," "an" and "the" include both singular and the plural referents unless the context clearly dictates otherwise.

As used in the specification and the appended claims, the term "and/or" when referring to two species, A and B, means at least one of A and B. As used in the specification and the appended claims, the term "and/or" when referring to greater than two species, such as A, B, and C, means at least one of A, B, or C, or at least one of any combination of A, B, or C (with each species in singular or multiple possibility).

The term "amino acid residue" or "amino acid" includes reference to an amino acid that is incorporated into a protein, polypeptide, or peptide. The term "polypeptide" includes any polymer of amino acids or amino acid residues. The term "polypeptide sequence" refers to a series of amino acids or amino acid residues which physically comprise a polypeptide. A "protein" is a macromolecule comprising one or more polypeptides or polypeptide "chains." A "peptide" is a small polypeptide of sizes less than about a total of 15 to 20 amino acid residues. The term "amino acid sequence" refers to a series of amino acids or amino acid residues which physically comprise a peptide or polypeptide depending on the length. Unless otherwise indicated, polypeptide and protein sequences disclosed herein are written from left to right representing their order from an amino-terminus to a carboxy-terminus.

The terms "amino acid," "amino acid residue," "amino acid sequence," or polypeptide sequence include naturally occurring amino acids (including L and D isostereisomers) and, unless otherwise limited, also include known analogs of natural amino acids that can function in a similar manner as naturally occurring amino acids, such as selenocysteine, pyrrolysine, N-formylmethionine, gamma-carboxyglutamate, hydroxyprolinehypusine, pyroglutamic acid, and selenomethionine. The amino acids referred to herein are described by shorthand designations as follows in Table 1:

TABLE 1

Amino Acid Nomenclature

| Name | 3-letter | 1-letter |
|---|---|---|
| Alanine | Ala | A |
| Arginine | Arg | R |
| Asparagine | Asn | N |
| Aspartic Acid or Aspartate | Asp | D |
| Cysteine | Cys | C |
| Glutamic Acid or Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The phrase "conservative substitution" with regard to an amino acid residue of a peptide, peptide region, polypeptide region, protein, or molecule refers to a change in the amino acid composition of the peptide, peptide region, polypeptide region, protein, or molecule that does not substantially alter the function and structure of the overall peptide, peptide region, polypeptide region, protein, or molecule (see Creighton, Proteins: Structures and Molecular Properties (W. H. Freeman and Company, New York (2nd ed., 1992))).

The phrase "derived from" when referring to a polypeptide or polypeptide region means that the polypeptide or polypeptide region comprises amino acid sequences originally found in a "parental" protein and which may now comprise certain amino acid residue additions, deletions, truncations, rearrangements, or other alterations relative to the original polypeptide or polypeptide region as long as a certain function(s) and a structure(s) of the "parental" molecule are substantially conserved. The skilled worker will be able to identify a parental molecule from which a polypeptide or polypeptide region was derived using techniques known in the art, e.g., protein sequence alignment software.

As used herein, the term "comparable" means similar. When "comparable" refers to a particular value (e.g., a binding affinity), the term may encompass values which are within about 5%, about 10%, about 15%, about 20%, or about 25%, or more, of one another.

As used herein, the term "antibody" refers to immunoglobulin proteins and encompasses the broadest of antibody formats having antigen binding capability, such as, e.g., various protein structures comprising at least one immunoglobulin domain, including but not limited to monoclonal antibodies, polyclonal antibodies, human antibodies, humanized antibodies, chimeric antibodies, camelized antibodies, or antigen-binding antibody fragments (e.g. a Fab, Fv, scFv, sdAb fragment), so long as they exhibit the desired antigen-binding activity.

As used herein, the term "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. Antibody fragments can be made by various techniques, including but not limited to proteolytic digestion of an intact antibody as well as production by recombinant host cells (e.g. *E. coli* or phage), as described herein.

In some embodiments, an antibody or antibody fragment described herein is a single-domain antibody fragment, single-chain variable fragment, antibody variable fragment, Fd fragment, Fab (antigen-binding fragment), an autonomous VH domain, single domain immunoglobulin-derived region VHH, heavy-chain antibody domain derived from a camelid VHH fragment or VH domain fragment, heavy-chain antibody domain derived from cartilaginous fish VHH fragment or VH domain fragment, immunoglobulin new antigen receptor (IgNAR), VNAR fragment, disulfide stabilized antibody variable (Fv) fragment, Armadillo repeat polypeptide, fibronectin-derived $10^{th}$ fibronectin type III domain, tenascin type III domain, ankyrin repeat motif domain, low-density-lipoprotein-receptor-derived A-domain, lipocalin, Kunitz domain, Protein-A-derived Z domain, gamma-B crystalline-derived domain, ubiquitin-derived domain, Sac7d-derived polypeptide, Fyn-derived SH2 domain, miniprotein, C-type lectin-like domain scaffold and so forth.

In some embodiments, the antibody or antibody fragment is a multivalent antibody. For example, the antibody or antibody fragment may be a multimerizing scFv fragment such as diabody, triabody, tetrabody, bispecific tandem scFv fragment, bispecific tandem VHH fragment, bispecific minibody or bivalent minibody.

As used herein, the term "chimeric" antibody refers to an antibody in which a portion of the heavy and/or light chain is derived from a particular source or species, while the remainder of the heavy and/or light chain is derived from a different source or species.

As used herein, a "humanized antibody" is one which possesses an amino acid sequence and/or residues involved in antigen-binding (e.g. a CDR) that are derived from a non-human source and wherein one or more other amino acid sequences is derived from a human source (e.g. a framework sequence).

As used herein, a "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues (e.g. CDRs). A human single-domain antibody is one comprising only a human heavy chain or human light chain; however, the CDR sequence may be naturally occurring or synthetic (see e.g. U.S. Pat. No. 6,248,516).

As used herein, a "camelized antibody" is one which possesses an amino acid sequence derived from a non-camelid source and comprises two heavy chains and no light chains and comprises a hinge region derived from a camelid source or species.

The terms "toxin", "toxin agent", "toxin component", or "cytotoxin" as used herein refers to a substance that inhibits or prevents a cellular function and/or causes cell death or destruction, including tissue damage. The toxin component of a binding molecule or antibody toxin conjugate may include, but is not limited to, natural toxins, biotoxins, proteinaceous toxins, venom, cytotoxins, small molecule toxins, and synthetic toxicants derived from any of the aforementioned, such as, e.g. ABx toxin, ribosome inactivating protein toxin, abrin, anthrax toxin, Aspfl, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin; and the various toxin agents described herein or known to the skilled worker.

For purposes of the instant disclosure and with regard to a Shiga toxin polypeptide sequence or Shiga toxin derived polypeptide, the term "wild-type" generally refers to a naturally occurring, Shiga toxin protein sequence(s) found in a living species, such as, e.g., a pathogenic bacterium, wherein that Shiga toxin protein sequence(s) is one of the most frequently occurring variants. This is in contrast to infrequently occurring Shiga toxin protein sequences that, while still naturally occurring, are found in less than one percent of individual organisms of a given species when sampling a statistically powerful number of naturally occurring individual organisms of that species which comprise at least one Shiga toxin protein variant. A clonal expansion of a natural isolate outside its natural environment (regardless of whether the isolate is an organism or molecule comprising biological sequence information) does not alter the naturally occurring requirement as long as the clonal expansion does not introduce new sequence variety not present in naturally occurring populations of that species and/or does not change the relative proportions of sequence variants to each other.

The terms "associated," "associating," "linked," or "linking" refers to the state of two or more components of a molecule being joined, attached, connected, or otherwise coupled to form a single molecule or the act of making two molecules associated with each other to form a single molecule by creating an association, linkage, attachment, and/or any other connection between the two molecules. For example, the term "linked" may refer to two or more components associated by one or more atomic interactions such that a single molecule is formed and wherein the atomic interactions may be covalent and/or non-covalent. Non-limiting examples of covalent associations between two components include peptide bonds and cysteine-cysteine disulfide bonds. Non-limiting examples of non-covalent associations between two molecular components include ionic bonds.

The term "linked" refers to two or more molecular components associated by one or more atomic interactions such that a single molecule is formed and wherein the atomic interactions includes at least one covalent bond. The term "linking" refers to the act of creating a linked molecule as described above.

By "linker" herein is meant a domain linker that joins two protein domains together, such as are used in scFv and/or other protein and protein fusion structures. For example, a "binding region linker" may be used to link a Shiga Toxin A subunit effector polypeptide with a binding region, and a "scFv linker" may be used to link the VH and the VL in an scFv. A "cleavable spacer" is a type of linker that contains a cleavage site for one or more proteases. Generally, there are a number of suitable linkers that can be used, including traditional peptide bonds, generated by recombinant techniques that allows for recombinant attachment of the two domains with sufficient length and flexibility to allow each domain to retain its biological function. In some embodiments, the linker peptide can predominantly include the following amino acid residues: Gly, Ser, Ala, or Thr. The linker peptide should have a length that is adequate to link two molecules in such a way that they assume the correct conformation relative to one another so that they retain the desired activity. In some embodiments, the linker is from about 1 to about 50 amino acids in length. In some embodiments, the linker is from about 1 to about 30 amino acids in length. In one embodiment, linkers of 1 to 20 amino acids in length can be used, with from about 5 to about 10 amino acids finding use in some embodiments. Useful linkers include glycine-serine polymers, including for example (GS)n (SEQ ID NO: 201), (GSGGS)n (SEQ ID NO: 202), (GGGGS)n (SEQ ID NO: 203), and (GGGS)n (SEQ ID NO: 204), where n is an integer of at least one (and generally from 3 to 4), glycine-alanine polymers, alanine-serine polymers, and other flexible linkers. Alternatively, a variety of non-proteinaceous polymers, including but not limited to polyethylene glycol (PEG), polypropylene glycol, polyoxyalkylenes, or copolymers of polyethylene glycol and polypropylene glycol, can find use as linkers. Other linker sequences can include any sequence of any length of CL/CH1 domain but not all residues of CL/CH1 domain; for example, the first 5-12 amino acid residues of the CL/CH1 domains. Linkers can also be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences can also be derived from other proteins such as Ig-like proteins (e.g., TCR, FcR, KIR), hinge region-derived sequences, and other natural sequences from other proteins. While any suitable linker can be used, some embodiments utilize a glycine-serine polymer, including for example (GS)n (SEQ ID NO: 201), (GSGGS)n (SEQ ID NO: 202), (GGGGS)n (SEQ ID NO: 203), and (GGGS)n (SEQ ID NO: 204), where n is an integer of at least one (and generally from 2 to 3 to 4 to 5). "scFv linkers" generally include these glycine-serine polymers.

The term "fused" refers to two or more proteinaceous components associated by at least one covalent bond which is a peptide bond, regardless of whether the peptide bond involves the participation of a carbon atom of a carboxyl acid group or involves another carbon atom, such as, e.g., the α-carbon, β-carbon, γ-carbon, σ-carbon, etc. Non-limiting examples of two proteinaceous components fused together include, e.g., an amino acid, peptide, or polypeptide fused to a polypeptide via a peptide bond such that the resulting molecule is a single, continuous polypeptide. The term "fusing" refers to the act of creating a fused molecule as described above, such as, e.g., a fusion protein generated from the recombinant fusion of genetic regions which when translated produces a single proteinaceous molecule.

The symbol "::" means the polypeptide regions before and after it are physically linked together to form a continuous polypeptide.

As used herein, the terms "expressed," "expressing," or "expresses," and grammatical variants thereof, refer to translation of a polynucleotide or nucleic acid into a protein. The expressed protein may remain intracellular, become a component of the cell surface membrane or be secreted into an extracellular space.

As used herein, cells which express a significant amount of an extracellular target biomolecule at least one cellular surface are "target positive cells", "target+ cells", or "+ve cells" and are cells physically coupled to the specified, extracellular target biomolecule.

As used herein, the symbol "α" is shorthand for an immunoglobulin-type binding region capable of binding to the biomolecule following the symbol. The symbol "α" is used to refer to the functional characteristic of an immunoglobulin-type binding region based on its ability to bind to the biomolecule following the symbol with a binding affinity described by a dissociation constant ($K_D$) of $10^{-5}$ or less.

As used herein, the term "heavy chain variable ($V_H$) domain" or "light chain variable ($V_L$) domain" respectively refer to any antibody $V_H$ or $V_L$ domain (e.g. a human $V_H$ or $V_L$ domain) as well as any derivative thereof retaining at least qualitative antigen binding ability of the corresponding native antibody (e.g. a humanized $V_H$ or $V_L$ domain derived from a native murine $V_H$ or $V_L$ domain). A $V_H$ or $V_L$ domain consists of a "framework" region interrupted by the three CDRs or ABRs. As used herein, the term "framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in a $V_H$ (or $V_L$): FR1-H1(L1)-FR2-H2(L2)-FR3-H3(L3)-FR4. The framework regions serve to align the CDRs or ABRs for specific binding to an epitope of an antigen. From amino-terminus to carboxy-terminus, both $V_H$ and $V_L$ domains comprise the following framework (FR) and CDR regions or ABR regions: FR1, CDR1, FR2, CDR2, FR3, CDR3, and FR4; or, similarly, FR1, ABR1, FR2, ABR2, FR3, ABR3, and FR4. As used herein, the terms "HCDR1," "HCDR2," or "HCDR3" are used to refer to CDRs 1, 2, or 3, respectively, in a $V_H$ domain, and the terms "LCDR1," "LCDR2," and "LCDR3" are used to refer to CDRs 1, 2, or 3, respectively, in a $V_L$ domain. As used herein, the terms "HABR1," "HABR2," or "HABR3" are used to refer to ABRs 1, 2, or 3, respectively, in a $V_H$ domain, and the terms "LABR1," "LABR2," or "LABR3" are used to refer to CDRs 1, 2, or 3, respectively, in a $V_L$ domain. For camelid VHH fragments, IgNARs of cartilaginous fish, VNAR fragments, certain single domain antibodies, and derivatives thereof, there is a single, heavy chain variable domain comprising the same basic arrangement: FR1, CDR1, FR2, CDR2, FR3, CDR3, and FR4. As used herein, the terms "HCDR1," "HCDR2," or "HCDR3" may be used to refer to CDRs 1, 2, or 3, respectively, in a single heavy chain variable domain. A single $V_H$ or $V_L$ domain may be sufficient to confer antigen-binding specificity.

The term "effector" means providing a biological activity, such as cytotoxicity, biological signaling, enzymatic catalysis, subcellular routing, and/or intermolecular binding resulting in an allosteric effect(s) and/or the recruitment of one or more factors.

The phrases "Shiga toxin effector polypeptide," "Shiga toxin effector polypeptide region," and "Shiga toxin effector region" refer to a polypeptide or polypeptide region derived from at least one Shiga toxin A Subunit of a member of the Shiga toxin family wherein the polypeptide or polypeptide region is capable of exhibiting at least one Shiga toxin function. For example, SEQ ID NOs: 40-68 are derived from StxA and SLT-1A.

As described herein, a Shiga toxin effector function is a biological activity conferred by a polypeptide region derived from a Shiga toxin A Subunit. Non-limiting examples of Shiga toxin effector functions include promoting cell entry; lipid membrane deformation; promoting cellular internalization; stimulating clathrin-mediated endocytosis; directing intracellular routing to various intracellular compartments such as, e.g., the Golgi, endoplasmic reticulum, and cytosol; directing intracellular routing with a cargo; inhibiting a ribosome function(s); catalytic activities, such as, e.g., N-glycosidase activity and catalytically inhibiting ribosomes; reducing protein synthesis, inducing caspase activity, activating effector caspases, effectuating cytostatic effects, and cytotoxicity. Shiga toxin catalytic activities include, for example, ribosome inactivation, protein synthesis inhibition, N-glycosidase activity, polynucleotide:adenosine glycosidase activity, RNAase activity, and DNAase activity. Shiga toxins are ribosome inactivating proteins (RIPs). RIPs can depurinate nucleic acids, polynucleosides, polynucleotides, rRNA, ssDNA, dsDNA, mRNA (and polyA), and viral nucleic acids (see e.g., Barbieri L et al., *Biochem J* 286: 1-4 (1992); Barbieri L et al., *Nature* 372: 624 (1994); Ling J et al., *FEBS Lett* 345: 143-6 (1994); Barbieri L et al., *Biochem J* 319: 507-13 (1996); Roncuzzi L, Gasperi-Campani A, *FEBS Lett* 392: 16-20 (1996); Stirpe F et al., *FEBS Lett* 382: 309-12 (1996); Barbieri L et al., *Nucleic Acids Res* 25: 518-22 (1997); Wang P, Tumer N, *Nucleic Acids Res* 27: 1900-5 (1999); Barbieri L et al., *Biochim Biophys Acta* 1480: 258-66 (2000); Barbieri L et al., *J Biochem* 128: 883-9 (2000); Brigotti Metal., *Toxicon* 39: 341-8 (2001); Brigotti Metal., *FASEB J* 16: 365-72 (2002); Bagga S et al., *J Biol Chem* 278: 4813-20 (2003); Picard D et al., *J Biol Chem* 280: 20069-75 (2005)). Some RIPs show antiviral activity and superoxide dismutase activity (Erice A et al., *Antimicrob Agents Chemother* 37: 835-8 (1993); Au T et al., *FEBS Lett* 471: 169-72 (2000); Parikh B, Tumer N, *Mini Rev Med Chem* 4: 523-43 (2004); Sharma N et al., *Plant Physiol* 134: 171-81 (2004)). Shiga toxin catalytic activities have been observed both in vitro and in vivo. Non-limiting examples of assays for Shiga toxin effector activity measure various activities, such as, e.g., protein synthesis inhibitory activity, depurination activity, inhibition of cell growth, cytotoxicity, supercoiled DNA relaxation activity, and nuclease activity.

The term "IC50" or "$IC_{50}$" is used herein to refer to the half-maximal inhibitory concentration as measured using in an in vitro ribosome function assay. The term "CD50" or "$CD_{50}$" is used herein to refer to the half-maximal cytotoxicity concentration in an in vitro cell killing and/or survival assay. The term "EC50" or "$EC_{50}$" is used herein to refer to the concentration that gives half-maximal response (e.g., inhibition of signaling). The skilled artisan will readily understand the meaning of each of these terms, when taken in context. Each of $IC_{50}$, $CD_{50}$, and $EC_{50}$ may be measured by generating a multiple data points using different molecule concentrations or a concentration series. For some samples, accurate values for either $IC_{50}$ or $CD_{50}$ might be unobtainable due to the inability to collect the required data points for an accurate curve fit. For example, theoretically, neither an $IC_{50}$ nor $CD_{50}$ can be determined if greater than 50% ribosome inhibition or cell death, respectively, does not occur in a concentration series for a given sample. Data insufficient to accurately fit a curve should not be considered as representative of actual molecule activity.

As used herein, the retention of Shiga toxin effector function refers to being capable of exhibiting a level of Shiga toxin functional activity, as measured by an appropriate quantitative assay with reproducibility, comparable to a wild-type, Shiga toxin effector polypeptide control (e.g. a Shiga toxin A1 fragment) or PD-L1 binding molecule comprising a wild-type Shiga toxin effector polypeptide (e.g. a Shiga toxin A1 fragment) under the same conditions. For the Shiga toxin effector function of ribosome inactivation or ribosome inhibition, retained Shiga toxin effector function is exhibiting an $IC_{50}$ of 10,000 pM or less in an in vitro setting, such as, e.g., by using an assay known to the skilled worker and/or described herein. For the Shiga toxin effector function of cytotoxicity in a target positive cell-kill assay, retained Shiga toxin effector function is exhibiting a $CD_{50}$ of 1,000 nM or less, depending on the cell type and its expression of the appropriate extracellular target biomolecule, as shown, e.g., by using an assay known to the skilled worker and/or described herein.

As used herein, the term "equivalent" with regard to ribosome inhibition means an empirically measured level of ribosome inhibitory activity, as measured by an appropriate quantitative assay with reproducibility, which is reproducibly within 10% or less of the activity of the reference molecule (e.g., the second PD-L1 binding molecule or third PD-L1 binding molecule) under the same conditions.

As used herein, the term "equivalent" with regard to cytotoxicity means an empirically measured level of cytotoxicity, as measured by an appropriate quantitative assay with reproducibility, which is reproducibly within 10% or less of the activity of the reference molecule (e.g., the second PD-L1 binding molecule or third binding molecule) under the same conditions.

As used herein, the term "attenuated" with regard to cytotoxicity means a molecule exhibits or exhibited a $CD_{50}$ between 10-fold to 100-fold of a $CD_{50}$ exhibited by a reference molecule under the same conditions.

Inaccurate $IC_{50}$ and $CD_{50}$ values should not be considered when determining a level of Shiga toxin effector function activity. For some samples, accurate values for either $IC_{50}$ or $CD_{50}$ might be unobtainable due to the inability to collect the required data points for an accurate curve fit. For example, theoretically, neither an $IC_{50}$ nor $CD_{50}$ can be determined if greater than 50% ribosome inhibition or cell death, respectively, does not occur in a concentration series for a given sample. Data insufficient to accurately fit a curve as described in the analysis of the data from exemplary Shiga toxin effector function assays, such as, e.g., assays described in the Examples below, should not be considered as representative of actual Shiga toxin effector function.

A failure to detect activity in Shiga toxin effector function may be due to improper expression, polypeptide folding, and/or protein stability rather than a lack of cell entry, subcellular routing, and/or enzymatic activity. Assays for Shiga toxin effector functions may not require much polypeptide to measure significant amounts of Shiga toxin effector function activity. To the extent that an underlying cause of low or no effector function is determined empirically to relate to protein expression or stability, one of skill in the art may be able to compensate for such factors using protein chemistry and molecular engineering techniques known in the art, such that a Shiga toxin functional effector activity may be restored and measured. As examples, improper cell-based expression may be compensated for by using different expression control sequences; and improper polypeptide folding and/or stability may benefit from stabilizing terminal sequences, or compensatory mutations in non-effector regions which stabilize the three-dimensional structure of the molecule.

Certain Shiga toxin effector functions are not easily measurable, e.g. subcellular routing functions. For example, there is no routine, quantitative assay to distinguish whether the failure of a Shiga toxin effector polypeptide to be cytotoxic and/or deliver a heterologous epitope is due to improper subcellular routing, but at a time when tests are available, then Shiga toxin effector polypeptides may be analyzed for any significant level of subcellular routing as compared to the appropriate wild-type Shiga toxin effector polypeptide. However, if a Shiga toxin effector polypeptide component of a binding molecule exhibits cytotoxicity comparable or equivalent to a wild-type Shiga toxin A Subunit construct, then the subcellular routing activity level is inferred to be comparable or equivalent, respectively, to the subcellular routing activity level of a wild-type Shiga toxin A Subunit construct at least under the conditions tested.

When new assays for individual Shiga toxin functions become available, Shiga toxin effector polypeptides and/or binding molecules comprising Shiga toxin effector polypeptides may be analyzed for any level of those Shiga toxin effector functions, such as a being within 1000-fold or 100-fold or less the activity of a wild-type Shiga toxin effector polypeptide or exhibiting 3-fold to 30-fold or greater activity as compared to a functional knockout, Shiga toxin effector polypeptide.

Sufficient subcellular routing may be merely deduced by observing a molecule's cytotoxic activity levels in cytotoxicity assays, such as, e.g., cytotoxicity assays based on T-cell epitope presentation or based on a toxin effector function involving a cytosolic and/or endoplasmic reticulum-localized, target substrate.

As used herein, the retention of "significant" Shiga toxin effector function refers to a level of Shiga toxin functional activity, as measured by an appropriate quantitative assay with reproducibility comparable to a wild-type Shiga toxin effector polypeptide control (e.g. a Shiga toxin A1 fragment). For in vitro ribosome inhibition, significant Shiga toxin effector function is exhibiting an $IC_{50}$ of 300 pM or less depending on the source of the ribosomes used in the assay (e.g. a bacterial, archaeal, or eukaryotic (algal, fungal, plant, or animal) source). This is significantly greater inhibition as compared to the approximate $IC_{50}$ of 100,000 pM for the catalytically disrupted SLT-1A 1-251 double mutant (Y77S/E167D). For cytotoxicity in a target-positive cell-kill assay in laboratory cell culture, significant Shiga toxin effector function is exhibiting a $CD_{50}$ of 100, 50, 30 nM, or less, depending on the target biomolecule(s) of the binding region and the cell type, particularly that cell type's expression and/or cell-surface representation of the appropriate extracellular target biomolecule(s) and/or the extracellular epitope(s) targeted by the molecule being evaluated. This is significantly greater cytotoxicity to the appropriate, target-positive cell population as compared to a Shiga toxin A Subunit alone (or a wild-type Shiga toxin A1 fragment), without a cell targeting binding region, which has a $CD_{50}$ of 100-10,000 nM, depending on the cell line.

For purposes of the present disclosure and with regard to the Shiga toxin effector function of a molecule as described herein, the term "reasonable activity" refers to exhibiting at least a moderate level (e.g. within 11-fold to 1,000-fold) of Shiga toxin effector activity as defined herein in relation to a molecule comprising a naturally occurring Shiga toxin, wherein the Shiga toxin effector activity is selected from the group consisting of: internalization efficiency, subcellular routing efficiency to the cytosol, delivered epitope presentation by a target cell(s), ribosome inhibition, and cytotoxicity. For cytotoxicity, a reasonable level of Shiga toxin effector activity includes being within 1,000-fold of a wild-type, Shiga toxin construct, such as, e.g., exhibiting a $CD_{50}$ of 500 nM or less when a wild-type Shiga toxin construct exhibits a $CD_{50}$ of 0.5 nM (e.g. a binding molecule comprising a wild-type Shiga toxin A1 fragment).

For purposes of the present disclosure and with regard to the cytotoxicity of a molecule as described herein, the term "optimal" refers to a level of Shiga toxin catalytic domain mediated cytotoxicity that is within 2, 3, 4, 5, 6, 7, 8, 9, or 10-fold of the cytotoxicity of a molecule comprising wild-type Shiga toxin A1 fragment (e.g. a Shiga toxin A Subunit or certain truncated variants thereof) and/or a naturally occurring Shiga toxin.

It should be noted that even if the cytotoxicity of a Shiga toxin effector polypeptide is reduced relative to a wild-type Shiga toxin A Subunit or fragment thereof, in practice, applications using attenuated, Shiga toxin effector polypeptides might be equally or more effective than using wild-type Shiga toxin effector polypeptides because the highest potency variants might exhibit undesirable effects which are minimized or reduced in reduced cytotoxic-potency variants. Wild-type Shiga toxins are very potent, being able to kill an intoxicated cell after only one toxin molecule has reached the cytosol of the intoxicated cell or perhaps after only forty toxin molecules have been internalized into the intoxicated cell. Shiga toxin effector polypeptides with even considerably reduced Shiga toxin effector functions, such as, e.g., subcellular routing or cytotoxicity, as compared to wild-type Shiga toxin effector polypeptides might still be potent enough for practical applications, such as, e.g., applications involving targeted cell-killing, heterologous epitope delivery, and/or detection of specific cells and their subcellular compartments. In addition, certain reduced-activity Shiga toxin effector polypeptides may be particularly useful for delivering cargos (e.g. an additional exogenous material or T-cell epitope) to certain intracellular locations or subcellular compartments of target cells.

As used herein, the phrase "antibody effector function" refer to those biological activities attributable to a Fc region of an antibody or derivative thereof, which vary with the antibody isotype. Examples of antibody effector functions include: C1q binding and complement dependent cytotoxicity (CDC); Fc receptor binding (including the neonatal Fc receptor (FcRn) or Brambell receptor), antibody-dependent cell-mediated cytotoxicity (ADCC); phagocytosis; down-regulation of cell surface receptors (e.g. PD-L1); T-cell activation, and B-cell activation.

The term "selective cytotoxicity" with regard to the cytotoxic activity of a molecule refers to the relative level of cytotoxicity between a biomolecule target positive cell population (e.g. a targeted cell-type) and a non-targeted bystander cell population (e.g. a biomolecule target negative cell-type), which can be expressed as a ratio of the half-maximal cytotoxic concentration ($CD_{50}$) for a targeted cell type over the $CD_{50}$ for an untargeted cell type to provide a metric of cytotoxic selectivity or indication of the preferentiality of killing of a targeted cell versus an untargeted cell.

The cell surface representation and/or density of a given extracellular target biomolecule (or extracellular epitope of a given target biomolecule) may influence the applications for which certain binding molecules may be most suitably used. Differences in cell surface representation and/or density of a given target biomolecule between cells may alter, both quantitatively and qualitatively, the efficiency of cellular internalization and/or cytotoxicity potency of a given binding molecule. The cell surface representation and/or density of a given target biomolecule can vary greatly among target biomolecule positive cells or even on the same cell at different points in the cell cycle or cell differentiation.

The total cell surface representation of a given target biomolecule and/or of certain extracellular epitopes of a given target biomolecule on a particular cell or population of cells may be determined using methods known to the skilled worker, such as methods involving fluorescence-activated cell sorting (FACS) flow cytometry.

As used herein, the terms "disrupted," "disruption," or "disrupting," and grammatical variants thereof, with regard to a polypeptide region or feature within a polypeptide refers to an alteration of at least one amino acid within the region or composing the disrupted feature. Amino acid alterations include various mutations, such as, e.g., a deletion, inversion, insertion, or substitution which alter the amino acid sequence of the polypeptide. Amino acid alterations also include chemical changes, such as, e.g., the alteration one or more atoms in an amino acid functional group or the addition of one or more atoms to an amino acid functional group.

As used herein, "de-immunized" means reduced antigenic and/or immunogenic potential after administration to a chordate as compared to a reference molecule, such as, e.g., a wild-type peptide region, polypeptide region, or polypeptide. This includes a reduction in overall antigenic and/or immunogenic potential despite the introduction of one or more, de novo, antigenic and/or immunogenic epitopes as compared to a reference molecule. In some embodiments, "de-immunized" means a molecule exhibited reduced antigenicity and/or immunogenicity after administration to a mammal as compared to a "parental" molecule from which it was derived, such as, e.g., a wild-type Shiga toxin A1 fragment or binding molecule comprising the aforementioned. In some embodiments, the de-immunized, Shiga toxin effector polypeptide is capable of exhibiting a relative antigenicity compared to a reference "parental" molecule which is reduced by 10%, 20%, 30%, 40%, 50%, 60%, 70%, 80%, 90%, or greater than the antigenicity of the reference molecule under the same conditions measured by the same assay, such as, e.g., an assay known to the skilled worker and/or described herein like a quantitative ELISA or Western blot analysis. In some embodiments, the de-immunized, Shiga toxin effector polypeptide is capable of exhibiting a relative immunogenicity compared to a reference "parental" molecule which is reduced by 10%, 20%, 30%, 40%, 50%, 60%, 70%, 80%, 90%, 95%, 97%, 99%, or greater than the immunogenicity of the reference molecule under the same conditions measured by the same assay, such as, e.g., an assay known to the skilled worker and/or described herein like a quantitative measurement of anti-molecule antibodies produced in a mammal(s) after receiving parenteral administration of the molecule at a given time-point.

The relative immunogenicities of exemplary binding molecules were determined using an assay for in vivo antibody responses to the binding molecules after repeat, parenteral administrations over periods of time.

The phrase "B-cell and/or CD4+ T-cell de-immunized" means that the molecule has a reduced antigenic and/or immunogenic potential after administration to a mammal regarding either B-cell antigenicity or immunogenicity and/or CD4+ T-cell antigenicity or immunogenicity. In some embodiments, "B-cell de-immunized" means a molecule exhibited reduced B-cell antigenicity and/or immunogenicity after administration to a mammal as compared to a "parental" molecule from which it was derived, such as, e.g., a wild-type Shiga toxin A1 fragment. In some embodiments, "CD4+ T-cell de-immunized" means a molecule exhibited reduced CD4 T-cell antigenicity and/or immunogenicity after administration to a mammal as compared to a "parental" molecule from which it was derived, such as, e.g., a wild-type Shiga toxin A1 fragment.

The term "endogenous" with regard to a B-cell epitope, CD4+ T-cell epitope, B-cell epitope region, or CD4+ T-cell epitope region in a Shiga toxin effector polypeptide refers to an epitope present in a wild-type Shiga toxin A Subunit.

The phrase "CD8+ T-cell hyper-immunized" means that the molecule, when present inside a nucleated, chordate cell within a living chordate, has an increased antigenic and/or immunogenic potential regarding CD8+ T-cell antigenicity or immunogenicity. Commonly, CD8+ T-cell immunized molecules are capable of cellular internalization to an early endosomal compartment of a nucleated, chordate cell due either to an inherent feature(s) or as a component of a binding molecule.

The term "heterologous" means of a different source than an A Subunit of a naturally occurring Shiga toxin, e.g. a heterologous polypeptide is not naturally found as part of any A Subunit of a native Shiga toxin. The term "heterologous" with regard to T-cell epitope or T-cell epitope-peptide component of a binding molecule refers to an epitope or peptide sequence which did not initially occur in the polypeptide component to be modified, but which has been added to the polypeptide, whether added via the processes of embedding, fusion, insertion, and/or amino acid substitution as described herein, or by any other engineering means. The result is a modified polypeptide comprising a T-cell epitope foreign to the original, unmodified polypeptide, i.e. the T-cell epitope was not present in the original polypeptide.

The term "embedded" and grammatical variants thereof with regard to a T-cell epitope or T-cell epitope-peptide component of a binding molecule refers to the internal replacement of one or more amino acids within a polypeptide region with different amino acids in order to generate a new polypeptide sequence sharing the same total number of amino acid residues with the starting polypeptide region. Thus, the term "embedded" does not include any external, terminal fusion of any additional amino acid, peptide, or polypeptide component to the starting polypeptide nor any additional internal insertion of any additional amino acid residues, but rather includes only substitutions for existing amino acids. The internal replacement may be accomplished merely by amino acid residue substitution or by a series of substitutions, deletions, insertions, and/or inversions. If an insertion of one or more amino acids is used, then the equivalent number of proximal amino acids must be deleted next to the insertion to result in an embedded T-cell epitope. This is in contrast to use of the term "inserted" with regard to a T-cell epitope contained within a polypeptide component of a binding molecule to refer to the insertion of one or more amino acids internally within a polypeptide resulting in a new polypeptide having an increased number of amino acids residues compared to the starting polypeptide.

The term "inserted" and grammatical variants thereof with regard to a T-cell epitope contained within a polypeptide component of a binding molecule refers to the insertion of one or more amino acids within a polypeptide resulting in a new polypeptide sequence having an increased number of amino acids residues compared to the starting polypeptide. The "pure" insertion of a T-cell epitope-peptide is when the resulting polypeptide increased in length by the number of amino acid residues equivalent to the number of amino acid residues in the entire, inserted T-cell epitope-peptide. The phrases "partially inserted," "embedded and inserted," and grammatical variants thereof with regard to a T-cell epitope contained within a polypeptide component of a binding molecule, refers to when the resulting polypeptide increased in length, but by less than the number of amino acid residues equivalent to the length of the entire, inserted T-cell epitope-peptide. Insertions, whether "pure" or "partial," include any of the previously described insertions even if other regions of the polypeptide not proximal to the insertion site within the polypeptide are deleted thereby resulting in a decrease in the total length of the final polypeptide because the final polypeptide still comprises an internal insertion of one or more amino acids of a T-cell epitope-peptide within a polypeptide region.

As used herein, the term "T-cell epitope delivering" when describing a functional activity of a molecule means that a molecule provides the biological activity of localizing within a cell to a subcellular compartment that is competent to result in the proteasomal cleavage of a proteinaceous part of the molecule which comprises a T-cell epitope-peptide. The "T-cell epitope delivering" function of a molecule can be assayed by observing the MHC presentation of a T-cell epitope-peptide cargo of the molecule on a cell surface of a cell exogenously administered the molecule or in which the assay was begun with the cell containing the molecule in one or more of its endosomal compartments. Generally, the ability of a molecule to deliver a T-cell epitope to a proteasome can be determined where the initial location of the "T-cell epitope delivering" molecule is an early endosomal compartment of a cell, and then, the molecule is empirically shown to deliver the epitope-peptide to the proteasome of the cell. However, a "T-cell epitope delivering" ability may also be determined where the molecule starts at an extracellular location and is empirically shown, either directly or indirectly, to deliver the epitope into a cell and to proteasomes of the cell. For example, certain "T-cell epitope delivering" molecules pass through an endosomal compartment of the cell, such as, e.g. after endocytotic entry into that cell. Alternatively, "T-cell epitope delivering" activity may be observed for a molecule starting at an extracellular location whereby the molecule does not enter any endosomal compartment of a cell—instead the "T-cell epitope delivering" molecule enters a cell and delivers a T-cell epitope-peptide to proteasomes of the cell, presumably because the "T-cell epitope delivering" molecule directed its own routing to a subcellular compartment competent to result in proteasomal cleavage of its T-cell epitope-peptide component.

The phrase "proximal to an amino-terminus" with reference to the position of a Shiga toxin effector polypeptide region of a binding molecule refers to a distance wherein at least one amino acid residue of the Shiga toxin effector polypeptide region is within 1, 2, 3, 4, 5, 6, 7, 8, 9, 10, 11, 12 or more, e.g., up to 18-20 amino acid residues, of an amino-terminus of the binding molecule as long as the binding molecule is capable of exhibiting the appropriate level of Shiga toxin effector functional activity noted herein (e.g., a certain level of cytotoxic potency). Thus, in some embodiments, any amino acid residue(s) fused amino-terminal to the Shiga toxin effector polypeptide does not reduce any Shiga toxin effector function (e.g., by sterically hindering a structure(s) near the amino-terminus of the Shiga toxin effector polypeptide region) such that a functional activity of the Shiga toxin effector polypeptide is reduced below the appropriate activity level required herein.

The phrase "more proximal to an amino-terminus" with reference to the position of a Shiga toxin effector polypeptide region within a binding molecule as compared to another component (e.g., a cell-targeting, binding region, molecular moiety, and/or additional exogenous material) refers to a position wherein at least one amino acid residue of the amino-terminus of the Shiga toxin effector polypeptide is closer to the amino-terminus of a linear, polypeptide component of the binding molecule as compared to the other referenced component.

The phrase "active enzymatic domain derived from one A Subunit of a member of the Shiga toxin family" refers to having the ability to inhibit protein synthesis via a catalytic ribosome inactivation mechanism. The enzymatic activities of naturally occurring Shiga toxins may be defined by the ability to inhibit protein translation using assays known to the skilled worker, such as, e.g., in vitro assays involving RNA translation in the absence of living cells or in vivo assays involving RNA translation in a living cell. Using assays known to the skilled worker and/or described herein, the potency of a Shiga toxin enzymatic activity may be assessed directly by observing N-glycosidase activity toward ribosomal RNA (rRNA), such as, e.g., a ribosome nicking assay, and/or indirectly by observing inhibition of ribosome function and/or protein synthesis.

The term "Shiga toxin A1 fragment region" refers to a polypeptide region consisting essentially of a Shiga toxin A1 fragment and/or derived from a Shiga toxin A1 fragment of a Shiga toxin.

The terms "terminus," "amino-terminus," or "carboxy-terminus" with regard to a binding molecule refers generally to the last amino acid residue of a polypeptide chain of the binding molecule (e.g., a single, continuous polypeptide chain). A binding molecule may comprise more than one polypeptides or proteins, and, thus, a binding molecule may comprise multiple amino-terminals and carboxy-terminals. For example, the "amino-terminus" of a binding molecule may be defined by the first amino acid residue of a polypeptide chain representing the amino-terminal end of the polypeptide, which is generally characterized by a starting, amino acid residue which does not have a peptide bond with any amino acid residue involving the primary amino group of the starting amino acid residue or involving the equivalent nitrogen for starting amino acid residues which are members of the class of N-alkylated alpha amino acid residues. Similarly, the "carboxy-terminus" of a binding molecule may be defined by the last amino acid residue of a polypeptide chain representing the carboxyl-terminal end of the polypeptide, which is generally characterized by a final, amino acid residue which does not have any amino acid residue linked by a peptide bond to the alpha-carbon of its primary carboxyl group.

The terms "terminus," "amino-terminus," or "carboxy-terminus" with regard to a polypeptide region refers to the regional boundaries of that region, regardless of whether additional amino acid residues are linked by peptide bonds outside of that region. In other words, the terminals of the polypeptide region regardless of whether that region is fused to other peptides or polypeptides. For example, a fusion protein comprising two proteinaceous regions, e.g., a binding region comprising a peptide or polypeptide and a Shiga toxin effector polypeptide, may have a Shiga toxin effector polypeptide region with a carboxy-terminus ending at amino acid residue 251 of the Shiga toxin effector polypeptide region despite a peptide bond involving residue 251 to an amino acid residue at position 252 representing the beginning of another proteinaceous region, e.g., the binding region. In this example, the carboxy-terminus of the Shiga toxin effector polypeptide region refers to residue 251, which is not a terminus of the fusion protein but rather represents an internal, regional boundary. Thus, for polypeptide regions, the terms "terminus," "amino-terminus," and "carboxy-terminus" are used to refer to the boundaries of polypeptide regions, whether the boundary is a physically terminus or an internal, position embedded within a larger polypeptide chain.

The phrase "carboxy-terminus region of a Shiga toxin A1 fragment" refers to a polypeptide region derived from a naturally occurring Shiga toxin A1 fragment, the region beginning with a hydrophobic residue (e.g., V236 of StxA-A1 and SLT-1A1, and V235 of SLT-2A1) that is followed by a hydrophobic residue and the region ending with the furin-cleavage site conserved among Shiga toxin A1 fragment polypeptides and ending at the junction between the A1 fragment and the A2 fragment in native, Shiga toxin A Subunits. The carboxy-terminal region of a Shiga toxin A1 fragment includes a peptidic region derived from the carboxy-terminus of a Shiga toxin A1 fragment polypeptide, such as, e.g., a peptidic region comprising or consisting essentially of the carboxy-terminus of a Shiga toxin A1 fragment. Non-limiting examples of peptidic regions derived from the carboxy-terminus of a Shiga toxin A1 fragment include the amino acid residue sequences natively positioned from position 236 to position 239, 240, 241, 242, 243, 244, 245, 246, 247, 248, 249, 250, or 251 in Stx1A (SEQ ID NO:2) or SLT-1A (SEQ ID NO:1); and from position 235 to position 239, 240, 241, 242, 243, 244, 245, 246, 247, 248, 249, or 250 in SLT-2A (SEQ ID NO:3).

The phrase "proximal to the carboxy-terminus of an A1 fragment polypeptide" with regard to a linked molecular moiety and/or binding region refers to being within 1, 2, 3, 4, 5, 6, 7, 8, 9, 10, 11, or 12 amino acid residues from the amino acid residue defining the last residue of the Shiga toxin A1 fragment polypeptide.

The phrase "sterically covers the carboxy-terminus of the A1 fragment-derived region" includes any molecular moiety of a size of 4.5 kDa or greater (e.g., an immunoglobulin-type binding region) linked and/or fused to an amino acid residue in the carboxy-terminus of the A1 fragment-derived region, such as, e.g., the amino acid residue derived from the amino acid residue natively positioned at any one of positions 236 to 251 in Stx1A (SEQ ID NO:2) or SLT-1A (SEQ ID NO:1) or from 235 to 250 in SLT-2A (SEQ ID NO:3). The phrase "sterically covers the carboxy-terminus of the A1 fragment-derived region" also includes any molecular moiety of a size of 4.5 kDa or greater (e.g., an immunoglobulin-type binding region) linked and/or fused to an amino acid residue in the carboxy-terminus of the A1 fragment-derived region, such as, e.g., the amino acid residue carboxy-terminal to the last amino acid A1 fragment-derived region and/or the Shiga toxin effector polypeptide. The phrase "sterically covers the carboxy-terminus of the A1 fragment-derived region" also includes any molecular moiety of a size of 4.5 kDa or greater (e.g., an immunoglobulin-type binding region) physically preventing cellular recognition of the carboxy-terminus of the A1 fragment-derived region, such as, e.g. recognition by the ERAD machinery of a eukaryotic cell.

A binding region, such as, e.g., an immunoglobulin-type binding region, that comprises a polypeptide comprising at least forty amino acids and that is linked (e.g., fused) to the carboxy-terminus of the Shiga toxin effector polypeptide region comprising an A1 fragment-derived region is a molecular moiety which is "sterically covering the carboxy-terminus of the A1 fragment-derived region."

A binding region, such as, e.g., an immunoglobulin-type binding region, that comprises a polypeptide comprising at least forty amino acids and that is linked (e.g., fused) to the carboxy-terminus of the Shiga toxin effector polypeptide region comprising an A1 fragment-derived region is a molecular moiety "encumbering the carboxy-terminus of the A1 fragment-derived region."

The term "A1 fragment of a member of the Shiga toxin family" refers to the remaining amino-terminal fragment of a Shiga toxin A Subunit after proteolysis by furin at the furin-cleavage site conserved among Shiga toxin A Subunits and positioned between the A1 fragment and the A2 fragment in wild-type Shiga toxin A Subunits.

The phrase "furin-cleavage motif at the carboxy-terminus of the A1 fragment region" refers to a specific, furin-cleavage motif conserved among Shiga toxin A Subunits and bridging the junction between the A1 fragment and the A2 fragment in naturally occurring, Shiga toxin A Subunits.

The phrase "furin-cleavage site proximal to the carboxy-terminus of the A1 fragment region" refers to any identifiable, furin-cleavage site having an amino acid residue within a distance of less than 1, 2, 3, 4, 5, 6, 7, or more amino acid residues of the amino acid residue defining the last amino acid residue in the A1 fragment region or A1 fragment derived region, including a furin-cleavage motif located carboxy-terminal of an A1 fragment region or A1 fragment derived region, such as, e.g., at a position proximal to the linkage of the A1 fragment-derived region to another component of the molecule, such as, e.g., a molecular moiety of a binding molecule.

The phrase "disrupted furin-cleavage motif" refers to (i) a specific furin-cleavage motif as described herein in Section I-B and (ii) which comprises a mutation and/or truncation that can confer a molecule with a reduction in furin-cleavage as compared to a reference molecule, such as, e.g., a reduction in furin-cleavage reproducibly observed to be 30%, 40%, 50%, 60%, 70%, 80%, 90%, 95%, 97%, 98%, 99%, or less (including 100% for no cleavage) than the furin-cleavage of a reference molecule observed in the same assay under the same conditions. The percentage of furin-cleavage as compared to a reference molecule can be expressed as a ratio of cleaved:uncleaved material of the molecule of interest divided by the cleaved:uncleaved material of the reference molecule (see e.g. WO 2015/191764; WO 2016/196344). Non-limiting examples of suitable reference molecules include certain molecules comprising a wild-type Shiga toxin furin-cleavage motif and/or furin-cleavage site as described herein.

The phrase "furin-cleavage resistant" means a molecule or specific polypeptide region thereof exhibits reproducibly less furin cleavage than (i) the carboxy-terminus of a Shiga toxin A1 fragment in a wild-type Shiga toxin A Subunit or (ii) the carboxy-terminus of the Shiga toxin A1 fragment derived region of construct wherein the naturally occurring furin-cleavage site natively positioned at the junction between the A1 and A2 fragments is not disrupted; as assayed by any available means to the skilled worker, including by using a method described herein.

The phrase "active enzymatic domain derived form an A Subunit of a member of the Shiga toxin family" refers to a polypeptide structure having the ability to inhibit protein synthesis via catalytic inactivation of a ribosome based on a Shiga toxin enzymatic activity. The ability of a molecular structure to exhibit inhibitory activity of protein synthesis and/or catalytic inactivation of a ribosome may be observed using various assays known to the skilled worker, such as, e.g., in vitro assays involving RNA translation assays in the absence of living cells or in vivo assays involving the ribosomes of living cells. For example, using assays known to the skilled worker, the enzymatic activity of a molecule based on a Shiga toxin enzymatic activity may be assessed directly by observing N-glycosidase activity toward ribosomal RNA (rRNA), such as, e.g., a ribosome nicking assay, and/or indirectly by observing inhibition of ribosome function, RNA translation, and/or protein synthesis.

As used herein with respect to a Shiga toxin effector polypeptide, a "combination" describes a Shiga toxin effector polypeptide comprising two or more sub-regions wherein each sub-region comprises at least one of the following: (1) a disruption in an endogenous epitope or epitope region; (2) an embedded, heterologous, T-cell epitope-peptide; (3) an inserted, heterologous, T-cell epitope-peptide; and (4) a disrupted furin-cleavage motif at the carboxy-terminus of an A1 fragment region.

As used herein, a "binding molecule" is used interchangeably with a "PD-L1 binding molecule", and "PD-L1 binding molecule", which encompasses "DI-SLT-1A fusion proteins" and "SLT-1A fusion proteins". All of the aforementioned molecule types include various "PD-L1-binding proteins".

PD-L1 Binding Molecules

Provided herein are various binding molecules which bind PD-L1 and comprise a toxin component (referred to herein as "PD-L1 binding molecules" or "PD-L1 binding molecules". All of the aforementioned molecule types include various "PD-L1-binding proteins). The PD-L1 binding molecules are useful, for e.g., (1) as cytotoxic molecules for killing PD-L1 expressing cells, (2) for selectively killing specific PD-L1-positive cell type(s) amongst other cells, (3) as delivery vehicles for delivering a CD8+ T-cell epitope to the WIC class I presentation pathway of a PD-L1 expressing cell, (4) as nontoxic delivery vehicles for delivering an atom or molecule to the interior of a PD-L1 expressing cell, (5) as diagnostic molecules for the diagnosis, prognosis, or characterization of diseases and conditions involving PD-L1 expressing cell, and (6) as therapeutic molecules for treating a variety of diseases, disorders, and conditions involving PD-L1-expressing cells, such as various cancers and tumors.

In some embodiments, the binding molecule comprises a PD-L1 binding immunoglobulin domain and a Shiga toxin A Subunit effector polypeptide. Shiga toxin A Subunit effector polypeptides provide robust and powerful scaffolds for engineering novel, binding molecules (see e.g. WO 2014/164680, WO 2014/164693, WO 2015/138435, WO 2015/138452, WO 2015/113005, WO 2015/113007, WO 2015/191764, WO 2016/196344, WO 2017/019623, WO 2018/106895, and WO 2018/140427). The association of PD-L1 binding immunoglobulin-derived fragments as cell-targeting moieties with Shiga toxin A Subunit effector polypeptides enables the engineering of therapeutic and diagnostic molecules that target PD-L1.

I. The General Structure of the PD-L1 Binding Molecules

The PD-L1 binding molecules described herein each comprise (1) a PD-L1 binding region for cell-targeting and (2) a toxin.

In some embodiments, a binding molecule comprises (1) a binding region capable of specifically binding an extracellular part of PD-L1 associated with a cell surface and (2) a toxin effector polypeptide. In some embodiments, a binding molecule comprises (1) a binding region capable of specifically binding an extracellular part of PD-L1 associated with a cell surface and (2) a Shiga toxin effector polypeptide region comprising a Shiga toxin A Subunit effector polypeptide (referred to herein as a "Shiga toxin effector polypeptide"). In some embodiments, the binding molecule comprises two or more PD-L1 binding regions, whether the same or different, and two or more Shiga toxin effector polypeptide regions, whether the same or different. One non-limiting example of a binding molecule is a Shiga toxin effector polypeptide fused to an immunoglobulin-type binding region comprising a single-chain variable fragment, or a homo- or hetero-dimer of the aforementioned. The PD-L1 binding molecules described herein may optionally comprise a T-cell epitope for delivery to the interior of a target cell and subsequent cell-surface presentation.

In some embodiments, the binding molecule is a homo-dimer or a hetero-dimer. In some embodiments, the binding molecule is a homo-dimer comprising two monomers, wherein each monomer comprises a PD-L1 binding region and a Shiga toxin effector polypeptide. In some embodiments, a dimeric binding molecule exhibits properties which are more favorable than the properties of a monomeric variant comprising identical binding region and toxin region. For example, in some embodiments, a binding molecule in dimeric form may more efficiently deliver an antigenic epitope (i.e., a CD8+ T-cell epitope) to a target cell than a similar molecule in monomeric form.

In some embodiments, the Shiga toxin A Subunit effector polypeptide of the binding molecule combines structural elements resulting in two or more properties in a single molecule, such as, e.g., the ability to 1) exhibit reduced antigenicity and/or immunogenicity as compared to molecular variants lacking that particular structural element(s), 2) exhibit reduced protease-cleavage as compared to molecular variants lacking that particular structural element(s), 3) exhibit reduced non-specific toxicity to a multicellular organism at certain dosages as compared to molecular variants lacking that particular element(s), 4) deliver an embedded or inserted CD8+ T-cell epitope to the MHC class I system a cell for cell-surface presentation, and/or 5) exhibit potent cytotoxicity.

A. PD-L1 Binding Regions

In some embodiments, the PD-L1 binding molecule comprises a binding region comprising an immunoglobulin-type polypeptide capable of exhibiting specific and high-affinity binding to human PD-L1 and/or PD-L1 present on a cellular surface of a cell, such as, e.g., PD-L1 expressing cell or PD-L1 positive cell.

In some embodiments, a binding region of a binding molecule is a cell-targeting component, such as, e.g., a domain, molecular moiety, or agent, capable of binding specifically to an extracellular part of a PD-L1 target biomolecule on a cell surface (i.e. an extracellular target biomolecule) with high affinity. As used herein, the term "PD-L1 binding region" refers to a molecular moiety (e.g. a proteinaceous molecule) or agent capable of specifically binding an extracellular part of a PD-L1 molecule with high affinity, such as, e.g., having a dissociation constant with regard to PD-L1 of $10^{-5}$ to 10-12 moles per liter. As used herein, PD-L1 binding refers to the ability to bind to an extracellular part of PD-L1, including an isoform or variant of human PD-L1.

An extracellular part of a target biomolecule refers to a portion of its structure exposed to the extracellular environment when the molecule is physically coupled to a cell, such as, e.g., when the target biomolecule is expressed at a cellular surface by the cell. In this context, exposed to the extracellular environment means that part of the target biomolecule is accessible by, e.g., an antibody or at least a binding moiety smaller than an antibody such as a single-domain antibody domain, a nanobody, a heavy-chain antibody domain derived from camelids or cartilaginous fishes, a single-chain variable fragment, or any number of engineered alternative scaffolds to immunoglobulins (see below). The exposure to the extracellular environment of or accessibility to a part of target biomolecule physically coupled to a cell may be empirically determined by the skilled worker using methods well known in the art.

In some embodiments, a binding molecule comprises a binding region comprising one or more polypeptides capable of selectively and specifically binding an extracellular part of PD-L1.

In some embodiments, the PD-L1 binding region is an immunoglobulin-type binding region. In some embodiments, the immunoglobulin-type, PD-L1 binding region is derived from an immunoglobulin, PD-L1 binding region, such as an antibody paratope capable of binding an extracellular part of PD-L1. This engineered polypeptide may optionally include polypeptide scaffolds comprising or consisting essentially of complementary determining regions and/or antigen binding regions from immunoglobulins as described herein.

In some embodiments, the PD-L1 binding region comprises a heavy chain variable region (HVR-H) comprising three CDRs, each having at least 85%, 90%, 91%, 92%, 93%, 94%, 95%, 96%, 97%, 98%, or 99% identity to any one of SEQ ID NOs: 22-24 and 27-32; or consisting essentially of an amino acid sequence show in any one of SEQ ID NOs: 22-24 and 27-32. In some embodiments, the binding region further comprises: (a) a light chain variable region (HVR-L) comprising three CDRs, each having at least 85%, 90%, 91%, 92%, 93%, 94%, 95%, 96%, 97%, 98%, or 99% identity to any one of SEQ ID NO:19, SEQ ID NO:20, SEQ ID NO:21, SEQ ID NO:25, and SEQ ID NO:26; or consisting essentially of an amino acid sequence shown in any one of SEQ ID NO:19, SEQ ID NO:20, SEQ ID NO:21, SEQ ID NO:25, and SEQ ID NO:26. In some embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:19, SEQ ID NO:20, and SEQ ID NO:21; or consisting essentially of an amino acid sequence shown in any one of SEQ ID NO:19, SEQ ID NO:20, and SEQ ID NO:21. In some embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:25, SEQ ID NO:20, and SEQ ID NO:21; or consisting essentially of an amino acid sequence shown in any one of SEQ ID NO:25, SEQ ID NO:20, and SEQ ID NO:21. In some embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:19, SEQ ID NO:20, and SEQ ID NO:26; or consisting essentially of an amino acid sequence shown in any one of SEQ ID NO:19, SEQ ID NO:20, and SEQ ID NO:26.

In some embodiments, the PD-L1 binding region comprises a heavy chain variable region (HVR-H) comprising three CDRs, each having at least 85%, 90%, 91%, 92%, 93%, 94%, 95%, 96%, 97%, 98%, or 99% identity to any one of SEQ ID NOs: 22-24 and 27-32; or consisting essentially of an amino acid sequence show in any one of SEQ ID NOs: 22-24 and 27-32. In some embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:19, SEQ ID NO:20, SEQ ID NO:21, SEQ ID NO:25, and SEQ ID NO:26; or consisting essentially of an amino acid sequence shown in any one SEQ ID NO:19, SEQ ID NO:20, SEQ ID NO:21, SEQ ID NO:25, and SEQ ID NO:26. In some embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:19, SEQ ID NO:20, and SEQ ID NO:26; or consisting essentially of an amino acid sequence shown in any one of SEQ ID NO:19, SEQ ID NO:20, and SEQ ID NO:26. In some embodiments, the binding region comprises: (a) a light chain variable region (HVR-L) comprising three CDRs, each comprising or consisting essentially of an amino acid sequence shown in any one of SEQ ID NO:19, SEQ ID NO:20, SEQ ID NO:21, SEQ ID NO:25, and SEQ ID NO:26; and (b) a heavy chain variable region (HVR-H) comprising three CDRs, each comprising or consisting essentially of an amino acid sequence show in any one of SEQ ID NOs: 22-24 and 27-32. In some embodiments, the binding region comprises: a) a heavy chain variable region (HVR-H) comprising (i) a HCDR1 comprising or consisting essentially, or consisting of the amino acid sequence of SEQ ID NO:27; (ii) a HCDR2 comprising, consisting essentially of, or consisting of the amino acid sequence of SEQ ID NO:29 or 30; and (iii) a HCDR3 comprising, consisting essentially of, or consisting of the amino acid sequence of SEQ ID NO:32; and/or b) a light chain variable region (HVR-L) comprising (i) a LCDR1 comprising, consisting essentially of, or consisting of the amino acid sequence of SEQ ID NO:19; (ii) a LCDR2 comprising, consisting essentially of, or consisting of the amino acid sequence of SEQ ID NO:20; and (iii) a LCDR3 comprising, consisting essentially of or consisting of the amino acid sequence of SEQ ID NO:26. In some embodiments, the binding region comprises: a) a heavy chain variable region (HVR-H) comprising (i) a HCDR1 consisting of the amino acid sequence of SEQ ID NO:27; (ii) a HCDR2 consisting of the amino acid sequence of SEQ ID NO:29 or 30; and (iii) a HCDR3 consisting of the amino acid sequence of SEQ ID NO:32; and b) a light chain variable region (HVR-L) comprising (i) a LCDR1 consisting of the amino acid sequence of SEQ ID NO:19; (ii) a LCDR2 consisting of the amino acid sequence of SEQ ID NO:20; and (iii) a LCDR3 consisting of the amino acid sequence of SEQ ID NO:26. In some embodiments, the binding region comprises: a) a heavy chain variable region (HVR-H) comprising (i) a HCDR1 consisting of the amino acid sequence of SEQ ID NO:27; (ii) a HCDR2 consisting of the amino acid sequence of SEQ ID NO:29; and (iii) a HCDR3 consisting of the amino acid sequence of SEQ ID NO:32; and b) a light chain variable region (HVR-L) comprising (i) a LCDR1 consisting of the amino acid sequence of SEQ ID NO:19; (ii) a LCDR2 consisting of the amino acid sequence of SEQ ID NO:20; and (iii) a LCDR3 consisting of the amino acid sequence of SEQ ID NO:26.

In some embodiments, the binding region comprises: (a) a light chain region having at least 85%, 90%, 91%, 92%, 93%, 94%, 95%, 96%, 97%, 98%, or 99%, identity to any one of SEQ ID NOs: 33, 35-36, and 38, or consisting essentially of the amino acid sequence of any one of SEQ ID NOs: 33, 35-36, and 38; and/or (b) a heavy chain region having at least 85%, 90%, 91%, 92%, 93%, 94%, 95%, 96%, 97%, 98%, or 99% identity to any one of SEQ ID NOs: 34, 37, and 39, or consisting essentially of the amino acid sequence of any one of SEQ ID NOs: 34, 37, and 39. In some embodiments, the binding region comprises a polypeptide having at least 85%, 90%, 91%, 92%, 93%, 94%, 95%, 96%, 97%, 98%, or 99% identity to any one of SEQ ID NOs: 85-107 and 156-157 or consists essentially of the polypeptide shown in any one of SEQ ID NOs: 85-107 and 156-157. In some embodiments, the binding region is a single-chain variable fragment, such as, e.g., consisting of, comprising, or consisting essentially of the polypeptide of any one of SEQ ID NOs: 85-107 and 156-157. In some embodiments, the binding region comprises: (a) a light chain variable region (HVR-L) comprising three CDRs, each comprising, consisting essentially of, or consisting of an amino acid sequence shown in any one of SEQ ID NO:33, SEQ ID NO:35, SEQ ID NO:36, and SEQ ID NO:38; and (b) a heavy chain variable region (HVR-H) comprising three CDRs, each comprising, consisting essentially of, or consisting of an amino acid sequence show in any one of SEQ ID NO:34, SEQ ID NO:37, and SEQ ID NO:39.

In some embodiments, the binding region of the binding molecule may be, e.g., a monoclonal antibody or engineered antibody derivative. In some embodiments, the binding region is an antibody fragment, e.g., a Fv, Fab, Fab', scFv, diabody, Fab'-SH, or F(ab')2 fragment. In another embodiment, the binding region is a full-length antibody, e.g., an intact IgG1 antibody or other antibody class or isotype as defined herein and/or known to the skilled worker. The "class" of an antibody refers to the type of constant domain or constant region present in the heavy chain. There are five major classes of antibodies: IgA, IgD, IgE, IgG, and IgM, and several of these may be further divided into isotypes, e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

In some embodiments, the binding region is a synthetically engineered antibody derivate, such as, e.g. an autonomous $V_H$ domain (such as, e.g., from camelids, murine, or human sources), single-domain antibody domain (sdAb), heavy-chain antibody domains derived from a camelid ($V_HH$ fragment or $V_H$ domain fragment), heavy-chain antibody domains derived from a camelid $V_HH$ fragments or $V_H$ domain fragments, heavy-chain antibody domain derived from a cartilaginous fish, immunoglobulin new antigen receptor (IgNAR), VNAR fragment, single-chain variable (scFv) fragment, nanobody, "camelized" scaffolds comprising a $V_H$ domain, Fd fragment consisting of the heavy chain and $C_H1$ domains, single chain Fv-$C_H3$ minibody, Fc antigen binding domain (Fcabs), scFv-Fc fusion, multimerizing scFv fragment (diabodies, triabodies, tetrabodies), disulfide-stabilized antibody variable (Fv) fragment (dsFv), disulfide-stabilized antigen-binding (Fab) fragment consisting of the $V_L$, $V_H$, $C_L$ and $C_H1$ domains, single-chain variable-region fragments comprising a disulfide-stabilized heavy and light chain (sc-dsFvs), bivalent nanobodies, bivalent minibodies, bivalent F(ab')2 fragments (Fab dimers), bispecific tandem $V_HH$ fragments, bispecific tandem scFv fragments, bispecific nanobodies, bispecific minibodies, Fab-FCabs (mAb 2's), and any genetically manipulated counterparts of the foregoing that retain its paratope and binding function, such as, e.g., wherein the relative orientation or order of the heavy and light chains is reversed or "flipped".

According to one specific, but non-limiting aspect, the binding region may comprise an immunoglobulin-type binding region. The term "immunoglobulin-type binding region" as used herein refers to a polypeptide region capable of binding one or more target biomolecules, such as an antigen or epitope. Binding regions may be functionally defined by their ability to bind to target molecules. Immunoglobulin-type binding regions are commonly derived from antibody or antibody-like structures.

Immunoglobulin (Ig) proteins have a structural domain known as an Ig domain. Ig domains range in length from about 70-110 amino acid residues and possess a characteristic Ig-fold, in which typically 7 to 9 antiparallel beta strands arrange into two beta sheets which form a sandwich-like structure. The Ig fold is stabilized by hydrophobic amino acid interactions on inner surfaces of the sandwich and highly conserved disulfide bonds between cysteine residues in the strands. Ig domains may be variable (IgV or V-set), constant (IgC or C-set) or intermediate (IgI or I-set). Some Ig domains may be associated with a complementarity determining region (CDR), also called a "complementary determining region," which is important for the specificity of antibodies binding to their epitopes. Ig-like domains are also found in non-immunoglobulin proteins and are classified on that basis as members of the Ig superfamily of proteins. The HUGO Gene Nomenclature Committee (HGNC) provides a list of members of the Ig-like domain containing family.

An immunoglobulin-type binding region may be a polypeptide sequence of an antibody or antigen-binding fragment thereof wherein the amino acid sequence has been varied from that of a native antibody or an Ig-like domain of a non-immunoglobulin protein, for example by molecular engineering or selection by library screening. Because of the relevance of recombinant DNA techniques and in vitro library screening in the generation of immunoglobulin-type binding regions, antibodies can be redesigned to obtain desired characteristics, such as smaller size, cell entry, or other improvements for in vivo and/or therapeutic applications. The possible variations are many and may range from the changing of just one amino acid to the complete redesign of, for example, a variable region. Typically, changes in the variable region will be made in order to improve the antigen-binding characteristics, improve variable region stability, or reduce the potential for immunogenic responses.

There are numerous immunoglobulin-type binding regions contemplated as components of molecules described herein. In some embodiments, the immunoglobulin-type binding region is derived from an immunoglobulin binding region, such as an antibody paratope capable of binding an extracellular part of PD-L1. In certain other embodiments, the immunoglobulin-type binding region comprises an engineered polypeptide not derived from any immunoglobulin domain but which functions like an immunoglobulin binding region by providing high-affinity binding to an extracellular part of PD-L1. This engineered polypeptide may optionally include polypeptide scaffolds comprising or consisting essentially of complementary determining regions from immunoglobulins as described herein.

There are also numerous binding regions in the prior art that are useful for targeting polypeptides to specific cell-types via their high-affinity binding characteristics. In some embodiments, the binding region of the binding molecule is selected from the group which includes autonomous $V_H$ domains, single-domain antibody domains (sdAbs), heavy-chain antibody domains derived from camelids ($V_HH$ fragments or $V_H$ domain fragments), heavy-chain antibody domains derived from camelid $V_HH$ fragments or $V_H$ domain fragments, heavy-chain antibody domains derived from cartilaginous fishes, immunoglobulin new antigen receptors (IgNARs), $V_{NAR}$ fragments, single-chain variable (scFv) fragments, nanobodies, Fd fragments consisting of the heavy chain and $C_H1$ domains, single chain Fv-$C_H3$ minibodies, dimeric $C_H2$ domain fragments ($C_H2D$), Fc antigen binding domains (Fcabs), isolated complementary determining region 3 (CDR3) fragments, constrained framework region 3, CDR3, framework region 4 (FR3-CDR3-FR4) polypeptides, small modular immunopharmaceutical (SMIP) domains, scFv-Fc fusions, multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, $C_L$ and $C_H1$ domains, bivalent nanobodies, bivalent minibodies, bivalent F(ab')$_2$ fragments (Fab dimers), bispecific tandem $V_H$H fragments, bispecific tandem scFv fragments, bispecific nanobodies, bispecific minibodies, and any genetically manipulated counterparts of the foregoing that retain its paratope and binding function, such as, e.g., wherein the relative orientation or order of the heavy and light chains is reversed or flipped (see Ward E et al., *Nature* 341: 544-6 (1989); Davies J, Riechmann L, *Biotechnology* (NY) 13: 475-9 (1995); Reiter Y et al., *Mol Biol* 290: 685-98 (1999); Riechmann L, Muyldermans S, *J Immunol Methods* 231: 25-38 (1999); Tanha J et al., *J Immunol Methods* 263: 97-109 (2002); Vranken W et al., *Biochemistry* 41: 8570-9 (2002); Jespers L et al., *J Mol Biol* 337: 893-903 (2004); Jespers L et al., *Nat Biotechnol* 22: 1161-5 (2004); To R et al., *J Biol Chem* 280: 41395-403 (2005); Saerens D et al., *Curr Opin Pharmacol* 8: 600-8 (2008); Dimitrov D, *MAbs* 1: 26-8 (2009); Weiner L, *Cell* 148: 1081-4 (2012); Ahmad Z et al., *Clin Dev Immunol* 2012: 980250 (2012)).

There are a variety of binding regions comprising polypeptides derived from the constant regions of immunoglobulins, such as, e.g., engineered dimeric Fc domains, monomeric Fcs (mFcs), scFv-Fcs, $V_H$H-Fcs, $C_H2$ domains, monomeric $C_H3$s domains (m$C_H3$s), synthetically reprogrammed immunoglobulin domains, and/or hybrid fusions of immunoglobulin domains with ligands (Hofer T et al., *Proc Natl Acad Sci U.S.A* 105: 12451-6 (2008); Xiao J et al., *J Am Chem Soc* 131: 13616-13618 (2009); Xiao X et al., *Biochem Biophys Res Commun* 387: 387-92 (2009); Wozniak-Knopp G et al., *Protein Eng Des Sel* 23 289-97 (2010); Gong R et al., *PLoS ONE* 7: e42288 (2012); Wozniak-Knopp G et al., *PLoS ONE* 7: e30083 (2012); Ying T et al., *J Biol Chem* 287: 19399-408 (2012); Ying T et al., *J Biol Chem* 288: 25154-64 (2013); Chiang M et al., *J Am Chem Soc* 136: 3370-3 (2014); Rader C, *Trends Biotechnol* 32: 186-97 (2014); Ying T et al., *Biochimica Biophys Acta* 1844: 1977-82 (2014)).

In some embodiments, the binding region of the binding molecule is an intact antibody and/or comprises an Fc region. The term "Fc region" refers to part of the fragment crystallizable region, a C-terminal proximal region of certain heavy chains of native immunoglobulins that contains at least a portion of the constant region, such as, e.g., at least the second and third constant ($C_H$) domains and a glycosylation site. However, as used herein, the term "Fc region" includes native sequence Fc regions and variant or mutated Fc regions or fragments thereof. Unless otherwise specified herein, numbering of amino acid residues in the Fc region or constant region is according to the EU numbering system, also called the EU index, as described in Kabat, E. A., *Sequences of Proteins of Immunological Interest*, 5th Ed. Public Health Service, National Institutes of Health, Bethesda, MD, USA (1991).

In accordance with certain other embodiments, the binding region comprises an engineered, alternative scaffold to immunoglobulin domains. Engineered alternative scaffolds are known in the art which exhibit similar functional characteristics to immunoglobulin-derived structures, such as high-affinity and specific binding of target biomolecules, and might provide improved characteristics to certain immunoglobulin domains, such as, e.g., greater stability or reduced immunogenicity. Generally, alternative scaffolds to immunoglobulins are less than 20 kilodaltons, consist of a single polypeptide chain, lack cysteine residues, and exhibit relatively high thermodynamic stability.

Any of the aforementioned PD-L1 binding molecules may be suitable for use as a PD-L1 binding region or modified to create one or more PD-L1 binding regions for use in a binding molecule. Any of the above binding region structures may be used as a component of a molecule as long as the binding region component has a dissociation constant of $10^{-5}$ to $10^{-12}$ moles per liter, preferably less than 200 nanomolar (nM), towards an extracellular part of a PD-L1 molecule.

B. Shiga Toxin Effector Polypeptides

The binding molecules comprise at least one toxin component. In some embodiments, the binding molecule comprises the toxin component which is a Shiga toxin effector polypeptide derived from a Shiga toxin A Subunit. A Shiga toxin effector polypeptide is a polypeptide derived from a Shiga toxin A Subunit member of the Shiga toxin family that is capable of exhibiting one or more Shiga toxin functions (see e.g., Cheung M et al., Mol Cancer 9: 28 (2010); WO 2014/164680, WO 2014/164693, WO 2015/138435, WO 2015/138452, WO 2015/113005, WO 2015/113007, WO 2015/191764, WO 2016/196344, WO 2017/019623, WO 2018/106895, and WO 2018/140427). Shiga toxin functions include, e.g., increasing cellular internalization, directing subcellular routing from an endosomal compartment to the cytosol, avoiding intracellular degradation, catalytically inactivating ribosomes, and effectuating cytostatic and/or cytotoxic effects.

In some embodiments, the binding molecules described herein comprise a Shiga toxin effector polypeptide comprising any one of SEQ ID NO: 1-18, 40-68, 169, 170, or 173. In some embodiments, the binding molecules described herein comprise a Shiga toxin effector polypeptide comprising a variant of any one of SEQ ID NO: 1-18, 40-68, 169, 170, or 173. In some embodiments, the binding molecules described herein comprise a Shiga toxin effector polypeptide comprising a sequence with at least 90%, at least 95%, at least 96%, at least 97%, at least 98%, or at least 99% identity to any one of SEQ ID NO: 1-18, 40-68, 169, 170, or 173 In some embodiments, the binding molecules described herein comprise a Shiga toxin effector polypeptide comprising any one of SEQ ID NO: 1-18, 40-68, 169, 170, or 173 with one or more mutations, such as 2, 3, 4, 5, 6, 7, 8, or 10 mutations. In some embodiments, the Shiga toxin effector comprises any one of SEQ ID NO: 1-18, 40-68, 169, 170, or 173 with 1-5, 5-10, 11-5, 15-20, 10-25, 25-30, or more than 30 mutations. In some embodiments, the binding molecules described herein comprise a Shiga toxin effector polypeptide comprising a variant of any one of SEQ ID NO: 1-18, 40-68, 169, 170, or 173, wherein the variant comprises a S45C mutation. In some embodiments, mutations in the Shiga toxin effector polypeptide render the polypeptide catalytically inactive. In some embodiments, mutations in the Shiga toxin effector polypeptide do not affect the catalytic activity of the polypeptide. In some embodiments, mutations in the Shiga toxin effector polypeptide increase the catalytic activity of the polypeptide. In some embodiments, mutations in the Shiga toxin effector polypeptide decrease the catalytic activity of the polypeptide.

In some embodiments, the binding molecules described herein comprise a Shiga toxin effector polypeptide SEQ ID NO: 41. In some embodiments, the binding molecules described herein comprise a Shiga toxin effector polypeptide that is a variant of SEQ ID NO: 41. In some embodiments, the binding molecules described herein comprise a Shiga toxin effector polypeptide comprising a sequence with at least 90%, at least 95%, at least 96%, at least 97%, at least 98%, or at least 99% identity to SEQ ID NO: 41. In some embodiments, the binding molecules described herein comprise a Shiga toxin effector polypeptide comprising SEQ ID NO: 41 with one or more mutations, such as 2, 3, 4, 5, 6, 7, 8, or 10 mutations. In some embodiments, the Shiga toxin effector comprises SEQ ID NO: 41, with 1-5, 5-10, 11-5, 15-20, 10-25, 25-30, or more than 30 mutations. In some embodiments, mutations in the Shiga toxin effector polypeptide render the polypeptide catalytically inactive. In some embodiments, mutations in the Shiga toxin effector polypeptide do not affect the catalytic activity of the polypeptide. In some embodiments, mutations in the Shiga toxin effector polypeptide increase the catalytic activity of the polypeptide. In some embodiments, mutations in the Shiga toxin effector polypeptide decrease the catalytic activity of the polypeptide.

In some embodiments, the Shiga toxin effector comprises SEQ ID NO: 41 plus an E167D mutation, a R1705 mutation, or both an E167D and a R1705 mutation. In some embodiments, the Shiga toxin effector comprises any one of SEQ ID NO: 167,170, or 173.

The Shiga toxin family of protein toxins is composed of various naturally occurring toxins which are structurally and functionally related, e.g., Shiga toxin, Shiga-like toxin 1, and Shiga-like toxin 2 (Johannes L, Römer W, *Nat Rev Microbiol* 8: 105-16 (2010)). Holotoxin members of the Shiga toxin family contain targeting domains that preferentially bind a specific glycosphingolipid present on the surface of some host cells and an enzymatic domain capable of permanently inactivating ribosomes once inside a cell (Johannes L, Römer W, *Nat Rev Microbiol* 8: 105-16 (2010)). Members of the Shiga toxin family share the same overall structure and mechanism of action (Engedal N et al., *Microbial Biotech* 4: 32-46 (2011)). For example, Stx, SLT-1 and SLT-2 display indistinguishable enzymatic activity in cell free systems (Head S et al., *J Biol Chem* 266: 3617-21 (1991); Tesh V et al., *Infect Immun* 61: 3392-402 (1993); Brigotti M et al., *Toxicon* (1997)).

The Shiga toxin family encompasses true Shiga toxin (Stx) isolated from *S. dysenteriae* serotype 1, Shiga-like toxin 1 variants (SLT1 or Stx1 or SLT-1 or Slt-I) isolated from serotypes of enterohemorrhagic *E. coli*, and Shiga-like toxin 2 variants (SLT2 or Stx2 or SLT-2) isolated from serotypes of enterohemorrhagic *E. coli*. SLT1 differs by only one amino acid residue from Stx, and both have been referred to as Verocytotoxins or Verotoxins (VTs) (O'Brien A, *Curr Top Microbiol Immunol* 180: 65-94 (1992)). Although SLT1 and SLT2 variants are only about 53-60% similar to each other at the primary amino acid sequence level, they share mechanisms of enzymatic activity and cytotoxicity common to the members of the Shiga toxin family (Johannes L, Römer W, *Nat Rev Microbiol* 8: 105-16 (2010)). Over 39 different Shiga toxins have been described, such as the defined subtypes Stx1a, Stx1c, Stx1d, and Stx2a-g (Scheutz F et al., *J Clin Microbiol* 50: 2951-63 (2012)). Members of the Shiga toxin family are not naturally restricted to any bacterial species because Shiga-toxin-encoding genes can spread among bacterial species via horizontal gene transfer (Strauch E et al., *Infect Immun* 69: 7588-95 (2001); Bielaszewska M et al., *Appl Environ Micrbiol* 73: 3144-50 (2007); Zhaxybayeva O, Doolittle W, *Curr Biol* 21: R242-6 (2011)). As an example of interspecies transfer, a Shiga toxin was discovered in a strain of *A. haemolyticus* isolated from a patient (Grotiuz G et al., *J Clin Microbiol* 44: 3838-41 (2006)). Once a Shiga toxin encoding polynucleotide enters a new subspecies or species, the Shiga toxin amino acid sequence is presumed to be capable of developing slight sequence variations due to genetic drift and/or selective pressure while still maintaining a mechanism of cytotoxicity common to members of the Shiga toxin family (see Scheutz F et al., *J Clin Microbiol* 50: 2951-63 (2012)).

In some embodiments of the PD-L1 binding molecules described herein, the Shiga toxin A Subunit effector polypeptide component comprises a combination of two or more of the following Shiga toxin effector polypeptide sub-regions: (1) a de-immunized sub-region, (2) a protease-cleavage resistant sub-region near the carboxy-terminus of a Shiga toxin A1 fragment region, and (3) a T-cell epitope-peptide embedded or inserted sub-region.

1. De-Immunized, Shiga Toxin a Subunit Effector Polypeptides

In some embodiments, the Shiga toxin effector polypeptide of the binding molecule is de-immunized, such as, e.g., as compared to a wild-type Shiga toxin, wild-type Shiga toxin polypeptide, and/or Shiga toxin effector polypeptide comprising only wild-type polypeptide sequences. A Shiga toxin effector polypeptide and/or Shiga toxin A Subunit polypeptide, whether naturally occurring or not, can be de-immunized by a method described herein, described in WO 2015/113005, WO 2015/113007, WO 2016/196344, and WO 2018/140427, and/or known to the skilled worker, wherein the resulting molecule retains one or more Shiga toxin A Subunit functions. The de-immunized, Shiga toxin effector polypeptide may comprise a disruption of at least one, putative, endogenous, epitope region in order to reduce the antigenic and/or immunogenic potential of the Shiga toxin effector polypeptide after administration of the polypeptide to a chordate.

In some embodiments, the Shiga toxin effector polypeptide comprises a disruption of an endogenous epitope or epitope region, such as, e.g., a B-cell and/or CD4+ T-cell epitope. In some embodiments, the Shiga toxin effector polypeptide comprises a disruption of at least one, endogenous, epitope region described herein, wherein the disruption reduces the antigenic and/or immunogenic potential of the Shiga toxin effector polypeptide after administration of the polypeptide to a chordate, and wherein the Shiga toxin effector polypeptide is capable of exhibiting one or more Shiga toxin A Subunit functions, such as, e.g., a significant level of Shiga toxin cytotoxicity.

The term "disrupted" or "disruption" as used herein with regard to an epitope region refers to the deletion of at least one amino acid residue in an epitope region, inversion of two or more amino acid residues where at least one of the inverted amino acid residues is in an epitope region, insertion of at least one amino acid into an epitope region, and a substitution of at least one amino acid residue in an epitope region. An epitope region disruption by mutation includes amino acid substitutions with non-standard amino acids and/or non-natural amino acids. Epitope regions may alternatively be disrupted by mutations comprising the modification of an amino acid by the addition of a covalently-linked chemical structure which masks at least one amino acid in an epitope region, see, e.g. PEGylation (see Zhang C et al., *BioDrugs* 26: 209-15 (2012), small molecule adjuvants (Flower D, *Expert Opin Drug Discov* 7: 807-17 (2012), and site-specific albumination (Lim S et al., *J Control Release* 207-93 (2015)).

Certain epitope regions and disruptions are indicated herein by reference to specific amino acid positions of native Shiga toxin A Subunits provided in the Sequence Listing, noting that naturally occurring Shiga toxin A Subunits may comprise precursor forms containing signal sequences of about 22 amino acids at their amino-terminals which are removed to produce mature Shiga toxin A Subunits and are recognizable to the skilled worker. Further, certain epitope region disruptions are indicated herein by reference to specific amino acids (e.g. S for a serine residue) natively present at specific positions within native Shiga toxin A Subunits (e.g. S33 for the serine residue at position 33 from the amino-terminus) followed by the amino acid with which that residue has been substituted in the particular mutation under discussion (e.g. S33I represents the amino acid substitution of isoleucine for serine at amino acid residue 33 from the amino-terminus).

In some embodiments, the de-immunized, Shiga toxin effector polypeptide comprises a disruption of at least one epitope region provided herein. In some embodiments, the de-immunized, Shiga toxin effector polypeptide comprises a disruption of at least one epitope region described in WO 2015/113005 or WO 2015/113007.

In some embodiments, the de-immunized, Shiga toxin effector polypeptide comprises or consists essentially of a full-length Shiga toxin A Subunit (e.g. SLT-1A (SEQ ID NO:1), StxA (SEQ ID NO:2), or SLT-2A (SEQ ID NO:3)) comprising at least one disruption of the amino acid sequence selected from the group of natively positioned amino acids consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; 210-218 of SEQ ID NO:3; 240-258 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, or the equivalent position in a Shiga toxin A Subunit polypeptide, conserved Shiga toxin effector polypeptide sub-region, and/or non-native, Shiga toxin effector polypeptide sequence.

In some embodiments, a Shiga toxin effector polypeptide comprises the sequence of SEQ ID NO: 169. In some embodiments, a Shiga toxin effector polypeptide comprises the sequence of SEQ ID NO: 170. In some embodiments, a Shiga toxin effector polypeptide comprises the sequence of SEQ ID NO: 173.

In some embodiments, the Shiga toxin effector polypeptide comprises or consists essentially of a truncated Shiga toxin A Subunit. Truncations of Shiga toxin A Subunits might result in the deletion of an entire epitope region(s) without affecting Shiga toxin effector function(s). The smallest, Shiga toxin A Subunit fragment shown to exhibit significant enzymatic activity was a polypeptide composed of residues 75-247 of StxA (Al-Jaufy A et al., Infect Immun 62: 956-60 (1994)). Truncating the carboxy-terminus of SLT-1A, StxA, or SLT-2A to amino acids 1-251 removes two predicted B-cell epitope regions, two predicted $CD_4$ positive ($CD_4$+) T-cell epitopes, and a predicted, discontinuous, B-cell epitope. Truncating the amino-terminus of SLT-1A, StxA, or SLT-2A to 75-293 removes at least three, predicted, B-cell epitope regions and three predicted CD4+ T-cell epitopes. Truncating both amino- and carboxy-terminals of SLT-1A, StxA, or SLT-2A to 75-251 deletes at least five, predicted, B-cell epitope regions; four, putative, $CD_4$+ T-cell epitopes; and one, predicted, discontinuous, B-cell epitope.

In some embodiments, a Shiga toxin effector polypeptide comprises or consists essentially of a full-length or truncated Shiga toxin A Subunit with at least one mutation, e.g. deletion, insertion, inversion, or substitution, in a provided epitope region. In some embodiments, the polypeptides comprise a disruption which comprises a deletion of at least one amino acid within the epitope region. In some embodiments, the polypeptides comprise a disruption which comprises an insertion of at least one amino acid within the epitope region. In some embodiments, the polypeptides comprise a disruption which comprises an inversion of amino acids, wherein at least one inverted amino acid is within the epitope region. In some embodiments, the polypeptides comprise a disruption which comprises a mutation, such as an amino acid substitution to a non-standard amino acid or an amino acid with a chemically modified side chain.

In some embodiments, the Shiga toxin effector polypeptides comprise or consist essentially of a full-length or truncated Shiga toxin A Subunit with one or more mutations as compared to the native sequence which comprises at least one amino acid substitution selected from the group consisting of: A, G, V, L, I, P, C, M, F, S, D, N, Q, H, and K. In some embodiments, the polypeptide comprises or consists essentially of a full-length or truncated Shiga toxin A Subunit with a single mutation as compared to the native sequence wherein the substitution is selected from the group consisting of: D to A, D to G, D to V, D to L, D to I, D to F, D to S, D to Q, E to A, E to G, E to V, E to L, E to I, E to F, E to S, E to Q, E to N, E to D, E to M, E to R, G to A, H to A, H to G, H to V, H to L, H to I, H to F, H to M, K to A, K to G, K to V, K to L, K to I, K to M, K to H, L to A, L to G, N to A, N to G, N to V, N to L, N to I, N to F, P to A, P to G, P to F, R to A, R to G, R to V, R to L, R to I, R to F, R to M, R to Q, R to S, R to K, R to H, S to A, S to G, S to V, S to L, S to I, S to F, S to M, T to A, T to G, T to V, T to L, T to I, T to F, T to M, T to S, Y to A, Y to G, Y to V, Y to L, Y to I, Y to F, and Y to M.

In some embodiments, the Shiga toxin effector polypeptides comprise or consist essentially of a full-length or truncated Shiga toxin A Subunit with one or more mutations as compared to the native amino acid residue sequence which comprises at least one amino acid substitution of an immunogenic residue and/or within an epitope region, wherein at least one substitution occurs at the natively positioned group of amino acids selected from the group consisting of: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1 or SEQ ID NO:2; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

In some embodiments, the Shiga toxin effector polypeptides comprise or consist essentially of a full-length or truncated Shiga toxin A Subunit with at least one substitution of an immunogenic residue and/or within an epitope region, wherein at least one amino acid substitution is to a non-conservative amino acid (see, e.g., Table 4, infra) relative to a natively occurring amino acid positioned at one of the following native positions: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1 or SEQ ID NO:2; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

In some embodiments, the Shiga toxin effector polypeptides comprise or consist essentially of a full-length or truncated Shiga toxin A Subunit with at least one amino acid substitution selected from the group consisting of: K1 to A, G, V, L, I, F, M and H; T4 to A, G, V, L, I, F, M, and S; D6 to A, G, V, L, I, F, S, and Q; S8 to A, G, V, I, L, F, and M; T8 to A, G, V, I, L, F, M, and S; T9 to A, G, V, I, L, F, M, and S; S9 to A, G, V, L, I, F, and M; K11 to A, G, V, L, I, F, M and H; T12 to A, G, V, I, L, F, M, and S; S33 to A, G, V, L, I, F, and M; S43 to A, G, V, L, I, F, and M; G44 to A and L; S45 to A, G, V, L, I, F, and M; T45 to A, G, V, L, I, F, and M; G46 to A and P; D47 to A, G, V, L, I, F, S, and Q; N48 to A, G, V, L, and M; L49 to A or G; F50; A51 to V; D53 to A, G, V, L, I, F, S, and Q; V54 to A, G, and L; R55 to A, G, V, L, I, F, M, Q, S, K, and H; G56 to A and P; I57 to A, G, M, and F; L57 to A, G, M, and F; D58 to A, G, V, L, I, F, S, and Q; P59 to A, G, and F; E60 to A, G, V, L, I, F, S, Q, N, D, M, and R; E61 to A, G, V, L, I, F, S, Q, N, D, M, and R; G62 to A; D94 to A, G, V, L, I, F, S, and Q; R84 to A, G, V, L, I, F, M, Q, S, K, and H; V88 to A and G; I88 to A, G, and V; D94; S96 to A, G, V, I, L, F, and M; T104 to A, G, V, I, L, F, M, and S; A105 to L; T107 to A, G, V, I, L, F, M, and S; S107 to A, G, V, L, I, F, and M; L108 to A, G, and M; S109 to A, G, V, I, L, F, and M; T109 to A, G, V, I, L, F, M, and S; G110 to A; D111 to A, G, V, L, I, F, S, and Q; S112 to A, G, V, L, I, F, and M; D141 to A, G, V, L, I, F, S, and Q; G147 to A; V154 to A and G; R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; L185 to A, G, and V; S186 to A, G, V, I, L, F, and M; G187 to A; R188 to A, G, V, L, I, F, M, Q, S, K, and H; S189 to A, G, V, I, L, F, and M; D197 to A, G, V, L, I, F, S, and Q; D198 to A, G, V, L, I, F, S, and Q; R204 to A, G, V, L, I, F, M, Q, S, K, and H; R205 to A, G, V, L, I, F, M, Q, S, K and H; C242 to A, G, V, and S; S247 to A, G, V, I, L, F, and M; Y247 to A, G, V, L, I, F, and M; R248 to A, G, V, L, I, F, M, Q, S, K, and H; R250 to A, G, V, L, I, F, M, Q, S, K, and H; R251 to A, G, V, L, I, F, M, Q, S, K, and H; C262 to A, G, V, and S; D264 to A, G, V, L, I, F, S, and Q; G264 to A; and T286 to A, G, V, L, I, F, M, and S.

In some embodiments, the Shiga toxin effector polypeptides comprise or consist essentially of a full-length or truncated Shiga toxin A Subunit with at least one of the following amino acid substitutions K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R248A, R250A, R251A, or D264A, G264A, T286A, and/or T286I. These epitope disrupting substitutions may be combined to form a de-immunized, Shiga toxin effector polypeptide with multiple substitutions per epitope region and/or multiple epitope regions disrupted while still retaining Shiga toxin effector function. For example, substitutions at the natively positioned K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R248A, R250A, R251A, or D264A, G264A, T286A, and/or T286I may be combined, where possible, with substitutions at the natively positioned residues K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R248A, R250A, R251A, or D264A, G264A, T286A, and/or T286I to create de-immunized, Shiga toxin effector polypeptides.

Any of the de-immunized, Shiga toxin effector polypeptide sub-regions and/or epitope disrupting mutations described herein may be used alone or in combination with each individual embodiment as described herein, including methods described herein.

2. Protease-Cleavage Resistant, Shiga Toxin A Subunit Effector Polypeptides

In some embodiments, the Shiga toxin effector polypeptide of the binding molecule comprises (1) a Shiga toxin A1 fragment derived region having a carboxy-terminus and (2) a disrupted furin-cleavage motif at the carboxy-terminus of the Shiga toxin A1 fragment region. Improving the stability of connections between the Shiga toxin component and other components of binding molecules, e.g., cell-targeting binding regions, can improve their toxicity profiles after administration to organisms by reducing non-specific toxicities caused by the breakdown of the connection and loss of cell-targeting, such as, e.g., as a result of proteolysis.

Shiga toxin A Subunits of members of the Shiga toxin family comprise a conserved, furin-cleavage site at the carboxy-terminal of their A1 fragment regions important for Shiga toxin function. Furin-cleavage site motifs and furin-cleavage sites can be identified by the skilled worker using standard techniques and/or by using the information herein.

Furin-cleavage motifs and furin-cleavage sites in Shiga toxin A Subunits and Shiga toxin effector polypeptides can be identified by the skilled worker using standard methods and/or by using the information herein. Furin cleaves the minimal, consensus motif R-x-x-R (Schalken J et al., *J Clin Invest* 80: 1545-9 (1987); Bresnahan P et al., *J Cell Biol* 111: 2851-9 (1990); Hatsuzawa K et al., *J Biol Chem* 265: 22075-8 (1990); Wise R et al., *Proc Natl Acad Sci USA* 87: 9378-82 (1990); Molloy S et al., *J Biol Chem* 267: 16396-402 (1992)). Consistent with this, many furin inhibitors comprise peptides comprising the motif R-x-x-R. An example of a synthetic inhibitor of furin is a molecule comprising the peptide R—V-K-R (Henrich S et al., *Nat Struct Biol* 10: 520-6 (2003)). In general, a peptide or protein comprising a surface accessible, dibasic amino acid motif with two positively charged, amino acids separated by two amino acid residues can be predicted to be sensitive to furin-cleavage with cleavage occurring at the carboxy bond of the last basic amino acid in the motif.

Consensus motifs in substrates cleaved by furin have been identified with some degree of specificity. A furin-cleavage site motif has been described that comprises a region of twenty, continuous, amino acid residues, which can be labeled P14 through P6' (Tian S et al., *Int J Mol Sci* 12: 1060-5 (2011)) using the nomenclature described in Schechter I, Berger, A, Biochem *Biophys Res Commun* 32: 898-902 (1968). According to this nomenclature, the furin-cleavage site is at the carboxy bond of the amino acid residue designated P1, and the amino acid residues of the furin-cleavage motif are numbered P2, P3, P4, etc., in the direction going toward the amino-terminus from this reference P1 residue. The amino acid residues of the motif going toward the carboxy-terminus from the P1 reference residue are numbered with the prime notation P2', P3', P4', etc. Using this nomenclature, the P6 to P2' region delineates the core substrate of the furin cleavage motif which is bound by the enzymatic domain of furin. The two flanking regions P14 to P7 and P3' to P6' are often rich in polar, amino acid residues to increase the accessibility to the core furin cleavage site located between them.

The twenty amino acid residue, furin-cleavage motif and furin-cleavage site found in native, Shiga toxin A Subunits at the junction between the Shiga toxin A1 fragment and A2 fragment is well characterized in certain Shiga toxins. For example in StxA (SEQ ID NO:2) and SLT-1A (SEQ ID NO:1), this furin-cleavage motif is natively positioned from L238 to F257, and in SLT-2A (SEQ ID NO:3), this furin-cleavage motif is natively positioned from V237 to Q256. Based on amino acid homology, experiment, and/or furin-cleavage assays described herein, the skilled worker can identify furin-cleavage motifs in other native, Shiga toxin A Subunits or Shiga toxin effector polypeptides, where the motifs are actual furin-cleavage motifs or are predicted to result in the production of A1 and A2 fragments after furin cleavage of those molecules within a eukaryotic cell.

In some embodiments, the Shiga toxin effector polypeptide comprises (1) a Shiga toxin A1 fragment derived polypeptide having a carboxy-terminus and (2) a disrupted furin-cleavage motif at the carboxy-terminus of the Shiga toxin A1 fragment derived polypeptide. The carboxy-terminus of a Shiga toxin A1 fragment derived polypeptide may be identified by the skilled worker by using techniques known in the art, such as, e.g., by using protein sequence alignment software to identify (i) a furin-cleavage motif conserved with a naturally occurring Shiga toxin, (ii) a surface exposed, extended loop conserved with a naturally occurring Shiga toxin, and/or (iii) a stretch of amino acid residues which are predominantly hydrophobic (i.e. a hydrophobic "patch") that may be recognized by the ERAD system.

A protease-cleavage resistant, Shiga toxin effector polypeptide of the binding molecule (1) may be completely lacking any furin-cleavage motif at a carboxy-terminus of its Shiga toxin A1 fragment region and/or (2) comprise a disrupted furin-cleavage motif at the carboxy-terminus of its Shiga toxin A1 fragment region and/or region derived from the carboxy-terminus of a Shiga toxin A1 fragment. A disruption of a furin-cleavage motif include various alterations to an amino acid residue in the furin-cleavage motif, such as, e.g., a post-translation modification(s), an alteration of one or more atoms in an amino acid functional group, the addition of one or more atoms to an amino acid functional group, the association to a non-proteinaceous moiety(ies), and/or the linkage to an amino acid residue, peptide, polypeptide such as resulting in a branched proteinaceous structure.

Protease-cleavage resistant, Shiga toxin effector polypeptides may be created from a Shiga toxin effector polypeptide and/or Shiga toxin A Subunit polypeptide, whether naturally occurring or not, using a method described herein, described in WO 2015/191764, and/or known to the skilled worker, wherein the resulting molecule still retains one or more Shiga toxin A Subunit functions.

With regard to a furin-cleavage site or furin-cleavage motif, the term "disruption" or "disrupted" refers to an alteration from the naturally occurring furin-cleavage site and/or furin-cleavage motif, such as, e.g., a mutation, that results in a reduction in furin-cleavage proximal to the carboxy-terminus of a Shiga toxin A1 fragment region, or identifiable region derived thereof, as compared to the furin-cleavage of a wild-type Shiga toxin A Subunit or a polypeptide derived from a wild-type Shiga toxin A Subunit comprising only wild-type polypeptide sequences. An alteration to an amino acid residue in the furin-cleavage motif includes a mutation in the furin-cleavage motif, such as, e.g., a deletion, insertion, inversion, substitution, and/or carboxy-terminal truncation of the furin-cleavage motif, as well as a post-translation modification, such as, e.g., as a result of glycosylation, albumination, and the like which involve conjugating or linking a molecule to the functional group of an amino acid residue. Because the furin-cleavage motif is comprised of about twenty, amino acid residues, in theory, alterations, modifications, mutations, deletions, insertions, and/or truncations involving one or more amino acid residues of any one of these twenty positions might result in a reduction of furin-cleavage sensitivity (Tian S et al., *Sci Rep* 2: 261 (2012)). The disruption of a furin-cleavage site and/or furin-cleavage motif might or might not increase resistance to cleavage by other proteases, such as, e.g., trypsin and extracellular proteases common in the vascular system of mammals. The effects of a given disruption to cleavage sensitivity of a given protease may be tested by the skilled worker using techniques known in the art.

A "disrupted furin-cleavage motif" is furin-cleavage motif comprising an alteration to one or more amino acid residues derived from the 20 amino acid residue region representing a conserved, furin-cleavage motif found in native, Shiga toxin A Subunits at the junction between the Shiga toxin A1 fragment and A2 fragment regions and positioned such that furin cleavage of a Shiga toxin A Subunit results in the production of the A1 and A2 fragments; wherein the disrupted furin-cleavage motif exhibits reduced furin cleavage in an experimentally reproducible way as compared to a reference molecule comprising a wild-type, Shiga toxin A1 fragment region fused to a carboxy-terminal polypeptide of a size large enough to monitor furin cleavage using the appropriate assay known to the skilled worker and/or described herein.

In some embodiments, the Shiga toxin effector polypeptide comprises (1) a Shiga toxin A1 fragment derived polypeptide having a carboxy-terminus and (2) a disrupted furin-cleavage motif at the carboxy-terminus of the Shiga toxin A1 fragment polypeptide region; wherein the Shiga toxin effector polypeptide (and any binding molecule comprising it) is more furin-cleavage resistant as compared to a reference molecule, such as, e.g., a wild-type Shiga toxin polypeptide comprising the carboxy-terminus of an A1 fragment and/or the conserved, furin-cleavage motif between A1 and A2 fragments. For example, a reduction in furin cleavage of one molecule compared to a reference molecule may be determined using an in vitro, furin-cleavage assay described in WO 2015/191764, conducted using the same conditions, and then performing a quantitation of the band density of any fragments resulting from cleavage to quantitatively measure in change in furin cleavage.

In some embodiments, the Shiga toxin effector polypeptide is more resistant to furin-cleavage in vitro and/or in vivo as compared to a wild-type, Shiga toxin A Subunit.

In general, the protease-cleavage sensitivity of a binding molecule is tested by comparing it to the same molecule having its furin-cleavage resistant, Shiga toxin effector polypeptide replaced with a wild-type, Shiga toxin effector polypeptide comprising a Shiga toxin A1 fragment. In some embodiments, the PD-L1 binding molecules comprising a disrupted furin-cleavage motif exhibits a reduction in in vitro furin cleavage of 30%, 40%, 50%, 60%, 70%, 80%, 90%, 95%, 97%, 98% or greater compared to a reference molecule comprising a wild-type, Shiga toxin A1 fragment fused at its carboxy-terminus to a peptide or polypeptide.

Several furin-cleavage motif disruptions have been described. For example, mutating the two conserved arginines to alanines in the minimal R-x-x-R motif completely blocked processing by furin and/or furin-like proteases (see e.g Duda A et al., *J Virology* 78: 13865-70 (2004)). Because the furin-cleavage site motif is comprised of about twenty amino acid residues, in theory, certain mutations involving one or more of any one of these twenty, amino acid residue positions might abolish furin cleavage or reduce furin cleavage efficiency (see e.g. Tian S et al., *Sci Rep* 2: 261 (2012)).

In some embodiments, the molecules described herein comprise a Shiga toxin effector polypeptide derived from at least one A Subunit of a member of the Shiga toxin family wherein the Shiga toxin effector polypeptide comprises a disruption in one or more amino acids derived from the conserved, highly accessible, protease-cleavage sensitive loop of Shiga toxin A Subunits. For example, in StxA and SLT-1A, this highly accessible, protease-sensitive loop is natively positioned from amino acid residues 242 to 261, and in SLT-2A, this conserved loop is natively positioned from amino acid residues 241 to 260. Based on polypeptide sequence homology, the skilled worker can identify this conserved, highly accessible loop structure in other Shiga toxin A Subunits. Certain mutations to the amino acid residues in this loop can reduce the accessibility of certain amino acid residues within the loop to proteolytic cleavage and this might reduce furin-cleavage sensitivity.

In some embodiments, a PD-L1 binding molecule comprises a Shiga toxin effector polypeptide comprising a disrupted furin-cleavage motif comprising a mutation in the surface-exposed, protease sensitive loop conserved among Shiga toxin A Subunits. In some embodiments, a PD-L1 binding molecule comprises a Shiga toxin effector polypeptide comprising a disrupted furin-cleavage motif comprising a mutation in this protease-sensitive loop of Shiga toxin A Subunits, the mutation which reduce the surface accessibility of certain amino acid residues within the loop such that furin-cleavage sensitivity is reduced.

In some embodiments, the disrupted furin-cleavage motif of a Shiga toxin effector polypeptide comprises a disruption in terms of existence, position, or functional group of one or both of the consensus amino acid residues P1 and P4, such as, e.g., the amino acid residues in positions 1 and 4 of the minimal furin-cleavage motif R/Y-x-x-R. For example, mutating one or both of the two arginine residues in the minimal, furin consensus site R-x-x-R to alanine will disrupt a furin-cleavage motif and prevent furin-cleavage at that site. Similarly, amino acid residue substitutions of one or both of the arginine residues in the minimal furin-cleavage motif R-x-x-R to any non-conservative amino acid residue known to the skilled worker will reduced the furin-cleavage sensitivity of the motif. In particular, amino acid residue substitutions of arginine to any non-basic amino acid residue which lacks a positive charge, such as, e.g., A, G, P, S, T, D, E, Q, N, C, I, L, M, V, F, W, and Y, will result in a disrupted furin-cleavage motif In some embodiments, the disrupted furin-cleavage motif of a Shiga toxin effector polypeptide comprises a disruption in the spacing between the consensus amino acid residues P4 and P1 in terms of the number of intervening amino acid residues being other than two, and, thus, changing either P4 and/or P1 into a different position and eliminating the P4 and/or P1 designations. For example, deletions within the furin-cleavage motif of the minimal furin-cleavage site or the core, furin-cleavage motif will reduce the furin-cleavage sensitivity of the furin-cleavage motif.

In some embodiments, the disrupted furin-cleavage motif comprises one or more amino acid residue substitutions, as compared to a wild-type, Shiga toxin A Subunit. In some embodiments, the disrupted furin-cleavage motif comprises one or more amino acid residue substitutions within the minimal furin-cleavage site R/Y-x-x-R, such as, e.g., for StxA and SLT-1A derived Shiga toxin effector polypeptides, the natively positioned amino acid residue R248 substituted with any non-positively charged, amino acid residue and/or R251 substituted with any non-positively charged, amino acid residue; and for SLT-2A derived Shiga toxin effector polypeptides, the natively positioned amino acid residue Y247 substituted with any non-positively charged, amino acid residue and/or R250 substituted with any non-positively charged, amino acid residue.

In some embodiments, the disrupted furin-cleavage motif comprises an un-disrupted, minimal furin-cleavage site R/Y-x-x-R but instead comprises a disrupted flanking region, such as, e.g., amino acid residue substitutions in one or more amino acid residues in the furin-cleavage motif flanking regions natively positioned at, e.g., 241-247 and/or 252-259. In some embodiments, the disrupted furin cleavage motif comprises a substitution of one or more of the amino acid residues located in the P1-P6 region of the furin-cleavage motif; mutating P1' to a bulky amino acid, such as, e.g., R, W, Y, F, and H; and mutating P2' to a polar and hydrophilic amino acid residue; and substituting one or more of the amino acid residues located in the P1'-P6' region of the furin-cleavage motif with one or more bulky and hydrophobic amino acid residues In some embodiments, the disruption of the furin-cleavage motif comprises a deletion, insertion, inversion, and/or mutation of at least one amino acid residue within the furin-cleavage motif. In some embodiments, a protease-cleavage resistant, Shiga toxin effector polypeptide comprises a disruption of the amino acid sequence natively positioned at 249-251 of the A Subunit of Shiga-like toxin 1 (SEQ ID NO:1) or Shiga toxin (SEQ ID NO:2), or at 247-250 of the A Subunit of Shiga-like toxin 2 (SEQ ID NO:3) or the equivalent position in a conserved Shiga toxin effector polypeptide and/or non-native Shiga toxin effector polypeptide sequence. In some embodiments, protease-cleavage resistant, Shiga toxin effector polypeptides comprise a disruption which comprises a deletion of at least one amino acid within the furin-cleavage motif. In some embodiments, protease-cleavage resistant, Shiga toxin effector polypeptides comprise a disruption which comprises an insertion of at least one amino acid within the protease-cleavage motif region. In some embodiments, the protease-cleavage resistant, Shiga toxin effector polypeptides comprise a disruption which comprises an inversion of amino acids, wherein at least one inverted amino acid is within the protease motif region. In some embodiments, the protease-cleavage resistant, Shiga toxin effector polypeptides comprise a disruption which comprises a mutation, such as an amino acid substitution to a non-standard amino acid or an amino acid with a chemically modified side chain.

In some embodiments, the disrupted furin-cleavage motif comprises the deletion of nine, ten, eleven, or more of the carboxy-terminal amino acid residues within the furin-cleavage motif. In these embodiments, the disrupted furin-cleavage motif will not comprise a furin-cleavage site or a minimal furin-cleavage motif. In other words, certain embodiments lack a furin-cleavage site at the carboxy-terminus of the A1 fragment region.

In some embodiments, the disrupted furin-cleavage motif comprises both an amino acid residue deletion and an amino acid residue substitution as compared to a wild-type, Shiga toxin A Subunit. In some embodiments, the disrupted furin-cleavage motif comprises one or more amino acid residue deletions and substitutions within the minimal furin-cleavage site R/Y-x-x-R, such as, e.g., for StxA and SLT-1A derived Shiga toxin effector polypeptides, the natively positioned amino acid residue R248 substituted with any non-positively charged, amino acid residue and/or R251 substituted with any non-positively charged, amino acid residue; and for SLT-2A derived Shiga toxin effector polypeptides, the natively positioned amino acid residue Y247 substituted with any non-positively charged, amino acid residue and/or R250 substituted with any non-positively charged, amino acid residue.

In some embodiments, the disrupted furin-cleavage motif comprises an amino acid residue deletion and an amino acid residue substitution as well as a carboxy-terminal truncation as compared to a wild-type, Shiga toxin A Subunit. In some embodiments, the disrupted furin-cleavage motif comprises one or more amino acid residue deletions and substitutions within the minimal furin-cleavage site R/Y-x-x-R, such as, e.g., for StxA and SLT-1A derived Shiga toxin effector polypeptides, the natively positioned amino acid residue R248 substituted with any non-positively charged, amino acid residue and/or R251 substituted with any non-positively charged, amino acid residue; and for SLT-2A derived Shiga toxin effector polypeptides, the natively positioned amino acid residue Y247 substituted with any non-positively charged, amino acid residue and/or R250 substituted with any non-positively charged, amino acid residue.

In some embodiments, the disrupted furin-cleavage motif comprises both an amino acid substitution within the minimal furin-cleavage site R/Y-x-x-R and a carboxy-terminal truncation as compared to a wild-type, Shiga toxin A Subunit, such as, e.g., for StxA and SLT-1A derived Shiga toxin effector polypeptides, truncations ending at the natively amino acid position 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R248 and/or R251 substituted with any non-positively charged, amino acid residue where appropriate; and for SLT-2A derived Shiga toxin effector polypeptides, truncations ending at the natively amino acid position 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue Y247 and/or R250 substituted with any non-positively charged, amino acid residue where appropriate.

In some embodiments, the disrupted furin-cleavage motif comprises an insertion of one or more amino acid residues as compared to a wild-type, Shiga toxin A Subunit as long as the inserted amino residue(s) does not create a de novo furin-cleavage site. In some embodiments, the insertion of one or more amino acid residues disrupts the natural spacing between the arginine residues in the minimal, furin-cleavage site R/Y-x-x-R, such as, e.g., StxA and SLT-1A derived polypeptides comprising an insertion of one or more amino acid residues at 249 or 250 and thus between R248 and R251; or SLT-2A derived polypeptides comprising an insertion of one or more amino acid residues at 248 or 249 and thus between Y247 and R250.

In some embodiments, the disrupted furin-cleavage motif comprises both an amino acid residue insertion and a carboxy-terminal truncation as compared to a wild-type, Shiga toxin A Subunit. In some embodiments, the disrupted furin-cleavage motif comprises both an amino acid residue insertion and an amino acid residue substitution as compared to a wild-type, Shiga toxin A Subunit. In some embodiments, the disrupted furin-cleavage motif comprises both an amino acid residue insertion and an amino acid residue deletion as compared to a wild-type, Shiga toxin A Subunit.

In some embodiments, the disrupted furin-cleavage motif comprises an amino acid residue deletion, an amino acid residue insertion, and an amino acid residue substitution as compared to a wild-type, Shiga toxin A Subunit.

In some embodiments, the disrupted furin-cleavage motif comprises an amino acid residue deletion, insertion, substitution, and carboxy-terminal truncation as compared to a wild-type, Shiga toxin A Subunit.

In some embodiments, the Shiga toxin effector polypeptide comprising a disrupted furin-cleavage motif is directly fused by a peptide bond to a molecular moiety comprising an amino acid, peptide, and/or polypeptide wherein the fused structure involves a single, continuous polypeptide. In these fusion embodiments, the amino acid sequence following the disrupted furin-cleavage motif should not create a de novo, furin-cleavage site at the fusion junction.

Any of the above protease-cleavage resistant, Shiga toxin effector polypeptide sub-regions and/or disrupted furin-cleavage motifs may be used alone or in combination with each individual embodiment as described herein, including methods described herein.

3. T-Cell Hyper-Immunized, Shiga Toxin a Subunit Effector Polypeptides

In some embodiments, the Shiga toxin effector polypeptide of the binding molecule comprises an embedded or inserted epitope-peptide. In some embodiments, the epitope-peptide is a heterologous, T-cell epitope-peptide, such as, e.g., an epitope considered heterologous to Shiga toxin A Subunits. In some embodiments, the epitope-peptide is a CD8+ T-cell epitope. In some embodiments, the CD8+ T-cell epitope-peptide has a binding affinity to a MHC class I molecule characterized by a dissociation constant ($K_D$) of $10^{-4}$ molar or less and/or the resulting MHC class I-epitope-peptide complex has a binding affinity to a T-cell receptor (TCR) characterized by a dissociation constant ($K_D$) of $10^{-4}$ molar or less.

In some embodiments, the Shiga toxin effector polypeptide comprises an embedded or inserted, heterologous, T-cell epitope, such as, e.g., a human CD8+ T-cell epitope. In some embodiments, the heterologous, T-cell epitope is embedded or inserted so as to disrupt an endogenous epitope or epitope region (e.g. a B-cell epitope and/or CD4+ T-cell epitope) identifiable in a naturally occurring Shiga toxin polypeptide or parental Shiga toxin effector polypeptide from which the Shiga toxin effector polypeptide is derived.

In some embodiments, the Shiga toxin effector polypeptide (and any binding molecule comprising it) is CD8+ T-cell hyper-immunized, such as, e.g., as compared to a wild-type Shiga toxin polypeptide. Each CD8+ T-cell hyper-immunized, Shiga toxin effector polypeptide comprises an embedded or inserted T-cell epitope-peptide. Hyper-immunized, Shiga toxin effector polypeptides can be created from Shiga toxin effector polypeptides and/or Shiga toxin A Subunit polypeptides, whether naturally occurring or not, using a method described herein, described in WO 2015/113005, and/or known to the skilled worker, wherein the resulting molecule still retains one or more Shiga toxin A Subunit functions.

A T-cell epitope is a molecular structure which is comprised by an antigenic peptide and can be represented by a linear, amino acid sequence. Commonly, T-cell epitopes are peptides of sizes of eight to eleven amino acid residues (Townsend A, Bodmer H, Annu Rev Immunol 7: 601-24 (1989)); however, certain T-cell epitope-peptides have lengths that are smaller than eight or larger than eleven amino acids long (see e.g. Livingstone A, Fathman C, Annu Rev Immunol 5: 477-501 (1987); Green K et al., Eur J Immunol 34: 2510-9 (2004)). In some embodiments, the embedded or inserted epitope is at least seven amino acid residues in length. In some embodiments, the embedded or inserted epitope is bound by a TCR with a binding affinity characterized by a $K_D$ less than 10 mM (e.g. 1-100 µM) as calculated using the formula in Stone J et al., Immunology 126: 165-76 (2009). However, it should be noted that the binding affinity within a given range between the MHC-epitope and TCR may not correlate with antigenicity and/or immunogenicity (see e.g. Al-Ramadi B et al., J Immunol 155: 662-73 (1995)), such as due to factors like MHC-peptide-TCR complex stability, MHC-peptide density and MHC-independent functions of TCR cofactors such as CD8 (Baker B et al., Immunity 13: 475-84 (2000); Hornell T et al., J Immunol 170: 4506-14 (2003); Woolridge L et al., J Immunol 171: 6650-60 (2003)).

In some embodiments, the molecule comprises a CD8+ T-cell epitope. In some further embodiments, the CD8+ T-cell epitope is a CD8+ T-cell epitope with regard to a human immune system. In some embodiments, the CD8+ T-cell epitope is a peptide having at least seven, eight, nine, or ten amino acid residues. In some embodiments, the CD8+ T-cell epitope comprises or consists of nine amino acid residues. In some embodiments, the CD8+ T-cell epitope may bound by a human TCR with a binding affinity characterized by a K D less than 10 mM (e.g. 1-100 µM), e.g. as determined using an in vitro assay known to the skilled worker.

In some embodiments, the molecule comprises a CD8+ T-cell epitope having a sequence of NLVPMVATV (SEQ ID NO: 78). In some embodiments, the molecule comprises a CD8+ T-cell epitope having a sequence VTEHDTLLY (SEQ ID NO: 79). In some embodiments, the molecule comprises a CD8+ T-cell epitope having a sequence SIINFEKYL (SEQ ID NO: 80). In some embodiments, the molecule comprises a CD8+ T-cell epitope having a sequence GLDRNSGNY (SEQ ID NO: 81). In some embodiments, the molecule comprises a CD8+ T-cell epitope having a sequence GVMTRGRLK (SEQ ID NO: 82). In some embodiments, the molecule comprises a CD8+ T-cell epitope having a sequence GILGFVFTL (SEQ ID NO: 83). In some embodiments, the molecule comprises a CD8+ T-cell epitope having a sequence ILRGSVAHK (SEQ ID NO: 84).

In some embodiments, a binding molecule described herein comprises a Shiga toxin effector polypeptide comprising any one of SEQ ID NO: 1-18, 40-68, 169, 170, or 173 and a $CD_8$+ T-cell epitope comprising the sequence of any one of SEQ ID NO: 78-84. In some embodiments, a binding molecule comprises a Shiga toxin effector polypeptide comprising SEQ ID NO: 41 and a CD8+ T-cell epitope comprising the sequence of any one of SEQ ID NO: 78-84. In some embodiments, a binding molecule comprises a Shiga toxin effector polypeptide comprising SEQ ID NO: 41 and a CD8+ T-cell epitope comprising the sequence of SEQ ID NO: 78. In some embodiments, a binding molecule comprises a Shiga toxin effector polypeptide comprising SEQ ID NO: 41 and a CD8+ T-cell epitope comprising the sequence of SEQ ID NO: 79. In some embodiments, a binding molecule comprises a Shiga toxin effector polypeptide comprising SEQ ID NO: 41 and a CD8+ T-cell epitope comprising the sequence of SEQ ID NO: 80. In some embodiments, a binding molecule comprises a Shiga toxin effector polypeptide comprising SEQ ID NO: 41 and a CD8+ T-cell epitope comprising the sequence of SEQ ID NO: 81. In some embodiments, a binding molecule comprises a Shiga toxin effector polypeptide comprising SEQ ID NO: 41 and a CD8+ T-cell epitope comprising the sequence of SEQ ID NO: 82. In some embodiments, a binding molecule comprises a Shiga toxin effector polypeptide comprising SEQ ID NO: 41 and a CD8+ T-cell epitope comprising the sequence of SEQ ID NO: 83. In some embodiments, a binding molecule comprises a Shiga toxin effector polypeptide comprising SEQ ID NO: 41 and a CD8+ T-cell epitope comprising the sequence of SEQ ID NO: 84.

A heterologous, T-cell epitope is an epitope not already present in a wild-type Shiga toxin A Subunit; a naturally occurring Shiga toxin A Subunit; and/or a parental, Shiga toxin effector polypeptide used as a source polypeptide for modification by a method described herein, described in WO 2015/113005, and/or known to the skilled worker.

A heterologous, T-cell epitope-peptide may be incorporated into a source polypeptide via numerous methods known to the skilled worker, including, e.g., the processes of creating one or more amino acid substitutions within the source polypeptide, fusing one or more amino acids to the source polypeptide, inserting one or more amino acids into the source polypeptide, linking a peptide to the source polypeptide, and/or a combination of the aforementioned processes. The result of such a method is the creation of a modified variant of the source polypeptide which comprises one or more embedded or inserted, heterologous, T-cell epitope-peptides.

T-cell epitopes may be chosen or derived from a number of source molecules for use as described herein. T-cell epitopes may be created or derived from various naturally occurring proteins. T-cell epitopes may be created or derived from various naturally occurring proteins foreign to mammals, such as, e.g., proteins of microorganisms. T-cell epitopes may be created or derived from mutated human proteins and/or human proteins aberrantly expressed by malignant human cells. T-cell epitopes may be synthetically created or derived from synthetic molecules (see e.g., Carbone F et al., *J Exp Med* 167: 1767-9 (1988); Del Val M et al., *J Virol* 65: 3641-6 (1991); Appella E et al., *Biomed Pept Proteins Nucleic Acids* 1: 177-84 (1995); Perez S et al., *Cancer* 116: 2071-80 (2010)).

Although any T-cell epitope-peptide is contemplated as being used as a heterologous, T-cell epitope, certain epitopes may be selected based on desirable properties. One objective described herein is to create CD8+ T-cell hyper-immunized, Shiga toxin effector polypeptides for administration to vertebrates, meaning that the heterologous, T-cell epitope is highly immunogenic and can elicit robust immune responses in vivo when displayed complexed with a MHC class I molecule on the surface of a cell. In some embodiments, the Shiga toxin effector polypeptide comprises one or more, embedded or inserted, heterologous, T-cell epitopes which are CD8+ T-cell epitopes. A Shiga toxin effector polypeptide that comprises a heterologous, CD8+ T-cell epitope is considered a CD8+ T-cell hyper-immunized, Shiga toxin effector polypeptide.

T-cell epitope components may be chosen or derived from a number of source molecules already known to be capable of eliciting a vertebrate immune response. T-cell epitopes may be derived from various naturally occurring proteins foreign to vertebrates, such as, e.g., proteins of pathogenic microorganisms and non-self, cancer antigens. In particular, infectious microorganisms may contain numerous proteins with known antigenic and/or immunogenic properties. Further, infectious microorganisms may contain numerous proteins with known antigenic and/or immunogenic sub-regions or epitopes.

For example, the proteins of intracellular pathogens with mammalian hosts are sources for T-cell epitopes. There are numerous intracellular pathogens, such as viruses, bacteria, fungi, and single-cell eukaryotes, with well-studied antigenic proteins or peptides. T-cell epitopes can be selected or identified from human viruses or other intracellular pathogens, such as, e.g., bacteria like mycobacterium, fungi like toxoplasmae, and protists like trypanosomes.

For example, there are many immunogenic, viral peptide components of viral proteins from viruses that are infectious to humans. Numerous, human T-cell epitopes have been mapped to peptides within proteins from influenza A viruses, such as peptides in the proteins HA glycoproteins FE17, S139/1, CH65, C05, hemagglutinin 1 (HA1), hemagglutinin 2 (HA2), nonstructural protein 1 and 2 (NS1 and NS 2), matrix protein 1 and 2 (M1 and M2), nucleoprotein (NP), neuraminidase (NA)), and many of these peptides have been shown to elicit human immune responses, such as by using ex vivo assay. Similarly, numerous, human T-cell epitopes have been mapped to peptide components of proteins from human cytomegaloviruses (HCMV), such as peptides in the proteins pp65 (UL83), UL128-131, immediate-early 1 (IE-1; UL123), glycoprotein B, tegument proteins, and many of these peptides have been shown to elicit human immune responses, such as by using ex vivo assays.

Another example is there are many immunogenic, cancer antigens in humans. The $CD_8$+ T-cell epitopes of cancer and/or tumor cell antigens can be identified by the skilled worker using techniques known in the art, such as, e.g., differential genomics, differential proteomics, immunoproteomics, prediction then validation, and genetic approaches like reverse-genetic transfection (see e.g., Admon A et al., *Mol Cell Proteomics* 2: 388-98 (2003); Purcell A, Gorman J, *Mol Cell Proteomics* 3: 193-208 (2004); Comber J, Philip R, *Ther Adv Vaccines* 2: 77-89 (2014)). There are many antigenic and/or immunogenic T-cell epitopes already identified or predicted to occur in human cancer and/or tumor cells. For example, T-cell epitopes have been predicted in human proteins commonly mutated or overexpressed in neoplastic cells, such as, e.g., ALK, CEA, N-acetylglucosaminyl-transferase V (GnT-V), HCA587, PD-L1/neu, MAGE, Melan-A/MART-1, MUC-1, p53, and TRAG-3 (see e.g., van der Bruggen P et al., *Science* 254: 1643-7 (1991); Kawakami Y et al., *J Exp Med* 180: 347-52 (1994); Fisk B et al., *J Exp Med* 181: 2109-17 (1995); Guilloux Y et al., *J Exp Med* 183: 1173 (1996); Skipper J et al., *J Exp Med* 183: 527 (1996); Brossart P et al., 93: 4309-17 (1999); Kawashima I et al., *Cancer Res* 59: 431-5 (1999); Papadopoulos K et al., *Clin Cancer Res* 5: 2089-93 (1999); Zhu B et al., *Clin Cancer Res* 9: 1850-7 (2003); Li B et al., *Clin Exp Immunol* 140: 310-9 (2005); Ait-Tahar K et al., *Int J Cancer* 118: 688-95 (2006); Akiyama Y et al., *Cancer Immunol Immunother* 61: 2311-9 (2012)). In addition, synthetic variants of T-cell epitopes from human cancer cells have been created (see e.g., Lazoura E, Apostolopoulos V, *Curr Med Chem* 12: 629-39 (2005); Douat-Casassus C et al., *J Med Chem* 50: 1598-609 (2007)).

In addition, multiple, immunogenic, T-cell epitopes for MHC class I presentation may be embedded in the same Shiga toxin effector polypeptide for use, such as, e.g., in the targeted delivery of a plurality of T-cell epitopes simultaneously.

Any of the protease-cleavage resistant, Shiga toxin effector polypeptide sub-regions and/or disrupted furin-cleavage motifs described herein may be used alone or in combination with each individual embodiment described herein, including methods described herein.

C. Additional Exogenous Materials

In some embodiments, the binding molecules comprises an additional exogenous material. An "additional exogenous material" as used herein refers to one or more atoms or molecules that can be transported to the interior of a cell by a binding molecule. In some embodiments, an additional exogenous material is any material transported into the interior of a cell by a binding molecule, whether or not it is typically present in the native target cell or in a native Shiga toxin. In some embodiments, an additional exogenous material is a material that is not generally present in Shiga toxins and/or native target cells. In one sense, the entire binding molecule is an exogenous material which will enter the cell; thus, the "additional" exogenous materials are heterologous materials linked to but other than the core binding molecule itself. Non-limiting examples of additional exogenous materials are radionucleides, peptides, detection promoting agents, proteins, small molecule chemotherapeutic agents, and polynucleotides.

In some embodiments of the binding molecules, the additional exogenous material is one or more radionucleides, such as, e.g., $^{211}$At, $^{131}$I, $^{125}$I, $^{90}$Y, $^{111}$In, $^{186}$Re, $^{188}$Re, $^{153}$Sm, $^{212}$Bi, $^{32}$P, $^{60}$C, and/or radioactive isotopes of lutetium.

In some embodiments, the additional exogenous material comprises a proapoptotic peptide, polypeptide, or protein, such as, e.g., BCL-2, caspases (e.g. fragments of caspase-3 or caspase-6), cytochromes, granzyme B, apoptosis-inducing factor (AIF), BAX, tBid (truncated Bid), and proapoptotic fragments or derivatives thereof (see e.g., Ellerby H et al., *Nat Med* 5: 1032-8 (1999); Mai J et al., *Cancer Res* 61: 7709-12 (2001); Jia L et al., *Cancer Res* 63: 3257-62 (2003); Liu Y et al., *Mol Cancer Ther* 2: 1341-50 (2003); Perea S et al., *Cancer Res* 64: 7127-9 (2004); Xu Y et al., *J Immunol* 173: 61-7 (2004); Dalken B et al., *Cell Death Differ* 13: 576-85 (2006); Wang T et al., *Cancer Res* 67: 11830-9 (2007); Kwon Metal., *Mol Cancer Ther* 7: 1514-22 (2008); Qiu X et al., *Mol Cancer Ther* 7: 1890-9 (2008); Shan L et al., *Cancer Biol Ther* 11: 1717-22 (2008); Wang F et al., *Clin Cancer Res* 16: 2284-94 (2010); Kim J et al., *J Virol* 85: 1507-16 (2011)).

In some embodiments, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA). In some embodiments, the additional exogenous material is an antigen, such as antigens derived from pathogens, bacterial proteins, viral proteins, proteins mutated in cancer, proteins aberrantly expressed in cancer, or T-cell complementary determining regions. For example, exogenous materials include antigens, such as those characteristic of antigen-presenting cells infected by bacteria, and T-cell complementary determining regions capable of functioning as exogenous antigens. Exogenous materials comprising polypeptides or proteins may optionally comprise one or more antigens whether known or unknown to the skilled worker.

In some embodiments of the binding molecules, all heterologous antigens and/or epitopes associated with the Shiga toxin effector polypeptide are arranged in the binding molecule amino-terminal to the carboxy-terminus of the Shiga toxin A1 fragment region of the Shiga toxin effector polypeptide. In some embodiments, all heterologous antigens and/or epitopes associated with the Shiga toxin effector polypeptide are associated, either directly or indirectly, with the Shiga toxin effector polypeptide at a position amino-terminal to the carboxy-terminus of the Shiga toxin A1 fragment region of the Shiga toxin effector polypeptide. In some embodiments, all additional exogenous material(s) which is an antigen is arranged amino-terminal to the Shiga toxin effector polypeptide, such as, e.g., fused directly or indirectly to the amino terminus of the Shiga toxin effector polypeptide.

In some embodiments of the binding molecules, the additional exogenous material is a cytotoxic agent, such as, e.g., a small molecule chemotherapeutic agent, anti-neoplastic agent, cytotoxic antibiotic, alkylating agent, antimetabolite, topoisomerase inhibitor, and/or tubulin inhibitor. Non-limiting examples of cytotoxic agents suitable for use with as described herein include aziridines, cisplatins, tetrazines, procarbazine, hexamethylmelamine, vinca alkaloids, taxanes, camptothecins, etoposide, doxorubicin, mitoxantrone, teniposide, novobiocin, aclarubicin, anthracyclines, actinomycin, amanitin, amatoxins, bleomycin, centanamycin (indolecarboxamide), plicamycin, mitomycin, daunorubicin, epirubicin, idarubicins, dolastatins, maytansines, maytansionoids, duromycin, docetaxel, duocarmycins, adriamycin, calicheamicin, auristatins, pyrrolobenzodiazepines, pyrrolobenzodiazepine dimers (PBDs), carboplatin, 5-fluorouracil (5-FU), capecitabine, mitomycin C, paclitaxel, 1,3-Bis (2-chloroethyl)-1-nitrosourea (BCNU), rifampicin, cisplatin, methotrexate, gemcitabine, aceglatone, acetogenins (e.g. bullatacin and bullatacinone), aclacinomysins, AG1478, AG1571, aldophosphamide glycoside, alkyl sulfonates (e.g., busulfan, improsulfan, and piposulfan), alkylating agents (e.g. thiotepa and cyclophosphamide), aminolevulinic acid, aminopterin, amsacrine, ancitabine, anthramycin, arabinoside, azacitidine, azaserine, aziridines (e.g., benzodopa, carboquone, meturedopa, and uredopa), azauridine, bestrabucil, bisantrene, bisphosphonates (e.g. clodronate), bleomycins, bortezomib, bryostatin, cactinomycin, callystatin, carabicin, carminomycin, carmofur, carmustine, carzinophilin, CC-1065, chlorambucil, chloranbucil, chlornaphazine, chlorozotocin, chromomycinis, chromoprotein enediyne antibiotic chromophores, CPT-11, cryptophycins (e.g. cryptophycin 1 and cryptophycin 8), cyclophosphamide, cytarabine, dacarbazine, dactinomycin, daunomycin, defofamine, demecolcine, detorubicin, diaziquone, 6-diazo-5-oxo-L-norleucine, dideoxyuridine, difluoromethylornithine (DMFO), doxifluridine, doxorubicins (e.g., morpholinodoxorubicin, cyanomorpholino-doxorubicin, 2-pyrrolinodoxorubicin, and deoxydoxorubicin), dynemicins, edatraxate, edatrexate, eleutherobins, elformithine, elliptinium acetate, enediyne antibiotics (e.g. calicheamicins), eniluracil, enocitabine, epirubicins, epothilone, esorubicins, esperamicins, estramustine, ethylenimines, 2-ethylhydrazide, etoglucid, fludarabine, folic acid analogues (e.g., denopterin, methotrexate, pteropterin, and trimetrexate), folic acid replenishers (e.g. frolinic acid), fotemustine, fulvestrant, gacytosine, gallium nitrate, gefitinib, gemcitabine, hydroxyurea, ibandronate, ifosfamide, imatinib mesylate, erlotinib, fulvestrant, letrozole, PTK787/ZK 222584 (Novartis, Basel, CH), oxaliplatin, leucovorin, rapamycin, lapatinib, lonafarnib, sorafenib, methylamelamines (e.g., altretamine, triethylenemelamine, triethy lenephosphoramide, triethylenethiophosphoramide and trimethylomelamine), pancratistatins, sarcodictyins, spongistatins, nitrogen mustards (e.g., chlorambucil, chlornaphazine, cyclophosphamide, mechlorethamine, mechlorethamine oxide hydrochloride, melphalan, novembichin, phenesterine, prednimustine, trofosfamide, and uracil mustard), nitrosureas (e.g., carmustine, fotemustine, lomustine, nimustine, and ranimnustine), dynemicins, neocarzinostatin chromophores, anthramycin, detorubicin, epirubicins, marcellomycins, mitomycins (e.g. mitomycin C), mycophenolic acid, nogalamycins, olivomycins, peplomycins, potfiromycins, puromycins, quelamycins, rodorubicins, ubenimex, zinostatins, zorubicins, purine analogs (e.g., fludarabine, 6-mercaptopurine, thiamiprine, and thioguanine), pyrimidine analogs (e.g., ancitabine, azacitidine, 6-azauridine, dideoxyuridine, doxifluridine, enocitabine, and floxuridine), aceglatone, lentinan, lonidainine, maytansinoids (e.g. maytansins and ansamitocins), mitoguazone, mitoxantrone, mopidanmol, nitraerine, pentostatin, phenamet, pirarubicin, podophyllinic acid, 2-ethylhydrazide, rhizoxin, sizofuran, spirogermanium, tenuazonic acid, triaziquone, 2,2',2"trichlorotriethylamine, trichothecenes (e.g., T-2 toxin, verracurin A, roridin A, and anguidine), urethan, vindesine, mannomustine, mitobronitol, mitolactol, pipobroman, arabinoside, cyclophosphamide, toxoids (e.g. paclitaxel and doxetaxel), 6-thioguanine, mercaptopurine, platinum, platinum analogs (e.g. cisplatin and carboplatin), etoposide (VP-16), mitoxantrone, vinorelbine, novantrone, daunomycin, xeloda, topoisomerase inhibitor RFS 2000, retinoids (e.g. retinoic acid), capecitabine, lomustine, losoxantrone, mercaptopurines, nimustine, nitraerine, rapamycin, razoxane, roridin A, spongistatins, streptonigrins, streptozocins, sutent, T-2 toxin, thiamiprine, thiotepa, toxoids (e.g. paclitaxel and doxetaxel), tubercidins, verracurin A, vinblastine, vincristine, and structural analogs of any of the aforementioned (e.g. synthetic analogs), and/or derivatives of any of the aforementioned (see e.g., Lindell T et al., *Science* 170: 447-9 (1970); Remillard S et al., *Science* 189: 1002-5 (1975); Ravry M et al., *Am J Clin Oncol* 8: 148-50 (1985); Ravry Metal., *Cancer Treat Rep* 69: 1457-8 (1985); Sternberg C et al., *Cancer* 64: 2448-58 (1989); Bai R et al., *Biochem Pharmacol* 39: 1941-9 (1990); Boger D, Johnson D, *Proc Natl Acad Sci USA* 92: 3642-9 (1995); Beck J et al., *Leuk Lymphoma* 41: 117-24 (2001); Cassady J et al., *Chem Pharm Bull* (Tokyo) 52: 1-26 (2004); Sapra P et al., *Clin Cancer Res* 11: 5257-64 (2005); Okeley N et al., *Clinc Cancer Res* 16: 888-97 (2010); Oroudjev E et al., *Mol Cancer Ther* 9: 2700-13 (2010); Ellestad G, *Chirality* 23: 660-71 (2011); Kantarjian H et al., *Lancet Oncol* 13: 403-11 (2012); Moldenhauer G et al., *J Natl Cancer Inst* 104: 622-34 (2012); Meulendijks D et al., *Invest New Drugs* 34: 119-28 (2016)).

A non-limiting list of illustrative carboxy-terminal exogenous materials are provided below in Table 2. These carboxy-terminal exogenous materials may, for example, be delivered into a target cell by a binding molecule.

TABLE 2

Illustrative Carboxy-Terminal Moieties

| Sequence | SEQ ID NO: |
|---|---|
| HHAANLVPMVATV | 176 |
| HHAANLVPMVATVRRNLVPMVATVRRNLVP | 177 |
| NLVPMVATVRRNLVPMVATVRRNLVPMVATV | 175 |
| NLVPMVATVRRNLVPMVATVRRNLVP | 174 |
| NLVPMVATVRRNLVPMVATV | 178 |
| NLVPMVATVHHAANLVPMVATV | 179 |
| RRNLVPMVATV | 180 |
| RRNLVPMVATVRRNLVPMVATVRRNLVP | 181 |
| NLVPMVATVRRNLVPMVATVHHAANLVPMVATV | 182 |
| NLVPMVATVRRAANLVPMVATVHHAANLVP | 183 |
| NLVPMVATVHHAANLVPMVATVRRNLVPMVATV | 184 |
| NLVPMVATVHHAANLVPMVATVRRNLVP | 185 |
| NLVPMVATVHHAANLVPMVATVHHAANLVPMVATV | 186 |
| NLVPMVATVHHAANLVPMVATVHHAANLVP | 187 |

In some embodiments, a binding molecule comprises a Shiga toxin effector polypeptide and a carboxy-terminal moiety, such as a carboxy terminal moiety comprising the sequence of any one of SEQ ID NO: 174-187. In some embodiments, a binding molecule comprises a Shiga toxin effector polypeptide and a carboxy terminal moiety, wherein the Shiga toxin effector polypeptide comprises the sequence of any one of SEQ ID NO: 1-18, 40-68, 169, 170, or 173. In some embodiments, a binding molecule comprises a Shiga toxin effector polypeptide and a carboxy terminal moiety, wherein the Shiga toxin effector polypeptide comprises the sequence of SEQ ID NO: 41. In some embodiments, a binding molecule comprises a Shiga toxin effector polypeptide and a carboxy terminal moiety, wherein the Shiga toxin effector polypeptide comprises the sequence of SEQ ID NO: 41, and the carboxy terminal moiety comprises the sequence of any one of SEQ ID NO: 174-178.

II. Linkages Connecting Components and/or their Subcomponents

Individual PD-L1 binding regions, toxin components, and/or other components of the binding molecules described herein may be suitably linked to each, such as, e.g., fused directly or indirectly linked to each other via one or more linkers well known in the art and/or described herein. Individual polypeptide subcomponents of the binding regions, e.g. heavy chain variable regions ($V_H$), light chain variable regions ($V_L$), CDR, and/or ABR regions, may be suitably linked to each other via one or more linkers (e.g., scFv linkers) well known in the art and/or described herein, including via chemical conjugation. Proteinaceous components, e.g., multi-chain binding regions, may be suitably linked to each other or other polypeptide components directly via peptide bonds and/or indirectly via one or more linkers well known in the art. Peptide components, e.g., KDEL family endoplasmic reticulum retention/retrieval signal motifs (see SEQ ID NO: 205-252), may be suitably linked to another component directly via peptide bonds or indirectly via one or more linkers, such as a proteinaceous linker, which are well known in the art. For example, in some embodiments of the binding molecule, an individual PD-L1 binding region and a Shiga toxin effector polypeptide (and/or additional components of the binding molecule, such as, e.g., a T-cell epitope, additional exogenous material, and/or KDEL motif (SEQ ID NO: 205)) are suitably linked and/or conjugated to each other via one or more binding region linkers well known in the art and/or described herein.

Suitable linkers are generally those which allow each polypeptide component to fold with a three-dimensional structure very similar to the polypeptide components produced individually without any linker or other component. Suitable linkers include single amino acids, peptides, polypeptides, and linkers lacking any of the aforementioned, such as various non-proteinaceous carbon chains, whether branched or cyclic.

Suitable linkers may be proteinaceous and comprise one or more amino acids, peptides, and/or polypeptides. Proteinaceous linkers are suitable for both recombinant fusion proteins and chemically linked conjugates. A proteinaceous linker typically has from about 2 to about 50 amino acid residues, such as, e.g., from about 5 to about 30 or from about 6 to about 25 amino acid residues. The length of the linker selected will depend upon a variety of factors, such as, e.g., the desired property or properties for which the linker is being selected. In some embodiments, the linker is proteinaceous and is linked near the terminus of a protein component, typically within about 20 amino acids of the terminus.

Suitable linkers may be non-proteinaceous, such as, e.g. chemical linkers. Various non-proteinaceous linkers known in the art may be used to link cell-targeting binding regions to the Shiga toxin effector polypeptide components of the binding molecules, such as linkers commonly used to conjugate immunoglobulin polypeptides to heterologous polypeptides. For example, polypeptide regions may be linked using the functional side chains of their amino acid residues and carbohydrate moieties such as, e.g., a carboxy, amine, sulfhydryl, carboxylic acid, carbonyl, hydroxyl, and/or cyclic ring group. For example, disulfide bonds and thioether bonds may be used to link two or more polypeptides. In addition, non-natural amino acid residues may be used with other functional side chains, such as ketone groups (see e.g. Axup J et al., *Proc Natl Acad Sci U.S.A.* 109: 16101-6 (2012); Sun S et al., *Chembiochem* July 18 (2014); Tian F et al., *Proc Natl Acad Sci USA* 111: 1766-71 (2014)). In addition, non-natural amino acid residues may be used with other functional side chains, such as ketone groups, alkyne groups, or azides (see e.g. the use of antibodies engineered to comprise p-acetyl-L-phenylalanine or p-azidomethyl-N-phenylalanine residues for conjugation to cargos U.S. Patent Application Publication Ser. No. 14/786,402 US 2017/0362334)). Examples of non-proteinaceous chemical linkers include but are not limited to N-hydroxysuccinimide esters (NETS esters) such as sulfo-NHS esters, isothiocyanates, isocyanates, acyl azides, sulfonyl chlorides, aldehydes, glyoxals, epoxides, oxiranes, carbonates, aryl halides, imidoesters, carbodiimides, anhydrides, and fluorophenyl esters. Further examples of non-proteinaceous chemical linkers include but are not limited to N-succinimidyl (4-iodoacetyl)-aminobenzoate, S—(N-succinimidyl) thioacetate (SATA), N-succinimidyl-oxycarbonyl-cu-methyl-a-(2-pyridyldithio) toluene (SMPT), N-succinimidyl 4-(2-pyridyldithio)-pentanoate (SPP), succinimidyl 4-(N-maleimidomethyl) cyclohexane carboxylate (SMCC or MCC), sulfosuccinimidyl (4-iodoacetyl)-aminobenzoate, 4-succinimidyl-oxycarbonyl-a-(2-pyridyldithio) toluene, sulfosuccinimidyl-6-(α-methyl-α-(pyridyldithiol)-toluamido) hexanoate, N-succinimidyl-3-(-(2-pyridyldithio)-proprionate (SPDP), succinimidyl 6(3(-(-2-pyridyldithio)-proprionamido) hexanoate, sulfosuccinimidyl 6(3(-(-2-pyridyldithio)-propionamido) hexanoate, maleimidocaproyl (MC), maleimidocaproyl-valine-citrulline-p-aminobenzyloxycarbonyl (MC-vc-PAB), 3-maleimidobenzoic acid N-hydroxysuccinimide ester (MBS), alpha-alkyl derivatives, sulfoNHS-ATMBA (sulfosuccinimidyl N-[3-(acetylthio)-3-methylbutyryl-beta-alanineD, sulfodichlorophenol, 2-iminothiolane, 3-(2-pyridyldithio)-propionyl hydrazide, Ellman's reagent, dichlorotriazinic acid, and S-(2-thiopyridyl)-L-cysteine.

Suitable linkers, whether proteinaceous or non-proteinaceous, may include, e.g., protease sensitive, environmental redox potential sensitive, pH sensitive, acid cleavable, photocleavable, and/or heat sensitive linkers.

Proteinaceous linkers may be chosen for incorporation into recombinant fusion binding molecules. For recombinant fusion cell-targeting proteins, linkers typically comprise about 2 to 50 amino acid residues, preferably about 5 to 30 amino acid residues. Commonly, proteinaceous linkers comprise a majority of amino acid residues with polar, uncharged, and/or charged residues, such as, e.g., threonine, proline, glutamine, glycine, and alanine. Non-limiting examples of proteinaceous linkers include alanine-serine-glycine-glycine-proline-glutamate (ASGGPE) (SEQ ID NO: 267), valine-methionine (VM), alanine-methionine (AM), AM$(G_{2\ to\ 4}S)_x$AM where G is glycine, S is serine, and x is an integer from 1 to 10 (SEQ ID NO: 268).

Proteinaceous linkers may be selected based upon the properties desired. Proteinaceous linkers may be chosen by the skilled worker with specific features in mind, such as to optimize one or more of the fusion molecule's folding, stability, expression, solubility, pharmacokinetic properties, pharmacodynamic properties, and/or the activity of the fused domains in the context of a fusion construct as compared to the activity of the same domain by itself. For example, proteinaceous linkers may be selected based on flexibility, rigidity, and/or cleavability. The skilled worker may use databases and linker design software tools when choosing linkers. In certain linkers may be chosen to optimize expression. In certain linkers may be chosen to promote intermolecular interactions between identical polypeptides or proteins to form homomultimers or different polypeptides or proteins to form heteromultimers. For example, proteinaceous linkers may be selected which allow for desired non-covalent interactions between polypeptide components of the binding molecules, such as, e.g., interactions related to the formation dimers and other higher order multimers.

Flexible proteinaceous linkers are often greater than 12 amino acid residues long and rich in small, non-polar amino acid residues, polar amino acid residues, and/or hydrophilic amino acid residues, such as, e.g., glycines, serines, and threonines. Flexible proteinaceous linkers may be chosen to increase the spatial separation between components and/or to allow for intramolecular interactions between components. For example, various "GS" linkers are known to the skilled worker and are composed of multiple glycines and/or one or more serines, sometimes in repeating units, such as, e.g., $(G_xS)_n$, $(S_xG)_n$, $(GGGGS)_n$, and $(G)_n$, in which x is 1 to 6 and n is 1 to 30 (SEQ ID NOs. 262-264, 266). Non-limiting examples of flexible proteinaceous linkers include GKSSGSGSESKS (SEQ ID NO: 188), EGKSSGSGSESKEF (SEQ ID NO: 189), GSTSGSGKSSEGKG (SEQ ID NO: 190), GSTSGSGKSSEGSGSTKG (SEQ ID NO: 191), GSTSGSGKPGSGEGSTKG (SEQ ID NO: 192), SRSSG (SEQ ID NO: 193), and SGSSC (SEQ ID NO: 194).

Rigid proteinaceous linkers are often stiff alpha-helical structures and rich in proline residues and/or one or more strategically placed prolines. Rigid linkers may be chosen to prevent intramolecular interactions between linked components.

Suitable linkers may be chosen to allow for in vivo separation of components, such as, e.g., due to cleavage and/or environment-specific instability. In vivo cleavable proteinaceous linkers are capable of unlinking by proteolytic processing and/or reducing environments often at a specific site within an organism or inside a certain cell type. In vivo cleavable proteinaceous linkers often comprise protease sensitive motifs and/or disulfide bonds formed by one or more cysteine pairs. In vivo cleavable proteinaceous linkers may be designed to be sensitive to proteases that exist only at certain locations in an organism, compartments within a cell, and/or become active only under certain physiological or pathological conditions (such as, e.g., involving proteases with abnormally high levels, proteases overexpressed at certain disease sites, and proteases specifically expressed by a pathogenic microorganism). For example, there are proteinaceous linkers known in the art which are cleaved by proteases present only intracellularly, proteases present only within specific cell types, and proteases present only under pathological conditions like cancer or inflammation, such as, e.g., R-x-x-R motif and AMGRSGGGCAGNRVGSSLSCGGLNLQAM (SEQ ID NO: 195).

In some embodiments of the binding molecules, a linker may be used which comprises one or more protease sensitive sites to provide for cleavage by a protease present within a target cell. In some embodiments, a linker may be used which is not cleavable to reduce unwanted toxicity after administration to a vertebrate organism.

Suitable linkers may include, e.g., protease sensitive, environmental redox potential sensitive, pH sensitive, acid cleavable, photocleavable, and/or heat sensitive linkers, whether proteinaceous or non-proteinaceous (see e.g., Doronina S et al., *Bioconjug Chem* 17: 114-24 (2003); Saito G et al., *Adv Drug Deliv Rev* 55: 199-215 (2003); Jeffrey S et al., *J Med Chem* 48: 1344-58 (2005); Sanderson R et al., *Clin Cancer Res* 11: 843-52 (2005); Erickson H et al., *Cancer Res* 66: 4426-33 (2006); Chen X et al., *Adv Drug Deliv Rev* 65: 1357-69 (2013)). Suitable cleavable linkers may include linkers comprising cleavable groups which are known in the art.

Suitable linkers may include pH sensitive linkers. For example, certain suitable linkers may be chosen for their instability in lower pH environments to provide for dissociation inside a subcellular compartment of a target cell (see e.g., van Der Velden V et al., *Blood* 97: 3197-204 (2001); Ulbrich K, Subr V, *Adv Drug Deliv Rev* 56: 1023-50 (2004)). For example, linkers that comprise one or more trityl groups, derivatized trityl groups, bismaleimideothoxy propane groups, adipic acid dihydrazide groups, and/or acid labile transferrin groups, may provide for release of components of the binding molecules, e.g. a polypeptide component, in environments with specific pH ranges. In certain linkers may be chosen which are cleaved in pH ranges corresponding to physiological pH differences between tissues, such as, e.g., the pH of tumor tissue is lower than in healthy tissues.

Photocleavable linkers are linkers that are cleaved upon exposure to electromagnetic radiation of certain wavelength ranges, such as light in the visible range. Photocleavable linkers may be used to release a component of a binding molecule, e.g. a polypeptide component, upon exposure to light of certain wavelengths. Non-limiting examples of photocleavable linkers include a nitrobenzyl group as a photocleavable protective group for cysteine, nitrobenzyloxycarbonyl chloride cross-linkers, hydroxypropylmethacrylamide copolymer, glycine copolymer, fluorescein copolymer, and methylrhodamine copolymer. Photocleavable linkers may have particular uses in linking components to form binding molecules designed for treating diseases, disorders, and conditions that can be exposed to light using fiber optics.

In some embodiments of the binding molecules, a PD-L1 binding region is linked to a Shiga toxin effector polypeptide using any number of means known to the skilled worker, including both covalent and noncovalent linkages.

In some embodiments of the binding molecules, the molecule comprises a binding region which is a scFv with a linker (i.e., a scFv linker) connecting a heavy chain variable ($V_H$) domain and a light chain variable ($V_L$) domain. There are numerous linkers known in the art suitable for this purpose, such as, e.g., the 15-residue $(Gly_4Ser)_3$ (SEQ ID NO: 269) peptide. Suitable scFv linkers which may be used in forming non-covalent multivalent structures include GGS, GGGS (SEQ ID NO: 196), GGGGS (SEQ ID NO: 72), GGGGSGGG (SEQ ID NO: 197), GGSGGGG (SEQ ID NO: 198), GSTSGGGSGGGSGGGGSS (SEQ ID NO: 199), and GSTSGSGKPGSSEGSTKG (SEQ ID NO: 200).

Suitable methods for linkage of the components of the binding molecules may be by any method presently known in the art for accomplishing such, so long as the attachment does not substantially impede the binding capability of the cell-targeting binding region, the cellular internalization of the Shiga toxin effector polypeptide component, and/or when appropriate the desired Shiga toxin effector function(s) as measured by an appropriate assay, including assays described herein.

The components of the binding molecule, e.g. a Shiga toxin A Subunit effector polypeptide and/or immunoglobulin-type PD-L1-binding region, may be linked via a binding region linker. In some embodiments, the components may be engineered to provide a suitable attachment moiety for the linkage of additional components, e.g. an additional exogenous material (see WO 2018/106895).

Figure 1:
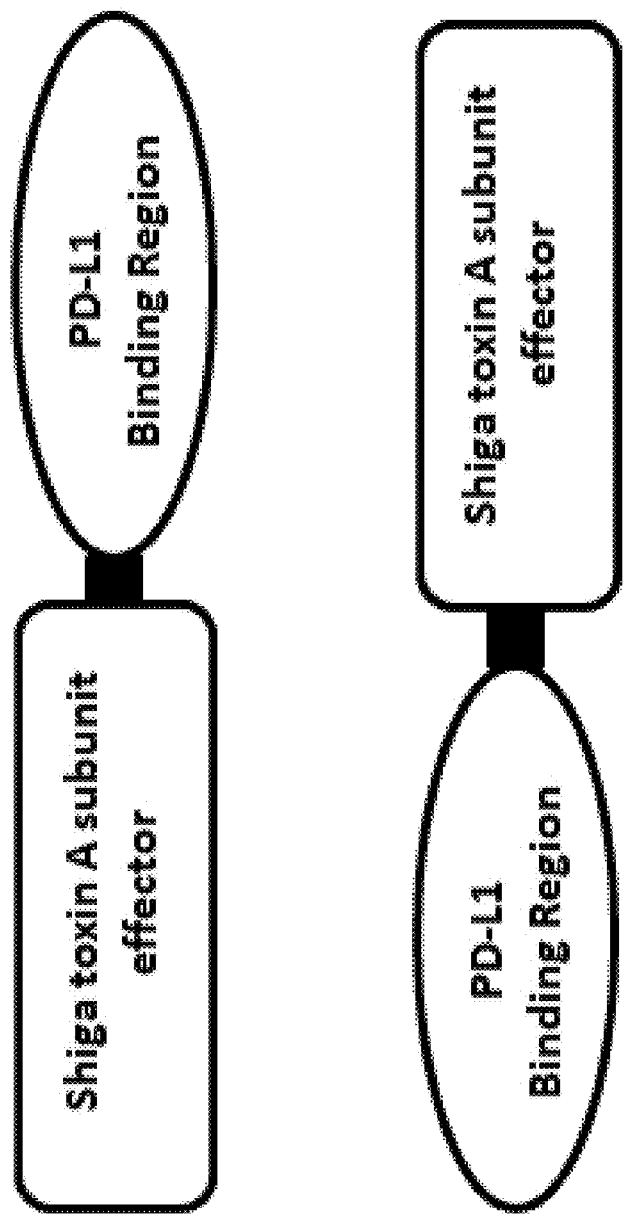
Figure 1:
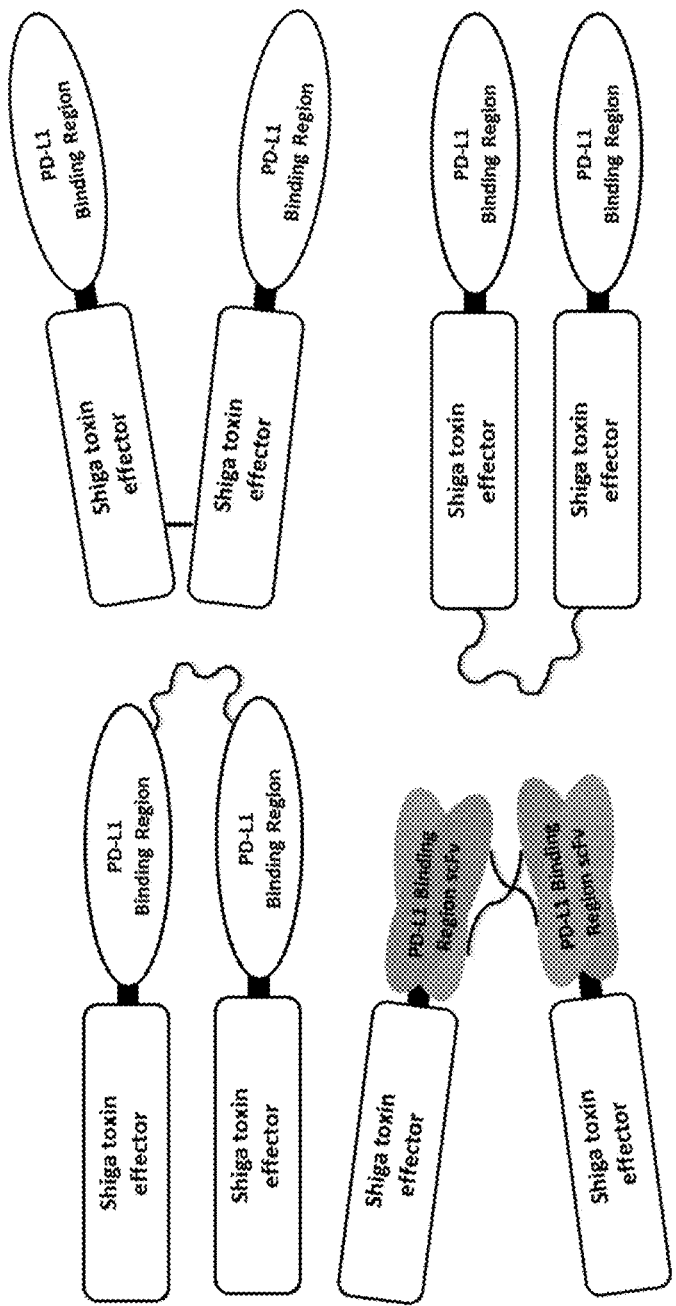
Figure 1:
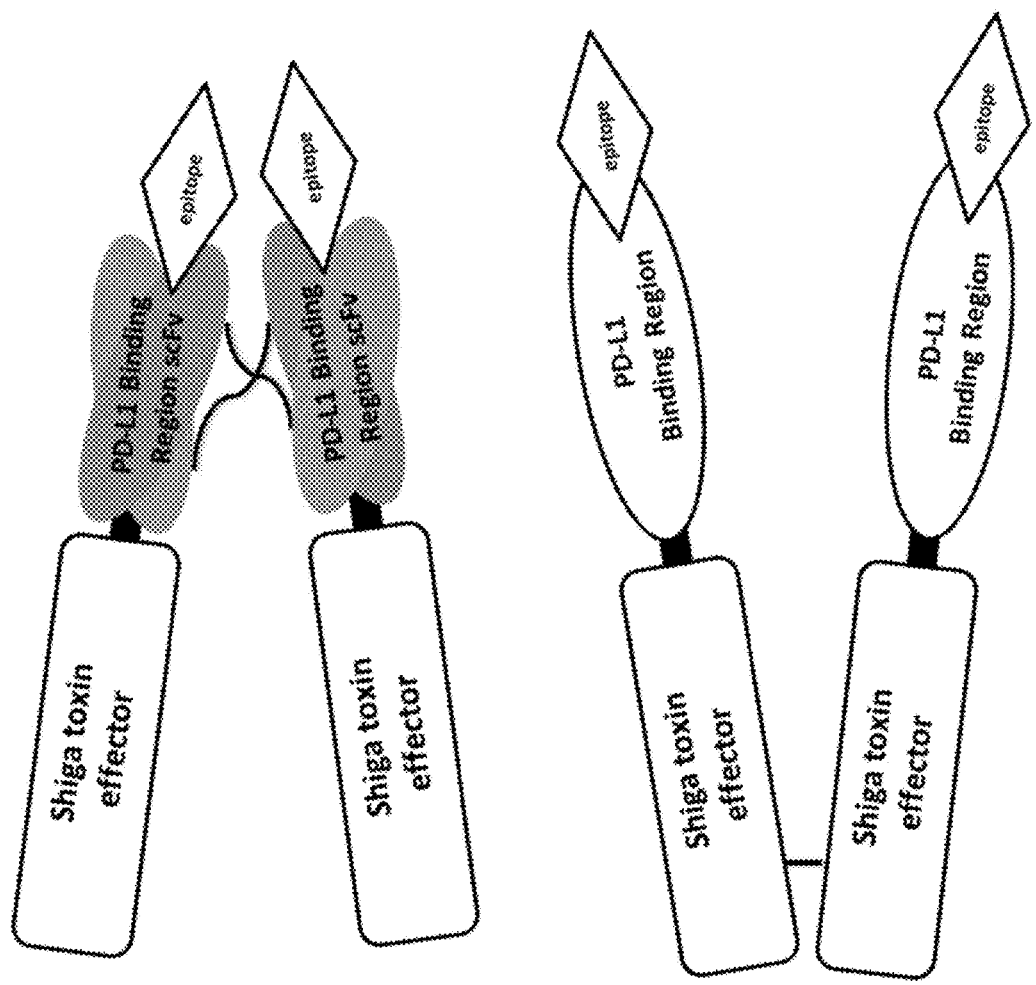

For the purposes of the binding molecules, the specific order or orientation is not fixed for the components: the Shiga toxin effector polypeptide(s), the binding region(s), and any optional linker(s), in relation to each other or the entire binding molecule (see e.g. FIG. 1) unless specifically noted. The components of the binding molecules may be arranged in any order provided that the desired activity(ies) of the binding region and Shiga toxin effector polypeptide are not eliminated.

III. Examples of Structural Variations of the Binding Molecules

In some embodiments, a Shiga toxin effector polypeptide of the binding molecule comprises or consists essentially of a truncated Shiga toxin A Subunit. Truncations of Shiga toxin A Subunits might result in the deletion of an entire epitope(s) and/or epitope region(s), B-cell epitopes, CD4+ T-cell epitopes, and/or furin-cleavage sites without affecting Shiga toxin effector functions, such as, e.g., catalytic activity and cytotoxicity. The smallest Shiga toxin A Subunit fragment shown to exhibit full enzymatic activity was a polypeptide composed of residues 1-239 of Slt1A (LaPointe P et al., *J Biol Chem* 280: 23310-18 (2005)). The smallest Shiga toxin A Subunit fragment shown to exhibit significant enzymatic activity was a polypeptide composed of residues 75-247 of StxA (Al-Jaufy A et al., *Infect Immun* 62: 956-60 (1994)).

Although Shiga toxin effector polypeptides may commonly be smaller than the full-length Shiga toxin A Subunit, it is preferred that the Shiga toxin effector polypeptide region of a binding molecule maintain the polypeptide region from amino acid position 77 to 239 (SLT-1A (SEQ ID NO:1) or StxA (SEQ ID NO:2)) or the equivalent in other A Subunits of members of the Shiga toxin family (e.g. 77 to 238 of (SEQ ID NO:3)). For example, in some embodiments, the Shiga toxin effector polypeptide derived from SLT-1A may comprise or consist essentially of amino acids 75 to 251 of SEQ ID NO:1, 1 to 241 of SEQ ID NO:1, 1 to 251 of SEQ ID NO:1, or amino acids 1 to 261 of SEQ ID NO:1, wherein relative to a wild-type Shiga toxin A Subunit at least one amino acid residue is mutated or has been deleted in an endogenous epitope and/or epitope region, and/or wherein there is a disrupted, furin-cleavage motif region at the carboxy-terminus of a Shiga toxin A1 fragment derived region. Similarly, Shiga toxin effector polypeptide regions derived from StxA may comprise or consist essentially of amino acids 75 to 251 of SEQ ID NO:2, 1 to 241 of SEQ ID NO:2, 1 to 251 of SEQ ID NO:2, or amino acids 1 to 261 of SEQ ID NO:2, wherein relative to a wild-type Shiga toxin A Subunit at least one amino acid residue is mutated or has been deleted in an endogenous epitope and/or epitope region, and/or wherein there is a disrupted, furin-cleavage motif region at the carboxy-terminus of a Shiga toxin A1 fragment derived region. Additionally, Shiga toxin effector polypeptide regions derived from SLT-2 may comprise or consist essentially of amino acids 75 to 251 of SEQ ID NO:3, 1 to 241 of SEQ ID NO:3, 1 to 251 of SEQ ID NO:3, or amino acids 1 to 261 of SEQ ID NO:3, wherein relative to a wild-type Shiga toxin A Subunit at least one amino acid residue is mutated or has been deleted in an endogenous epitope and/or epitope region, and/or wherein there is a disrupted, furin-cleavage motif region at the carboxy-terminus of a Shiga toxin A1 fragment derived region.

Also provided herein are variants of Shiga toxin effector polypeptides and binding molecules, wherein the Shiga toxin effector polypeptide differs from a naturally occurring Shiga toxin A Subunit by only or up to 1, 2, 3, 4, 5, 6, 7, 8, 9, 10, 15, 20, 25, 30, 35, 40 or more amino acid residues (but by no more than that which retains at least 85%, 90%, 95%, 99% or more amino acid sequence identity). Thus, a molecule derived from an A Subunit of a member of the Shiga toxin family may comprise additions, deletions, truncations, or other alterations from the original sequence as long as at least 85%, 90%, 95%, 99% or more amino acid sequence identity is maintained to a naturally occurring Shiga toxin A Subunit and wherein relative to a wild-type Shiga toxin A Subunit at least one amino acid residue is mutated or has been deleted in an endogenous epitope and/or epitope region, and/or wherein there is a disrupted, furin-cleavage motif region at the carboxy-terminus of a Shiga toxin A1 fragment derived region.

Accordingly, in some embodiments, the Shiga toxin effector polypeptide of a molecule described herein comprises or consists essentially of amino acid sequences having at least 55%, 60%, 65%, 70%, 75%, 80%, 85%, 90%, 95%, 97%, 98%, 99%, 99.5% or 99.7% overall sequence identity to a naturally occurring Shiga toxin A Subunit, such as SLT-1A (SEQ ID NO:1), StxA (SEQ ID NO:2), and/or SLT-2A (SEQ ID NO:3) wherein relative to a wild-type Shiga toxin A Subunit at least one amino acid residue is mutated or has been deleted in an endogenous epitope and/or epitope region, and/or wherein there is a disrupted, furin-cleavage motif region at the carboxy-terminus of a Shiga toxin A1 fragment derived region.

Optionally, either a full-length or a truncated version of the Shiga toxin A Subunit may comprise the Shiga toxin effector polypeptide region of a molecule of the present, wherein the Shiga toxin derived polypeptide comprises one or more mutations (e.g. substitutions, deletions, insertions, or inversions) as compared to a naturally occurring Shiga toxin. It is preferred in some embodiments that the Shiga toxin effector polypeptides have sufficient sequence identity to a naturally occurring Shiga toxin A Subunit to retain cytotoxicity after entry into a cell, either by well-known methods of host cell transformation, transfection, infection or induction, or by internalization mediated by a cell-targeting binding region linked with the Shiga toxin effector polypeptide. The most critical residues for enzymatic activity and/or cytotoxicity in the Shiga toxin A Subunits have been mapped to the following residue-positions: asparagine-75, tyrosine-77, glutamate-167, arginine-170, and arginine-176 among others (Di R et al., *Toxicon* 57: 525-39 (2011)). In any one of the embodiments described herein, the Shiga toxin effector polypeptides may preferably but not necessarily maintain one or more conserved amino acids at positions, such as those found at positions 77, 167, 170, and 176 in StxA, SLT-1A, or the equivalent conserved position in other members of the Shiga toxin family which are typically required for cytotoxic activity. The capacity of a cytotoxic molecule to cause cell death, e.g. its cytotoxicity, may be measured using any one or more of a number of assays well known in the art.

A. Examples of De-Immunized, Shiga Toxin Effector Polypeptides

In some embodiments, the de-immunized, Shiga toxin effector polypeptide of the binding molecule may consist essentially of a truncated Shiga toxin A Subunit having two or more mutations. Truncations of Shiga toxin A Subunits might result in the deletion of an entire epitope(s) and/or epitope region(s), B-cell epitopes, CD4+ T-cell epitopes, and/or furin-cleavage sites without affecting Shiga toxin effector functions, such as, e.g., catalytic activity and cytotoxicity. Truncating the carboxy-terminus of SLT-1A, StxA, or SLT-2A to amino acids 1-251 removes two predicted B-cell epitope regions, two predicted CD4 positive (CD4+) T-cell epitopes, and a predicted discontinuous B-cell epitope. Truncating the amino-terminus of SLT-1A, StxA, or SLT-2A to 75-293 removes at least three predicted B-cell epitope regions and three predicted CD4+ T-cell epitopes. Truncating both amino- and carboxy-terminals of SLT-1A, StxA, or SLT-2A to 75-251 deletes at least five predicted B-cell epitope regions, four putative CD4+ T-cell epitopes and one predicted discontinuous B-cell epitope.

In some embodiments, a de-immunized, Shiga toxin effector polypeptide may comprise or consist essentially of a full-length or truncated Shiga toxin A Subunit with at least one mutation (relative to a wild-type Shiga toxin polypeptide), e.g. deletion, insertion, inversion, or substitution, in a provided, endogenous, B-cell and/or CD4+ T-cell epitope region. In some embodiments, the Shiga toxin effector polypeptide comprises a disruption which comprises a mutation (relative to a wild-type Shiga toxin polypeptide) which includes a deletion of at least one amino acid residue within the endogenous, B-cell and/or CD4+ T-cell epitope region. In some embodiments, the Shiga toxin effector polypeptide comprises a disruption which comprises an insertion of at least one amino acid residue within the endogenous, B-cell and/or CD4+ T-cell epitope region. In some embodiments, the Shiga toxin effector polypeptide comprises a disruption which comprises an inversion of amino acid residues, wherein at least one inverted amino acid residue is within the endogenous, B-cell and/or CD4+ T-cell epitope region. In some embodiments, the Shiga toxin effector polypeptide comprises a disruption which comprises a mutation (relative to a wild-type Shiga toxin polypeptide), such as, e.g., an amino acid substitution, an amino acid substitution to a non-standard amino acid, and/or an amino acid residue with a chemically modified side chain. Non-limiting examples of de-immunized, Shiga toxin effector sub-regions suitable for use as described herein are described in WO 2015/113005, WO 2015/113007, WO 2015/191764, WO 2016/196344, and WO 2018/140427.

In other embodiments, the de-immunized, Shiga toxin effector polypeptide comprises a truncated Shiga toxin A Subunit which is shorter than a full-length Shiga toxin A Subunit wherein at least one amino acid residue is disrupted in a natively positioned, B-cell and/or CD4+ T-cell epitope region.

To create a de-immunized, Shiga toxin effector polypeptide, in principle modifying any amino acid residue in a provided epitope region by various means can result in a disruption of an epitope, such as, e.g., a modification which represents a deletion, insertion, inversion, rearrangement, substitution, and chemical modification of a side chain relative to a wild-type Shiga toxin polypeptide. However, modifying certain amino acid residues and using certain amino acid modifications are more likely to successfully reduce antigenicity and/or immunogenicity while maintaining a certain level of a Shiga toxin effector function(s). For example, terminal truncations and internal amino acid substitutions are preferred because these types of modifications maintain the overall spacing of the amino acid residues in a Shiga toxin effector polypeptide and thus are more likely to maintain Shiga toxin effector polypeptide structure and function.

In some embodiments, the de-immunized, Shiga toxin effector polypeptide comprising or consisting essentially of amino acids 75 to 251 of SLT-1A (SEQ ID NO:1), StxA (SEQ ID NO:2), and/or SLT-2A (SEQ ID NO:3) wherein at least one amino acid residue is disrupted in a natively positioned, epitope region. Among certain other embodiments are de-immunized, Shiga toxin effector polypeptides which comprise or consist essentially of amino acids 1 to 241 of SLT-1A (SEQ ID NO:1), StxA (SEQ ID NO:2), and/or SLT-2A (SEQ ID NO:3) wherein at least one amino acid residue is disrupted in a natively positioned, epitope region. Further embodiments are de-immunized, Shiga toxin effector polypeptides which comprise or consist essentially of amino acids 1 to 251 of SLT-1A (SEQ ID NO:1), StxA (SEQ ID NO:2), and/or SLT-2A (SEQ ID NO:3) wherein at least one amino acid residue is disrupted in a natively positioned, epitope region provided. Further embodiments are Shiga toxin effector polypeptides comprising amino acids 1 to 261 of SLT-1A (SEQ ID NO:1), StxA (SEQ ID NO:2), and/or SLT-2A (SEQ ID NO:3) wherein at least one amino acid residue is disrupted in a natively positioned, epitope region.

There are numerous, diverse, internal amino acid substitutions that can be used to create de-immunized, Shiga toxin effector polypeptides. Of the possible substitute amino acids to use within an epitope region, the following substitute amino acid residues are predicted to be the most likely to reduce the antigenicity and/or immunogenicity of an epitope—G, D, E, S, T, R, K, and H. Except for glycine, these amino acid residues may all be classified as polar and/or charged residues. Of the possible amino acids to substitute with, the following amino acids A, G, V, L, I, P, C, M, F, S, D, N, Q, H, and K are predicted to be the most likely to reduce antigenicity and/or immunogenicity while providing the retention of a significant level of a Shiga toxin effector function(s), depending on the amino acid substituted for. Generally, the substitution should change a polar and/or charged amino acid residue to a non-polar and uncharged residue (see e.g. WO 2015/113007). In addition, it may be beneficial to epitope disruption to reduce the overall size and/or length of the amino acid residue's R-group functional side chain (see e.g. WO 2015/113007). However despite these generalities of substitutions most likely to confer epitope disruption, because the aim is to preserve significant Shiga toxin effector function(s), the substitute amino acid might be more likely to preserve Shiga toxin effector function(s) if it resembles the amino acid substituted for, such as, e.g., a nonpolar and/or uncharged residue of similar size substituted for a polar and/or charged residue.

WO 2015/113007 and WO 2016/196344 reported the results from the empirically testing of many different mutations and combinations of mutations for effect(s) on the Shiga toxin effector functions of various Shiga toxin effector polypeptides and binding molecules. Table 3 summarizes the results described in WO 2015/113007 and WO 2016/196344 where an amino acid substitution, alone or in combination with one or more other substitutions, did not prevent the exhibition of a potent level of a Shiga toxin effector function(s). Table 3 uses the epitope region numbering scheme described in WO 2016/196344.

TABLE 3

Amino Acid Substitutions in Shiga Toxin Effector Polypeptides

| Epitope Region Disrupted | Substitution | natively positioned amino acid positions B-Cell Epitope Region | T-Cell Epitope |
|---|---|---|---|
| 1 | K1A | 1-15 | |
| 1 | K1M | 1-15 | |
| 1 | T4I | 1-15 | 4-33 |
| 1 | D6R | 1-15 | 4-33 |
| 1 | S8I | 1-15 | 4-33 |
| 1 | T9V | 1-15 | 4-33 |
| 1 | T9I | 1-15 | 4-33 |
| 1 | K11A | 1-15 | 4-33 |
| 1 | K11H | 1-15 | 4-33 |
| 1 | T12K | 1-15 | 4-33 |
| 2 | S33I | 27-37 | 4-33 |
| 2 | S33C | 27-37 | 4-33 |
| 3 | S43N | 39-48 | 34-78 |
| 3 | G44L | 39-48 | 34-78 |
| 3 | T45V | 39-48 | 34-78 |
| 3 | T45I | 39-48 | 34-78 |
| 3 | S45V | 39-48 | 34-78 |
| 3 | S45I | 39-48 | 34-78 |
| 3 | G46P | 39-48 | 34-78 |
| 3 | D47G | 39-48 | 34-78 |
| 3 | D47M | 39-48 | 34-78 |

TABLE 3-continued

Amino Acid Substitutions in Shiga Toxin Effector Polypeptides

| Epitope Region Disrupted | Substitution | B-Cell Epitope Region | T-Cell Epitope |
|---|---|---|---|
| 3 | N48V | 39-48 | 34-78 |
| 3 | N48F | 39-48 | 34-78 |
| — | L49A | immunogenic residue | 34-78 |
| — | F50T | | 34-78 |
| — | A51V | | 34-78 |
| 4 | D53A | 53-66 | 34-78 |
| 4 | D53G | 53-66 | 34-78 |
| 4 | D53N | 53-66 | 34-78 |
| 4 | V54L | 53-66 | 34-78 |
| 4 | V54I | 53-66 | 34-78 |
| 4 | R55A | 53-66 | 34-78 |
| 4 | R55V | 53-66 | 34-78 |
| 4 | R55L | 53-66 | 34-78 |
| 4 | G56P | 53-66 | 34-78 |
| 4 | I57M | 53-66 | 34-78 |
| 4 | I57F | 53-66 | 34-78 |
| 4 | D58A | 53-66 | 34-78 |
| 4 | D58V | 53-66 | 34-78 |
| 4 | D58F | 53-66 | 34-78 |
| 4 | P59A | 53-66 | 34-78 |
| 4 | P59F | 53-66 | 34-78 |
| 4 | E60I | 53-66 | 34-78 |
| 4 | E60T | 53-66 | 34-78 |
| 4 | E60R | 53-66 | 34-78 |
| 4 | E61A | 53-66 | 34-78 |
| 4 | E61V | 53-66 | 34-78 |
| 4 | E61L | 53-66 | 34-78 |
| 4 | G62A | 53-66 | 34-78 |
| — | R84A | | 77-103 |
| — | V88A | | 77-103 |
| 5 | D94A | 94-115 | 77-103 |
| 5 | S96I | 94-115 | 77-103 |
| 5 | T104N | 94-115 | |
| 5 | A105L | 94-115 | |
| 5 | T107P | 94-115 | |
| 5 | L108M | 94-115 | |
| 5 | S109V | 94-115 | |
| 5 | G110A | 94-115 | |
| 5 | D111T | 94-115 | |
| 5 | S112V | 94-115 | |
| 6 | D141A | 141-153 | 128-168 |
| 6 | G147A | 141-153 | 128-168 |
| — | V154A | | 128-168 |
| 7 | R179A | 179-190 | 160-183 |
| 7 | T180G | 179-190 | 160-183 |
| 7 | T181I | 179-190 | 160-183 |
| 7 | D183A | 179-190 | 160-183 |
| 7 | D183G | 179-190 | 160-183 |
| 7 | D184A | 179-190 | |
| 7 | D184F | 179-190 | |
| 7 | L185V | 179-190 | |
| 7 | S186A | 179-190 | |
| 7 | S186F | 179-190 | |
| 7 | G187A | 179-190 | |
| 7 | G187T | 179-190 | |
| 7 | R188A | 179-190 | |
| 7 | R188L | 179-190 | |
| 7 | S189A | 179-190 | |
| — | D198A | immunogenic residue | |
| — | R205A | immunogenic residue | |
| — | C242S | | 236-258 |
| 8 | R248A | 243-257 | 236-258 |
| 8 | R251A | 243-257 | 236-258 |

Based on the empirical evidence in WO 2015/113007 and WO 2016/196344, certain amino acid positions in the A Subunits of Shiga toxins are predicted to tolerate epitope disruptions while still retaining significant Shiga toxin effector functions. For example, the following natively occurring positions tolerate amino acid substitutions, either alone or in combination, while retaining a Shiga toxin effector function(s) such as cytotoxicity—1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1 or SEQ ID NO:2; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

The empirical data in WO 2015/113007 and WO 2016/196344 point towards other epitope disrupting substitutions and combinations of epitope disrupting substitutions that can reduce antigenicity and/or immunogenicity of a Shiga toxin effector polypeptide while retaining the ability of the Shiga toxin effector polypeptide to exhibit a significant Shiga toxin effector function such as, e.g., new combinations of the aforementioned truncations and positions tolerating substitutions as well as new substitutions at identical positions or conserved positions in related Shiga toxin A Subunits.

It is predictable that other amino acid substitutions to amino acid residues of a conservative functional group of a substitution tested herein may reduce antigenicity and/or immunogenicity while preserving a significant Shiga toxin effector function. For example, other substitutions known to the skilled worker to be similar to any of K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R248A, R250A, R251A, or D264A, G264A, T286A, and/or T286I may disrupt an endogenous epitope while maintaining at least one Shiga toxin effector function. In particular, amino acid substitutions to conservative amino acid residues similar to K1A, T4I, S8I, T8V, T9I, S9I, K11A, K11H, S33I, S33C, S43N, G44L, S45V, S45I, T45V, T45I, G46P, D47M, N48V, N48F, L49A, A51V, D53A, D53N, V54L, V54I, R55A, R55V, R55L, G56P, I57F, I57M, D58A, D58V, D58F, P59A, E60I, E60T, E61A, E61V, E61L, G62A, R84A, V88A, D94A, S96I, T104N, T107P, L108M, S109V, T109V, G110A, D111T, S112V, D141A, G147A, V154A, R179A, T180G, T181I, D183A, D183G, D184A, D184F, L185V, S186A, S186F, G187A, R188A, R188L, S189A, D198A, R204A, R205A, C242S, S247I, Y247A, R248A, R250A, R251A, D264A, G264A, T286A, and T286I may have the same or similar effects. In some embodiments, a Shiga toxin effector polypeptide may comprise similar conservative amino acid substitutions to empirically tested ones, such as, e.g., K1 to G, V, L, I, F, and H; T4 to A, G, V, L, F, M, and S; S8 to A, G, V, L, F, and M; T9 to A, G, L, F, M, and S; S9 to A, G, L, I, F, and M; K11 to G, V, L, I, F, and M; S33 to A, G, V, L, F, and M; S43 to A, G, V, L, I, F, and M; S45 to A, G, L, F, and M; T45 to A, G, L, F, and M; D47 to A, V, L, I, F, S, and Q; N48 to A, G, L, and M; L49 to G; Y49 to A; D53 to V, L, I, F, S, and Q; R55 to G, I, F, M, Q, S, K, and H; D58 to G, L, I, S, and Q; P59 to G; E60 to A, G, V, L, F, S, Q, N, D, and M; E61 to G, I, F, S, Q, N, D, M, and R; R84 to G, V, L, I, F, M, Q, S, K, and H; V88 to G; 188 to G; D94 to G, V, L, I, F, S, and Q; S96 to A, G, V, L, F, and M; T107 to A, G, V, L, I, F, M, and S; S107 to A, G, V, L, I, F, and M; S109 to A, G, I, L, F, and M; T109 to A, G, I, L, F, M, and S; S112 to A, G, L, I, F, and M; D141 to V, L, I, F, S, and Q; V154 to G; R179 to G, V, L, I, F, M, Q, S, K, and H; T180 to A, V, L, I, F, M, and S; T181 to A, G, V, L, F, M, and S; D183 to V, L, I, F, S, and Q; D184 to G, V, L, I, S, and Q; S186 to G, V, I, L, and M; R188 to G, V, I, F, M, Q, S, K, and H; S189 to G, V, I, L, F, and M; D197 to V, L, I, F, S, and Q; D198 to A, V, L, I, F, S, and Q; R204 to G, V, L, I, F, M, Q, S, K, and H; R205 to G, V, L, I, F, M, Q, S, K and H; 5247 to A, G, V, I, L, F, and M; Y247 to A, G, V, L, I, F, and M; R248 to G, V, L, I, F, M, Q, S, K, and H; R250 to G, V, L, I, F, M, Q, S, K, and H; R251 to G, V, L, I, F, M, Q, S, K, and H; D264 to A, G, V, L, I, F, S, and Q; and T286 to A, G, V, L, I, F, M, and S.

Similarly, amino acid substitutions which remove charge, polarity, and/or reduce side chain length can disrupt an epitope while maintaining at least one Shiga toxin effector function. In some embodiments, a Shiga toxin effector polypeptide may comprise one or more epitopes disrupted by substitutions such that side chain charge is removed, polarity is removed, and/or side chain length is reduced such as, e.g., substituting the appropriate amino acid selected from the following group A, G, V, L, I, P, C, M, F, S, D, N, Q, H, or K for the amino acid residue at position 1 of SEQ ID NO:1 or SEQ ID NO:2; 4 of SEQ ID NO:1, SEQ ID NO:2, or SEQ ID NO:3; 6 of SEQ ID NO:1 or SEQ ID NO:2; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 12 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1, SEQ ID NO:2, or SEQ ID NO:3; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1, SEQ ID NO:2, or SEQ ID NO:3; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1, SEQ ID NO:2, or SEQ ID NO:3; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 197 of SEQ ID NO:3; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2. In some embodiments, a Shiga toxin effector polypeptide may comprise one or more of the following amino acid substitutions: K1 to A, G, V, L, I, F, M and H; T4 to A, G, V, L, I, F, M, and S; D6 to A, G, V, L, I, F, S, and Q; S8 to A, G, V, I, L, F, and M; T8 to A, G, V, I, L, F, M, and S; T9 to A, G, V, I, L, F, M, and S; S9 to A, G, V, L, I, F, and M; K11 to A, G, V, L, I, F, M and H; T12 to A, G, V, I, L, F, M, and S; S33 to A, G, V, L, I, F, and M; S43 to A, G, V, L, I, F, and M; G44 to A and L; S45 to A, G, V, L, I, F, and M; T45 to A, G, V, L, I, F, and M; G46 to A and P; D47 to A, G, V, L, I, F, S, and Q; N48 to A, G, V, L, and M; L49 to A or G; F50; A51 to V; D53 to A, G, V, L, I, F, S, and Q; V54 to A, G, and L; R55 to A, G, V, L, I, F, M, Q, S, K, and H; G56 to A and P; 157 to A, G, M, and F; L57 to A, G, M, and F; D58 to A, G, V, L, I, F, S, and Q; P59 to A, G, and F; E60 to A, G, V, L, I, F, S, Q, N, D, M, and R; E61 to A, G, V, L, I, F, S, Q, N, D, M, and R; G62 to A; D94 to A, G, V, L, I, F, S, and Q; R84 to A, G, V, L, I, F, M, Q, S, K, and H; V88 to A and G; 188 to A, G, and V; D94; S96 to A, G, V, I, L, F, and M; T104 to A, G, V, I, L, F, M, and S; A105 to L; T107 to A, G, V, I, L, F, M, and S; S107 to A, G, V, L, I, F, and M; L108 to A, G, and M; S109 to A, G, V, I, L, F, and M; T109 to A, G, V, I, L, F, M, and S; G110 to A; D111 to A, G, V, L, I, F, S, and Q; S112 to A, G, V, L, I, F, and M; D141 to A, G, V, L, I, F, S, and Q; G147 to A;

V154 to A and G; R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; L185 to A, G, and V; S186 to A, G, V, I, L, F, and M; G187 to A; R188 to A, G, V, L, I, F, M, Q, S, K, and H; S189 to A, G, V, I, L, F, and M; D197 to A, G, V, L, I, F, S, and Q; D198 to A, G, V, L, I, F, S, and Q; R204 to A, G, V, L, I, F, M, Q, S, K, and H; R205 to A, G, V, L, I, F, M, Q, S, K and H; C242 to A, G, V, and S; S247 to A, G, V, I, L, F, and M; Y247 to A, G, V, L, I, F, and M; R248 to A, G, V, L, I, F, M, Q, S, K, and H; R250 to A, G, V, L, I, F, M, Q, S, K, and H; R251 to A, G, V, L, I, F, M, Q, S, K, and H; C262 to A, G, V, and S; D264 to A, G, V, L, I, F, S, and Q; G264 to A; and T286 to A, G, V, L, I, F, M, and S.

In addition, any amino acid substitution in one epitope region of a Shiga toxin effector polypeptide which disrupts an epitope while retaining significant Shiga toxin effector function is combinable with any other amino acid substitution in the same or a different epitope region which disrupts an epitope while retaining significant Shiga toxin effector function to form a de-immunized, Shiga toxin effector polypeptide with multiple epitope regions disrupted while still retaining a significant level of Shiga toxin effector function. In some embodiments, a Shiga toxin effector polypeptide may comprise a combination of two or more of the aforementioned substitutions and/or the combinations of substitutions described in WO 2015/113007, WO 2016/196344, and/or WO 2018/140427.

Based on work described in WO 2015/113007, WO 2016/196344, and WO 2018/140427, certain amino acid regions in the A Subunits of Shiga toxins are predicted to tolerate epitope disruptions while still retaining significant Shiga toxin effector functions. For example, the epitope regions natively positioned at 1-15, 39-48, 53-66, 55-66, 94-115, 180-190, 179-190, and 243-257 tolerated multiple amino acid substitution combinations simultaneously without compromising Shiga toxin enzymatic activity and cytotoxicity.

B. Examples of Furin-Cleavage Resistant, Shiga Toxin Effector Polypeptides

In some embodiments, the Shiga toxin effector polypeptide may comprise a disrupted, furin cleavage motif and/or furin cleavage site at the carboxy-terminus of a Shiga toxin A1 fragment derived region. In some embodiments, the Shiga toxin effector polypeptide does not comprise any known compensatory structure which may provide furin cleavage proximal to the carboxy-terminus of the Shiga toxin A1 fragment derived region. Non-limiting examples of disrupted furin cleavage motifs and furin cleave sites are described in WO 2015/191764.

Certain furin-cleavage motif disruptions are indicated herein by reference to specific amino acid positions of native Shiga toxin A Subunits provided in the Sequence Listing, noting that naturally occurring Shiga toxin A Subunits includes precursor forms containing signal sequences of about 22 amino acids at their amino-terminals which are removed to produce mature Shiga toxin A Subunits and are recognizable to the skilled worker. Further, certain furin-cleavage motif disruptions comprising mutations are indicated herein by reference to specific amino acids (e.g. R for an arginine residue) natively present at specific positions within native Shiga toxin A Subunits (e.g. R251 for the arginine residue at position 251 from the amino-terminus) followed by the amino acid with which that residue has been substituted in the particular mutation under discussion (e.g. R251A represents the amino acid substitution of alanine for arginine at amino acid residue 251 from the amino-terminus).

In some embodiments, the Shiga toxin effector polypeptide comprises a disrupted furin-cleavage motif at the carboxy-terminus of a Shiga toxin A1 fragment derived region, and such embodiments are referred to herein as "furin-cleavage resistant" or "protease-cleavage resistant," Shiga toxin effector polypeptides to describe their property(ies) relative to wild-type, Shiga toxin A Subunits and/or wild-type, Shiga toxin A1 fragment fusion proteins.

In some embodiments, the protease-cleavage resistant, Shiga toxin effector polypeptide consists essentially of a truncated Shiga toxin A Subunit having two or more mutations.

In some embodiments, the protease-cleavage resistant, Shiga toxin effector polypeptide comprises the disrupted furin-cleavage motif comprising the amino acid residue substitution (relative to a wild-type Shiga toxin polypeptide) of one or both of the arginine residues in the minimal, furin-cleavage site consensus motif with A, G, or H. In some embodiments, the protease-cleavage resistant, Shiga toxin effector polypeptide comprises a disruption which comprises an amino acid substitution within a furin-cleavage motif region, where in the substitution occurs at the natively positioned amino acid selected from the group consisting of: 247 of SEQ ID NO:3, 248 of SEQ ID NO:1 or SEQ ID NO:2, 250 of SEQ ID NO:3, 251 of SEQ ID NO:1 or SEQ ID NO:2, or the equivalent position in a conserved Shiga toxin effector polypeptide and/or non-native Shiga toxin effector polypeptide sequence. In some embodiments, the substitution is to any non-conservative amino acid and the substitution occurs at the natively positioned amino acid residue position. In some embodiments, the mutation comprises an amino acid substitution selected from the group consisting of: R247A, R248A, R250A R251A, or the equivalent position in a conserved Shiga toxin effector polypeptide and/or non-native Shiga toxin effector polypeptide sequence.

In some embodiments, the protease-cleavage resistant Shiga toxin effector polypeptide comprises the disrupted furin-cleavage motif comprising the mutation which is a deletion. In some embodiments, the disrupted furin-cleavage motif comprises a mutation which is a deletion of the region natively positioned at 247-252 in StxA (SEQ ID NO:2) and SLT-1A (SEQ ID NO:3), or the region natively positioned at 246-251 in SLT-2A (SEQ ID NO:3); a deletion of the region natively positioned at 244-246 in StxA (SEQ ID NO:2) and SLT-1A (SEQ ID NO:3), or the region natively positioned at 243-245 in SLT-2A (SEQ ID NO:3); or a deletion of the region natively positioned at 253-259 in StxA (SEQ ID NO:2) and SLT-1A (SEQ ID NO:3), or the region natively positioned at 252-258 in SLT-2A (SEQ ID NO:3).

In some embodiments, the protease-cleavage resistant Shiga toxin effector polypeptide comprises the disrupted furin-cleavage motif comprising the mutation which is a carboxy-terminal truncation as compared to a wild-type Shiga toxin A Subunit, the truncation which results in the deletion of one or more amino acid residues within the furin-cleavage motif. In some embodiments, the disrupted furin-cleavage motif comprises the carboxy-terminal truncation which deletes one or more amino acid residues within the minimal cleavage site Y/R-x-x-R, such as, e.g., for StxA and SLT-1A derived Shiga toxin effector polypeptides, truncations ending at the natively amino acid residue position 250, 249, 248, 247, 246, 245, 244, 243, 242, 241, 240, or less; and for SLT-2A derived Shiga toxin effector polypeptides, truncations ending at the natively amino acid residue position 249, 248, 247, 246, 245, 244, 243, 242, 241, or less. Some embodiments comprise the disrupted furin-cleavage motif comprising a combination of any of the aforementioned mutations, where possible.

In some embodiments, the disrupted furin-cleavage motif comprises the mutation(s) that is a partial, carboxy-terminal truncation of the furin-cleavage motif; however, some molecules described herein do not comprise the disrupted furin-cleavage motif which is a complete, carboxy-terminal truncation of the entire 20 amino acid residue, furin-cleavage motif. For example, certain Shiga toxin effector polypeptides comprise the disrupted furin-cleavage motif comprising a partial, carboxy-terminal truncation of the Shiga toxin A1 fragment region up to native position 240 in StxA (SEQ ID NO:2) or SLT-1A (SEQ ID NO:1) but not a carboxy-terminal truncation at position 239 or less. Similarly, certain Shiga toxin effector polypeptides comprise the disrupted furin-cleavage motif comprising a partial, carboxy-terminal truncation of the Shiga toxin A1 fragment region up to native position 239 in SLT-2A (SEQ ID NO:3) but not a carboxy-terminal truncation at position 238 or less. In the largest carboxy-terminal truncation of the furin-cleavage resistant, Shiga toxin effector polypeptide, mutations comprising the disrupted furin-cleavage motif, positions P14 and P13 of the furin-cleavage motif are still present.

In some embodiments, the disrupted furin-cleavage motif comprises both an amino acid residue substitution within the furin-cleavage motif and a carboxy-terminal truncation as compared to a wild-type, Shiga toxin A Subunit. In some embodiments, the disrupted furin-cleavage motif comprises both an amino acid residue substitution within the minimal furin-cleavage site R/Y-x-x-R and a carboxy-terminal truncation as compared to a wild-type, Shiga toxin A Subunit, such as, e.g., for StxA and SLT-1A derived Shiga toxin effector polypeptides, truncations ending at the natively amino acid residue position 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R248 and/or R251 substituted with any non-positively charged, amino acid residue where appropriate; and for SLT-2A derived Shiga toxin effector polypeptides, truncations ending at the natively amino acid residue position 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue Y247 and/or R250 substituted with any non-positively charged, amino acid residue where appropriate. In some embodiments, the truncated Shiga toxin effector polypeptide comprising a disrupted furin-cleavage motif also comprises the furin-cleavage motif, amino acid residues at positions P9, P8, and/or P7 in order to maintain optimal cytotoxicity.

In some embodiments, the disrupted furin-cleavage motif comprises a mutation(s) which is one or more internal, amino acid residue deletions, as compared to a wild-type, Shiga toxin A Subunit. In some embodiments, the disrupted furin-cleavage motif comprises a mutation(s) which has one or more amino acid residue deletions within the minimal furin-cleavage site R/Y-x-x-R. For example, StxA and SLT-1A derived Shiga toxin effector polypeptides comprising internal deletions of the natively positioned amino acid residues R248 and/or R251, which may be combined with deletions of surrounding residues such as, e.g., 249, 250, 247, 252, etc.; and SLT-2A derived Shiga toxin effector polypeptides comprising internal deletions of the natively positioned amino acid residues Y247 and/or R250, which may be combined with deletions of surrounding residues such as, e.g., 248, 249, 246, 251, etc. In some embodiments, the disrupted furin-cleavage motif comprises a mutation which is a deletion of four, consecutive, amino acid residues which deletes the minimal furin-cleavage site R/Y-x-x-R, such as, e.g., StxA and SLT-1A derived Shiga toxin effector polypeptides lacking R248-R251 and SLT-2A derived Shiga toxin effector polypeptides lacking Y247-R250. In some embodiments, the disrupted furin-cleavage motif comprises a mutation(s) having one or more amino acid residue deletions in the amino acid residues flanking the core furin-cleavage motif, such as, e.g., a deletion of 244-247 and/or 252-255 in SLT-1A or StxA. In some embodiments, the disrupted furin-cleavage motif comprises a mutation which is an internal deletion of the entire surface-exposed, protease-cleavage sensitive loop as compared to a wild-type, Shiga toxin A Subunit, such as, e.g., for StxA and SLT-1A derived Shiga toxin effector polypeptides, a deletion of natively positioned amino acid residues 241-262; and for SLT-2A derived Shiga toxin effector polypeptides, a deletion of natively positioned amino acid residues 240-261.

In some embodiments, the disrupted furin-cleavage motif comprises both a mutation which is an internal, amino acid residue deletion within the furin-cleavage motif and a mutation which is carboxy-terminal truncation as compared to a wild-type, Shiga toxin A Subunit. In some embodiments, the disrupted furin-cleavage motif comprises both a mutation which is an amino acid residue deletion within the minimal furin-cleavage site R/Y-x-x-R and a mutation which is a carboxy-terminal truncation as compared to a wild-type, Shiga toxin A Subunit. For example, protease-cleavage resistant, Shiga toxin effector polypeptides may comprise a disrupted furin-cleavage motif comprising mutation(s) which are deletions of the natively positioned amino acid residues 248-249 and/or 250-251 in a truncated StxA or SLT-1A polypeptide which still has amino acid residue 247 and/or 252, or the amino acid residues 247-248 and/or 249-250 in a truncated SLT-2A which still has amino acid residue 246 and/or 251. In some embodiments, the disrupted furin-cleavage motif comprises a mutation having a deletion of four, consecutive, amino acid residues which deletes the minimal furin-cleavage site R/Y-x-x-R and a carboxy-terminal truncation as compared to a wild-type, Shiga toxin A Subunit, such as, e.g., for StxA and SLT-1A derived Shiga toxin effector polypeptides, truncations ending at the natively amino acid residue position 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and lacking R248-R251; and for SLT-2A derived Shiga toxin effector polypeptides, truncations ending at the natively amino acid residue position 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and lacking Y247-R250.

C. Examples of Shiga Toxin Effector Polypeptides Having an Embedded Epitope

In some embodiments, the Shiga toxin effector polypeptide may comprise one or more embedded or inserted, heterologous, T-cell epitopes for purposes of de-immunization and/or delivery to a MHC class I presentation pathway of a target cell. In some embodiments and/or certain Shiga toxin effector polypeptide sub-regions, embedding or partial embedding a T-cell epitope may be preferred over inserting a T-cell epitope because, e.g., embedding-type modifications are more likely to be successful in diverse sub-regions of a Shiga toxin effector polypeptide whereas successful insertions may be more limited to a smaller subset of Shiga toxin effector polypeptide sub-regions. The term "successful" is used here to mean the modification to the Shiga toxin effector polypeptide (e.g. introduction of a heterologous, T-cell epitope) results in a modified Shiga toxin effector polypeptide which retains one or more Shiga toxin effector functions at the requisite level of activity either alone or as a component of a binding molecule.

Any of the Shiga toxin effector polypeptide sub-regions described in WO 2015/113007 may be suitable. In some embodiments, and any of the Shiga toxin effector polypeptides described in WO 2015/113007 may be modified into a Shiga toxin effector polypeptide of a binding molecule, e.g., by the addition of one or more new epitope region disruptions for de-immunization (such one as described herein) and/or a furin-cleavage motif disruption (such as one described herein).

In some embodiments, the Shiga toxin effector polypeptide consists essentially of a truncated Shiga toxin A Subunit comprising an embedded or inserted, heterologous, T-cell epitope and one or more other mutations. In some embodiments, the Shiga toxin effector polypeptide comprises an embedded or inserted, heterologous, T-cell epitope and is smaller than a full-length, Shiga toxin A Subunit, such as, e.g., consisting of the polypeptide represent by amino acids 77 to 239 of SLT-1A (SEQ ID NO:1) or StxA (SEQ ID NO:2) or the equivalent in other A Subunits of members of the Shiga toxin family (e.g. amino acids 77 to 238 of SLT-2A (SEQ ID NO:3)). For example, in some embodiments, the Shiga toxin effector polypeptides is derived from amino acids 75 to 251 of SEQ ID NO:1, 1 to 241 of SEQ ID NO:1, 1 to 251 of SEQ ID NO:1, or amino acids 1 to 261 of SEQ ID NO:1, wherein the Shiga toxin effector polypeptide comprises at least one embedded or inserted, heterologous T-cell epitope and at least one amino acid is disrupted in an endogenous, B-cell and/or CD4+ T-cell epitope region and wherein the disrupted amino acid does not overlap with the embedded or inserted epitope. Similarly in other embodiments, the Shiga toxin effector polypeptide is derived from amino acids 75 to 251 of SEQ ID NO:2, 1 to 241 of SEQ ID NO:2, 1 to 251 of SEQ ID NO:2, or amino acids 1 to 261 of SEQ ID NO:2, wherein the Shiga toxin effector polypeptide comprises at least one embedded or inserted, heterologous T-cell epitope and at least one amino acid is disrupted in an endogenous, B-cell and/or CD4+ T-cell epitope region and wherein the disrupted amino acid does not overlap with the embedded or inserted epitope. Additionally, the Shiga toxin effector polypeptide may be derived from amino acids 75 to 251 of SEQ ID NO:3, 1 to 241 of SEQ ID NO:3, 1 to 251 of SEQ ID NO:3, or amino acids 1 to 261 of SEQ ID NO:3, wherein the Shiga toxin effector polypeptide comprises at least one embedded or inserted, heterologous T-cell epitope and at least one amino acid is disrupted in an endogenous, B-cell and/or CD4+ T-cell epitope region and wherein the disrupted amino acid does not overlap with the embedded or inserted epitope. In some embodiments, the Shiga toxin effector polypeptide comprises an embedded or inserted, heterologous, T-cell epitope and a disrupted furin-cleavage motif at the carboxy-terminus of a Shiga toxin A1 fragment derived region. For example in some embodiments, the Shiga toxin effector polypeptide is derived from amino acids 75 to 251 of SEQ ID NO:1, 1 to 241 of SEQ ID NO:1, 1 to 251 of SEQ ID NO:1, or amino acids 1 to 261 of SEQ ID NO:1, wherein the Shiga toxin effector polypeptide comprises at least one embedded or inserted, heterologous T-cell epitope and a disrupted furin-cleavage motif at the carboxy-terminus of a Shiga toxin A1 fragment derived region. Similarly in other embodiments, the Shiga toxin effector polypeptide is derived from amino acids 75 to 251 of SEQ ID NO:2, 1 to 241 of SEQ ID NO:2, 1 to 251 of SEQ ID NO:2, or amino acids 1 to 261 of SEQ ID NO:2, wherein the Shiga toxin effector polypeptide comprises at least one embedded or inserted, heterologous T-cell epitope and a disrupted furin-cleavage motif at the carboxy-terminus of a Shiga toxin A1 fragment derived region. Additionally, the Shiga toxin effector polypeptide may be derived from amino acids 75 to 251 of SEQ ID NO:3, 1 to 241 of SEQ ID NO:3, 1 to 251 of SEQ ID NO:3, or amino acids 1 to 261 of SEQ ID NO:3, wherein the Shiga toxin effector polypeptide comprises at least one embedded or inserted, heterologous T-cell epitope and a disrupted furin-cleavage motif at the carboxy-terminus of a Shiga toxin A1 fragment derived region.

D. Examples of Combination Shiga Toxin Effector Polypeptides

A combination Shiga toxin effector polypeptide comprises two or more sub-regions (i.e. non-overlapping sub-regions) wherein each sub-region comprises at least one of the following: (1) a disruption in an endogenous epitope or epitope region; (2) an embedded, heterologous, T-cell epitope-peptide; (3) an inserted, heterologous, T-cell epitope-peptide; and (4) a disrupted furin-cleavage motif at the carboxy-terminus of an A1 fragment derived region.

Certain embodiments of the combination Shiga toxin effector polypeptides comprise both (1) a disruption in an endogenous epitope or epitope region and (2) a disrupted furin-cleavage motif at the carboxy-terminus of an A1 fragment derived region. It is predicted that any of the individual, de-immunized, Shiga toxin effector sub-regions described in WO 2015/113007, WO 2016/196344, and WO 2018/140427 (see e.g. Table 3, supra) may generally be combined with any Shiga toxin effector sub-region comprising a disrupted furin-cleavage motif described herein, described in WO 2015/191764, and/or known in the art in order to create a Shiga toxin effector polypeptide for use as a component of a binding molecule.

In some embodiments, the Shiga toxin effector polypeptide comprises a disruption of at least one, endogenous, B-cell and/or T-cell epitope region which does not overlap with an embedded or inserted, heterologous, CD8+ T-cell epitope; wherein the disruption comprises one or more amino acid residue substitutions relative to a wild-type Shiga toxin. In some embodiments the substitution is selected from the group consisting of: K1 to A, G, V, L, I, F, M and H; T4 to A, G, V, L, I, F, M, and S; D6 to A, G, V, L, I, F, S, Q and R; S8 to A, G, V, I, L, F, and M; T9 to A, G, V, I, L, F, M, and S; S9 to A, G, V, L, I, F, and M; K11 to A, G, V, L, I, F, M and H; T12 to A, G, V, I, L, F, M, S, and K; S12 to A, G, V, I, L, F, and M; S33 to A, G, V, L, I, F, M, and C; S43 to A, G, V, L, I, F, and M; G44 to A or L; S45 to A, G, V, L, I, F, and M; T45 to A, G, V, L, I, F, and M; G46 to A and P; D47 to A, G, V, L, I, F, S, M, and Q; N48 to A, G, V, L, M and F; L49 to A, V, C, and G; Y49 to A, G, V, L, I, F, M, and T; F50 to A, G, V, L, I, and T; A51; D53 to A, G, V, L, I, F, S, and Q; V54 to A, G, I, and L; R55 to A, G, V, L, I, F, M, Q, S, K, and H; G56 to A and P; I57 to A, G, V, and M; L57 to A, V, C, G, M, and F; D58 to A, G, V, L, I, F, S, and Q; P59 to A, G, and F; E60 to A, G, V, L, I, F, S, Q, N, D, M, T, and R; E61 to A, G, V, L, I, F, S, Q, N, D, M, and R; G62 to A; R84 to A, G, V, L, I, F, M, Q, S, K, and H; V88 to A and G; 188 to A, V, C, and G; D94 to A, G, V, L, I, F, S, and Q; S96 to A, G, V, I, L, F, and M; T104 to A, G, V, L, I, F, M; and N; A105 to L; T107 to A, G, V, L, I, F, M, and P; S107 to A, G, V, L, I, F, M, and P; L108 to A, V, C, and G; S109 to A, G, V, I, L, F, and M; T109 to A, G, V, I, L, F, M, and S; G110 to A; S112 to A, G, V, L, I, F, and M; D111 to A, G, V, L, I, F, S, Q, and T; S112 to A, G, V, L, I, F, and M; D141 to A, G, V, L, I, F, S, and Q; G147 to A; V154 to A and G. R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; L185 to A, G, V and C; 5186 to A, G, V, I, L, F, and M; G187 to A; R188 to A, G, V, L, I, F, M, Q, S, K, and H; S189 to A, G, V, I, L, F, and M; D198 to A, G, V, L, I, F, S, and Q; R204 to A, G, V, L, I, F, M, Q, S, K, and H; R205 to A, G, V, L, I, F, M, Q, S, K and H; 5247 to A, G, V, I, L, F, and M; Y247 to A, G, V, L, I, F, and M; R248 to A, G, V, L, I, F, M, Q, S, K, and H; R250 to A, G, V, L, I, F, M, Q, S, K, and H; R251 to A, G, V, L, I, F, M, Q, S, K, and H; D264 to A, G, V, L, I, F, S, and Q; G264 to A; and T286 to A, G, V, L, I, F, and S. In some embodiments, there are multiple disruptions of multiple, endogenous B-cell and/or CD8+ T-cell epitope regions wherein each disruption involves at least one amino acid residue substitution selected from the group consisting of: K1 to A, G, V, L, I, F, M and H; T4 to A, G, V, L, I, F, M, and S; D6 to A, G, V, L, I, F, S, Q and R; S8 to A, G, V, I, L, F, and M; T9 to A, G, V, I, L, F, M, and S; S9 to A, G, V, L, I, F, and M; K11 to A, G, V, L, I, F, M and H; T12 to A, G, V, I, L, F, M, S, and K; S12 to A, G, V, I, L, F, and M; S33 to A, G, V, L, I, F, M, and C; S43 to A, G, V, L, I, F, and M; G44 to A or L; S45 to A, G, V, L, I, F, and M; T45 to A, G, V, L, I, F, and M; G46 to A and P; D47 to A, G, V, L, I, F, S, M, and Q; N48 to A, G, V, L, M and F; L49 to A, V, C, and G; Y49 to A, G, V, L, I, F, M, and T; F50 to A, G, V, L, I, and T; A51; D53 to A, G, V, L, I, F, S, and Q; V54 to A, G, I, and L; R55 to A, G, V, L, I, F, M, Q, S, K, and H; G56 to A and P; 157 to A, G, V, and M; L57 to A, V, C, G, M, and F; D58 to A, G, V, L, I, F, S, and Q; P59 to A, G, and F; E60 to A, G, V, L, I, F, S, Q, N, D, M, T, and R; E61 to A, G, V, L, I, F, S, Q, N, D, M, and R; G62 to A; R84 to A, G, V, L, I, F, M, Q, S, K, and H; V88 to A and G; 188 to A, V, C, and G; D94 to A, G, V, L, I, F, S, and Q; S96 to A, G, V, I, L, F, and M; T104 to A, G, V, L, I, F, M; and N; A105 to L; T107 to A, G, V, L, I, F, M, and P; S107 to A, G, V, L, I, F, M, and P; L108 to A, V, C, and G; S109 to A, G, V, I, L, F, and M; T109 to A, G, V, I, L, F, M, and S; G110 to A; S112 to A, G, V, L, I, F, and M; D111 to A, G, V, L, I, F, S, Q, and T; S112 to A, G, V, L, I, F, and M; D141 to A, G, V, L, I, F, S, and Q; G147 to A; V154 to A and G. R179 to A, G, V, L, I, F, M, Q, S, K, and H; T180 to A, G, V, L, I, F, M, and S; T181 to A, G, V, L, I, F, M, and S; D183 to A, G, V, L, F, S, and Q; D184 to A, G, V, L, I, F, S, and Q; L185 to A, G, V and C; 5186 to A, G, V, I, L, F, and M; G187 to A; R188 to A, G, V, L, I, F, M, Q, S, K, and H; S189 to A, G, V, I, L, F, and M; D198 to A, G, V, L, I, F, S, and Q; R204 to A, G, V, L, I, F, M, Q, S, K, and H; R205 to A, G, V, L, I, F, M, Q, S, K and H; S247 to A, G, V, I, L, F, and M; Y247 to A, G, V, L, I, F, and M; R248 to A, G, V, L, I, F, M, Q, S, K, and H; R250 to A, G, V, L, I, F, M, Q, S, K, and H; R251 to A, G, V, L, I, F, M, Q, S, K, and H; D264 to A, G, V, L, I, F, S, and Q; G264 to A; and T286 to A, G, V, L, I, F, M, and S.

Certain embodiments, the Shiga toxin effector polypeptide comprises both (1) an embedded or inserted, heterologous, T-cell epitope-peptide and (2) a disrupted furin-cleavage motif at the carboxy-terminus of an A1 fragment derived region. Any of the Shiga toxin effector polypeptide sub-regions comprising an embedded or inserted, heterologous, T-cell epitope described in WO 2015/113007 may generally be combined with any protease-cleavage resistant, Shiga toxin effector polypeptide sub-region (e.g., modified, Shiga toxin A Subunit sub-regions described herein, described in WO 2015/191764, and/or known in the art) in order to create a combination, Shiga toxin effector polypeptide which, as a component of a binding molecule, is both protease-cleavage resistant and capable of delivering a heterologous, T-cell epitope to the MHC class I presentation pathway of a target cell. Non-limiting examples of this type of combination Shiga toxin effector polypeptide are shown in SEQ ID NOs: 19-21.

Certain embodiments of the combination Shiga toxin effector polypeptides comprise both (1) a disruption in an endogenous epitope or epitope region and (2) an embedded, heterologous, T-cell epitope-peptide. However, the Shiga toxin effector sub-regions comprising inserted or embedded, heterologous, T-cell epitopes described herein or in WO 2015/191764 are generally not combinable with every de-immunized, Shiga toxin effector sub-regions described herein, except where empirically shown to be successfully combined such that the resulting combination molecule retained a sufficient level of a Shiga toxin effector function(s). The disclosure herein shows how such embodiments may be made and tested to empirically demonstrate success.

The term "successful" is used here to mean two or more amino acid residue substitutions in a Shiga toxin effector polypeptide results in a functional feature, such as, e.g., de-immunization, reduced furin-cleavage, and/or ability to deliver an embedded or inserted epitope, while the modified Shiga toxin effector polypeptide retains one or more Shiga toxin effector functions. The approaches and assays described herein show how to design, make and empirically test embodiments described herein, which represent combination, Shiga toxin effector polypeptides and binding molecules comprising the same.

The combination, Shiga toxin effector polypeptide may combine the features of their respective sub-regions, such as, e.g., a furin-cleavage motif disruption, individual epitope disruptions, and/or a heterologous T-cell epitope cargo, and these combinations sometimes result in Shiga toxin effector polypeptides with synergistic reductions in immunogenicity as compared to the sum of their partially de-immunized sub-regions.

De-immunized, Shiga toxin effector polypeptides which exhibit no cytotoxicity or reduced cytotoxicity at certain concentrations, e.g. Shiga toxin effector polypeptides comprising R179A, may still be useful as de-immunized, Shiga toxin effector polypeptides for delivering exogenous materials into cells. Similarly, CD8+ T-cell hyper-immunized, Shiga toxin effector polypeptides of the which exhibit no cytotoxicity or reduced cytotoxicity at certain concentrations, e.g. a Shiga toxin effector polypeptide comprising an epitope embedded into its catalytic domain (see e.g. WO 2015/113005: Example 1-F), may still be useful for delivering a T-cell epitope(s) to a desired subcellular compartment of a cell in which the Shiga toxin effector polypeptide is present or as a component of a binding molecule for delivery of a T-cell epitope(s) into a target cell.

E. Examples of Binding Molecules

The following embodiments describe in more detail certain structures of exemplary binding molecules which target cells physically coupled to PD-L1 at a cellular surface, e.g. cells which express PD-L1 and/or PD-L1 positive cells.

Provided herein are various embodiments of PD-L1 binding molecules, and compositions thereof, wherein each PD-L1 binding molecule comprises (1) at least one toxin component and (2) at least one PD-L1 binding region capable of specifically binding an extracellular part of a PD-L1 molecule. For each PD-L1 binding molecule described herein, the at least one binding region is heterologous to the toxin from which the toxin effector polypeptide is derived, such as, e.g., a PD-L1 binding region comprising an immunoglobulin domain unrelated to the toxin. In some embodiments, the at least one toxin component comprises a toxin effector polypeptide. In some embodiments, the toxin effector polypeptide is a Shiga toxin A Subunit effector polypeptide derived from the A Subunit of a Shiga toxin.

In some embodiments, the PD-L1 binding molecule comprises (1) at least one Shiga toxin A Subunit effector polypeptide derived from the A Subunit of at least one member of the Shiga toxin family and (2) at least one PD-L1 binding region capable of specifically binding an extracellular part of a PD-L1 molecule.

In some embodiments, the PD-L1 binding region comprises a heavy chain variable region (HVR-H) comprising three CDRs, each having at least 85%, 90%, 91%, 92%, 93%, 94%, 95%, 96%, 97%, 98%, or 99% identity to any one of SEQ ID NOs: 22-24 and 27-32; or consisting essentially of an amino acid sequence show in any one of SEQ ID NOs: 22-24 and 27-32. In some embodiments, the binding region further comprises: (a) a light chain variable region (HVR-L) comprising three CDRs, each having at least 85%, 90%, 91%, 92%, 93%, 94%, 95%, 96%, 97%, 98%, or 99% identity to any one of SEQ ID NO:19, SEQ ID NO:20, SEQ ID NO:21, SEQ ID NO:25, and SEQ ID NO:26; or consisting essentially of an amino acid sequence shown in any one of SEQ ID NO:19, SEQ ID NO:20, SEQ ID NO:21, SEQ ID NO:25, and SEQ ID NO:26. In some embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:19, SEQ ID NO:20, and SEQ ID NO:21; or consisting essentially of an amino acid sequence shown in any one of SEQ ID NO:19, SEQ ID NO:20, and SEQ ID NO:21. In certain other further embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:25, SEQ ID NO:20, and SEQ ID NO:21; or consisting essentially of an amino acid sequence shown in any one of SEQ ID NO:25, SEQ ID NO:20, and SEQ ID NO:21. In certain other further embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:19, SEQ ID NO:20, and SEQ ID NO:26; or consisting essentially of an amino acid sequence shown in any one of SEQ ID NO:19, SEQ ID NO:20, and SEQ ID NO:26.

In some embodiments, the binding region comprises: (a) a light chain variable region (HVR-L) comprising three CDRs, each comprising or consisting essentially of an amino acid sequence shown in any one of SEQ ID NO:19, SEQ ID NO:20, SEQ ID NO:21, SEQ ID NO:25, and SEQ ID NO:26; and (b) a heavy chain variable region (HVR-H) comprising three CDRs, each comprising or consisting essentially of an amino acid sequence show in any one of SEQ ID NOs: 22-24 and 27-32.

In some embodiments, the binding region comprises: (a) a light chain region having at least 85%, 90%, 91%, 92%, 93%, 94%, 95%, 96%, 97%, 98%, or 99%, identity to any one of SEQ ID NOs: 33, 35-36, and 38, or consisting essentially of the amino acid sequence of any one of SEQ ID NOs: 33, 35-36, and 38; and/or (b) a heavy chain region having at least 85%, 90%, 91%, 92%, 93%, 94%, 95%, 96%, 97%, 98%, or 99% identity to any one of SEQ ID NOs: 34, 37, and 39, or consisting essentially of the amino acid sequence of any one of SEQ ID NOs: 34, 37, and 39. In some embodiments, the binding region comprises a polypeptide having at least 85%, 90%, 91%, 92%, 93%, 94%, 95%, 96%, 97%, 98%, or 99% identity to any one of SEQ ID NOs: 85-107 and 156-157 or consists essentially of the polypeptide shown in any one of SEQ ID NOs: 85-107 and 156-157. In some embodiments, the binding region is a single-chain variable fragment, such as, e.g., consisting of, comprising, or consisting essentially of the polypeptide of any one of SEQ ID NOs: 85-107 and 156-157.

In some embodiments, a PD-L1 binding molecule comprising a Shiga toxin A subunit effector polypeptide and a binding region capable of specifically binding an extracellular part of PD-L1; wherein the binding region comprises (a) a heavy chain variable region (VH) comprising (i) a CDR1 comprising the amino acid sequence EYTMH (SEQ ID NO:27), (ii) a CDR2 comprising the amino acid sequence GINPNNGGTWYNQKFKG (SEQ ID NO:29), and (iii) a CDR3 comprising the amino acid sequence PYYYGSREDYFDY (SEQ ID NO:32); and (b) a light chain variable region (VL) comprising (i) a CDR1 comprising the amino acid sequence SASSSVSYMY (SEQ ID NO:19), (ii) a CDR2 comprising the amino acid sequence LTSNLAS (SEQ ID NO:20), and (iii) a CDR3 comprising the amino acid sequence QQWSSNPPT (SEQ ID NO:26). In some embodiments, a PD-L1 binding molecule comprising a Shiga toxin A subunit effector polypeptide and a binding region capable of specifically binding an extracellular part of PD-L1; wherein the binding region comprises (a) a heavy chain variable region (VH) comprising (i) a CDR1 consisting of the amino acid sequence EYTMH (SEQ ID NO:27), (ii) a CDR2 consisting of the amino acid sequence GINPNNGGTWYNQKFKG (SEQ ID NO:29), and (iii) a CDR3 consisting of the amino acid sequence PYYYGSREDYFDY (SEQ ID NO:32); and (b) a light chain variable region (VL) comprising (i) a CDR1 consisting of the amino acid sequence SASSSVSYMY (SEQ ID NO:19), (ii) a CDR2 consisting of the amino acid sequence LTSNLAS (SEQ ID NO:20), and (iii) a CDR3 consisting of the amino acid sequence QQWSSNPPT (SEQ ID NO:26). In some embodiments, a PD-L1 binding molecule comprising a Shiga toxin A subunit effector polypeptide and a binding region capable of specifically binding an extracellular part of PD-L1; wherein the binding region comprises (a) a heavy chain variable region (VH) comprising (i) a CDR1 having the amino acid sequence EYTMH (SEQ ID NO:27), (ii) a CDR2 having the amino acid sequence GINPNNGGTWYNQKFKG (SEQ ID NO:29), and (iii) a CDR3 having the amino acid sequence PYYYGSREDYFDY (SEQ ID NO:32); and (b) a light chain variable region (VL) comprising (i) a CDR1 having the amino acid sequence SASSSVSYMY (SEQ ID NO:19), (ii) a CDR2 having the amino acid sequence LTSNLAS (SEQ ID NO:20), and (iii) a CDR3 having the amino acid sequence QQWSSNPPT (SEQ ID NO:26).

In some embodiments, the Shiga toxin A subunit effector polypeptide comprises the sequence of SEQ ID NO: 41, or a sequence at least 90% or at least 95% identical thereto.

In some embodiments, the VH comprises the sequence of SEQ ID NO: 34, or a sequence at least 90% or at least 95% identical thereto. In some embodiments, the VL comprises the sequence of SEQ ID NO: 35, or a sequence at least 90% or at least 95% identical thereto. In some embodiments, the VH comprises the sequence of SEQ ID NO: 34 and the VL comprises the sequence of SEQ ID NO: 35.

In some embodiments, the binding region comprises a scFv linker that links the VH and the VL. In some embodiments, the scFv linker is 3 to 12 amino acids in length. In some embodiments, the scFv linker is 3 to about 12 amino acids in length. In some embodiments, the scFv linker is about 3 to about 12 amino acids in length. In some embodiments, the scFv linker is about 10-20 amino acids in length. In some embodiments, the scFv linker is greater than 20 amino acids in length. In some embodiments, the scFv linker is a flexible linker. In some embodiments, the scFv linker comprises the sequence of SEQ ID NO: 72, or a sequence at least 90% or at least 95% identical thereto. In some embodiments, the binding region is a single chain variable fragment (scFv). In some embodiments, the binding region comprises the sequence of SEQ ID NO: 106, or a sequence at least 90% or at least 95% identical thereto.

As used herein, the term "binding domain linker" refers to a linker which links the Shiga toxin A subunit effector polypeptide and the binding region (e.g., the scFv). In some embodiments, the PD-L1 binding molecule comprises a binding domain linker. In some embodiments, the binding domain linker comprises the sequence of SEQ ID NO: 73, or a sequence at least 90% or at least 95% identical thereto. In some embodiments, the binding domain linker comprises the sequence of any one of SEQ ID NO: 74-77, or a sequence at least 90% or at least 95% identical thereto.

In some embodiments, a binding molecule comprises a CD8+ T-cell epitope that is heterologous to Shiga toxin A subunits. In some embodiments, the CD8+ T-cell epitope comprises the sequence NLVPMVATV (SEQ ID NO: 78), or a sequence at least 90% or at least 95% identical thereto. In some embodiments, the CD8+ T-cell epitope is linked to the binding region via a cleavable spacer. In some embodiments, a binding molecule has spacer having the sequence HHAA (SEQ ID NO: 265).

In some embodiments, the binding molecule comprises, from N-terminus to C-terminus, a Shiga toxin A subunit effector polypeptide, a binding domain linker, and a binding region. In some embodiments, the binding molecule comprises, from N-terminus to C-terminus, a Shiga toxin A subunit effector polypeptide, a binding domain linker, a VH and a VL. In some embodiments, the binding molecule comprises, from N-terminus to C-terminus, a Shiga toxin A subunit effector polypeptide, a binding domain linker, a VH, a scFv linker, and a VL.

In some embodiments, a binding molecule comprises, from N-terminus to C-terminus, a Shiga toxin A subunit effector polypeptide, a binding domain linker, a binding region, and a CD8+ T-cell epitope. In some embodiments, the binding molecule comprises, from N-terminus to C-terminus, a Shiga toxin A subunit effector polypeptide, a binding domain linker, a VH, a scFv linker, a VL, and a CD8+ T-cell epitope. In some embodiments, a binding molecule comprises, from N-terminus to C-terminus, a Shiga toxin A subunit effector polypeptide, a binding domain linker, a binding region, a cleavable spacer and a CD8+ T-cell epitope.

In some embodiments, a binding molecule is a single continuous polypeptide. In some embodiments, a binding molecule comprises the sequence of SEQ ID NO: 128, or a sequence at least 90% or at least 95% identical thereto. In some embodiments, a binding molecule comprises the sequence of any one of SEQ ID NO: 108-155, 158-159, or 160-168, or a sequence at least 90% or at least 95% identical thereto.

In some embodiments, a binding molecule comprises two or more (e.g., three, four, five, six, seven, or eight) polypeptides. In some embodiments, each of polypeptides comprises the sequence of SEQ ID NO: 128. In some embodiments, the two polypeptides are non-covalently linked to each other, for example via the binding region.

In some embodiments, the binding molecule is cytotoxic. In some embodiments, the PD-L1 binding molecule is non-cytotoxic. For example, the PD-L1 binding molecule may be non-cytotoxic if the Shiga toxin subunit effector polypeptide is truncated or comprises one or more mutations which eliminate its cytotoxic activity.

In some embodiments of the PD-L1 binding molecule, upon administration of the PD-L1 binding molecule to a PD-L1-expressing cell results in (i) the internalization of the PD-L1 binding molecule by the cell and (ii) the death of the cell. In some embodiments of the PD-L1 binding molecule, upon administration of the PD-L1 binding molecule to a PD-L1-expressing cell results in (i) the internalization of the PD-L1 binding molecule by the cell and (ii) the death of the cell due to a catalytically active Shiga toxin A subunit effector polypeptide. In some embodiments of the PD-L1 binding molecule, upon administration of the PD-L1 binding molecule to a PD-L1-expressing cell results in (i) the internalization of the PD-L1 binding molecule by the cell and (ii) the death of the cell due to delivery and presentation of T-cell epitope cargo. In some embodiments, the PD-L1 binding molecule is capable, when introduced to cells, of exhibiting a cytotoxicity with a half-maximal inhibitory concentration ($CD_{50}$) value of 300 nM or less and/or capable of exhibiting a significant level of Shiga toxin cytotoxicity.

In some embodiments of the PD-L1 binding molecule, the Shiga toxin A Subunit effector polypeptide is capable of exhibiting a ribosome inhibition activity with a half-maximal inhibitory concentration ($IC_{50}$) value of less than 10,000, 5,000, 1,000, 500, or 200 picomolar.

In some embodiments of the PD-L1 binding molecule, the at least one Shiga toxin A Subunit derived polypeptide comprises a combination of features (e.g., de-immunized sub-region(s), heterologous epitope comprising sub-region(s), a protease-cleavage resistant sub-region, and/or a carboxy-terminal, endoplasmic reticulum retention/retrieval signal motif). Certain PD-L1 binding molecules described herein provide a combination of several properties in a single molecule, such as, e.g., efficient cellular internalization, potent cell-targeted cytotoxicity, selective cytotoxicity, de-immunization, low non-specific toxicity at high dosages, high stability, CD8+ T-cell hyper-immunization, and/or the ability to deliver a heterologous, T-cell epitope(s) to the MHC I class pathway of a target cell.

In some embodiments, the PD-L1 binding molecules are useful for administration to chordates, such as, e.g., when it is desirable to (1) reduce or eliminate a certain immune response(s) resulting from the administered molecule, (2) reduce or eliminate non-specific toxicities resulting from the administered molecule, (3) specifically kill a PD-L1-expressing target cell(s) in vivo, and/or (4) target a beneficial immune response(s) to a target cell-type, a tumor mass comprising a target cell-type, and/or a tissue locus comprising such a target cell-type, such as via stimulating intercellular engagement of a CD8+ T-cell(s) of the chordate with a specific MHC class I-epitope complex displaying target cell-type.

In some embodiments, the PD-L1 binding molecule comprises or consists essentially of the polypeptide shown in any one of SEQ ID NOs: 85-107 and 156-157, and optionally the PD-L1 binding molecule comprises an amino-terminal methionine residue.

As used herein, the term "Cmax" refers to the peak serum concentration that a binding molecule achieves after it has been administered to a subject. In some embodiments, the PD-L1 binding molecules described herein have a Cmax in the range of about 1000 to about 50,000 ng/mL. For example, the PD-L1 binding molecules may have a Cmax in the range of about 1 to about 1,000 ng/mL, about 1,000 to about 3,000 ng/mL, about 2,000 to about 5,000 ng/mL, about 5000 to about 10,000 ng/mL, about 10,000 ng/mL to about 15,000 ng/mL, about 15,000 ng/mL to about 20,000 ng/mL, about 20,000 ng/mL to about 25,000 ng/mL, about 25,000 ng/mL to about 30,000 ng/mL, or about 30,000 ng/mL to about 35,000 ng/mL, or about 35,000 ng/mL to about 50,000 ng/mL. In some embodiments the Cmax is about 1,000, about 2,000, about 3,000, about 4,000, about 5,000, about 6.00, about 7,000, about 8,000, about 9,000, or about 10,000 ng/mL. In some embodiments, the Cmax is about 21,000, about 22,000, about 23,000, about 24,000, about 25,000, about 26,000, about 27,000, about 28,000, about 29,000, or about 30,000 ng/mL. In some embodiments, the Cmax is 2,096, 27,063, or 22,375 ng/mL.

As used herein the term "half-life" or "Ti/2" refers to the time taken for half the initial dose of PD-L1 binding molecule administered to be eliminated from the body. In some embodiments, the half-life of a PD-L1 molecule described herein is about 1 minute to about 1 hour, about 1 hour to about 3 hours, about 3 hours to about 5 hours, or about 5 hours to about 10 hours. In some embodiments, the half-life of a PD-L1 binding molecule is about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes. In some embodiments, the half-life of a PD-L1 binding molecule is about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.6 hours, or about 10 hours. In some embodiments, the half-life of a PD-L1 binding molecule is about 2.8 hours, about 3.7 hours, or about 5.6 hours.

In some embodiments of the PD-L1 binding molecule, upon administration of the PD-L1 binding molecule to a PD-L1-expressing cell results in (i) the internalization of the PD-L1 binding molecule by the cell and (ii) the cell presenting on a cellular surface a heterologous, CD8+ T-cell epitope-peptide cargo delivered by the PD-L1 binding molecule complexed with a MHC class I molecule.

Other Structural Variations

In some embodiments, fragments, variants, and/or derivatives of the binding molecules are used, which contain a functional binding site to any extracellular part of a PD-L1 target biomolecule, and even more preferably capable of binding a target biomolecule with high affinity (e.g. as shown by K D). For example, any binding region which binds an extracellular part of a target biomolecule with a dissociation constant ($K_D$) of $10^{-5}$ to $10^{-12}$ moles/liter, preferably less than 200 nM, may be substituted for use in making binding molecules and methods as described herein.

The skilled worker will recognize that variations may be made to the Shiga toxin effector polypeptides, antibodies, and binding molecules, and polynucleotides encoding any of the former, without diminishing their biological activities, e.g., by maintaining the overall structure and function of the Shiga toxin effector polypeptide, such as in conjunction with one or more 1) endogenous epitope disruptions which reduce antigenic and/or immunogenic potential, 2) furin-cleavage motif disruptions which reduce proteolytic cleavage, and/or 3) embedded or inserted epitopes which reduce antigenic and/or immunogenic potential or are capable of being delivered to a MHC I molecule for presentation on a cell surface. For example, some modifications may facilitate expression, facilitate purification, improve pharmacokinetic properties, and/or improve immunogenicity. Such modifications are well known to the skilled worker and include, for example, a methionine added at the amino-terminus to provide an initiation site, additional amino acids placed on either terminus to create conveniently located restriction sites or termination codons, and biochemical affinity tags fused to either terminus to provide for convenient detection and/or purification. A common modification to improve the immunogenicity of a polypeptide produced using a non-chordate system (e.g. a prokaryotic cell) is to remove, after the production of the polypeptide, the starting methionine residue, which may be formylated during production, such as, e.g., in a bacterial host system, because, e.g., the presence of N-formylmethionine (fMet) might induce undesirable immune responses in chordates.

Also contemplated herein is the inclusion of additional amino acid residues at the amino and/or carboxy termini of a binding molecule, or a proteinaceous component of a binding molecule, such as sequences for epitope tags or other moieties. The additional amino acid residues may be used for various purposes including, e.g., facilitating cloning, facilitating expression, post-translational modification, facilitating synthesis, purification, facilitating detection, and administration. Non-limiting examples of epitope tags and moieties are chitin binding protein domains, enteropeptidase cleavage sites, Factor Xa cleavage sites, FIAsH tags, FLAG tags, green fluorescent proteins (GFP), glutathione-S-transferase moieties, HA tags, maltose binding protein domains, myc tags, polyhistidine tags, ReAsH tags, strep-tags, strep-tag II, TEV protease sites, thioredoxin domains, thrombin cleavage site, and V5 epitope tags.

In certain of the above embodiments, the polypeptide sequence of the Shiga toxin effector polypeptides and/or binding molecules are varied by one or more conservative amino acid substitutions introduced into the polypeptide region(s) as long as all required structural features are still present and the Shiga toxin effector polypeptide is capable of exhibiting any required function(s), either alone or as a component of a binding molecule. As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids (see, for example, Table 4). An example of a conservative substitution with a residue normally not found in endogenous, mammalian peptides and proteins is the conservative substitution of an arginine or lysine residue with, for example, ornithine, canavanine, aminoethylcysteine, or another basic amino acid. For further information concerning phenotypically silent substitutions in peptides and proteins see, e.g., Bowie J et al., *Science* 247: 1306-10 (1990).

TABLE 4

Examples of Conservative Amino Acid Substitutions

| I | II | III | IV | V | VI | VII | VIII | IX | X | XI | XII | XIII | XIV |
|---|----|-----|----|---|----|----|------|----|---|----|-----|------|-----|
| A | D | H | C | F | N | A | C | F | A | C | A | A | D |
| G | E | K | I | W | Q | G | M |   | H | C | D | C | C | E |
| P | Q | R | L | Y | S | I | P |   | W | F | E | D | D | G |
| S | N |   | M |   | T | L |   |   | Y | G | H | G | E | K |
| T |   |   | V |   |   | V |   |   |   | H | K | N | G | P |
|   |   |   |   |   |   |   |   |   |   | I | N | P | H | Q |
|   |   |   |   |   |   |   |   |   |   | L | Q | S | K | R |
|   |   |   |   |   |   |   |   |   |   | M | R | T | N | S |
|   |   |   |   |   |   |   |   |   |   | R | S | V | Q | T |
|   |   |   |   |   |   |   |   |   |   | T | T |   | R |   |
|   |   |   |   |   |   |   |   |   |   | V |   |   | S |   |
|   |   |   |   |   |   |   |   |   |   | W |   |   | P |   |
|   |   |   |   |   |   |   |   |   |   | Y |   |   | T |   |

In the conservative substitution scheme in Table 4, exemplary conservative substitutions of amino acids are grouped by physicochemical properties—I: neutral, hydrophilic; II: acids and amides; III: basic; IV: hydrophobic; V: aromatic, bulky amino acids, VI hydrophilic uncharged, VII aliphatic uncharged, VIII non-polar uncharged, IX cycloalkenyl-associated, X hydrophobic, XI polar, XII small, XIII turn-permitting, and XIV flexible. For example, conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

Additional conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

Variants of the Shiga toxin effector polypeptides and binding molecules may be prepared by changing a polypeptide described herein by altering one or more amino acid residues or deleting or inserting one or more amino acid residues, such as within the binding region or Shiga toxin effector polypeptide region, in order to achieve desired properties, such as changed cytotoxicity, changed cytostatic effects, changed immunogenicity, and/or changed serum half-life. The Shiga toxin effector polypeptides and binding molecules may further be with or without a signal sequence. In some embodiments, the binding molecules may comprise functional fragments or variants of a polypeptide region described herein that have, at most, 20, 15, 10, 9, 8, 7, 6, 5, 4, 3, 2, or 1 amino acid substitutions compared to a polypeptide sequence recited herein.

In some embodiments, the Shiga toxin effector polypeptides and binding molecules may comprise functional fragments or variants of a polypeptide region described herein that have, at most, 20, 15, 10, 9, 8, 7, 6, 5, 4, 3, 2, or 1 amino acid substitutions compared to a polypeptide sequence recited herein, as long as it (1) comprises at least one embedded or inserted, heterologous T-cell epitope and at least one amino acid is disrupted in an endogenous, B-cell and/or CD4+ T-cell epitope region, wherein the disrupted amino acid does not overlap with the embedded or inserted epitope; (2) comprises at least one embedded or inserted, heterologous T-cell epitope and a disrupted furin-cleavage motif at the carboxy-terminus of a Shiga toxin A1 fragment derived region; or (3) comprises a disrupted furin-cleavage motif at the carboxy-terminus of a Shiga toxin A1 fragment derived region and comprises at least one amino acid is disrupted in an endogenous, B-cell and/or CD4+ T-cell epitope region, wherein the disrupted amino acid does not overlap with the disrupted furin-cleavage motif Accordingly, in some embodiments, the Shiga toxin effector polypeptide comprises or consists essentially of amino acid sequences having at least 55%, 60%, 65%, 70%, 75%, 80%, 85%, 90%, 95%, 97%, 98%, or 99%, overall sequence identity to a naturally occurring Shiga toxin A Subunit or fragment thereof, such as, e.g., Shiga toxin A Subunit, such as SLT-1A (SEQ ID NO:1), StxA (SEQ ID NO:2), and/or SLT-2A (SEQ ID NO:3), wherein the Shiga toxin effector polypeptide (1) comprises at least one embedded or inserted, heterologous T-cell epitope and at least one amino acid is disrupted in an endogenous, B-cell and/or CD4+ T-cell epitope region, and wherein the disrupted amino acid does not overlap with the embedded or inserted epitope; (2) comprises at least one embedded or inserted, heterologous T-cell epitope and a disrupted furin-cleavage motif at the carboxy-terminus of a Shiga toxin A1 fragment derived region; or (3) comprises a disrupted furin-cleavage motif at the carboxy-terminus of a Shiga toxin A1 fragment derived region and comprises at least one amino acid is disrupted in an endogenous, B-cell and/or CD4+ T-cell epitope region, and wherein the disrupted amino acid does not overlap with the disrupted furin-cleavage motif In some embodiments, the Shiga toxin effector polypeptide has one or more amino acid residues may be mutated, inserted, or deleted in order to increase the enzymatic activity of the Shiga toxin effector polypeptide. In some embodiments, the Shiga toxin effector polypeptide has one or more amino acid residues may be mutated or deleted in order to reduce or eliminate catalytic and/or cytotoxic activity of the Shiga toxin effector polypeptide. For example, the catalytic and/or cytotoxic activity of the A Subunits of members of the Shiga toxin family may be diminished or eliminated by mutation or truncation.

The cytotoxicity of the A Subunits of members of the Shiga toxin family may be altered, reduced, or eliminated by mutation and/or truncation. The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan M, Hovde C, *Infect Immun* 66: 5252-9 (1998)). Mutating both glutamate-167 and arginine-170 eliminated the enzymatic activity of Slt-I A1 in a cell-free ribosome inactivation assay (LaPointe P et al., *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe P et al., *J Biol Chem* 280: 23310-18 (2005)). A truncation analysis demonstrated that a fragment of StxA from residues 75 to 268 still retains significant enzymatic activity in vitro (Haddad J et al., *J Bacteriol* 175: 4970-8 (1993)). A truncated fragment of Slt-I A1 containing residues 1-239 displayed significant enzymatic activity in vitro and cytotoxicity by de novo expression in the cytosol (LaPointe P et al., *J Biol Chem* 280: 23310-18 (2005)). Expression of a Slt-I A1 fragment truncated to residues 1-239 in the endoplasmic reticulum was not cytotoxic because it could not retrotranslocate to the cytosol (LaPointe P et al., *J Biol Chem* 280: 23310-18 (2005)).

The most critical residues for enzymatic activity and/or cytotoxicity in the Shiga toxin A Subunits were mapped to the following residue-positions: asparagine-75, tyrosine-77, tyrosine-114, glutamate-167, arginine-170, arginine-176, and tryptophan-203 among others (Di R et al., *Toxicon* 57: 525-39 (2011)). In particular, a double-mutant construct of Stx2A containing glutamate-E1 67-to-lysine and arginine-176-to-lysine mutations was completely inactivated; whereas, many single mutations in Stx1 and Stx2 showed a 10-fold reduction in cytotoxicity. Further, truncation of Stx1A to 1-239 or 1-240 reduced its cytotoxicity, and similarly, truncation of Stx2A to a conserved hydrophobic residue reduced its cytotoxicity. The most critical residues for binding eukaryotic ribosomes and/or eukaryotic ribosome inhibition in the Shiga toxin A Subunit have been mapped to the following residue-positions arginine-172, arginine-176, arginine-179, arginine-188, tyrosine-189, valine-191, and leucine-233 among others (McCluskey A et al., *PLoS One* 7: e31191 (2012). However, certain modification may increase a Shiga toxin functional activity exhibited by a Shiga toxin effector polypeptide. For example, mutating residue-position alanine-231 in Stx1A to glutamate increased Stx1A's enzymatic activity in vitro (Suhan M, Hovde C, *Infect Immun* 66: 5252-9 (1998)).

In some embodiments, the Shiga toxin effector polypeptide derived from SLT-1A (SEQ ID NO:1) or StxA (SEQ ID NO:2) has one or more amino acid residues mutated include substitution of the asparagine at position 75, tyrosine at position 77, tyrosine at position 114, glutamate at position 167, arginine at position 170, arginine at position 176, and/or substitution of the tryptophan at position 203. Examples of such substitutions will be known to the skilled worker based on the prior art, such as asparagine at position 75 to alanine, tyrosine at position 77 to serine, substitution of the tyrosine at position 114 to serine, substitution of the glutamate position 167 to glutamate, substitution of the arginine at position 170 to alanine, substitution of the arginine at position 176 to lysine, substitution of the tryptophan at position 203 to alanine, and/or substitution of the alanine at 231 with glutamate. Other mutations which either enhance or reduce Shiga toxin enzymatic activity and/or cytotoxicity are within the scope of the disclosure and may be determined using well known techniques and assays disclosed herein.

The Shiga toxin effector polypeptides and binding molecules may optionally be conjugated to one or more additional agents, which may include therapeutic agents, diagnostic agents, and/or other additional exogenous materials known in the art, including such agents as described herein. In some embodiments, the Shiga toxin effector polypeptide or binding molecule is PEGylated or albuminated, such as, e.g., to provide de-immunization, disrupt furin-cleavage by masking the extended loop and/or the furin-cleavage motif at the carboxy-terminus of a Shiga toxin A1 fragment derived region, improve pharmacokinetic properties, and/or improve immunogenicity (see e.g., Wang Q et al., *Cancer Res* 53: 4588-94 (1993); Tsutsumi Y et al., *Proc Natl Acad Sci USA* 97: 8548-53 (2000); Buse J, El-Aneed A, *Nanomed* 5: 1237-60 (2010); Lim S et al., *J Control Release* 207-93 (2015)).

1. Antibody Component Variants

In some embodiments, amino acid sequence variants of the antibody component of the binding molecules (e.g. an antibody-toxin conjugate) described herein are contemplated. For example, it may be desirable to improve the binding affinity and/or other biological properties of the antibody-toxin conjugate. Amino acid sequence variants of an antibody may be prepared by introducing appropriate modifications into the nucleotide sequence encoding the antibody component, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding and/or toxin delivery.

a) Substitution, Insertion, and Deletion Variants

In some embodiments, antibody variants having one or more amino acid substitutions are provided. Sites of interest for substitutional mutagenesis include the HVRs and FRs. Amino acid substitutions may be introduced into an antibody of interest and the antibody-toxin conjugate products screened for a desired activity, e.g., retained/improved antigen binding, decreased immunogenicity, or improved ADCC or CDC.

One type of substitutional variant involves substituting one or more hypervariable region residues of a parent antibody (e.g. to create a humanized antibody). Generally, the resulting variant(s) selected for further study will have modifications (e.g. improvements) in certain biological properties (e.g. increased affinity or reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques. Briefly, one or more HVR residues are mutated and the variant antibodies displayed and screened for a particular biological activity (e.g. binding affinity) (see e.g. WO 2015/120058).

Alterations (e.g. substitutions) may be made in HVRs, e.g., to improve antibody affinity using methods known to the skilled worker. For example, alterations may be made in HVR "hotspots" or residues encoded by codons that undergo mutation at high frequency during the somatic maturation process (Chowdhury P, *Methods Mol Biol* 207: 179-196 (2008)), and/or SDRs (a-CDRs), with the resulting variant heavy and/or light chains being tested for binding affinity. In some embodiments, substitutions, insertions, or deletions may occur within one or more HVRs so long as such alterations do not substantially reduce the ability of the antibody to bind antigen. For example, conservative alterations that do not substantially reduce binding affinity may be made in HVRs, including outside of HVR "hotspots" or SDRs. In some embodiments of the variant VH and VL sequences provided above, each HVR either is unaltered, or contains no more than one, two, or three amino acid substitutions.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an amino-terminal methionyl residue. Other insertional variants of the antibody molecule include the fusion to the amino- and/or carboxyl-terminus of the antibody to an enzyme (e.g. for antibody-directed enzyme prodrug therapy) or a polypeptide which increases the serum half-life of the antibody.

b) De-Immunized and/or Chimeric Variants

In some embodiments, the antibody component of the binding molecule (e.g. an antibody-toxin conjugate) is chimeric. For example, the chimeric antibody comprises a non-human variable region (e.g., a variable region derived from a mouse, rat, hamster, rabbit, or non-human primate)

and a human constant region. In a further example, a chimeric antibody is a "class switched" antibody in which the class or isotype has been changed from that of the parent antibody from which it was derived. In some embodiments, the chimeric antibody is a humanized antibody. Chimeric antibodies include antigen-binding fragments thereof.

In some embodiments, the antibody component of the binding molecule (e.g. an antibody-toxin conjugate) is humanized. Typically, a non-human antibody is humanized to reduce immunogenicity in humans, while retaining the specificity and affinity of the parental non-human antibody. Typically, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a constant region from a human antibody. In some embodiments, some FR residues in a humanized antibody have been substituted with corresponding residues from a non-human antibody (e.g. the antibody from which the HVR residues are derived), e.g., to restore or improve antibody specificity and/or affinity.

c) Fc Region Variants

In some embodiments, the antibody component of the binding molecule (e.g. an antibody-toxin conjugate) comprises an Fc region. For example, the Fc region variant may comprise a human Fc region sequence (e.g., a Fc region from a human IgG1, IgG2, IgG3, or IgG4) and may optionally comprise one or more amino acid alterations (e.g. a substitution at one or more amino acid positions). In some embodiments, the antibody component comprises an Fc region that has ADCC and/or CDC activity. Such antibodies are particularly useful for mediating killing of target expressing cells. Antibodies with improved Fc effector functions can be generated, for example, through changes in amino acid residues involved in the interaction between the Fc domain and an Fc receptor (FcR) (e.g. FcγRI, FcγRIIA, FcγRIIB, or FcγRIII with FcRn), which may lead to increased cytotoxicity and/or altered pharmacokinetics, such as increased serum half-life. Certain antibody variants with improved or diminished binding to FcRs are known to skilled worker and/or described in Shields R et al., *J Biol Chem* 9: 6591-6604 (2001).

In some embodiments, the antibody component comprises an Fc region that lacks one or more effector functions (e.g. lacks ADCC and/or CDC activity). Fc regions lacking or having substantially reduced effector function may be obtained, for example, by introducing one or more amino acid substitutions into a native Fc region sequence, such that the Fc region does not bind, or has substantially reduced binding, to cytolytic Fc receptors (e.g. DANA mutant) and/or the C1q complement protein (see e.g. Wilson N et al., *Cancer Cell* 19: 101-113 (2011); Idusogie E et al. *J Immunol* 164: 4178-4184 (2000)). In some embodiments, the antibody component is varied in that it possesses some but not all antibody effector functions, which make it a desirable candidate for applications in which the half-life of the binding molecule in vivo is important yet certain effector functions (e.g. CDC or ADCC) are undesirable or deleterious.

In some embodiments, the antibody component comprises an Fc region with one or more amino acid substitutions which improve ADCC, e.g., substitutions at positions 298, 333, and/or 334 of the Fc region (EU numbering of residues).

In some embodiments, the antibody component comprises an Fc region with one or more amino acid substitutions resulting in altered C1q binding and/or CDC effector function (e.g. either improved or diminished) (see e.g. WO 1999/051642; U.S. Pat. No. 6,194,551).

d) Glycosylation Variants

In some embodiments, the antibody component of the binding molecule (e.g. an antibody-toxin conjugate) is altered to increase or decrease the extent to which the antibody is glycosylated. Addition or deletion of glycosylation sites to an antibody may be conveniently accomplished by altering the amino acid sequence such that one or more glycosylation sites is created or removed. For example, an antibody component comprising a glycosylated Fc region may be altered such that the carbohydrate attached thereto is altered. In another example, the carbohydrate attached to an antibody component may be altered using methods known to the skilled worker.

e) Cysteine Engineered Antibody Variants

In some embodiments, the antibody component of the binding molecule (e.g. an antibody-toxin conjugate) possesses one or more engineered cysteine residues. In some embodiments of the antibody, it may be desirable to create cysteine engineered antibodies, such as, e.g, in which one or more residues of an antibody are substituted with cysteine residues (e.g. a ThioFab). In some embodiments, the substituted residues occur at sites of the antibody that are readily available for conjugation (see e.g. Junutula J et al., Nature Biotech 26: 925-32 (2008); Dornan D et al, *Blood* 114: 2721-29 (2009)). By substituting those residues with cysteine, reactive thiol groups are thereby positioned at accessible sites of the antibody and may be used to conjugate the antibody to other moieties, such as drug moieties or linker-drug moieties, to create an immunoconjugates as described further herein. In some embodiments of the antibody, it may be desirable to create cysteine engineered antibodies via one or more cysteine residue substitutions that do not significantly perturb antibody folding and assembly nor significantly alter antigen binding and/or antibody effector functions.

2. Immunoconjugates

Also provided herein are various embodiments of PD-L1 binding molecules, wherein each PD-L1 binding molecule comprises (1) at least one toxin component and (2) at least one PD-L1 binding region capable of specifically binding an extracellular part of a PD-L1 molecule, including immunoconjugates comprising an anti-PD-L1 antibody conjugated to one or more toxins components (e.g. protein toxins, enzymatically active toxins of bacterial, fungal, plant, or animal origin, or fragments thereof). An "immunoconjugate" is an antibody (including an antigen-binding antibody fragment) conjugated to one or more heterologous molecule(s), including but not limited to a cytotoxic agent.

In some embodiments of the binding molecule, the immunoconjugate is an antibody-toxin conjugate, which is an antibody conjugated to a toxin, such as, e.g., diphtheria A chain, exotoxin A chain (from *P. aeruginosa*), ricin A chain, abrin A chain, modeccin A chain, alpha-sarcin, *Aleurites fordii* protein, dianthin protein, *Phytolaca americana* protein (e.g. PAPI, PAPII, or PAP-S), *Momordica charantia* inhibitor, curcin, crotin, *Sapaonaria officinalis* inhibitor, gelonin, mitogellin, restrictocin, phenomycin, enomycin, Shiga toxin A Subunit, and tricothecenes. Biological immunoconjugates comprising a toxin (e.g. a Shiga toxin A subunit fragment) linked to a PD-L1 binding region (e.g. an antibody or antibody fragment) are useful as therapeutic or diagnostic biological molecules. In addition, such therapeutic or diagnostic molecules may be improved by having a Shiga toxin effector polypeptide conjugated to an additional agent such as, e.g., a solubility-altering agent, pharmacokinetic-altering agent, immunogenicity-altering agent, and/or a pharmacodynamic-altering agent (see e.g. WO 2018/106895). Typically, biopharmaceutical immunoconjugates are created by conjugating an antibody to other agents or cargos using chemical reactions involving a functional group(s) of the biological molecule and a functional group of the agent or cargo, or alternatively of a linker designed to bridge between the biological molecule and the agent or cargo (see section II. Linkages Connecting Components and/or Their Subcomponents, supra).

In some embodiments, the binding molecule is an immunoconjugate utilizing a cysteine engineered into the PD-L1 binding region, such as, e.g., wherein the binding molecule comprises a cysteine engineered antibody. In some embodiments, the binding molecule is an immunoconjugate utilizing a cysteine engineered into the framework region (e.g. FR1) of an immunoglobulin variable region for conjugation (see e.g. WO 2011/000054).

In some embodiments, the binding molecule is an immunoconjugate utilizing a carbohydrate moiety attached to a Fc region, such as, e.g., wherein the binding molecule comprises a glycosylated antibody or antibody fragment.

In some embodiments, the binding molecule is an immunoconjugate comprising an antibody or antibody fragment and a Shiga toxin A subunit effector polypeptide.

The toxin component of a binding molecule or antibody toxin conjugate as described herein may include, but is not limited to, natural toxins, biotoxins, proteinaceous toxins, venom, cytotoxins, small molecule toxins, and synthetic toxicants derived from any of the aforementioned, such as, e.g., aconitine, adriamycin, amanitin, amatoxin, anthracycline, aroin, apitoxin, atropine, bufotoxin, cardiac glycoside, calicheamicin, celandine, cicutoxin, colchicine, coniine, convallatoxin, crotamine, curare, curcin, dauricine, *digitalis*, dolastatin, duocarmycin, evomonoside, grayanotoxin, gel semine, gel seminine, hellebrin, helleborin, hyoscyamine, ligatoxin, ligustrin, maytansine, mitomycin C, muscarine, phallotoxin, phoratoxin, phytotoxin, picrotoxin, sea nettle toxin, taxine alkaloid, thionin, *vinca* alkaloid, viscotoxin, and various toxin agents described herein. Pharmaceutically active cytotoxins suitable for use as a toxin component also include, but are not limited to ABx toxins, ribosome inactivating protein toxin, anthrax toxin, cholix toxin, claudin, diphtheria toxin, heat-labile enterotoxin, pertussis toxin, *Pseudomonas* exotoxin A, ricin, Shiga toxin, and subtilase cytotoxin; alkylating agents (such as, e.g. bendamustine, busulfan, carmustine, chlorambucil, cyclophosphamide, etramustine, ifosfamide, lomustine, mechlorethamine, melphalan, mustine, thiotepa, and treosulfan), antibiotics (such as, e.g. anthracyclines), anti-microtubule agens (such as, e.g. *vinca* alkaloids like vincristine, vinblastine, and etoposide or toxoids like paclitaxel and docetaxel), intercalating agents (such as, e.g. daunorubicin, bleomycin, dactinomycin, doxorubicin, epirubicin, mitoxatrone, idarubicin, plicamycin, mitomycin, and steptozotocin), anti-metabolites (such as, e.g. methotrexate, pyrimidine antagonists, and purine antagonists), growth inhibitory agents (such as topoisomerase inhibitors and spindle poisons like camptothecin, colchicine, daunorubicin, fisetin, genistein, irinotecan, lamellarins, myricetin, paclitaxel, thaspine, tricitrinol B, topotecan, *vinca* alkaloids); enzymes and fragments thereof such as nucleolytic enzymes like asparaginase and certain RNAses such as, e.g., bacterial RNases, fungal ribotoxins, argonaute polypeptides, binase, amphibian RNases, ranpirnase, ONCONASE® (Ranpirnase), and mammalian RNases, such as, e.g., bovine semen RNase and the human RNases; toxins such as small molecule toxins or enzymatically active toxins of bacterial, fungal, plant or animal origin, including fragments and/or variants thereof, such as, e.g., abrins, agrostin, amarandins, amaranthin, *Amaranthus* antiviral/RIP, angiogenin, *A. patens* RIPs, Articulatin D, asparins, aspergillin, Aspfl, balsamin, *B. hispida* RIP, bouganin, *Bougainvillea* x *buttiana* antiviral protein1, benincasins, bouganin, *B. rubra* RIPs, bryodins (e.g. bryodin 1, bryodin 2), *B. spectabilis* RIPs, *B. vulgaris* RIPs, *C. album* RIPs, camphorin, *C. aculeatum*-systemic resistance inducing protein, *C. cristata* RIPs, *C. figarei* RIPs, charantin, charybdin, cinnamomin, clavin, *C. moschata* RIP, cochinin B, colocins, crotins, cucurmosin, curcins, *Dianthus* spp. RIPs, *Corynebacterium* spp. diphtheria toxins (diphtheria toxins in *C. ulcerans, C. omega, C. pseudotuberculosis*), dodecandrins, ebulins, ebulitins, *E. hyemalis* RIPs, euserratins, eutirucallin, flammin, flammulin, foetidissimin, gelonin, gigantin, gypsophilin, *H. crepitans* RIPs, Heterotepalin, hispin, hirsutellin A, *H. orientalis* RIPs, *H. vulgare* RIPs, hypsin, insularin, *I. hollandica* RIPs, lagenin, lamjapin, lanceolin, *L. cylindrical* RIPs, luffacylin, luffaculin, luffagulin, luffins, *L. usitatissimum* RIPs, lychnin, lyophyllin, manutins, marmorin, mapalmin, *M. charantia* lectin, *M. crystallinum* RIPs, melonin, mexin, *Mirabilis* spp. RIPs, mitogillin, modeccins, MORs, *Mormordica* spp. RIPs, momorsgrovin, moschatin, musarmins, *N. tabacum* RIPs, nigrins, nigritins, ocymoidin, pachyerosin, *P. californicum* lectin, pepocin, petroglaucin, petrograndin, *Phytolacca* spp. RIPs, pisavin, pleuturegin, Pluturegin, *A. thaliana* pectin methyl transferase (PME), *P. multiforum* RIPs, pokeweed antiviral protein (PAP), porrectin, *Aeromonas* spp. *Pseudomonas* toxins (*A. hydrophila pseudomonas*-like toxin), pulchellin, quinqueginsin, *R. communis* agglutinins, restrictocin, ricins, riproximin, saporins, sarcins, sativin, *S. cereale* RIPs, sechiumin, Shiga toxin, Shiga-like toxins, sieboldin b, *S. nigra* RIPs (e.g. *S. nigra* agglutinins I-V), *S. ocymoides* RIPs, *Spinacia oleracea* protein, stellarin, stenodactylin, texanin, tricholin, *Trichosanthes* spp. RIPs (e.g. karasurins, kirilowins, trichoanguin, trichokirins, trichosanthins, TYchi), *Triticum* spp. RIPs, *V. album* RIPs, velin, velutin, verotoxins, *V. hispanica* RIPs, vircumin, volkensin, *V. volvacea* RIPs, Volvarin, *Yucca* leaf protein, *Z. diploperennis* RIPs, *Z. mays* RIPs, and any ribotoxic fragment of any of the foregoing; and the various antitumor or anticancer agents described herein.

There are numerous proteinaceous toxins suitable for use as a toxin component as described herein. For example, argonaute enzymatic domains or hybrid enzymatic domains composed of fungal ribotoxins and argonaute sequences may be engineered for ribosome inactivation (see Pichinuk E, Wreschner D, *Protein Sci* 19: 1272-8 (2010)). Examples of RNases with enzymatic domains useful as ribotoxic regions include bacterial RNases, such as, e.g., binase, amphibian RNases, such as e.g., ranpirnase and ONCONASE® (Ranpirnase), and mammalian RNases, such as, e.g., bovine semen RNase and the human RNases: RNase2, RNase3, and RNase5 (Newton D et al., *J Biol Chem* 269: 739-45 (1994); Netwon D et al., *J Immunol Meth* 231: 159-67 (1999); Yoon J et al., *Life Sci* 64: 1435-45 (1999); Hugh M et al., *Cancer Res* 61: 8737-42 (2001); Makarov A, Ilinskaya N, *FEBS Lett* 540: 15-20 (2003)).

TABLE 5

Exemplary Protein Toxins and Sources of Toxin Effector Polypeptides

| Protein Toxin | Substrate - Subcellular Location |
| --- | --- |
| Abrins | sarcin-ricin loop - cytosol |
| Anthrax lethal factor | MAPKK - cytosol |
| Aspf1 | sarcin-ricin loop - cytosol |
| Bouganin | sarcin-ricin loop - cytosol |
| Bryodins | sarcin-ricin loop - cytosol |
| Cholix toxin | heterotrimeric G protein - cytosol |
| Cinnamomin | sarcin-ricin loop - cytosol |
| Claudin | sarcin-ricin loop - cytosol |
| Clavin | sarcin-ricin loop - cytosol |
| *C. difficile* Tcd A | Ras GTPases - cytosol |
| *C. difficile* Tcd A | Rho GTPases - cytosol |
| *C. perfringens* iota | Rho GTPases - cytosol |
| cytolethal distending | DNA - nucleus |
| Dianthins | sarcin-ricin loop - cytosol |
| Diphtheria toxins | elongation factor-2 (EF2) - cytosol |
| Ebulins | sarcin-ricin loop - cytosol |
| Gelonin | sarcin-ricin loop - cytosol |
| Gigantin | sarcin-ricin loop - cytosol |
| heat-labile enterotoxins | heterotrimeric G protein - cytosol |
| Maize RIPs | sarcin-ricin loop - cytosol |
| Mitogillin | sarcin-ricin loop - cytosol |
| Nigrins | sarcin-ricin loop - cytosol |
| Pertussis toxins | heterotrimeric G protein - cytosol |
| PD-Ls | sarcin-ricin loop - cytosol |
| PAPs | sarcin-ricin loop - cytosol |
| *Pseudomonas* toxins | elongation factor-2 (EF2) - cytosol |
| Pulchellin | sarcin-ricin loop - cytosol |
| Restrictocin | sarcin-ricin loop - cytosol |
| Ricins | sarcin-ricin loop - cytosol |
| Saporins | sarcin-ricin loop - cytosol |
| Sarcins | sarcin-ricin loop - cytosol |
| Shiga toxins | sarcin-ricin loop - cytosol |
| Subtilase cytotoxins | endoplasmic chaperon - ER |
| Trichosanthins | sarcin-ricin loop - cytosol |

IV. General Functions of the Binding Molecules

The binding molecules are useful in diverse applications involving, e.g., cell-killing; cell growth inhibition; intracellular, cargo delivery; biological information gathering; immune response stimulation, and/or remediation of a health condition. The binding molecules are useful as therapeutic and/or diagnostic molecules, such as, e.g., as cell-targeting, cytotoxic, therapeutic molecules; cell-targeting, nontoxic, delivery vehicles; and/or cell-targeting, diagnostic molecules; for examples in applications involving the in vivo targeting of specific cell types for the diagnosis or treatment of a variety of diseases, including cancers, immune disorders, and microbial infections.

In some embodiments, the binding molecules are capable of binding an extracellular part of PD-L1 molecules associated with cell surfaces of particular cell types and entering those cells. Once internalized within a targeted cell type, certain embodiments of the binding molecules are capable of killing the cell via the action(s) of the toxin component. For example, once internalized within a targeted cell type, certain embodiments of the binding molecules are capable of routing an enzymatically active, cytotoxic, Shiga toxin effector polypeptide fragment into the cytosol of the target cell and eventually killing the cell. In another example, once internalized within a targeted cell type, certain embodiments of the binding molecules are capable of delivering a $CD_8+$ T-cell epitope cargo to the MHC class I presentation pathway of the target cell due to the action of the toxin component, leading to cell-surface presentation of that epitope complexed with a MHC class I molecule, and eventually resulting in the death of the cell. In another example, once internalized within a targeted cell type, certain embodiments of the binding molecules are capable of delivering a cytotoxic cargo to the target cell due to the action of the toxin component thereby resulting in the death of the cell.

Alternatively, nontoxic or reduced-toxicity variants of the binding molecules may be used to deliver additional exogenous materials into target cells, such as epitopes, peptides, proteins, polynucleotides, and detection-promoting agents. This system is modular, in that any number of diverse toxin components may be associated with a PD-L1 binding region(s) to produce variants of the binding molecule with different functional characteristics, such as, e.g. de-immunized toxin effectors for applications involving administration of the binding molecule to a chordate, reduced protease-cleavage sensitive toxin effectors to improve stability particularly in vivo, and toxin effectors comprising a CD8+ T-cell epitope for immunotherapy applications.

A. Cell-Kill Via Toxin Component Cytotoxicity

Some embodiments of the binding molecules are cytotoxic. Some embodiments of the binding molecules are cytotoxic only due to the presence of one or more Shiga toxin effector polypeptide components. The A Subunits of members of the Shiga toxin family each comprise an enzymatically active polypeptide region capable of killing a eukaryotic cell once in the cell's cytosol. Because members of the Shiga toxin family are adapted to killing eukaryotic cells, molecules derived from Shiga toxins, such as, e.g., PD-L1 binding molecules comprising certain embodiments of the Shiga toxin effector polypeptides can exhibit potent cell-kill activities.

In some embodiments, upon contacting a cell physically coupled with PD-L1 bound by the binding region of the binding molecule (e.g. a PD-L1 positive cell), the binding molecule is capable of causing death of the cell. For some embodiments, the $CD_{50}$ value of the binding molecule is less than 5, 2.5, 1, 0.5, or 0.25 nM, which is vastly more potent than an untargeted, wild-type, Shiga toxin effector polypeptide (e.g. SEQ ID NOs: 1-18).

Cell-kill may be accomplished using a molecule described herein under varied conditions of target cells, such as, e.g., an ex vivo manipulated target cell, a target cell cultured in vitro, a target cell within a tissue sample cultured in vitro, or a target cell in an in vivo setting like within a multicellular organism.

In some embodiments, the Shiga toxin effector polypeptides and binding molecules comprise (1) a de-immunized, Shiga toxin effector sub-region, (2) a protease-cleavage resistant region near the carboxy-terminus of a Shiga toxin A1 fragment derived region, (3) a carboxy-terminal, endoplasmic reticulum retention/retrieval signal motif; and/or (4) a heterologous, T-cell epitope embedded or inserted region; however, for some embodiments, these structural modifications do not significantly alter the potency of Shiga toxin cytotoxicity as compared to reference molecules comprising a wild-type Shiga toxin A Subunit polypeptide, such as, e.g., a wild-type Shiga toxin A1 fragment. Thus, Shiga toxin effector polypeptides and binding molecules which are de-immunized, protease cleavage resistant, and/or carrying embedded or inserted, heterologous, epitopes can maintain potent cytotoxicity while providing one or more various other functionalities or properties.

Already cytotoxic binding molecules comprising Shiga toxin effector polypeptides may be engineered by the skilled worker using the information and methods provided herein to be more cytotoxic and/or to have redundant, backup cytotoxicities operating via completely different mechanisms. These multiple cytotoxic mechanisms may complement each other by their diversity of functions (such as by providing potent killing via two mechanisms of cell-killing, direct and indirect, as well as mechanisms of immuno-stimulation to the local area), redundantly backup each other (such as by providing one cell-killing mechanism in the absence of the other mechanisms—like if a target cell is resistant to or acquires some immunity to a subset of previously active mechanisms), and/or protect against developed resistance (by limiting resistance to the less probable situation of the malignant or infected cell blocking multiple, different cell-killing mechanisms simultaneously).

B. Delivery of a T-Cell Epitope for MHC Class I Presentation on a Cell Surface

In some embodiments, the binding molecules comprise a T-cell epitope, which enables the engineering of "T-cell epitope delivering" molecules with virtually unlimited choices of epitope-peptide cargos for delivery and cell-surface presentation by a nucleated, chordate cell. In some embodiments, the binding molecules comprises a toxin effector comprising a T-cell epitope. In some embodiments, the binding molecules are capable via their toxin component of delivering one or more T-cell epitopes to the proteasome of a cell. The delivered T-cell epitope are then proteolytic processed and presented by the MHC class I pathway on the surface of the cell. By engineering MHC class I epitopes into binding molecules, the targeted delivery and presentation of immuno-stimulatory antigens may be accomplished in order to harness and direct a beneficial function(s) of a chordate immune system.

In some embodiments, the Shiga toxin effector polypeptide or binding molecule is capable of delivering a T-cell epitope to a MHC class I molecule of a cell for cell-surface presentation. In some embodiments, the Shiga toxin effector polypeptide or binding molecule comprises a heterologous, T-cell epitope, whether as an additional exogenous material or embedded or inserted within a Shiga toxin effector polypeptide. For some embodiments, the Shiga toxin effector polypeptide or binding molecule is capable of delivering an embedded or inserted T-cell epitope to a MHC class I molecule for cell-surface presentation.

In some embodiments, the Shiga toxin effector polypeptide is capable of delivering a T-cell epitope, which is embedded or inserted in the Shiga toxin effector polypeptide, to a MHC class I molecule of a cell in which the Shiga toxin effector polypeptide is present for presentation of the T-cell epitope by the MHC class I molecule on a surface of the cell. For some embodiments, the T-cell epitope is a heterologous, T-cell epitope. For some embodiments, the T-cell epitope functions as CD8+ T-cell epitope, whether already known or identified in the future using methods which are routine to the skilled worker.

In some embodiments, the binding molecule is capable of delivering a T-cell epitope, which is associated with the binding molecule, to a MHC class I molecule of a cell for presentation of the T-cell epitope by the MHC class I molecule on a surface of the cell. For some embodiments, the T-cell epitope is a heterologous, T-cell epitope which is embedded or inserted in the Shiga toxin effector polypeptide. For some embodiments, the T-cell epitope functions as CD8+ T-cell epitope, whether already known or identified in the future using methods which are routine to the skilled worker.

In some embodiments, upon contacting a cell with the binding molecule, the binding molecule is capable of delivering a T-cell epitope-peptide, which is associated with the binding molecule, to a MHC class I molecule of the cell for presentation of the T-cell epitope-peptide by the MHC class I molecule on a surface of the cell. For some embodiments, the T-cell epitope-peptide is a heterologous epitope which is embedded or inserted in a Shiga toxin effector polypeptide. For some embodiments, the T-cell epitope-peptide functions as CD8+ T-cell epitope, whether already known or identified in the future using methods which are routine to the skilled worker.

The addition of a heterologous epitope into or presence of a heterologous epitope in a binding molecule, whether as an additional exogenous material or embedded or inserted within a Shiga toxin effector polypeptide, enables methods of using such binding molecules for the cell-targeted delivery of a chosen epitope for cell-surface presentation by a nucleated, target cell within a chordate.

One function of certain, CD8+ T-cell hyper-immunized, Shiga toxin effector polypeptides and binding molecules is the delivery of one or more T-cell epitope-peptides to a MHC class I molecule for MHC class I presentation by a cell. Delivery of exogenous, T-cell epitope-peptides to the MHC class I system of a target cell can be used to induce the target cell to present the T-cell epitope-peptide in association with MHC class I molecules on the cell surface, which subsequently leads to the activation of CD8+ effector T-cells to attack the target cell.

The skilled worker, using techniques known in the art, can associate, couple, and/or link certain, Shiga toxin effector polypeptides to various other PD-L1-targeting binding regions to create binding molecules which target specific, extracellular, target biomolecules physically coupled to cells and promote target-cell internalization of these binding molecules. All nucleated vertebrate cells are believed to be capable of presenting intracellular epitopes using the MHC class I system. Thus, extracellular target biomolecules of the binding molecules may in principle target any nucleated vertebrate cell for T-cell epitope delivery to a MHC class I presentation pathway of such a cell.

The epitope-delivering functions of the Shiga toxin effector polypeptides and binding molecules can be detected and monitored by a variety of standard methods known in the art to the skilled worker and/or described herein. For example, the ability of binding molecules to deliver a T-cell epitope-peptide and drive presentation of the epitope-peptide by the MHC class I system of target cells may be investigated using various in vitro and in vivo assays, including, e.g., the direct detection/visualization of MHC class I/peptide complexes, measurement of binding affinities for the heterologous, T-cell epitope-peptide to MHC class I molecules, and/or measurement of functional consequences of MHC class I-peptide complex presentation on target cells by monitoring cytotoxic T-lymphocyte (CTL) responses (see e.g. Examples, infra).

Certain assays to monitor this function of the polypeptides and molecules involve the direct detection of a specific MHC class I/peptide antigen complex in vitro or ex vivo. Common methods for direct visualization and quantitation of peptide-MHC class I complexes involve various immuno-detection reagents known to the skilled worker. For example, specific monoclonal antibodies can be developed to recognize a particular MHC/class I/peptide antigen complex. Similarly, soluble, multimeric T cell receptors, such as the TCR-STAR reagents (Altor Bioscience Corp., Mirmar, FL, U.S.A.) can be used to directly visualize or quantitate specific WIC I/antigen complexes (Zhu X et al., *J Immunol* 176: 3223-32 (2006)). These specific mAbs or soluble, multimeric T-cell receptors may be used with various detection methods, including, e.g. immunohistochemistry, flow cytometry, and enzyme-linked immuno assay (ELISA).

An alternative method for direct identification and quantification of MHC I/peptide complexes involves mass spectrometry analyses, such as, e.g., the ProPresent Antigen Presentation Assay (ProImmune, Inc., Sarasota, FL, U.S.A.) in which peptide-MCH class I complexes are extracted from the surfaces of cells, then the peptides are purified and identified by sequencing mass spectrometry (Falk K et al., *Nature* 351: 290-6 (1991)).

In certain assays to monitor the T-cell epitope delivery and WIC class I presentation function of the polypeptides and molecules described herein involve computational and/or experimental methods to monitor WIC class I and peptide binding and stability. Several software programs are available for use by the skilled worker for predicting the binding responses of peptides to MHC class I alleles, such as, e.g., The Immune Epitope Database and Analysis Resource (IEDB) Analysis Resource MHC-I binding prediction Consensus tool (Kim Y et al., *Nucleic Acid Res* 40: W525-30 (2012). Several experimental assays have been routinely applied, such as, e.g., cell surface binding assays and/or surface plasmon resonance assays to quantify and/or compare binding kinetics (Miles K et al., *Mot Immunol* 48: 728-32 (2011)). Additionally, other WIC-peptide binding assays based on a measure of the ability of a peptide to stabilize the ternary WIC-peptide complex for a given MHC class I allele, as a comparison to known controls, have been developed (e.g., WIC-peptide binding assay from ProImmmune, Inc.).

Alternatively, measurements of the consequence of WIC class I/peptide antigen complex presentation on the cell surface can be performed by monitoring the cytotoxic T-cell (CTL) response to the specific complex. These measurements by include direct labeling of the CTLs with WIC class I tetramer or pentamer reagents. Tetramers or pentamers bind directly to T cell receptors of a particular specificity, determined by the Major Histocompatibility Complex (MHC) allele and peptide complex. Additionally, the quantification of released cytokines, such as interferon gamma or interleukins by ELISA or enzyme-linked immunospot (ELIspot) is commonly assayed to identify specific CTL responses. The cytotoxic capacity of CTL can be measured using a number of assays, including the classical 51 Chromium (Cr) release assay or alternative non-radioactive cytotoxicity assays (e.g., CYTOTOX96 ® non-radioactive kits and CELLTOX™ CELLTITER-GLO® (cell viability) kits available from Promega Corp., Madison, WI, U.S.A.), Granzyme B ELISpot, Caspase Activity Assays or LAMP-1 translocation flow cytometric assays. To specifically monitor the killing of target cells, carboxyfluorescein diacetate succinimidyl ester (CF SE) can be used to easily and quickly label a cell population of interest for in vitro or in vivo investigation to monitor killing of epitope specific CSFE labeled target cells (Durward M et al., *J Vis Exp* 45 pii 2250 (2010)).

In vivo responses to MHC class I presentation can be followed by administering a MHC class Pantigen promoting agent (e.g., a peptide, protein or inactivated/attenuated virus vaccine) followed by challenge with an active agent (e.g. a virus) and monitoring responses to that agent, typically in comparison with unvaccinated controls. Ex vivo samples can be monitored for CTL activity with methods similar to those described previously (e.g. CTL cytotoxicity assays and quantification of cytokine release).

HLA-A, HLA-B, and/or HLA-C molecules are isolated from the intoxicated cells after lysis using immune affinity (e.g., an anti-MHC antibody "pulldown" purification) and the associated peptides (i.e., the peptides presented by the isolated MHC molecules) are recovered from the purified complexes. The recovered peptides are analyzed by sequencing mass spectrometry. The mass spectrometry data is compared against a protein database library consisting of the sequence of the exogenous (non-self) peptide (T-cell epitope X) and the international protein index for humans (representing "self" or non-immunogenic peptides). The peptides are ranked by significance according to a probability database. All detected antigenic (non-self) peptide sequences are listed. The data is verified by searching against a scrambled decoy database to reduce false hits (see e.g. Ma B, Johnson R, *Mol Cell Proteomics* 11: O111.014902 (2012)). The results will demonstrate that peptides from the T-cell epitope X are presented in MHC complexes on the surface of intoxicated target cells.

The set of presented peptide-antigen-MHC complexes can vary between cells due to the antigen-specific HLA molecules expressed. T-cells can then recognize specific peptide-antigen-MHC complexes displayed on a cell surface using different TCR molecules with different antigen-specificities.

Because multiple T-cell epitopes may be delivered by a binding molecule, such as, e.g., by embedding two or more different T-cell epitopes in a single proteasome delivering effector polypeptide, a single binding molecule may be effective chordates of the same species with different MHC class variants, such as, e.g., in humans with different HLA alleles. This may allow for the combining within a single molecule of different T-cell epitopes with different effectiveness in different sub-populations of subjects based on MHC complex protein diversity and polymorphisms. For example, human MHC complex proteins, HLA proteins, vary among humans based on genetic ancestry, e.g. African (sub-Saharan), Amerindian, Caucasiod, Mongoloid, New Guinean and Australian, or Pacific islander.

The applications involving the T-cell epitope delivering polypeptides and molecules are vast. Every nucleated cell in a mammalian organism may be capable of WIC class I pathway presentation of immunogenic, T-cell epitope-peptides on their cell outer surfaces complexed to MHC class I molecules. In addition, the sensitivity of T-cell epitope recognition is so exquisite that only a few MHC-I peptide complexes are required to be presented to result in an immune response, e.g., even presentation of a single complex can be sufficient for recognition by an effector T-cell (Sykulev Y et al., *Immunity* 4: 565-71 (1996)).

The activation of T-cell responses are desired characteristics of certain anti-cancer, anti-neoplastic, anti-tumor, and/or anti-microbial biologic drugs to stimulate the patient's own immune system toward targeted cells. Activation of a robust and strong T-cell response is also a desired characteristic of many vaccines. The presentation of a T-cell epitope by a target cell within an organism can lead to the activation of robust immune responses to a target cell and/or its general locale within an organism. Thus, the targeted delivery of a T-cell epitope for presentation may be utilized for as a mechanism for activating T-cell responses during a therapeutic regime.

The presentation of a T-cell immunogenic epitope-peptide by the WIC class I system targets the presenting cell for killing by CTL-mediated lysis and also triggers immune stimulation in the local microenvironment. By engineering immunogenic epitope sequences within Shiga toxin effector polypeptide components of target-cell-internalizing therapeutic molecules, the targeted delivery and presentation of immuno-stimulatory antigens may be accomplished. The presentation of immuno-stimulatory non-self antigens, such as e.g. known viral antigens with high immunogenicity, by target cells signals to other immune cells to destroy the target cells as well as to recruit more immune cells to the area.

The presentation of an immunogenic, T-cell epitope-peptide by the MHC class I complex targets the presenting cell for killing by CTL-mediated cytolysis. The presentation by targeted cells of immuno-stimulatory non-self antigens, such as, e.g., known viral epitope-peptides with high immunogenicity, can signal to other immune cells to destroy the target cells and recruit more immune cells to the target cell site within a chordate.

Thus, already cytotoxic molecules, such as e.g. therapeutic or potentially therapeutic molecules comprising Shiga toxin effector polypeptides, may be engineered using methods as described herein into more cytotoxic molecules and/or to have an additional cytotoxic mechanism operating via delivery of a T-cell epitope, presentation, and stimulation of effector T-cells. These multiple cytotoxic mechanisms may complement each other (such as by providing both direct target-cell-killing and indirect (CTL-mediated) cell-killing, redundantly backup each other (such as by providing one mechanism of cell-killing in the absence of the other), and/or protect against the development of therapeutic resistance (by limiting resistance to the less probable situation of the malignant or infected cell evolving to block two different cell-killing mechanisms simultaneously).

In addition, a cytotoxic molecule comprising a Shiga toxin effector polypeptide region that exhibits catalytic-based cytotoxicity may be engineered by the skilled worker using routine methods into enzymatically inactive variants. For example, the cytotoxic Shiga toxin effector polypeptide component of a cytotoxic molecule may be conferred with reduced activity and/or rendered inactive by the introduction of one or mutations and/or truncations such that the resulting molecule can still be cytotoxic via its ability to deliver a T-cell epitope to the MHC class I system of a target cell and subsequent presentation to the surface of the target cell. In another example, a T-cell epitope may be inserted or embedded into a Shiga toxin effector polypeptide such that the Shiga toxin effector polypeptide is inactivated by the added epitope (see e.g. WO 2015/113005: Example 1-F). This approach removes one cytotoxic mechanism while retaining or adding another and may also provide a molecule capable of exhibiting immuno-stimulation to the local area of a target cell(s) within an organism via delivered T-cell epitope presentation or "antigen seeding." Furthermore, non-cytotoxic variants of the binding molecules which comprise embedded or inserted, heterologous, T-cell epitopes may be useful in applications involving immune-stimulation within a chordate and/or labeling of target cells within a chordate with MHC class I molecule displayed epitopes.

The ability to deliver a T-cell epitope of certain Shiga toxin effector polypeptides and binding molecules may be accomplished under varied conditions and in the presence of non-targeted bystander cells, such as, e.g., an ex vivo manipulated target cell, a target cell cultured in vitro, a target cell within a tissue sample cultured in vitro, or a target cell in an in vivo setting like within a multicellular organism.

C. Cell-Kill Via Targeted Cytotoxicity and/or Engagement of Cytotoxic T-Cells

In some embodiments, the binding molecule can provide 1) delivery of a T-cell epitope for MHC class I presentation by a target cell and/or 2) potent cytotoxicity. In some embodiments of the binding molecules, upon contacting a cell physically coupled with an extracellular PD-L1 bound by the cell-targeting binding region, the binding molecule is capable of causing death of the cell. The mechanism of cell-kill may be direct, e.g. via the enzymatic activity of a toxin effector polypeptide region, or indirect via CTL-mediated cytolysis.

1. Indirect Cell-Kill Via T-Cell Epitope Delivery and MHC Class I Presentation

Certain embodiments of the binding molecules are cytotoxic because they comprise a CD8+ T-cell epitope capable of being delivered to the MHC class I presentation pathway of a target cell and presented on a cellular surface of the target cell. For example, T-cell epitope delivering, CD8+ T-cell hyper-immunized, Shiga toxin effector polypeptides, with or without endogenous epitope de-immunization, may be used as components of binding molecules for applications involving indirect cell-killing.

In certain embodiments of the binding molecules, upon contacting a cell physically coupled with extracellular PD-L1 bound by the cell-targeting binding region, the binding molecule is capable of indirectly causing the death of the cell, such as, e.g., via the presentation of one or more T-cell epitopes by the target cell and the subsequent recruitment of CTLs which kill the target cell. In some embodiments, the recruitment involves an endogenous CTL specific to an antigen cargo of the binding molecule.

The presentation of an antigenic peptide complexed with a MHC class I molecule by a cell sensitizes the presenting cell to targeted killing by cytotoxic T-cells (CTLs) via the induction of apoptosis, lysis, and/or necrosis. In addition, the CTLs which recognize the target cell may release immuno-stimulatory cytokines, such as, e.g., interferon gamma (IFN-gamma), tumor necrosis factor alpha (TNF), macrophage inflammatory protein-1 beta (MIP-1beta), and interleukins such as IL-17, IL-4, and IL-22. Furthermore, CTLs activated by recognition of a presented epitope may indiscriminately kill other cells proximal to the presenting cell regardless of the peptide-MHC class I complex repertoire presented by those proximal cells (Wiedemann A et al., *Proc Natl Acad Sci USA* 103: 10985-90 (2006)).

Because of MHC allele diversity within different species, a binding molecule comprising only a single epitope may exhibit varied effectiveness to different patients or subjects of the same species. However, certain embodiments of the binding molecules may each comprise multiple, T-cell epitopes that are capable of being delivered to the MHC class I system of a target cell simultaneously. Thus, in some embodiments of the binding molecules, a binding molecule is used to treat different subjects with considerable differences in their MHC molecules' epitope-peptide binding affinities (i.e. considerable differences in their MHC alleles and/or MHC genotypes). In addition, certain embodiments of the binding molecules reduce or prevent target cell adaptations to escape killing (e.g. a target cancer cell mutating to escape therapeutic effectiveness or "mutant escape") by using multiple cell-killing mechanisms simultaneously (e.g. direct killing and indirect killing via multiple different T-cell epitopes simultaneously).

In some embodiments, the binding molecules induce target cell-killing via at least two distinct mechanisms of action, Shiga toxin A Subunit effector activity and antigenic peptide delivery to promote immune activation, which may function cooperatively to induce more target cell death in the presence of certain MHC class I epitope-specific restricted CD8+ T-cells. In some embodiments of the binding molecules which induce target cell-killing via two distinct mechanisms of action, Shiga toxin A Subunit effector activity and antigenic peptide delivery to promote immune activation, the resulting target cell killing is additive or synergistic as compared to either killing mechanism in isolation.

2. Direct Cell-Kill Via Cell-Targeted, Shiga Toxin Cytotoxicity

Certain embodiments of the binding molecules are cytotoxic because they comprise a catalytically active toxin component and regardless of the presence of an immunogenic, CD8+ T-cell epitope in the molecule. For example, CD8+ T-cell hyper-immunized, Shiga toxin effector or Diphtheria toxin effector polypeptides, with or without endogenous epitope de-immunization, may be used as components of binding molecules for applications involving direct cell-killing, such as, e.g., via the ribotoxic, enzymatic activity of a Shiga toxin effector polypeptide or ribosome binding and interference with ribosome function due to a non-catalytic mechanism(s) (see e.g. WO 2015/113005). Certain binding molecules can permanently inactivate ribosomes within target cells.

In some embodiments of the CD8+ T-cell hyper-immunized, binding molecules, upon contacting a cell physically coupled with extracellular PD-L1 bound by the cell-targeting binding region, the binding molecule is capable of directly causing the death of the cell, such as, e.g., without the involvement of a untargeted, cytotoxic T-cell (see Section V-D, supra).

In some embodiments, the binding molecules is capable, upon contacting a PD-L1 positive peripheral blood mononuclear cell, the binding molecule, of causing the death of the PD-L1 positive peripheral blood mononuclear cell, such as, e.g., in vivo.

C. Selective Cytotoxicity Among Cell Types

Certain binding molecules have uses in the selective killing of specific target cells in the presence of untargeted, bystander cells. By targeting the delivery of a toxin component to specific cells via a cell-targeting binding region(s), the binding molecules can exhibit cell-type specific, restricted cell-kill activities resulting in the exclusive or preferential killing selected cell types in the presence of untargeted cells. Similarly, by targeting the delivery of immunogenic T-cell epitopes to the MHC class I pathway of target cells, the subsequent presentation of T-cell epitopes and CTL-mediated cytolysis of target cells induced by the binding molecules can be restricted to exclusively or preferentially killing selected cell types in the presence of untargeted cells. In addition, both the cell-targeted delivery of a cytotoxic, toxin component and an immunogenic, T-cell epitope can be accomplished by a single binding molecule such that deliver of both potentially cytotoxic components is restricted exclusively or preferentially to target cells in the presence of untargeted cells.

In some embodiments, the binding molecule is cytotoxic at certain concentrations. In some embodiments, upon administration of the binding molecule to a mixture of cell types, the cytotoxic binding molecule is capable of selectively killing those cells which are physically coupled with extracellular PD-L1 bound by the binding region compared to cell types not physically coupled with any extracellular PD-L1. In some embodiments, the cytotoxic binding molecule is capable of selectively or preferentially causing the death of a specific cell type within a mixture of two or more different cell types. This enables targeting cytotoxic activity to specific cell types with a high preferentiality, such as a 3-fold cytotoxic effect, over "bystander" cell types that do not express the target biomolecule. Alternatively, the expression of the target biomolecule of the binding region may be non-exclusive to one cell type if the target biomolecule is expressed in low enough amounts and/or physically coupled in low amounts with cell types that are not to be targeted. This enables the targeted cell-killing of specific cell types with a high preferentiality, such as a 3-fold cytotoxic effect, over "bystander" cell types that do not express significant amounts of the target biomolecule or are not physically coupled to significant amounts of the target biomolecule.

For some embodiments, upon administration of the cytotoxic binding molecule to two different populations of cell types, the cytotoxic binding molecule is capable of causing cell death as defined by the half-maximal cytotoxic concentration ($CD_{50}$) on a population of target cells, whose members express an extracellular target biomolecule of the binding region of the cytotoxic binding molecule, at a dose at least three-times lower than the $CD_{50}$ dose of the same cytotoxic binding molecule to a population of cells whose members do not express an extracellular target biomolecule of the binding region of the cytotoxic binding molecule.

In some embodiments, the cytotoxic activity of a binding molecule toward populations of cell types physically coupled with an extracellular PD-L1 bound by the binding region is at least 3-fold higher than the cytotoxic activity toward populations of cell types not physically coupled with any extracellular PD-L1 bound by the binding region. As described herein, selective cytotoxicity may be quantified in terms of the ratio (a/b) of (a) cytotoxicity towards a population of cells of a specific cell type physically coupled with extracellular PD-L1 bound by the binding region to (b) cytotoxicity towards a population of cells of a cell type not physically coupled with any extracellular PD-L1 bound by binding region. In some embodiments, the cytotoxicity ratio is indicative of selective cytotoxicity which is at least 3-fold, 5-fold, 10-fold, 15-fold, 20-fold, 25-fold, 30-fold, 40-fold, 50-fold, 75-fold, 100-fold, 250-fold, 500-fold, 750-fold, or 1000-fold higher for populations of cells or cell types physically coupled with a target biomolecule of the binding region compared to populations of cells or cell types not physically coupled with a target biomolecule of the binding region.

In some embodiments, the preferential cell-killing function or selective cytotoxicity of a binding molecule is due to an additional exogenous material (e.g. a cytotoxic material) and/or heterologous, T-cell epitope present in a Shiga toxin effector polypeptide and not necessarily a result of the catalytic activity of a Shiga toxin effector polypeptide region.

This preferential cell-killing function allows a targeted cell to be killed by certain cytotoxic, binding molecules under varied conditions and in the presence of non-targeted bystander cells, such as ex vivo manipulated mixtures of cell types, in vitro cultured tissues with mixtures of cell types, or in vivo in the presence of multiple cell types (e.g. in situ or in a native location within a multicellular organism).

Although PD-L1-expressing cells may be selectively targeted, certain binding molecules may selectively kill PD-L1-expressing tumor cells in the presence of PD-L1-expressing peripheral blood mononuclear cell types.

D. PD-L1/PD-1 Signaling Interference

In addition to cytotoxic, cytostatic, and immune stimulation applications, binding molecules optionally may be used for inhibiting PD-1 signaling, such as, e.g., in applications involving immune checkpoint inhibition and anti-cancer immunotherapy. In some embodiments, the PD-L1 binding molecules can block the PD-1/PD-L1 interaction when exogenously administered to cells. Although some embodiments of the binding molecules exhibit half-maximal inhibitory concentrations for PD-L1 signaling inhibition ($EC_{50}$) that are much less potent (e.g. greater than 500 nM or 1 μM)

than their cytotoxic $CD_{50}$ (e.g. 0.1 to 50 nM), for a given target cell type, this is not always the case. Some embodiments of the binding molecules can exhibit $EC_{50}$ values equivalent to their $CD_{50}$ values, indicating potent levels of both PD-1 signaling inhibition and cytotoxicity could occur concurrently. In some embodiments, the binding molecules exhibit $EC_{50}$ values (e.g. 1 to 200 nM) that are greater than their cytotoxic $CD_{50}$ values (e.g. greater than 1,000 or 10,000 nM), such as, e.g., binding molecules comprising inactivated toxins like PD-L1 binding molecules comprising an inactive or reduced-activity Shiga toxin effector polypeptide such as 116296 (SEQ ID NO:127)). Certain binding molecules exhibiting $EC_{50}$ values greater than their cytotoxic $CD_{50}$ value may be used at certain concentrations for effectuating PD-1 signaling inhibition in the absence of any significant cytotoxic activity.

E. Delivery of Additional Exogenous Material into the Interior of Targeted Cells In addition to cytotoxic, cytostatic, immune stimulation, and anti-cancer immunotherapy applications, binding molecules optionally may be used for targeted intracellular delivery functions, such as, e.g., in applications involving information gathering and diagnostic functions.

Because the binding molecules, including reduced cytotoxicity and/or nontoxic forms thereof, are capable of entering cells physically coupled with an extracellular PD-L1 molecule recognized by the binding molecule's binding region, certain embodiments of the binding molecules may be used to deliver additional exogenous materials into the interior of targeted cell types. For example, non-toxic variants of the cytotoxic, binding molecules, or optionally cytotoxic variants, may be used to deliver additional exogenous materials to and/or label the interiors of cells physically coupled with an extracellular PD-L1 bound by the binding region of the binding molecule. Various types of cells and/or cell populations which express target biomolecules to at least one cellular surface may be targeted by the binding molecules for receiving exogenous materials. The functional components are modular, in that various toxin components, additional exogenous materials, and binding regions may be associated with each other to provide binding molecules suitable for diverse applications involving cargo delivery, such as, e.g., non-invasive, in vivo imaging of tumor cells.

This delivery of exogenous material function of certain binding molecules may be accomplished under varied conditions and in the presence of non-targeted bystander cells, such as, e.g., an ex vivo manipulated target cell, a target cell cultured in vitro, a target cell within a tissue sample cultured in vitro, or a target cell in an in vivo setting like within a multicellular organism. Furthermore, the selective delivery of exogenous material to certain cells by certain binding molecules may be accomplished under varied conditions and in the presence of non-targeted bystander cells, such as ex vivo manipulated mixtures of cell types, in vitro cultured tissues with mixtures of cell types, or in vivo in the presence of multiple cell types (e.g., in situ or in a native location within a multicellular organism).

Toxin effector polypeptides and binding molecules which are not capable, such as a certain concentration ranges, of killing a target cell and/or delivering an embedded or inserted epitope for cell-surface presentation by a MHC molecule of a target cell may still be useful for delivering exogenous materials into cells, such as, e.g., detection promoting agents.

In some embodiments, the Shiga toxin effector exhibits low to zero cytotoxicity and thus are referred to herein as "noncytotoxic and/or reduced cytotoxic." In some embodiments, the binding molecule exhibits low to zero cytotoxicity and may be referred to as "noncytotoxic" and/or "reduced cytotoxic variants." For example, some molecules do not exhibit a significant level of Shiga toxin based cytotoxicity wherein at doses of less than 1000 nM, 500 nM, 100 nM, 75 nM, 50 nM, there is no significant amount of cell death as compared to the appropriate reference molecule, such as, e.g., as measured by an assay known to the skilled worker and/or described herein. In some embodiments, the molecules do not exhibit any toxicity at dosages of 1-100 µg per kg of a mammalian recipient. Reduced-cytotoxic variants may still be cytotoxic at certain concentrations or dosages but exhibit reduced cytotoxicity, such as, e.g., are not capable of exhibiting a significant level of Shiga toxin cytotoxicity in certain situations.

Certain binding molecules comprising the same, can be rendered non-cytotoxic, such as, e.g., via the addition of one or more amino acid substitutions known to the skilled worker to inactivate a toxin effector polypeptide, including exemplary substitutions described herein. The non-cytotoxic and reduced cytotoxic variants of the binding molecules may be in certain situations more suitable for delivery of additional exogenous materials than more cytotoxic variants.

Diagnostic Functions

In certain binding molecules have uses in the in vitro and/or in vivo detection of specific cells, cell types, and/or cell populations, as well as specific subcellular compartments of any of the aforementioned. Reduced-cytotoxicity and/or nontoxic forms of the cytotoxic, binding molecules that are conjugated to detection promoting agents optionally may be used for diagnostic functions, such as for companion diagnostics used in conjunction with a therapeutic regimen comprising the same or a related binding region, such as, e.g., a binding region with high-affinity binding to the same target biomolecule, an overlapping epitope, and/or the same epitope.

In some embodiments, the binding molecules described herein are used for both diagnosis and treatment, or for diagnosis alone. When the same cytotoxic binding molecule is used for both diagnosis and treatment, in some embodiments the binding molecule variant which incorporates a detection promoting agent for diagnosis may have its cytotoxicity reduced or may be rendered nontoxic by catalytic inactivation of its Shiga toxin effector polypeptide region(s) via one or more amino acid substitutions, including exemplary substitutions described herein. For example, certain nontoxic variants of the binding molecules exhibit less than 5%, 4%, 3%, 2%, or 1% death of target cells after administration of a dose less than 1 mg/kg. Reduced-cytotoxicity variants may still be cytotoxic at certain concentrations or dosages but exhibit reduced cytotoxicity, such as, e.g., are not capable of exhibiting a significant level of Shiga toxin cytotoxicity as described herein.

The ability to conjugate detection promoting agents known in the art to various binding molecules provides useful compositions for the detection of certain cells, such as, e.g., cancer, tumor, immune, and/or infected cells. These diagnostic embodiments of the binding molecules may be used for information gathering via various imaging techniques and assays known in the art. For example, diagnostic embodiments of the binding molecules may be used for information gathering via imaging of intracellular organelles (e.g. endocytotic, Golgi, endoplasmic reticulum, and cytosolic compartments) of individual cancer cells, immune cells, and/or infected cells in a patient or biopsy sample.

Various types of information may be gathered using the diagnostic embodiments of the binding molecules whether for diagnostic uses or other uses. This information may be useful, for example, in diagnosing neoplastic cell types, determining therapeutic susceptibilities of a patient's disease, assaying the progression of anti-neoplastic therapies over time, assaying the progression of immunomodulatory therapies over time, assaying the progression of antimicrobial therapies over time, evaluating the presence of infected cells in transplantation materials, evaluating the presence of unwanted cell types in transplantation materials, and/or evaluating the presence of residual tumor cells after surgical excision of a tumor mass.

For example, subpopulations of patients might be ascertained using information gathered using the diagnostic variants of the binding molecules, and then individual patients could be further categorized into subpopulations based on their unique characteristic(s) revealed using those diagnostic embodiments. For example, the effectiveness of specific pharmaceuticals or therapies might be a criterion used to define a patient subpopulation. For example, a nontoxic diagnostic variant of a particular cytotoxic, binding molecule may be used to differentiate which patients are in a class or subpopulation of patients predicted to respond positively to a cytotoxic variant of that binding molecule. Accordingly, associated methods for patient identification, patient stratification, and diagnosis using binding molecules, including non-toxic variants of cytotoxic, binding molecules, are also provided herein.

The expression of the target biomolecule by a cell need not be native in order for cell-targeting by a binding molecule, such as, e.g., for direct cell-kill, indirect cell-kill, delivery of exogenous materials like T-cell epitopes, and/or information gathering. Cell surface expression of the target biomolecule could be the result of an infection, the presence of a pathogen, and/or the presence of an intracellular microbial pathogen. Expression of a target biomolecule could be artificial such as, for example, by forced or induced expression after infection with a viral expression vector, see e.g. adenoviral, adeno-associated viral, and retroviral systems. Expression of PD-L1 can be induced by exposing a cell to ionizing radiation (Wattenberg Metal., *Br J Cancer* 110: 1472-80 (2014)).

Targeting Immunosuppressive Immune Cells

In some embodiments, the PD-L1 binding molecules described herein are capable of specifically binding PD-L1 on the surface of a cell, such as an immunosuppressive immune cell (IIC). Upon binding to PD-L1 on the cell, the binding molecules may be internalized and the activity of the Shiga toxin A subunit effector polypeptide effectively and specifically kills the cell. In some embodiments, this direct cell kill activity depletes immunosuppressive immune cells, such as Tregs in the tumor microenvironment (TME). Once immunosuppression in the TME is lifted, non-suppressive immune cells (e.g., cytotoxic T cells) can attack the tumor.

In some embodiments, the binding molecules described herein bind to PD-L1 that is on an IIC and on a tumor cell. Thus, in some embodiments, in addition to depleting immunosuppressive immune cells in the TME, the binding molecules also bind to and directly kill tumor cells. This dual mechanism of action can enhance effectiveness of the disclosed binding molecules in cancer therapy.

In some embodiments, the binding molecules described herein cause expansion of one or more types of cells, such as immune cells. For example, in some embodiments, the PD-L1 binding molecules cause expansion of B-cells, T-cells, or eosinophils.

In some embodiments, the binding molecules described herein comprise an antigenic epitope, such as a CD8+ T-cell epitope. In some embodiments, after the binding molecule binds to PD-L1 and is internalized into the cell, the antigenic epitope is delivered to the MHC class I system of the cell, targeting the cell for immune-mediated destruction. Therefore, in addition to depleting immunosuppressive immune cells in the TME, and in some embodiments directly killing tumor cells, the binding molecules also enhance recognition of the tumor by the immune system.

In some embodiments, the binding molecules modulate expression of PD-L1 to which the binding molecules' binding region binds. In some embodiments, the binding molecules reduce or downregulate expression of PD-L1. In some embodiments, the binding molecules reduce cell-surface density of PD-L1. In some embodiments, modulation of expression of PD-L1 reduces immunosuppression. In some embodiments, modulation of expression of PD-L1 leads to cell death.

Thus, the disclosed binding molecules are useful (1) for selectively killing a cell type(s) expressing a PD-1 amongst other cells, and (2) as therapeutic molecules for treating a variety of diseases, disorders, and conditions, including cancers. FIG. 35 further illustrates the mechanisms of action by which an illustrative binding molecule can induce anti-tumor effects in a subject.

The binding molecules described herein comprise a binding region capable of specifically binding PD-L1 on the surface of a cell, e.g., a PD-L1 positive cell. In some embodiments, the PD-L1 positive cell is a tumor cell. In some embodiments, the PD-L1 positive cell is an immunosuppressive immune cell, such as an immunosuppressive T cell, an immunosuppressive B cell, an immunosuppressive plasma cell, or an immunosuppressive myeloid cell. In some embodiments, the immunosuppressive immune cell is a Treg, an MDSC, or a TAM. In some embodiments, the immunosuppressive immune cell is a TAN or a CAF. In some embodiments, the binding region does not specifically bind to a resident memory T cell, a tumor-excluded dendritic cell, and/or a CD14+ monocyte.

As used herein, the terms "does not directly kill" or "indirectly kills" refers to a process wherein a binding molecule comprising a Shiga toxin A subunit effector polypeptide and a binding region binds to a target cell (e.g., a ICC), which leads to the downstream killing of a second cell (e.g., a cancer cell). For example, a binding molecule can indirectly kill a tumor cell by binding to and killing an immunosuppressive immune cell in the tumor microenvironment (TME). Once immunosuppression is lifted in the TME, the cancer cell can be killed by non-suppressive immune cells (e.g., cytotoxic T cells, etc).

In some embodiments, methods for reducing the immunosuppressive activity of an immune cell in a subject in need thereof comprise administering to the subject an effective amount of (i) a binding molecule, (ii) a nucleic acid encoding the binding molecule (e.g., an expression vector), or (iii) a composition comprising the binding molecule or the nucleic acid encoding the same.

In some embodiments, the binding molecule binds to PD-L1 that is present on the surface of an immunosuppressive immune cell in the subject, but is not present on the surface of the subject's cancer cells. In some embodiments, the binding molecule directly kills the immunosuppressive immune cell, but does not directly kill the subject's cancer cells.

In some embodiments, the binding molecule binds to PD-L1 that is present on the surface of an immunosuppressive cell in the subject, and the subject's cancer cells. In some embodiments, the binding molecule directly kills the immunosuppressive immune cell and the subject's cancer cells.

In some embodiments, the subject has cancer. In some embodiments, the cancer is characterized by the presence of at least one immunosuppressive cell, for example in the tumor microenvironment. In some embodiments, the cancer is characterized by a high mutational burden (TMB) and/or a high frequency of indels. Mutational burden can be analyzed by various methods, including hybrid-based next-generation sequencing, and is reported as the total number of sequence variants or mutations per tumor genomic region analyzed (e.g., mutations per megabase). Cancers can be classified as having a "high" mutational burden if they have greater than or equal to 20 mutations per magabase. High mutational burden is typical of cancers developed as a consequence of exposure to powerful carcinogens, such as tobacco smoke and polycyclic aromatic hydrocarbons (e.g., in lung and bladder cancers), as well as exposure to mutagens (e.g., UV light in melanoma). Indels (insertions and deletions) are one type of mutation commonly seen in cancer cells. Indels that produce frameshift mutations can generate highly immunogenic tumor neoantigens. Therefore, the presence of a high frequency of indels can lead to a better response to the therapeutic approaches described herein. Cancers are classified as having a "high" frequency of indels if they have greater than or equal to 0.1, 0.5, 1, 2, 3, 4, 5, 6, 7, 8 9, or 10 indels per magabase. In some embodiments, a cancer is classified as having a high frequency of indels if it has 0.1-1, 1-10, 10-50, 50-100, or greater than 100 indels per megabase.

V. Production, Manufacture, and Purification of Shiga Toxin Effector Polypeptides and Binding Molecules The Shiga toxin effector polypeptides and certain binding molecules may be produced using techniques well known to those of skill in the art. For example, Shiga toxin effector polypeptides and binding molecules may be manufactured by standard synthetic methods, by use of recombinant expression systems, or by any other suitable method. Thus, Shiga toxin effector polypeptides and binding molecules may be synthesized in a number of ways, including, e.g. methods comprising: (1) synthesizing a polypeptide or polypeptide component of a binding molecule using standard solid-phase or liquid-phase methodology, either stepwise or by fragment assembly, and isolating and purifying the final polypeptide compound product; (2) expressing a polynucleotide that encodes a protein or protein component of a binding molecule in a host cell and recovering the expression product from the host cell or host cell culture; or (3) cell-free, in vitro expression of a polynucleotide encoding a polypeptide or polypeptide component of a binding molecule, and recovering the expression product; or by any combination of the methods of (1), (2) or (3) to obtain fragments of the protein component, subsequently joining (e.g. ligating) the peptide or polypeptide fragments to obtain a polypeptide component, and recovering the polypeptide component.

It may be preferable to synthesize a binding molecule, or a protein component of a binding molecule, by means of solid-phase or liquid-phase peptide synthesis. Polypeptides and binding molecules may suitably be manufactured by standard synthetic methods. Thus, peptides may be synthesized by, e.g. methods comprising synthesizing the peptide by standard solid-phase or liquid-phase methodology, either stepwise or by fragment assembly, and isolating and purifying the final peptide product. In this context, reference may be made to WO 1998/011125 or, inter alia, Fields G et al., *Principles and Practice of Solid-Phase Peptide Synthesis* (Synthetic Peptides, Grant G, ed., Oxford University Press, U.K., 2nd ed., 2002) and the synthesis examples therein.

Shiga toxin effector polypeptides and binding molecules may be prepared (produced and purified) using recombinant techniques well known in the art. In general, methods for preparing proteins by culturing host cells transformed or transfected with a vector comprising the encoding polynucleotide and purifying or recovering the protein from cell culture are described in, e.g., Sambrook J et al., *Molecular Cloning: A Laboratory Manual* (Cold Spring Harbor Laboratory Press, NY, U.S., 1989); Dieffenbach C et al., *PCR Primer: A Laboratory Manual* (Cold Spring Harbor Laboratory Press, N.Y., U.S., 1995). Any suitable host cell may be used to produce a polypeptide and/or cell-targeting protein. Host cells may be cells stably or transiently transfected, transformed, transduced or infected with one or more expression vectors which drive expression of a polypeptide. In addition, a Shiga toxin effector polypeptide and/or binding molecule may be produced by modifying the polynucleotide encoding a polypeptide or cell-targeting protein that result in altering one or more amino acids or deleting or inserting one or more amino acids in order to achieve desired properties, such as changed cytotoxicity, changed cytostatic effects, and/or changed serum half-life.

There are a wide variety of expression systems which may be chosen to produce a polypeptide or cell-targeting protein as described herein. For example, host organisms for expression of cell-targeting proteins include prokaryotes, such as *E. coli* and *B. subtilis*, eukaryotic cells, such as yeast and filamentous fungi (like *S. cerevisiae, P. pastoris, A. awamori*, and *K. lactis*), algae (like *C. reinhardtii*), insect cell lines, mammalian cells (like CHO cells), plant cell lines, and eukaryotic organisms such as transgenic plants (like *A. thaliana* and *N. benthamiana*).

Accordingly, also provided are methods for producing a Shiga toxin effector polypeptide and/or binding molecule according to above recited methods and using a polynucleotide encoding part or all of a polypeptide or a protein component of a cell-targeting protein, an expression vector comprising at least one polynucleotide capable of encoding part or all of a polypeptide or cell-targeting protein when introduced into a host cell, and/or a host cell comprising a polynucleotide or expression vector.

When a protein is expressed using recombinant techniques in a host cell or cell-free system, it is advantageous to separate (or purify) the desired protein away from other components, such as host cell factors, in order to obtain preparations that are of high purity or are substantially homogeneous. Purification can be accomplished by methods well known in the art, such as centrifugation techniques, extraction techniques, chromatographic and fractionation techniques (e.g. size separation by gel filtration, charge separation by ion-exchange column, hydrophobic interaction chromatography, reverse phase chromatography, chromatography on silica or cation-exchange resins such as DEAE and the like, chromatofocusing, and Protein A Sepharose chromatography to remove contaminants), and precipitation techniques (e.g. ethanol precipitation or ammonium sulfate precipitation). Any number of biochemical purification techniques may be used to increase the purity of a polypeptide and/or binding molecule. In some embodiments, the polypeptides and binding molecules may optionally be purified in homo-multimeric forms (e.g. a molecular complex comprising two or more polypeptides or binding molecules).

Antibodies may be produced using recombinant methods and compositions (see e.g. U.S. Pat. No. 4,816,567). In some embodiments, isolated nucleic acid encoding an antibody or antibody fragment described herein is provided. Such nucleic acid may encode an amino acid sequence comprising the VL and/or an amino acid sequence comprising the VH of the antibody (e.g. a light and/or heavy chain of an antibody). A method of making an antibody as described herein comprises culturing a host cell comprising a nucleic acid encoding the antibody, as provided above, under conditions suitable for expression of the antibody, and optionally recovering the antibody from the host cell (or host cell culture medium). For recombinant production of an antibody, nucleic acid encoding an antibody, e.g. as described above, is isolated and inserted into one or more vectors for further cloning and/or expression in a host cell. Such nucleic acid may be readily isolated and sequenced using routine methods known to the skilled worker.

Suitable host cells for cloning or expression of antibody-encoding vectors include prokaryotic or eukaryotic cells described herein and/or known to the skilled worker. For example, antibodies may be produced in bacteria, in particular when glycosylation and/or Fc effector function are not required (see e.g. U.S. Pat. Nos. 5,648,237, 5,789,199, and 5,840,523). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see e.g. Gerngross T, *Nat Biotech* 22: 1409-14 (2004); Li H et al., *Nat Biotech* 24: 210-15 (2006)).

Suitable host cells for the expression of glycosylated antibody are also derived from multicellular organisms (invertebrates and vertebrates). Examples of invertebrate cells include plant and insect cells. Plant cells may be utilized as hosts (see e.g. U.S. Pat. Nos. 5,959,177, 6,040,498, 6,420,548, 7,125,978, and 6,417,429). Numerous baculoviral strains have been identified which may be used in conjunction with insect cells, particularly for transfection of *Spodoptera frugiperda* cells. Vertebrate cells may be used as hosts. For example, mammalian cell lines that are adapted to grow in suspension may be useful. Other examples of useful mammalian host cell lines are monkey kidney CV1 line transformed by SV40 (COS-7); human embryonic kidney line 293 cells; baby hamster kidney cells (BHK); mouse sertoli cells (e.g. TM4 cells); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TM cells; MRC 5 cells; and FS4 cells (Graham F et al., *J Gen Virol* 36: 59-74 (1977); Mather J et al., *Biol Reprod* 23: 243-52 (1980); Mather J et al., *Ann NY Acad Sci* 383: 44-68 (1992)). Other useful mammalian host cell lines include Chinese hamster ovary (CHO) cells, including DHFR-CHO, and myeloma cell lines such as Y0, NS0 and Sp2/0 cells (see e.g. Urlaub G et al., *Proc Natl Acad Sci U.S.A.* 77: 4216-20 (1980)). For a review of certain mammalian host cell lines suitable for antibody production, see Yazaki and Wu, *Methods in Molecular Biology*, Vol. 248 (B. K. C. Lo, ed., Humana Press, Totowa, N.J.), pp. 255-268 (2003).

Antibodies provided herein may be identified, screened for, or characterized for their physical/chemical properties and/or biological activities by various assays known in the art.

Methods of immuno-conjugation include but are not limited to reactive thiols, aldehyde-tagged, sortase-mediated conjugation, MTGase-mediated conjugation, transglutaminase conjugation, bis-linkages, and using a spacer or multifunctional linker (see e.g. WO 2009/052249, WO 2012/097333, WO2013/173391, WO 2014/140317, WO 2014/159835, WO 2015/155753, WO 2015/191883, WO 2016/102632, WO 2018/185526).

An antibody-toxin conjugate or immunoconjugate may be prepared by several routes employing organic chemistry reactions, conditions, and reagents known to those skilled in the art, including reaction of a nucleophilic group of an antibody with a bivalent linker reagent to form a covalent bond between the linker and the antibody, followed by reaction with a toxin component; and reaction of a nucleophilic group of a toxin component with a bivalent linker reagent, to form a covalent bond between the linker and the toxin, followed by reaction with a nucleophilic group of an antibody.

Nucleophilic groups on antibodies include but are not limited to: (i) amino-terminal amine groups, (ii) side chain amine groups, e.g. of a lysine residue, (iii) side chain thiol groups, e.g. of a cysteine residue, and (iv) sugar hydroxyl or amino groups of a carbohydrate moiety when the antibody is glycosylated. Amine, hydroxyl, and thiol groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, e.g. cysteine disulfide bridges. Antibodies may be made reactive for conjugation with linker reagents by treatment with a reducing agent such as dithiothreitol (DTT) or tricarbonylethylphosphine (TCEP), such that the antibody is fully or partially reduced (see e.g. WO 2013/173391, WO 2013/173392, WO 2013/173393, WO 2013/190272, WO 2014/064424, WO 2014/114207, WO 2015/155753, WO 2018/185526). Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g. by preparing variant antibodies comprising one or more non-native cysteine amino acid residues).

Antibody-toxin conjugates or immunoconjugates may also be produced by reaction between an electrophilic group on an antibody, such as an aldehyde or ketone carbonyl group, with a nucleophilic group on a linker reagent or toxin component. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or toxin component. In another embodiment, the sugars of glycosylated antibodies may be oxidized, e.g. with periodate oxidizing reagents, to form aldehyde or ketone groups which may react with the amine group of linker reagents or toxin components. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the toxin component. In another embodiment, antibodies containing amino-terminal serine or threonine residues can react with sodium meta-periodate, resulting in production of an aldehyde in place of the first amino acid (see e.g. U.S. Pat. No. 5,362,852). Such an aldehyde can be reacted with a toxin component or linker nucleophile.

Carbohydrate(s) on the Fc region of an antibody is a natural site for attaching compounds. Generally, the carbohydrate is modified by periodate oxidation to generate reactive aldehydes, which can then be used to attach reactive amine containing compounds by Schiff base formation. As the aldehydes can react with amine groups, reactions are carried out at low pH so that lysine residues in the antibody or antigen binding domain are protonated and unreactive. Hydrazide groups are most suitable for attachment to the aldehydes generated since they are reactive at low pH to form a hydrazone linkage. The linkage can then be further stabilized by reduction with sodium cyanoborohydride to form a hydrazine linkage.

Exemplary nucleophilic groups on a toxin component include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Conjugate loading may be expressed as an average number of conjugate moieties per antibody (x). Conjugate loading may range from 1 to 20 conjugate moieties per antibody. The average number of conjugate moieties per antibody in preparations of antibody-toxin conjugates or immunoconjugates from conjugation reactions may be characterized by conventional means such as mass spectroscopy, ELISA assay, and high-performance liquid chromatography (HPLC). The quantitative distribution of immunoconjugate in terms of x may also be determined, such as, e.g., by separation, purification, and characterization of homogeneous immunoconjugate where p is a certain value from immunoconjugate with other conjugate loadings may be achieved by means such as reverse phase HPLC or electrophoresis.

In the Examples below are descriptions of non-limiting examples of methods for producing exemplary binding molecules, as well as specific but non-limiting aspects of production methods.

VI. Pharmaceutical and Diagnostic Compositions Comprising Binding Molecules

Also provided are Shiga toxin effector polypeptides and binding molecules for use, alone or in combination with one or more additional therapeutic agents, in a pharmaceutical composition, for treatment or prophylaxis of conditions, diseases, disorders, or symptoms described in further detail below (e.g. cancers, malignant tumors, non-malignant tumors, growth abnormalities, immune disorders, and microbial infections). Also provided herein are pharmaceutical compositions comprising a binding molecule, or a pharmaceutically acceptable salt or solvate thereof, together with at least one pharmaceutically acceptable carrier, excipient, or vehicle. In some embodiments, the pharmaceutical composition may comprise homo-multimeric and/or hetero-multimeric forms of a binding molecule. The pharmaceutical compositions are useful in methods of treating, ameliorating, or preventing a disease, condition, disorder, or symptom described in further detail below. Each such disease, condition, disorder, or symptom is envisioned to be a separate embodiment with respect to uses of a pharmaceutical composition according as described herein. Also provided are pharmaceutical compositions for use in at least one method of treatment, as described in more detail below.

As used herein, the terms "patient" and "subject" are used interchangeably to refer to any organism, commonly vertebrates such as humans and animals, which presents symptoms, signs, and/or indications of at least one disease, disorder, or condition. These terms include mammals such as the non-limiting examples of primates, livestock animals (e.g. cattle, horses, pigs, sheep, goats, etc.), companion animals (e.g. cats, dogs, etc.) and laboratory animals (e.g. mice, rabbits, rats, etc.).

As used herein, "treat," "treating," or "treatment" and grammatical variants thereof refer to an approach for obtaining beneficial or desired clinical results. The terms may refer to slowing the onset or rate of development of a condition, disorder or disease, reducing or alleviating symptoms associated with it, generating a complete or partial regression of the condition, or some combination of any of the above. In some embodiments, beneficial or desired clinical results include, but are not limited to, reduction or alleviation of symptoms, diminishment of extent of disease, stabilization (e.g. not worsening) of state of disease, delay or slowing of disease progression, amelioration or palliation of the disease state, and remission (whether partial or total), whether detectable or undetectable. "Treat," "treating," or "treatment" can also mean prolonging survival relative to expected survival time if not receiving treatment. A subject (e.g. a human) in need of treatment may thus be a subject already afflicted with the disease or disorder in question. The terms "treat," "treating," or "treatment" includes inhibition or reduction of an increase in severity of a pathological state or symptoms relative to the absence of treatment, and is not necessarily meant to imply complete cessation of the relevant disease, disorder, or condition. With regard to tumors and/or cancers, treatment includes reduction in overall tumor burden and/or individual tumor size.

As used herein, the terms "prevent," "preventing," "prevention" and grammatical variants thereof refer to an approach for preventing the development of, or altering the pathology of, a condition, disease, or disorder. Accordingly, "prevention" may refer to prophylactic or preventive measures. In some embodiments, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" includes slowing the onset of disease relative to the absence of treatment and is not necessarily meant to imply permanent prevention of the relevant disease, disorder or condition. Thus "preventing" or "prevention" of a condition may in certain contexts refer to reducing the risk of developing the condition or preventing or delaying the development of symptoms associated with the condition.

As used herein, an "effective amount" or "therapeutically effective amount" is an amount or dose of a composition (e.g. a therapeutic composition, compound, or agent) that produces at least one desired therapeutic effect in a subject, such as preventing or treating a target condition or beneficially alleviating a symptom associated with the condition. The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic composition (including activity, pharmacokinetics, pharmacodynamics, and bioavailability), the physiological condition of the subject (including age, sex, disease type, disease stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a composition and adjusting the dosage accordingly (see e.g. *Remington: The Science and Practice of Pharmacy* (Gennaro A, ed., Mack Publishing Co., Easton, PA, U.S., 19th ed., 1995)).

An effective amount of an agent, e.g., a pharmaceutical formulation of a binding molecule, refers to an amount effective, at dosages and for periods of time necessary, to achieve the desired therapeutic or prophylactic result. The effective amount of the drug for treating cancer may reduce the number of cancer cells; reduce the tumor size; inhibit (e.g. slow to some extent and preferably stop) cancer cell infiltration into peripheral organs; inhibit (e.g. slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

Diagnostic compositions comprise a binding molecule and one or more detection promoting agents. When producing or manufacturing a diagnostic composition, a binding molecule may be directly or indirectly linked to one or more detection promoting agents. There are numerous standard techniques known to the skilled worker for incorporating, affixing, and/or conjugating various detection promoting agents to proteins or proteinaceous components of molecules, especially to immunoglobulins and immunoglobulin-derived domains.

There are numerous detection promoting agents known to the skilled worker, such as isotopes, dyes, colorimetric agents, contrast enhancing agents, fluorescent agents, bioluminescent agents, and magnetic agents, which can be operably linked to the polypeptides or binding molecules for information gathering methods, such as for diagnostic and/or prognostic applications to diseases, disorders, or conditions of an organism (see e.g. Cai W et al., *J Nucl Med* 48: 304-10 (2007); Nayak T, Brechbiel M, *Bioconjug Chem* 20: 825-41 (2009); Paudyal P et al., *Oncol Rep* 22: 115-9 (2009); Qiao J et al., *PLoS ONE* 6: e18103 (2011); Sano K et al., *Breast Cancer Res* 14: R61 (2012)). These agents may be associated with, linked to, and/or incorporated within the polypeptide or binding molecule at any suitable position. For example, the linkage or incorporation of the detection promoting agent may be via an amino acid residue(s) of a molecule or via some type of linkage known in the art, including via linkers and/or chelators. The incorporation of the agent is in such a way to enable the detection of the presence of the diagnostic composition in a screen, assay, diagnostic procedure, and/or imaging technique.

Similarly, there are numerous imaging approaches known to the skilled worker, such as non-invasive in vivo imaging techniques commonly used in the medical arena, for example: computed tomography imaging (CT scanning), optical imaging (including direct, fluorescent, and bioluminescent imaging), magnetic resonance imaging (MRI), positron emission tomography (PET), single-photon emission computed tomography (SPECT), ultrasound, and x-ray computed tomography imaging.

VII. Production or Manufacture of Pharmaceutical and/or Diagnostic Compositions Comprising Binding Molecules Pharmaceutically acceptable salts or solvates of any of the Shiga toxin effector polypeptides and binding molecules are also provided herein.

The term "solvate" refers to a complex of defined stoichiometry formed between a solute (in casu, a proteinaceous compound or pharmaceutically acceptable salt thereof) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

Polypeptides and proteins, or salts thereof, may be formulated as pharmaceutical compositions prepared for storage or administration, which typically comprise a therapeutically effective amount of a molecule, or a salt thereof, in a pharmaceutically acceptable carrier. The term "pharmaceutically acceptable carrier" includes any of the standard pharmaceutical carriers. Pharmaceutically acceptable carriers for therapeutic molecule use are well known in the pharmaceutical art, and are described, for example, in *Remington's Pharmaceutical Sciences* (Mack Publishing Co. (A. Gennaro, ed., 1985). As used herein, "pharmaceutically acceptable carrier" includes any and all physiologically acceptable, i.e. compatible, solvents, dispersion media, coatings, antimicrobial agents, isotonic, and absorption delaying agents, and the like. Pharmaceutically acceptable carriers or diluents include those used in formulations suitable for oral, rectal, nasal or parenteral (including subcutaneous, intramuscular, intravenous, intradermal, and transdermal) administration. Exemplary pharmaceutically acceptable carriers include sterile aqueous solutions or dispersions and sterile powders for the extemporaneous preparation of sterile injectable solutions or dispersions. Examples of suitable aqueous and nonaqueous carriers that may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants. In some embodiments, the carrier is suitable for intravenous, intramuscular, subcutaneous, parenteral, spinal or epidermal administration (e.g. by injection or infusion). Depending on selected route of administration, the protein or other pharmaceutical component may be coated in a material intended to protect the compound from the action of low pH and other natural inactivating conditions to which the active protein may encounter when administered to a patient by a particular route of administration.

The formulations of the pharmaceutical compositions may conveniently be presented in unit dosage form and may be prepared by any of the methods well known in the art of pharmacy. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration. Subcutaneous or transdermal modes of administration may be particularly suitable for therapeutic proteins described herein.

The pharmaceutical compositions may also contain adjuvants such as preservatives, wetting agents, emulsifying agents and dispersing agents. Preventing the presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

A pharmaceutical composition also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

Also provided herein are pharmaceutical compositions comprising one or a combination of different binding molecules, or an ester, salt or amide of any of the foregoing, and at least one pharmaceutically acceptable carrier.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In some embodiments, isotonic agents, e.g., sugars and polyalcohols such as mannitol, sorbitol, or sodium chloride, may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a polypeptide or binding molecule in the required amount in an appropriate solvent with one or a combination of ingredients described above, as required, followed by sterilization microfiltration. Dispersions may be prepared by incorporating the active compound into a sterile vehicle that contains dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a polypeptide and/or binding molecule is designed to be administered by, e.g. intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition may also contain stabilizers, preservatives, buffers, antioxidants, or other additives well known to those of skill in the art.

As described elsewhere herein, a polypeptide and/or binding molecule may be prepared with carriers that will protect the active therapeutic agent against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see e.g. *Sustained and Controlled Release Drug Delivery Systems* (Robinson J, ed., Marcel Dekker, Inc., NY, U.S., 1978)).

In some embodiments, the composition (e.g. a pharmaceutical and/or diagnostic composition) may be formulated to ensure a desired in vivo distribution of a binding molecule. For example, the blood-brain barrier excludes many large and/or hydrophilic compounds. To target a therapeutic molecule or composition to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 catenin and the like.

Pharmaceutical compositions include parenteral formulations designed to be used as implants or particulate systems. Examples of implants are depot formulations composed of polymeric or hydrophobic components such as emulsions, ion exchange resins, and soluble salt solutions. Examples of particulate systems are microspheres, microparticles, nanocapsules, nanospheres, and nanoparticles (see e.g. Honda M et al., *Int J Nanomedicine* 8: 495-503 (2013); Sharma A et al., *Biomed Res Int* 2013: 960821 (2013); Ramishetti S, Huang L, *Ther Deliv* 3: 1429-45 (2012)). Controlled release formulations may be prepared using polymers sensitive to ions, such as, e.g. liposomes, polaxamer 407, and hydroxyapatite.

VIII. Polynucleotides, Expression Vectors, and Host Cells

Beyond the polypeptides and binding molecules, the polynucleotides that encode the polypeptide components and binding molecules, or functional portions thereof, are also provided herein. The term "polynucleotide" is equivalent to the term "nucleic acid," each of which includes one or more of: polymers of deoxyribonucleic acids (DNAs), polymers of ribonucleic acids (RNAs), analogs of these DNAs or RNAs generated using nucleotide analogs, and derivatives, fragments and homologs thereof. The polynucleotide may be single-, double-, or triple-stranded. Such polynucleotides are specifically disclosed to include all polynucleotides capable of encoding an exemplary protein, for example, taking into account the wobble known to be tolerated in the third position of RNA codons, yet encoding for the same amino acid as a different RNA codon (see Stothard P, *Biotechniques* 28: 1102-4 (2000)).

In some embodiments, provided herein are polynucleotides which encode a Shiga toxin effector polypeptide and/or binding molecule, or a fragment or derivative thereof. The polynucleotides may include, e.g., a nucleic acid sequence encoding a polypeptide at least 50%, 55%, 60%, 65%, 70%, 75%, 80%, 85%, 90%, 95%, 99% or more, identical to a polypeptide comprising one of the amino acid sequences of a polypeptide or binding molecule. Also provided herein are polynucleotides comprising nucleotide sequences that hybridize under stringent conditions to a polynucleotide which encodes a Shiga toxin effector polypeptide component and/or binding molecule, or a fragment or derivative thereof, or the antisense or complement of any such sequence.

Derivatives or analogs of the molecules described herein (e.g., PD-L1 binding molecules) include, inter alia, polynucleotide (or polypeptide) molecules having regions that are substantially homologous to the polynucleotides (or binding molecules), e.g. by at least about 45%, 50%, 70%, 80%, 95%, 98%, or even 99% identity (with a preferred identity of 80-99%) over a polynucleotide (or polypeptide) sequence of the same size or when compared to an aligned sequence in which the alignment is done by a computer homology program known in the art. An exemplary program is the GAP program (Wisconsin Sequence Analysis Package, Version 8 for UNIX, Genetics Computer Group, University Research Park, Madison, WI, U.S.) using the default settings, which uses the algorithm of Smith T, Waterman M, *Adv Appl Math* 2: 482-9 (1981). Also included are polynucleotides capable of hybridizing to the complement of a sequence encoding the cell-targeting proteins under stringent conditions (see e.g. Ausubel F et al., *Current Protocols in Molecular Biology* (John Wiley & Sons, New York, NY, U.S., 1993)), and below. Stringent conditions are known to those skilled in the art and may be found, e.g., in *Current Protocols in Molecular Biology* (John Wiley & Sons, NY, U.S., Ch. Sec. 6.3.1-6.3.6 (1989)).

Also provided herein are expression vectors that comprise the polynucleotides described herein. The polynucleotides capable of encoding the Shiga toxin effector polypeptide components and/or binding molecules may be inserted into known vectors, including bacterial plasmids, viral vectors and phage vectors, using material and methods well known in the art to produce expression vectors. Such expression vectors will include the polynucleotides necessary to support production of contemplated Shiga toxin effector polypeptides and/or binding molecules within any host cell of choice or cell-free expression systems (e.g. pTxb1 and pIVEX2.3). The specific polynucleotides comprising expression vectors for use with specific types of host cells or cell-free expression systems are well known to one of ordinary skill in the art, can be determined using routine experimentation, and/or may be purchased.

The term "expression vector," as used herein, refers to a polynucleotide, linear or circular, comprising one or more expression units. The term "expression unit" denotes a polynucleotide segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. An expression vector contains one or more expression units. Thus, in some embodiments, an expression vector encoding a Shiga toxin effector polypeptide and/or binding molecule comprising a single polypeptide chain includes at least an expression unit for the single polypeptide chain, whereas a protein comprising, e.g. two or more polypeptide chains (e.g. one chain comprising a $V_L$ domain and a second chain comprising a $V_H$ domain linked to a toxin effector polypeptide) includes at least two expression units, one for each of the two polypeptide chains of the protein. For expression of multi-chain cell-targeting proteins, an expression unit for each polypeptide chain may also be separately contained on different expression vectors (e.g. expression may be achieved with a single host cell into which expression vectors for each polypeptide chain has been introduced).

Expression vectors capable of directing transient or stable expression of polypeptides and proteins are well known in the art. The expression vectors generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

The term "host cell" refers to a cell which can support the replication or expression of the expression vector. Host cells may be prokaryotic cells, such as *E. coli* or eukaryotic cells (e.g. yeast, insect, amphibian, bird, or mammalian cells). Creation and isolation of host cell lines comprising a polynucleotide or capable of producing a polypeptide and/or binding molecule can be accomplished using standard techniques known in the art.

Shiga toxin effector polypeptides and/or proteins described herein may be variants or derivatives of the polypeptides and molecules described herein that are produced by modifying the polynucleotide encoding a polypeptide and/or proteinaceous component of a binding molecule by altering one or more amino acids or deleting or inserting one or more amino acids that may render it more suitable to achieve desired properties, such as more optimal expression by a host cell.

IX. PD-L1 Binding Molecules Immobilized on Solid Substrates

In some embodiments, a molecule described herein (e.g. a binding molecule, fusion protein, or polynucleotide), or any effector fragment thereof, is immobilized on a solid substrate. Solid substrates contemplated herein include, but are not limited to, microbeads, nanoparticles, polymers, matrix materials, microarrays, microtiter plates, or any solid surface known in the art (see e.g. U.S. Pat. No. 7,771,955). In accordance with these embodiments, a molecule may be covalently or non-covalently linked to a solid substrate, such as, e.g., a bead, particle, or plate, using techniques known to the skilled worker (see e.g. Jung Y et al., *Analyst* 133: 697-701 (2008)). Immobilized molecules may be used for screening applications using techniques known in the art (see e.g. Bradbury A et al., *Nat Biotechnol* 29: 245-54 (2011); Sutton C, *Br J Pharmacol* 166: 457-75 (2012); Diamante L et al., *Protein Eng Des Sel* 26: 713-24 (2013); Houlihan G et al., *J Immunol Methods* 405: 47-56 (2014)).

Non-limiting examples of solid substrates to which a molecule may be immobilized on include: microbeads, nanoparticles, polymers, nanopolymers, nanotubes, magnetic beads, paramagnetic beads, superparamagnetic beads, streptavidin coated beads, reverse-phase magnetic beads, carboxy terminated beads, hydrazine terminated beads, silica (sodium silica) beads and iminodiacetic acid (IDA)-modified beads, aldehyde-modified beads, epoxy-activated beads, diaminodipropylamine (DADPA)-modified beads (beads with primary amine surface group), biodegradable polymeric beads, polystyrene substrates, amino-polystyrene particles, carboxyl-polystyrene particles, epoxy-polystyrene particles, dimethylamino-polystyrene particles, hydroxy-polystyrene particles, colored particles, flow cytometry particles, sulfonate-polystyrene particles, nitrocellulose surfaces, reinforced nitrocellulose membranes, nylon membranes, glass surfaces, activated glass surfaces, activated quartz surfaces, polyvinylidene difluoride (PVDF) membranes, polyacrylamide-based substrates, poly-vinyl chloride substrates, poly-methyl methacrylate substrates, poly(dimethyl siloxane) substrates, and photopolymers which contain photoreactive species (such as nitrenes, carbenes, and ketyl radicals) capable of forming covalent linkages. Other examples of solid substrates to which a molecule may be immobilized on are commonly used in molecular display systems, such as, e.g., cellular surfaces, phages, and virus particles.

X. Delivery Devices and Kits

In some embodiments, the disclosure relates to a device comprising one or more compositions of matter, such as a pharmaceutical composition or diagnostic composition, for delivery to a subject in need thereof. Thus, a delivery device comprising one or more compositions can be used to administer to a patient a composition of matter by various delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

Also provided herein are kits comprising at least one composition as described herein, and optionally, packaging and instructions for use. Kits may be useful for drug administration and/or diagnostic information gathering. A kit may optionally comprise at least one additional reagent (e.g., standards, markers and the like). Kits typically include a label indicating the intended use of the contents of the kit. The kit may further comprise reagents and other tools for detecting a cell type (e.g. a tumor cell) in a sample or in a subject, or for diagnosing whether a patient belongs to a group that responds to a therapeutic strategy which makes use of a compound, composition, or related method, e.g., such as a method described herein.

XI. Methods for Using Binding Molecules and/or Pharmaceutical and/or Diagnostic Compositions Thereof Generally, it is an object of the present disclosure to provide pharmacologically active agents, as well as compositions comprising the same, that can be used in the prevention and/or treatment of diseases, disorders, and conditions, such as certain cancers, tumors, growth abnormalities, immune disorders, or further pathological conditions mentioned herein. Accordingly, provided herein are methods of using the polypeptides, binding molecules, and pharmaceutical compositions for the targeted killing of cells, for delivering additional exogenous materials into targeted cells, for labeling of the interiors of targeted cells, for collecting diagnostic information, for the delivering of T-cell epitopes to the WIC class I presentation pathway of target cells, and for treating diseases, disorders, and conditions as described herein. For example, the methods described herein may be used to prevent or treat cancers, cancer initiation, tumor initiation, metastasis, and/or disease reoccurrence.

In particular, it is an object of the disclosure to provide such pharmacologically active agents, compositions, and/or methods that have certain advantages compared to the agents, compositions, and/or methods that are known in the art. Accordingly, the present disclosure provides methods of using Shiga toxin effector polypeptides and binding molecules with specified protein sequences and pharmaceutical compositions thereof. For example, any of the amino acid sequences described herein may be specifically utilized as a component of the binding molecule used in the following methods or any method for using a binding molecule known to the skilled worker, such as, e.g., various methods described in WO 2014/164680, WO 2014/164693, WO 2015/138435, WO 2015/138452, WO 2015/113005, WO 2015/113007, WO 2015/191764, US20150259428, WO 2016/196344, WO 2017/019623, WO 2018/106895, and WO 2018/140427.

Provided herein are methods of killing a cell comprising the step of contacting the cell, either in vitro or in vivo, with a Shiga toxin effector polypeptide, binding molecule, or pharmaceutical composition as described herein. The Shiga toxin effector polypeptides, binding molecules, and pharmaceutical compositions described herein can be used to kill a specific cell type upon contacting a cell or cells with one of the claimed compositions of matter. In some embodiments, a binding molecule or pharmaceutical composition can be used to kill specific cell types in a mixture of different cell types, such as mixtures comprising cancer cells, infected cells, and/or hematological cells. In some embodiments, a binding molecule, or pharmaceutical composition can be used to kill cancer cells in a mixture of different cell types. In some embodiments, a cytotoxic Shiga binding molecule, or pharmaceutical composition can be used to kill specific cell types in a mixture of different cell types, such as pre-transplantation tissues. In some embodiments, a Shiga toxin effector polypeptide, binding molecule, or pharmaceutical composition can be used to kill specific cell types in a mixture of cell types, such as pre-administration tissue material for therapeutic purposes. In some embodiments, a binding molecule or pharmaceutical composition can be used to selectively kill cells infected by viruses or microorganisms, or otherwise selectively kill cells expressing a particular extracellular target biomolecule, such as a cell surface biomolecule. The Shiga toxin effector polypeptides, binding molecules, and pharmaceutical compositions have varied applications, including, e.g., uses in depleting unwanted cell types from tissues either in vitro or in vivo, uses in modulating immune responses to treat graft versus host, uses as antiviral agents, uses as anti-parasitic agents, and uses in purging transplantation tissues of unwanted cell types.

In some embodiments, certain Shiga toxin effector polypeptides, binding molecules, and pharmaceutical compositions, alone or in combination with other compounds or pharmaceutical compositions, can show potent cell-kill activity when administered to a population of cells, in vitro or in vivo in a subject such as in a patient in need of treatment. By targeting the delivery of enzymatically active Shiga toxin A Subunit effector polypeptides and/or T-cell epitopes using high-affinity binding regions to specific cell types, cell-kill activities can be restricted to specifically and selectively killing certain cell types within an organism, such as certain cancer cells, neoplastic cells, malignant cells, non-malignant tumor cells, and/or infected cells.

In some embodiments, a method of killing a cell in a patient in need thereof comprises the step of administering to the patient at least one binding molecule or a pharmaceutical composition thereof.

In some embodiments, the binding molecule or pharmaceutical compositions thereof can be used to kill a cancer cell in a patient by targeting an extracellular PD-L1 found physically coupled with a cancer or tumor cell. The terms "cancer cell" or "cancerous cell" refers to various neoplastic cells which grow and divide in an abnormally accelerated and/or unregulated fashion and will be clear to the skilled person. The term "tumor cell" includes both malignant and non-malignant cells. Generally, cancers and/or tumors can be defined as diseases, disorders, or conditions that are amenable to treatment and/or prevention. The cancers and tumors (either malignant or non-malignant) which are comprised of cancer cells and/or tumor cells which may benefit from methods and compositions will be clear to the skilled person. Neoplastic cells are often associated with one or more of the following: unregulated growth, lack of differentiation, local tissue invasion, angiogenesis, and metastasis. The diseases, disorders, and conditions resulting from cancers and/or tumors (either malignant or non-malignant) which may benefit from the methods and compositions described herein for targeting certain cancer cells and/or tumor cells will be clear to the skilled person.

In some embodiments, the binding molecules and compositions described herein may be used to kill cancer stem cells, tumor stem cells, pre-malignant cancer-initiating cells, and tumor-initiating cells, which commonly are slow dividing and resistant to cancer therapies like chemotherapy and radiation. For example, acute myeloid leukemias (AMLs) may be treated by killing AML stem cells and/or dormant AML progenitor cells (see e.g. Shlush L et al., *Blood* 120: 603-12 (2012)).

Because of the Shiga toxin A Subunit based mechanism of action, compositions of matter described herein may be more effectively used in methods involving their combination with, or in complementary fashion with other therapies, such as, e.g., chemotherapies, immunotherapies, radiation, stem cell transplantation, and immune checkpoint inhibitors, and/or effective against chemoresistant/radiation-resistant and/or resting tumor cells/tumor initiating cells/stem cells. Similarly, compositions of matter may be more effectively used in methods involving in combination with other cell-targeted therapies targeting other than the same epitope on, non-overlapping, or different targets for the same disease disorder or condition.

Certain embodiments of the binding molecules, or pharmaceutical compositions thereof, can be used to kill an immune cell (whether healthy or malignant) in a patient by targeting an extracellular PD-L1 found physically coupled with an immune cell.

It is within the scope of the present disclosure to utilize a binding molecule, or pharmaceutical composition thereof, for the purposes of purging patient cell populations (e.g. bone marrow) of malignant, neoplastic, or otherwise unwanted T-cells and/or B-cells and then reinfusing the T-cell and/or B-cells depleted material into the patient (see e.g. van Heeckeren W et al., *Br J Haematol* 132: 42-55 (2006); (see e.g. Alpdogan O, van den Brink M, *Semin Oncol* 39: 629-42 (2012)).

It is within the scope of the present disclosure to utilize the binding molecule, or pharmaceutical composition thereof, for the purposes of ex vivo depletion of T cells and/or B-cells from isolated cell populations removed from a patient. In one non-limiting example, the binding molecule can be used in a method for prophylaxis of organ and/or tissue transplant rejection wherein the donor organ or tissue is perfused prior to transplant with a cytotoxic, binding molecule or a pharmaceutical composition thereof in order to purge the organ of donor T-cells and/or B-cells (see e.g. Alpdogan 0, van den Brink M, *Semin Oncol* 39: 629-42 (2012)).

It is also within the scope of the present disclosure to utilize the binding molecule, or pharmaceutical composition thereof, for the purposes of depleting T-cells and/or B-cells from a donor cell population as a prophylaxis against graft-versus-host disease, and induction of tolerance, in a patient to undergo a bone marrow and or stem cell transplant (see e.g. van Heeckeren W et al., *Br J Haematol* 132: 42-55 (2006); (see e.g. Alpdogan 0, van den Brink M, *Semin Oncol* 39: 629-42 (2012)).

In some embodiments of the Shiga toxin effector polypeptide or binding molecule, or pharmaceutical compositions thereof, can be used to kill an infected cell in a patient by targeting an extracellular PD-L1 found physically coupled with an infected cell.

In some embodiments of the binding molecules, or pharmaceutical compositions thereof, can be used to "seed" a locus within a chordate with non-self, T-cell epitope-peptide presenting cells in order to activate the immune system to enhance policing of the locus. In some embodiments of this "seeding" method, the locus is a tumor mass or infected tissue site. In preferred embodiments of this "seeding" method, the non-self, T-cell epitope-peptide is selected from the group consisting of: peptides not already presented by the target cells of the binding molecule, peptides not present within any protein expressed by the target cell, peptides not present within the proteome or transcriptome of the target cell, peptides not present in the extracellular microenvironment of the site to be seeded, and peptides not present in the tumor mass or infect tissue site to be targeting.

This "seeding" method functions to label one or more target cells within a chordate with one or more MHC class I presented T-cell epitopes for recognition by effector T-cells and activation of downstream immune responses. By exploiting the cell internalizing, intracellularly routing, and T-cell epitope delivering functions of the binding molecules, the target cells which display the delivered T-cell epitope are harnessed to induce recognition of the presenting target cell by host T-cells and induction of further immune responses including target-cell-killing by CTLs. This "seeding" method of using a binding molecule can provide a temporary vaccination-effect by inducing adaptive immune responses to attack the cells within the seeded microenvironment, such as, e.g. a tumor mass or infected tissue site, whether presenting a binding molecule-delivered T-cell epitope(s) or not. This "seeding" method may also induce the breaking of immuno-tolerance to a target cell population, a tumor mass, and/or infected tissue site within a chordate.

In some embodiments, methods involving the seeding of a locus within a chordate with one or more antigenic and/or immunogenic epitopes may be combined with the administration of immunologic adjuvants, whether administered locally or systemically, to stimulate the immune response to certain antigens, such as, e.g., the co-administration of a composition described herein with one or more immunologic adjuvants like a cytokine, bacterial product, or plant saponin. Other examples of immunologic adjuvants which may be suitable for use in the methods described herein include aluminum salts and oils, such as, e.g., alums, aluminum hydroxide, mineral oils, squalene, paraffin oils, peanut oils, and thimerosal.

Additionally, provided herein is a method of treating a disease, disorder, or condition in a patient comprising the step of administering to a patient in need thereof an effective amount of at least one of the binding molecules, or a pharmaceutical composition thereof. In some embodiments, the disease, disorder, or condition involves a PD-L1 expressing cell. Contemplated diseases, disorders, and conditions that can be treated using this method include cancers, malignant tumors, non-malignant tumors, growth abnormalities, immune disorders, and microbial infections. Administration of a "therapeutically effective dosage" of a composition described herein can result in a decrease in severity of disease symptoms, an increase in frequency and duration of disease symptom-free periods, or a prevention of impairment or disability due to the disease affliction.

The therapeutically effective amount of a composition will depend on the route of administration, the type of organism being treated, and the physical characteristics of the specific patient under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by herein and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

An acceptable route of administration may refer to any administration pathway known in the art, including but not limited to aerosol, enteral, nasal, ophthalmic, oral, parenteral, rectal, vaginal, or transdermal (e.g. topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

For administration of a pharmaceutical composition, the dosage range will generally be from about 0.001 to 10 milligrams per kilogram (mg/kg), and more, usually 0.001 to 0.5 mg/kg, of the subject's body weight. Exemplary dosages may be 0.01 mg/kg body weight, 0.03 mg/kg body weight, 0.07 mg/kg body weight, 0.09 mg/kg body weight or 0.1 mg/kg body weight or within the range of 0.01 to 0.1 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular patient.

Pharmaceutical compositions will typically be administered to the same patient on multiple occasions. Intervals between single dosages can be, for example, two to five days, weekly, monthly, every two or three months, every six months, or yearly. Intervals between administrations can also be irregular, based on regulating blood levels or other markers in the subject or patient. Dosage regimens for a composition include, for example, intravenous administration of 0.01 mg/kg body weight or 0.03 mg/kg body weight with the composition administered every two to four weeks for six dosages, then every three months at 0.03 mg/kg body weight or 0.01 mg/kg body weight.

A pharmaceutical composition may be administered via one or more routes of administration, using one or more of a variety of methods known in the art. As will be appreciated by the skilled worker, the route and/or mode of administration will vary depending upon the desired results. Routes of administration for binding molecules and pharmaceutical compositions include, e.g. intravenous, intramuscular, intradermal, intraperitoneal, subcutaneous, spinal, or other parenteral routes of administration, for example by injection or infusion. For other embodiments, a binding molecule or pharmaceutical composition may be administered by a non-parenteral route, such as a topical, epidermal or mucosal route of administration, for example, intranasally, orally, vaginally, rectally, sublingually, or topically.

Therapeutic binding molecules or pharmaceutical compositions may be administered with one or more of a variety of medical devices known in the art. For example, in one embodiment, a pharmaceutical composition may be administered with a needleless hypodermic injection device. Examples of well-known implants and modules useful are known in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

The binding molecule or pharmaceutical composition may be administered alone or in combination with one or more other therapeutic or diagnostic agents. A combination therapy may include a binding molecule, or pharmaceutical composition thereof, combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutic molecules which may complement or otherwise be beneficial in a therapeutic or prophylactic treatment regimen.

Treatment of a patient with binding molecule or pharmaceutical composition may, in some embodiments, lead to cell death of targeted cells and/or the inhibition of growth of targeted cells. As such, cytotoxic, binding molecules, and pharmaceutical compositions comprising them, will be useful in methods for treating a variety of pathological disorders in which killing or depleting target cells may be beneficial, such as, inter alia, cancer, tumors, other growth abnormalities, immune disorders, and infected cells. Also provided herein are methods for suppressing cell proliferation, and treating cell disorders, including neoplasia, overactive B-cells, and overactive T-cells.

In some embodiments, the binding molecules and pharmaceutical compositions described herein can be used to treat or prevent cancers, tumors (malignant and non-malignant), growth abnormalities, immune disorders, and microbial infections. In some embodiments, the above ex vivo method can be combined with the above in vivo method to provide methods of treating or preventing rejection in bone marrow transplant recipients, and for achieving immunological tolerance.

In some embodiments, methods for treating malignancies or neoplasms and other blood cell associated cancers in a mammalian subject, such as a human, comprise the step of administering to a subject in need thereof a therapeutically effective amount of a cytotoxic binding molecule or pharmaceutical composition.

The binding molecules and pharmaceutical compositions have varied applications, including, e.g., uses in removing unwanted T-cells, uses in modulating immune responses to treat graft versus host, uses as antiviral agents, uses as antimicrobial agents, and uses in purging transplantation tissues of unwanted cell types. The binding molecules and pharmaceutical compositions described herein are commonly anti-neoplastic agents—meaning they are capable of treating and/or preventing the development, maturation, or spread of neoplastic or malignant cells by inhibiting the growth and/or causing the death of cancer or tumor cells.

In some embodiments, the binding molecule or pharmaceutical composition is used to treat a B-cell-, plasma cell- or antibody-mediated disease or disorder, such as for example leukemia, lymphoma (e.g., primary mediastinal B cell lymphoma, Hodgkin's lymphoma, or non-Hodgkin's lymphoma), myeloma, rheumatic disease, spondylitis, Human Immunodeficiency Virus-related diseases, amyloidosis, hemolytic uremic syndrome, polyarteritis, septic shock, Crohn's Disease, rheumatoid arthritis, ankylosing spondylitis, psoriatic arthritis, ulcerative colitis, psoriasis, asthma, Sjögren's syndrome, graft-versus-host disease, graft rejection, diabetes, vasculitis, scleroderma, and systemic lupus erythematosus.

In some embodiments, certain embodiments of the binding molecules and pharmaceutical compositions described herein are antimicrobial agents—meaning they are capable of treating and/or preventing the acquisition, development, or consequences of microbiological pathogenic infections, such as caused by viruses, bacteria, fungi, prions, or protozoans.

It is within the scope of the present disclosure to provide a prophylaxis or treatment for diseases or conditions mediated by T-cells or B-cells by administering a binding molecule described herein, or a pharmaceutical composition thereof, to a patient for the purpose of killing T-cells or B-cells in the patient. This usage is compatible with preparing or conditioning a patient for bone marrow transplantation, stem cell transplantation, tissue transplantation, or organ transplantation, regardless of the source of the transplanted material, e.g. human or non-human sources.

It is within the scope of the present disclosure to provide a bone marrow recipient for prophylaxis or treatment of host-versus-graft disease via the targeted cell-killing of host T-cells using a cytotoxic binding molecule or pharmaceutical composition as described herein.

In some embodiments, a method of treating cancer comprises administering to a subject in need thereof an effective amount of a PDL-1 binding molecule or a pharmaceutical composition comprising the same. In some embodiments, a method of treating cancer comprises administering to a subject in need thereof an effective amount of a nucleic acid (e.g., an expression vector) encoding a PD-L1 binding molecule. In some embodiments, the cancer is any one of the following: bladder cancer (e.g., urothelial carcinoma), breast cancer (e.g., HER2 positive breast cancer, triple negative breast cancer), colon cancer (e.g., colorectal cancer such as metastatic microsatellite instability-high or mismatch repair deficient colorectal cancer), endometrial cancer, esophageal cancer, fallopian tube cancer, gastrointestinal cancer (e.g., gastric cancer, biliary tract neoplasm, gastroesophageal junction cancer), glioblastoma, glioma, head and neck cancer (e.g., squamous cell carcinoma of the head and neck), kidney cancer (e.g., renal cell carcinoma), liver cancer (e.g., hepatocellular carcinoma), lung cancer (e.g., non-small cell lung cancer, small-cell lung cancer), lymphoma (e.g., diffuse large B-cell lymphoma, Hodgkin lymphoma, non-Hodgkin lymphoma, primary mediastinal large B-cell lymphoma), Merkel cell carcinoma, mesothelioma (e.g., pleural mesothelioma), myeloma (e.g., multiple myeloma), nasopharyngeal neoplasm, ovarian cancer, pancreatic cancer, peritoneal neoplasm, prostate cancer, skin cancer (e.g., squamous cell cancer of the skin, melanoma, transitional cell carcinoma, or urothelial cancer.

Some embodiments of the binding molecules and pharmaceutical compositions can be utilized in a method of treating cancer comprising administering to a patient, in need thereof, a therapeutically effective amount of a binding molecule and/or pharmaceutical composition. In some embodiments, the cancer being treated is selected from the group consisting of: bone cancer (such as multiple myeloma or Ewing's sarcoma), breast cancer (such as HER2 positive breast cancer or triple negative breast cancer), central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer (such as hepatocellular carcinoma), lung/pleura cancer (such as mesothelioma, small cell lung cancer, or non-small cell lung cancer), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), urothelial cancer, gastric cancer, esophageal cancer, head and neck squamous cell cancer, cervical cancer, Merkel cell carcinoma, endometrial cancer, and uterine cancer.

In some embodiments of the methods of treating cancer described herein, the subject received at least one line or regimen of prior treatment, before administration with a binding molecule. In some embodiments, subject has cancer, and the cancer is relapsed or refractory to at least one prior treatment, such as checkpoint inhibitor therapy. In some embodiments, the cancer is relapsed or refractory to ipilimumab, nivolumab, pembrolizumab, atexolizumab, durvalumab, avelumab, tremelimumab or cemiplimab. In some embodiments, the cancer is one of the cancers listed in Table 6, below, and is relapsed or refractory to at least one prior treatment marked with an "X" in the table.

In some embodiments, the Shiga toxin effector polypeptide or binding molecule is used as a component of a pharmaceutical composition or medicament for the treatment or prevention of a cancer, tumor, other growth abnormality, immune disorder, and/or microbial infection. For example, immune disorders presenting on the skin of a patient may be treated with such a medicament in efforts to reduce inflammation. In another example, skin tumors may be treated with such a medicament in efforts to reduce tumor size or eliminate the tumor completely.

Certain cytotoxic binding molecules, and compositions thereof, may be used in molecular neurosurgery applications such as immunolesioning and neuronal tracing (see, Wiley R, Lappi D, *Adv Drug Deliv Rev* 55: 1043-54 (2003), for review). For example, the targeting domain may be selected or derived from various ligands, such as neurotransmitters and neuropeptides, which target specific neuronal cell types by binding neuronal surface receptors, such as a neuronal circuit specific G-protein coupled receptor. Similarly, the targeting domain may be selected from or derived from antibodies that bind neuronal surface receptors. Because certain Shiga toxin effector polypeptides robustly direct their own retrograde axonal transport, certain binding molecules may be used to kill a neuron(s) which expresses the extracellular target at a site of cytotoxic protein injection distant from the cell body (see Llewellyn-Smith I et al., *J Neurosci Methods* 103: 83-90 (2000)). These targeted cytotoxic molecules that specifically target neuronal cell types have uses in neuroscience research, such as for elucidating mechanisms of sensations (see e.g. Mishra S, Hoon M, *Science* 340: 968-71 (2013), and creating model systems of neurodegenerative diseases, such as Parkinson's and Alzheimer's (see e.g. Hamlin A et al., *PLoS One* e53472 (2013)).

TABLE 6

Cancers treatable with a binding molecule of the disclosure that can be relapsed or refractory to prior treatments

| Cancer | Ipilimumab | Nivolumab | Pembroizumab | Atezolizumab | Durvalumab | Avelumab | Cemiplimab |
|---|---|---|---|---|---|---|---|
| Melanoma | X | X | X | | | | |
| Merkel Cell | | | X | | | X | |
| Cutaneous Squamous Cell Carcinoma | | | | | | | X |
| Non-small cell lung cancer | | X | X | X | X | | |
| Small cell lung cancer | | X | X | X | | | |
| Squamous cell carcinoma of the head and neck | | X | X | | X | | |
| Esophageal cancer | | | X | | | | |
| Gastric cancer | | X | X | | | | |
| Colorectal cancer | | X | X | | | | |
| Hepatocellular carcinoma | | X | | | | | |
| Bladder cancer | | X | X | X | X | X | |
| Renal Cell Carcinoma | X | X | X | | | X | |

In some embodiments, a method of treating cancer comprises administering to a subject in need thereof an effective amount of a PDL-1 binding molecule or a pharmaceutical composition comprising the same, wherein the cancer is metastatic.

Some embodiments of the binding molecules and pharmaceutical compositions can be utilized in a method of treating an immune disorder comprising administering to a patient, in need thereof, a therapeutically effective amount of the binding molecules and/or pharmaceutical composition. In some embodiments, the immune disorder is related to an inflammation associated with a disease selected from the group consisting of: rheumatic disease, spondylitis, amyloidosis, ankylosing spondylitis, asthma, Crohn's disease, diabetes, graft rejection, graft-vs.-host disease, Hashimoto's thyroiditis, hemolytic uremic syndrome, HIV-related diseases, lupus erythematosus, 287318279 multiple sclerosis, polyarteritis, psoriasis, psoriatic arthritis, rheumatoid arthritis, scleroderma, septic shock, Sjögren's syndrome, ulcerative colitis, and vasculitis.

In some embodiments, a method of using a Shiga toxin effector polypeptide, binding molecule, pharmaceutical composition, and/or diagnostic composition as described herein to label or detect the interiors of neoplastic cells and/or immune cell types is provided. This method may be based on the ability of certain binding molecules to enter specific cell types and route within cells via retrograde intracellular transport, to the interior compartments of specific cell types are labeled for detection. This can be performed on cells in situ within a patient or on cells and tissues removed from an organism, e.g. biopsy material.

In some embodiments, a method of using a Shiga toxin effector polypeptide, binding molecule, pharmaceutical composition, and/or diagnostic composition to detect the presence of a cell type for the purpose of information gathering regarding diseases, conditions and/or disorders is provided. The method comprises contacting a cell with a diagnostically effective amount of a binding molecule in order to detect the molecule by an assay or diagnostic technique. The phrase "diagnostically effective amount" refers to an amount that provides adequate detection and accurate measurement for information gathering purposes by the particular assay or diagnostic technique utilized. Generally, the diagnostically effective amount for whole organism in vivo diagnostic use will be a non-cumulative dose of between 0.001 to 10 milligrams of the detection promoting agent linked binding molecule per kg of subject per subject. Typically, the amount of Shiga toxin effector polypeptide or binding molecule used in these information gathering methods will be as low as possible, provided that it is still a diagnostically effective amount. For example, for in vivo detection in an organism, the amount of Shiga toxin effector polypeptide, binding molecule, or pharmaceutical composition administered to a subject will be as low as feasibly possible.

The cell-type specific targeting of binding molecules combined with detection promoting agents provides a way to detect and image cells physically coupled with an extracellular PD-L1 bound by the binding region of the molecule. Imaging of cells using the binding molecules may be performed in vitro or in vivo by any suitable technique known in the art. Diagnostic information may be collected using various methods known in the art, including whole body imaging of an organism or using ex vivo samples taken from an organism. The term "sample" used herein refers to any number of things, but not limited to, fluids such as blood, urine, serum, lymph, saliva, anal secretions, vaginal secretions, and semen, and tissues obtained by biopsy procedures. For example, various detection promoting agents may be utilized for non-invasive in vivo tumor imaging by techniques such as magnetic resonance imaging (MM), optical methods (such as direct, fluorescent, and bioluminescent imaging), positron emission tomography (PET), single-photon emission computed tomography (SPECT), ultrasound, x-ray computed tomography, and combinations of the aforementioned (see, Kaur S et al., *Cancer Lett* 315: 97-111 (2012), for review).

Also provided is a method of using a Shiga toxin effector polypeptide, binding molecule, or pharmaceutical composition in a diagnostic composition to label or detect the interiors of a hematologic cell, cancer cell, tumor cell, infected cell, and/or immune cell (see e.g., Koyama Y et al., *Clin Cancer Res* 13: 2936-45 (2007); Ogawa M et al., *Cancer Res* 69: 1268-72 (2009); Yang L et al., *Small* 5: 235-43 (2009)). Based on the ability of certain binding molecules to enter specific cell types and route within cells via retrograde intracellular transport, the interior compartments of specific cell types are labeled for detection. This can be performed on cells in situ within a patient or on cells and tissues removed from an organism, e.g. biopsy material.

Diagnostic compositions may be used to characterize a disease, disorder, or condition as potentially treatable by a related pharmaceutical composition. Some compositions of matter may described herein be used to determine whether a patient belongs to a group that responds to a therapeutic strategy which makes use of a compound, composition or related method as described herein or is well suited for using a delivery device as described herein.

Diagnostic compositions may be used after a disease, e.g. a cancer, is detected in order to better characterize it, such as to monitor distant metastases, heterogeneity, and stage of cancer progression. The phenotypic assessment of disease disorder or infection can help prognostic and prediction during therapeutic decision making. In disease reoccurrence, certain methods may be used to determine if local or systemic problem.

Diagnostic compositions may be used to assess responses to therapies regardless of the type of the type of therapy, e.g. small molecule drug, biological drug, or cell-based therapy. For example, certain embodiments of the diagnostics may be used to measure changes in tumor size, changes in antigen positive cell populations including number and distribution, or monitoring a different marker than the antigen targeted by a therapy already being administered to a patient (see Smith-Jones P et al., *Nat. Biotechnol* 22: 701-6 (2004); Evans M et al., *Proc. Natl. Acad. Sci. USA* 108: 9578-82 (2011)).

In some embodiments of the method used to detect the presence of a cell type may be used to gather information regarding diseases, disorders, and conditions, such as, for example bone cancer (such as multiple myeloma or Ewing's sarcoma), breast cancer, central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer, lung/pleura cancer (such as mesothelioma, small cell lung carcinoma, or non-small cell lung carcinoma), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), uterine cancer, AIDS, rheumatic disease, spondylitis, amyloidosis, ankylosing spondylitis, asthma, autism, cardiorheumatic disease, Crohn's disease, diabetes, erythematosus, gastritis, graft rejection, graft-versus-host disease, Grave's disease, Hashimoto's thyroiditis, hemolytic uremic syndrome, HIV-related diseases, lupus erythematosus, lymphoproliferative disorders (including post-transplant lymphoproliferative disorders), multiple sclerosis, myasthenia gravis, neuroinflammation, polyarteritis, psoriasis, psoriatic arthritis, rheumatoid arthritis, scleroderma, septic shock, Sjögren's syndrome, systemic lupus erythematosus, ulcerative colitis, vasculitis, cell proliferation, inflammation, leukocyte activation, leukocyte adhesion, leukocyte chemotaxis, leukocyte maturation, leukocyte migration, neuronal differentiation, acute lymphoblastic leukemia (ALL), T acute lymphocytic leukemia/lymphoma (ALL), acute myelogenous leukemia, acute myeloid leukemia (AML), B-cell chronic lymphocytic leukemia (B-CLL), B-cell prolymphocytic lymphoma, Burkitt's lymphoma (BL), chronic lymphocytic leukemia (CLL), chronic myelogenous leukemia (CIVIL-BP), chronic myeloid leukemia (CIVIL), diffuse large B-cell lymphoma, follicular lymphoma, hairy cell leukemia (HCL), Hodgkin's Lymphoma (HL), intravascular large B-cell lymphoma, lymphomatoid granulomatosis, lymphoplasmacytic lymphoma, MALT lymphoma, mantle cell lymphoma, multiple myeloma (MM), natural killer cell leukemia, nodal marginal B-cell lymphoma, Non-Hodgkin's lymphoma (NHL), plasma cell leukemia, plasmacytoma, primary effusion lymphoma, pro-lymphocytic leukemia, promyelocytic leukemia, small lymphocytic lymphoma, splenic marginal zone lymphoma, T-cell lymphoma (TCL), heavy chain disease, monoclonal gammopathy, monoclonal immunoglobulin deposition disease, myelodusplastic syndromes (MDS), smoldering multiple myeloma, and Waldenstrom macroglobulinemia.

In some embodiments, the Shiga toxin effector polypeptides and binding molecules, or pharmaceutical compositions thereof, are used for both diagnosis and treatment, or for diagnosis alone. In some situations, it would be desirable to determine or verify the HLA variant(s) and/or HLA alleles expressed in the subject and/or diseased tissue from the subject, such as, e.g., a patient in need of treatment, before selecting a Shiga toxin effector polypeptide or binding molecule for use in treatment(s).

Any embodiment of the binding molecule (e.g. an embodiment of any one of Embodiment Sets #1-13 in the Summary) may be used with each individual embodiment of the methods described herein.

The present invention is further illustrated by the following numbered embodiments, and the non-limiting examples of binding molecules capable of specifically targeting PD-L1 and comprising one or more proteinaceous toxin components.

NUMBERED EMBODIMENTS

Different embodiments of the PD-L1 binding molecules are described below with reference to sets of embodiments numbered #1-3.

Embodiment Set #1—PD-L1 Binding Molecule Comprising a De-Immunized Shiga Toxin Effector Polypeptide Comprising an Embedded or Inserted, Heterologous, T-Cell Epitope and a Non-Overlapping De-Immunized Sub-Region Provided herein are binding molecules comprising (i) a binding region capable of specifically binding an extracellular target biomolecule (PD-L1) and (ii) a de-immunized, Shiga toxin effector polypeptide. For example, in some embodiments of Embodiment Set #1, the binding molecule comprises (i) a binding region capable of specifically binding an extracellular target biomolecule and (ii) a de-immunized, Shiga toxin effector polypeptide comprising at least one inserted or embedded, heterologous epitope (a) and at least one disrupted, endogenous, B-cell and/or CD4+ T-cell epitope region (b), wherein the heterologous epitope does not overlap with the embedded or inserted, heterologous, T-cell epitope. In some embodiments, the Shiga toxin effector polypeptide is capable of exhibiting at least one Shiga toxin effector function, such as, e.g., directing intracellular routing to the endoplasmic reticulum and/or cytosol of a cell in which the polypeptide is present, inhibiting a ribosome function, enzymatically inactivating a ribosome, causing cytostasis, and/or causing cytotoxicity. In some embodiments, the heterologous, T-cell epitope is a CD8+ T-cell epitope, such as, e.g., with regard to a human immune system. In some embodiments, the heterologous, T-cell epitope is capable of being presented by a MHC class I molecule of a cell. In some embodiments, the binding molecule is capable of one or more the following: entering a cell, inhibiting a ribosome function, causing cytostasis, causing cell death, and/or delivering the embedded or inserted, heterologous, T-cell epitope to a MHC class I molecule for presentation on a cellular surface. In some embodiments, the binding molecule is capable, when introduced to cells, of exhibiting a cytotoxicity comparable or better than a reference molecule, such as, e.g., a second binding molecule consisting of the binding molecule except for all of its Shiga toxin effector polypeptide component(s) each comprise a wild-type Shiga toxin A1 fragment.

In some embodiments of Embodiment Set #1, the binding molecule comprises a molecular moiety located carboxy-terminal to the carboxy-terminus of the Shiga toxin A1 fragment region.

In some embodiments of Embodiment Set #1, the binding molecule is capable, when introduced to a chordate, of exhibiting improved in vivo tolerability and/or stability compared to a reference molecule, such as, e.g., a second binding molecule consisting of the binding molecule except for all of its Shiga toxin effector polypeptide component(s) each comprise a wild-type Shiga toxin A1 fragment and/or wild-type Shiga toxin furin-cleavage site at the carboxy terminus of its A1 fragment region. In some embodiments, the Shiga toxin effector polypeptide is not cytotoxic and the molecular moiety is cytotoxic.

In some embodiments of Embodiment Set #1, the binding region and Shiga toxin effector polypeptide are linked together, either directly or indirectly.

In some embodiments of Embodiment Set #1, the binding region comprises a polypeptide comprising an immunoglobulin-type binding region. In some embodiments, the binding region comprises a polypeptide selected from the group consisting of: an autonomous $V_H$ domain, single-domain antibody fragment (sdAb), nanobody, heavy chain-antibody domain derived from a camelid ($V_HH$ or $V_H$ domain fragment), heavy-chain antibody domain derived from a cartilaginous fish ($V_HH$ or $V_H$ domain fragment), immunoglobulin new antigen receptor (IgNAR), $V_{NAR}$ fragment, single-chain variable fragment (scFv), antibody variable fragment (Fv), complementary determining region 3 fragment (CDR3), constrained FR3-CDR3-FR4 polypeptide (FR3-CDR3-FR4), Fd fragment, small modular immunopharmaceutical (SMIP) domain, antigen-binding fragment (Fab), Armadillo repeat polypeptide (ArmRP), fibronectin-derived $10^{th}$ fibronectin type III domain (10Fn3), tenascin type III domain (TNfn3), ankyrin repeat motif domain, low-density-lipoprotein-receptor-derived A-domain (LDLR-A), lipocalin (anticalin), Kunitz domain, Protein-A-derived Z domain, gamma-B crystallin-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality.

In some embodiments of Embodiment Set #1, the binding molecule is capable of exhibiting (i) a catalytic activity level comparable to a wild-type Shiga toxin A1 fragment or wild-type Shiga toxin effector polypeptide, (ii) a ribosome inhibition activity with a half-maximal inhibitory concentration ($IC_{50}$) value of 10,000 picomolar or less, and/or (iii) a significant level of Shiga toxin catalytic activity.

In some embodiments of Embodiment Set #1, the binding molecule and/or its Shiga toxin effector polypeptide is capable of exhibiting subcellular routing efficiency comparable to a reference binding molecule comprising a wild-type Shiga toxin A1 fragment or wild-type Shiga toxin effector polypeptide and/or capable of exhibiting a significant level of intracellular routing activity to the endoplasmic reticulum and/or cytosol from an endosomal starting location of a cell.

In some embodiments of Embodiment Set #1, whereby administration of the binding molecule to a cell physically coupled with the extracellular target biomolecule of the binding molecule's binding region, the binding molecule is capable of causing death of the cell. In some embodiments, administration of the binding molecule to two different populations of cell types which differ with respect to the presence or level of the extracellular target biomolecule, the binding molecule is capable of causing cell death to the cell-types physically coupled with an extracellular target biomolecule of the cytotoxic binding molecule's binding region at a $CD_{50}$ at least three times or less than the $CD_{50}$ to cell types which are not physically coupled with an extracellular target biomolecule of the binding molecule's binding region. In some embodiments, whereby administration of the binding molecule to a first population of cells whose members are physically coupled to extracellular target biomolecules of the binding molecule's binding region, and a second population of cells whose members are not physically coupled to any extracellular target biomolecule of the binding region, the cytotoxic effect of the binding molecule to members of said first population of cells relative to members of said second population of cells is at least 3-fold greater. In some embodiments, whereby administration of the binding molecule to a first population of cells whose members are physically coupled to a significant amount of the extracellular target biomolecule of the binding molecule's binding region, and a second population of cells whose members are not physically coupled to a significant amount of any extracellular target biomolecule of the binding region, the cytotoxic effect of the binding molecule to members of said first population of cells relative to members of said second population of cells is at least 3-fold greater. In some embodiments, whereby administration of the binding molecule to a first population of target biomolecule positive cells, and a second population of cells whose members do not express a significant amount of a target biomolecule of the binding molecule's binding region at a cellular surface, the cytotoxic effect of the binding molecule to members of the first population of cells relative to members of the second population of cells is at least 3-fold greater.

In some embodiments of Embodiment Set #1, the binding molecule is capable, when introduced to cells, of exhibiting a cytotoxicity with a half-maximal inhibitory concentration ($CD_{50}$) value of 300 nM or less and/or capable of exhibiting a significant level of Shiga toxin cytotoxicity.

In some embodiments of Embodiment Set #1, the binding molecule is capable of delivering an embedded or inserted, heterologous, CD8+ T-cell epitope to a MHC class I presentation pathway of a cell for cell-surface presentation of the epitope bound by a MHC class I molecule.

In some embodiments of Embodiment Set #1, the binding molecule comprises a molecular moiety associated with the carboxy-terminus of the Shiga toxin effector polypeptide. In some embodiments, the molecular moiety comprises or consists of the binding region. In some embodiments, the molecular moiety comprises at least one amino acid and the Shiga toxin effector polypeptide is linked to at least one amino acid residue of the molecular moiety. In some embodiments, the molecular moiety and the Shiga toxin effector polypeptide are fused forming a continuous polypeptide.

In some embodiments of Embodiment Set #1, the binding molecule further comprises a cytotoxic molecular moiety associated with the carboxy-terminus of the Shiga toxin effector polypeptide. In some embodiments, the cytotoxic molecular moiety is a cytotoxic agent, such as, e.g., a small molecule chemotherapeutic agent, anti-neoplastic agent, cytotoxic antibiotic, alkylating agent, antimetabolite, topoisomerase inhibitor, and/or tubulin inhibitor known to the skilled worker and/or described herein. For some embodiments, the cytotoxic molecular moiety is cytotoxic at concentrations of less than 10,000, 5,000, 1,000, 500, or 200 pM.

In some embodiments of Embodiment Set #1, the binding region is linked, either directly or indirectly, to the Shiga toxin effector polypeptide by at least one covalent bond which is not a disulfide bond. In some embodiments, the binding region is fused, either directly or indirectly, to the carboxy-terminus of the Shiga toxin effector polypeptide to form a single, continuous polypeptide. In some embodiments, the binding region is an immunoglobulin-type binding region.

In some embodiments of Embodiment Set #1, the disrupted furin-cleavage motif comprises one or more mutations in the minimal, furin-cleavage site relative to a wild-type Shiga toxin A Subunit. In some embodiments, the disrupted furin-cleavage motif is not an amino-terminal truncation of sequences that overlap with part or all of at least one amino acid residue of the minimal furin-cleavage site. In some embodiments, the mutation in the minimal, furin-cleavage site is an amino acid deletion, insertion, and/or substitution of at least one amino acid residue in the R/Y-x-x-R furin cleavage motif. In some embodiments, the disrupted furin-cleavage motif comprises at least one mutation relative to a wild-type Shiga toxin A Subunit, the mutation altering at least one amino acid residue in the region natively positioned 1) at 248-251 of the A Subunit of Shiga-like toxin 1 (SEQ ID NO: 1) or Shiga toxin (SEQ ID NO: 2), or 2) at 247-250 of the A Subunit of Shiga-like toxin 2 (SEQ ID NO:3), or the equivalent amino acid sequence position in any Shiga toxin A Subunit. In some embodiments, the mutation is an amino acid residue substitution of an arginine residue with a non-positively charged, amino acid residue.

In some embodiments of Embodiment Set #1, the binding molecule is capable, when introduced to cells, of exhibiting cytotoxicity comparable to a cytotoxicity of a reference molecule, such as, e.g., a second binding molecule consisting of the binding molecule except for all of its Shiga toxin effector polypeptide component(s) each comprise a wild-type Shiga toxin A1 fragment.

In some embodiments, the binding region comprises or consists essentially of the polypeptide comprising the amino acid sequence of any one of SEQ ID NOs: 85-107 and 156-157.

In some embodiments, the binding region comprises a polypeptide that is at least 85%, 90%, 95%, 97%, 98%, 98.5%, or 99% identical to any one of SEQ ID NOs: 85-107 and 156-157. In some embodiments, the polypeptide comprises: (a) a light chain variable region (HVR-L) comprising three CDRs, each comprising or consisting essentially of an amino acid sequence shown in any one of SEQ ID NO:19, SEQ ID NO:20, SEQ ID NO:21, SEQ ID NO:25, and SEQ ID NO:26; and (b) a heavy chain variable region (HVR-H) comprising three CDRs, each comprising or consisting essentially of an amino acid sequence show in any one of SEQ ID NOs: 22-24 and 27-32.

In some embodiments of Embodiment Set #1, the binding molecule comprises or consists essentially of the polypeptide shown in any one of SEQ ID NOs: 108-155.

In some embodiments of Embodiment Set #1, the binding region sterically covers the carboxy-terminus of the A1 fragment region.

In some embodiments of Embodiment Set #1, the molecular moiety sterically covers the carboxy-terminus of the A1 fragment region. In some embodiments, the molecular moiety comprises the binding region.

In some embodiments of Embodiment Set #1, the binding molecule comprises a binding region and/or molecular moiety located carboxy-terminal to the carboxy-terminus of the Shiga toxin A1 fragment region. In some embodiments, the mass of the binding region and/or molecular moiety is at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater.

In some embodiments of Embodiment Set #1, the binding molecule comprises a binding region with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the binding molecule retains the appropriate level of the Shiga toxin biological activity noted herein (e.g., cytotoxicity and/or intracellular routing).

In some embodiments of Embodiment Set #1, the binding region is comprised within a relatively large, molecular moiety comprising such as, e.g., a molecular moiety with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the binding molecule retains the appropriate level of the Shiga toxin biological activity noted herein.

In some embodiments of Embodiment Set #1, the amino-terminus of the Shiga toxin effector polypeptide is at and/or proximal to an amino-terminus of a polypeptide component of the binding molecule. In some embodiments, the binding region is not located proximally to the amino-terminus of the binding molecule relative to the Shiga toxin effector polypeptide. In some embodiments, the binding region and Shiga toxin effector polypeptide are physically arranged or oriented within the binding molecule such that the binding region is not located proximally to the amino-terminus of the Shiga toxin effector polypeptide. In some embodiments, the binding region is located within the binding molecule more proximal to the carboxy-terminus of the Shiga toxin effector polypeptide than to the amino-terminus of the Shiga toxin effector polypeptide. For some embodiments, the binding molecule is capable, when introduced to cells, of exhibiting cytotoxicity that is greater than that of a third binding molecule having an amino-terminus and comprising the binding region and the Shiga toxin effector polypeptide which is not positioned at or proximal to the amino-terminus of the third binding molecule. For some embodiments, the binding molecule exhibits cytotoxicity with better optimized, cytotoxic potency, such as, e.g., 4-fold, 5-fold, 6-fold, 9-fold, or greater cytotoxicity as compared to the cytotoxicity of the third binding molecule. For some embodiments, the cytotoxicity of the binding molecule to a population of target positive cells is 3-fold, 4-fold, 5-fold, 6-fold, 7-fold, 8-fold, 9-fold, 10-fold or greater than the cytotoxicity of the third binding molecule to a second population of target positive cells as assayed by $CD_{50}$ values. In some embodiments, the third binding molecule does not comprise any carboxy-terminal, endoplasmic reticulum retention/retrieval signal motif of the KDEL family (See SEQ ID NO: 205-252).

In some embodiments of Embodiment Set #1, the amino-terminus of the Shiga toxin effector polypeptide is at and/or proximal to an amino-terminus of a polypeptide component of the binding molecule. In some embodiments, the binding region is not located proximally to the amino-terminus of the binding molecule relative to the Shiga toxin effector polypeptide. In some embodiments, the binding region and Shiga toxin effector polypeptide are physically arranged or oriented within the binding molecule such that the binding region is not located proximally to the amino-terminus of the Shiga toxin effector polypeptide. In some embodiments, the binding region is located within the binding molecule more proximal to the carboxy-terminus of the Shiga toxin effector polypeptide than to the amino-terminus of the Shiga toxin effector polypeptide. For some embodiments, the binding molecule is not cytotoxic and is capable, when introduced to cells, of exhibiting a greater subcellular routing efficiency from an extracellular space to a subcellular compartment of an endoplasmic reticulum and/or cytosol as compared to the cytotoxicity of a third binding molecule having an amino-terminus and comprising the binding region and the Shiga toxin effector polypeptide which is not positioned at or proximal to the amino-terminus of the third binding molecule. In some embodiments, the third binding molecule does not comprise any carboxy-terminal, endoplasmic reticulum retention/retrieval signal motif of the KDEL family (See SEQ ID NO: 205-252).

In some embodiments of Embodiment Set #1, the amino-terminus of the Shiga toxin effector polypeptide is at and/or proximal to an amino-terminus of a polypeptide component of the binding molecule. In some embodiments, the binding region is not located proximally to the amino-terminus of the binding molecule relative to the Shiga toxin effector polypeptide. In some embodiments, the binding region and Shiga toxin effector polypeptide are physically arranged or oriented within the binding molecule such that the binding region is not located proximally to the amino-terminus of the Shiga toxin effector polypeptide. In some embodiments, the binding region is located within the binding molecule more proximal to the carboxy-terminus of the Shiga toxin effector polypeptide than to the amino-terminus of the Shiga toxin effector polypeptide. In some embodiments, the binding molecule exhibits low cytotoxic potency (i.e. is not capable when introduced to certain positive target cell types of exhibiting a cytotoxicity greater than 1% cell death of a cell population at a binding molecule concentration of 1000 nM, 500 nM, 100 nM, 75 nM, or 50 nM) and is capable, when introduced to cells, of exhibiting a greater subcellular routing efficiency from an extracellular space to a subcellular compartment of an endoplasmic reticulum and/or cytosol as compared to the cytotoxicity of a third binding molecule having an amino-terminus and comprising the binding region and the Shiga toxin effector polypeptide which is not positioned at or proximal to the amino-terminus of the third binding molecule. In some embodiments, the third binding molecule does not comprise any carboxy-terminal, endoplasmic reticulum retention/retrieval signal motif of the KDEL family (See SEQ ID NO: 205-252).

In some embodiments of Embodiment Set #1, the binding molecule, or a polypeptide component thereof, comprises a carboxy-terminal, endoplasmic reticulum retention/retrieval signal motif of a member of the KDEL family. For some embodiments, the carboxy-terminal endoplasmic reticulum retention/retrieval signal motif is selected from the group consisting of: KDEL (SEQ ID NO: 205), HDEF (SEQ ID NO: 206), HDEL (SEQ ID NO: 207), RDEF (SEQ ID NO: 208), RDEL (SEQ ID NO: 209), WDEL (SEQ ID NO: 210), YDEL (SEQ ID NO: 211), HEEF (SEQ ID NO: 212), HEEL (SEQ ID NO: 213), KEEL (SEQ ID NO: 214), REEL (SEQ ID NO: 215), KAEL (SEQ ID NO: 216), KCEL (SEQ ID NO: 217), KFEL (SEQ ID NO: 218), KGEL (SEQ ID NO: 219), KHEL (SEQ ID NO: 220), KLEL (SEQ ID NO: 221), KNEL (SEQ ID NO: 222), KQEL (SEQ ID NO: 223), KREL (SEQ ID NO: 224), KSEL (SEQ ID NO: 225), KVEL (SEQ ID NO: 226), KWEL (SEQ ID NO: 227), KYEL (SEQ ID NO: 228), KEDL (SEQ ID NO: 229), KIEL (SEQ ID NO: 230), DKEL (SEQ ID NO: 231), FDEL (SEQ ID NO: 232), KDEF (SEQ ID NO: 233), KKEL (SEQ ID NO: 234), HADL (SEQ ID NO: 235), HAEL (SEQ ID NO: 236), HIEL (SEQ ID NO: 237), HNEL (SEQ ID NO: 238), HTEL (SEQ ID NO: 239), KTEL (SEQ ID NO: 240), HVEL (SEQ ID NO: 241), NDEL (SEQ ID NO: 242), QDEL (SEQ ID NO: 243), REDL (SEQ ID NO: 244), RNEL (SEQ ID NO: 245), RTDL (SEQ ID NO: 246), RTEL (SEQ ID NO: 247), SDEL (SEQ ID NO: 248), TDEL (SEQ ID NO: 249), SKEL (SEQ ID NO: 250), STEL (SEQ ID NO: 251), and EDEL (SEQ ID NO: 252). In some embodiments, the binding molecule is capable, when introduced to cells, of exhibiting cytotoxicity that is greater than that of a fourth binding molecule consisting of the binding molecule except for it does not comprise any carboxy-terminal, endoplasmic reticulum retention/retrieval signal motif of the KDEL family (See SEQ ID NO: 205-252). In some embodiments, the binding molecule is capable of exhibiting a cytotoxicity with better optimized, cytotoxic potency, such as, e.g., 4-fold, 5-fold, 6-fold, 9-fold, or greater cytotoxicity as compared to a reference molecule, such as, e.g., the fourth binding molecule. In some embodiments, the cytotoxicity of the binding molecule to a population of target positive cells is 3-fold, 4-fold, 5-fold, 6-fold, 7-fold, 8-fold, 9-fold, 10-fold or greater than the cytotoxicity of the fourth binding molecule to a second population of target positive cells as assayed by $CD_{50}$ values.

Embodiment Set #2—Binding Molecule Comprising a Shiga Toxin Effector Polypeptide Comprising (i) an Embedded or Inserted, Heterologous, T-Cell Epitope and (ii) a Disrupted, Furin-Cleavage Motif Also provided herein are binding molecules comprising (i) a binding region capable of specifically binding an extracellular target biomolecule (PD-L1); (ii) a Shiga toxin effector polypeptide comprising an inserted or embedded, heterologous, epitope; and (iii) a disrupted furin-cleavage motif. In some embodiments, the cell-binding molecule comprises (i) a binding region capable of specifically binding an extracellular target biomolecule; (ii) a Shiga toxin effector polypeptide comprising (a) an inserted or embedded, heterologous, epitope; (b) a Shiga toxin A1 fragment derived region having a carboxy terminus; and (c) a disrupted furin-cleavage motif at the carboxy-terminus of the A1 fragment region. For some embodiments, the Shiga toxin effector polypeptide is capable of exhibiting at least one Shiga toxin effector function, such as, e.g., directing intracellular routing to the endoplasmic reticulum and/or cytosol of a cell in which the polypeptide is present, inhibiting a ribosome function, enzymatically inactivating a ribosome, causing cytostasis, and/or causing cytotoxicity. In some embodiments, the heterologous, T-cell epitope is a CD8+ T-cell epitope, such as, e.g., with regard to a human immune system. For some embodiments, the heterologous, T-cell epitope is capable of being presented by a WIC class I molecule of a cell. In some embodiments, the cell-binding molecule is capable of one or more of the following: entering a cell, inhibiting a ribosome function, causing cytostasis, causing cell death, and/or delivering the embedded or inserted, heterologous, T-cell epitope to a WIC class I molecule for presentation on a cellular surface. For some embodiments, the binding molecule is capable, when introduced to cells, of exhibiting a cytotoxicity comparable or better than a reference molecule, such as, e.g., a second binding molecule consisting of the binding molecule except for all of its Shiga toxin effector polypeptide components comprise a wild-type Shiga toxin furin-cleavage site at the carboxy terminus of its A1 fragment region.

In some embodiments of Embodiment Set #2, the embedded or inserted, heterologous, T-cell epitope disrupts the endogenous, B-cell and/or T-cell epitope region selected from the group of natively positioned Shiga toxin A Subunit regions consisting of: (i) 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3, or the equivalent region in a Shiga toxin A Subunit or derivative thereof; (ii) 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; and (iii) 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, or the equivalent region in a Shiga toxin A Subunit or derivative thereof.

In some embodiments of Embodiment Set #2, the disrupted furin-cleavage motif comprises one or more mutations, relative to a wild-type Shiga toxin A Subunit, the mutation altering at least one amino acid residue in a region natively positioned at 248-251 of the A Subunit of Shiga-like toxin 1 (SEQ ID NO:1) or Shiga toxin (SEQ ID NO:2), or at 247-250 of the A Subunit of Shiga-like toxin (SEQ ID NO:3); or the equivalent region in a Shiga toxin A Subunit or derivative thereof. In some embodiments, the disrupted furin-cleavage motif comprises one or more mutations, relative to a wild-type Shiga toxin A Subunit, in a minimal furin cleavage site of the furin-cleavage motif. In some embodiments the minimal furin cleavage site is represented by the consensus amino acid sequence R/Y-x-x-R and/or R-x-x-R.

In some embodiments of Embodiment Set #2, the binding molecule comprises a molecular moiety located carboxy-terminal to the carboxy-terminus of the Shiga toxin A1 fragment region.

In some embodiments of Embodiment Set #2, the binding region sterically covers the carboxy-terminus of the A1 fragment region.

In some embodiments of Embodiment Set #2, the molecular moiety sterically covers the carboxy-terminus of the A1 fragment region. In some embodiments, the molecular moiety comprises the binding region.

In some embodiments of Embodiment Set #2, the binding molecule comprises a binding region and/or molecular moiety located carboxy-terminal to the carboxy-terminus of the Shiga toxin A1 fragment region. In some embodiments, the mass of the binding region and/or molecular moiety is at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater.

In some embodiments of Embodiment Set #2, the binding molecule comprises a binding region with a mass of at least 4.5 kDa, 6, kDa, 9 kDa, 12 kDa, 15 kDa, 20 kDa, 25 kDa, 28 kDa, kDa, 41 kDa, 50 kDa, 100 kDa, or greater, as long as the binding molecule retains the appropriate level of the Shiga toxin biological activity noted herein (e.g., cytotoxicity and/or intracellular routing).

In some embodiments of Embodiment Set #2, the binding region is comprised within a relatively large, molecular moiety comprising such as, e.g., a molecular moiety with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the binding molecule retains the appropriate level of the Shiga toxin biological activity noted herein.

In some embodiments of Embodiment Set #2, the disrupted furin-cleavage motif comprises an amino acid residue substitution in the furin-cleavage motif relative to a wild-type Shiga toxin A Subunit. In some embodiments, the substitution of the amino acid residue in the furin-cleavage motif is of an arginine residue with a non-positively charged, amino acid residue selected from the group consisting of: alanine, glycine, proline, serine, threonine, aspartate, asparagine, glutamate, glutamine, cysteine, isoleucine, leucine, methionine, valine, phenylalanine, tryptophan, and tyrosine. In some embodiments, the substitution of the amino acid residue in the furin-cleavage motif is of an arginine residue with a histidine.

In some embodiments of Embodiment Set #2, the binding molecule is capable, when introduced to cells, of exhibiting cytotoxicity comparable to the cytotoxicity of a second binding molecule consisting of the binding molecule except for all of its Shiga toxin effector polypeptide component(s) each comprise a wild-type Shiga toxin A1 fragment and/or wild-type Shiga toxin furin-cleavage site at the carboxy terminus of its A1 fragment region. In some embodiments, the binding molecule is capable, when introduced to cells, of exhibiting cytotoxicity that is in a range of from 0.1-fold, 0.5-fold, or 0.75-fold to 1.2-fold, 1.5-fold, 1.75-fold, 2-fold, 3-fold, 4-fold, or 5-fold of the cytotoxicity exhibited by the second binding molecule.

In some embodiments of Embodiment Set #2, the binding molecule is capable, when introduced to a chordate, of exhibiting improved, in vivo tolerability compared to in vivo tolerability of the second binding molecule.

In some embodiments of Embodiment Set #2, the binding molecule is de-immunized due to the embedded or inserted, heterologous, epitope. In some embodiments, the binding molecule is capable of exhibiting less relative antigenicity and/or relative immunogenicity as compared to a reference molecule, such as, e.g., a third cell-binding molecule consisting of the binding molecule except for it lacks one or more embedded or inserted epitopes present in the cell binding molecule.

In some embodiments of Embodiment Set #2, the binding molecule is de-immunized due to the furin-cleavage motif disruption. In some embodiments, the binding molecule is capable of exhibiting less relative antigenicity and/or relative immunogenicity as compared to a fourth cell-binding molecule consisting of the binding molecule except for the furin-cleavage motif is wild-type and/or all the Shiga toxin effector polypeptide components consist of a wild-type Shiga toxin A1 fragment.

Embodiment Set #3—Binding Molecule Comprising a De-Immunized Shiga Toxin Effector Polypeptide Comprising a Disrupted, Furin-Cleavage Motif Also provided herein are binding molecules, each comprising (i) a binding region capable of specifically binding an extracellular target biomolecule (PD-L1) and (ii) a de-immunized, Shiga toxin effector polypeptide comprising a disrupted furin-cleavage motif. In some embodiments, the binding molecule comprises (i) a binding region capable of specifically binding an extracellular target biomolecule and (ii) a de-immunized, Shiga toxin effector polypeptide comprising (a) a Shiga toxin A1 fragment derived region having a carboxy terminus, (b) a disrupted furin-cleavage motif at the carboxy-terminus of the A1 fragment region, and (c) at least one disrupted, endogenous, B-cell and/or CD4+ T-cell epitope and/or epitope region. For some embodiments, the Shiga toxin effector polypeptide is capable of exhibiting at least one Shiga toxin effector function, such as, e.g., directing intracellular routing to the endoplasmic reticulum and/or cytosol of a cell in which the polypeptide is present, inhibiting a ribosome function, enzymatically inactivating a ribosome, causing cytostasis, and/or causing cytotoxicity. In some embodiments, the binding molecule is capable of one or more the following: entering a cell, inhibiting a ribosome function, causing cytostasis, and/or causing cell death. For some embodiments, the binding molecule is capable, when introduced to cells, of exhibiting a cytotoxicity comparable or better than a reference molecule, such as, e.g., a second binding molecule consisting of the binding molecule except for all of its Shiga toxin effector polypeptide components comprise a wild-type Shiga toxin furin-cleavage site at the carboxy terminus of its A1 fragment region.

In some embodiments of Embodiment Set #3, the Shiga toxin effector polypeptide comprises a mutation, relative to a wild-type Shiga toxin A Subunit, in the B-cell and/or T-cell epitope region selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2, and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; 285-293 of SEQ ID NO:1 or SEQ ID NO:2; 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; 236-258 of SEQ ID NO:1 or SEQ ID NO:2; and 274-293 of SEQ ID NO:1 or SEQ ID NO:2; or the equivalent region in a Shiga toxin A Subunit or derivative thereof. In some embodiments, there is no disruption which is a carboxy-terminal truncation of amino acid residues that overlap with part or all of at least one disrupted, endogenous, B-cell and/or T-cell epitope and/or epitope region.

In some embodiments of Embodiment Set #3, the disrupted furin-cleavage motif comprises one or more mutations, relative to a wild-type Shiga toxin A Subunit, the mutation altering at least one amino acid residue in a region natively positioned at 248-251 of the A Subunit of Shiga-like toxin 1 (SEQ ID NO:1) or Shiga toxin (SEQ ID NO:2), or at 247-250 of the A Subunit of Shiga-like toxin (SEQ ID NO:3); or the equivalent region in a Shiga toxin A Subunit or derivative thereof. In some embodiments, the disrupted furin-cleavage motif comprises one or more mutations, relative to a wild-type Shiga toxin A Subunit, in a minimal furin cleavage site of the furin-cleavage motif. In some embodiments the minimal furin cleavage site is represented by the consensus amino acid sequence R/Y-x-x-R and/or R-x-x-R.

In some embodiments of Embodiment Set #3, the binding molecule comprises a molecular moiety located carboxy-terminal to the carboxy-terminus of the Shiga toxin A1 fragment region.

In some embodiments of Embodiment Set #3, the binding region sterically covers the carboxy-terminus of the A1 fragment region.

In some embodiments of Embodiment Set #3, the molecular moiety sterically covers the carboxy-terminus of the A1 fragment region. In some embodiments, the molecular moiety comprises the binding region.

In some embodiments of Embodiment Set #3, the binding molecule comprises a binding region and/or molecular moiety located carboxy-terminal to the carboxy-terminus of the Shiga toxin A1 fragment region. In some embodiments, the mass of the binding region and/or molecular moiety is at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater.

In some embodiments of Embodiment Set #3, the binding molecule comprises a binding region with a mass of at least 4.5 kDa, 6, kDa, 9 kDa, 12 kDa, 15 kDa, 20 kDa, 25 kDa, 28 kDa, kDa, 41 kDa, 50 kDa, 100 kDa, or greater, as long as the binding molecule retains the appropriate level of the Shiga toxin biological activity noted herein (e.g., cytotoxicity and/or intracellular routing).

In some embodiments of Embodiment Set #3, the binding region is comprised within a relatively large, molecular moiety comprising such as, e.g., a molecular moiety with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the binding molecule retains the appropriate level of the Shiga toxin biological activity noted herein.

In some embodiments of Embodiment Set #3, the disrupted furin-cleavage motif comprises an amino acid residue substitution in the furin-cleavage motif relative to a wild-type Shiga toxin A Subunit. In some embodiments, the substitution of the amino acid residue in the furin-cleavage motif is of an arginine residue with a non-positively charged, amino acid residue selected from the group consisting of: alanine, glycine, proline, serine, threonine, aspartate, asparagine, glutamate, glutamine, cysteine, isoleucine, leucine, methionine, valine, phenylalanine, tryptophan, and tyrosine. In some embodiments, the substitution of the amino acid residue in the furin-cleavage motif is of an arginine residue with a histidine.

In some embodiments of Embodiment Set #3, the binding molecule is capable, when introduced to cells, of exhibiting cytotoxicity comparable to the cytotoxicity of a reference molecule, such as, e.g., a fifth binding molecule consisting of the binding molecule except for all of its Shiga toxin effector polypeptide component(s) each comprise a wild-type Shiga toxin A1 fragment and/or wild-type Shiga toxin furin-cleavage site at the carboxy terminus of its A1 fragment region. In some embodiments, the binding molecule is capable, when introduced to cells, of exhibiting cytotoxicity that is in a range of from 0.1-fold, 0.5-fold, or 0.75-fold to 1.2-fold, 1.5-fold, 1.75-fold, 2-fold, 3-fold, 4-fold, or 5-fold of the cytotoxicity exhibited by the fifth binding molecule.

In some embodiments of Embodiment Set #3, the binding molecule is capable, when introduced to a chordate, of exhibiting improved, in vivo tolerability compared to in vivo tolerability of the fifth binding molecule.

In some embodiments of Embodiment Set #3, the binding molecule is de-immunized due to the furin-cleavage motif disruption. In some embodiments, the binding molecule is capable of exhibiting less relative antigenicity and/or relative immunogenicity as compared to a reference binding molecule consisting of the binding molecule except for the furin-cleavage motif is wild-type and/or all the Shiga toxin effector polypeptide components consist of a wild-type Shiga toxin A1 fragment, such as, e.g., the fifth binding molecule.

Further Embodiments of Embodiment Sets #1-#3

In some embodiments of Embodiment Sets #1 to #3, the Shiga toxin effector polypeptide is fused to the binding region, either directly or indirectly, such as, e.g., via a linker known to the skilled worker.

In some embodiments of Embodiment Sets #1 to #3, the binding molecule comprises a molecular moiety located carboxy-terminal to the carboxy-terminus of the Shiga toxin A1 fragment region.

In some embodiments of Embodiment Sets #1 to #3, the Shiga toxin effector polypeptide has a Shiga toxin A1 fragment derived region having a carboxy terminus and further comprises a disrupted furin-cleavage motif at the carboxy-terminus of the A1 fragment region.

In some embodiments of Embodiment Sets #1 to #3, the binding molecule, or a polypeptide component thereof, comprises a carboxy-terminal, endoplasmic reticulum retention/retrieval signal motif of a member of the KDEL family. For some embodiments, the carboxy-terminal endoplasmic reticulum retention/retrieval signal motif is selected from the group consisting of: KDEL (SEQ ID NO: 205), HDEF (SEQ ID NO: 206), HDEL (SEQ ID NO: 207), RDEF (SEQ ID NO: 208), RDEL (SEQ ID NO: 209), WDEL (SEQ ID NO: 210), YDEL (SEQ ID NO: 211), HEEF (SEQ ID NO: 212), HEEL (SEQ ID NO: 213), KEEL (SEQ ID NO: 214), REEL (SEQ ID NO: 215), KAEL (SEQ ID NO: 216), KCEL (SEQ ID NO: 217), KFEL (SEQ ID NO: 218), KGEL (SEQ ID NO: 219), KHEL (SEQ ID NO: 220), KLEL (SEQ ID NO: 221), KNEL (SEQ ID NO: 222), KQEL (SEQ ID NO: 223), KREL (SEQ ID NO: 224), KSEL (SEQ ID NO: 225), KVEL (SEQ ID NO: 226), KWEL (SEQ ID NO: 227), KYEL (SEQ ID NO: 228), KEDL (SEQ ID NO: 229), KIEL (SEQ ID NO: 230), DKEL (SEQ ID NO: 231), FDEL (SEQ ID NO: 232), KDEF (SEQ ID NO: 233), KKEL (SEQ ID NO: 234), HADL (SEQ ID NO: 235), HAEL (SEQ ID NO: 236), HIEL (SEQ ID NO: 237), HNEL (SEQ ID NO: 238), HTEL (SEQ ID NO: 239), KTEL (SEQ ID NO: 240), HVEL (SEQ ID NO: 241), NDEL (SEQ ID NO: 242), QDEL (SEQ ID NO: 243), REDL (SEQ ID NO: 244), RNEL (SEQ ID NO: 245), RTDL (SEQ ID NO: 246), RTEL (SEQ ID NO: 247), SDEL (SEQ ID NO: 248), TDEL (SEQ ID NO: 249), SKEL (SEQ ID NO: 250), STEL (SEQ ID NO: 251), and EDEL (SEQ ID NO: 252). In some embodiments, the binding molecule is capable, when introduced to cells, of exhibiting cytotoxicity that is greater than that of a reference molecule, such as, e.g., a sixth binding molecule consisting of the binding molecule except for it does not comprise any carboxy-terminal, endoplasmic reticulum retention/retrieval signal motif of the KDEL family (See SEQ ID NO: 205-252). In some embodiments, the binding molecule is capable of exhibiting a cytotoxicity with better optimized, cytotoxic potency, such as, e.g., 4-fold, 5-fold, 6-fold, 9-fold, or greater cytotoxicity as compared to a reference molecule, such as, e.g., the sixth binding molecule. In some embodiments, the cytotoxicity of the binding molecule to a population of target positive cells is 3-fold, 4-fold, 5-fold, 6-fold, 7-fold, 8-fold, 9-fold, 10-fold or greater than the cytotoxicity of the sixth binding molecule to a second population of target positive cells as assayed by $CD_{50}$ values.

In some embodiments of Embodiment Sets #1 to #3, the Shiga toxin effector polypeptide further comprises at least one inserted or embedded, heterologous epitope.

In some embodiments of Embodiment Sets #1 to #3, the Shiga toxin effector polypeptide further comprises at least one, two, or three disrupted, endogenous, B-cell and/or CD4+ T-cell epitope regions. In some embodiments, the Shiga toxin effector polypeptide comprises a disruption of at least one, two, or three endogenous, B-cell and/or T-cell epitopes and/or epitope regions. In some embodiments, the Shiga toxin effector polypeptide further comprises at least one disrupted, endogenous, B-cell and/or CD4+ T-cell epitope region which does not overlap with at least one inserted or embedded, heterologous epitope.

In some embodiments of Embodiment Sets #1 to #3, the amino-terminus of the Shiga toxin effector polypeptide is at and/or proximal to an amino-terminus of a polypeptide component of the binding molecule. In some embodiments, the binding region is not located proximally to the amino-terminus of the binding molecule relative to the Shiga toxin effector polypeptide. In some embodiments, the binding region and Shiga toxin effector polypeptide are physically arranged or oriented within the binding molecule such that the binding region is not located proximally to the amino-terminus of the Shiga toxin effector polypeptide. In some embodiments, the binding region is located within the binding molecule more proximal to the carboxy-terminus of the Shiga toxin effector polypeptide than to the amino-terminus of the Shiga toxin effector polypeptide. For some embodiments, the binding molecule is not cytotoxic and is capable, when introduced to cells, of exhibiting a greater subcellular routing efficiency from an extracellular space to a subcellular compartment of an endoplasmic reticulum and/or cytosol as compared to the cytotoxicity of a reference molecule, such as, e.g., a seventh binding molecule having an amino-terminus and comprising the binding region and the Shiga toxin effector polypeptide which is not positioned at or proximal to the amino-terminus. For some embodiments, the binding molecule exhibits cytotoxicity with better optimized, cytotoxic potency, such as, e.g., 4-fold, 5-fold, 6-fold, 9-fold, or greater cytotoxicity as compared to the cytotoxicity of the seventh binding molecule. For some embodiments, the cytotoxicity of the binding molecule to a population of target positive cells is 3-fold, 4-fold, 5-fold, 6-fold, 7-fold, 8-fold, 9-fold, 10-fold or greater than the cytotoxicity of the seventh binding molecule to a second population of target positive cells as assayed by $CD_{50}$ values. In some embodiments, the seventh cell-binding molecule does not comprise any carboxy-terminal, endoplasmic reticulum retention/retrieval signal motif of the KDEL family (See SEQ ID NO: 205-252).

In some embodiments of Embodiment Sets #1 to #3, the Shiga toxin effector polypeptide further comprises a disruption in the B-cell and/or T-cell epitope region selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2, and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; 285-293 of SEQ ID NO:1 or SEQ ID NO:2; 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; 236-258 of SEQ ID NO:1 or SEQ ID NO:2; and 274-293 of SEQ ID NO:1 or SEQ ID NO:2; or the equivalent region in a Shiga toxin A Subunit or derivative thereof. In some embodiments, there is no disruption which is a carboxy-terminal truncation of amino acid residues that overlap with part or all of at least one disrupted, endogenous, B-cell and/or T-cell epitope and/or epitope region.

In some embodiments of Embodiment Sets #1 to #3, the Shiga toxin effector polypeptide further comprises a mutation, relative to a wild-type Shiga toxin A Subunit, in the B-cell immunogenic, amino acid residue selected from the group of natively positioned Shiga toxin A Subunit amino acid residues: L49, D197, D198, R204, and R205.

In some embodiments of Embodiment Sets #1 to #3, the embedded or inserted, heterologous, T-cell epitope disrupts the endogenous, B-cell and/or T-cell epitope region is selected from the group of natively positioned Shiga toxin A Subunit regions consisting of: (i) 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3; or the equivalent region in a Shiga toxin A Subunit or derivative thereof, wherein there is no disruption which is an amino-terminal truncation of sequences that overlap with part or all of at least one disrupted epitope region; (ii) 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; and (iii) 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; or the equivalent region in a Shiga toxin A Subunit or derivative thereof.

In some embodiments of Embodiment Sets #1 to #3, the Shiga toxin effector polypeptide comprises a mutation, relative to a wild-type Shiga toxin A Subunit, in the B-cell and/or T-cell epitope region selected from the group of natively positioned Shiga toxin A Subunit regions consisting of: (i) 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3; or the equivalent region in a Shiga toxin A Subunit or derivative thereof, wherein there is no disruption which is an amino-terminal truncation of sequences that overlap with part or all of at least one disrupted epitope region; (ii) 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; and (iii) 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; or the equivalent region in a Shiga toxin A Subunit or derivative thereof, wherein there is no disruption which is an amino-terminal truncation of sequences that overlap with part or all of at least one disrupted epitope region.

In some embodiments of Embodiment Sets #1 to #3, the Shiga toxin effector polypeptide comprises a disruption of at least one endogenous epitope region selected from the group of natively positioned Shiga toxin A Subunits consisting of: 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; or 210-218 of SEQ ID NO:3.

In some embodiments of Embodiment Sets #1 to #3, the Shiga toxin effector polypeptide comprises disruptions of at least four, five, six, seven, eight, or more endogenous, B-cell and/or T-cell epitope regions.

In some embodiments of Embodiment Sets #1 to #3, one or more disruptions comprises an amino acid residue substitution relative to a wild-type Shiga toxin A Subunit.

In some embodiments of Embodiment Sets #1 to #3, one or more endogenous, B-cell and/or T-cell epitope regions comprises a plurality of amino acid residue substitutions relative to a wild-type Shiga toxin A Subunit.

In some embodiments of Embodiment Sets #1 to #3, at least one, two, three, or four disruptions comprise a plurality of amino acid residue substitutions in the endogenous, B-cell and/or T-cell epitope region relative to a wild-type Shiga toxin A Subunit.

In some embodiments of Embodiment Sets #1 to #3, at least one disruption comprises at least one, two, three, four, five, six, seven, eight, or more amino acid residue substitutions relative to a wild-type Shiga toxin A Subunit, and optionally wherein at least one substitution occurs at the natively positioned Shiga toxin A Subunit amino acid residue selected form the group consisting of: 1 of SEQ ID NO:1 or SEQ ID NO:2; 4 of SEQ ID NO:1, SEQ ID NO:2, or SEQ ID NO:3; 6 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 12 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1, SEQ ID NO:2, or SEQ ID NO:3; 47 of SEQ ID NO:1 or SEQ ID NO:2; 48 of SEQ ID NO:1, SEQ ID NO:2, or SEQ ID NO:3; 49 of SEQ ID NO:1, SEQ ID NO:2, or SEQ ID NO:3; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1, SEQ ID NO:2, or SEQ ID NO:3; 55 of SEQ ID NO:1 or SEQ ID NO:2; 56 of SEQ ID NO:1, SEQ ID NO:2, or SEQ ID NO:3; 57 of SEQ ID NO:1, SEQ ID NO:2, or SEQ ID NO:3; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1, SEQ ID NO:2, or SEQ ID NO:3; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1, SEQ ID NO:2, or SEQ ID NO:3; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1, SEQ ID NO:2, or SEQ ID NO:3; 112 of SEQ ID NO:1, SEQ ID NO:2, or SEQ ID NO:3; 141 of SEQ ID NO:1, SEQ ID NO:2, or SEQ ID NO:3; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 197 of SEQ ID NO:3; 198 of SEQ ID NO:1 or SEQ ID NO:2; 204 of SEQ ID NO:3; 205 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2; or the equivalent amino acid residue in a Shiga toxin A Subunit or derivative thereof. In some embodiments, at least two disruptions each comprise at least one amino acid residue substitutions relative to a wild-type Shiga toxin A Subunit selected form the group consisting of: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 45 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 53 of SEQ ID NO:1 or SEQ ID NO:2; 55 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 109 of SEQ ID NO:1, SEQ ID NO:2, or SEQ ID NO:3; 110 of SEQ ID NO:1 or SEQ ID NO:2; 112 of SEQ ID NO:1, SEQ ID NO:2, or SEQ ID NO:3; 147 of SEQ ID NO:1, SEQ ID NO:2, or SEQ ID NO:3; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 204 of SEQ ID NO:3; 205 of SEQ ID NO:1 or SEQ ID NO:2; 247 of SEQ ID NO:1 or SEQ ID NO:2; 247 of SEQ ID NO:3; 250 of SEQ ID NO:3; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2; or the equivalent amino acid residue in a Shiga toxin A Subunit or derivative thereof.

In some embodiments of Embodiment Sets #1 to #3, the Shiga toxin effector polypeptide comprises disruption of at least three, endogenous, B-cell and/or T-cell epitope regions selected from the group of consisting of: (i) 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3, or the equivalent region in a Shiga toxin A Subunit or derivative thereof, wherein there is no disruption which is an amino-terminal truncation of amino acid residues that overlap with part or all of at least one disrupted, endogenous, B-cell and/or T-cell epitope region; (ii) 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; and (iii) 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; or the equivalent region in a Shiga toxin A Subunit or derivative thereof, wherein there is no disruption which is a carboxy-terminal truncation of amino acid residues that overlap with part or all of at least one disrupted, endogenous, B-cell and/or T-cell epitope and/or epitope region.

In some embodiments of Embodiment Sets #1 to #3, the Shiga toxin effector polypeptide comprises disruptions of at least two, endogenous, B-cell and/or T-cell epitope regions, wherein each disruption comprises one or more amino acid residue substitutions, and wherein the endogenous, B-cell and/or T-cell epitope regions are selected from the group of natively positioned Shiga toxin A Subunit regions consisting of: 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; or the equivalent region in a Shiga toxin A Subunit or derivative thereof.

In some embodiments of Embodiment Sets #1 to #3, the embedded or inserted, heterologous, T-cell epitope does not disrupt any endogenous, B-cell and/or CD4+ T-cell epitope region described herein.

In some embodiments of Embodiment Sets #1 to #3, at least one disruption comprises one or more amino acid residue substitutions relative to a wild-type Shiga toxin A Subunit is selected from the group consisting of: D to A, D to G, D to V, D to L, D to I, D to F, D to S, D to Q, D to M, D to R, E to A, E to G, E to V, E to L, E to I, E to F, E to S, E to Q, E to N, E to D, E to M, E to R, F to A, F to G, F to V, F to L, F to I, G to A, G to P, H to A, H to G, H to V, H to L, H to I, H to F, H to M, I to A, I to V, I to G, I to C, K to A, K to G, K to V, K to L, K to I, K to M, K to H, L to A, L to V, L to G, L to C, N to A, N to G, N to V, N to L, N to I, N to F, P to A, P to G, P to F, R to A, R to G, R to V, R to L, R to I, R to F, R to M, R to Q, R to S, R to K, R to H, S to A, S to G, S to V, S to L, S to I, S to F, S to M, T to A, T to G, T to V, T to L, T to I, T to F, T to M, T to S, V to A, V to G, Y to A, Y to G, Y to V, Y to L, Y to I, Y to F, Y to M, and Y to T. In some embodiments, the one or more amino acid residue substitutions relative to a wild-type Shiga toxin A Subunit is selected from the group consisting of: D to A, D to G, D to V, D to L, D to I, D to F, D to S, D to Q, E to A, E to G, E to V, E to L, E to I, E to F, E to S, E to Q, E to N, E to D, E to M, E to R, G to A, H to A, H to G, H to V, H to L, H to I, H to F, H to M, K to A, K to G, K to V, K to L, K to I, K to M, K to H, L to A, L to G, N to A, N to G, N to V, N to L, N to I, N to F, P to A, P to G, P to F, R to A, R to G, R to V, R to L, R to I, R to F, R to M, R to Q, R to S, R to K, R to H, S to A, S to G, S to V, S to L, S to I, S to F, S to M, T to A, T to G, T to V, T to L, T to I, T to F, T to M, T to S, Y to A, Y to G, Y to V, Y to L, Y to I, Y to F, and Y to M.

In some embodiments of Embodiment Sets #1 to #3, at least one of the disruption(s) comprises one or more amino acid residue substitutions relative to a wild-type Shiga toxin A Subunit selected from the group consisting of: K1 to A, G, V, L, I, F, M and H; T4 to A, G, V, L, I, F, M, and S; D6 to A, G, V, L, I, F, S, Q and R; S8 to A, G, V, I, L, F, and M; T9 to A, G, V, I, L, F, M, and S; S9 to A, G, V, L, I, F, and M; K11 to A, G, V, L, I, F, M and H; T12 to A, G, V, I, L, F, M, S, and K; S12 to A, G, V, I, L, F, and M; S33 to A, G, V, L, I, F, M, and C; S43 to A, G, V, L, I, F, and M; G44 to A or L; S45 to A, G, V, L, I, F, and M; T45 to A, G, V, L, I, F, and M; G46 to A and P; D47 to A, G, V, L, I, F, S, M, and Q; N48 to A, G, V, L, M and F; L49 to A, V, C, and G; Y49 to A, G, V, L, I, F, M, and T; F50 to A, G, V, L, I, and T; A51; D53 to A, G, V, L, I, F, S, and Q; V54 to A, G, I, and L; R55 to A, G, V, L, I, F, M, Q, S, K, and H; G56 to A and P; I57 to A, G, V, and M; L57 to A, V, C, G, M, and F; D58 to A, G, V, L, I, F, S, and Q; P59 to A, G, and F; E60 to A, G, V, L, I, F, S, Q, N, D, M, T, and R; E61 to A, G, V, L, I, F, S, Q, N, D, M, and R; G62 to A; R84 to A, G, V, L, I, F, M, Q, S, K, and H; V88 to A and G; 188 to A, V, C, and G; D94 to A, G, V, L, I, F, S, and Q; S96 to A, G, V, I, L, F, and M; T104 to A, G, V, L, I, F, M; and N; A105 to L; T107 to A, G, V, L, I, F, M, and P; S107 to A, G, V, L, I, F, M, and P; L108 to A, V, C, and G; S109 to A, G, V, I, L, F, and M; T109 to A, G, V, I, L, F, M, and S; G110 to A; S112 to A, G, V, L, I, F, and M; D111 to A, G, V, L, I, F, S, Q, and T; S112 to A, G, V, L, I, F, and M; D141 to A, G, V, L, I, F, S, and Q; G147 to A; V154 to A and G. R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; L185 to A, G, V and C; S186 to A, G, V, I, L, F, and M; G187 to A; R188 to A, G, V, L, I, F, M, Q, S, K, and H; S189 to A, G, V, I, L, F, and M; D197 to A, G, V, L, I, F, S, and Q; D198 to A, G, V, L, I, F, S, and Q; R204 to A, G, V, L, I, F, M, Q, S, K, and H; R205 to A, G, V, L, I, F, M, Q, S, K and H; 5247 to A, G, V, I, L, F, and M; Y247 to A, G, V, L, I, F, and M; R248 to A, G, V, L, I, F, M, Q, S, K, and H; R250 to A, G, V, L, I, F, M, Q, S, K, and H; R251 to A, G, V, L, I, F, M, Q, S, K, and H; D264 to A, G, V, L, I, F, S, and Q; G264 to A; and T286 to A, G, V, L, I, F, M, and S.

In some embodiments of Embodiment Sets #1 to #3, the binding molecule is capable, when introduced to a chordate, of exhibiting improved in vivo tolerability and/or stability compared to a reference molecule, such as, e.g., a twenty-fourth binding molecule consisting of the binding molecule except for all of its Shiga toxin effector polypeptide component(s) each comprise a wild-type Shiga toxin A1 fragment and/or wild-type Shiga toxin furin-cleavage site at the carboxy terminus of its A1 fragment region. In some embodiments, the Shiga toxin effector polypeptide is not cytotoxic and the molecular moiety is cytotoxic.

In some embodiments of Embodiment Sets #1 to #3, the binding region and Shiga toxin effector polypeptide are linked together, either directly or indirectly.

In some embodiments of Embodiment Sets #1 to #3, the binding region comprises at least one peptide and/or polypeptide. In some embodiments, the binding region is or comprises an immunoglobulin-type binding region. In some embodiments, the binding region comprising a polypeptide selected from the group consisting of: an autonomous $V_H$ domain, single-domain antibody fragment (sdAb), nanobody, heavy chain-antibody domain derived from a camelid ($V_HH$ or $V_H$ domain fragment), heavy-chain antibody domain derived from a cartilaginous fish ($V_HH$ or $V_H$ domain fragment), immunoglobulin new antigen receptor (IgNAR), $V_{NAR}$ fragment, single-chain variable fragment (scFv), antibody variable fragment (Fv), complementary determining region 3 fragment (CDR3), constrained FR3-CDR3-FR4 polypeptide (FR3-CDR3-FR4), Fd fragment, small modular immunopharmaceutical (SMIP) domain, antigen-binding fragment (Fab), Armadillo repeat polypeptide (ArmRP), fibronectin-derived $10^{th}$ fibronectin type III domain (10Fn3), tenascin type III domain (TNfn3), ankyrin repeat motif domain, low-density-lipoprotein-receptor-derived A-domain (LDLR-A), lipocalin (anticalin), Kunitz domain, Protein-A-derived Z domain, gamma-B crystallin-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality.

In some embodiments of Embodiment Sets #1 to #3, the binding molecule is capable of exhibiting (i) a catalytic activity level comparable to a wild-type Shiga toxin A1 fragment or wild-type Shiga toxin effector polypeptide, (ii) a ribosome inhibition activity with a half-maximal inhibitory concentration ($IC_{50}$) value of 10,000 picomolar or less, and/or (iii) a significant level of Shiga toxin catalytic activity.

In some embodiments of Embodiment Sets #1 to #3, the binding molecule and/or its Shiga toxin effector polypeptide is capable of exhibiting subcellular routing efficiency comparable to a reference binding molecule comprising a wild-type Shiga toxin A1 fragment or wild-type Shiga toxin effector polypeptide and/or capable of exhibiting a significant level of intracellular routing activity to the endoplasmic reticulum and/or cytosol from an endosomal starting location of a cell.

In some embodiments of Embodiment Sets #1 to #3, whereby administration of the binding molecule to a cell physically coupled with the extracellular target biomolecule of the binding molecule's binding region, the binding molecule is capable of causing death of the cell. In some embodiments, administration of the binding molecule to two different populations of cell types which differ with respect to the presence or level of the extracellular target biomolecule, the binding molecule is capable of causing cell death to the cell-types physically coupled with an extracellular target biomolecule of the cytotoxic binding molecule's binding region at a $CD_{50}$ at least three times or less than the $CD_{50}$ to cell types which are not physically coupled with an extracellular target biomolecule of the binding molecule's binding region. In some embodiments, whereby administration of the binding molecule to a first population of cells whose members are physically coupled to extracellular target biomolecules of the binding molecule's binding region, and a second population of cells whose members are not physically coupled to any extracellular target biomolecule of the binding region, the cytotoxic effect of the binding molecule to members of said first population of cells relative to members of said second population of cells is at least 3-fold greater. In some embodiments, whereby administration of the binding molecule to a first population of cells whose members are physically coupled to a significant amount of the extracellular target biomolecule of the binding molecule's binding region, and a second population of cells whose members are not physically coupled to a significant amount of any extracellular target biomolecule of the binding region, the cytotoxic effect of the binding molecule to members of said first population of cells relative to members of said second population of cells is at least 3-fold greater. In some embodiments, whereby administration of the binding molecule to a first population of target biomolecule positive cells, and a second population of cells whose members do not express a significant amount of a target biomolecule of the binding molecule's binding region at a cellular surface, the cytotoxic effect of the binding molecule to members of the first population of cells relative to members of the second population of cells is at least 3-fold greater.

In some embodiments of Embodiment Sets #1 to #3, the binding molecule is capable, when introduced to cells, of exhibiting a cytotoxicity with a half-maximal inhibitory concentration ($CD_{50}$) value of 300 nM or less and/or capable of exhibiting a significant level of Shiga toxin cytotoxicity.

In some embodiments of Embodiment Sets #2 to #11, the binding molecule is capable of delivering an embedded or inserted, heterologous, CD8+ T-cell epitope to a MHC class I presentation pathway of a cell for cell-surface presentation of the epitope bound by a MHC class I molecule.

In some embodiments of Embodiment Sets #2 to #11, the binding molecule comprises a molecular moiety associated with the carboxy-terminus of the Shiga toxin effector polypeptide. In some embodiments, the molecular moiety comprises or consists of the binding region. In some embodiments, the molecular moiety comprises at least one amino acid and the Shiga toxin effector polypeptide is linked to at least one amino acid residue of the molecular moiety. In some embodiments, the molecular moiety and the Shiga toxin effector polypeptide are fused forming a continuous polypeptide.

In some embodiments of Embodiment Sets #1 to #3, the binding molecule further comprises a cytotoxic molecular moiety associated with the carboxy-terminus of the Shiga toxin effector polypeptide. In some embodiments, the cytotoxic molecular moiety is a cytotoxic agent, such as, e.g., a small molecule chemotherapeutic agent, anti-neoplastic agent, cytotoxic antibiotic, alkylating agent, antimetabolite, topoisomerase inhibitor, and/or tubulin inhibitor known to the skilled worker and/or described herein. For some embodiments, the cytotoxic molecular moiety is cytotoxic at concentrations of less than 10,000, 5,000, 1,000, 500, or 200 pM.

In some embodiments of Embodiment Sets #1 to #3, the binding region is linked, either directly or indirectly, to the Shiga toxin effector polypeptide by at least one covalent bond which is not a disulfide bond. In some embodiments, the binding region is fused, either directly or indirectly, to the carboxy-terminus of the Shiga toxin effector polypeptide to form a single, continuous polypeptide. In some embodiments, the binding region is an immunoglobulin-type binding region.

In some embodiments of Embodiment Sets #1 to #3, the disrupted furin-cleavage motif comprises one or more mutations in the minimal, furin-cleavage site relative to a wild-type Shiga toxin A Subunit. In some embodiments, the disrupted furin-cleavage motif is not an amino-terminal truncation of sequences that overlap with part or all of at least one amino acid residue of the minimal furin-cleavage site. In some embodiments, the mutation in the minimal, furin-cleavage site is an amino acid deletion, insertion, and/or substitution of at least one amino acid residue in the R/Y-x-x-R furin cleavage motif. In some embodiments, the disrupted furin-cleavage motif comprises at least one mutation relative to a wild-type Shiga toxin A Subunit, the mutation altering at least one amino acid residue in the region natively positioned 1) at 248-251 of the A Subunit of Shiga-like toxin 1 (SEQ ID NO: 1) or Shiga toxin (SEQ ID NO: 2), or 2) at 247-250 of the A Subunit of Shiga-like toxin 2 (SEQ ID NO:3), or the equivalent amino acid sequence position in any Shiga toxin A Subunit. In some embodiments, the mutation is an amino acid residue substitution of an arginine residue with a non-positively charged, amino acid residue.

In some embodiments of Embodiment Sets #1 to #3, the binding molecule is capable, when introduced to cells, of exhibiting cytotoxicity comparable to a cytotoxicity of a reference molecule, such as, e.g., a eighth binding molecule consisting of the binding molecule except for all of its Shiga toxin effector polypeptide component(s) each comprise a wild-type Shiga toxin A1 fragment.

In some embodiments of Embodiment Sets #1 to #3, the binding region comprises or consists essentially of the polypeptide represented by any one of SEQ ID NOs: 85-107 and 156-157.

In some embodiments of Embodiment Sets #1 to #3, the binding region sterically covers the carboxy-terminus of the A1 fragment region.

In some embodiments of Embodiment Sets #1 to #3, the molecular moiety sterically covers the carboxy-terminus of the A1 fragment region. In some embodiments, the molecular moiety comprises the binding region.

In some embodiments of Embodiment Sets #1 to #3, the binding molecule comprises a binding region and/or molecular moiety located carboxy-terminal to the carboxy-terminus of the Shiga toxin A1 fragment region. In some embodiments, the mass of the binding region and/or molecular moiety is at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater.

In some embodiments of Embodiment Sets #1 to #3, the binding molecule comprises a binding region with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the binding molecule retains the appropriate level of the Shiga toxin biological activity noted herein (e.g., cytotoxicity and/or intracellular routing).

In some embodiments of Embodiment Sets #1 to #3, the binding region is comprised within a relatively large, molecular moiety comprising such as, e.g., a molecular moiety with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the binding molecule retains the appropriate level of the Shiga toxin biological activity noted herein.

In some embodiments of Embodiment Sets #1 to #3, the binding molecule exhibits low cytotoxic potency (i.e. is not capable when introduced to certain positive target cell types of exhibiting a cytotoxicity greater than 1% cell death of a cell population at a binding molecule concentration of 1000 nM, 500 nM, 100 nM, 75 nM, or 50 nM) and is capable, when introduced to cells, of exhibiting a greater subcellular routing efficiency from an extracellular space to a subcellular compartment of an endoplasmic reticulum and/or cytosol as compared to the cytotoxicity of a reference molecule, such as, e.g., a ninth binding molecule having an amino-terminus and comprising the binding region and the Shiga toxin effector polypeptide which is not positioned at or proximal to the amino-terminus. In some embodiments, the ninth cell-binding molecule does not comprise any carboxy-terminal, endoplasmic reticulum retention/retrieval signal motif of the KDEL family (See SEQ ID NO: 205-252).

In some embodiments of Embodiment Sets #1 to #3, In some embodiments, the molecular moiety comprises a peptide and/or polypeptide derived from the Shiga toxin A2 fragment of a naturally occurring Shiga toxin.

The embodiments described herein are not intended to cover any naturally occurring Shiga holotoxin or Shiga toxin A Subunit. In some embodiments of Embodiment Sets #1 to #3, the binding molecule does not comprise a naturally occurring Shiga toxin B Subunit. In some embodiments, the binding molecule does not comprise any polypeptide comprising or consisting essentially of a functional binding domain of a native Shiga toxin B subunit. Rather, in some embodiments of the binding molecules, the Shiga toxin A Subunit derived regions are functionally associated with heterologous binding regions to effectuate cell-targeting.

In some embodiments of Embodiment Sets #1 to #3, the Shiga toxin effector polypeptide comprises at least two, embedded or inserted, heterologous epitopes.

In some embodiments of Embodiment Sets #1 to #3, the Shiga toxin effector polypeptide does not comprise the set of amino acid residue substitutions relative to a wild-type Shiga toxin A Subunit selected from the following sets: (1) R248H and R251H; (2) R248G and R251G; (3) A246G, S247A, A253G, and S254A; and (4) A246G, S247A, R248G, R251G, A253G, and S254A.

In some embodiments of Embodiment Sets #1 to #3, the Shiga toxin effector polypeptide does not comprise a deletion of the region natively positioned at 247-252 in a wild-type Shiga toxin A Subunit. In some embodiments of Embodiment Sets #1 to #3, the Shiga toxin effector polypeptide does not comprise deletions of the regions natively positioned at 245-247 and 253-255 in a wild-type Shiga toxin A Subunit.

In some embodiments of Embodiment Sets #1 to #3, the Shiga toxin effector polypeptide comprises one or more mutations relative to a naturally occurring A Subunit of a member of the Shiga toxin family which changes an enzymatic activity of the Shiga toxin effector polypeptide, the mutation selected from at least one amino acid residue deletion, insertion, or substitution. In some embodiments, the mutation relative to the naturally occurring A Subunit reduces of eliminates a cytotoxic activity of the Shiga toxin effector polypeptide but the Shiga toxin effector polypeptide retains at least one other Shiga toxin effector function, such as, e.g., promoting cellular internalization and/or directing intracellular routing to a certain subcellular compartment(s). In some embodiments, the mutation relative to the naturally occurring A Subunit is selected from at least one amino acid residue substitution, such as, e.g., A231E, R75A, Y77S, Y114S, E167D, R170A, R176K, and/or W203A in SEQ ID NO:1, SEQ ID NO:2, or SEQ ID NO:3.

In some embodiments of Embodiment Sets #1 to #3, the Shiga toxin effector polypeptide is capable of: (i) routing to a subcellular compartment of a cell in which the Shiga toxin effector polypeptide is present selected from the following: cytosol, endoplasmic reticulum, and lysosome; (ii) intracellular delivery of the epitope from an early endosomal compartment to a proteasome of a cell in which the Shiga toxin effector polypeptide is present; and/or (iii) intracellular delivery of the epitope to a MHC class I molecule from an early endosomal compartment of a cell in which the Shiga toxin effector polypeptide is present. In some embodiments, the Shiga toxin effector polypeptide is capable of intracellular delivery of the CD 8+ T-cell epitope for presentation by a MHC class I molecule on the surface of a cell in which the Shiga toxin effector polypeptide is present.

Embodiment Set #4—Binding Molecule Comprising an Antibody-Toxin Conjugate

Also provided herein are various embodiments of PD-L1 binding molecules, wherein each PD-L1 binding molecule comprises (1) at least one toxin component and (2) at least one PD-L1 binding region capable of specifically binding an extracellular part of a PD-L1 molecule. In some embodiments, the PD-L1 binding molecule comprises a pharmaceutically active toxin. In some embodiments, the PD-L1 binding molecule is conjugated with a pharmaceutically active toxin to form an "antibody drug conjugate" (ADC).

In some embodiments, the PD-L1 binding molecule comprises (1) a toxin and (2) a PD-L1 binding region comprising an anti-PD-L1 antibody. In some embodiments, the toxin is a pharmaceutically active cytotoxin. In some embodiments, the PD-L1 binding molecule is an "antibody drug conjugate" (ADC), wherein the antibody and toxin components are linked as described herein. As used herein, the term "antibody," refers to immunoglobulin proteins, i.e., polypeptides of the immunoglobulin family, or antigen-binding fragments thereof, that contain an antigen binding site that immunospecifically binds to a specific antigen, such as, e.g., a polyclonal antibody, monoclonal antibody, human antibody, camelized antibody, humanized antibody, or antigen-binding antibody fragment (e.g. a Fab, Fv, scFv, sdAb fragment). As used herein, the term "conjugate" is used broadly and means the covalent or non-covalent association of any toxin agent with an antibody regardless of the method of association. The toxin agent component of an ADC includes, but is not limited to, natural toxins, biotoxins, proteinaceous toxins, venom, cytotoxins, small molecule toxins, and synthetic toxicants derived from any of the aforementioned. The ADCs may be used for therapeutic and diagnostic purposes.

In some embodiments, the PD-L1 binding region comprises a heavy chain variable region (HVR-H) comprising three CDRs, each having at least 85%, 90%, 91%, 92%, 93%, 94%, 95%, 96%, 97%, 98%, or 99% identity to any one of SEQ ID NOs: 22-24 and 27-32; or consisting essentially of an amino acid sequence show in any one of SEQ ID NOs: 22-24 and 27-32. In some embodiments, the binding region further comprises: (a) a light chain variable region (HVR-L) comprising three CDRs, each having at least 85%, 90%, 91%, 92%, 93%, 94%, 95%, 96%, 97%, 98%, or 99% identity to any one of SEQ ID NO:19, SEQ ID NO:20, SEQ ID NO:21, SEQ ID NO:25, and SEQ ID NO:26; or consisting essentially of an amino acid sequence shown in any one of SEQ ID NO:19, SEQ ID NO:20, SEQ ID NO:21, SEQ ID NO:25, and SEQ ID NO:26. In some embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:19, SEQ ID NO:20, and SEQ ID NO:21; or consisting essentially of an amino acid sequence shown in any one of SEQ ID NO:19, SEQ ID NO:20, and SEQ ID NO:21. In certain other further embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:25, SEQ ID NO:20, and SEQ ID NO:21; or consisting essentially of an amino acid sequence shown in any one of SEQ ID NO:25, SEQ ID NO:20, and SEQ ID NO:21. In certain other further embodiments, the binding region further comprises: (a) a light chain variable region (HVR-L) comprising three CDRs, having at least 85%, 90%, 91%, 92%, 93%, 94%, 95%, 96%, 97%, 98%, or 99% identity to SEQ ID NO:19, SEQ ID NO:20, and SEQ ID NO:26; or consisting essentially of an amino acid sequence shown in any one of SEQ ID NO:19, SEQ ID NO:20, and SEQ ID NO:26.

In some embodiments, the binding region comprises: (a) a light chain variable region (HVR-L) comprising three CDRs, each comprising or consisting essentially of an amino acid sequence shown in any one of SEQ ID NO:19, SEQ ID NO:20, SEQ ID NO:21, SEQ ID NO:25, and SEQ ID NO:26; and (b) a heavy chain variable region (HVR-H) comprising three CDRs, each comprising or consisting essentially of an amino acid sequence show in any one of SEQ ID NOs: 22-24 and 27-32.

In some embodiments, the binding region comprises: (a) a light chain region having at least 85%, 90%, 91%, 92%, 93%, 94%, 95%, 96%, 97%, 98%, or 99%, identity to any one of SEQ ID NOs: 33, 35-36, and 38, or consisting essentially of the amino acid sequence of any one of SEQ ID NOs: 33, 35-36, and 38; and/or (b) a heavy chain region having at least 85%, 90%, 91%, 92%, 93%, 94%, 95%, 96%, 97%, 98%, or 99% identity to any one of SEQ ID NOs: 34, 37, and 39, or consisting essentially of the amino acid sequence of any one of SEQ ID NOs: 34, 37, and 39. In some embodiments, the binding region comprises a polypeptide having at least 85%, 90%, 91%, 92%, 93%, 94%, 95%, 96%, 97%, 98%, or 99% identity to any one of SEQ ID NOs: 85-107 and 156-157 or consists essentially of the polypeptide shown in any one of SEQ ID NOs: 85-107 and 156-157. In some embodiments, the binding region is a single-chain variable fragment, such as, e.g., consisting of, comprising, or consisting essentially of the polypeptide of any one of SEQ ID NOs: 85-107 and 156-157.

In some embodiments of the PD-L1 binding molecule, upon administration of the PD-L1 binding molecule to a PD-L1-expressing cell results in (i) the internalization of the toxin component of the PD-L1 binding molecule by the cell and (ii) the death of the cell. For some embodiments, upon administration of the PD-L1 binding molecule to a PD-L1-expressing cell results in (i) the internalization of the PD-L1 binding molecule by the cell and (ii) the death of the cell due to a catalytically active toxin component. In some embodiments, the PD-L1 binding molecule of Embodiment Set #4 is capable, when introduced to cells, of exhibiting a cytotoxicity with a half-maximal inhibitory concentration ($CD_{50}$) value of 500 nM, 100 nM, 50 nM, 10 nM, 1 nM or less.

In some embodiments of the PD-L1 binding molecule, the PD-L1 binding region is in the form of a full-length antibody, bispecific antibody, dual variable domain antibodies, multiple chain or single chain antibody, and/or an antibody fragment(s) that specifically bind human PD-L1, including but not limited to Fab, Fab', (Fab')$_2$, Fv, scFv (single chain Fv), single domain antibody (e.g. a heavy-chain antibody domain fragment derived from camelid or cartilaginous fish), surrobody (including a surrogate light chain construct), camelized antibody, humanized antibody, and the like. The PD-L1 binding region can be of, or derived from, any antibody isotype, including for example, IgA (e.g. IgA$_1$, IgA$_2$, or sIgA), IgD, IgE, IgG (e.g. IgG$_1$, IgG$_2$, IgG$_3$, or IgG$_4$), or IgM. The PD-L1 binding region can be of, or derived from, any antibody of any species, including but not limited to species of mammalian origin (e.g., simians, rodents, goats, and rabbits). The PD-L1 binding region can comprise modifications and/or mutations that alter the properties of the antibodies and/or antigen-binding fragments, such as those that increase half-life, increase or decrease ADCC, CDC, PD-L1 antagonism, PD-L1 agonist activity, etc., as is known in the art.

In some embodiments, the binding molecule further comprises an additional exogenous material, which may be present for delivery to a target cell. In some embodiments, the additional exogenous material is associated, linked, and/or coupled to the binding molecule, either directly or indirectly.

In some embodiments, the binding molecule further comprises a detection promoting agent. In some embodiments, the detection promoting agent is associated, linked, and/or coupled to the binding molecule, either directly or indirectly.

In some embodiments, the binding region is not multispecific or bispecific, i.e. the PD-L1 binding region is monospecific. In some embodiments, the PD-L1 binding molecule is capable of specifically binding an extracellular part of a PD-L1 molecule but lacks high affinity and specific binding to any other cell-surface target i.e. the PD-L1 binding molecule is capable of exhibiting monospecific binding to PD-L1 and/or a single epitope within the extracellular part of a PD-L1 molecule. In some embodiments, the PD-L1 binding molecule comprises only one immunoglobulin-type binding region capable of exhibiting specific and high-affinity binding to PD-L1 present on a cellular surface of a cell, i.e. a single antigen binding site per molecule providing monospecific binding characteristics. In some embodiments of Embodiment Sets #1 to #4, the PD-L1 binding molecule comprises only one species of immunoglobulin-type binding region capable of exhibiting specific and high-affinity binding to PD-L1 present on a cellular surface of a cell, i.e. two or more identical copies of a single antigen binding site, such as, e.g., wherein the PD-L1 binding molecule exhibits multivalent PD-L1 binding characteristics but only monospecificity in binding to PD-L1.

Also provided herein is a pharmaceutical composition comprising any one of the above binding molecules and at least one pharmaceutically acceptable excipient or carrier.

Also provided herein is a diagnostic composition comprising any one of the above binding molecules and a detection promoting agent. Some embodiments are binding molecules wherein the detection promoting agent is a heterologous epitope and the binding molecule comprises the heterologous epitope.

Beyond the binding molecules, and compositions thereof, polynucleotides capable of encoding a binding molecule are also provided herein, as well as expression vectors which comprise a polynucleotide and host cells comprising any polynucleotide and/or expression vector. Host cells comprising an expression vector may be used, e.g., in methods for producing a molecule described herein or a polypeptide component or fragment thereof by recombinant expression.

Also provided herein is a method of killing a cell (e.g. a PD-L1-expressing cell), the method comprising the step of contacting the cell with any of the above binding molecules or the above pharmaceutical compositions described herein. In some embodiments, the step of contacting the cell(s) occurs in vitro. In certain other embodiments, the step of contacting the cell(s) occurs in vivo. In some embodiments of the cell-killing methods, the method is capable of selectively killing cell(s) and/or cell types preferentially over other cell(s) and/or cell types when contacting a mixture of cells which differ with respect to the extracellular presence and/or expression level of an extracellular target biomolecule of the binding region of the binding molecule.

Also provided herein is a method of inhibiting a PD-L1/PD1 interaction and/or downstream signaling, the method comprising the step of contacting a PD-L1 expressing cell with any of the above binding molecules or the above pharmaceutical compositions described herein. In some embodiments, the step of contacting the cell(s) occurs in vitro. In certain other embodiments, the step of contacting the cell(s) occurs in vivo.

Also provided herein is a method of concurrently inhibiting a PD-L1/PD1 interaction and inducing death of a PD-L1-expressing cell, the method comprising the step of contacting a PD-L1 expressing cell with any of the above binding molecules or the above pharmaceutical compositions. In some embodiments, the step of contacting the cell(s) occurs in vitro. In certain other embodiments, the step of contacting the cell(s) occurs in vivo.

In some embodiments, a method of treating a disease, disorder, or condition comprises administering to a subject in need thereof an effective amount of a PDL-1 binding molecule or a pharmaceutical composition comprising the same. In some embodiments, the cancer is any one of the following: bladder cancer (e.g., urothelial carcinoma), breast cancer (e.g., HER2 positive breast cancer, triple negative breast cancer), colon cancer (e.g., colorectal cancer such as metastatic microsatellite instability-high or mismatch repair deficient colorectal cancer), endometrial cancer, esophageal cancer, fallopian tube cancer, gastrointestinal cancer (e.g., gastric cancer, biliary tract neoplasm, gastroesophageal junction cancer), glioblastoma, glioma, head and neck cancer (e.g., squamous cell carcinoma of the head and neck), kidney cancer (e.g., renal cell carcinoma), liver cancer (e.g., hepatocellular carcinoma), lung cancer (e.g., non-small cell lung cancer, small-cell lung cancer), lymphoma (e.g., diffuse large B-cell lymphoma, Hodgkin lymphoma, non-Hodgkin lymphoma, primary mediastinal large B-cell lymphoma), Merkel cell carcinoma, mesothelioma (e.g., pleural mesothelioma), myeloma (e.g., multiple myeloma), nasopharyngeal neoplasm, ovarian cancer, pancreatic cancer, peritoneal neoplasm, prostate cancer, skin cancer (e.g., squamous cell cancer of the skin, melanoma, transitional cell carcinoma, or urothelial cancer.

In some embodiments, methods of treating diseases, disorders, and/or conditions in patients comprise the step of administering to a patient in need thereof a therapeutically effective amount of a binding molecule and/or pharmaceutical composition. In some embodiments, the disease, disorder, or condition to be treated using a method is selected from: a cancer, tumor, growth abnormality, immune disorder, or microbial infection. In some embodiments of these methods, the cancer to be treated is selected from the group consisting of: lung cancer, melanoma, bladder cancer, Hodgkin's lymphoma, and breast cancer. In some embodiments of these methods, the immune disorder to be treated is an immune disorder associated with a disease selected from the group consisting of: rheumatic disease, spondylitis, amyloidosis, ankylosing spondylitis, asthma, Crohn's disease, diabetes, graft rejection, graft-versus-host disease, Hashimoto's thyroiditis, hemolytic uremic syndrome, HIV-related disease, lupus erythematosus, multiple sclerosis, polyarteritis nodosa, polyarthritis, psoriasis, psoriatic arthritis, rheumatoid arthritis, scleroderma, septic shock, Sjögren's syndrome, ulcerative colitis, and vasculitis.

Certain embodiments of the binding molecules may be utilized for the delivery of additional exogenous material into a cell physically coupled with an extracellular target biomolecule of the binding molecule. Additionally, the present disclosure provides a method for delivering exogenous material to the inside of a cell(s) comprising contacting the cell(s), either in vitro or in vivo, with a binding molecule, pharmaceutical composition, and/or diagnostic composition. Also provided is a method for delivering exogenous material to the inside of a cell(s) in a patient, the method comprising the step of administering to the patient a binding molecule (with or without cytotoxic activity), wherein the target cell(s) is physically coupled with an extracellular target biomolecule of the binding molecule.

Also provided herein is a method of delivering into a cell a T-cell epitope capable of being presented by a MHC class I molecule of the cell, the method comprising the step of contacting the cell with the binding molecule which is associated with a heterologous, T-cell epitope and/or a composition thereof (e.g., a pharmaceutical or diagnostic composition as described herein).

In some embodiments, a method for making the PD-L1 binding molecules described herein comprises expressing a PD-L1 binding molecule and recovering the PD-L1 binding molecule. In some embodiments, expressing the PD-L1 binding molecule comprises culturing a host cell comprising a nucleic acid (e.g., an expression vector) encoding the PD-L1 binding molecule under conditions wherein the PD-L1 binding molecule is expressed.

In some embodiments, a method for purifying the PD-L1 binding molecules described herein from an expression system composition comprising the PD-L1 binding molecule and at least one other biomolecule comprises (i) contacting the expression system composition with a bacterial protein L to create a PD-L1 binding molecule-protein L complex, and (ii) recovering the PD-L1 binding molecule-protein L complex. In some embodiments, the expression system composition is a cellular lysate. In some embodiments, the protein L is isolated or derived from *F. magna*. In some embodiments, the protein L is conjugated to a resin.

In some embodiments, a method of producing a molecule described herein comprises the step of purifying the molecule or a polypeptide component of thereof using a bacterial cell-wall protein domain interaction, such as, e.g., protein L from *P. magnus* or derivatives and binding domain fragments thereof or protein A from *S. aureus* or derivatives and binding domain fragments thereof. In some embodiments, the purifying step of the method involves the Shiga toxin effector polypeptide comprising or consisting essentially of any one of the polypeptides shown in SEQ ID NOs: 1-18 and 40-68. In some embodiments, the purifying step of the method involves the binding molecule comprising or consisting essentially of any one of the polypeptides shown in SEQ ID NOs: 108-155.

In embodiments, a method of making a PD-L1 binding molecule comprises culturing a host cell under conditions wherein the PD-L1 binding molecule is expressed and recovering the protein. In some embodiments, the binding molecules comprise an epitope that allows them to be purified using affinity chromatography. In some embodiments, the binding molecules comprise an Ig binding domain, such as a bacterial Ig binding domain, or a fragment or functional variant thereof.

In some embodiments, the Ig binding domain used in the purification methods described herein is Protein L, or a derivative or binding domain fragments thereof. Protein L, which was first isolated from *Finegoldia magna* (formerly *Peptostreptococcus magnus*), is an immunoglobulin-binding protein that has the unique ability to bind to bind through kappa light chain interactions without interfering with the antigen-binding site of an antibody, scFv, Fab fragment, or other binding protein. Protein L binds native kappa light chain subtypes I, III and IV. Protein L does not bind to native kappa light chain subtypes II or native lambda light chains. Protein L binds to human IgG, IgA, IgM, IgE, and IgD. In some embodiments, the protein L is isolated or derived from *F. magna*. Protein L can be produced recombinantly in, for example, *E. coli*. In some embodiments, Protein L comprises the sequence of SEQ ID NO: 279, or a sequence at least 90%, at least 95%, at least 96%, at least 97%, at least 98%, or at least 99% identical thereto.

In some embodiments, the Ig binding domain is Protein G from group C and G Streptococcal bacteria, or Protein A from *S. aureus*, or derivatives and binding domain fragments of any of the foregoing.

In some embodiments, a purification method comprises contacting a binding molecule comprising an Ig binding domain epitope with an Ig binding domain (e.g., protein L or a fragment or derivative thereof).

In some embodiments, the method comprises three steps: a binding step, a washing step, and an elution step. In the binding step, a protein comprising a chimeric immunoglobulin binding domain is contacted with protein L immobilized on a matrix. The matrix can be any solid support such as a bead, a resin, etc. In some embodiments, the matrix can be packed into a column or into a cartridge.

In the washing step, the matrix is washed to remove impurities. The washing step can be repeated, for example at least 2 times, at least 3 times, at least 4 times, or at least 5 times, until substantially all impurities are removed. In some embodiments, the washing step is repeated until at least 80%, at least 85%, at least 90%, at least 95%, at least 96%, at least 97%, at least 98%, or at least 99% of impurities are removed.

In the elution step, the protein comprising the chimeric immunoglobulin binding domain is eluted from the protein L-matrix. The protein can be eluted using, for example, a high salt wash solution (e.g., 1 M NaCl) or a change in pH. After elution, the protein can be collected and further purified and/or desalted as appropriate, according to standard methods.

In some embodiments, a method for purifying a PD-L1 binding molecule from an expression system composition comprising the PD-L1 binding molecule and at least one other biomolecule comprises (i) contacting the expression system composition with a bacterial protein L to create a PD-L1 binding molecule-protein L complex, and (ii) recovering the PD-L1 binding molecule-protein L complex. In some embodiments, the expression system composition is a cellular lysate. In some embodiments, the protein L is isolated or derived from *F. magna*. In some embodiments, the protein L is conjugated to a resin.

In some embodiments, a method of making a binding molecule comprises culturing a host cell under conditions wherein the binding molecule is expressed and recovering the protein. In some embodiments, a method of purifying a binding molecule comprises comprising contacting the binding molecule with a bacterial protein L. In some embodiments, the protein L is isolated or derived from *F. magna*. In some embodiments, the protein L is conjugated to a resin.

Also provided herein are kits comprising a composition of matter as described herein, and optionally, instructions for use, additional reagent(s), and/or pharmaceutical delivery device(s). The kit may further comprise reagents and other tools for detecting a cell type (e.g. a tumor cell) in a sample or in a subject.

Additional Numbered Embodiments

1. A PD-L1 binding molecule comprising a Shiga toxin A subunit effector polypeptide and a binding region capable of specifically binding an extracellular part of PD-L1; wherein the binding region comprises: (a) a heavy chain variable region (VH) comprising: (i) a CDR1 comprising the amino acid sequence EYTMH (SEQ ID NO:27), (ii) a CDR2 comprising the amino acid sequence GINPNNGGTWYN-QKFKG (SEQ ID NO:29), and (iii) a CDR3 comprising the amino acid sequence PYYYGSREDYFDY (SEQ ID NO:32); and (b) a light chain variable region (VL) comprising: (i) a CDR1 comprising the amino acid sequence SASSSVSYMY (SEQ ID NO:19), (ii) a CDR2 comprising the amino acid sequence LTSNLAS (SEQ ID NO:20), and (iii) a CDR3 comprising the amino acid sequence QQWSSNPPT (SEQ ID NO:26).

2. The PD1-L1 binding molecule of embodiment 1, wherein the Shiga toxin A subunit effector polypeptide comprises the sequence of SEQ ID NO: 41, or a sequence at least 90% or at least 95% identical thereto.

3. The PD-L1 binding molecule of any one of embodiments 1-2, wherein the VH comprises the sequence of SEQ ID NO: 34, or a sequence at least 90% or at least 95% identical thereto.

4. The PD-L1 binding molecule of any one of embodiments 1-3, wherein the VL comprises the sequence of SEQ ID NO: 35, or a sequence at least 90% or at least 95% identical thereto.

5. The PD-L1 binding molecule of any one of embodiments 1-2, wherein the VH comprises the sequence of SEQ ID NO: 34 and the VL comprises the sequence of SEQ ID NO: 35.

6. The PD-L1 binding molecule of any one of embodiments 1-5, wherein the binding region comprises a scFv linker that links the VH and the VL.

7. The PD-L1 binding molecule of embodiment 6, wherein the scFv linker is about 3 to about 12 amino acids in length.

8. The PD-L1 binding molecule of any one of embodiments 6-7, wherein the scFv linker is a flexible linker.

9. The PD-L1 binding molecule of embodiment 6, wherein the scFv linker comprises the sequence of SEQ ID NO: 72, or a sequence at least 90% or at least 95% identical thereto.

10. The PD-L1 binding molecule of any one of embodiments 1-9, wherein the binding region is a single chain variable fragment (scFv).

11. The PD-L1 binding molecule of any one of embodiments 1-9, wherein the binding region comprises the sequence of SEQ ID NO: 106, or a sequence at least 90% or at least 95% identical thereto.

12. The PD-L1 binding molecule of any one of embodiments 1-11, wherein the PD-L1 binding molecule comprises a binding domain linker which links the Shiga toxin A subunit effector polypeptide and the binding region.

13. The PD-L1 binding molecule of embodiment 12, wherein the binding domain linker comprises the sequence of SEQ ID NO: 73, or a sequence at least 90% or at least 95% identical thereto.

14. The PD-L1 binding molecule of any one of embodiments 12-13, wherein the binding molecule comprises, from N-terminus to C-terminus, the Shiga toxin A subunit effector polypeptide, the binding domain linker, and the binding region.

15. The PD-L1 binding molecule of any one of embodiments 12-13, wherein the binding molecule comprises, from N-terminus to C-terminus, the Shiga toxin A subunit effector polypeptide, the binding domain linker, the VH and the VL.

16. The PD-L1 binding molecule of any one of embodiments 12-13, wherein the binding molecule comprises, from N-terminus to C-terminus, the Shiga toxin A subunit effector polypeptide, the binding domain linker, the VH, the scFv linker, and the VL.

17. The PD-L1 binding molecule of any one of embodiments 1-16, wherein the PD-L1 binding molecule comprises a CD8+ T-cell epitope that is heterologous to Shiga toxin A subunits.

18. The PD-L1 binding molecule of embodiment 17, wherein the CD8+ T-cell epitope comprises the sequence NLVPMVATV (SEQ ID NO: 78), or a sequence at least 90% or at least 95% identical thereto.

19. The PD-L1 binding molecule of any one of embodiments 17-18 wherein the CD8+ T-cell epitope is linked to the binding region via a cleavable spacer.

20. The PD-L1 binding molecule of embodiment 19, wherein the cleavable spacer has the sequence HHAA (SEQ ID NO: 265).

21. The PD-L1 binding molecule of any one of embodiments 17-20, wherein the binding molecule comprises, from N-terminus to C-terminus, the Shiga toxin A subunit effector polypeptide, the binding domain linker, the binding region, and the CD8+ T-cell epitope.

22. The PD-L1 binding molecule of any one of embodiments 17-20, wherein the binding molecule comprises, from N-terminus to C-terminus, the Shiga toxin A subunit effector polypeptide, the binding domain linker, the VH, the scFv linker, the VL, and the CD8+ T-cell epitope.

23. The PD-L1 binding molecule of any one of embodiments 19-20, wherein the binding molecule comprises, from N-terminus to C-terminus, the Shiga toxin A subunit effector polypeptide, the binding domain linker, the binding region, the cleavable spacer and the CD8+ T-cell epitope.

24. The PD-L1 binding molecule of any one of embodiments 1-23, wherein the PD-L1 binding molecule comprises the sequence of SEQ ID NO: 128, or a sequence at least 90% or at least 95% identical thereto.

25. The PD-L1 binding molecule of any one of embodiments 1-24, wherein the PD-L1 binding molecule is a single continuous polypeptide.

26. The PD-L1 binding molecule of any one of embodiments 1-24, wherein the PD-L1 binding molecule comprises two polypeptides.

27. The PD-L1 binding molecule of embodiment 26, wherein each of the two polypeptide comprises the sequence of SEQ ID NO: 128.

28. The PD-L1 binding molecule of any one of embodiments 26-27, wherein the two polypeptides are non-covalently linked to each other.

29. The PD-L1 binding molecule of any one of embodiments 26-27, wherein the two polypeptides are non-covalently linked to each other via the binding region.

30. The PD-L1 binding molecule of any one of embodiments 1-29, wherein the binding molecule is cytotoxic.

31. The PD-L1 binding molecule of any one of embodiments 1-29, wherein the binding molecule is non-cytotoxic.

32. A pharmaceutical composition comprising the PD-L1 binding molecule of any one of embodiments 1-31, and at least one pharmaceutically acceptable excipient or carrier.

33. A polynucleotide encoding the PD-L1 binding molecule of any one of embodiments 1-31, or a complement thereof.

34. An expression vector comprising a polynucleotide according to embodiment 33.

35. A host cell comprising a polynucleotide according to embodiment 33 or an expression vector according to embodiment 34.

36. A method for making the PD-L1 binding molecule of any one of embodiments 1-31, the method comprising (a) expressing a PD-L1 binding molecule of any one of embodiments 1-31 and (b) recovering the PD-L1 binding molecule.

37. The method of embodiment 36, wherein expressing the PD-L1 binding molecule comprises culturing the host cell of embodiment 35 under conditions wherein the PD-L1 binding molecule is expressed.

38. A method for purifying the PD-L1 binding molecule of any one of embodiments 1-31 from an expression system composition comprising the PD-L1 binding molecule and at least one other biomolecule, the method comprising (i) contacting the expression system composition with a bacterial protein L to create a PD-L1 binding molecule-protein L complex, and (ii) recovering the PD-L1 binding molecule-protein L complex.

39. The method of embodiment 38, wherein the expression system composition is a cellular lysate.

40. The method of any one of embodiments 38-39, wherein the protein L is isolated or derived from *F. magna*.

41. The method of any one of embodiments 38-40, wherein the protein L is conjugated to a resin.

42. A method of killing a PD-L1 expressing cell, the method comprising the step of contacting the cell with a PD-L1 binding molecule according to any one of embodiments 1-31 or a pharmaceutical composition according to embodiment 32.

43. A method of treating a disease, disorder, or condition in a subject, the method comprising a step of administering to a subject in need thereof a therapeutically effective amount of a PD-L1 binding molecule according to any one of embodiments 1-31 or a pharmaceutical composition according to embodiment 32.

44. The method of embodiment 43, wherein the disease, disorder, or condition is an immune disorder or microbial infection.

45. A method of treating cancer, the method comprising administering to a subject in need thereof an effective amount of the PD-L1 binding molecule of any one of embodiments 1-31, or the pharmaceutical composition of embodiment 32.

46. The method of embodiment 45, wherein the cancer is characterized by a high mutational burden and/or a high frequency of indels.

47. The method of any one of embodiments 45-46, wherein the cancer is a solid tumor.

48. The method of any one of embodiments 45-47, wherein the cancer is bladder cancer, breast cancer, colon cancer, endometrial cancer, esophageal cancer, fallopian tube cancer, gastrointestinal cancer, glioma, head and neck cancer, kidney cancer, liver cancer, lung cancer, lymphoma, Merkel cell carcinoma, mesothelioma, myeloma, nasopharyngeal neoplasm, ovarian cancer, pancreatic cancer, peritoneal neoplasm, prostate cancer, skin cancer, transitional cell carcinoma, or urothelial cancer.

49. The method of any one of embodiments 45-47, wherein the cancer is bladder cancer, and the bladder cancer is urothelial carcinoma.

50. The method of any one of embodiments 45-47, wherein the cancer is breast cancer, and the breast cancer is HER2 positive breast cancer or triple negative breast cancer.

51. The method of any one of embodiments 45-47, wherein the cancer is colon cancer, and the colon cancer is colorectal cancer.

52. The method of any one of embodiments 45-47, wherein the cancer is gastrointestinal cancer, and the gastrointestinal cancer is gastric cancer, biliary tract neoplasm, or gastroesophageal junction cancer.

53. The method of any one of embodiments 45-47, wherein the cancer is glioma, and the glioma is glioblastoma.

54. The method of any one of embodiments 45-47, wherein the cancer is head and neck cancer, and the head and neck cancer is squamous cell carcinoma of the head and neck.

55. The method of any one of embodiments 45-47, wherein the cancer is kidney cancer, and the kidney cancer is renal cell carcinoma.

56. The method of any one of embodiments 45-47, wherein the cancer is liver cancer, and the liver cancer is hepatocellular carcinoma.

57. The method of any one of embodiments 45-47, wherein the cancer is lung cancer, and the lung cancer is non-small cell lung cancer or small-cell lung cancer.

58. The method of any one of embodiments 45-47, wherein the cancer is lymphoma, and the lymphoma is Hodgkin lymphoma, non-Hodgkin lymphoma, primary mediastinal large B-cell lymphoma, or diffuse large B-cell lymphoma.

59. The method of any one of embodiments 45-47, wherein the cancer is mesothelioma, and the mesothelial carcinoma is pleural mesothelioma.

60. The method of any one of embodiments 45-47, wherein the cancer is myeloma, and the myeloma is multiple myeloma.

61. The method of any one of embodiments 45-47, wherein the cancer is skin cancer, and the skin cancer is squamous cell cancer of the skin or melanoma.

62. The method of any one of embodiments 45-61, wherein the cancer is relapsed or refractory to a treatment involving at least one of ipilimumab, nivolumab, pembrolizumab, atezolizumab, durvalumab, avelumab, tremelimumab and cemiplimab.

63. The method of any one of embodiments 45-62, wherein the cancer is metastatic.

64. A cytotoxic PD-L1 binding molecule comprising: a Shiga toxin A subunit effector polypeptide comprising an amino acid sequence at least 98% identical to SEQ ID NO: 41; a single chain variable fragment (scFv) capable of specifically binding an extracellular part of PD-L1;

wherein the scFv comprises: (a) a heavy chain variable region (VH) comprising: (i) a CDR1 comprising the amino acid sequence EYTMH (SEQ ID NO:27), (ii) a CDR2 comprising the amino acid sequence GINPNNGGTWYNQKFKG (SEQ ID NO:29), and (iii) a CDR3 comprising the amino acid sequence PYYYGSREDYFDY (SEQ ID NO:32); and (b) a light chain variable region (VL) comprising: (i) a CDR1 comprising the amino acid sequence SASSSVSYMY (SEQ ID NO:19), (ii) a CDR2 comprising the amino acid sequence LTSNLAS (SEQ ID NO:20), and (iii) a CDR3 comprising the amino acid sequence QQWSSNPPT (SEQ ID NO:26); and a scFv linker between the VH and the VL which is 3 to 12 amino acids in length; and a human CD8+ T-cell epitope.

65. The PD-L1 binding molecule of embodiment 64, wherein the VH comprises the sequence of SEQ ID NO: 34, or a sequence at least 90% identical thereto.

66. The PD-L1 binding molecule of embodiment 64 or 65, wherein the VL comprises the sequence of SEQ ID NO: 35, or a sequence at least 90% identical thereto.

67. The PD-L1 binding molecule of embodiment 64, wherein the VH comprises the sequence of SEQ ID NO: 34 and the VL comprises the sequence of SEQ ID NO: 35.

68. The PD-L1 binding molecule of any one of embodiments 64-67, wherein the scFv linker comprises the sequence of SEQ ID NO: 72, or a sequence at least 90% identical thereto.

69. The PD-L1 binding molecule of any one of embodiments 64-68, wherein the scFv comprises the sequence of SEQ ID NO: 106, or a sequence at least 90% identical thereto.

70. The PD-L1 binding molecule of any one of embodiments 64-69, wherein the PD-L1 binding molecule comprises a binding domain linker which links the Shiga toxin A subunit effector polypeptide and the scFv.

71. The PD-L1 binding molecule of embodiment 70, wherein the binding domain linker comprises the sequence of SEQ ID NO: 73, or a sequence at least 90% identical thereto.

72. The PD-L1 binding molecule of any one of embodiments 64-71, wherein the CD8+ T-cell epitope comprises the sequence NLVPMVATV (SEQ ID NO: 78).

73. The PD-L1 binding molecule any one of embodiments 64-72, wherein the CD8+ T-cell epitope is linked to the scFv via a spacer.

74. The PD-L1 binding molecule of embodiment 73, wherein the spacer has the sequence HHAA (SEQ ID NO: 265).

75. The PD-L1 binding molecule of any one of embodiments 64-74, wherein the PD-L1 binding molecule comprises the sequence of SEQ ID NO: 128, or a sequence at least 90% or at least 95% identical thereto.

76. The PD-L1 binding molecule of any one of embodiments 64-75, wherein the PD-L1 binding molecule is a single continuous polypeptide.

77. The PD-L1 binding molecule of embodiment 76, wherein the PD-L1 binding molecule is a single continuous polypeptide comprising, in order from N-terminus to C-terminus, the Shiga toxin A subunit effector polypeptide, the scFv, and the CD8+ T-cell epitope.

78. The PD-L1 binding molecule of embodiment 76, wherein the binding molecule is a single continuous polypeptide comprising, from N-terminus to C-terminus, the Shiga toxin A subunit effector polypeptide, a binding domain linker, the scFv, and the CD8+ T-cell epitope.

79. The PD-L1 binding molecule of embodiment 76, wherein the binding molecule is a single continuous polypeptide comprising, in order from N-terminus to C-terminus, the Shiga toxin A subunit effector polypeptide, a binding domain linker, the VH, the scFv linker, the VL, and the CD8+ T-cell epitope.

80. The PD-L1 binding molecule of embodiment 76, wherein the binding molecule is a single continuous polypeptide comprising, from N-terminus to C-terminus, the Shiga toxin A subunit effector polypeptide, a binding domain linker, the scFv, a spacer, and the CD8+ T-cell epitope.

81. The PD-L1 binding molecule of any one of embodiments 64-75, wherein the PD-L1 binding molecule comprises two polypeptides.

82. The PD-L1 binding molecule of embodiment 81, wherein the two polypeptides are non-covalently linked to each other.

83. The PD-L1 binding molecule of embodiment 81 or 82, wherein the two polypeptides are non-covalently linked to each other via the binding region.

84. The PD-L1 binding molecule of any one of embodiments 81-83, wherein each of the two polypeptides comprises, in order from N-terminus to C-terminus, the Shiga toxin A subunit effector polypeptide, the scFv, and the CD8+ T-cell epitope.

85. The PD-L1 binding molecule of any one of embodiments 81-83, wherein each of the two polypeptides comprises, from N-terminus to C-terminus, the Shiga toxin A subunit effector polypeptide, a binding domain linker, the scFv, and the CD8+ T-cell epitope.

86. The PD-L1 binding molecule of any one of embodiments 81-83, wherein each of the two polypeptides comprises, in order from N-terminus to C-terminus, the Shiga toxin A subunit effector polypeptide, a binding domain linker, the VH, the scFv linker, the VL, and the CD8+ T-cell epitope.

87. The PD-L1 binding molecule of any one of embodiments 81-83, wherein each of the two polypeptides comprises, from N-terminus to C-terminus, the Shiga toxin A subunit effector polypeptide, a binding domain linker, the scFv, a spacer, and the CD8+ T-cell epitope.

88. The PD-L1 binding molecule of embodiment any one of embodiments 81-87, wherein each of the two polypeptide comprises the sequence of SEQ ID NO: 128.

89. A protein comprising the sequence of SEQ ID NO: 128.

90. A protein consisting of the sequence of SEQ ID NO: 128.

EXAMPLES

The following examples demonstrate certain embodiments of the present invention. However, it is to be understood that these examples are for illustration purposes only and do not intend, nor should any be construed, to be wholly definitive as to conditions and scope of this invention. The experiments in the following examples were carried out using standard techniques, which are well known and routine to those of skill in the art, except where otherwise described.

The following examples describe several, exemplary, PD-L1 binding molecules. Each exemplary PD-L1 binding molecule below comprises at least one toxin linked, either directly or indirectly, to a cell-targeting PD-L1 binding region (See, e.g., FIG. 1). Exemplary, cytotoxic, binding molecules described below bound to cell-surface PD-L1 molecules expressed by targeted, tumor cell-types and entered those target cells. Some of the internalized, PD-L1 binding molecules shown in the Examples had toxin components which effectively routed to the cytosolic compartments of target cells where the toxin inactivated ribosomes and subsequently caused the apoptotic death of the target cells. Some exemplary binding molecules were able to effectively deliver an immunogenic, T-cell epitope-peptide to the intracellular MHC class I pathway of tumor target cells resulting in cell-surface presentation, intercellular T-cell engagement, and immune response including cytokine secretion and/or target cell killing.

The protein toxin effector polypeptides used in exemplary PD-L1 binding molecules in the Examples were de-immunized while retaining catalytic and/or cytotoxic activity, unless indicated herein as "inactivated". Some exemplary PD-L1 binding molecules comprise at least one Shiga toxin effector polypeptide component which (1) is de-immunized; (2) is positioned on or proximal to an amino-terminus of a polypeptide component of the binding molecule; (3) is furin-cleavage resistant as described herein; and/or (4) comprises an embedded or inserted CD8+ T-cell epitope.

Example 1. PD-L1 Binding Domain Discovery

The PD-L1 binding domains were identified by Abeome Corporation (Bogart, Georgia, U.S.A.) or derived from PD-L1 binding proteins identified by Abeome Corporation (see e.g. PCT/US2019/022971). PD-L1 binding proteins were identified using methods described in the literature regarding Abeome Corporation's method of screening transgenic murine B-cells expressing affinity maturated, monoclonal anti-PD-L1 antibodies for PD-L1 binding affinity. Certain anti-PD-L1 antibody candidates were optionally humanized using recombinant methods to make murine/human chimeric sequences, and the resulting chimeric anti-PD-L1 monoclonal antibodies were screened for both PD-L1 binding affinity and inhibition of PD-L1/PD-1 binding. For certain molecules, amino acid residues identified as putative post-translational modification sites and/or potentially disadvantageous to manufacturing, such as noncanonical or unpaired cysteine residues and N-glycosylation sites, were altered or removed. If greater PD-L1 binding affinity was desired, then mutagenesis of complementarity determining regions (CDRs) was undertaken using Abeome Corporation's proprietary methods.

The transgenic murine B-cells expressing anti-PD-L1 antibodies were obtained from transgenic AbeoMice™ immunized subcutaneously on a prime/boost schedule using a recombinant PD-L1 extracellular domain (comprising the first 239 amino acids of human PD-L1) as the immunogen. Lymphoid tissue samples and bone marrow were harvested and pooled, and B-cells expressing monoclonal antibodies (mAbs) on the cell surface were sorted and screened for binding to human PD-L1. The variable regions from monoclonal antibodies of certain B-cell clones were identified and cloned as chimeric mAbs. Candidate mAbs were characterized for PD-L1 binding and the ability to disrupt the PD-1/PD-L1 interaction and/or PD-1 signaling axis.

Example 2. PD-L1 Binding Molecules Comprising Shiga Toxin a Subunit Components

I. Construction and Testing of PD-L1-Targeting Immunotoxins

PD-L1 binding molecules comprising Shiga toxin components and candidate mAb immunoglobulin domains of Example 1 were designed, expressed, and purified as previously described in WO 2016/196344 and WO 2018/140427. Various mutations to the Shiga toxin A1 fragment were utilized in the toxin components of the PD-L1-targeting immunotoxins described in these examples. For example, all the Shiga toxin A1 fragments used in the exemplary PD-L1-targeting immunotoxins of Example 2 were de-immunized (referred to herein as "DI-SLT-A1"). Exemplary PD-L1-targeting immunotoxins were constructed as fusion proteins, each comprising an exemplary anti-PD-L1 scFv derived from the variable regions PD-L1 binding domains identified in Example 1 and one or more variants of a "DI-SLT-A1". These PD-L1-targeting immunotoxins ae referred to herein as "DI-SLT-A1 fusion proteins". Protein preparations of 116297 comprise a mixture of monomers (i.e., monomers of a protein comprising SEQ ID NO: 128), homodimers (i.e., dimers of two proteins each comprising the sequence of SEQ ID NO: 128), and homomultimers of sizes greater than dimers (i.e. multimers of three or more proteins each comprising the sequence of SEQ ID NO: 128) with homodimers being vastly predominant. Preparations of 115749 comprise predominantly monomers (i.e., monomers of a protein comprising SEQ ID NO: 113).

PD-L1-targeting immunotoxins (DI-SLT-A1 fusion proteins) comprising exemplary anti-PD-L1 scFv's were tested for binding to PD-L1 recombinant protein in an enzyme-linked immuno assay (ELISA) format. Briefly, NUNC MAXISORP® plates were coated with recombinant human or cynomolgus macaque PD-L1 extracellular domain (ECD) protein, washed with PBS, and blocked to reduce nonspecific background noise. DI-SLT-A1 fusion proteins were incubated with PD-L1 ECD protein, the samples washed, and then DI-SLT-A1 fusion protein levels were detected using an anti DI-SLT-A1 mAb conjugated to horseradish peroxidase (HRP). The ELISA signal was detected after incubation with TMB-Ultra (3',5,5'-tetramethylbenzidine) and subsequent neutralization with hydrochloric acid. The absorbance values (Abs) at 450 nanometer (nm) were read using a plate reader, and the background ELISA signal from a buffer only control was subtracted. The mean fluorescent intensity (MFI) values were plotted as a function of the log transformed DI-SLT-A1 fusion protein concentration to determine the Bmax and $K_D$ using a non-linear curve regression analysis (Prism (GraphPad Prism, San Diego, CA, U.S.A., Prism software function sigmoidal 4PL). Some results from these binding experiments are shown Table 7 and FIGS. 2, 3, 15, and 34. Table 7 shows the dissociation constant ($K_D$) as measured in nanogram per milliliter (ng/mL) and Bmax as measured in MFI.

Figure 2:
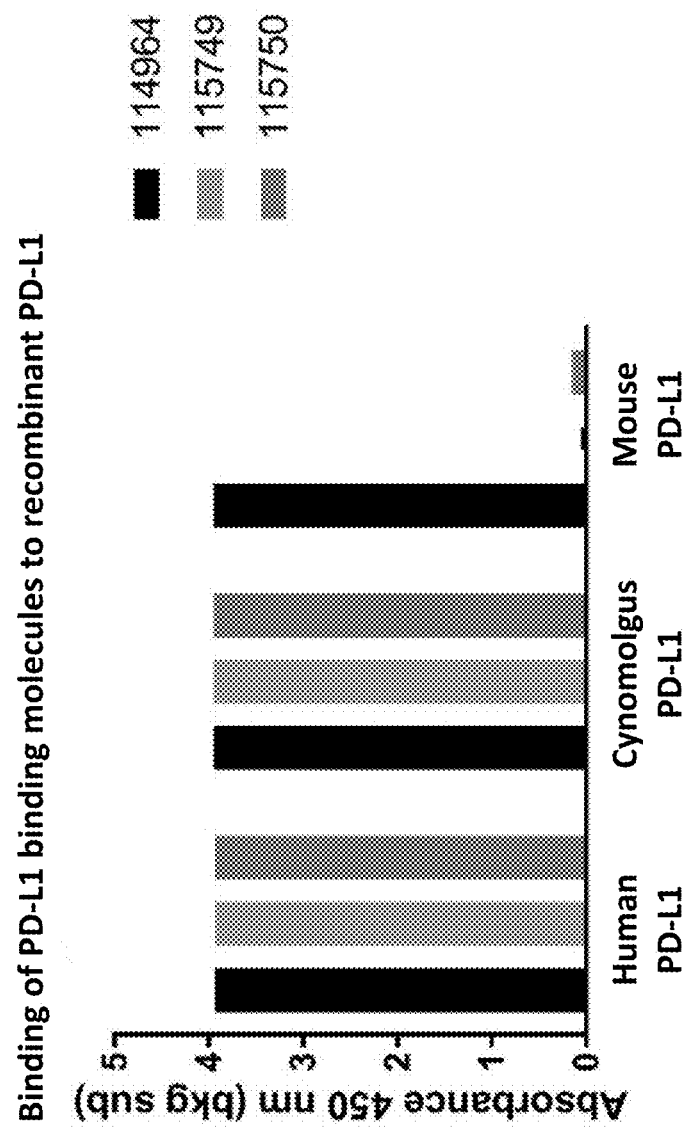

The DI-SLT-A1 fusion proteins 115749 (SEQ ID NO:113) and 115750 (SEQ ID NO:114) were tested for binding to PD-L1 from different species and were determined to bind to human and cynomolgus macaque PD-L1, but not mouse PD-L1 as shown in FIG. 2. A control DI-SLT-A1 fusion protein (114964) targeting PD-L1, comprising immunoglobulin binding domains present in atezolizumab known to bind to PD-L1 from human, macaque, and mouse, was used as a positive control.

Both PD-L1 binding molecules 115749 (SEQ ID NO:113) and 115750 (SEQ ID NO:114) bound to human PD-L1 and cynomolgus macaque PD-L1 but did not bind to murine PD-L1 in this assay (FIG. 2; Table 7).

Closely related DI-SLT-A1 fusion proteins, differing only in the scFv interdomain linker between the light chain domain and the heavy chain domain, were tested in a similar assay to characterize their binding affinities to PD-L1. In this experiment, a dilution series of the DI-SLT-A1 fusion proteins were tested for binding to human or cynomolgus macaque PD-L1 recombinant proteins. Some results from these binding experiments are shown Table 7 and FIGS. 3, 15, and 34.

Figure 3:
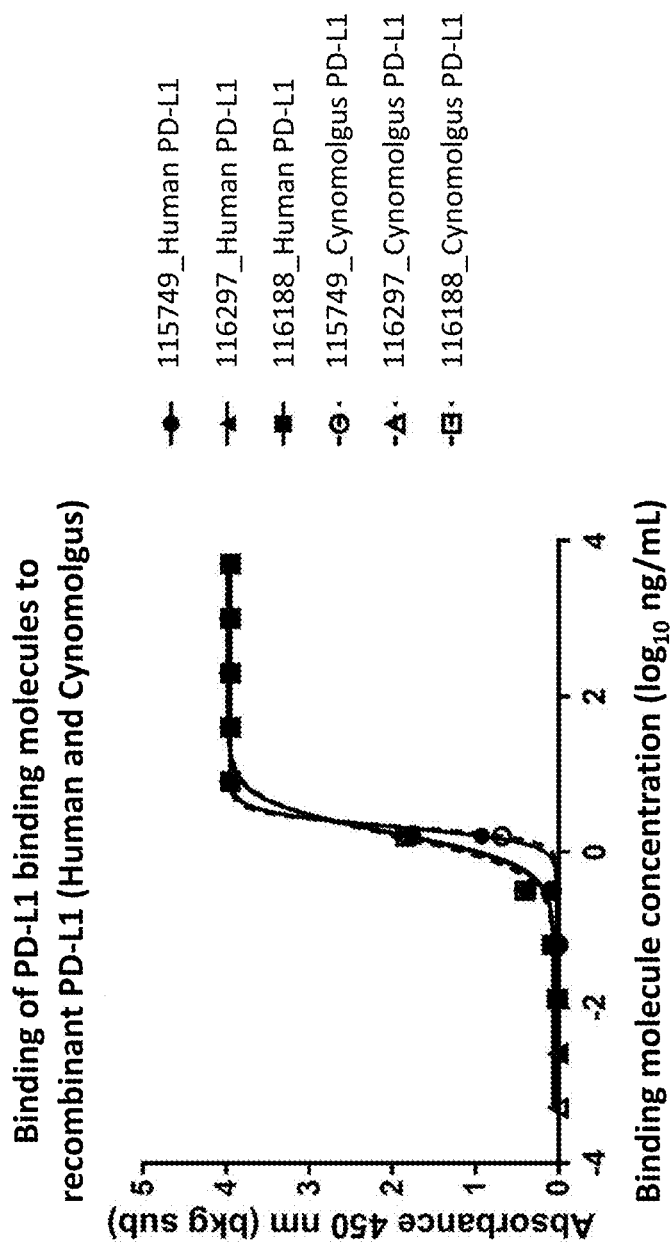
Figure 15:
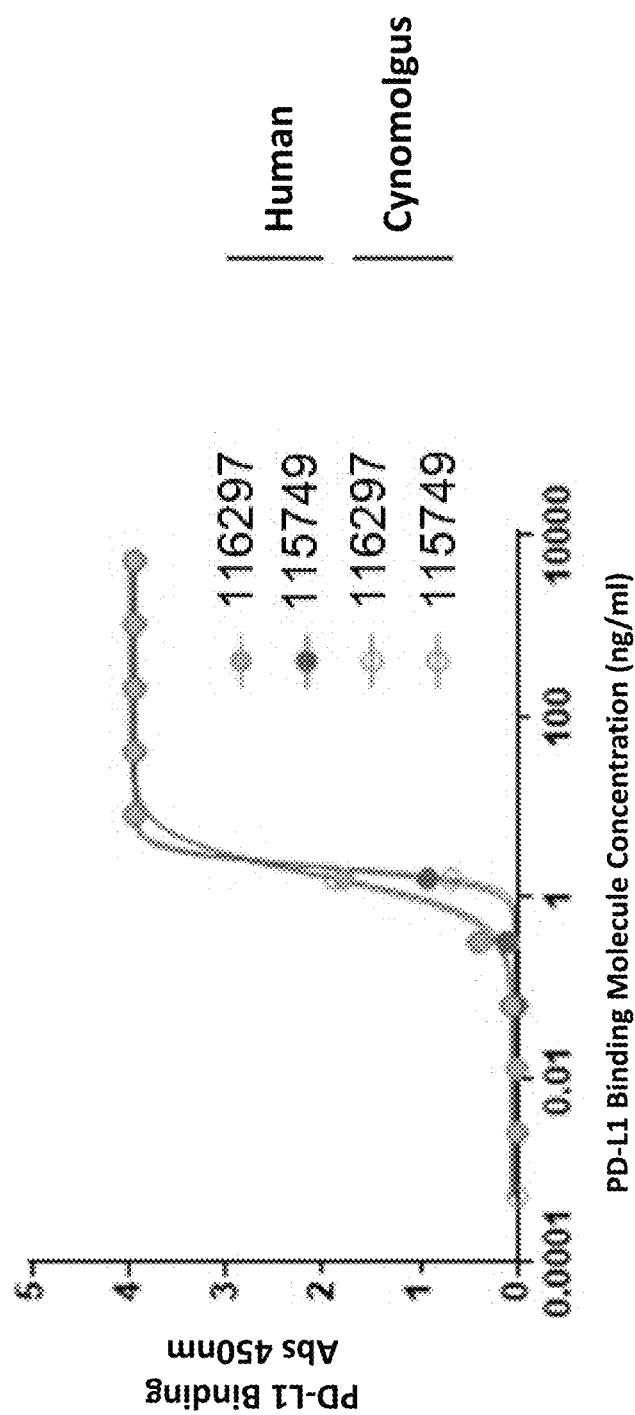

Both PD-L1 binding molecules 115749 (SEQ ID NO:113) and 116297 (SEQ ID NO:128) bound to recombinant human PD-L1 and cynomolgus macaque PD-L1 (Table 7; FIGS. 3, 15, and 34).

TABLE 7

Binding Properties of Exemplary PD-L1 Binding DI-SLT-1A Fusion Proteins to Recombinant PD-L1 Proteins from Human or Cynomolgus Macaque Origins

| DI-SLT-1A fusion protein | recombinant protein | $K_D$ (ng/mL) | Bmax (MFI) |
|---|---|---|---|
| 115749 (SEQ ID NO: 113) | human PD-L1-Fc | 2.10 | 3.95 |
|  | cynomolgus PD-L1-Fc | 2.16 | 3.95 |
| 116297 (SEQ ID NO: 128) | human PD-L1-Fc | 1.75 | 3.98 |
|  | cynomolgus PD-L1-Fc | 1.66 | 3.99 |

The PD-L1 binding molecules 115749 (SEQ ID NO:113), 116188 (SEQ ID NO:126), and 116297 (SEQ ID NO:128)

each bound both human and cynomolgus macaque PD-L1 proteins with similar binding characteristics (FIGS. 3, 13, 15, 17A-17B, and 34). The results shown in Table 7 and FIGS. 3 and 15 demonstrate that both 115749 (SEQ ID NO:113) and 116297 (SEQ ID NO:128) bind human and cynomolgus macaque PD-L1 with similar affinities and Bmax values. Additionally, the results in FIG. 3 show that 116188 (SEQ ID NO:126), a related variant of 116297 (SEQ ID NO:128), demonstrated similar binding characteristics to PD-L1. In another experiment using the same assay, the affinity of 115749 (SEQ ID NO:113) for PD-L1 recombinant proteins was shown to be comparable to the affinity of 115961 (SEQ ID NO:123) to the same PD-L1 recombinant proteins.

Figure 17A:
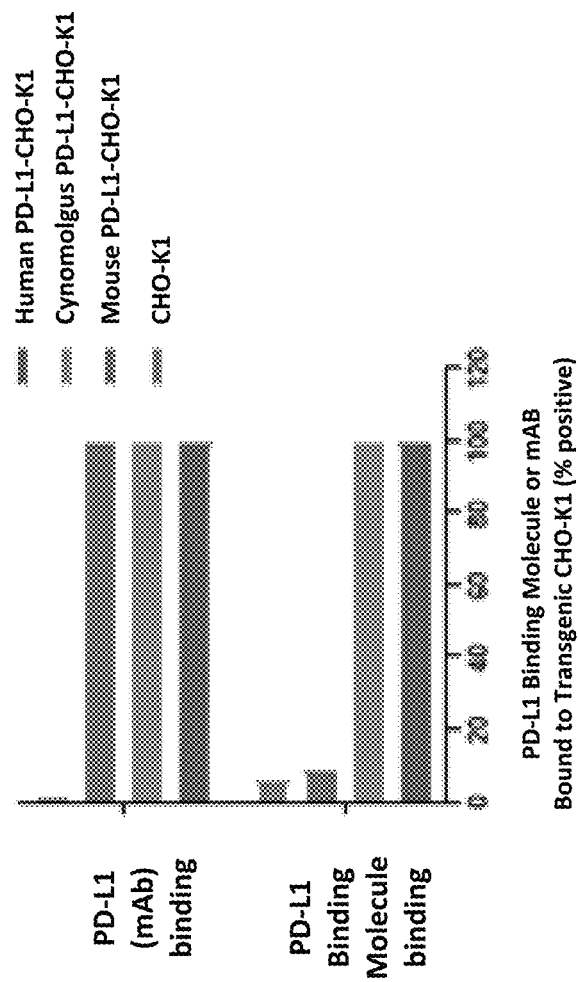
Figure 17B:
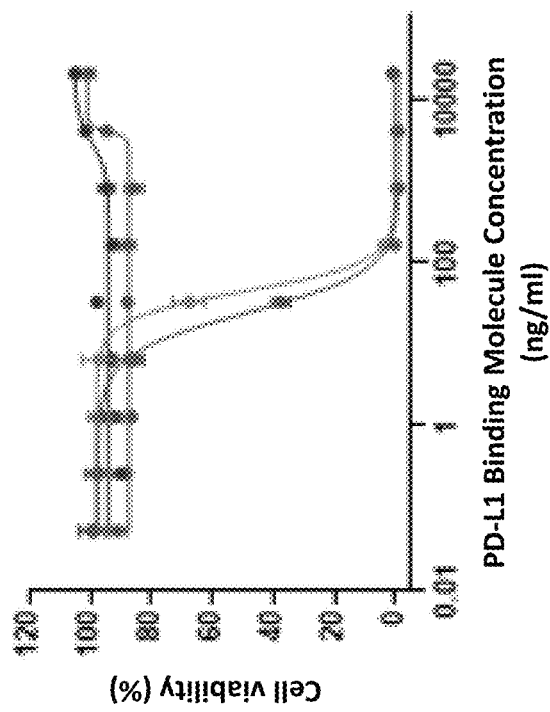

The exemplary PD-L1 binding molecule 116297 (SEQ ID NO:128) bound to recombinant human and cynomolgus protein with similar affinity (FIGS. 3, 13, 15, 17A-17B, and 34); however, 116297 (SEQ ID NO:128) did not bind rodent PD-L1 (FIG. 17A-17B).

Figure 4:
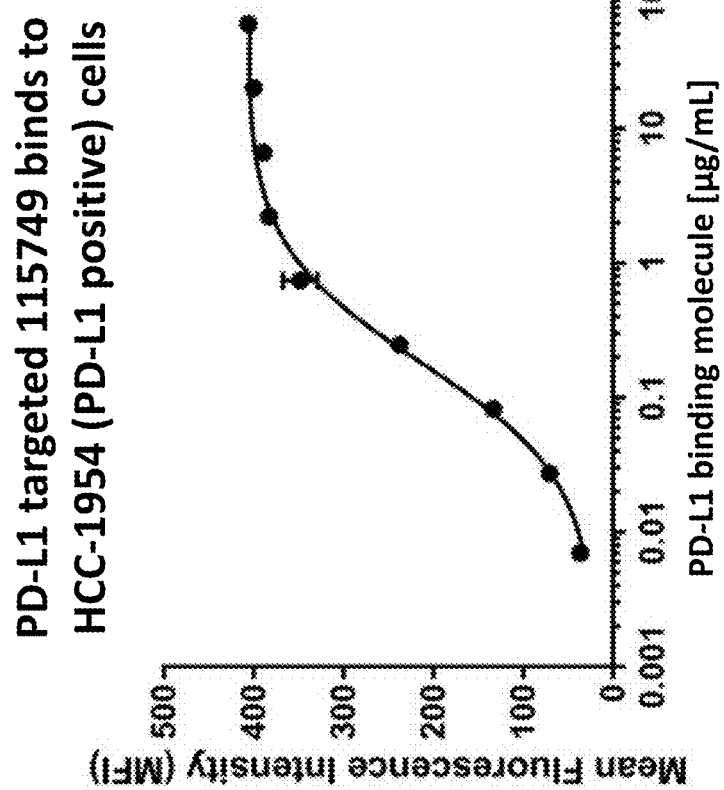
Figure 5:
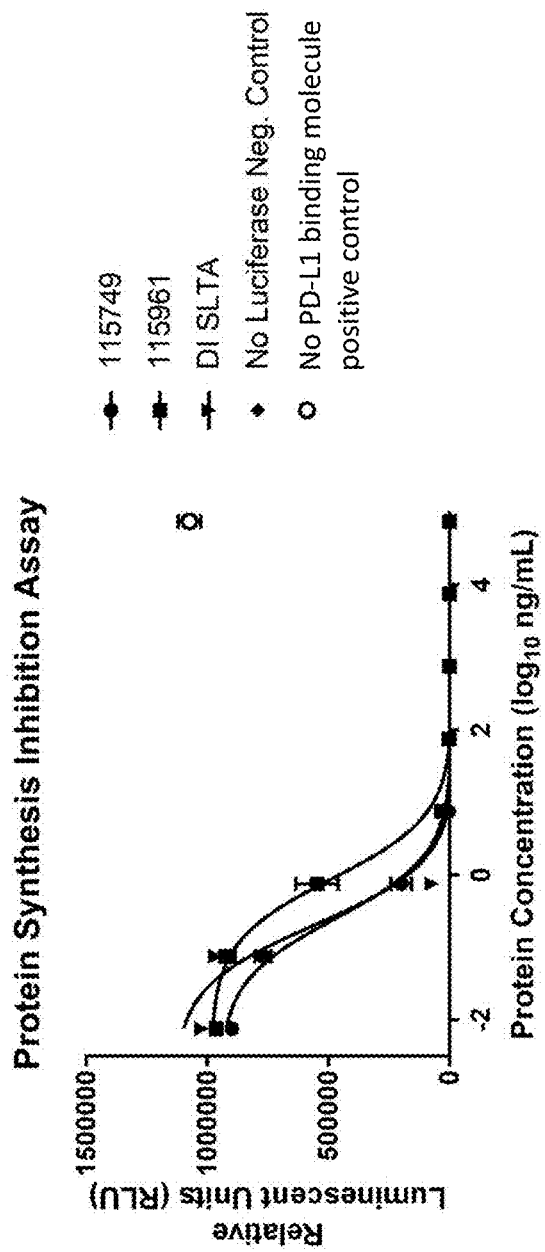

The binding of 115749 (SEQ ID NO:113) to PD-L1 expressing HCC1954 cells was measured by flow cytometry. Cells were treated with IFN-gamma (IFN-γ) for one day prior to the binding assay performed as follows. The fusion protein 115749 (SEQ ID NO:113) was added to the cells and the samples were incubated for one hour on ice. The cells were washed, and DI-SLT-A1 fusion protein was detected with using an anti-DI SLT-A1 mAb conjugated to FITC. FIG. 4 shows results from this assay. The PD-L1 binding molecule 115749 (SEQ ID NO:113) exhibited dose-dependent binding of to the PD-L1 expressing HCC1954 cells (FIG. 4).

Figure 14:
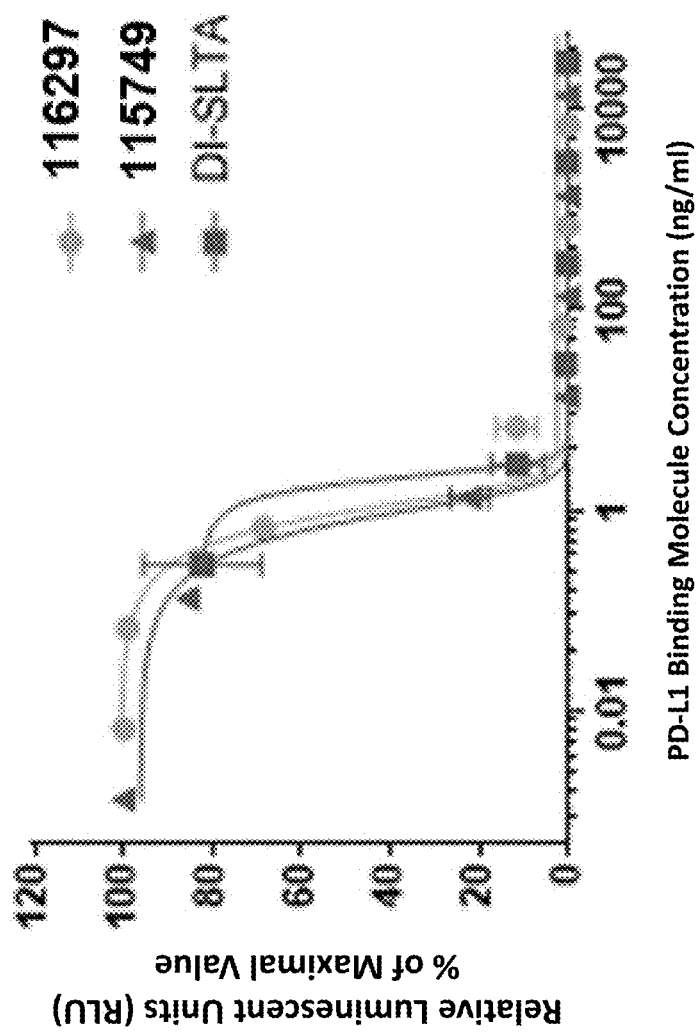

Notably, in a PD-L1 expressing cell binding assay, the binding affinities of 116297, 115749, 115695, and 116555 are comparable (See, e.g., FIG. 15). In a PD-L1 positive cell-kill assay, the $CD_{50}$ values for 116297 and 115765 are comparable (See, e.g., FIG. 14).

II. Determining Toxin Enzymatic Activity and Immunotoxin Cytotoxicity

DI-SLT-A1 fusion proteins comprising exemplary PD-L1 binding regions, were demonstrated to have ribosome inactivation activity similar to the DI SLT-A1 Shiga toxin effector polypeptide alone. The ribosome inhibition assay used a cell-free, in vitro protein translation assay using the TNT® Quick Coupled Transcription/Translation kit (L1170 Promega Madison, WI, U.S.A.). The kit includes Luciferase T7 Control DNA (L4821 Promega Madison, WI, U.S.A.) and TNT® Quick Master Mix. The ribosome activity reaction was prepared according to manufacturer instructions. A series (typically 10-fold) of dilutions were prepared in appropriate buffer and a series of identical TNT reaction mixture components were created for each dilution. The protein samples were combined with each of the TNT reaction mixtures along with the Luciferase T7 Control DNA. The test samples were incubated for 1.5 hours at 30° C. After the incubation, Luciferase Assay Reagent (E1483 Promega, Madison, WI, U.S.A.) was added to all test samples and the amount of luciferase protein translation was measured by luminescence according to the manufacturer instructions. The level of translational inhibition was determined by non-linear regression analysis of log-transformed concentrations of total protein versus relative luminescence units. Using statistical software (GraphPad Prism, San Diego, CA, U.S.A.), the half maximal inhibitory concentration ($IC_{50}$) value was calculated for each sample using the Prism software function of log(inhibitor) vs. response (three parameters) [Y=Bottom+((Top−Bottom)/(1+10^(X−Log $IC_{50}$)))] under the heading dose-response-inhibition. Some results of this ribosome inhibition assay are shown in Table 8, FIG. 5, FIGS. 13-14, and FIG. 33.

TABLE 8

Catalytic Activity of Exemplary, PD-L1-Targeting DI-SLT-1A Fusion Proteins Assayed via Protein Synthesis Inhibition

| DI-SLT-1A fusion protein | $IC_{50}$ (ng/mL) |
|---|---|
| 115749 (SEQ ID NO: 113) | 0.25 |
| 115961 (SEQ ID NO: 123) | 0.88 |
| DI-SLT-1A only | 0.20 |

The exemplary PD-L1 binding molecules 115749 (SEQ ID NO:113) and 115961 (SEQ ID NO:123) exhibited ribosome inhibition activities comparable to a positive "control" molecule, a Shiga toxin effector polypeptide (DI-SLTA) alone, not coupled with any targeting agent or binding region (i.e., a polypeptide comprising SEQ ID NO: 41), although 115961 (SEQ ID NO:123) was slightly less potent (FIG. 5; Table 8). 115749 (SEQ ID NO:113) retained the Shiga toxin function of potent protein synthesis inhibition, such as, e.g. at the level of DI-SLTA alone (i.e., a polypeptide comprising SEQ ID NO: 41) (Table 8; FIG. 5).

FIGS. 13, 14, and 33 also report the results of a ribosome inhibition assay for 116297 (SEQ ID NO:128). The exemplary PD-L1 binding molecule 116297 (SEQ ID NO:128) exhibited a ribosome inhibition activity level (IC50 0.36 ng/mL) comparable to that of 115749 (SEQ ID NO:113) (IC50 0.25 ng/mL) (see Table 8). 116297 (SEQ ID NO:128) exhibited a ribosome inhibitory activity comparable to 115749 (SEQ ID NO:113) and a positive "control" molecule, a Shiga toxin effector polypeptide (DI-SLTA) alone, not coupled with any targeting agent or binding region (i.e., a polypeptide comprising SEQ ID NO: 41) (FIGS. 14 and 33).

DI-SLT-A1 fusion proteins comprising exemplary scFv and other PD-L1 targeted binding domains were tested for specific cytotoxicity towards cells that express PD-L1 on the cell surface. Briefly, cells were plated and then incubated with a dilution series of DI-SLT-A1 fusion protein, incubated for 3 to 5 days and then readout for viability with CELLTITER-GLO® (cell viability assay. Relative Luminescence values (RLU) were measured and normalized to cells only control wells. Viability was plotted as a function of log transformed concentration and the $CD_{50}$ was calculated with non-linear regression (log(inhibitor) vs. response (three parameters)) in GraphPad Prism. When $CD_{50}$ values could not be calculated based on the shape of the curve over the concentrations tested, then a maximum $CD_{50}$ value was noted as being beyond the maximum tested value, e.g., greater than 20,000 ng/mL (">20,000 ng/mL"), for samples which did not kill 50% of the cells at the highest, tested, sample concentration. CHO-K1 cell lines transfected to express human, cynomolgus macaque, or mouse PD-L1 were incubated with 115749 (SEQ ID NO:113) or 115750 (SEQ ID NO:114) (in a dilution series) for 4 days prior to reading the cell viability (CELLTITER-GLO® (cell viability assay), Promega, Madison, WI, U.S.A.). Some results of this cytotoxicity experiment are shown in Table 9 and FIG. 6A-6B.

TABLE 9

Cytotoxicities of Exemplary, PD-L1 Targeting DI-SLT-1A Fusion Proteins to Cells Expressing Human or Cynomolgus Macaque PD-L1 Assayed via an In Vitro Cell Viability Assay

| DI-SLT-1A fusion protein | $CD_{50}$ (ng/mL) | | |
|---|---|---|---|
| | Human PD-L1/ CHO-K1 | Cynomolgus PD-L1/CHO-K1 | Mouse PD-L1/ CHO-K1 |
| 115749 | 48.85 | 7.09 | >20,000 |
| 115750 | 50.78 | 6.74 | >20,000 |

Figure 6A:
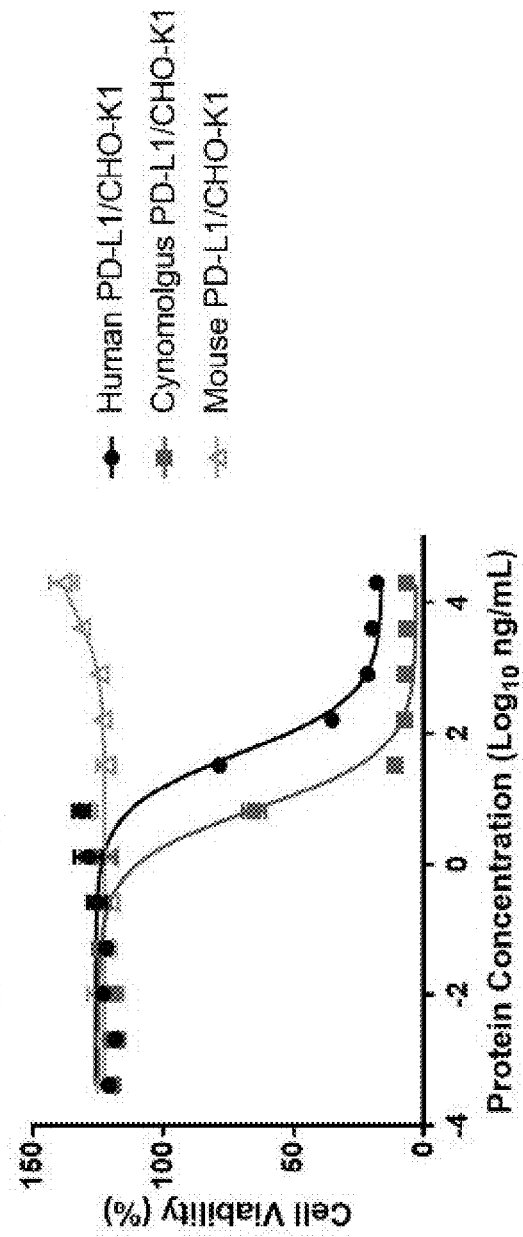
Figure 6B:
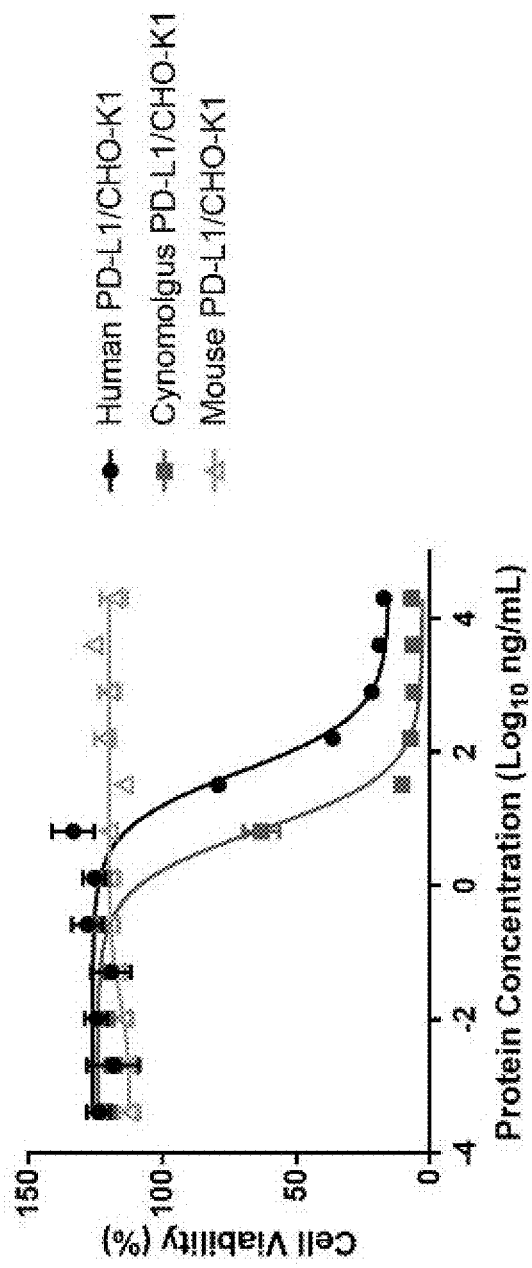

FIG. 6A shows the PD-L1 binding molecule 115749 (SEQ ID NO:113) and FIG. 6B shows the PD-L1 binding molecule 115750 (SEQ ID NO:114) killed cells expressing human or cynomolgus macaque PD-L1 but not murine PD-L1. The results shown in Table 9 and FIG. 6A-6B demonstrated that the specificity of the cytotoxicities of 115749 (SEQ ID NO:113) and 115750 (SEQ ID NO:114) correlate with the presence of PD-L1 from human and cynomolgus macaque, but not from mouse.

Using the in vitro cell viability assay described above, the exemplary PD-L1 binding molecule 116297 (SEQ ID NO:128) killed cells expressing human or cynomolgus PD-L1, but not mouse PD-L1 (FIG. 17A-17B).

Human immortalized cancer cells were incubated with 115749 (SEQ ID NO:113) or 115750 (SEQ ID NO:114) or DI-SLT-1A Shiga toxin effector polypeptide (in a dilution series) for 5 days (media was refreshed once during this time for all samples) prior to reading the cell viability (CELL-TITER-GLO® (cell viability assay), Promega, Madison, WI, U.S.A.) using the assay described above. In a separate flow cytometry experiment, these cell lines were profiled for the PD-L1 expression on the cell surface. Experiments involving these cell lines were run within 1 week of each other. Some results of this cytotoxicity experiment are shown in Table 10 and FIG. 7.

TABLE 10

Cytotoxicities of Exemplary, PD-L1 Targeting DI-SLT-1A Fusion Proteins to PD-L1 Expressing Human Tumor Cells Assayed via an In Vitro Cell Viability Assay

| | $CD_{50}$ (ng/mL) | | | | |
|---|---|---|---|---|---|
| PD-L1 expression | HCC1954 positive | HCC-827 positive | JIMT-1 positive | MDA-MB-231 positive | MDA-MB-468 negative |
| 115749 | 14.26 | 439 | 480 | 70.04 | >20,000 |
| 115750 | 8.27 | 371 | 351 | 44.08 | >20,000 |
| DI-SLT-1A only | 4,783 | >20,000 | 19,049 | 6,360 | DNT |

* "DNT" denotes did not test.

Figure 7:
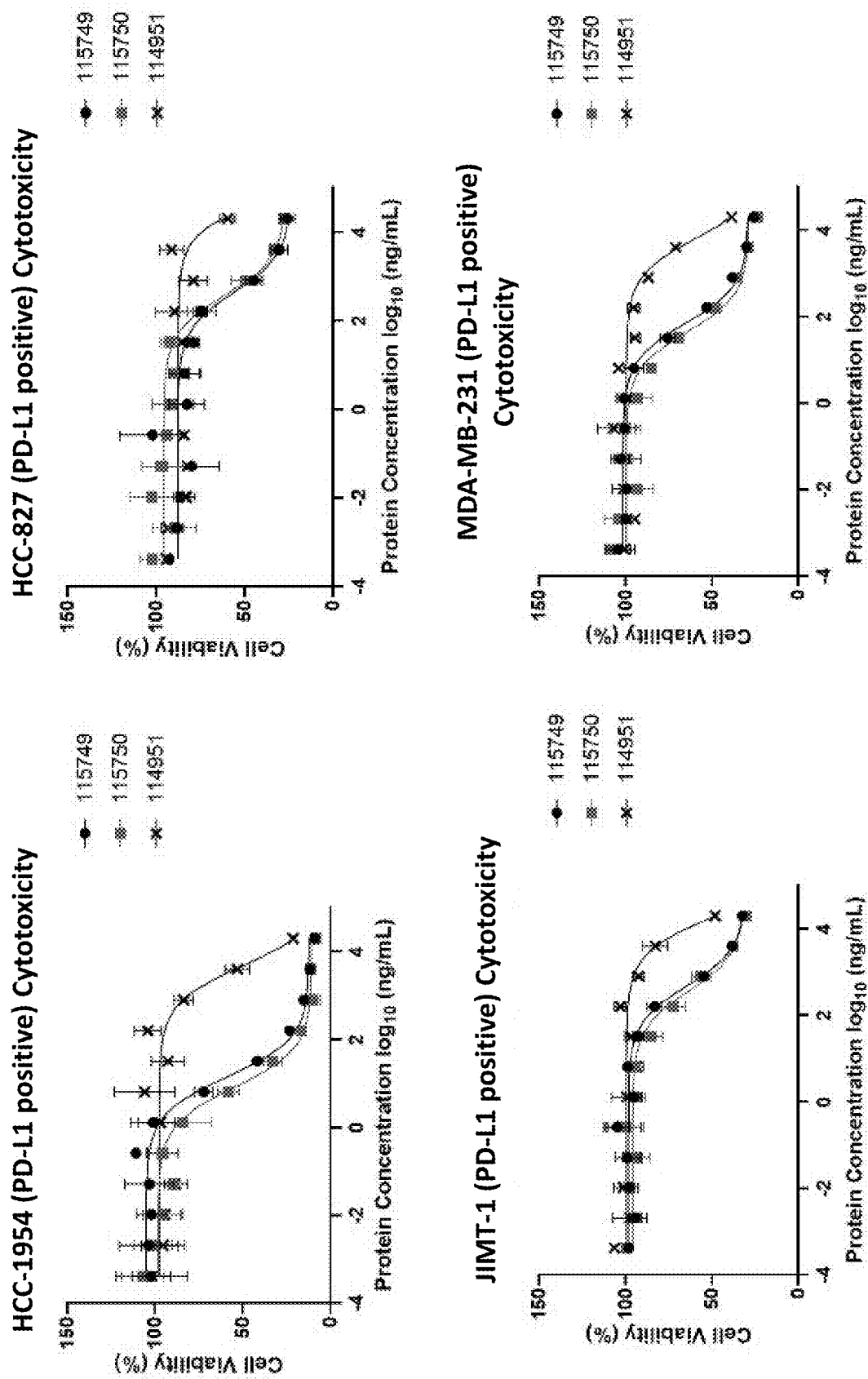
Figure 7:
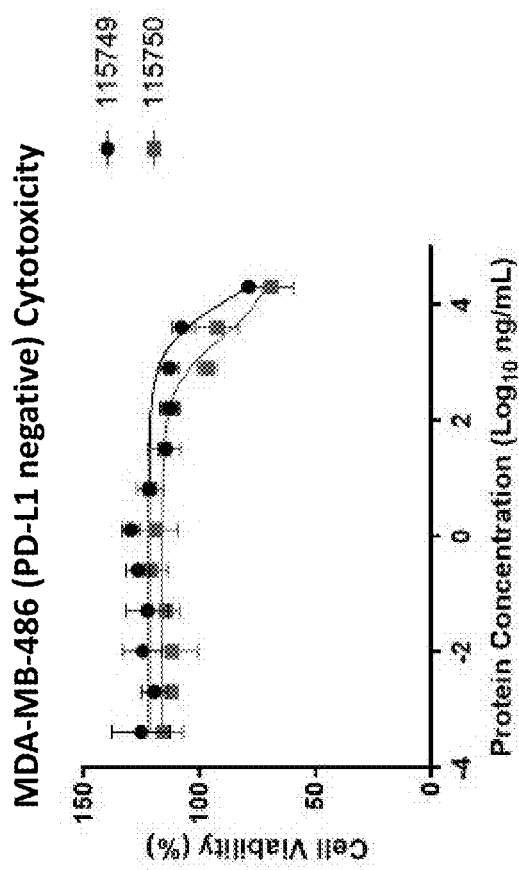
Figure 16:
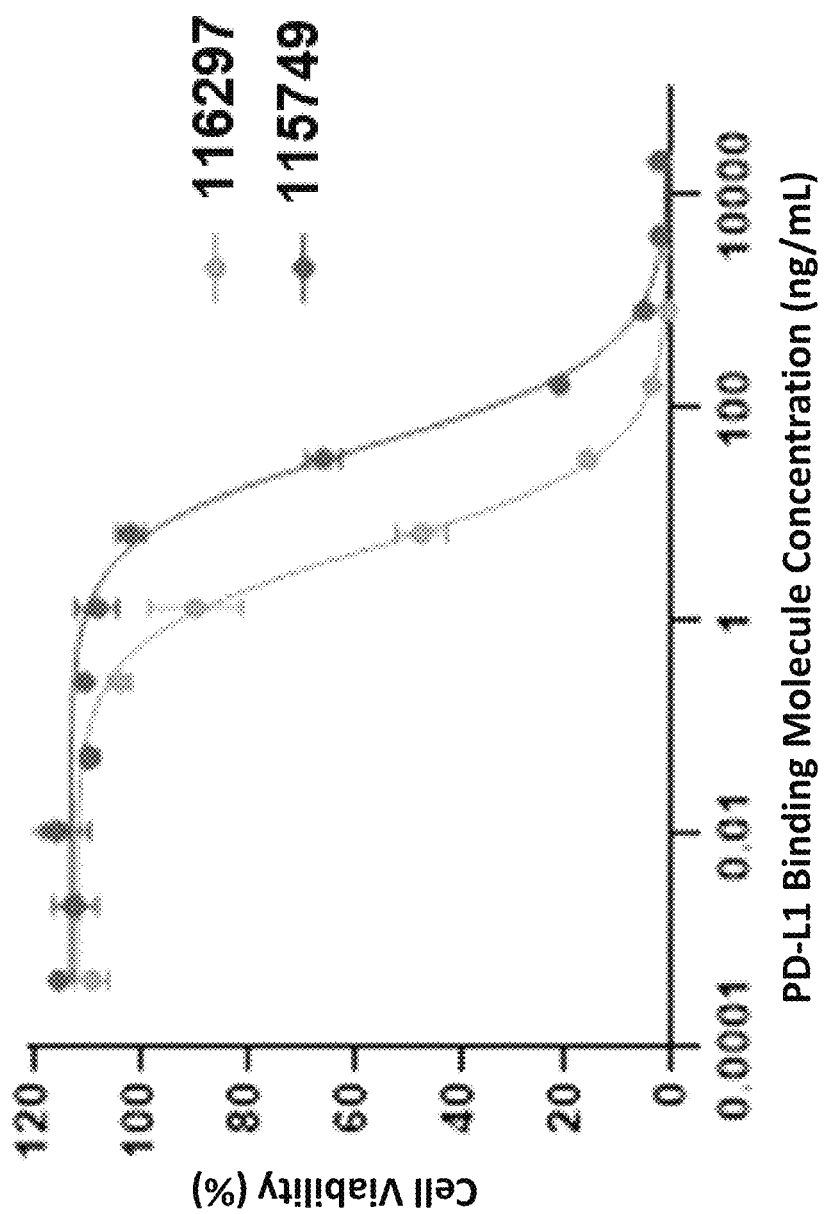

The results shown in Table 10 and FIG. 7 demonstrate that 115749 (SEQ ID NO:113) is cytotoxic over a range of concentrations to human cancer cell lines expressing PD-L1, whereas the untargeted DI SLT-1A alone ("DI-SLT-1A only", i.e., a polypeptide comprising SEQ ID NO: 41) exhibited relatively low cytotoxicity at the concentrations tested (DI SLT-1A was cytotoxic only at high concentrations and only for certain cell lines). FIG. 16 shows that 116297 (SEQ ID NO:128) can exhibit greater cytotoxicity than 115749 (SEQ ID NO:113).

Additional cell viability experiments were conducted essentially as described above for related DI-SLT-A1 fusion proteins. Some results of these experiments for representative PD-L1 positive cell lines, HCC-1954 and MDA-MB-231, are shown in Table 11 and FIG. 8. DI-SLT-A1 fusion proteins tested in these cytotoxicity experiments have the same or similar CDR sequences in the variable regions of their immunoglobulin-type binding domains.

TABLE 11

Cytotoxicities of Exemplary, PD-L1 Targeting DI-SLT-1A Fusion Proteins to PD-L1 Expressing Human Tumor Cells Assayed via an In Vitro Cell Viability Assay

| DI-SLT-1A fusion protein | $CD_{50}$ (ng/mL) | |
|---|---|---|
| | HCC1954 | MDA-MB-231 |
| 115744 (SEQ ID NO: 108) | 24 | 453 |
| 115745 (SEQ ID NO: 109) | 1 | 7.85 |
| 115747 (SEQ ID NO: 111) | 376 | 287 |
| 115748 (SEQ ID NO: 112) | 254 | 708 |
| 115749 (SEQ ID NO: 113) | 9 | 34 |
| 115750 (SEQ ID NO: 114) | 13 | 47 |
| 115751 (SEQ ID NO: 115) | 14.36 | 177.3 |
| 115752 (SEQ ID NO: 116) | 26.54 | 99.43 |
| 115753 (SEQ ID NO: 117) | 20.14 | 103.2 |
| 115754 (SEQ ID NO: 118) | 12.25 | 54.03 |
| 115755 (SEQ ID NO: 119) | 42.24 | 138.3 |
| 115756 (SEQ ID NO: 120) | 19.81 | 60.76 |
| 115757 (SEQ ID NO: 121) | 18.61 | 68.31 |
| 115758 (SEQ ID NO: 122) | 18.9 | 59.64 |

Figure 8:
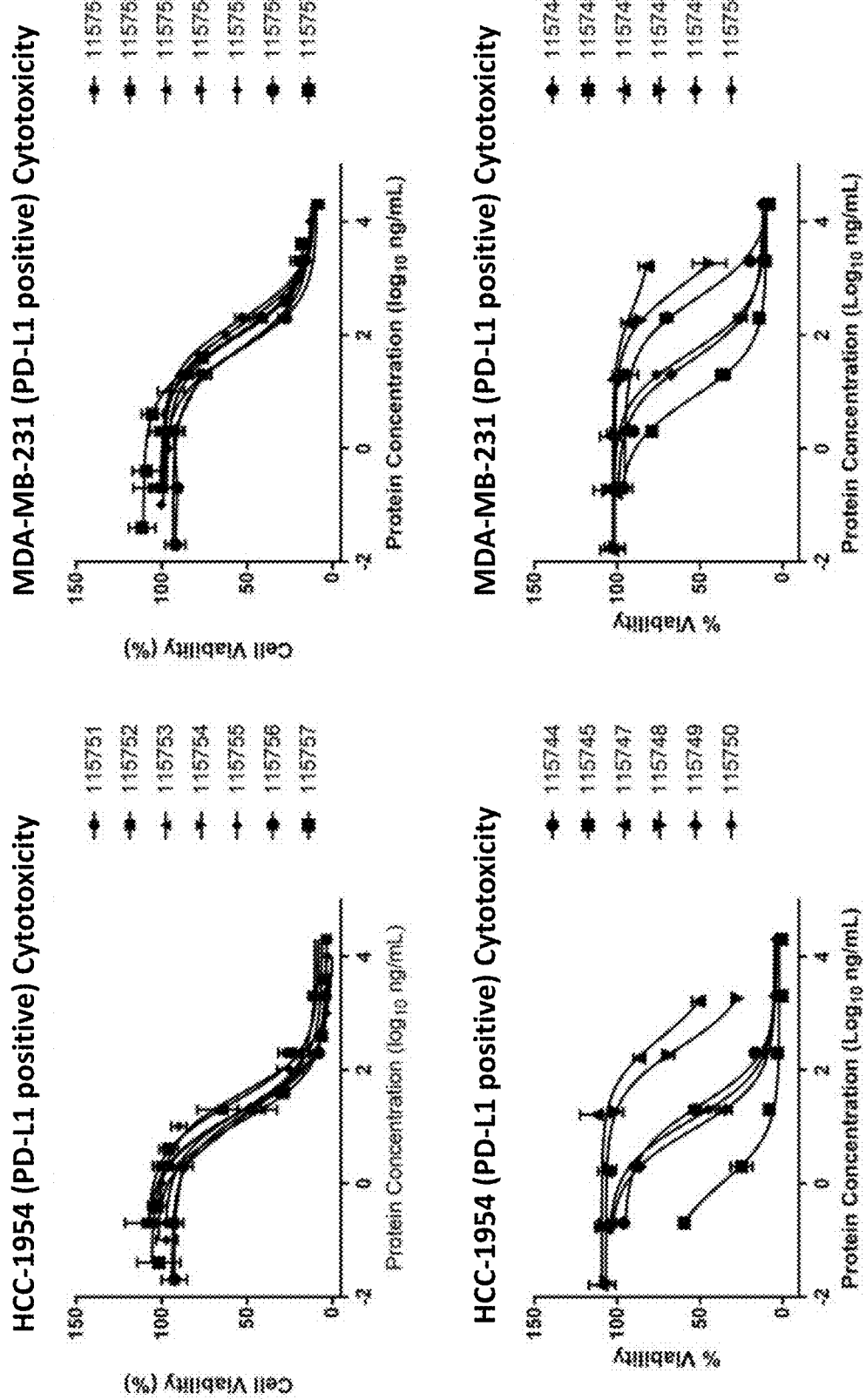

The PD-L1 binding molecules 115744 (SEQ ID NO:108), 115745 (SEQ ID NO:109), 115747 (SEQ ID NO:111), 115748 (SEQ ID NO:112), 115749 (SEQ ID NO:113), 115750 (SEQ ID NO:114), 115751 (SEQ ID NO:115), 115752 (SEQ ID NO:116), 115753 (SEQ ID NO:117), 115754 (SEQ ID NO:118), 115755 (SEQ ID NO:119), 115756 (SEQ ID NO:120), and 115757 (SEQ ID NO:121) exhibited cytotoxicity to two, different PD-L1-expressing cell-types: HCC-1954 and MDA-MB-231 cells (Table 11; FIG. 8).

Additional cell viability experiments were conducted in a similar format for related DI-SLT-A1 fusion proteins. DI-SLT-A1 fusion proteins tested in these experiments have the same or similar CDR sequences in the variable regions of their immunoglobulin-type binding domains. Some results of these experiments for representative PD-L1 positive cell lines, HCC-1954 and MDA-MB-231, are shown in Table 12 and FIG. 9. As used in Table 12, "DI-SLTA-1A only" refers to a polypeptide comprising SEQ ID NO: 41.

TABLE 12

Cytotoxic Activities of Exemplary PD-L1 Binding DI-SLT-A1 Fusion Proteins to PD-L1 Positive or Negative Human Tumor Cells

| | $CD_{50}$ (ng/mL) | | | | | |
|---|---|---|---|---|---|---|
| Cell Line | HCC1954 | HCC-827 | JIMT-1 | MDA-MB-231 | MCF-7 | SKBR3 |
| PD-L1 | positive | positive | positive | positive | low/negative | negative |
| 116297 | 5.9 | 57.4 | 25.2 | 6.9 | >20,000 | >20,000 |

TABLE 12-continued

Cytotoxic Activities of Exemplary PD-L1 Binding DI-SLT-A1 Fusion Proteins to PD-L1 Positive or Negative Human Tumor Cells

| | $CD_{50}$ (ng/mL) | | | | | |
|---|---|---|---|---|---|---|
| Cell Line | HCC1954 | HCC-827 | JIMT-1 | MDA-MB-231 | MCF-7 | SKBR3 |
| 116299 | 8.2 | 31.0 | 36.2 | 9.8 | >20,000 | >20,000 |
| DI-SLT-1A only | >20,000 | 8,505 | >20,000 | 1,208 | >20,000 | >20,000 |

The PD-L1 binding molecules 116297 (SEQ ID NO:128) and 116299 (SEQ ID NO:129) exhibited cytotoxicity to four, different PD-L1-expressing cell-types: HCC 1954, JIMT-1, HCC 827, and MDA-MB-231 (FIG. 9; Table 12). The PD-L1 binding molecules characterized in Tables 10-12 and FIGS. 7-9 exhibited $CD_{50}$ values of around 1 to 480 ng/mL in the absence of cytotoxic T-cells. Without being bound by theory, these results suggest that certain PD-L1 binding molecules are cytotoxic in vivo to "cold" tumor cells or to tumor cells in tumors characterized as "non-inflamed" or excluded from immunosurveillance, e.g. "immune-excluded tumors". For example, some PD-L1 binding molecules may be cytotoxic to tumor cells in vivo in the absence of tumor infiltrating lymphocytes and regardless of the immune modulatory status of the tumor microenvironment. Without being bound by theory, some PD-L1 binding molecules may be cytotoxic to tumor cells in vivo regardless of the mutational burden of the tumor cell. Thus, the targeted cell-killing mechanism(s) of action allow for targeted tumor cell killing in vivo regardless of tumor immune status (e.g. immune-excluded, non-inflamed, and/or "cold").

Human immortalized cancer cells were incubated with 116297 (SEQ ID NO:128), 115749 (SEQ ID NO:113), 115765 (SEQ ID NO: 161), or 114895 (SEQ ID NO: 163) for 5 days (media was refreshed once during this time for all samples) prior to reading the cell viability (CELLTITER-GLO® (cell viability assay), Promega, Madison, WI, U.S.A.) using the assay described above. Results of this cytotoxicity experiment are shown in FIG. 43A-43B. These results demonstrate that 116297 (SEQ ID NO:128) is cytotoxic over a range of concentrations to human cancer cell lines (HCC1954 (FIG. 43A) and MDA-MB-231 (FIG. 43B)) expressing PD-L1, and can exhibit greater cytotoxicity than 115749 (SEQ ID NO:113), 115765 (SEQ ID NO:161), and 114895 (SEQ ID NO: 163).

Figure 18A:
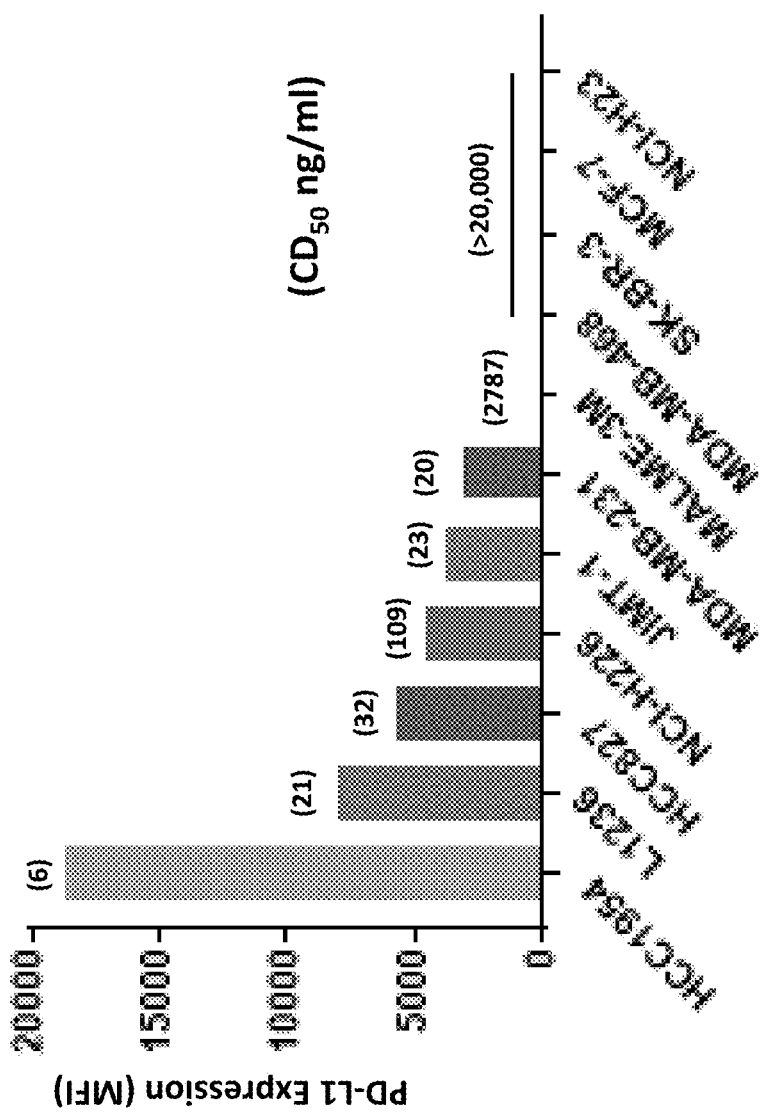
Figure 18B:
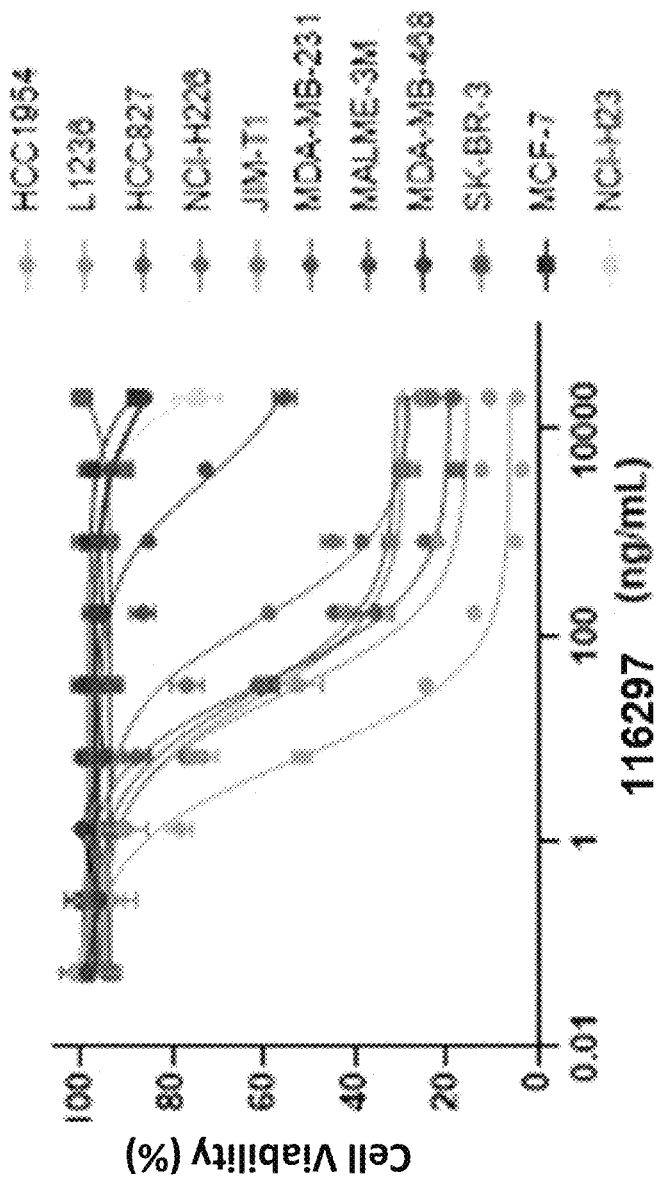

FIG. 18 reports cell-surface PD-L1 expression levels (FIG. 18A) and $CD_{50}$ values (FIG. 18B) for 116297 (SEQ ID NO:128) for a variety of clinically relevant tumor cell lines. PD-L1 is expressed on the cell surface of various human tumor cells, including cells from cell lines of human lung, skin, and breast cancer origin. 116297 (SEQ ID NO:128) exhibited broad anti-tumor cytotoxicity. 116297 (SEQ ID NO:128) specifically and potently kills target cells expressing PD-L1.

Figure 19:
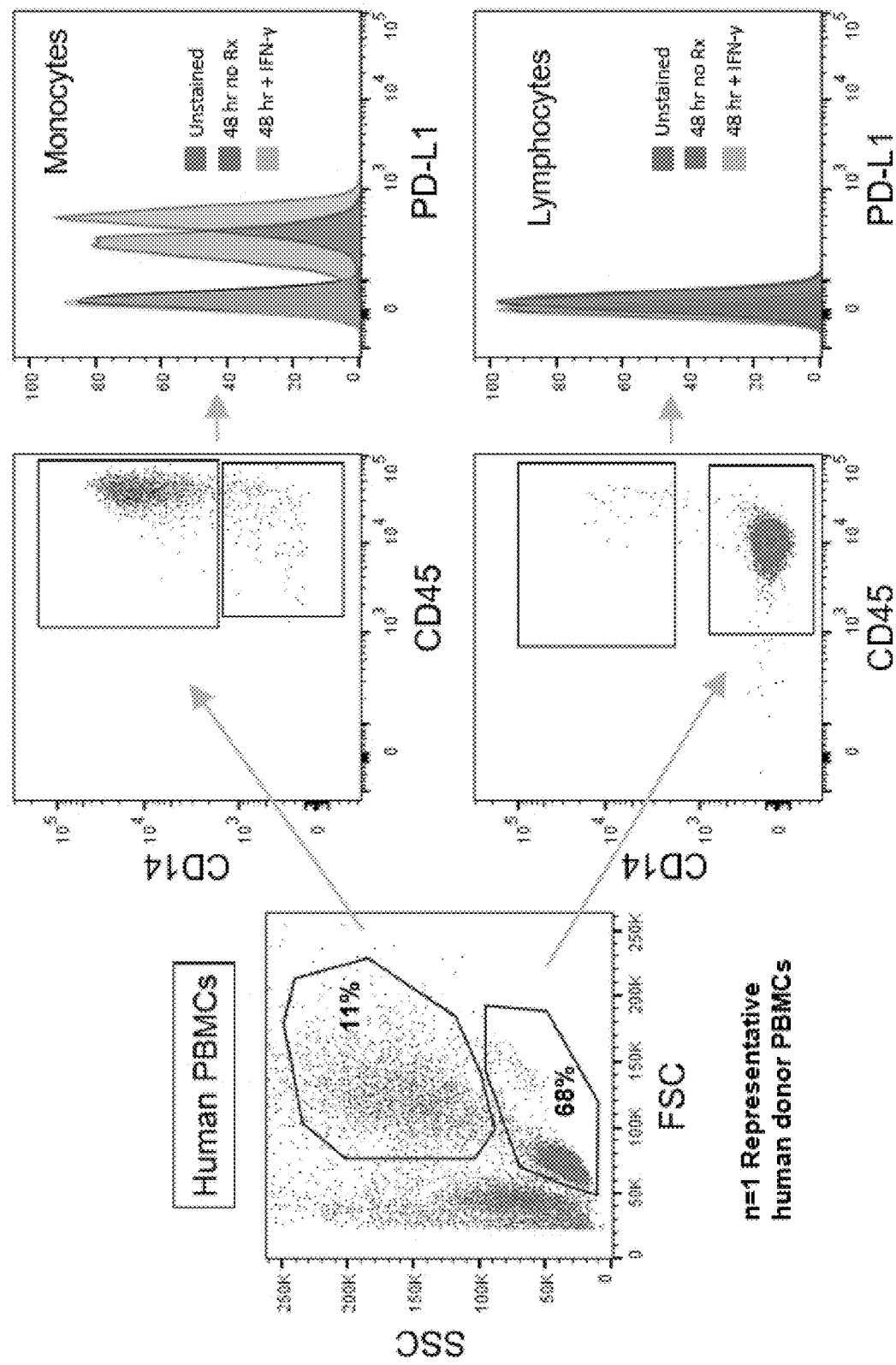
Figures 21A, 21B:
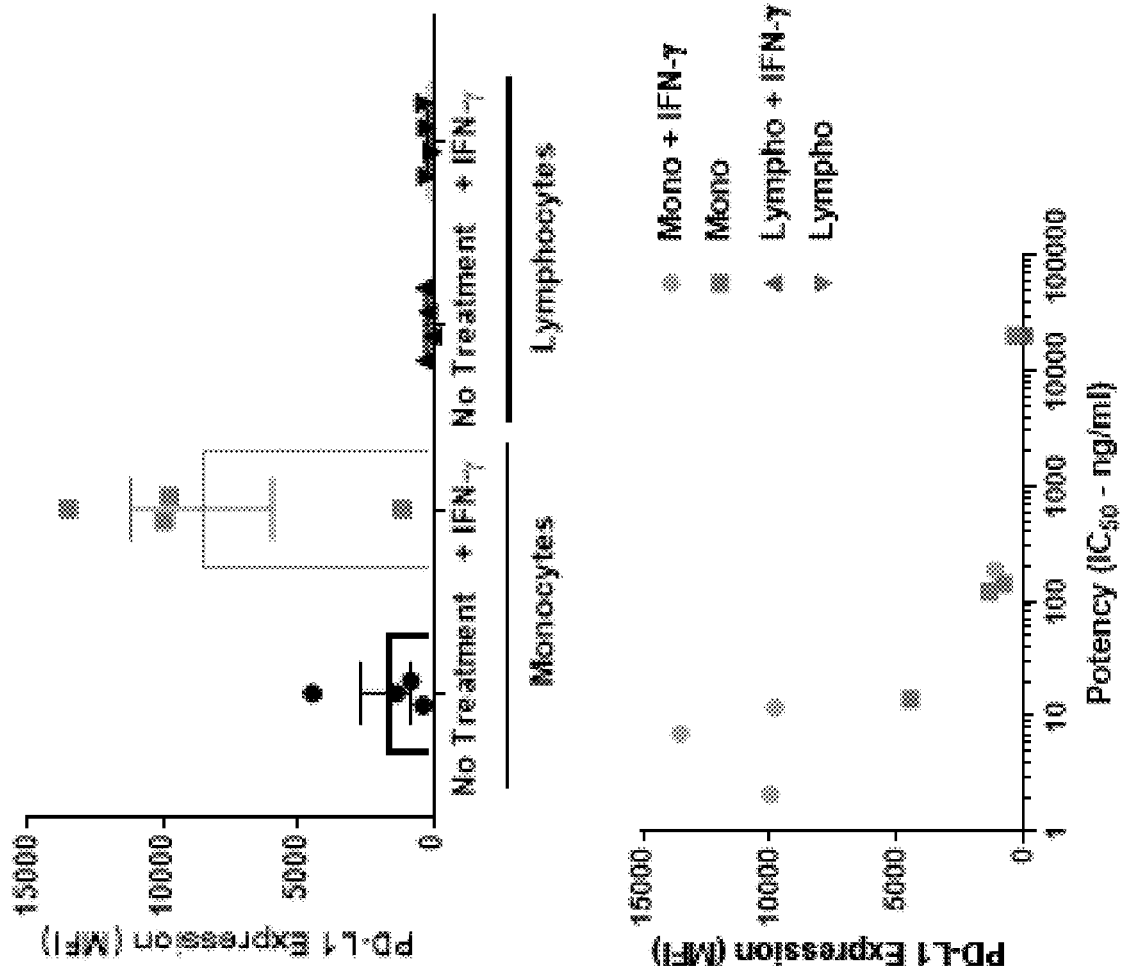

FIGS. 19, 20A-20B, and 21A-21B show that PD-L1 expression levels on subsets of immune cells from PBMC samples are related to the cytotoxic potency of 116297 (SEQ ID NO:128) treatment. FIG. 19 demonstrates that human donor PBMC samples include monocytes and lymphocytes, wherein the monocytes can be induced by interferon gamma treatment to elevate their expression of PD-L1. FIG. 20A demonstrates that 116297 (SEQ ID NO:128) cytotoxicity against PBMCs is limited to IFN-γ treated monocytes expressing higher levels of PD-L1. FIG. 20A-20B, and FIG. 21A-21B show 116297 (SEQ ID NO:128) can exhibit selective cytotoxicity to "PD-L1 high-expressing" monocytes without cytotoxicity to PD-L1 negative lymphocytes. FIG. 21B shows plots of the PD-L1 expression level versus the CD50 values of 116297 (SEQ ID NO:128) under the conditions tested. FIG. 21A-21B demonstrates that there is a general correlation between higher PD-L1 expression and greater cytotoxic potency (i.e. lower $CD_{50}$ values) of 116297 (SEQ ID NO:128). PD-L1 expression on monocytes is enhanced by the inflammatory cytokine IFN-γ. FIG. 20A-20B shows 116297 (SEQ ID NO:128) exhibits cytotoxicity to PD-L1 positive human immune cells ex vivo. Direct killing of immune cells by 116297 (SEQ ID NO:128) requires PD-L1 expression. 116297 (SEQ ID NO:128) does not target bulk lymphocyte populations, which do not express PD-L1 in the presence or absence of IFN-γ. 116297 (SEQ ID NO:128) is designed to deplete both tumor cells (TC) and immune cells (IC) expressing PD-L1 in the tumor environment. IFN-γ induction of PD-L1 expression by monocytes ex vivo is consistent with adaptive PD-L1 expression on ICs in tumors (see e.g. Kowanetz M et al., *Proc Natl Acad Sci U.S.A* 115: E10119-E10126 (2018)). Other PD-L1 targeted agents have demonstrated activity in patients with PD-L1 positivity on tumor cells or immune cells (Kowanetz M et al., *Proc Natl Acad Sci U.S.A* 115: E10119-E10126 (2018); Tang F, Zheng P, *Cell Biosci* 8: 34 (2018)).

III. Testing CD8+ T-Cell Epitope Delivery and Induction of Immune Responses

Exemplary molecules were tested for functional presentation of an antigen on the surface of target cells. In this Example, a viral CD8+ T-cell epitope-peptide which is known to be immunogenic in humans was selected for fusing to DI-SLT-A1 fusion proteins. The CD8+ T-cell epitope-peptide NLVPMVATV (SEQ ID NO:78) used in this Example was chosen based on this peptide's ability to bind to human MHC class I molecules and thus provoke human, CTL-mediated immune response(s). This viral epitope-peptide was fused to PD-L1 targeting proteins comprising Shiga toxin effector polypeptides that have the intrinsic ability to intracellularly route to the cytosol via retrograde transport via the endoplasmic reticulum (see e.g. WO 2016/196344 and WO 2018/140427).

To test the functional presentation of the immunogenic, viral epitope-peptide, a co-incubation assay was utilized. Target cancer cell line MDA-MB-231(NR) (MDA-MB-231 cells, which express PD-L1 and HLA-A02 and were transfected with an INCUCYTE® NucLight Red Lentivirus reagent (Essen Bioscience, Ann Arbor, MI, U.S.A.) for fluorescent quantification) were treated with exemplary DI-SLT-A1 fusion proteins or related control DI-SLT-A1 fusion proteins that do not have the immunogenic viral peptide and then exposed to lymphocytes enriched for NLVPMVATV (SEQ ID NO:78) peptide specific CTLs (enriched from HLA-A02 positive, CMV seropositive donor peripheral blood mononuclear cells (PBMCs) cultured in standard conditions). The lymphocytes enriched for NLVPMVATV (SEQ ID NO:78) peptide specific CTLs are referred to hereafter as CMV-CTLs.

Stimulation of the CMV-CTL signaling was measured by IFN-γ levels in the supernatant (ELISA) and specific target cell lysis directed by the engaged CMV-CTLs was measured by target cell viability (both kinetically by fluorescence in an INCUCYTE® S3 Live-Cell Analysis System (Essen Bioscience, Ann Arbor, MI, U.S.A.) reading and with endpoint CELLTITER-GLO® (cell viability assay). Briefly, PD-L1 positive cell line MDA-MB-231(NR) was incubated for up to 24 hours with either phosphate buffered saline (PBS) alone ("buffer only") or a DI-SLT-A1 fusion protein. After incubation, cells were washed and media containing CMV-CTLs were co-incubated with target cells. After 24 to 48 hours, supernatants were harvested and IFN-γ concentrations were measured by a cytokine-specific IFN-γ ELISA Kit (Biolegend, Inc., San Diego, CA, U.S.A.), according to the manufacturer's instructions. In some experiments, after harvesting of supernatants, adherent target cells were washed to remove PBMCs and cell viability was assessed by CELLTITER-GLO® (cell viability assay) Luminescent Cell Viability Assay (G7573, Promega Corp., Madison, WI, U.S.A.) according to the manufacturer's instructions and measured in RLU.

Figure 10A:
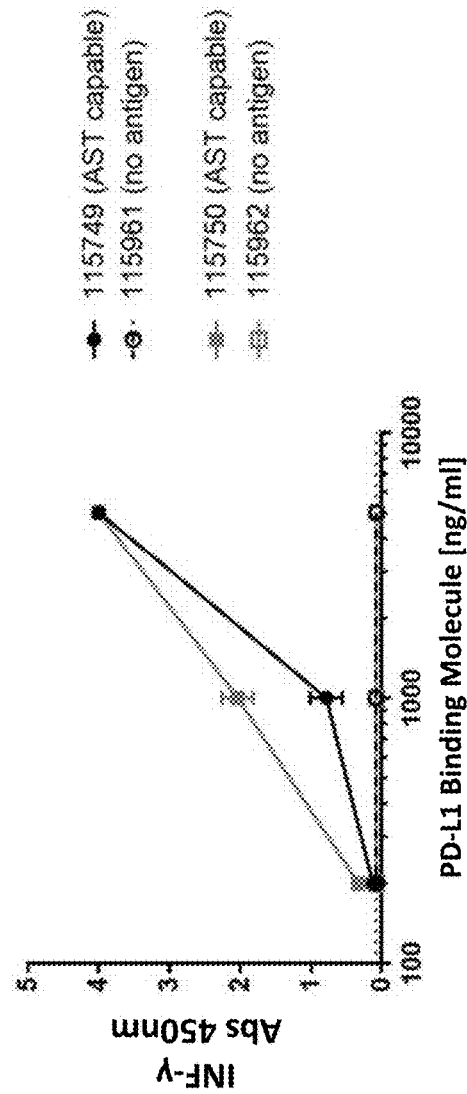

MDA-MB-231(NR) target cells (30,000 cells per well were plated in the presence of IFN-γ 24 hours prior to assay) were incubated for 24 hours with matched pairs of DI-SLT-A1 fusion proteins having either (1) a heterologous, CD8+ T-cell epitope cargo ("antigen delivering") (e.g. 115749 (SEQ ID NO:113)) or (2) lacking a viral antigen cargo (referred to herein as "no antigen" or "control binding molecule") (e.g. 115961 (SEQ ID NO:123), which is closely related to 115749 (SEQ ID NO:113)). In addition to the matched pair of 115749 (SEQ ID NO:113) with viral antigen cargo and related 115961 (SEQ ID NO:123) without viral antigen cargo, another matched pair tested was DI-SLT-A1 fusion protein 115750 (SEQ ID NO:114) with viral antigen cargo and the related DI-SLT-A1 fusion protein 115962 (SEQ ID NO:124), which lacks any viral antigen cargo. Results are shown in FIG. 10A.

Cells were washed and then CMV-CTLs were added at a ratio of 1:1 CMV-CTLs to target cells. At 48 hours, supernatants were removed for IFN-γ secretion and media replaced. The viability of the treated cells as compared to untreated controls was monitored over time, and the viability after 80 hours is shown. Some results of this immunogenicity experiment are shown in Table 13, FIGS. 10A and 10B, and FIG. 24B.

TABLE 13

Functional Response by CMV-CTLs to Target Cell Treatment with DI-SLT-1A Fusion Proteins Comprising a Viral Antigen Cargo

| | Endpoint at 5,000 µg/mL | | Change calculated relative to "no antigen" control binding molecule | |
| --- | --- | --- | --- | --- |
| | IFN-γ secretion (Abs 450 nm, max 4.0) | Cell Viability (% of T0 control) | Fold change IFN-γ increase | Fold change cell kill increase |
| No fusion protein | | 167% | N/A | N/A |

TABLE 13-continued

Functional Response by CMV-CTLs to Target Cell Treatment with DI-SLT-1A Fusion Proteins Comprising a Viral Antigen Cargo

| | Endpoint at 5,000 µg/mL | | Change calculated relative to "no antigen" control binding molecule | |
| --- | --- | --- | --- | --- |
| | IFN-γ secretion (Abs 450 nm, max 4.0) | Cell Viability (% of T0 control) | Fold change IFN-γ increase | Fold change cell kill increase |
| 115749 | 4.00 | 45.8% | 50 | 100 |
| 115961 (no antigen) | 0.08 | 144% | N/A | N/A |
| 115750 | 4.00 | 42.0% | 50 | 100 |
| 115962 (no antigen) | 0.08 | 142% | N/A | N/A |

Figure 10B:
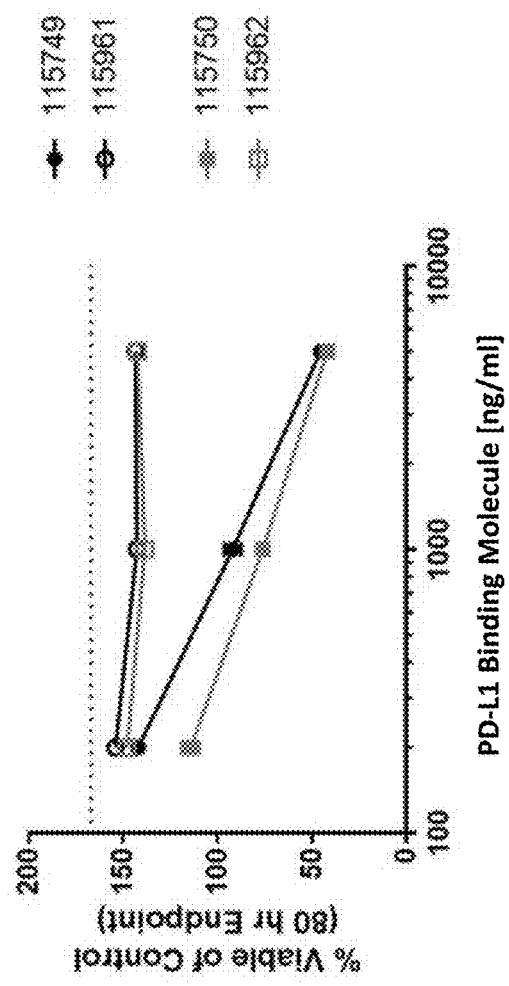

The data shown in Table 13 and FIGS. 10A and 10B demonstrate that the antigen cargo carrying DI-SLT-A1 fusion proteins 115749 (SEQ ID NO:113) and 115750 (SEQ ID NO:114) were able to stimulate the CMV-CTL cells to drive cytokine (IFN-γ) secretion and target cell killing, and that this property was not present in the control DI-SLT-A1 fusion proteins, 115961 (SEQ ID NO:123) and 115962 (SEQ ID NO:124), all of which do not comprise any viral antigen cargo.

Using a similar immunogenicity assay, the induction of IFN-γ secretion was measured after administration of additional pairs of DI-SLT-A1 fusion proteins, one comprising a fused viral antigen and the other a control DI-SLT-A1 fusion protein lacking any viral antigen cargo. MDA-MB-231(NR) target cells (10,000 cells per well were plated in the presence of IFN-γ 24 hours prior to assay) were incubated for 24 hours with matched pairs of DI-SLT-A1 fusion proteins with and without antigen delivering capability, e.g. antigen delivering 115749 (SEQ ID NO:113) paired with related DI-SLT-A1 fusion protein 115961 (SEQ ID NO:123) without viral antigen; and antigen delivering 116297 (SEQ ID NO:128) or 116299 (SEQ ID NO:129) paired with related DI-SLT-A1 fusion protein 116187 (SEQ ID NO:125) without antigen cargo. Cells were washed and then CMV-CTLs were added at a ratio of 1:1 CMV-CTLs to target cells. At 40 hours, 35% of the supernatants were removed for IFN-γ secretion, and the media was replaced. The viability of the treated cells as compared to untreated controls was monitored over time. Some results of this immunogenicity experiment are shown in Table 14 and FIG. 11.

TABLE 14

Functional Response by CMV-CTLs to Target Cell Treatment with DI-SLT-1A Fusion Proteins Comprising an Antigen Cargo

| | IFN-γ secretion (Abs 450 nm, max 4.0; 35% supernatant) |
| --- | --- |
| 115749 (SEQ ID NO: 113) | 2.60 |
| 115961 (SEQ ID NO: 123) (no antigen) | 0.15 |
| 116297 (SEQ ID NO: 128) | 2.90 |
| 116299 (SEQ ID NO: 129) | 2.59 |
| 116187 (SEQ ID NO: 125) (no antigen) | 0.20 |
| DI-SLT-1A only | 0.08 |

Figure 11:
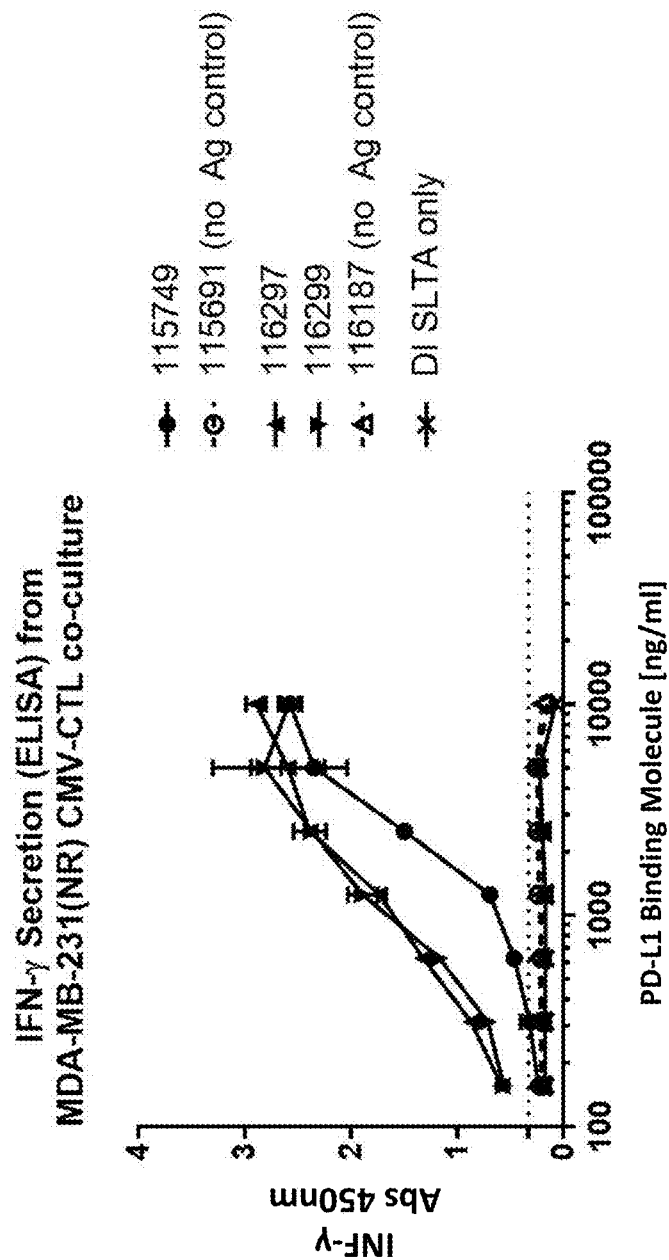

The data in Table 14 and FIG. 11 demonstrate that the DI-SLT-A1 fusion proteins 115749 (SEQ ID NO:113), 116297 (SEQ ID NO:128) and 116299 (SEQ ID NO:129) are able to stimulate the CMV-CTL cells to drive cytokine (IFN-γ) secretion, and that this function is absent in the control DI-SLT-A1 fusion proteins, 115961 (SEQ ID NO:123) and 116187 (SEQ ID NO:125), which do not contain the viral antigen. As used in Table 14, the term "DI-SLT-1A only" refers to a polypeptide comprising SEQ ID NO: 41.

In the co-culture experiments, the CMV seropositive donor PBMCs in the presence of PD-L1 expressing tumor cells exposed to PD-L1 binding molecule can expand a CTL population like the CTL memory expansion that occurs during a natural infection and/or made to resemble endogenous memory T cells.

A CTL-based cytotoxicity assay was used to assess the consequences of CD8+ T-cell epitope presentation. The assay involves tissue-cultured target cells and T-cells. Target cells were intoxicated with exemplary PD-L1 binding molecules by incubating the cells (typically for 4 hours or 16 hours or more) in standard conditions, including at 37° C. and an atmosphere with 5% carbon dioxide, to allow for intoxication by the PD-L1-targeting. After incubation, the target cells were washed. Next, CTLs were added to the treated target cells and incubated to allow for the CTLs to recognize and bind any target cells displaying CD8+ T-cell epitope-peptide/MHC class I complexes (pMHC Is). Then certain functional consequences of pMHC I recognition were investigated using standard methods known to the skilled worker, including epitope-presenting target cell killing by CTL-mediated cytolysis, and the release of cytokines, such as IFN-γ or interleukins by ELISA.

Co-Culture Cell-Kill Assays: PD-L1 positive cells were plated at 10,000 to 20,000 cells per well in 96-well plates and incubated with exemplary PD-L1 binding molecules at a concentration of 5,000 ng/mL. After 24 hours, the PD-L1 binding molecule was washed away and then cells were co-cultured with T-cells or just cell-culture medium. PD-L1 positive/HLA:A2 positive MDA-MB-231 cells that express a fluorescent tag were used as targets in INCUCYTE® assays (Essen BioScience, Ann Arbor, MI, U.S.A.). Cell viability over time was measured using an IncuCyte-S3-Live cell imager (Essen BioScience, Ann Arbor, MI, U.S.A.), and phase and fluorescent images of the cell samples were captured every four to six hours. Percent viability was measured by fluorescent cell counts via INCUCYTE® S3 software package (Essen BioScience, Ann Arbor, MI, U.S.A). Viability data was plotted as total fluorescent cell counts and normalized to time zero.

Figure 22:
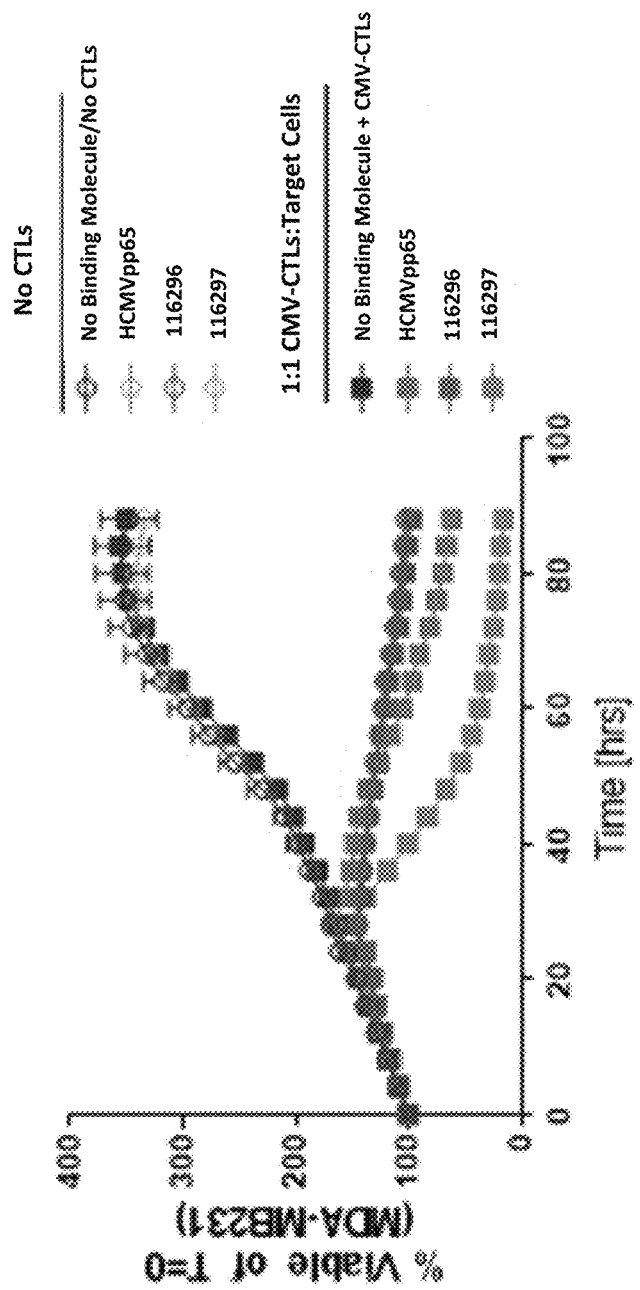
Figure 24A:
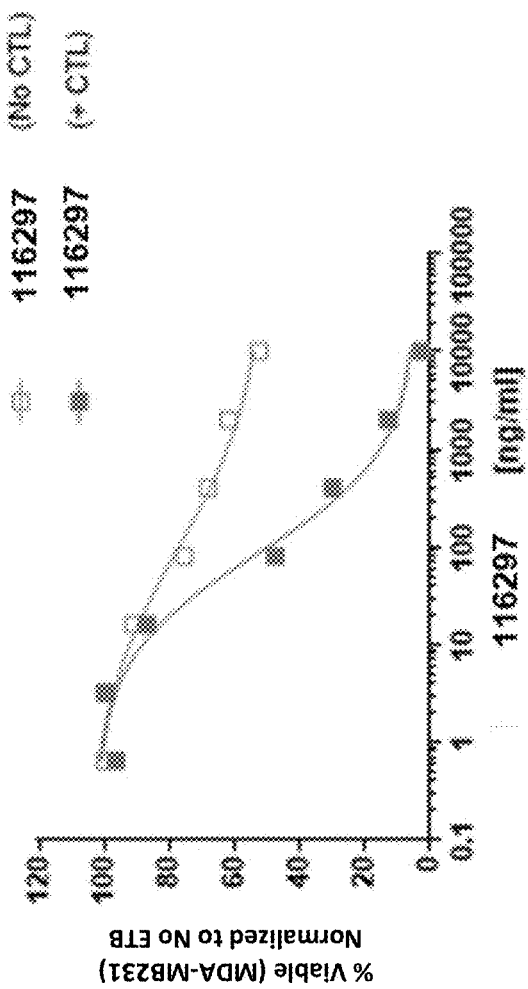
Figure 24B:
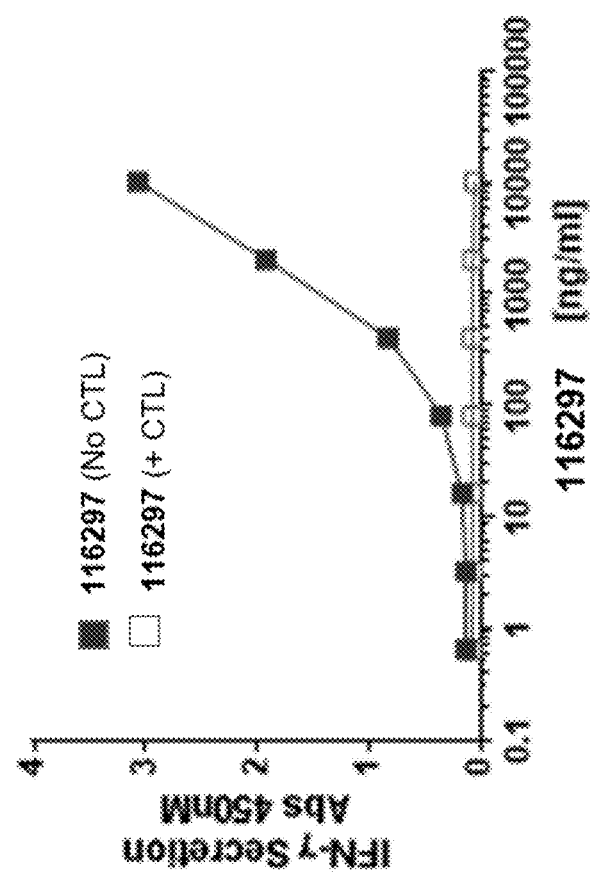

FIGS. 22, 23, and 24A-24B show that 116297 (SEQ ID NO:128) exhibits at least two mechanisms of targeted cell killing: direct cell kill and antigen-specific CTL-dependent cell kill. FIG. 22 demonstrates that 116297 (SEQ ID NO:128), but not 116296 (SEQ ID NO:127), exhibits greater target cell (MDA-MB-231 (HLA:A02 positive)) cytotoxicity in the presence of antigen-specific CTLs (co-culture). The cytotoxic effect of 116297 (SEQ ID NO:128) in the presence of antigen specific CTLs is greater than in the absence of CTLs. The cytotoxic effect of 116297 (SEQ ID NO:128) in the absence of CTLs (red, open circle) is equivalent to the cytotoxic effect of 116296 (SEQ ID NO:127) in the presence (green square) or absence of CTLs (green, open circle). 116297 (SEQ ID NO:128) cytotoxic effects to HLA*A02+/PD-L1+ target cells were increased when viral antigen specific cytotoxic T-cells (CMV-CTLs) were present. As a control, a control PD-L1 binding molecule lacking any viral antigen cargo did not exhibit increases in cytotoxicity in the presence of CMV-CTLs. FIG. 24 demonstrates that incubation of 116297 (SEQ ID NO:128) with tumor cells results in dose-dependent cytotoxicity and inducement of interferon gamma secretion in the presence of CTLs. FIGS. 22 and 24A-24B show that antigen cargo delivery is present as a second cytotoxic mechanism of action in addition to direct cytotoxicity via internalized Shiga toxin effector polypeptide.

Figure 25:
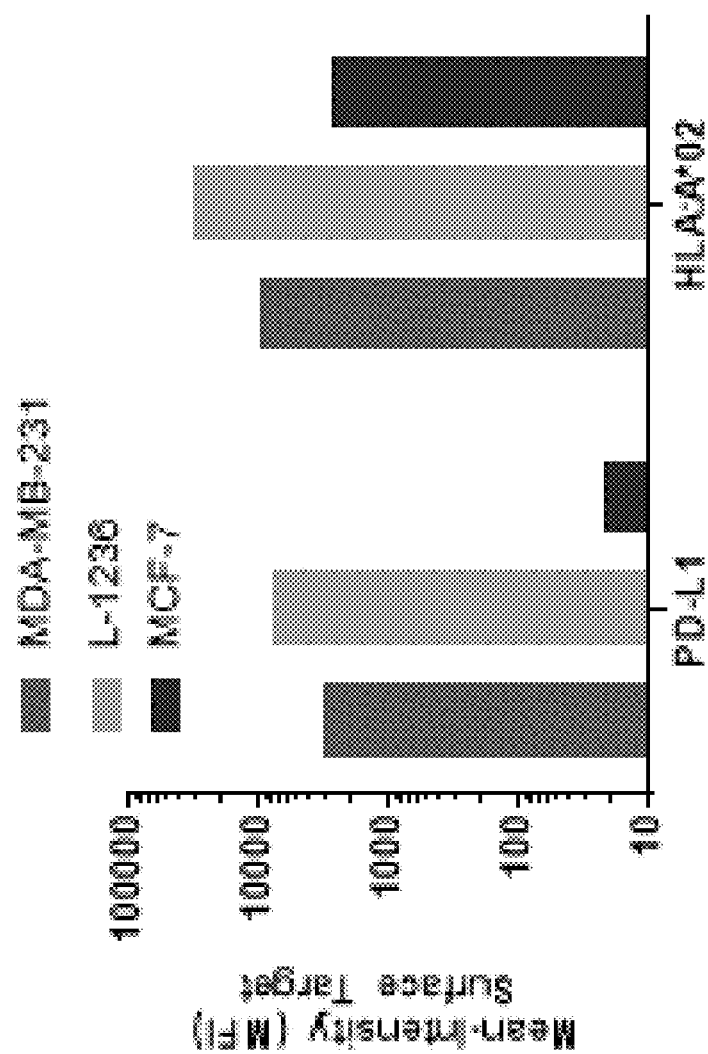
FIG. 25 shows expression as measured using mean fluorescent intensity (MFI) of surface targets PD-L1 and HLA:A*02 in several cell types.
Figure 26:
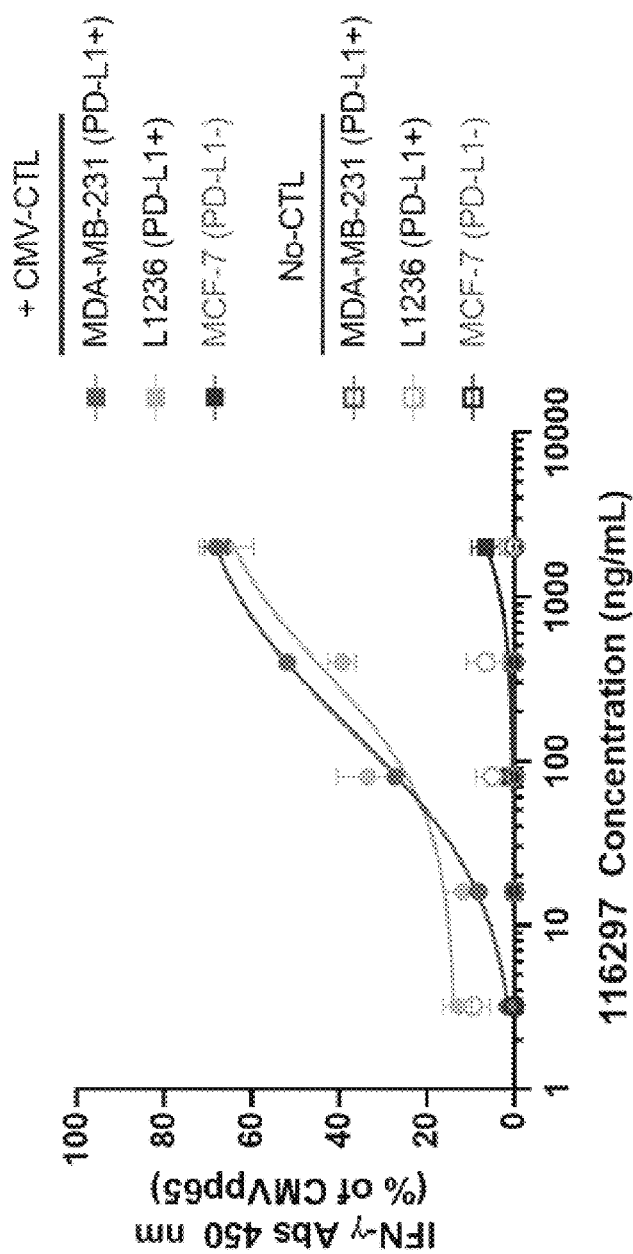
FIG. 26 shows secretion of IFN-γ in a model wherein HLA:A*02 and PD-L1 positive tumor cells in co-culture with antigen-specific CTLs ("CMV-CTL") after treatment with various concentrations of 116297 (SEQ ID NO:128).
Figure 27:
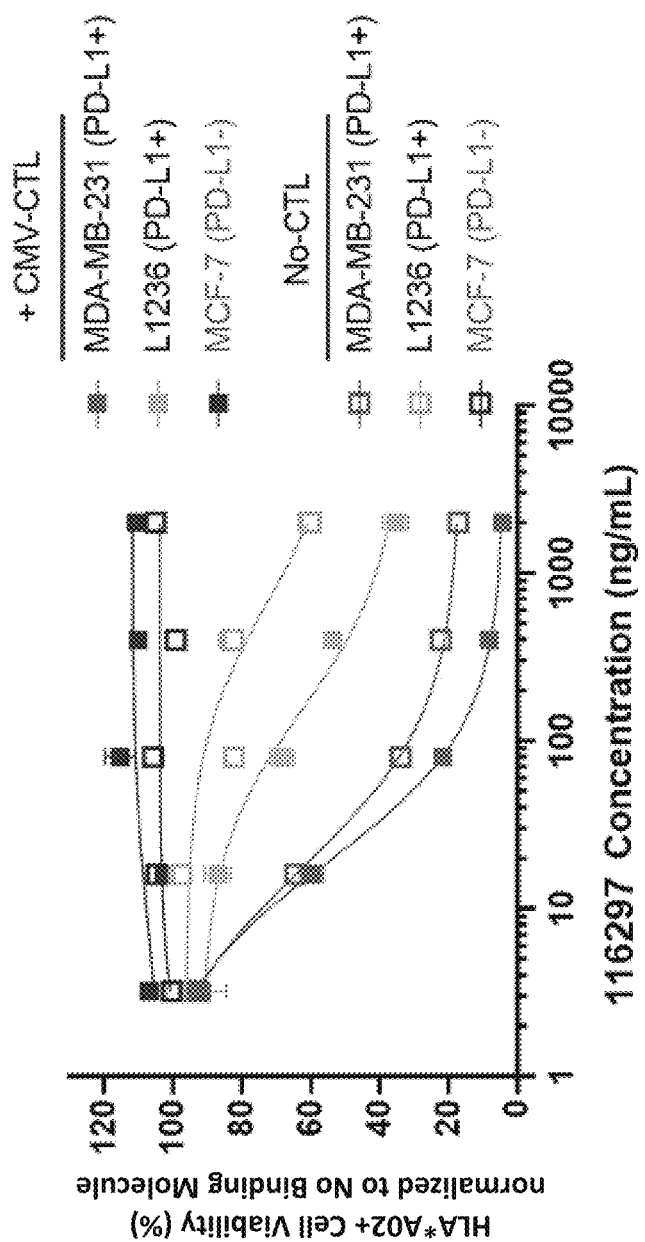
FIG. 27 shows viability of HLA:A*02 positive tumor cells in co-culture with antigen-specific CTLs ("CMV-CTL") after administration of various concentrations of 116297 (SEQ ID NO:128).

FIGS. 23, 25-27 demonstrate that expression of PD-L1 and HLA:A*02 by tumor target cells is required, but is not sufficient, for antigen seeding, i.e. greater 116297 (SEQ ID NO:128) induced cytotoxicity is observed in the presence of CTLs. These results suggest that in these co-culture experiments CTL activation and CTL-mediated cytotoxicity induced by 116297 (SEQ ID NO:128) requires target cell expression of PD-L1 and HLA:A*02 and CTL-antigen specificity. FIG. 25 shows the surface molecule expression of PD-L1 and HLA:A*02 on MDA-MB-231 (PD-L1 positive, HLA:A*02 positive); L1236 ((PD-L1 positive, HLA:A*02 positive); or MCF-7 (PD-L1 negative, HLA:A*02 positive) cells. FIG. 26 shows that 116297 (SEQ ID NO:128) administration to HLA:A*02 and PD-L1+ tumor cells in co-culture with antigen-specific CTLs ("CMV-CTL") induce of interferon gamma secretion. FIG. 27 shows that 116297 (SEQ ID NO:128) administration to HLA:A*02 and PD-L1+ tumor cells in co-culture with antigen-specific CTLs ("CMV-CTL") induces more cytotoxicity than in the No-CTL samples. FIG. 27 shows that the cytotoxic potency of 116297 (SEQ ID NO:128) to PD-L1 positive target cells is increased in the presence of CTLs.

Figure 9:
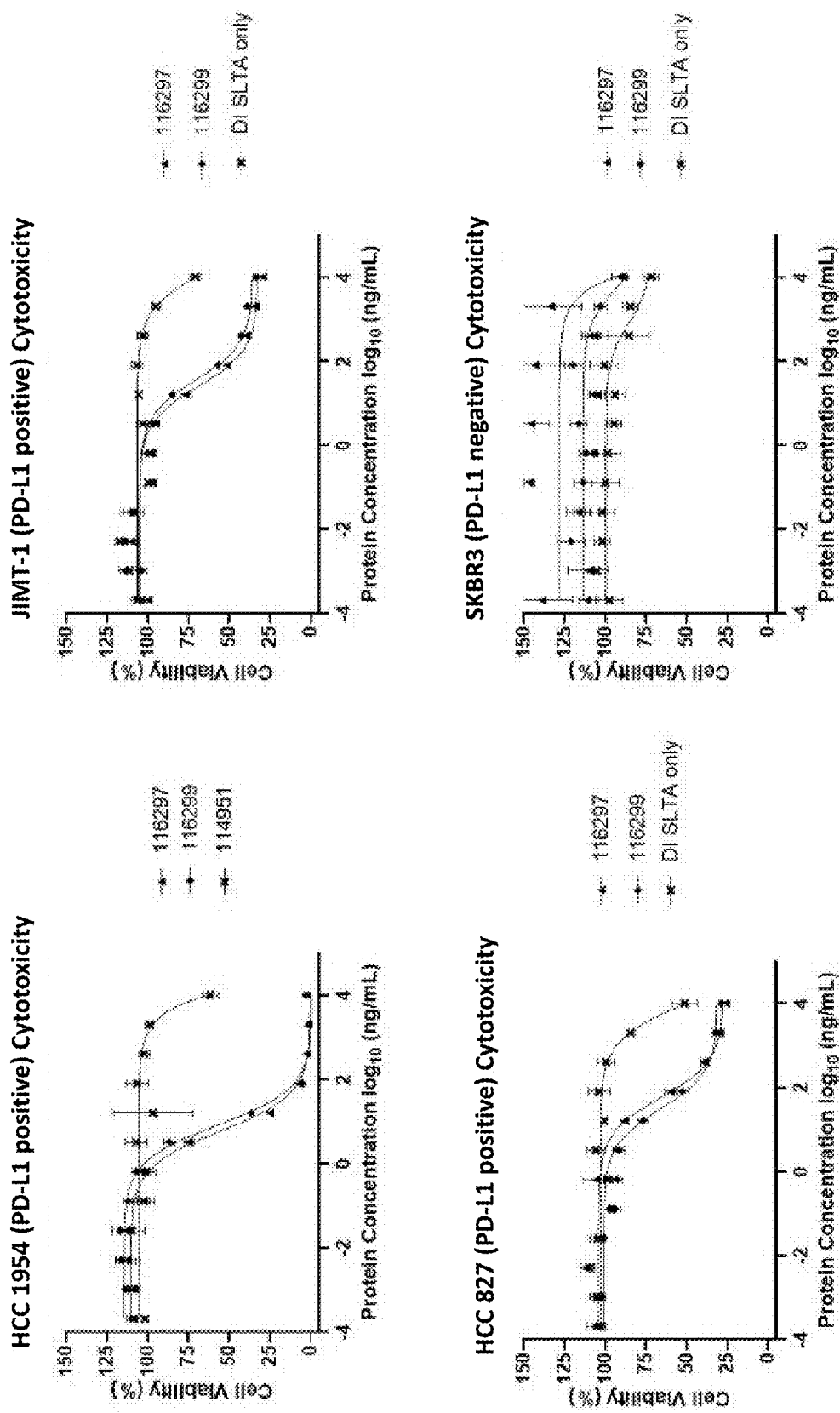
Figure 9:
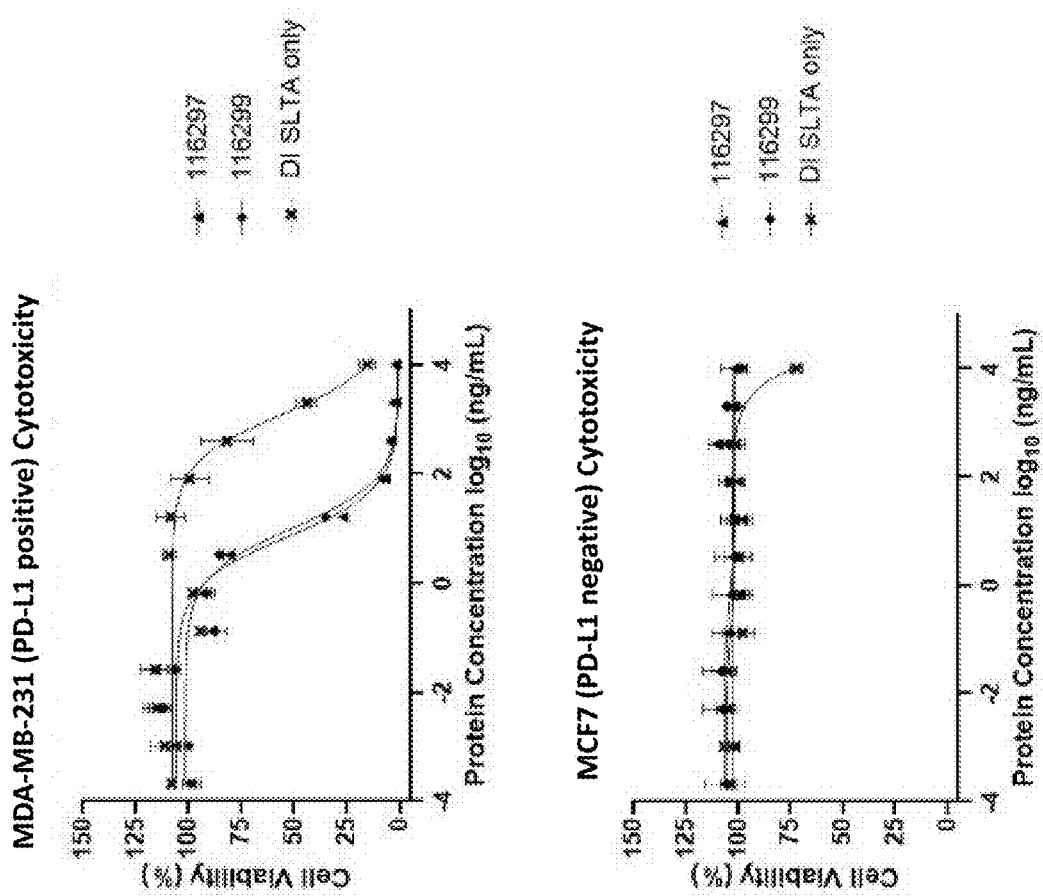

The results of these experiments showed the exemplary PD-L1 binding molecules 116296 (SEQ ID NO:127) and 116297 (SEQ ID NO:128) were cytotoxic to PD-L1 positive/HLA:A02 positive MDA-MB-231 cells both in the absence and presence of human donor cytotoxic T-cells (See, e.g., FIG. 9, FIG. 11, FIG. 24A). In the presence of donor CTLs, significantly more MDA-MB-231 cells were killed as a result of the prior administration of 116297 (SEQ ID NO:128) but not the administration of 116296 (SEQ ID NO:127).

IV. Testing PD-L1/PD-1 Signaling Interference by PD-L1 Binding Molecules

Without being bound by any theory, the ability of a PD-L1-targeting DI-SLT-A1 fusion protein to block the PD-1/PD-L1 interaction is not required for the cytotoxic mechanism of action of any of the exemplary DI-SLT-A1 fusion proteins in killing PD-L1 expressing target cells, which presumably requires cellular internalization and ribosome inhibition by the Shiga toxin A subunit component. However, for certain antibodies, the ability to block the PD-1/PD-L1 signaling axis is believed to be important for their therapeutic benefit (see Ribas A, Wolchok *J, Science* 359: 1350-55 (2018)).

To test the ability of DI-SLT-A1 fusion proteins to perturb the PD-1/PD-L1 interaction, a commercially available cell-based PD-1 signaling bioassay (Promega PD-1/PD-L1 Blockage Bioassay, Promega Corp., Madison, WI, U.S.A.) was used according to manufacturer's instructions. This assay is based on a Jurkat NFAT-Luc reporter system activated by the release of PD-1 inhibition. Target cells expressing PD-L1 (PD-L1 aAPC/CHO-K1 cells) were incubated with test proteins (e.g. antibody or PD-L1 binding molecule) for 30 minutes and then co-cultured for six hours at 37° C. with Jurkat T-cells expressing PD-1 (PD-1 Effector Cells) expressing an NFAT-Luc reporter under the control of a TCR. BioGlo reagent (luciferin) was added to wells of plate, and plates were read for luminescence using a luminometer according to standard procedure. The increase in signal (measured in RLU) indicates the blockage of the PD-1/PD-L1 interaction. The PD-L1-targeted monoclonal antibody known to block this interaction, anti-hPD-L1-hIgG1

Figure 12:
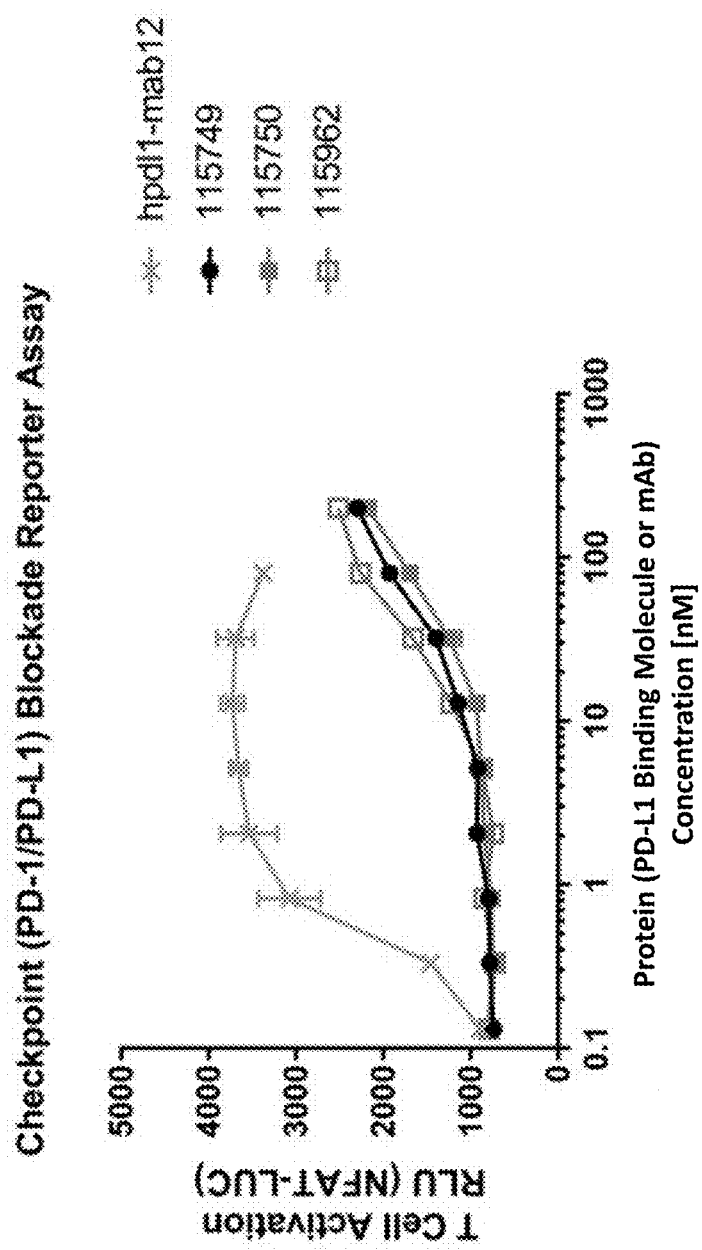

(N298A) (catalog number hpdl1-mabl2, InvivoGen, San Diego, CA, U.S.A.), was tested as a control. The results of these PD-1/PD-L1 interaction experiments are shown in FIG. 12.

The PD-L1 targeted DI-SLT-A1 fusion proteins 115749 (SEQ ID NO:113), 115750 (SEQ ID NO:114), and 115962 (SEQ ID NO:124) all showed the ability to block this interaction at some concentrations, but the activity was much lower than the anti-hPD-L1-hIgG1 control, as shown in FIG. 12. The half-maximal effective concentration for inhibition of PD-1/PD-L1 signaling ($EC_{50}$) for 115749 (SEQ ID NO:113), 115750 (SEQ ID NO:114), and 115962 (SEQ ID NO:124) was greater than 200 nM in this assay (see FIG. 12). Certain other embodiments of the PD-L1 binding molecules showed the ability to block the PD-1/PD-L1 interaction at half-maximal inhibitory concentrations of 1 to 50 nM or less.

V. Animal Models for Testing Binding Molecules and Induction of Immune Responses In Vivo Animal models were used to determine the in vivo effects exemplary cell-targeting fusion proteins on neoplastic cells and/or the immune system.

A. Murine Studies

Various mice strains were used to test the effects on xenograft tumors of the cell-targeting fusion proteins after administration to mice injected with human neoplastic cells which express PD-L1 on their cell surfaces, CTG-1444 or CTG-0192 (non-small cell lung cancer (NSCLC) tumor cells derived from patients and passaged in vivo in mice). The NSCLC tumor cells tested in this experiment were HLA: A0201 positive.

Immunocompromised (Nude) or immune deficient (NOG) mouse strains were used as xenograft models. The mice were first administered CD8+ human cytotoxic T-cells (CTLs) capable of recognizing the CD8+ T-cell epitope as an adoptive transfer model of a human T-cell system. Human tumor cells were administered to the immunodeficient mice to create either a subcutaneous tumor or disseminated tumors as patient-derived xenograft model of human NSCLC.

Intravenous administration of 116297 (SEQ ID NO:128) showed in vivo efficacy against human patient derived non-small cell lung cancer xenografts in two different murine models (see FIGS. 28A-28C and 29A-29C). In the first xenograft model, administration of 116297 (SEQ ID NO:128) reduced tumor growth and prolonged endpoint survival against an aggressive form of NSCLC xenograft in immunocompromised NOG mice (FIG. 28B). The 116297 (SEQ ID NO:128) dosing schedule was 6 mg/kg on study Days 1 and 2 mg/kg on study Days 3, 5, 8, 10, 12, 22, 24, and 28. Both 115749 (SEQ ID NO:113) and 116297 (SEQ ID NO:128) administration resulted in a survival benefit (FIG. 28C). 116297 (SEQ ID NO:128) administration resulted in tumor volumes 67% of the vehicle control group, and 115749 (SEQ ID NO:113) administration resulted in tumor volumes 85% of the vehicle control group (FIG. 28C). In the second xenograft model using immunocompromised NOG mice, administration of 116297 (SEQ ID NO:128) promoted tumor regression and increased endpoint survival against a NSCLC xenograft derived from NSCLC cells expressing relatively low levels of cell surface PD-L1 (FIGS. 29A-29C and 30). The 116297 (SEQ ID NO:128) dosing schedule was 6 mg/kg on study Days 1 and 15 and 2 mg/kg on study Days 3, 5, 8, 10, 12, 17, 19, 22, and 4. 116297 (SEQ ID NO:128) administration resulted in tumor volumes 21% of the vehicle control group whereas 115749 (SEQ ID NO:113) administration did not reduce tumor growth (FIG. 29A-C and FIG. 30). During the 60-day study, administration of 116297 (SEQ ID NO:128) increased survival compared to vehicle control (FIGS. 29A-29C and 30).

FIG. 30 shows that 116297 (SEQ ID NO:128) exhibited activity in vivo toward human patient derived tumors in xenograft (PDX) animal models. 116297 (SEQ ID NO:128) administration resulted in potent and sustained responses to PD-L1 positive, non-small cell lung cancer (NSCLC) patient derived xenografts. Treatment with 116297 (SEQ ID NO:128) resulted in systemic regressions and delays in tumor growth in this NSCLC PDX mouse model (NOG mice).

B. Non-Human Primate Studies

Exemplary, PD-L1 binding molecule 116297 (SEQ ID NO:128) was administered to cynomolgus macaques and certain pharmacodynamic effects were observed. Because 116297 (SEQ ID NO:128) targets both human and cynomolgus PD-L1 and kills cells expressing cynomolgus PD-L1 (see FIGS. 13, 15, 17A-17B, and 34), cynomolgus macaques were considered a relevant model for tolerability and pharmacodynamic studies. Cynomolgus PD-L1 shares about 93% sequence homology with human PD-L1.

Intravenous administration of 116297 (SEQ ID NO:128) once per week for 4 weeks resulted in an increase in TNF-alpha, IFN-gamma, and interleukin-2 (IL-2) (i.e. type I cytokines) in one of two animals tested (see FIG. 31). The increase in type I cytokine levels is an indication of T cell activation as a result of 116297 (SEQ ID NO:128) administration.

FIG. 17A reports that 116297 (SEQ ID NO:128) binds to both human (Hu) and cynomolgus (Cyno) PD-L1 expressed by transgenic CHO-K1 cells. 116297 (SEQ ID NO:128) did not bind to mouse PD-L1 expressed by transgenic CHO-K1 cells under these conditions. A control anti-human-PD-L1 antibody ("PD-L1 mAb") atezolizumab was used in the binding assay. Similarly, FIG. 17B shows that 116297 (SEQ ID NO:128) is cytotoxic to transgenic $C_H$0-1 cells expressing either human (Hu) or cynomolgus (Cyno) PD-L1 but not expressing mouse PD-L1.

FIG. 31 shows 116297 (SEQ ID NO:128) administration resulted in increases in type I cytokines in sera of non-human primates. Weekly, intravenous, repeated dosing of 116297 (SEQ ID NO:128) was tested in an exploratory study (n=2 per dose level cohort) in cynomolgus macaques at doses of 50 μg/kg, 150 μg/kg, and 450 μg/kg for 4 weeks (dosing on days 1, 8, 15, and 22). This study showed that 116297 (SEQ ID NO:128) administration increased the levels of serum type I cytokines TNF-α, IFN-γ, and IL-2 on days 15 and 23 in one of two cynomolgus macaques in the highest two dosing cohorts (150 and 450 μg/kg). Immune related events driven by PD-L1 and PD-1 targeted agents are associated with patient benefit (see e.g. Das S, Johnson D, *J Immunother Cancer* 7: 306 (2019)). In FIG. 31, μg refers to micrograms (μg) administered per kilogram of the subject's body weight, and pg/ml refers to picograms per milliliter (pg/mL).

FIG. 32 is a schematic drawing showing potential mechanisms of action of exemplary PD-L1 binding molecules, such as, e.g., 116297 (SEQ ID NO:128). 116297 (SEQ ID NO:128) is designed to deplete PD-L1 positive tumor and immune cells. A PD-L1 binding molecule may comprise a continuous polypeptide comprising a deimmunized Shiga toxin A subunit effector polypeptide (DI SLTA), an anti-PD-L1 single-chain variable fragment (scFv), and a CD8+ T-cell epitope peptide cargo (e.g. a human CMV-pp65 derived peptide) (see FIG. 32). This potential mechanism of action is unique in that it comprises two distinct mechanisms of action: potent killing of PD-L1 expressing tumor and immune cells and altering the tumor immunophenotype. Briefly, the first mechanism of action involves targeting potent cytotoxicity to PD-L1 expressing target cells. First, the scFv fragment region of the PD-L1 binding molecules binds cell-surface PD-L1; then the Shiga toxin effector polypeptide component induces internalization into the cell and intracellular routing via the Golgi to the endoplasmic reticulum, and finally to the cytosol; once in the cytosol, the Shiga toxin effector polypeptide potently kills the target cell through enzymatic and irreversible ribosomal destruction. Once the PD-L1 binding molecule is in the endoplasmic reticulum or cytosol, the antigenic peptide cargo may be cleaved away from the rest of the PD-L1 binding molecule allowing for transport of the antigenic peptide to the lumen of the endoplasmic reticulum and/or binding of the antigenic peptide by a MHC class I molecule. This allows for an unloaded MHC class I molecule to become loaded with the antigenic peptide cargo, for example, to form a "epitope-peptide loaded MHC-I". The antigen loaded MHC class I molecule can then be transported from the endoplasmic reticulum through the Golgi to the cell surface to present the CD*+ T-cell epitope for recognition by the adaptive immune system. Once on the cell-surface, the epitope-loaded MHC class I molecule complex may be recognized by CD8+ T-cells, e.g., leading to cytotoxic T-cell engagement and killing of the antigen-presenting target cell. The presentation of delivered antigens by tumor cells may result in an "altered immune phenotype" and result in antigen seeding as described herein. The re-direction of endogenous cytotoxic T-cells to the tumor target cells via delivery and presentation of a CD8+ T-cell epitope may represent an altered immune phenotype for the tumor or specific locus within the treated subject. For example, the delivery and presentation of a class I CMV CD8+ T-cell epitope may re-direct endogenous CMV-specific cytotoxic T-cells (CTLs) to the tumor cells. In FIG. 32, "CTL" refers to CMV-specific T-cells which express a TCR recognizing the MHC class I displayed CMV viral epitope-peptide complex. In FIG. 32, the phrase "altered immune phenotype" or "alteration of tumor immunophenotype" refers to the results of delivery of viral CD8+ T-cell epitope (antigen) to re-direct endogenous CMV-specific T-cells to the tumor—"Antigen seeding technology" or simply "AST". A PD-L1 binding molecule having its viral epitope-peptide cargo removed can be active in the cytosol, having a primary mechanism of action (MOA) involving the inhibition of protein synthesis leading to target cell killing. This primary mechanism of action is independent of a subject's immune function status.

This potential mechanism of action may also involve the killing of PD-L1-expressing immune cells, including repressive immune cells, leading to favorable improvements in anti-tumor immunosurveillance via the removal of repressive and/or anergic cells at tumor site(s) or in certain tumor microenvironments. 116297 (SEQ ID NO:128) is designed to deplete PD-L1 positive tumor and PD-L1 positive repressive (i.e., immunosuppressive) immune cells. PD-L1 positivity on tumor cells (TC) and immune cells (IC) are independently correlated with durable clinical responses to atezolizumab (an anti PD-L1 antibody therapeutic) by patients diagnosed with non-small cell lung cancer (NSCLC) (Kowanetz Metal., *Proc Natl Acad Sci U.S.A* 115: E10119-E10126 (2018)). The cytotoxic potential of 116297 (SEQ ID NO:128) might be therapeutically leveraged for both (1) direct targeting of PD-L1 positive tumor cells to reduce tumor burdens in patients and (2) targeting of inhibitory immune cells to reduce their undesirable effects on tumor microenvironments of patients. For example, the cytotoxic potential of 116297 (SEQ ID NO:128) might be leveraged for both direct targeting of PD L1+TCs to reduce tumor burden, and reduction of inhibitory cells and their associated effects on the TME by depletion of PD L1+ICs at the tumor.

FIG. 33 shows the results of a ribosome inhibition assay for the exemplary PD-L1 binding molecule 116297 (SEQ ID NO:128). The PD-L1 binding molecule 116297 (SEQ ID NO:128) exhibited a ribosome inhibition activity level comparable to that of a positive "control" molecule, a Shiga toxin effector polypeptide (DI-SLTA) alone, not coupled with any targeting agent or cell-binding region or domain (i.e., a polypeptide comprising SEQ ID NO: 41). Thus, 116297 (SEQ ID NO:128) appears to retain the potent enzymatic activity of protein synthesis inhibition present in the catalytic domain of the DI-SLTA only construct in its de-immunized Shiga toxin effector polypeptide component.

FIG. 34 shows results of a PD-L1 target binding assay for the exemplary PD-L1 binding molecule 116297 (SEQ ID NO:128). FIG. 34 shows that the PD-L1 binding molecule 116297 (SEQ ID NO:128) bound to recombinant human PD-L1 and cynomolgus macaque PD-L1 but did not exhibit high-affinity binding to recombinant mouse PD-L1 in this assay.

Figure 35:
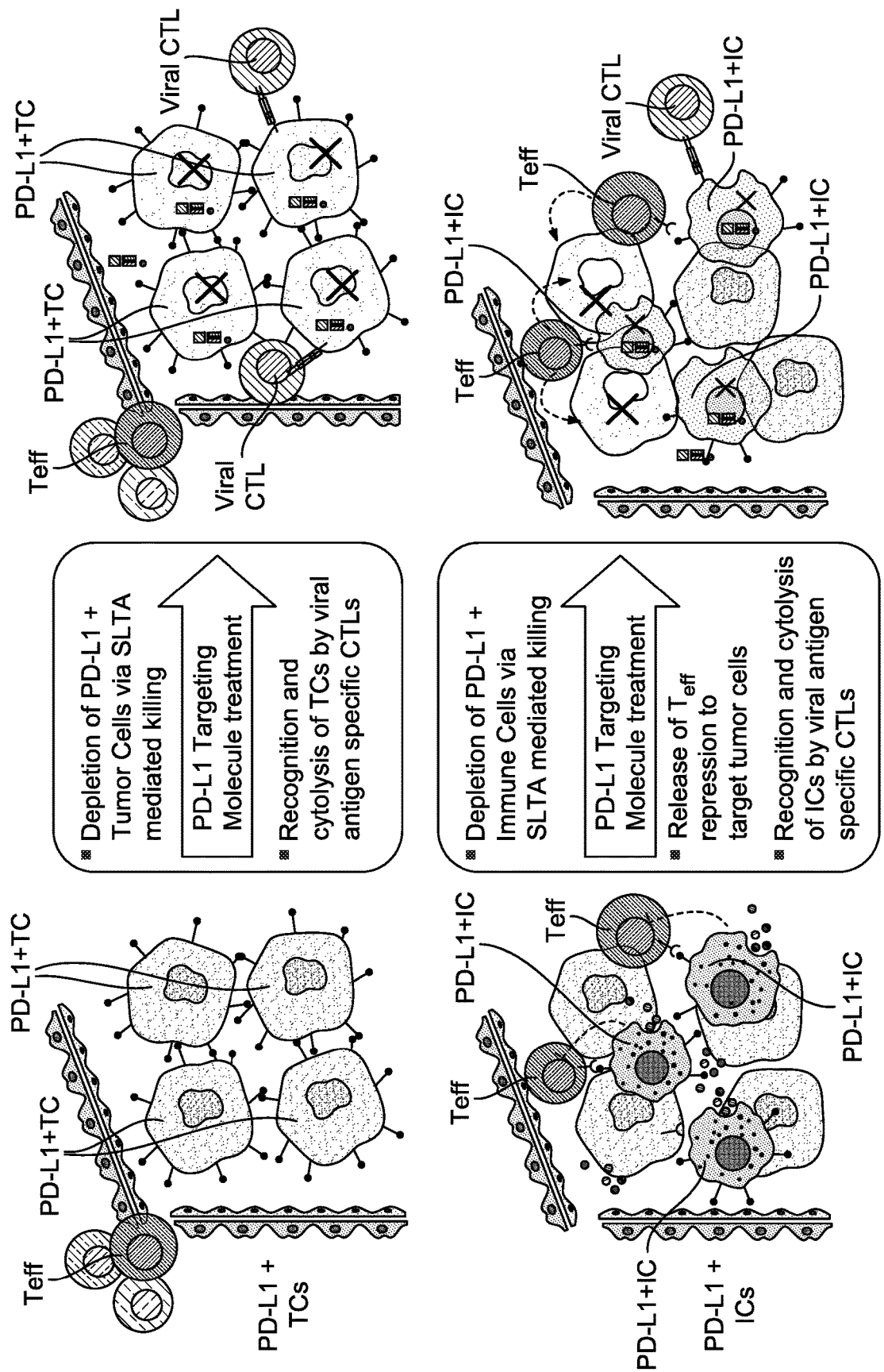
Figure 36:
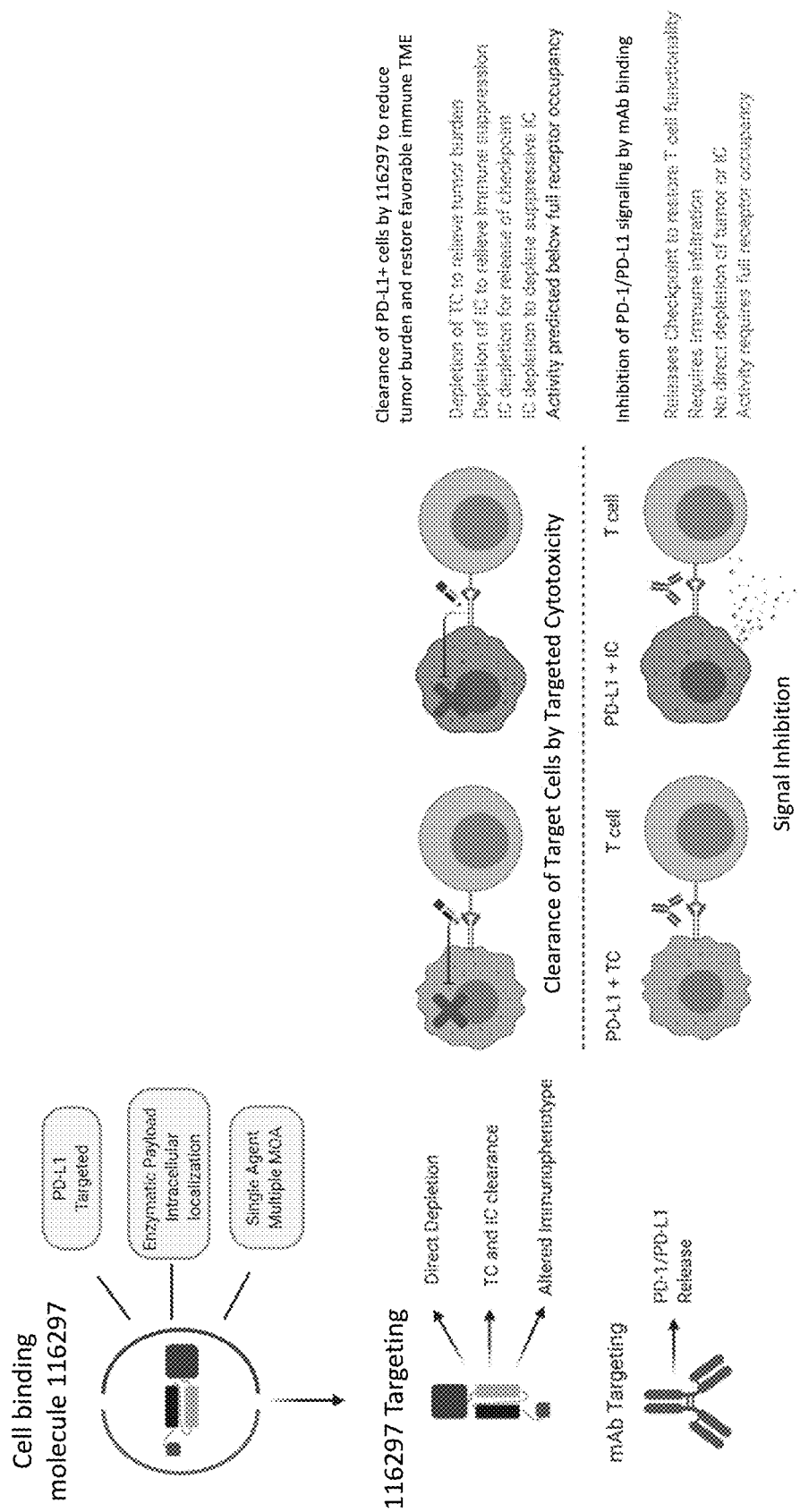

FIG. 35 shows how PD-L1 binding molecule treatment(s) may induce anti-tumor effects, such as, e.g., by directly killing PD-L1-expressing tumor cells and PD-L1 positive immune cells resulting in alterations of tumor immunophenotypes. 116297 (SEQ ID NO:128) is a unique agent designed to deplete tumor and repressive immune cells. 116297 (SEQ ID NO:128) specifically and directly kills PD-L1+ target cells, demonstrated in vitro for tumor cells and ex vivo for immune cells. 116297 (SEQ ID NO:128) can deliver a viral antigen cargo for presentation in complex with MHC class I molecules on the surfaces of HLA*A02+/PD-L1+ target cells, which may lead to alterations in the immunophenotype of the tissue site, tumor, and/or tumor microenvironment thereby allowing for beneficial anti-tumor surveillance by effector T-cells. 116297 (SEQ ID NO:128) is tolerated in a pharmacodynamic relevant primate model at doses relevant to predicted potencies in human cancer patients. In FIG. 35, "Teff" refers to an effector T-cell, "viral CTL" refers to a viral antigen specific CTL, and "SLTA" refers to the Shiga toxin A subunit effector polypeptide component of a PD-L1 binding molecule.

Figure 37A:
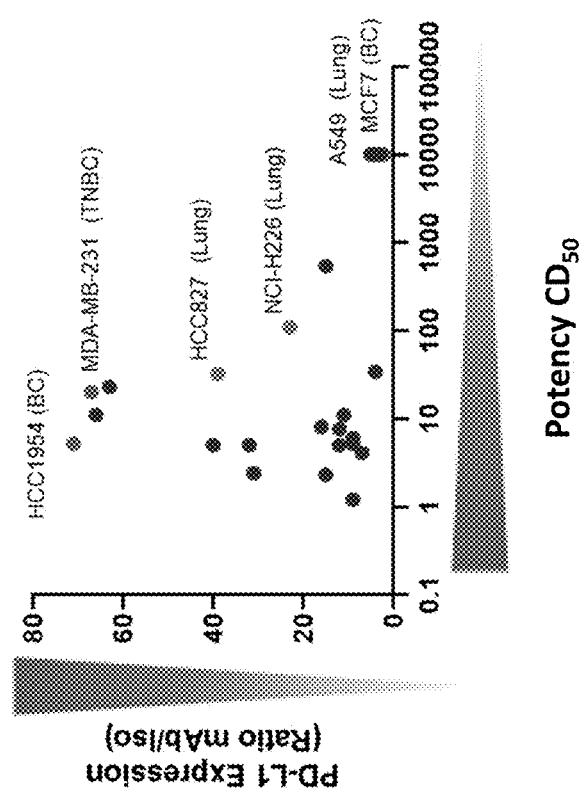
Figure 37B:
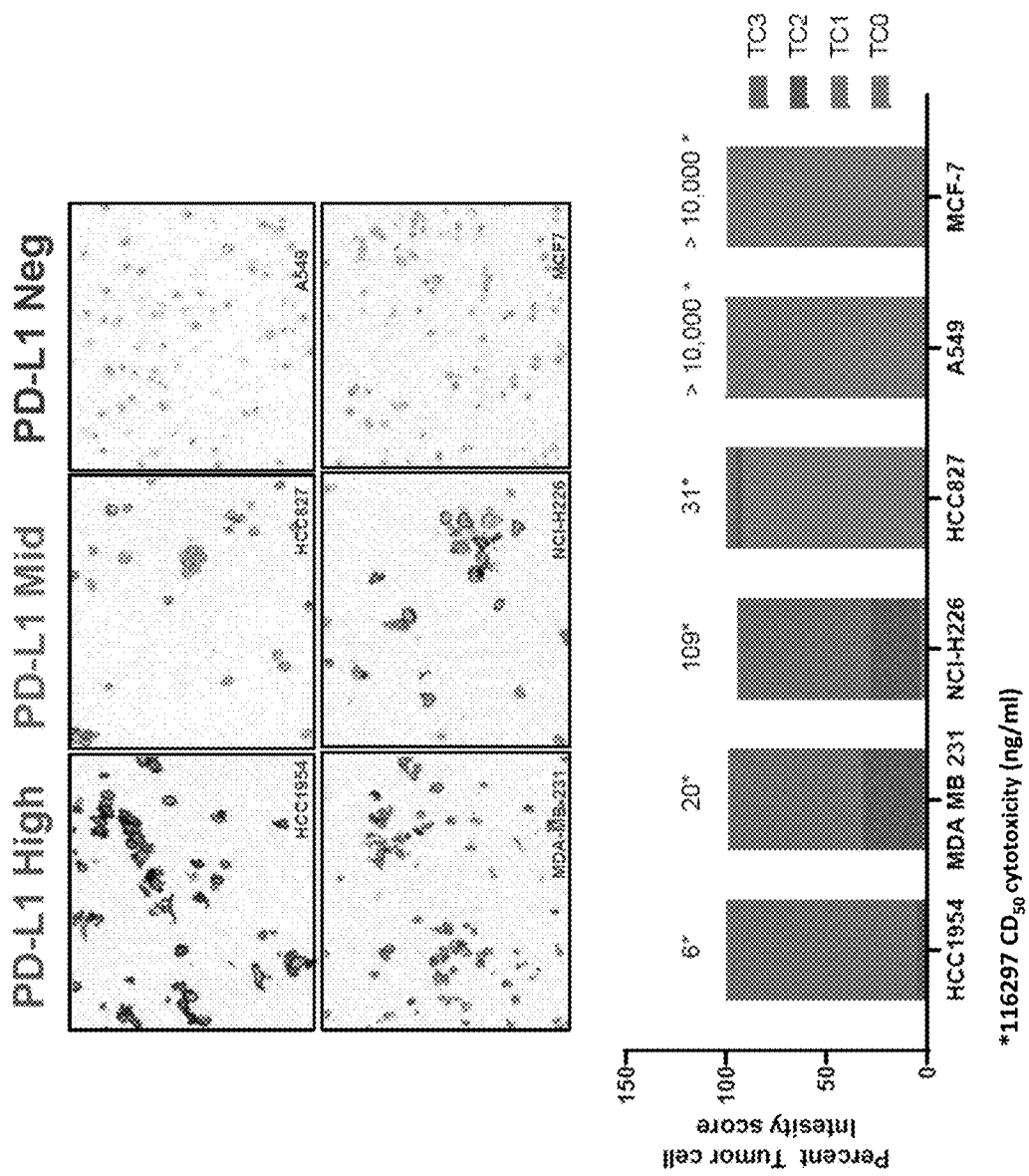

Example 4. 116297 Targets PD-L1 Positive Tumor Cells (TC) for Depletion Via Distinct Modes of Action In this example, 116297 was tested for cytotoxicity to tumor cells having different levels of PD-L1 expression and via different mechanisms of action. Initially, 29 representative lung, skin, breast, and ovary tumor cell lines (TCs) were evaluated for surface PD-L1 expression by immunohistochemistry and scored for intensity (TC1=low expression, TC2=medium expression, TC3=high expression). Representative results are shown in FIG. 37B.

The 29 cell lines were then evaluated for PD-L1 expression by flow cytometry and for cytotoxic sensitivity to 116297 in vitro. Results from various illustrative cell lines are shown in FIG. 37A, including HCC1954 (breast cancer), MDA-MB-231 (triple negative breast cancer), HCC827 (lung cancer), NCI-H225 (lung cancer), A549 (lung cancer), and MCF7 (breast cancer). These data show that 116297 is cytotoxic to tumor cell lines across a range of PD-L1 expression levels.

Figure 37C:
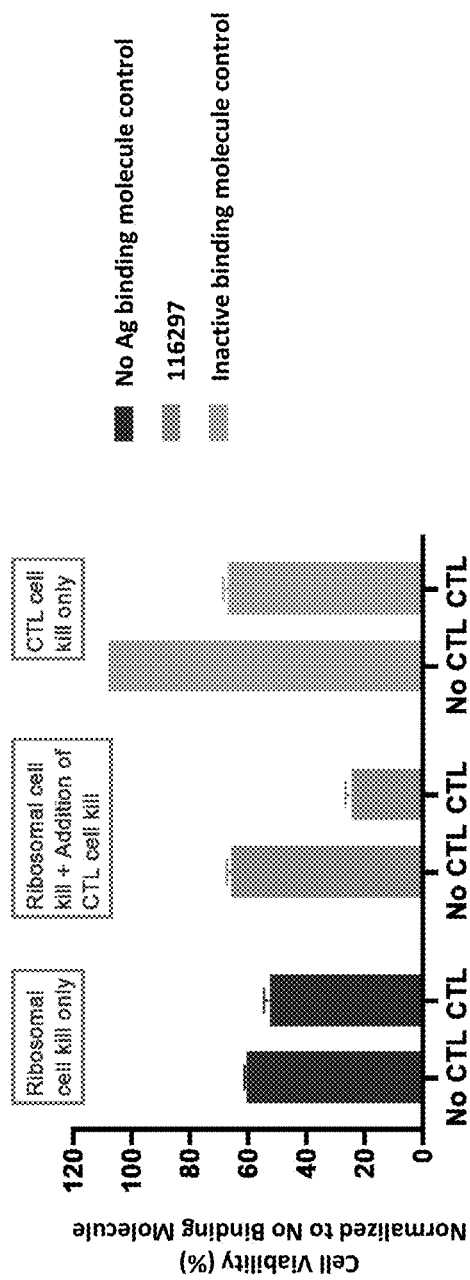
Figure 37D:
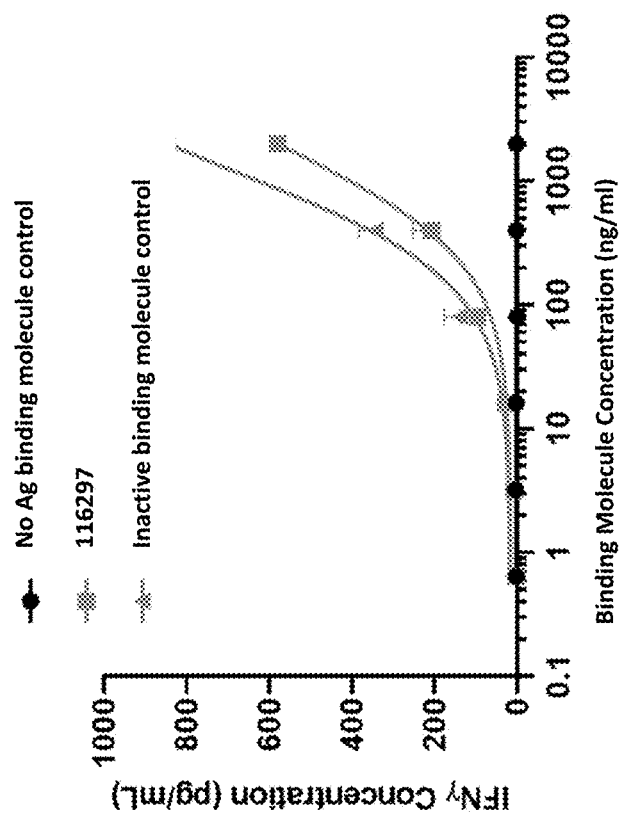

Ribosomal inhibition-based cytotoxicity and CTL-mediated cytotoxicity was investigated for 116297. CTL-mediated cytotoxicity in this experiment is based on antigen-seeded PD-L1/HLA*A02 positive target cells presenting on a cell surface the delivered CMV CD8+ T-cell epitope peptide cargo. MDA-MB-231 cells were treated with a PD-L1 binding molecule 116297, "No Ag" PD-L1 binding molecule control (a molecule related to 116297 but lacking the antigenic peptide domain), or CMV epitope-peptide carrying "inactive" PD-L1 binding molecule control, 116555, and then cultured for 5 days in the presence or absence of CMV-HLA:A02 restricted T cells to test cell viability and T cell activation via IFN-gamma secretion. As shown in FIG. 37C, the PD-L1 binding molecules killed cells according to various mechanisms of action: ribosomal inhibition ("No Ag" PD-L1 binding molecule control) and antigenic peptide delivery ("inactive" PD-L1 binding molecule control). 116297 killed cells according to both mechanisms of action. As shown in FIG. 37D, 116297 stimulated CMV-specific CTLs to secrete IFN-gamma in response to PD-L1/HLA*A02 target cells presenting the delivered CMV CD8+ T-cell peptide via the MHC class I system.

Example 5. 116297 Controls PD-L1 Positive Tumors In Vivo

Figure 38B:
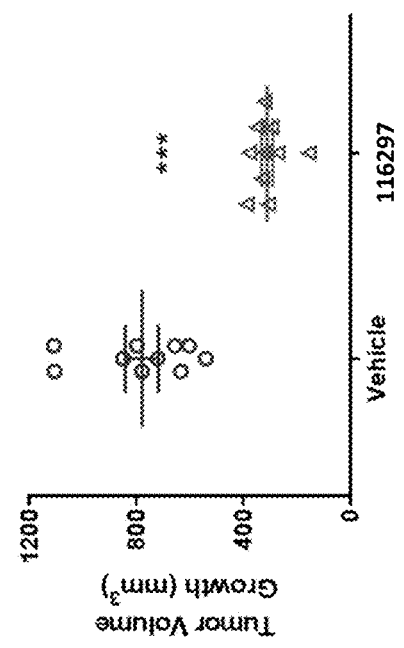
Figure 38A:
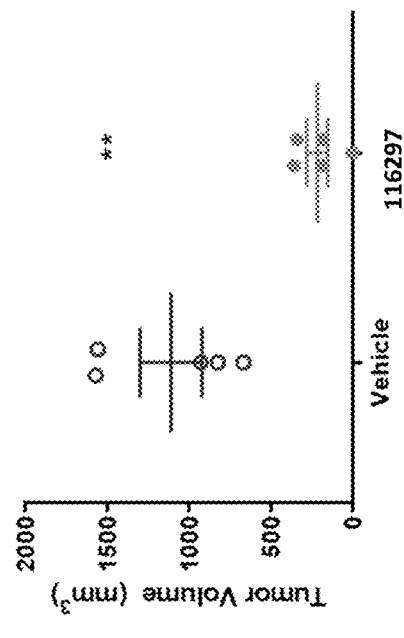
Figures 38C, 38D:
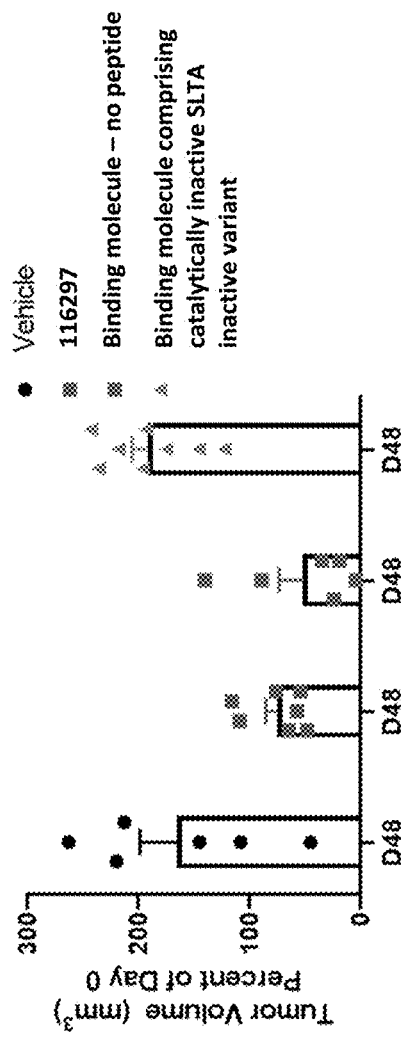

In this example, 116297 was evaluated for the ability to control PD-L1 positive tumors in immunodeficient mice implanted with human tumors. 116297 treatment resulted in significant control of tumors in mice with limited toxicity (FIG. 38A-38B). 116297 administration suppressed the growth of tumors in mice implanted with PD-L1 positive, human triple negative breast cancer (TNBC, MDA-MB-231 cells (FIG. 38A)) or PD-L1 positive, human non-small cell lung cancer (NSCLC) patient derived cells (FIG. 38B). Additionally, 116297 activity in these mouse xenograft models was compared to treatments with related molecules lacking either the viral antigen (No CMV peptide) or lacking Shiga toxin catalytic activity (116555, a catalytically inactive variant of 116297) to demonstrate the mechanism(s) of action of 116927 in vivo (FIG. 38C). Model and efficacy endpoints are summarized in FIG. 38D. These data indicate that 116297 controls tumor growth in vivo across relevant tumor models and activity is dependent on a catalytically active Shiga toxin component.

Figure 39A:
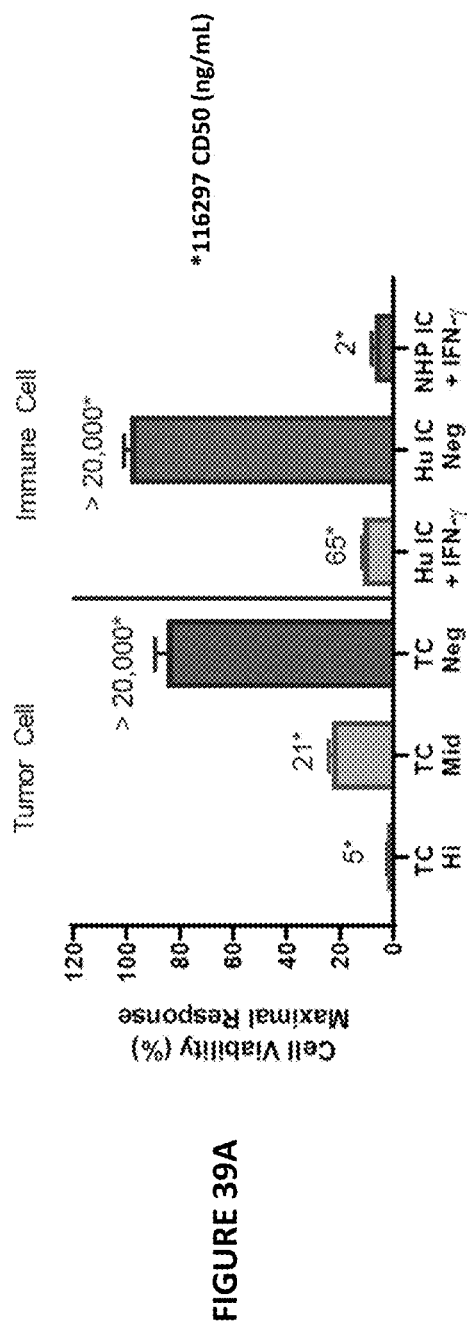
Figure 39B:
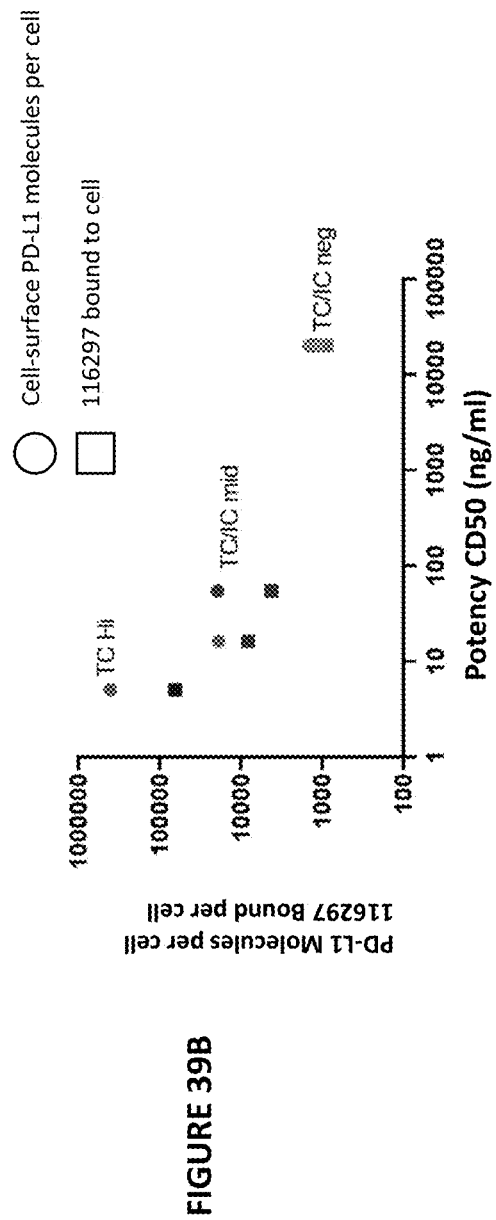

Example 6. 116297 Binds and Targets Tumor Cells and Immune Cells with Similar Potency Profiled Ex Vivo In this example, 116297 cytotoxicity to tumor cells having varying PD-L1 expression was evaluated using a CELLTITER-GLO® (Promega, cell viability) assay, cells representative of high PD-L1 expression (HCC1954), mid/hi PD-L1 expression (MDA-MB-231), and PD-L1 negative (MCF7). The cell-surface density of PD-L1 was determined for tumor cells and immune cell subsets by flow cytometry, to evaluate the relationship between target expression, 116297 cell binding, and cytotoxic potency. FIG. 39B shows the number of cell surface PD-L1 molecules per cell (circles) or the number of 116927 molecules bound per cell (squares) plotted against 116297 cytotoxic potency as represented by $CD_{50}$ values. The cytotoxicity ($CD_{50}$) of 116297 was also measured on isolated human $CD_{14}$ positive monocytes, which were either untreated or treated with IFN-gamma to induce PD-L1 expression. 16297 potency ($CD_{50}$) was correlated with PD-L1 surface expression and binding to PD-L1 positive tumor cells and immune cells. As shown in FIG. 39A, 116297 potently depleted human tumor cells and immune cell subsets in a PD-L1 expression level dependent manner.

Example 7. 116297 Targets Human PD-L1 Positive Tumor Cells for Depletion in Non-Human Primates A non-human primate (NHP) study was used to determine pharmacokinetics (PK) of 116297 in vivo, and to estimate maximum cell-kill and receptor occupancy for tumor cell and immune cell subsets. 116297 or the binding molecule-SLTA-catalytically inactive control 116555 (SEQ ID NO: 160) were administered intravenously to NHPs at 50 µg/kg (116297) or 450 µg/kg (116297 and 116555) weekly for 4 doses.

Figure 40A:
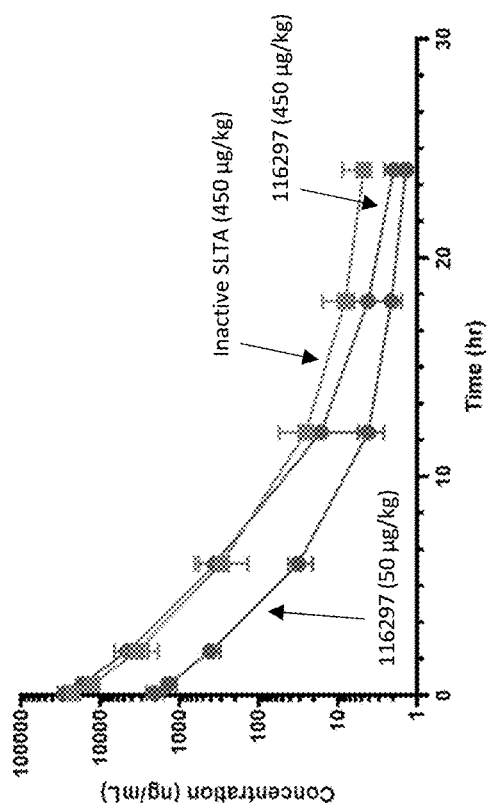
Figure 40B:
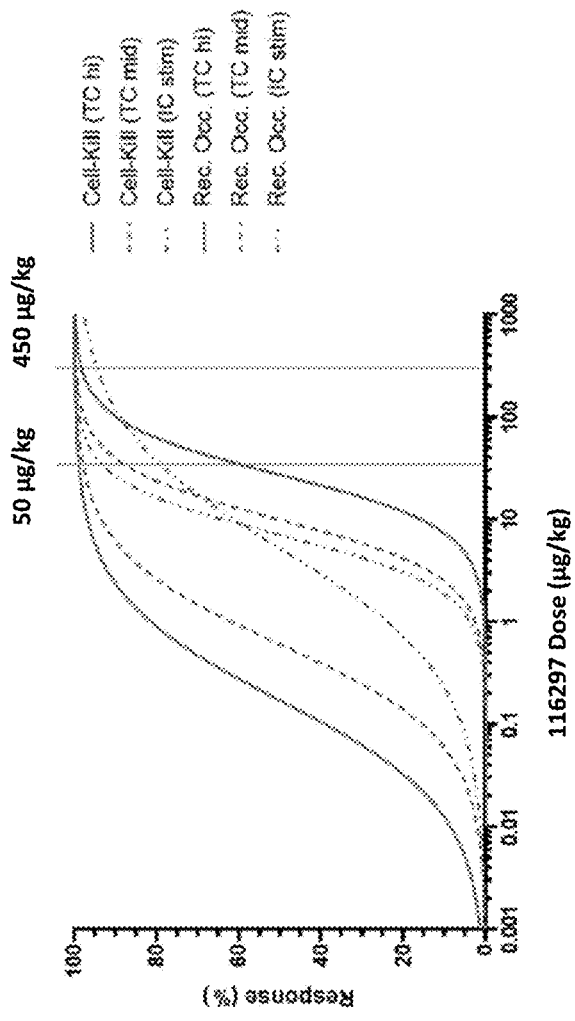

On the first day of the study, blood samples were taken periodically for 24 hours after administration of 116297 or 116555. Pharmacokinetic curves were calculated and are shown in FIG. 40A. 116297 had a half-life of about 2.8 hours for dosing at 50m/kg and about 3.7 hours for dosing at 450 µg/kg. 116555 was observed to have a half-life of about 5.6 hours after a dose of 450 µg/kg.

Human serum exposure was then simulated from the NHP PK data from the study described above and correlated with the in vitro $CD_{50}$ values and PD-L1 binding data to predict maximum cell-kill and receptor occupancy for TC and IC subsets. Results are shown in Figure Example 8. 116297 Elicits a Distinct Profile of Immune Related Adverse Events in Non-Human Primates A non-human primate (NHP) study was also used to observe and measure immune related adverse effects (irAE) in vivo. 116297 or the 116555 (binding molecule-SLTA-catalytically inactive control) were administered to NHP at 50 µg/kg (116297) or 450 µg/kg (116297 and 11655) weekly for 4 doses. This dosing regimen is illustrated in FIG. 41A.

Levels of immune cell subsets from circulation, including peripheral monocytes (FIG. 41B) and peripheral T lymphocytes (FIG. 41C) were evaluated by flow cytometry. Monocyte samples were obtained at day 8, and lymphocyte samples were obtained at day 15. As shown in in FIG. 41B, 116297 treatment resulted in the depletion of CD14 positive monocytes in NHPs after two administrations of the molecule. CD14 positive monocyte killing by 116297 treatment was dose-dependent and required a catalytically active Shiga toxin component, as 116555 treatment did not result in monocyte depletion. As shown in FIG. 41C, 116297 expanded T and B lymphocytes in NHPs after two administrations of the molecule. In contrast, administration of 116555 did not result in depletion of immune cells in NHPs. This NHP study shows the 116297 effect on monocytes was dose-dependent and that the effect of immune cell depletion was not caused by blockade of the PD-L1/PD-1 interaction but rather required the catalytic activity of the Shiga toxin A subunit component.

Serum cytokine responses were evaluated across two independent NHP studies. In FIG. 41D, results from these studies is displayed as percent of responder for study 1 (n=2 NHP) and study 2 (n=8 NHP (116297) and n=5 (116555)). The data reflects induction of cytokines after dose 3 in the studies. 116297 depletion of immune cells and lymphocyte activation was associated with an immune checkpoint inhibitor inflammatory signature. Notably, 116297 treatment elicited a cytokine profile in NHPs associated with T cell activation and responses observed with immune checkpoint inhibitors in the clinic. Administration of 116297 also resulted in an immune activation profile associated with the development of irAEs, including dermatitis (skin flaking) and myocarditis.

NHP studies were also used to observe and measure immune related adverse events (irAEs) in vivo. 116297 was administered to NHPs at 50 μg/kg or 450 μg/kg and compared to administration of at 450 μg/kg of 116555 (catalytically inactive control), all at weekly dosing for 4 doses total. In additional studies, 115749 was administered to NHPs at 150, 450, or 750 μg/kg; 115765 was administered to NHPs at 25, 150, or 450 μg/kg; and 115695 was administered to NHPs at 50, 150, or 450 μg/kg, all dosed every 3 days for 2 weeks.

Levels of immune cell subsets from circulation, including peripheral monocytes (FIG. 41B) and peripheral T lymphocytes (FIG. 41C) were evaluated by flow cytometry. As shown in FIG. 41B, 11629 depleted CD14+ monocytes in NHPs as observed after two administrations of the molecule. Cell-kill was dose-dependent and required a catalytically active Shiga toxin component as the catalytically inactivated variant, 116555, failed to elicit this response. As shown in FIG. 41C, 116297 administration resulted increases in T and B lymphocyte populations in NHPs as observed after two administrations of the molecule; such increases in lymphocyte populations was not observed after administering the catalytically inactive 116555 control PD-L1 binding molecule to NHPs. These responses were not observed with treatment of NHPs with 115749, 115765, or 115695 (see FIG. 44).

Serum cytokine responses were also evaluated across independent NHP studies. In FIG. 41D, the data is displayed as percent of responder for study 1 (sample size of 2 animals) and study 2 (8 animals tested with 116297 and 5 animals tested with 116555). The data reflects induction of cytokines at times after dose 3 of 116297 in the studies. 116297 depletion of immune cells and lymphocyte activation was associated with an immune checkpoint inhibitor inflammatory signature. Notably, 116297 treatment elicited a cytokine profile in NHPs associated with T cell activation and responses observed with immune checkpoint inhibitors in the clinic. Neither 115749, 115765, nor 115695 treatment elicited cytokine responses associated with irAEs in NHPs at any dose tested (FIG. 44).

Targeting of immune cells in patients has shown clinical benefit. For example, administration of a single agent, or combination ICI (immune checkpoint inhibitor) treatment can lead to immune activation and immune related adverse events (irAE) in correlative to favorable response. In this NHP study, however, the irAE response was only observed after combination ICI mAbs treatments at high doses, but not after a single agent ICI mAb treatment. This data suggests that the NHP model has a higher threshold for response.

As shown in FIG. 42A, 116297 treatment stimulated immune activation and resulted in pharmacodynamic and irAE profiles consistent with approved ICI combination therapies in humans (or ICI combination treatment at high doses in NHPs) but not consistent with single agent ICI NHP studies. The 116297 treatment immune related responses are dose-dependent and mediated by Shiga toxin catalytic activity. These responses are probably not mediated solely by PD-L1 signaling inhibition and/or antigen delivery because 116555 treatment at the dose(s) tested did not trigger immune activation or PD response in vivo.

116297-based therapies might represent a unique therapeutic approach with the potential for potent responses in humans as a single agent therapy, as suggested by data shown in FIG. 42B. Notably, myocarditis and dermatitis are common immune-related adverse events (irAE) observed with combination immune checkpoint inhibitors in clinical settings and are associated with beneficial therapeutic responses. irAEs in the form of myocarditis or dermatitis were also observed with 116297 treatment in a dose-dependent manner and resolved with cessation of dosing. Adverse events associated with 116927 might benefit from the relatively short half-life of the molecule (on the order of hours) (see FIG. 40A). 116297 induced irAEs were associated with infiltration of T lymphocytes into the cardiac tissue and which was not observed in the absence of Shiga toxin catalytic activity as treatment with 116555 did not elicit myocarditis, dermatitis, or infiltration of T lymphocytes into the cardiac tissue. Additionally, other PD-L1 binding molecules, 115765 (SEQ ID NO: 161) or 115695 (SEQ ID NO: 162) did not elicit these responses. Administration of 115749, which comprises the same Ig heavy and light variable domain regions but a different scFv linker as 116297, did not elicit myocarditis but did result in dermatitis (see FIG. 44).

Taken together, these data indicate that 116297 possess unique properties amongst the PD-L1 binding molecules tested. 116297 exhibited the most potent in vitro cytotoxicity against a variety of PD-L1 positive tumor cells, and treatment with 116297 results in tumor growth delay and survival benefits in NSCLC PDX in vivo model (see, e.g., FIG. 29A-29C). 116297 directly killed PD-L1 positive immune cells. 116297 treatment elicits an immune mediated irAE profile in NHPs that is similar to an irAE profile associated with clinical benefit in patients treated with immune checkpoint inhibitors. Targeting cells for depletion with 116297 may lead to unique benefits in the clinic not observed with antibody block which mediates activity through steric block alone, as shown in FIG. 42A. 116297 stimulates immune activation and a pharmacodynamic and irAE profile consistent with combination but not single agent checkpoint inhibitors in NHPs.

Because irAEs have not be seen in NHP models with monotherapy mAb checkpoint inhibitors, the irAE responses induced by 116297 treatment suggests the possibility of benefits to patients as a unique PD-L1 targeted monotherapy. 116297 targets PD-L1 with multiple mechanisms of action, which might provide improved responses than have been observed with government regulatory approved PD-L1 monoclonal antibodies administered at approved dosages.

Example 9. Comparison of the Activities of PD-L1 Binding Molecules

The purpose of this study was to compare the ability of 116297 and other PD-L1 binding molecules to induce an antigen-specific T-lymphocyte (AST) response in target cells, as a function of time target cells are exposed to the molecules.

PD-L1 binding molecules comprising distinct binding domains were compared against each other in a co-culture cell viability assay. Briefly, PD-L1 binding molecules were incubated with PD-L1 positive and HLA:A*02 positive target cells at high density for either 4 hours or 24 hours (See Table 15). The binding molecules were then washed off. Each PD-L1 binding molecule tested comprised a peptide antigen (NLVPMVATV, SEQ ID NO: 78) for delivery to the target cells. Subsequently, cytotoxic T lymphoctyes (CTLs) restricted to the peptide antigen delivered by the binding molecules were co-cultured with the pre-treated target cells, at an effector cell to target cell ratio of 1:1. After 48 hours of co-culture, supernatants were harvested and used for detection of IFN-γ as a readout for CTL activation by ELISA. Viability was also measured at 60-72 hours using an IncuCtye S3 (Sartorius) system, as determined by confluency of the monolayer. PD-L1 binding molecules were compared for their ability to promote direct cell kill or mediate T cell activation (i.e., IFN-γ secretion) after acute incubation and washout (4 h) or sustained incubation with target (24 h).

TABLE 15

PD-L1 and HLA:A*02 Positive Target Cells and HLA:A*02 NLVPMVATV (SEQ ID NO: 78) Restricted Effector Cells

| Donor ID or Cell Line | Cell Type | Characteristics |
|---|---|---|
| MDA-MB-231 | Epithelial; adenocarcinoma | PD-L1 + and HLA:A*02 + 10,000 cells/well in 40 µL media in a 96-well plate |
| HCMV-CTL | Primary T Cell | HLA:A*02 NLVPMVATV restricted Used at 1:1 Effector to target ratio |

Results are shown in FIG. 45A, 45B and summarized below in Table 16. The PD-L1 binding molecules tested demonstrated T cell dependent activation and cell kill. The potency of T cell activation, as measured by IFN-γ secretion as well as the cell-kill response elicited in the presence of CTLs was increased overall for 24 hour 'sustained' incubation experiments as compared to 4 hour 'acute' PD-L1 binding molecule incubation experiments (FIG. 45A).

Of note, 116297 and 116555 (which contains two point mutations in Shiga toxin effector polypeptide component to reduce the enzymatic activity of the molecule) elicited increased IFN-γ secretion from T cells after 'acute' stimulation (~20 µg/mL), compared to other PD-L1 binding molecules tested, and that IFN-γ secretion was further increased to −40-80 μg/mL after 'sustained' PD-L1 binding molecule exposure. This was not observed with two other PD-L1 binding molecules, comprised of non-related binding domains (115765 and 114895), which only elicited IFN-γ secretion of ~20 μg/mL after sustained but not acute exposure (FIG. 45A).

Further, 116297 demonstrated an ability to elicit CTL mediated cell kill of 40% of a PD-L1-expressing cell population after a 4-hour incubation and washout. This 40% cell-kill level was not observed with other PD-L1 binding molecules tested comprising different binding domains.

Other PD-L1 binding molecules tested (115765 and 115749) required 24 hours of sustained exposure to induce CTL mediated killing of at least 40% of a population of target cells (FIG. 45B).

The data described above indicates that 116297 displays more rapid and potent T cell activation compared to other PD-L1 binding molecules comprising different scFv binding domains or scFv linkers. The data described above for the catalytically inactivated variant of 116297, 116555, provides supporting evidence of desirable properties exhibited by PD-L1 binding molecules tested are correlated with the binding domain structure of 116297 and 116555. The absence of this activity in experiments using 115749 (which retains the same heavy and light chain variable regions as 116297 binding domain but differs in the scFv linker resulting in a monomeric and not homodimeric molecule) suggests that the activities and potency of 116297 might be attributable to the combination of the structure/function of its binding domain and its overall homodimeric structure.

TABLE 16

| Assay results | | | | |
|---|---|---|---|---|
| | T-cell activation (IFN-γ, pg/mL) | | T-cell cytotoxicity (Max % kill) | |
| PD-L1 binding molecule | Acute (4 h) | Sustained (24 h) | Acute (4 h) | Sustained (24 h) |
| 116297 | 38 | 82 | 67 | 54 |
| 116555 | 34 | 154 | 95 | 65 |
| 115749 | 13 | 29 | 96 | 53 |
| 115765 | 15 | 46 | 96 | 48 |
| 114895 | 1.7 | 59 | 99 | 50 |
| | T-cell activation (IFN-γ, pg/mL) | | T-cell cytotoxicity (CD50 ng/mL) | |
| PD-L1 binding molecule | Acute (4 h) | Sustained (24 h) | Acute (4 h) | Sustained (24 h) |
| 116297 | >10,000 | 502 | >10,000 | 218 |
| 116555 | >10,000 | 5038 | >10,000 | 685 |
| 115749 | >10,000 | >10,000 | >10,000 | 869 |
| 115765 | >10,000 | >10,000 | >10,000 | 1338 |
| 114895 | >10,000 | >10,000 | >10,000 | 2488 |

The ability of 116297 and other unique PD-L1 binding molecules to specifically deplete immune cells was also tested. The goal of these studies was to determine whether 116297 displays activities that correlate to monocyte depletion and the development of immune-related adverse events (irAE) in non-human primates (NHPs) that were not observed with other PD-L1 binding molecules.

PD-L1 binding molecules were incubated with either (i) primary human monocytes (IC) treated with IFN-γ (100 IU/mL) to induce PD-L1 expression, (ii) HCC1954 tumor cells, which express high levels of PD-L1, or (iii) MCF7 tumor cells, which do not express PD-L1 (See Table 17). The PD-L1 binding molecules were added to cells using a dose series, with the final PD-L1 binding molecule concentration ranging from 0.631-20,000 ng/mL (6- or 8-fold dilutions) and left in culture throughout the duration of the study. On Day 5 of the assay, cells were evaluated for viability using a standard CELLTITER-GLO® (cell viability) assay, as described above.

TABLE 17

| Target cells | | |
|---|---|---|
| Donor ID or Cell Line | Cell Type | Cell Number for Cytotoxicity Assay |
| Donor 1 CC00152 | CD14 + Monocyte | 5,000 cells/well in 20 μL media in a 384-well plate |
| Donor 1 M6206 | CD14 + Monocyte | 5,000 cells/well in 20 μL media in a 384-well plate |
| Donor 3 M6541 | CD14 + Monocyte | 5,000 cells/well in 20 μL media in a 384-well plate |
| Donor 4 M7488 | CD14 + Monocyte | 5,000 cells/well in 20 μL media in a 384-well plate |
| HCC1954 | Epithelial; ductal carcinoma | 1,000 cells/well in 20 μL media in a 384-well plate |

TABLE 17-continued

| Donor ID or Cell Line | Cell Type | Cell Number for Cytotoxicity Assay |
|---|---|---|
| MCF7 | Epithelial; adenocarcinoma | 1,000 cells/well in 20 μL media in a 384-well plate |

Results are shown in FIG. 46A, 46B and summarized in Table 18. 116297 elicited a dose-dependent depletion of a representative IC population of primary monocytes by reducing viability by ~60% at 20 μg/mL and 40% at 2 μg/mL across cells from four individual donors. Similar responses were observed with the PD-L1 binding molecules 114963 (SEQ ID NO: 260), 114964 (SEQ ID NO: 261), and 115695 (SEQ ID NO: 162) which lack a C-terminal CD8+ T-cell epitope-peptide cargo. Of note, additional PD-L1 binding molecules displayed reduced potency on monocytes compared to 116297, including 115749 a monomeric variant of 116297, which contains the same binding domain and antigenic peptide cargo as 116297, as well as additional PD-L1 binding molecules 115765 and 114895, which comprise different binding domains and comprising the same peptide antigen cargo.

114962 (SEQ ID NO: 259) which lacks a C-terminal peptide-antigen cargo failed to target monocytes for cell depletion as did 116555, an analogue of 116297 having point mutations (Y77S, E167D) which render the enzymatic potency of SLTA-I severely attenuated. A negative control, DI-SLTA alone did not show direct activity on monocytes tested in the assay.

In contrast to differential activity of different PD-L1 binding molecules toward monocytes, PD-L1 binding molecules showed similar potency toward the TC line, HCC1954, which expresses the PD-L1 target, and similar lack of activity toward the PD-L1 negative control line MCF7.

TABLE 18

| PD-L1 binding molecule | Cytotoxicity (CD50 ng/mL) | | Cytotoxicity (Max % kill) | |
|---|---|---|---|---|
| | TC | IC | TC | IC |
| 116297 | 7.2 | 8531 | 98 | 38 |
| 116555 | >20,000 | >20,000 | 0 | 9 |
| 115749 | 35 | >20,000 | 97 | 15 |
| 115695 | 29 | 5969 | 99 | 34 |
| 115765 | 4.7 | >20,000 | 99 | 27 |
| 114895 | 87 | >20,000 | 98 | 0 |
| 114963 | 6.4 | 10,248 | 99 | 3 |
| 114964 | 8.4 | 2218 | 98 | 36 |
| 114962 | 35.6 | >20,000 | 96 | 0 |

All PD-L1 binding molecules tested elicited potent cell kill of the TC control line (Max response >90%) and displayed potencies at less than 10 ng/mL with the exception of 114962, 115749, and 114895 (>35 ng/mL). 116297, 115695, 114964, and 115963 each showed comparable selective cytotoxicity for PD-L1 positive cell. 115765, 115749 and 114895 showed reduced activity compared to 116297 at 20 μg/mL and were not able to deplete monocytes (responses similar to the catalytically inactive 116555) at the lower 2 μg/mL concentration.

Together these data demonstrate that while PD-L1 binding molecules show similar potency ranges against TC's in vitro, potency toward IC subsets, such as monocytes, is present only in a subset of these molecules. This subset of molecules includes 116297, 115695, 114964, and 115963. Of note, only 116297 within this subset represents a PD-L1 binding molecule with the capacity to deliver direct cytotoxicity via SLTA enzymatic activity and indirect cytotoxicity via delivery of CD8+ T-cell epitope-peptide and CTL engagement. Further, this in vitro activity of 116297 correlates with the observation of in vivo depletion of monocytes by 116297 in NHPs, which was not observed with other molecules tested, e.g. 115695, 115749, or 115765 treatment did not result in IC depletion, immune related adverse event generation, or immune stimulatory activity in in vivo NHPs studies.

Example 10. PD-L1 Binding Molecules that Bind to PD-L1 and Comprise a Shiga Toxin a Subunit Scaffold In this example, a binding region which binds an extracellular part of a PD-L1 target biomolecule comprising a heavy chain variable region comprising three CDRs, each comprising or consisting essentially of an amino acid sequence show in any one of SEQ ID NOs: 27, 29, 30, and/or 32, and a light chain variable region comprising three CDRs having at least 95%, 96%, 97%, 98%, or 99% identity to SEQ ID NO:19, SEQ ID NO:20, SEQ ID NO:21, SEQ ID NO:25, and/or SEQ ID NO:26, is fused to a toxin or a fragment or derivative thereof. In some embodiments, the binding region is fused to a Shiga toxin effector polypeptide (such as, e.g., any one of SEQ ID NOs: 1-18 and 40-68). The Shiga toxin effector region is derived from the A subunit of a Shiga toxin or Shiga-like toxin (e.g. any one of SEQ ID NOs: 1-18), optionally such that it comprises a combination of sub-regions described herein to provide two or more of the following: 1) de-immunization, 2) protease-cleavage resistance, and/or 3) an embedded or inserted, heterologous, T-cell epitope (such as e.g., a Shiga toxin effector polypeptide described in any one of WO 2014/164680, WO 2014/164693, WO 2015/138435, WO 2015/138452, WO 2015/113005, WO 2015/113007, WO 2015/191764, WO 2016/196344, WO 2017/019623, WO 2018/106895, and WO 2018/140427).

The resulting fusion protein is produced and purified as a single-chain polypeptide or multimer, which is optionally multivalent (e.g. comprising two or more PD-L1 binding regions). The exemplary proteins of this example are optionally created with a carboxy-terminal KDEL-type signal motif using techniques known in the art and optionally linked to an additional exogenous material, such as, a CD8+ T-cell epitope-peptide cargo and/or detection promoting agent(s). The exemplary proteins of this example are tested as described in the previous examples using cells expressing the appropriate PD-L1 molecule. The exemplary PD-L1 targeting fusion proteins of this example may be used, e.g., to kill PD-L1 expressing cells, to label subcellular compartments of target cells and to diagnose and treat diseases, conditions, and/or disorders, such as, e.g. various cancers and tumors.

SUMMARY 116927 was selected from amongst other PD-L1 binding molecules tested based on its cytotoxic potency to PD-L1 expressing cells in vitro and has additionally shown unexpected activities in a non-human primate model. 116297 administration to PD-L1 expressing cells resulted in the most potent Shiga toxin A subunit catalytic activity-mediated cytotoxic potency to two PD-L1 positive tumor lines, a PD-L1 high (+++) and intermediate (++) when compared to other PD-L1 targeted molecules having different immunoglobulin binding domains (e.g. 115765 or 114895) or a different scFv-linker (115749) (see FIG. 43A, 43B). The greater relative cytotoxic potency of 116297 to other PD-L1 targeted molecules was maintained as PD-L1 cell-surface expression levels decreased, suggesting 116297 might have a larger therapeutic window and/or might be able to more potently kill PD-L1 expressing cells with more moderate PD-L1 expression as compared to other PD-L1 binding molecules (see FIG. 43A, 43B). Furthermore, 116297 (SEQ ID NO:128) might be cytotoxic to tumor cells in vivo in the absence of tumor infiltrating lymphocytes and regardless of the immune modulatory status of the tumor microenvironment, e.g. regardless if the tumor is characterized as "hot" or "cold", non-inflamed, or immune-excluded tumors.

116297 (SEQ ID NO:128) was capable of exhibiting survival benefits and anti-tumor activity in human patient derived xenograft mouse models. Intravenous administration of 116297 (SEQ ID NO:128) at 450 µg/kg over 4 weeks was tolerated by non-human primates. 116297 (SEQ ID NO:128) exhibits potent cytotoxic activity against clinically relevant tumor cells 116297 (SEQ ID NO:128) with some relation to PD-L1 expression level. 116297 (SEQ ID NO:128) is capable of exhibiting three distinct mechanisms of action: #1) direct cell-kill of PD-L1 expressing cells via cellular internalization and catalytic activity; #2) indirect cell-kill of PD-L1 expressing cells via antigen delivery, presentation, and CTL recognition; and #3) blockade of the PD-1/PD-L1 interaction. While 116297 (SEQ ID NO:128) might kill healthy peripheral immune cells that express PD-L1, this could be limited to a subset of monocytes which have elevated PD-L1 expression and could provide a benefit at tumor sites if these immune cells with elevated PD-L1 levels are inhibiting immune responses to tumor cells.

Monoclonal antibodies (mAbs) targeting PD-L1 act as immune checkpoint inhibitors and operate by physically inhibiting the interaction between PD-L1 and PD-1 to prevent immune checkpoint activation and restore T cell functionality toward tumor cells.

MAbs that act as immune checkpoint inhibitors (ICIs), including mAbs targeting PD-1, PD-L1, and CTLA-4 are reported to provide good clinical benefit. Although the majority of patients receiving ICIs do not experience immune related adverse events (irAEs), the clinical benefit of ICI treatments has been correlated with immune related responses, such as irAEs (see Das S et al. J Immunother Cancer 7: 306 (2019)). In non-human primate (NHP) studies, approved ICI single agent treatments do not result in any irAE at any dose. However, in NHP models single agent ICI mAb administration can result in irAEs when given in combinations of two or more ICI mAbs and at doses that are well above the expected clinical dose (Changhua J et al., Clin Cancer Res 25: 4735-48 (2019)). As described in the Examples herein, it was unexpectedly observed that 116297 administration as a single agent to NHPs resulted in irAEs in a significant proportion of the animals.

As described in the Examples, 116297 administration to NHPs can result in immune activation and the presentation of irAEs which are similar to those correlated with beneficial responses in patients treated with ICIs (see FIG. 42B; Nakamura Y, Front Med (Lausanne) 6: 119 (2019)). The activities of 116297 are differentiated from the ICI mAbs as 116297 produces these effects as a single agent. Furthermore, these responses are associated with depletion of monocytes which are shown to be depleted in a PD-L1 expression-dependent manner and therefore link the ability of 116297 to induce immune activation and irAEs to the pharmacodynamic effects associated with PD-L1 targeting.

116297 treatment of NHPs resulted in dose-dependent peripheral expansion of immune subsets including T-lymphocytes, B-lymphocytes, NK cells, and eosinophils. Immune expansion was associated with cytokine secretion, including IL-6, IL-10, IFN-gamma, TNF-alpha, and IL-2 (see FIG. 42B). The functional immune activities observed were further associated with immune infiltration into cardiac tissue (myocarditis) and the development of dermatitis irAEs that are similar to irAEs which have been observed after ICI treatment in the clinical setting (Nakamura et al. 2019). These irAEs induced by the PD-L1 binding molecule were resolved with dose cessation in line with the short half-life of 116297.

As shown in the Examples, the properties of 116297 are dependent on the Shiga toxin A subunit catalytic mechanism of cell kill because administration of a PD-L1 binding molecule variant, 116555, having point mutations that inactivated the catalytic activity of the Shiga toxin component did not display any immune activation, cellular depletion, or presentation of any irAEs in NHP (see FIGS. 41B, 41C, and 41D).

Additionally, the properties of 116297 were correlated with the scFv CDRs, heavy and light chains, and/or the scFv linker, as molecules with different variable domains (115765 and 115695) did not have the same effects in the primate model despite being dosed at comparable doses and greater frequency in NHPs compared to 116297 (FIG. 44). 115765 and 115695 did not display signs of direct clearance of immune subsets, immune subset expansion, or tissue infiltration to promote irAE development in NHP studies.

115749, a monomeric and monovalent PD-L1 binding molecule, which contains the same binding domain as 116297 but differs in the scFv-linker length did not display immune depletion or activation but some signs of irAE development (dermatitis), suggesting a dependence to the specific binding properties of the Ig domains shared between 116297 and 115749 and demonstrating that full immune activation and irAE development in NHPs might be due to additional structure/function unique to 116297 beyond the heavy and light chains.

While some embodiments of the invention have been described by way of illustration, it will be apparent that the invention may be put into practice with many modifications, variations and adaptations, and with the use of numerous equivalents or alternative solutions that are within the scope of persons skilled in the art, without departing from the spirit of the invention.

All publications, patents, and patent applications are herein incorporated by reference in their entirety to the same extent as if each individual publication, patent or patent application was specifically and individually indicated to be incorporated by reference in its entirety. The international patent application publications WO 2014/164680, WO 2014/164693, WO 2015/138435, WO 2015/138452, WO 2015/113005, WO 2015/113007, WO 2015/191764, WO 2016/196344, WO 2017/019623, WO 2018/106895, WO 2018/140427, WO 2019/183093, and WO 2020/154475, are each incorporated herein by reference in its entirety. The disclosures of U.S. patent applications US2015/259428, US2016/17784, US2017/143814, and U.S. 62/644,832, are

What is claimed is:

1. A method of treating cancer in a human subject in need thereof, the method comprising administering to the subject a therapeutically effective amount of a PD-L1 binding molecule comprising a Shiga toxin effector polypeptide and a binding region capable of specifically binding an extracellular part of PD-L1;

wherein the binding region comprises:

(a) a heavy chain variable region ($V_H$) comprising:

(i) a CDR1 comprising the amino acid sequence EYTMH (SEQ ID NO:27), (ii) a CDR2 comprising the amino acid sequence GINPNNGGTWYNQKFKG (SEQ ID NO:29), and (iii) a CDR3 comprising the amino acid sequence PYYYGSREDYFDY (SEQ ID NO:32); and (b) a light chain variable region ($V_L$) comprising:

(i) a CDR1 comprising the amino acid sequence SASSSVSYMY (SEQ ID NO:19), (ii) a CDR2 comprising the amino acid sequence LTSNLAS (SEQ ID NO:20), and (iii) a CDR3 comprising the amino acid sequence QQWSSNPPT (SEQ ID NO:26); and wherein the subject has the cancer, and wherein the cancer comprises PD-L1 expressing tumor cells.

2. The method of claim 1, wherein the Shiga toxin effector polypeptide comprises the sequence of SEQ ID NO: 41, or a sequence at least 90% identical thereto.

3. The method of claim 1, wherein the $V_H$ comprises the sequence of SEQ ID NO: 34.

4. The method of claim 1, wherein the $V_L$ comprises the sequence of SEQ ID NO: 35.

5. The method of claim 1, wherein the $V_H$ comprises the sequence of SEQ ID NO: 34 and the $V_L$ comprises the sequence of SEQ ID NO: 35.

6. The method of claim 1, wherein the binding region comprises a scFv linker that links the $V_H$ and the $V_L$.

7. The method of claim 6, wherein the scFv linker comprises the sequence of SEQ ID NO: 72.

8. The method of claim 1, wherein the binding region is a single chain variable fragment (scFv).

9. The method of claim 1, wherein the binding region comprises the sequence of SEQ ID NO: 106, or a sequence at least 90% identical thereto.

10. The method of claim 1, wherein the PD-L1 binding molecule comprises a binding domain linker which links the Shiga toxin effector polypeptide and the binding region.

11. The method of claim 10, wherein the binding domain linker comprises the sequence of SEQ ID NO: 73.

12. The method of claim 10, wherein the PD-L1 binding molecule comprises, from N-terminus to C-terminus, the Shiga toxin effector polypeptide, the binding domain linker, the $V_H$, and the $V_L$.

13. The method of claim 1, wherein the PD-L1 binding molecule comprises a CD8+ T-cell epitope that is heterologous to Shiga toxin A subunits.

14. The method of claim 13, wherein the CD8+ T-cell epitope comprises the sequence NLVPMVATV (SEQ ID NO: 78).

15. The method of claim 13, wherein the CD8+ T-cell epitope is linked to the binding region via a spacer.

16. The method of claim 15, wherein the spacer has the sequence HHAA (SEQ ID NO: 265).

17. The method of claim 13, wherein the PD-L1 binding molecule comprises, from N-terminus to C-terminus, the Shiga toxin effector polypeptide, a binding domain linker, the $V_H$, an scFv linker, the $V_L$, and the CD8+ T-cell epitope.

18. The method of claim 1, wherein the PD-L1 binding molecule comprises the sequence of SEQ ID NO: 128, or a sequence at least 95% identical thereto.

19. The method of claim 1, wherein the PD-L1 binding molecule is a single continuous polypeptide.

20. The method of claim 1, wherein the PD-L1 binding molecule comprises two polypeptides.

21. The method of claim 20, wherein each of the two polypeptides comprises the sequence of SEQ ID NO: 128.

22. The method of claim 20, wherein the two polypeptides are non-covalently linked to each other.

23. The method of claim 20, wherein the two polypeptides are non-covalently linked to each other via the binding region.

24. The method of claim 1, wherein the PD-L1 binding molecule is cytotoxic.

25. The method of claim 1, wherein the PD-L1 binding molecule is non-cytotoxic.

26. The method of claim 1, wherein the cancer is characterized by a high mutational burden and/or a high frequency of indels.

27. The method of claim 1, wherein the cancer is a solid tumor.

28. The method of claim 1, wherein the cancer is bladder cancer, breast cancer, colon cancer, endometrial cancer, esophageal cancer, fallopian tube cancer, gastrointestinal cancer, glioma, head and neck cancer, kidney cancer, liver cancer, lung cancer, lymphoma, Merkel cell carcinoma, mesothelioma, myeloma, nasopharyngeal neoplasm, ovarian cancer, pancreatic cancer, peritoneal neoplasm, prostate cancer, skin cancer, transitional cell carcinoma, or urothelial cancer.

29. The method of claim 1, wherein the cancer is bladder cancer, and the bladder cancer is urothelial carcinoma.

30. The method of claim 1, wherein the cancer is breast cancer, and the breast cancer is HER2 positive breast cancer or triple negative breast cancer.

31. The method of claim 1, wherein the cancer is colon cancer, and the colon cancer is colorectal cancer.

32. The method of claim 1, wherein the cancer is gastrointestinal cancer, and the gastrointestinal cancer is gastric cancer, biliary tract neoplasm, or gastroesophageal junction cancer.

33. The method of claim 1, wherein the cancer is glioma, and the glioma is glioblastoma.

34. The method of claim 1, wherein the cancer is head and neck cancer, and the head and neck cancer is squamous cell carcinoma of the head and neck.

35. The method of claim 1, wherein the cancer is kidney cancer, and the kidney cancer is renal cell carcinoma.

36. The method of claim 1, wherein the cancer is liver cancer, and the liver cancer is hepatocellular carcinoma.

37. The method of claim 1, wherein the cancer is lung cancer, and the lung cancer is non-small cell lung cancer or small-cell lung cancer.

38. The method of claim 1, wherein the cancer is lymphoma, and the lymphoma is Hodgkin lymphoma, non-Hodgkin lymphoma, primary mediastinal large B-cell lymphoma, or diffuse large B-cell lymphoma.

39. The method of claim 1, wherein the cancer is mesothelioma, and the mesothelioma is pleural mesothelioma.

40. The method of claim 1, wherein the cancer is myeloma, and the myeloma is multiple myeloma.

41. The method of claim 1, wherein the cancer is skin cancer, and the skin cancer is squamous cell cancer of the skin or melanoma.

42. The method of claim 1, wherein the cancer is relapsed or refractory to treatment with at least one of ipilimumab, nivolumab, pembrolizumab, atezolizumab, durvalumab, avelumab, tremelimumab and cemiplimab.

43. The method of claim 1, wherein the cancer is metastatic.

* * * * *

SEQUENCE LISTING

<160> NUMBER OF SEQ ID NOS: 269

<210> SEQ ID NO 1
<211> LENGTH: 293
<212> TYPE: PRT
<213> ORGANISM: Unknown
<220> FEATURE:
<223> OTHER INFORMATION: Shiga-like toxin 1 Subunit A (SLT-1A)

<400> SEQUENCE: 1

```
Lys Glu Ph

```
<220> FEATURE:
<223> OTHER INFORMATION: Shiga toxin Subunit A (StxA)

<400> SEQUENCE: 2

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290

<210> SEQ ID NO 3
<211> LENGTH: 297
<212> TYPE: PRT
<213> ORGANISM: Unknown
<220> FEATURE:
<223> OTHER INFORMATION: Shiga-like toxin 2 Subunit A (SLT-2A)

<400> SEQUENCE: 3

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
```

-continued

```
                35                  40                  45
Tyr Ile Ser Leu Asn Val Arg Gly Leu Asp Pro Tyr Ser Glu Arg Phe
 50                  55                  60

Asn His Leu Arg Leu Ile Met Glu Arg Asn Asn Leu Tyr Val Ala Gly
 65                  70                  75                  80

Phe Ile Asn Thr Glu Thr Asn Ile Phe Tyr Arg Phe Ser Asp Phe Ser
                 85                  90                  95

His Ile Ser Val Pro Asp Val Ile Thr Val Ser Met Thr Thr Asp Ser
                100                 105                 110

Ser Tyr Ser Ser Leu Gln Arg Ile Ala Asp Leu Glu Arg Thr Gly Met
            115                 120                 125

Gln Ile Gly Arg His Ser Leu Val Gly Ser Tyr Leu Asp Leu Met Glu
        130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
            260                 265                 270

Asn Val Leu Trp Glu Ala Asn Thr Ile Ala Ala Leu Leu Asn Arg Lys
        275                 280                 285

Pro Gln Asp Leu Thr Glu Pro Asn Gln
    290                 295

<210> SEQ ID NO 4
<211> LENGTH: 251
<212> TYPE: PRT
<213> ORGANISM: Unknown
<220> FEATURE:
<223> OTHER INFORMATION: Shiga toxin subtype c Subunit A (Stx1cA)

<400> SEQUENCE: 4

Lys Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Thr Gly Asp Asn
            35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
```

```
                100             105             110
Ser Tyr Thr Thr Leu Gln Arg Val Ala Gly Ile Ser Arg Thr Gly Met
            115                 120             125

Gln Ile Asn Arg His Ser Leu Thr Thr Ser Tyr Leu Asp Leu Met Ser
            130                 135             140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170             175

Gly Phe Arg Thr Thr Leu Asp Asp Leu Ser Gly Arg Ser Tyr Val Met
            180                 185             190

Thr Ala Glu Asp Val Asp Leu Thr Leu Asn Trp Gly Arg Leu Ser Ser
            195                 200             205

Val Leu Pro Asp Tyr His Gly Gln Asp Ser Val Arg Val Gly Arg Ile
            210                 215             220

Ser Phe Gly Ser Val Asn Ala Ile Leu Gly Ser Val Ala Leu Ile Leu
225                 230                 235                 240

Asn Cys His His His Ala Ser Arg Val Ala Arg
                245                 250

<210> SEQ ID NO 5
<211> LENGTH: 251
<212> TYPE: PRT
<213> ORGANISM: Unknown
<220> FEATURE:
<223> OTHER INFORMATION: Shiga toxin subtype d Subunit A (Stx1dA)

<400> SEQUENCE: 5

Lys Glu Phe Thr Leu Asp Phe Ser Thr Ala Lys Lys Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Ile Met Gly Leu Glu Pro Glu Glu Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Arg Ala Val Thr Leu Ser Gly Asp Ser
            100                 105             110

Ser Tyr Thr Thr Leu Gln Arg Val Ala Gly Ile Ser Arg Thr Gly Met
            115                 120             125

Gln Ile Asn Arg His Ser Leu Thr Thr Ser Tyr Leu Asp Leu Met Ser
            130                 135             140

Tyr Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170             175

Gly Phe Arg Thr Thr Leu Asp Asp Leu Ser Gly Arg Ser Tyr Val Met
            180                 185             190

Thr Ala Glu Asp Val Asp Leu Thr Leu Asn Trp Gly Arg Leu Ser Ser
            195                 200             205

Ile Leu Pro Asp Tyr His Gly Gln Asp Ser Val Arg Val Gly Arg Ile
```

```
        210                 215                 220
Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 6
<211> LENGTH: 251
<212> TYPE: PRT
<213> ORGANISM: Unknown
<220> FEATURE:
<223> OTHER INFORMATION: Shiga toxin subtype e Subunit A (Stx1eA)

<400> SEQUENCE: 6

```
Gln Asp Phe Thr Val Asp Phe Ser Thr Ala Lys Lys Tyr Val Asp Ser
1               5                   10                  15

Leu Asn Ala Ile Arg Ser Ala Ile Gly Thr Pro Leu His Ser Ile Ser
                20                  25                  30

Ser Gly Gly Thr Ser Leu Leu Met Ile Asp Asn Gly Thr Gly Asp Asn
            35                  40                  45

Leu Phe Ala Val Asp Ile Arg Gly Leu Asp Pro Glu Glu Glu Arg Phe
50                  55                  60

Asp Asn Leu Arg Leu Ile Ile Glu Arg Asn Asn Leu Tyr Val Thr Gly
65                  70                  75                  80

Phe Val Asn Arg Thr Ser Asn Ile Phe Tyr Arg Phe Ala Asp Phe Ser
                85                  90                  95

His Val Thr Phe Pro Gly Thr Arg Ala Val Thr Leu Ser Gly Asp Ser
                100                 105                 110

Ser Tyr Thr Thr Leu Gln Arg Val Ala Gly Ile Gly Arg Thr Gly Met
            115                 120                 125

Gln Ile Asn Arg His Ser Leu Thr Thr Ser Tyr Leu Asp Leu Met Ser
130                 135                 140

Tyr Ser Gly Ser Ser Leu Thr Gln Pro Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Val Ser Gly His Ser Tyr Thr Met
                180                 185                 190

Thr Val Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Gly Val Asn Ala Ile Leu Gly Ser Val Ala Leu Ile Leu
225                 230                 235                 240

Asn Cys His His His Thr Ser Arg Val Ser Arg
                245                 250
```

<210> SEQ ID NO 7
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 1

<400> SEQUENCE: 7

```
Arg Glu Phe Thr Ile Asp Phe Ser Thr Gln Gln Ser Tyr Val Ser Ser
1               5                   10                  15
```

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
 50                  55                  60

Asp His Leu Arg Leu Ile Ile Glu Gln Asn Asn Leu Tyr Val Ala Gly
 65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Val Ser Met Thr Thr Asp Ser
            100                 105                 110

Ser Tyr Thr Thr Leu Gln Arg Val Ala Ala Leu Glu Arg Ser Gly Met
                115                 120                 125

Gln Ile Ser Arg His Ser Leu Val Ser Ser Tyr Leu Ala Leu Met Glu
130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
                180                 185                 190

Pro Gly Asp Val Asp Leu Thr Leu Asn Trp Gly Arg Ile Ser Asn Val
                195                 200                 205

Leu Pro Glu Tyr Arg Gly Glu Asp Gly Val Arg Val Gly Arg Ile Ser
            210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 8
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 2

<400> SEQUENCE: 8

Arg Glu Phe Thr Ile Asp Phe Ser Thr Gln Gln Ser Tyr Val Ser Ser
 1               5                  10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
 50                  55                  60

Asp His Leu Arg Leu Ile Ile Glu Gln Asn Asn Leu Tyr Val Ala Gly
 65                  70                  75                  80

Phe Val Asn Thr Ala Thr Asn Thr Phe Tyr Arg Phe Ser Asp Phe Ala
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met

```
            115                 120                 125
Gln Ile Ser Arg His Ser Leu Val Ser Ser Tyr Leu Ala Leu Met Glu
        130                 135                 140
Phe Ser Gly Asn Thr Met Thr Arg Asp Ala Ser Arg Ala Val Leu Arg
145                 150                 155                 160
Phe Val Thr Val Thr Ala Glu Ala Leu Arg Phe Arg Gln Ile Gln Arg
                165                 170                 175
Glu Phe Arg Gln Ala Leu Ser Glu Thr Ala Pro Val Tyr Thr Met Thr
            180                 185                 190
Pro Gly Asp Val Asp Leu Thr Leu Asn Trp Gly Arg Ile Ser Asn Val
        195                 200                 205
Leu Pro Glu Tyr Arg Gly Glu Asp Gly Val Arg Val Gly Arg Ile Ser
210                 215                 220
Phe Asn Asn Ile Ser Ala Ile Leu Gly Thr Val Ala Val Ile Leu Asn
225                 230                 235                 240
Cys His His Gln Gly Ala Arg Ser Val Arg
                245                 250

<210> SEQ ID NO 9
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 3

<400> SEQUENCE: 9

Arg Glu Phe Thr Ile Asp Phe Ser Thr Gln Gln Ser Tyr Val Ser Ser
1               5                   10                  15
Leu Asn Ser Ile Arg Thr Glu Ile Ser Thr Pro Leu Glu His Ile Ser
            20                  25                  30
Gln Gly Thr Thr Ser Val Ser Val Ile Asn His Thr Pro Pro Gly Ser
        35                  40                  45
Tyr Phe Ala Val Asp Ile Arg Gly Leu Asp Ile Tyr Gln Ala Arg Phe
    50                  55                  60
Asp His Leu Arg Leu Ile Ile Glu Gln Asn Asn Leu Tyr Val Ala Gly
65                  70                  75                  80
Phe Val Asn Thr Ala Thr Asn Thr Phe Tyr Arg Phe Ser Asp Phe Thr
                85                  90                  95
His Ile Ser Val Pro Gly Val Thr Thr Val Ser Met Thr Thr Asp Ser
            100                 105                 110
Ser Tyr Thr Thr Leu Gln Arg Val Ala Ala Leu Glu Arg Ser Gly Met
        115                 120                 125
Gln Ile Ser Arg His Ser Leu Val Ser Ser Tyr Leu Ala Leu Met Glu
    130                 135                 140
Phe Ser Gly Asn Thr Met Thr Arg Asp Ala Ser Arg Ala Val Leu Arg
145                 150                 155                 160
Phe Val Thr Val Thr Ala Glu Ala Leu Arg Phe Arg Gln Ile Gln Arg
                165                 170                 175
Glu Phe Arg Gln Ala Leu Ser Glu Thr Ala Pro Val Tyr Thr Met Thr
            180                 185                 190
Pro Gly Asp Val Asp Leu Thr Leu Asn Trp Gly Arg Ile Ser Asn Val
        195                 200                 205
Leu Pro Glu Tyr Arg Gly Glu Asp Gly Val Arg Val Gly Arg Ile Ser
210                 215                 220
```

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 10
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 4

<400> SEQUENCE: 10

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Ser Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 11
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 5

<400> SEQUENCE: 11

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Met Ala Gly
65                  70                  75                  80

Phe Val Asn Thr Ala Thr Asn Thr Phe Tyr Arg Phe Ser Asp Phe Thr
                85                  90                  95

His Ile Ser Val Pro Ser Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 12
<211> LENGTH: 250
<212> TYPE: PRT
<213> ORGANISM: Artificial Sequence
<220> FEATURE:
<223> OTHER INFORMATION: Shiga toxin subtype 2c Subunit A (Stx2cA)
      variant 6

<400> SEQUENCE: 12

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

```
Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Val Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Ser Thr Val Ala Val Ile Leu Asn
225                 230                 235                 240

Cys His His Gln Gly Ala Arg Ser Val Arg
                245                 250

<210> SEQ ID NO 13
<211> LENGTH: 250
<212> TYPE: PRT
<213> ORGANISM: Artificial Sequence
<220> FEATURE:
<223> OTHER INFORMATION: Shiga toxin subtype 2d Subunit A (Stx2dA)
      variant 1

<400> SEQUENCE: 13

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Ala
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Ile Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
```

Cys His His Gln Gly Ala Arg Ser Val Arg
                245                 250

<210> SEQ ID NO 14
<211> LENGTH: 250
<212> TYPE: PRT
<213> ORGANISM: Artificial Sequence
<220> FEATURE:
<223> OTHER INFORMATION: Shiga toxin subtype 2d Subunit A (Stx2dA)
      variant 2

<400> SEQUENCE: 14

Arg Glu Phe Met Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Glu Glu Val Asp Leu Thr Leu Asn Trp Gly Arg Ile Ser Asn Val
        195                 200                 205

Leu Pro Glu Phe Arg Gly Glu Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 15
<211> LENGTH: 250
<212> TYPE: PRT
<213> ORGANISM: Artificial Sequence
<220> FEATURE:
<223> OTHER INFORMATION: Shiga toxin subtype 2d Subunit A (Stx2dA)
      variant 3

<400> SEQUENCE: 15

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser

```
            20                  25                  30
Gln Gly Thr Thr Ser Val Ser Val Ile Asn His Thr Pro Pro Gly Ser
            35                  40                  45

Tyr Phe Ala Val Asp Ile Arg Gly Leu Asp Val Tyr Gln Ala Arg Phe
        50                  55                  60

Asp His Leu Arg Leu Ile Ile Glu Gln Asn Asn Leu Tyr Val Ala Gly
 65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Thr Val Ser Met Thr Thr Asp Ser
               100                 105                 110

Ser Tyr Thr Thr Leu Gln Arg Val Ala Ala Leu Glu Arg Ser Gly Met
               115                 120                 125

Gln Ile Ser Arg His Ser Leu Val Ser Ser Tyr Leu Ala Leu Met Glu
               130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
                180                 185                 190

Pro Gly Asp Val Asp Leu Thr Leu Asn Trp Gly Arg Ile Ser Asn Val
                195                 200                 205

Ile Pro Glu Tyr Arg Gly Glu Asp Gly Val Arg Val Gly Arg Ile Ser
            210                 215                 220

Phe Asn Asn Ile Ser Ala Ile Leu Ser Thr Val Ala Val Ile Leu Asn
225                 230                 235                 240

Cys His His Gln Gly Ala Arg Ser Val Arg
                245                 250

<210> SEQ ID NO 16
<211> LENGTH: 250
<212> TYPE: PRT
<213> ORGANISM: Artificial Sequence
<220> FEATURE:
<223> OTHER INFORMATION: Shiga toxin subtype 2e Subunit A (Stx2eA)
      variant 1

<400> SEQUENCE: 16

Gln Glu Phe Thr Ile Asp Phe Ser Thr Gln Gln Ser Tyr Val Ser Ser
1               5                   10                  15

Leu Asn Ser Ile Arg Thr Ala Ile Ser Thr Pro Leu Glu His Ile Ser
                20                  25                  30

Gln Gly Ala Thr Ser Val Ser Val Ile Asn His Thr Pro Pro Gly Ser
            35                  40                  45

Tyr Ile Ser Val Gly Ile Arg Gly Leu Asp Val Tyr Gln Glu Arg Phe
        50                  55                  60

Asp His Leu Arg Leu Ile Ile Glu Arg Asn Asn Leu Tyr Val Ala Gly
 65                  70                  75                  80

Phe Val Asn Thr Thr Thr Asn Thr Phe Tyr Arg Phe Ser Asp Phe Ala
                85                  90                  95

His Ile Ser Leu Pro Gly Val Thr Thr Ile Ser Met Thr Thr Asp Ser
               100                 105                 110

Ser Tyr Thr Thr Leu Gln Arg Val Ala Ala Leu Glu Arg Ser Gly Met
               115                 120                 125
```

```
Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Leu Ala Leu Ser Glu Thr Ala Pro Val Tyr Thr Met Thr
            180                 185                 190

Pro Glu Asp Val Asp Leu Thr Leu Asn Trp Gly Arg Ile Ser Asn Val
            195                 200                 205

Leu Pro Glu Tyr Arg Gly Glu Ala Gly Val Arg Val Gly Arg Ile Ser
        210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 17
<211> LENGTH: 250
<212> TYPE: PRT
<213> ORGANISM: Artificial Sequence
<220> FEATURE:
<223> OTHER INFORMATION: Shiga toxin subtype 2e Subunit A (Stx2eA)
      variant 2

<400> SEQUENCE: 17

Gln Glu Phe Thr Ile Asp Phe Ser Thr Gln Gln Ser Tyr Val Ser Ser
1               5                   10                  15

Leu Asn Ser Ile Arg Thr Ala Ile Ser Thr Pro Leu Glu His Ile Ser
            20                  25                  30

Gln Gly Ala Thr Ser Val Ser Val Ile Asn His Thr Pro Pro Gly Ser
        35                  40                  45

Tyr Ile Ser Val Gly Ile Arg Gly Leu Asp Val Tyr Gln Ala His Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Ala
                85                  90                  95

His Ile Ser Leu Pro Gly Val Thr Thr Ile Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Glu Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Glu Asp Val Asp Leu Thr Leu Asn Trp Gly Arg Ile Ser Asn Val
            195                 200                 205

Leu Pro Glu Tyr Arg Gly Glu Asp Gly Val Arg Val Gly Arg Ile Ser
        210                 215                 220

Phe Asn Asn Ile Ser Ala Ile Leu Gly Thr Val Ala Val Ile Leu Asn
225                 230                 235                 240
```

```
Cys His His Gln Gly Ala Arg Ser Val Arg
                245                 250

<210> SEQ ID NO 18
<211> LENGTH: 250
<212> TYPE: PRT
<213> ORGANISM: Artificial Sequence
<220> FEATURE:
<223> OTHER INFORMATION: Shiga toxin subtype 2f Subunit A (Stx2fA)

<400> SEQUENCE: 18

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Pro Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Thr Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg
                245                 250

<210> SEQ ID NO 19
<211> LENGTH: 10
<212> TYPE: PRT
<213> ORGANISM: Unknown
<220> FEATURE:
<223> OTHER INFORMATION: light chain HVR CDR1

<400> SEQUENCE: 19

Ser Ala Ser Ser Ser Val Ser Tyr Met Tyr
1               5                   10

<210> SEQ ID NO 20
<211> LENGTH: 7
<212> TYPE: PRT
```

<213> ORGANISM: Unknown
<220> FEATURE:
<223> OTHER INFORMATION: light chain HVR CDR2

<400> SEQUENCE: 20

Leu Thr Ser Asn Leu Ala Ser
1               5

<210> SEQ ID NO 21
<211> LENGTH: 9
<212> TYPE: PRT
<213> ORGANISM: Unknown
<220> FEATURE:
<223> OTHER INFORMATION: light chain HVR CDR3

<400> SEQUENCE: 21

Gln Gln Trp Ser Ser Tyr Pro Pro Thr
1               5

<210> SEQ ID NO 22
<211> LENGTH: 5
<212> TYPE: PRT
<213> ORGANISM: Unknown
<220> FEATURE:
<223> OTHER INFORMATION: heavy chain HVR CDR1

<400> SEQUENCE: 22

Glu Asn Ser Met His
1               5

<210> SEQ ID NO 23
<211> LENGTH: 17
<212> TYPE: PRT
<213> ORGANISM: Unknown
<220> FEATURE:
<223> OTHER INFORMATION: heavy chain HVR CDR2

<400> SEQUENCE: 23

Gly Ile Asn Pro Asn Asn Gly Gly Thr Ser Tyr Asn Gln Lys Phe Lys
1               5                   10                  15

Gly

<210> SEQ ID NO 24
<211> LENGTH: 13
<212> TYPE: PRT
<213> ORGANISM: Unknown
<220> FEATURE:
<223> OTHER INFORMATION: heavy chain HVR CDR3

<400> SEQUENCE: 24

Pro Tyr Tyr Tyr Gly Tyr Arg Glu Asp Tyr Phe Asp Tyr
1               5                   10

<210> SEQ ID NO 25
<211> LENGTH: 10
<212> TYPE: PRT
<213> ORGANISM: Unknown
<220> FEATURE:
<223> OTHER INFORMATION: light chain HVR CDR1

<400> SEQUENCE: 25

Arg Ala Ser Ser Ser Val Ser Tyr Met Tyr
1               5                   10

<210> SEQ ID NO 26
<211> LENGTH: 9

```
<212> TYPE: PRT
<213> ORGANISM: Unknown
<220> FEATURE:
<223> OTHER INFORMATION: light chain HVR CDR3

<400> SEQUENCE: 26

Gln Gln Trp Ser Ser Asn Pro Pro Thr
1               5

<210> SEQ ID NO 27
<211> LENGTH: 5
<212> TYPE: PRT
<213> ORGANISM: Unknown
<220> FEATURE:
<223> OTHER INFORMATION: heavy chain HVR CDR1

<400> SEQUENCE: 27

Glu Tyr Thr Met His
1               5

<210> SEQ ID NO 28
<211> LENGTH: 17
<212> TYPE: PRT
<213> ORGANISM: Unknown
<220> FEATURE:
<223> OTHER INFORMATION: heavy chain HVR CDR2

<400> SEQUENCE: 28

Gly Ile Asp Pro Asn Asn Gly Gly Thr Trp Tyr Asn Gln Lys Phe Lys
1               5                   10                  15

Gly

<210> SEQ ID NO 29
<211> LENGTH: 17
<212> TYPE: PRT
<213> ORGANISM: Unknown
<220> FEATURE:
<223> OTHER INFORMATION: heavy chain HVR CDR2

<400> SEQUENCE: 29

Gly Ile Asn Pro Asn Asn Gly Gly Thr Trp Tyr Asn Gln Lys Phe Lys
1               5                   10                  15

Gly

<210> SEQ ID NO 30
<211> LENGTH: 17
<212> TYPE: PRT
<213> ORGANISM: Unknown
<220> FEATURE:
<223> OTHER INFORMATION: heavy chain HVR CDR2

<400> SEQUENCE: 30

Gly Ile Asn Pro Asn Asn Gly Gly Thr Trp Tyr Asn Arg Lys Phe Lys
1               5                   10                  15

Gly

<210> SEQ ID NO 31
<211> LENGTH: 17
<212> TYPE: PRT
<213> ORGANISM: Unknown
<220> FEATURE:
<223> OTHER INFORMATION: heavy chain HVR CDR2

<400> SEQUENCE: 31

Gly Ile Asn Pro Asn Asn Gly Gly Thr Ser Tyr Asn Gln Lys Phe Gln
1               5                   10                  15
```

-continued

```
1               5                   10                  15

Gly

<210> SEQ ID NO 32
<211> LENGTH: 13
<212> TYPE: PRT
<213> ORGANISM: Unknown
<220> FEATURE:
<223> OTHER INFORMATION: heavy chain HVR CDR3

<400> SEQUENCE: 32

Pro Tyr Tyr Tyr Gly Ser Arg Glu Asp Tyr Phe Asp Tyr
1               5                   10

<210> SEQ ID NO 33
<211> LENGTH: 106
<212> TYPE: PRT
<213> ORGANISM: Artificial Sequence
<220> FEATURE:
<223> OTHER INFORMATION: light chain 1

<400> SEQUENCE: 33

Asp Ile Val Met Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Leu Lys
            100                 105

<210> SEQ ID NO 34
<211> LENGTH: 122
<212> TYPE: PRT
<213> ORGANISM: Artificial Sequence
<220> FEATURE:
<223> OTHER INFORMATION: heavy chain 1

<400> SEQUENCE: 34

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Arg His Gly Lys Ser Leu Glu Trp Ile
        35                  40                  45

Gly Gly Ile Asn Pro Asn Asn Gly Gly Thr Trp Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Tyr Tyr Tyr Gly Ser Arg Glu Asp Tyr Phe Asp Tyr Trp
            100                 105                 110
```

```
Gly Gln Gly Thr Thr Leu Thr Val Ser Ser
            115                 120

<210> SEQ ID NO 35
<211> LENGTH: 106
<212> TYPE: PRT
<213> ORGANISM: Artificial Sequence
<220> FEATURE:
<223> OTHER INFORMATION: light chain 2

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Leu Lys
            100                 105

<210> SEQ ID NO 36
<211> LENGTH: 106
<212> TYPE: PRT
<213> ORGANISM: Artificial Sequence
<220> FEATURE:
<223> OTHER INFORMATION: light chain 3

<400> SEQUENCE: 36

Asp Ile Val Leu Asn Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 37
<211> LENGTH: 122
<212> TYPE: PRT
<213> ORGANISM: Artificial Sequence
<220> FEATURE:
<223> OTHER INFORMATION: heavy chain 2

<400> SEQUENCE: 37

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
```

```
                    20                  25                  30
Thr Met His Trp Val Lys Gln Ser His Gly Lys Ser Leu Glu Trp Ile
            35                  40                  45
Gly Gly Ile Asn Pro Asn Asn Gly Gly Thr Trp Tyr Asn Arg Lys Phe
        50                  55                  60
Lys Gly Lys Ala Ala Leu Thr Val Asp Lys Ser Ser Thr Ala Tyr
65                  70                  75                  80
Met Glu Leu Arg Ser Leu Thr Ser Glu Asp Ser Ala Val Tyr Phe Cys
                85                  90                  95
Ala Arg Pro Tyr Tyr Tyr Gly Ser Arg Glu Asp Tyr Phe Asp Tyr Trp
            100                 105                 110
Gly Gln Gly Thr Thr Leu Thr Val Ser Ser
            115                 120

<210> SEQ ID NO 38
<211> LENGTH: 106
<212> TYPE: PRT
<213> ORGANISM: Artificial Sequence
<220> FEATURE:
<223> OTHER INFORMATION: light chain 4

<400> SEQUENCE: 38

Asp Ile Gln Met Thr Gln Ser Pro Ser Ser Leu Ser Ala Ser Val Gly
1               5                   10                  15
Asp Arg Val Thr Ile Thr Cys Ser Ala Ser Ser Ser Val Ser Tyr Met
                20                  25                  30
Tyr Trp Tyr Gln Gln Lys Pro Arg Ser Ser Pro Lys Pro Trp Ile Tyr
            35                  40                  45
Leu Thr Ser Asn Leu Ala Ser Gly Val Pro Ala Arg Phe Ser Gly Ser
        50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Asn Pro Pro Thr
                85                  90                  95
Phe Gly Gly Gly Thr Lys Leu Glu Ile Lys
            100                 105

<210> SEQ ID NO 39
<211> LENGTH: 122
<212> TYPE: PRT
<213> ORGANISM: Artificial Sequence
<220> FEATURE:
<223> OTHER INFORMATION: heavy chain 3

<400> SEQUENCE: 39

Glu Val Gln Leu Gln Gln Ser Gly Pro Glu Leu Val Lys Pro Gly Ala
1               5                   10                  15
Ser Val Lys Ile Ser Cys Lys Thr Ser Gly Tyr Thr Phe Thr Glu Tyr
                20                  25                  30
Thr Met His Trp Val Lys Gln Ser His Gly Lys Ser Leu Glu Trp Ile
            35                  40                  45
Gly Gly Ile Asn Pro Asn Asn Gly Gly Thr Trp Tyr Asn Arg Lys Phe
        50                  55                  60
Lys Gly Lys Ala Ala Leu Thr Val Asp Lys Ser Ser Thr Ala Tyr
65                  70                  75                  80
Met Glu Leu Arg Ser Leu Thr Ser Glu Asp Ser Ala Val Tyr Phe Cys
                85                  90                  95
```

Ala Arg Pro Tyr Tyr Gly Ser Arg Glu Asp Tyr Phe Asp Tyr Trp
            100                 105                 110

Gly Gln Gly Thr Thr Leu Thr Val Ser Ser
            115                 120

<210> SEQ ID NO 40
<211> LENGTH: 251
<212> TYPE: PRT
<213> ORGANISM: Artificial Sequence
<220> FEATURE:
<223> OTHER INFORMATION: Shiga toxin effector polypeptide 1

<400> SEQUENCE: 40

Ala Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 41
<211> LENGTH: 251
<212> TYPE: PRT
<213> ORGANISM: Artificial Sequence
<220> FEATURE:
<223> OTHER INFORMATION: Shiga toxin effector polypeptide 2

<400> SEQUENCE: 41

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

```
Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 42
<211> LENGTH: 251
<212> TYPE: PRT
<213> ORGANISM: Artificial Sequence
<220> FEATURE:
<223> OTHER INFORMATION: Shiga toxin effector polypeptide 3

<400> SEQUENCE: 42

Lys Glu Phe Thr Leu Asp Ph

```
His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 43
<211> LENGTH: 251
<212> TYPE: PRT
<213> ORGANISM: Artificial Sequence
<220> FEATURE:
<223> OTHER INFORMATION: Shiga toxin effector polypeptide 4

<400> SEQUENCE: 43

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu

<210> SEQ ID NO 44
<211> LENGTH: 251
<212> TYPE: PRT
<213> ORGANISM: Artificial Sequence
<220> FEATURE:
<223> OTHER INFORMATION: Shiga toxin effector polypeptide 5

<400> SEQUENCE: 44

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
        50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 45
<211> LENGTH: 251
<212> TYPE: PRT
<213> ORGANISM: Artificial Sequence
<220> FEATURE:
<223> OTHER INFORMATION: Shiga toxin effector polypeptide 6

<400> SEQUENCE: 45

Ala Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ile Gly Asp Asn
            35                  40                  45

Leu Phe Ala Val Asp Ile Leu Gly Phe Asp Phe Thr Leu Gly Arg Phe

-continued

```
                50                  55                  60
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
            130                 135                 140

His Ser Ala Thr Ser Leu Thr Gln Ser Val Ala Arg Ala Met Leu Arg
145                 150                 155                 160

Phe Val Thr Val Thr Ala Asp Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250
```

<210> SEQ ID NO 46
<211> LENGTH: 251
<212> TYPE: PRT
<213> ORGANISM: Artificial Sequence
<220> FEATURE:
<223> OTHER INFORMATION: Shiga toxin effector polypeptide 7

<400> SEQUENCE: 46

```
Lys Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
                 20                  25                  30

Ser Gly Gly Thr Ser Leu Leu Met Ile Asp Ser Gly Ile Gly Asp Asn
             35                  40                  45

Leu Phe Ala Val Asp Ile Leu Gly Phe Asp Phe Thr Leu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
            130                 135                 140

His Ser Gly Thr Ser Leu Thr Gln Ser Val Ala Arg Ala Met Leu Arg
145                 150                 155                 160

Phe Val Thr Val Thr Ala Asp Ala Leu Arg Phe Arg Gln Ile Gln Arg
```

```
                    165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 47
<211> LENGTH: 251
<212> TYPE: PRT
<213> ORGANISM: Artificial Sequence
<220> FEATURE:
<223> OTHER INFORMATION: Shiga toxin effector polypeptide 8

<400> SEQUENCE: 47

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Ala Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Asp Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 48
<211> LENGTH: 251
<212> TYPE: PRT
```

<213> ORGANISM: Artificial Sequence
<220> FEATURE:
<223> OTHER INFORMATION: Shiga toxin effector polypeptide 9

<400> SEQUENCE: 48

```
Lys Glu Phe Thr Leu Asp Phe Ser Thr Ala Lys Thr Tyr Val Asp Ser
1               5                   10

```
Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Asp Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 50
<211> LENGTH: 251
<212> TYPE: PRT
<213> ORGANISM: Artificial Sequence
<220> FEATURE:
<223> OTHER INFORMATION: Shiga toxin effector polypeptide 11

<400> SEQUENCE: 50

Lys Glu Phe Ile Leu Arg Phe Ser Val Ala His Lys Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190
```

```
Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 51
<211> LENGTH: 251
<212> TYPE: PRT
<213> ORGANISM: Artificial Sequence
<220> FEATURE:
<223> OTHER INFORMATION: Shiga toxin effector polypeptide 12

<400> SEQUENCE: 51

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Asn Leu Val Pro Met Val
        35                  40                  45

Ala Thr Val Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 52
<211> LENGTH: 251
<212> TYPE: PRT
<213> ORGANISM: Artificial Sequence
<220> FEATURE:
<223> OTHER INFORMATION: Shiga toxin effector polypeptide 13

<400> SEQUENCE: 52
```

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Asn Leu Val Pro Met
        35                  40                  45

Val Ala Thr Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 53
<211> LENGTH: 251
<212> TYPE: PRT
<213> ORGANISM: Artificial Sequence
<220> FEATURE:
<223> OTHER INFORMATION: Shiga toxin effector polypeptide 14

<400> SEQUENCE: 53

Lys Glu Phe Thr Leu Asp Phe Ser Thr Ala Lys Thr Tyr Val Asp Ser
1               5                   10                  15

Leu Asn Val Ile Arg Ser Ala Ile Gly Thr

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 54
<211> LENGTH: 251
<212> TYPE: PRT
<213> ORGANISM: Artificial Sequence
<220> FEATURE:
<223> OTHER INFORMATION: Shiga toxin effector polypeptide 15

<400> SEQUENCE: 54

Lys Glu Phe Thr Leu As

-continued

```
Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 55
<211> LENGTH: 251
<212> TYPE: PRT
<213> ORGANISM: Artificial Sequence
<220> FEATURE:
<223> OTHER INFORMATION: Shiga toxin effector polypeptide 16

<400> SEQUENCE: 55

Lys Glu Phe Thr Leu Asp Phe Ser Thr Ala Lys Thr T

```
            20                  25                  30
Ser Gly Gly Thr Ser Leu Leu Met Ile Asp Ser Gly Ser Gly Asp Asn
            35                  40                  45

Leu Phe Ala Val Asp Ile Leu Gly Phe Asp Phe Thr Leu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
            130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 57
<211> LENGTH: 251
<212> TYPE: PRT
<213> ORGANISM: Artificial Sequence
<220> FEATURE:
<223> OTHER INFORMATION: Shiga toxin effector polypeptide 18

<400> SEQUENCE: 57

Lys Glu Phe Thr Leu Asp Phe Ser Thr

```
            130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 58
<211> LENGTH: 251
<212> TYPE: PRT
<213> ORGANISM: Artificial Sequence
<220> FEATURE:
<223> OTHER INFORMATION: Shiga toxin effector polypeptide 19

<400> SEQUENCE: 58

-continued

```
                245                 250

<210> SEQ ID NO 59
<211> LENGTH: 252
<212> TYPE: PRT
<213> ORGANISM: Artificial Sequence
<220> FEATURE:
<223> OTHER INFORMATION: Shiga toxin effector polypeptide 20

<400> SEQUENCE: 59

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Gly Ile Leu Gly Phe Val Phe Thr Leu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala
                245                 250

<210> SEQ ID NO 60
<211> LENGTH: 251
<212> TYPE: PRT
<213> ORGANISM: Artificial Sequence
<220> FEATURE:
<223> OTHER INFORMATION: Shiga toxin effector polypeptide 21

<400> SEQUENCE: 60

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45
```

Leu Phe Ala Val Asn Leu Val Pro Met Val Ala Thr Val Gly Arg Phe
            50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 61
<211> LENGTH: 251
<212> TYPE: PRT
<213> ORGANISM: Artificial Sequence
<220> FEATURE:
<223> OTHER INFORMATION: Shiga toxin effector polypeptide 22

<400> SEQUENCE: 61

Lys Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Asn Leu Val Pro Met Val Ala Thr Val
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
            165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
            245                 250

<210> SEQ ID NO 62
<211> LENGTH: 251
<212> TYPE: PRT
<213> ORGANISM: Artificial Sequence
<220> FEATURE:
<223> OTHER INFORMATION: Shiga toxin effector polypeptide 23

<400> SEQUENCE: 62

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser

<212> TYPE: PRT
<213> ORGANISM: Artificial Sequence
<220> FEATURE:
<223> OTHER INFORMATION: Shiga toxin effector polypeptide 24

<400> SEQUENCE: 63

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ile Leu Arg Phe Ser Val Ala His Lys Ala Ser
                245                 250                 255

Ala Val Ala Ala
            260

<210> SEQ ID NO 64
<211> LENGTH: 262
<212> TYPE: PRT
<213> ORGANISM: Artificial Sequence
<220> FEATURE:
<223> OTHER INFORMATION: Shiga toxin effector polypeptide 25

<400> SEQUENCE: 64

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Ile Leu Gly Phe Asp Phe Thr Leu Gly Arg Phe
    50                  55                  60

```
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Arg Asn Leu Val Pro Met Val Ala Thr Val
                245                 250                 255

Ala Ser Ala Val Ala Ala
            260

<210> SEQ ID NO 65
<211> LENGTH: 251
<212> TYPE: PRT
<213> ORGANISM: Artificial Sequence
<220> FEATURE:
<223> OTHER INFORMATION: Shiga toxin effector polypeptide 26

<400> SEQUENCE: 65

Lys Glu Phe Thr Le

```
Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 66
<211> LENGTH: 251
<212> TYPE: PRT
<213> ORGANISM: Artificial Sequence
<220> FEATURE:
<223> OTHER INFORMATION: Shiga toxin effector polypeptide 27

<400> S

<211> LENGTH: 260
<212> TYPE: PRT
<213> ORGANISM: Artificial Sequence
<220> FEATURE:
<223> OTHER INFORMATION: Shiga toxin effector polypeptide 28

<400> SEQUENCE: 67

Lys Glu Phe Thr Leu Asp Phe Ser Th

```
                 50                  55                  60
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
            130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Arg Asn Leu Val Pro Met Val Ala Thr Val
                245                 250                 255

Ala Ser Ala Val Ala Ala
            260

<210> SEQ ID NO 69
<211> LENGTH: 25
<212> TYPE: PRT
<213> ORGANISM: Artificial Sequence
<220> FEATURE:
<223> OTHER INFORMATION: linker 1

<400> SEQUENCE: 69

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 70
<211> LENGTH: 20
<212> TYPE: PRT
<213> ORGANISM: Artificial Sequence
<220> FEATURE:
<223> OTHER INFORMATION: linker 2

<400> SEQUENCE: 70

Gly Gly Gly Gly Ser Gly Gly Gly Gly Ser Gly Gly Gly Gly Ser Gly
1               5                   10                  15

Gly Gly Gly Ser
            20

<210> SEQ ID NO 71
<211> LENGTH: 18
<212> TYPE: PRT
<213> ORGANISM: Artificial Sequence
<220> FEATURE:
```

<223> OTHER INFORMATION: linker 3

<400> SEQUENCE: 71

Gly Ser Thr Ser Gly Ser Gly Lys Pro Gly Ser Gly Glu Gly Ser Thr
1               5                   10                  15

Lys Gly

<210> SEQ ID NO 72
<211> LENGTH: 5
<212> TYPE: PRT
<213> ORGANISM: Artificial Sequence
<220> FEATURE:
<223> OTHER INFORMATION: linker 4

<400> SEQUENCE: 72

Gly Gly Gly Gly Ser
1               5

<210> SEQ ID NO 73
<211> LENGTH: 16
<212> TYPE: PRT
<213> ORGANISM: Artificial Sequence
<220> FEATURE:
<223> OTHER INFORMATION: linker 5

<400> SEQUENCE: 73

Glu Phe Pro Lys Pro Ser Thr Pro Pro Gly Ser Gly Gly Ala Pro
1               5                   10                  15

<210> SEQ ID NO 74
<211> LENGTH: 25
<212> TYPE: PRT
<213> ORGANISM: Artificial Sequence
<220> FEATURE:
<223> OTHER INFORMATION: linker 6

<400> SEQUENCE: 74

Glu Phe Pro Lys Pro Ser Thr Pro Pro Gly Ser Ser Gly Gly Ala Pro
1               5                   10                  15

Gly Ile Leu Gly Phe Val Phe Thr Leu
            20                  25

<210> SEQ ID NO 75
<211> LENGTH: 15
<212> TYPE: PRT
<213> ORGANISM: Artificial Sequence
<220> FEATURE:
<223> OTHER INFORMATION: linker 7

<400> SEQUENCE: 75

Gly Ser Thr Ser Gly Ser Gly Lys Pro Gly Ser Gly Glu Gly Ser
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: linker 8

<400> SEQUENCE: 76

Ser Pro Ser Thr Pro Pro Thr Pro Ser Pro Ser Thr Pro Pro Ala Ser
1               5                   10                  15

<210> SEQ ID NO 77

-continued

```
<211> LENGTH: 15
<212> TYPE: PRT
<213> ORGANISM: Artificial Sequence
<220> FEATURE:
<223> OTHER INFORMATION: linker 9

<400> SEQUENCE: 77

Ala His His Ser Glu Asp Pro Ser Ser Lys Ala Pro Lys Ala Pro
1               5                   10                  15

<210> SEQ ID NO 78
<211> LENGTH: 9
<212> TYPE: PRT
<213> ORGANISM: Unknown
<220> FEATURE:
<223> OTHER INFORMATION: T-cell epitope-peptide C1

<400> SEQUENCE: 78

Asn Leu Val Pro Met Val Ala Thr Val
1               5

<210> SEQ ID NO 79
<211> LENGTH: 9
<212> TYPE: PRT
<213> ORGANISM: Unknown
<220> FEATURE:
<223> OTHER INFORMATION: T-cell epitope-peptide C2

<400> SEQUENCE: 79

Val Thr Glu His Asp Thr Leu Leu Tyr
1               5

<210> SEQ ID NO 80
<211> LENGTH: 9
<212> TYPE: PRT
<213> ORGANISM: Unknown
<220> FEATURE:
<223> OTHER INFORMATION: T-cell epitope-peptide C4

<400> SEQUENCE: 80

Ser Ile Ile Asn Phe Glu Lys Tyr Leu
1               5

<210> SEQ ID NO 81
<211> LENGTH: 9
<212> TYPE: PRT
<213> ORGANISM: Unknown
<220> FEATURE:
<223> OTHER INFORMATION: T-cell epitope-peptide C1-2

<400> SEQUENCE: 81

Gly Leu Asp Arg Asn Ser Gly Asn Tyr
1               5

<210> SEQ ID NO 82
<211> LENGTH: 9
<212> TYPE: PRT
<213> ORGANISM: Unknown
<220> FEATURE:
<223> OTHER INFORMATION: T-cell epitope-peptide C1-3

<400> SEQUENCE: 82

Gly Val Met Thr Arg Gly Arg Leu Lys
1               5

<210> SEQ ID NO 83
<211> LENGTH: 9
```

```
<212> TYPE: PRT
<213> ORGANISM: Unknown
<220> FEATURE:
<223> OTHER INFORMATION: T-cell epitope-peptide F2

<400> SEQUENCE: 83

Gly Ile Leu Gly Phe Val Phe Thr Leu
1               5

<210> SEQ ID NO 84
<211> LENGTH: 9
<212> TYPE: PRT
<213> ORGANISM: Unknown
<220> FEATURE:
<223> OTHER INFORMATION: T-cell epitope-peptide F3

<400> SEQUENCE: 84

Ile Leu Arg Gly Ser Val Ala His Lys
1               5

<210> SEQ ID NO 85
<211> LENGTH: 233
<212> TYPE: PRT
<213> ORGANISM: Artificial Sequence
<220> FEATURE:
<223> OTHER INFORMATION: single-chain variable fragment I

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Ile Lys Gly Gly Gly Gly Ser Glu
            100                 105                 110

Val Gln Leu Gln Glu Ser Gly Pro Glu Leu Val Lys Pro Gly Ala Ser
        115                 120                 125

Val Lys Ile Ser Cys Lys Thr Ser Gly Tyr Thr Phe Thr Glu Asn Ser
    130                 135                 140

Met His Trp Val Lys Gln Ser His Gly Lys Ser Leu Glu Trp Ile Gly
145                 150                 155                 160

Gly Ile Asn Pro Asn Asn Gly Gly Thr Ser Tyr Asn Gln Lys Phe Lys
                165                 170                 175

Gly Lys Ala Thr Leu Thr Val Asp Lys Ser Ser Ser Thr Ala Tyr Met
            180                 185                 190

Glu Phe Arg Ser Leu Thr Ser Glu Asp Ser Ala Val Tyr Tyr Cys Ala
        195                 200                 205

Arg Pro Tyr Tyr Tyr Gly Tyr Arg Glu Asp Tyr Phe Asp Tyr Trp Gly
    210                 215                 220

Gln Gly Thr Thr Leu Thr Val Ser Ser
225                 230
```

```
<210> SEQ ID NO 86
<211> LENGTH: 233
<212> TYPE: PRT
<213> ORGANISM: Artificial Sequence
<220> FEATURE:
<223> OTHER INFORMATION: single-chain variable fragment II

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys Gly Gly Gly Gly Ser Glu
            100                 105                 110

Val His Leu Val Glu Ser Gly Pro Glu Leu Val Lys Pro Gly Ala Ser
        115                 120                 125

Val Lys Ile Ser Cys Lys Thr Ser Gly Tyr Thr Phe Thr Glu Tyr Thr
    130                 135                 140

Met His Trp Val Lys Gln Ser His Gly Lys Ser Leu Glu Trp Ile Gly
145                 150                 155                 160

Gly Ile Asp Pro Asn Asn Gly Gly Thr Trp Tyr Asn Gln Lys Phe Lys
                165                 170                 175

Gly Lys Ala Thr Leu Thr Val Asp Lys Ser Ser Thr Ala Tyr Met
            180                 185                 190

Glu Leu Arg Ser Leu Thr Ser Glu Asp Ser Ala Val Tyr Phe Cys Ala
        195                 200                 205

Arg Pro Tyr Tyr Tyr Gly Ser Arg Glu Asp Tyr Phe Asp Tyr Trp Gly
    210                 215                 220

Gln Gly Thr Thr Leu Thr Val Ser Ser
225                 230

<210> SEQ ID NO 87
<211> LENGTH: 233
<212> TYPE: PRT
<213> ORGANISM: Artificial Sequence
<220> FEATURE:
<223> OTHER INFORMATION: single-chain variable fragment III

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80
```

Asp Ala Ala Thr Tyr Tyr Cys Gln Gln Trp Ser Ser Asn Pro Pro Thr
                    85                  90                  95

Phe Gly Gly Gly Thr Lys Leu Glu Leu Lys Gly Gly Gly Ser Glu
            100                 105                 110

Val Gln Leu Gln Gln Ser Gly Pro Glu Leu Val Lys Pro Gly Ala Ser
            115                 120                 125

Val Lys Ile Ser Cys Lys Thr Ser Gly Tyr Thr Phe Thr Glu Tyr Thr
        130                 135                 140

Met His Trp Val Lys Gln Arg His Gly Lys Ser Leu Glu Trp Ile Gly
145                 150                 155                 160

Gly Ile Asn Pro Asn Asn Gly Gly Thr Trp Tyr Asn Gln Lys Phe Lys
                165                 170                 175

Gly Lys Ala Thr Leu Thr Val Asp Lys Ser Ser Thr Ala Tyr Met
            180                 185                 190

Glu Leu Arg Ser Leu Thr Ser Glu Asp Ser Ala Val Tyr Phe Cys Ala
        195                 200                 205

Arg Pro Tyr Tyr Tyr Gly Ser Arg Glu Asp Tyr Phe Asp Tyr Trp Gly
        210                 215                 220

Gln Gly Thr Thr Leu Thr Val Ser Ser
225                 230

<210> SEQ ID NO 88
<211> LENGTH: 233
<212> TYPE: PRT
<213> ORGANISM: Artificial Sequence
<220> FEATURE:
<223> OTHER INFORMATION: single-chain variable fragment IV

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys Gly Gly Gly Ser Glu
            100                 105                 110

Val Gln Leu Gln Gln Ser Gly Pro Glu Leu Val Lys Pro Gly Ala Ser
            115                 120                 125

Val Lys Ile Ser Cys Lys Thr Ser Gly Tyr Thr Phe Thr Glu Tyr Thr
        130                 135                 140

Met His Trp Val Lys Gln Ser His Gly Lys Ser Leu Glu Trp Ile Gly
145                 150                 155                 160

Gly Ile Asn Pro Asn Asn Gly Gly Thr Trp Tyr Asn Arg Lys Phe Lys
                165                 170                 175

Gly Lys Ala Ala Leu Thr Val Asp Lys Ser Ser Thr Ala Tyr Met
            180                 185                 190

Glu Leu Arg Ser Leu Thr Ser Glu Asp Ser Ala Val Tyr Phe Cys Ala
        195                 200                 205

Arg Pro Tyr Tyr Tyr Gly Ser Arg Glu Asp Tyr Phe Asp Tyr Trp Gly
                210                 215                 220

Gln Gly Thr Thr Leu Thr Val Ser Ser
225                 230

<210> SEQ ID NO 89
<211> LENGTH: 253
<212> TYPE: PRT
<213> ORGANISM: Artificial Sequence
<220> FEATURE:
<223> OTHER INFORMATION: single-chain variable fragment V

<400> SEQUENCE: 89

Glu Val Gln Leu Gln Glu Ser Gly Pro Glu Leu Val Lys Pro Gly Ala
1               5                   10                  15

Ser Val Lys Ile Ser Cys Lys Thr Ser Gly Tyr Thr Phe Thr Glu Asn
            20                  25                  30

Ser Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Pro Tyr Tyr Tyr Gly Tyr Arg Glu Asp Tyr Phe Asp Tyr Trp
            100                 105                 110

Gly Gln Gly Thr Thr Leu Thr Val Ser Ser Gly Gly Gly Gly Ser Gly
        115                 120                 125

Gly Gly Gly Ser Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Ser Ala Ser Ser Ser Val
                165                 170                 175

Ser Tyr Met Tyr Trp Tyr Gln Gln Lys Pro Arg Ser Ser Pro Lys Pro
            180                 185                 190

Trp Ile Tyr Leu Thr Ser Asn Leu Ala Ser Gly Val Pro Ala Arg Phe
        195                 200                 205

Ser Gly Ser Gly Ser Gly Thr Ser Tyr Ser Leu Thr Ile Ser Ser Met
    210                 215                 220

Glu Ala Glu Asp Ala Ala Thr Tyr Tyr Cys Gln Gln Trp Ser Ser Tyr
225                 230                 235                 240

Pro Pro Thr Phe Gly Gly Gly Thr Lys Leu Glu Ile Lys
                245                 250

<210> SEQ ID NO 90
<211> LENGTH: 253
<212> TYPE: PRT
<213> ORGANISM: Artificial Sequence
<220> FEATURE:
<223> OTHER INFORMATION: single-chain variable fragment VI

<400> SEQUENCE: 90

Glu Val His Leu Val Glu Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

```
Thr Met His Trp Val Lys Gln Ser His Gly Lys Ser Leu Glu Trp Ile
            35                  40                  45
Gly Gly Ile Asp Pro Asn Asn Gly Gly Thr Trp Tyr Asn Gln Lys Phe
        50                  55                  60
Lys Gly Lys Ala Thr Leu Thr Val Asp Lys Ser Ser Thr Ala Tyr
65                  70                  75                  80
Met Glu Leu Arg Ser Leu Thr Ser Glu Asp Ser Ala Val Tyr Phe Cys
                85                  90                  95
Ala Arg Pro Tyr Tyr Tyr Gly Ser Arg Glu Asp Tyr Phe Asp Tyr Trp
                100                 105                 110
Gly Gln Gly Thr Thr Leu Thr Val Ser Ser Gly Gly Gly Gly Ser Gly
            115                 120                 125
Gly Gly Gly Ser Gly Gly Gly Ser Gly Gly Gly Gly Ser Gly Gly
        130                 135                 140
Gly Gly Ser Asp Ile Gln Met Thr Gln Ser Pro Ser Ser Leu Ser Ala
145                 150                 155                 160
Ser Val Gly Asp Arg Val Thr Ile Thr Cys Ser Ala Ser Ser Ser Val
                165                 170                 175
Ser Tyr Met Tyr Trp Tyr Gln Gln Lys Pro Arg Ser Ser Pro Lys Pro
                180                 185                 190
Trp Ile Tyr Leu Thr Ser Asn Leu Ala Ser Gly Val Pro Ala Arg Phe
                195                 200                 205
Ser Gly Ser Gly Ser Gly Thr Ser Tyr Ser Leu Thr Ile Ser Ser Met
            210                 215                 220
Glu Ala Glu Asp Ala Ala Thr Tyr Tyr Cys Gln Gln Trp Ser Ser Asn
225                 230                 235                 240
Pro Pro Thr Phe Gly Gly Gly Thr Lys Leu Glu Ile Lys
                245                 250

<210> SEQ ID NO 91
<211> LENGTH: 253
<212> TYPE: PRT
<213> ORGANISM: Artificial Sequence
<220> FEATURE:
<223> OTHER INFORMATION: single-chain variable fragment VII

<400> SEQUENCE: 91

Glu Val Gln Leu Gln Gln Ser Gly Pro Glu Leu Val Lys Pro Gly Ala
1               5                   10                  15
Ser Val Lys Ile Ser Cys Lys Thr Ser Gly Tyr Thr Phe Thr Glu Tyr
            20                  25                  30
Thr Met His Trp Val Lys Gln Arg His Gly Lys Ser Leu Glu Trp Ile
            35                  40                  45
Gly Gly Ile Asn Pro Asn Asn Gly Gly Thr Trp Tyr Asn Gln Lys Phe
        50                  55                  60
Lys Gly Lys Ala Thr Leu Thr Val Asp Lys Ser Ser Thr Ala Tyr
65                  70                  75                  80
Met Glu Leu Arg Ser Leu Thr Ser Glu Asp Ser Ala Val Tyr Phe Cys
                85                  90                  95
Ala Arg Pro Tyr Tyr Tyr Gly Ser Arg Glu Asp Tyr Phe Asp Tyr Trp
                100                 105                 110
Gly Gln Gly Thr Thr Leu Thr Val Ser Ser Gly Gly Gly Gly Ser Gly
            115                 120                 125
Gly Gly Gly Ser Gly Gly Gly Gly Ser Gly Gly Gly Gly Ser Gly Gly
        130                 135                 140
```

```
Gly Gly Ser Asp Ile Gln Met Thr Gln Ser Pro Ser Ser Leu Ser Ala
145                 150                 155                 160

Ser Val Gly Asp Arg Val Thr Ile Thr Cys Ser Ala Ser Ser Ser Val
                165                 170                 175

Ser Tyr Met Tyr Trp Tyr Gln Gln Lys Pro Arg Ser Ser Pro Lys Pro
            180                 185                 190

Trp Ile Tyr Leu Thr Ser Asn Leu Ala Ser Gly Val Pro Ala Arg Phe
        195                 200                 205

Ser Gly Ser Gly Ser Gly Thr Ser Tyr Ser Leu Thr Ile Ser Ser Met
    210                 215                 220

Glu Ala Glu Asp Ala Ala Thr Tyr Tyr Cys Gln Gln Trp Ser Ser Asn
225                 230                 235                 240

Pro Pro Thr Phe Gly Gly Gly Thr Lys Leu Glu Leu Lys
                245                 250
```

<210> SEQ ID NO 92
<211> LENGTH: 253
<212> TYPE: PRT
<213> ORGANISM: Artificial Sequence
<220> FEATURE:
<223> OTHER INFORMATION: single-chain variable fragment VIII

<400> SEQUENCE: 92

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Trp Tyr Asn Arg Lys Phe
    50                  55                  60

Lys Gly Lys Ala Ala Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Tyr Tyr Gly Ser Arg Glu Asp Tyr Phe Asp Tyr Trp
            100                 105                 110

Gly Gln Gly Thr Thr Leu Thr Val Ser Ser Gly Gly Gly Gly Ser Gly
        115                 120                 125

Gly Gly Gly Ser Gly Gly Gly Ser Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Ser Ala Ser Ser Ser Val
                165                 170                 175

Ser Tyr Met Tyr Trp Tyr Gln Gln Lys Pro Arg Ser Ser Pro Lys Pro
            180                 185                 190

Trp Ile Tyr Leu Thr Ser Asn Leu Ala Ser Gly Val Pro Ala Arg Phe
        195                 200                 205

Ser Gly Ser Gly Ser Gly Thr Ser Tyr Ser Leu Thr Ile Ser Ser Met
    210                 215                 220

Glu Ala Glu Asp Ala Ala Thr Tyr Tyr Cys Gln Gln Trp Ser Ser Asn
225                 230                 235                 240

Pro Pro Thr Phe Gly Gly Gly Thr Lys Leu Glu Ile Lys
                245                 250
```

-continued

```
<210> SEQ ID NO 93
<211> LENGTH: 233
<212> TYPE: PRT
<213> ORGANISM: Artificial Sequence
<220> FEATURE:
<223> OTHER INFORMATION: single-chain variable fragment IX

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

Tyr Trp Tyr Gln Gln Lys Pro Gly Gln Ala Pro Arg Pro Leu Ile Tyr
                35                  40                  45

Leu Thr Ser Asn Leu Ala Ser Gly Ile Pro Asp Arg Phe Ser Gly Ser
        50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Ser Tyr Pro Pro Thr
                85                  90                  95

Phe Gly Gln Gly Thr Lys Val Glu Ile Lys Gly Gly Gly Ser Gln
                100                 105                 110

Val Gln Leu Val Gln Ser Gly Pro Glu Val Lys Lys Pro Gly Ala Ser
            115                 120                 125

Val Lys Val Ser Cys Lys Ala Ser Gly Tyr Thr Phe Thr Glu Asn Ser
130                 135                 140

Met His Trp Val Arg Gln Ser His Gly Lys Ser Leu Glu Trp Met Gly
145                 150                 155                 160

Gly Ile Asn Pro Asn Asn Gly Gly Thr Ser Tyr Asn Gln Lys Phe Lys
                165                 170                 175

Gly Lys Val Thr Met Thr Thr Asp Lys Ser Thr Ser Thr Ala Tyr Met
            180                 185                 190

Glu Leu Arg Ser Leu Thr Ser Asp Asp Thr Ala Val Tyr Tyr Cys Ala
        195                 200                 205

Arg Pro Tyr Tyr Tyr Gly Tyr Arg Glu Asp Tyr Phe Asp Tyr Trp Gly
    210                 215                 220

Gln Gly Thr Thr Leu Thr Val Ser Ser
225                 230

<210> SEQ ID NO 94
<211> LENGTH: 233
<212> TYPE: PRT
<213> ORGANISM: Artificial Sequence
<220> FEATURE:
<223> OTHER INFORMATION: single-chain variable fragment X

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

Tyr Trp Tyr Gln Gln Lys Pro Gly Gln Ala Pro Arg Pro Leu Ile Tyr
                35                  40                  45

Leu Thr Ser Asn Leu Ala Ser Gly Ile Pro Asp Arg Phe Ser Gly Ser
        50                  55                  60

Gly Ser Gly Thr Asp Tyr Thr Leu Thr Ile Ser Arg Leu Glu Pro Glu
```

```
                65                  70                  75                  80
Asp Phe Ala Val Tyr Tyr Cys Gln Gln Trp Ser Ser Tyr Pro Pro Thr
                    85                  90                  95
Phe Gly Gln Gly Thr Lys Val Glu Ile Lys Gly Gly Gly Ser Gln
                100                 105                 110
Val Gln Leu Val Gln Ser Gly Ala Glu Val Lys Lys Pro Gly Ala Ser
            115                 120                 125
Val Lys Val Ser Cys Lys Ala Ser Gly Tyr Thr Phe Thr Glu Asn Ser
        130                 135                 140
Met His Trp Val Arg Gln Ala His Gly Gln Arg Leu Glu Trp Ile Gly
145                 150                 155                 160
Gly Ile Asn Pro Asn Asn Gly Gly Thr Trp Tyr Asn Arg Lys Phe Lys
                165                 170                 175
Gly Lys Ala Ala Ile Thr Val Asp Thr Ser Ala Ser Thr Ala Tyr Met
            180                 185                 190
Glu Leu Ser Ser Leu Arg Ser Glu Asp Thr Ala Val Tyr Tyr Cys Ala
        195                 200                 205
Arg Pro Tyr Tyr Tyr Gly Tyr Arg Glu Asp Tyr Phe Asp Tyr Trp Gly
    210                 215                 220
Gln Gly Thr Thr Leu Thr Val Ser Ser
225                 230

<210> SEQ ID NO 95
<211> LENGTH: 233
<212> TYPE: PRT
<213> ORGANISM: Artificial Sequence
<220> FEATURE:
<223> OTHER INFORMATION: single-chain variable fragment XI

<400> SEQUENCE: 95

Asp Ile Gln Met Thr Gln Ser Pro Ser Ser Leu Ser Ala Ser Val Gly
1               5                   10                  15
Asp Arg Val Thr Ile Thr Cys Arg Ala Ser Ser Ser Val Ser Tyr Met
            20                  25                  30
Tyr Trp Tyr Gln Gln Lys Pro Gly Gln Ala Pro Arg Pro Leu Ile Tyr
        35                  40                  45
Leu Thr Ser Asn Leu Ala Ser Gly Ile Pro Asp Arg Phe Ser Gly Ser
    50                  55                  60
Gly Ser Gly Thr Asp Tyr Thr Leu Thr Ile Ser Arg Leu Glu Pro Glu
65                  70                  75                  80
Asp Phe Ala Val Tyr Tyr Cys Gln Gln Trp Ser Ser Tyr Pro Pro Thr
                85                  90                  95
Phe Gly Gln Gly Thr Lys Val Glu Ile Lys Gly Gly Gly Ser Gln
                100                 105                 110
Val Gln Leu Val Gln Ser Gly Ala Glu Val Lys Lys Pro Gly Ala Ser
            115                 120                 125
Val Lys Val Ser Cys Lys Ala Ser Gly Tyr Thr Phe Thr Glu Asn Ser
        130                 135                 140
Met His Trp Val Arg Gln Ala His Gly Gln Arg Leu Glu Trp Ile Gly
145                 150                 155                 160
Gly Ile Asn Pro Asn Asn Gly Gly Thr Ser Tyr Asn Gln Lys Phe Lys
                165                 170                 175
Gly Lys Ala Thr Ile Thr Val Asp Thr Ser Ala Ser Thr Ala Tyr Met
            180                 185                 190
Glu Leu Ser Ser Leu Arg Ser Glu Asp Thr Ala Val Tyr Tyr Cys Ala
```

195                 200                 205
Arg Pro Tyr Tyr Tyr Gly Tyr Arg Glu Asp Tyr Phe Asp Tyr Trp Gly
    210                 215                 220

Gln Gly Thr Thr Leu Thr Val Ser Ser
225                 230

<210> SEQ ID NO 96
<211> LENGTH: 233
<212> TYPE: PRT
<213> ORGANISM: Artificial Sequence
<220> FEATURE:
<223> OTHER INFORMATION: single-chain variable fragment XII

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

Tyr Trp Tyr Gln Gln Lys Pro Gly Gln Ala Pro Arg Pro Leu Ile Tyr
        35                  40                  45

Leu Thr Ser Asn Leu Ala Ser Gly Ile Pro Asp Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Ser Tyr Pro Pro Thr
                85                  90                  95

Phe Gly Gln Gly Thr Lys Val Glu Ile Lys Gly Gly Gly Gly Ser Gln
            100                 105                 110

Val Gln Leu Val Gln Ser Gly Ala Glu Val Lys Lys Pro Gly Ala Ser
        115                 120                 125

Val Lys Val Ser Cys Lys Thr Ser Gly Tyr Thr Phe Thr Glu Asn Ser
    130                 135                 140

Met His Trp Val Arg Gln Ala Pro Gly Gln Arg Leu Glu Trp Met Gly
145                 150                 155                 160

Gly Ile Asn Pro Asn Asn Gly Gly Thr Ser Tyr Asn Gln Lys Phe Gln
                165                 170                 175

Gly Arg Val Thr Leu Thr Val Asp Lys Ser Ser Ser Thr Ala Tyr Met
            180                 185                 190

Glu Leu Ser Ser Leu Arg Ser Glu Asp Thr Ala Val Tyr Tyr Cys Ala
        195                 200                 205

Arg Pro Tyr Tyr Tyr Gly Tyr Arg Glu Asp Tyr Phe Asp Tyr Trp Gly
    210                 215                 220

Gln Gly Thr Thr Leu Thr Val Ser Ser
225                 230

<210> SEQ ID NO 97
<211> LENGTH: 253
<212> TYPE: PRT
<213> ORGANISM: Artificial Sequence
<220> FEATURE:
<223> OTHER INFORMATION: single-chain variable fragment XIII

<400> SEQUENCE: 97

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Glu Asn
            20                  25                  30

```
Ser Met His Trp Val Arg Gln Ser His Gly Lys Ser Leu Glu Trp Met
        35                  40                  45

Gly Gly Ile Asn Pro Asn Asn Gly Gly Thr Ser Tyr Asn Gln Lys Phe
 50                  55                  60

Lys Gly Lys Val Thr Met Thr Thr Asp Lys Ser Thr Ser Thr Ala Tyr
65                   70                  75                  80

Met Glu Leu Arg Ser Leu Thr Ser Asp Asp Thr Ala Val Tyr Tyr Cys
                 85                  90                  95

Ala Arg Pro Tyr Tyr Tyr Gly Tyr Arg Glu Asp Tyr Phe Asp Tyr Trp
                100                 105                 110

Gly Gln Gly Thr Thr Leu Thr Val Ser Ser Gly Gly Gly Gly Ser Gly
            115                 120                 125

Gly Gly Gly Ser Gly Gly Gly Ser Gly Gly Gly Gly Ser Gly Gly
        130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Arg Ala Ser Ser Ser Val
                165                 170                 175

Ser Tyr Met Tyr Trp Tyr Gln Gln Lys Pro Gly Gln Ala Pro Arg Pro
            180                 185                 190

Leu Ile Tyr Leu Thr Ser Asn Leu Ala Ser Gly Ile Pro Asp Arg Phe
        195                 200                 205

Ser Gly Ser Gly Ser Gly Thr Asp Tyr Thr Leu Thr Ile Ser Arg Leu
    210                 215                 220

Glu Pro Glu Asp Phe Ala Val Tyr Tyr Cys Gln Gln Trp Ser Ser Tyr
225                 230                 235                 240

Pro Pro Thr Phe Gly Gln Gly Thr Lys Val Glu Ile Lys
                245                 250

<210> SEQ ID NO 98
<211> LENGTH: 253
<212> TYPE: PRT
<213> ORGANISM: Artificial Sequence
<220> FEATURE:
<223> OTHER INFORMATION: single-chain variable fragment XIV

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Asn
            20                  25                  30

Ser Met His Trp Val Arg Gln Ala His Gly Gln Arg Leu Glu Trp Ile
        35                  40                  45

Gly Gly Ile Asn Pro Asn Asn Gly Gly Thr Trp Tyr Asn Arg Lys Phe
 50                  55                  60

Lys Gly Lys Ala Ala Ile Thr Val Asp Thr Ser Ala Ser Thr Ala Tyr
65                   70                  75                  80

Met Glu Leu Ser Ser Leu Arg Ser Glu Asp Thr Ala Val Tyr Tyr Cys
                 85                  90                  95

Ala Arg Pro Tyr Tyr Tyr Gly Tyr Arg Glu Asp Tyr Phe Asp Tyr Trp
                100                 105                 110

Gly Gln Gly Thr Thr Leu Thr Val Ser Ser Gly Gly Gly Gly Ser Gly
            115                 120                 125

Gly Gly Gly Ser Gly Gly Gly Ser Gly Gly Gly Gly Ser Gly Gly
        130                 135                 140
```

Gly Gly Ser Asp Ile Gln Met Thr Gln Ser Pro Ser Ser Leu Ser Ala
145                 150                 155                 160

Ser Val Gly Asp Arg Val Thr Ile Thr Cys Arg Ala Ser Ser Ser Val
                165                 170                 175

Ser Tyr Met Tyr Trp Tyr Gln Gln Lys Pro Gly Gln Ala Pro Arg Pro
            180                 185                 190

Leu Ile Tyr Leu Thr Ser Asn Leu Ala Ser Gly Ile Pro Asp Arg Phe
        195                 200                 205

Ser Gly Ser Gly Ser Gly Thr Asp Tyr Thr Leu Thr Ile Ser Arg Leu
    210                 215                 220

Glu Pro Glu Asp Phe Ala Val Tyr Tyr Cys Gln Gln Trp Ser Ser Tyr
225                 230                 235                 240

Pro Pro Thr Phe Gly Gln Gly Thr Lys Val Glu Ile Lys
                245                 250

<210> SEQ ID NO 99
<211> LENGTH: 253
<212> TYPE: PRT
<213> ORGANISM: Artificial Sequence
<220> FEATURE:
<223> OTHER INFORMATION: single-chain variable fragment XV

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Asn
            20                  25                  30

Ser Met His Trp Val Arg Gln Ala His Gly Gln Arg Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Tyr Tyr Tyr Gly Tyr Arg Glu Asp Tyr Phe Asp Tyr Trp
            100                 105                 110

Gly Gln Gly Thr Thr Leu Thr Val Ser Ser Gly Gly Gly Gly Ser Gly
        115                 120                 125

Gly Gly Gly Ser Gly Gly Gly Ser Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Arg Ala Ser Ser Ser Val
                165                 170                 175

Ser Tyr Met Tyr Trp Tyr Gln Gln Lys Pro Gly Gln Ala Pro Arg Pro
            180                 185                 190

Leu Ile Tyr Leu Thr Ser Asn Leu Ala Ser Gly Ile Pro Asp Arg Phe
        195                 200                 205

Ser Gly Ser Gly Ser Gly Thr Asp Tyr Thr Leu Thr Ile Ser Arg Leu
    210                 215                 220

Glu Pro Glu Asp Phe Ala Val Tyr Tyr Cys Gln Gln Trp Ser Ser Tyr
225                 230                 235                 240

Pro Pro Thr Phe Gly Gln Gly Thr Lys Val Glu Ile Lys
                245                 250

```
<210> SEQ ID NO 100
<211> LENGTH: 253
<212> TYPE: PRT
<213> ORGANISM: Artificial Sequence
<220> FEATURE:
<223> OTHER INFORMATION: single-chain variable fragment XVI

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Asn
            20                  25                  30

Ser Met His Trp Val Arg Gln Ala Pro Gly Gln Arg Leu Glu Trp Met
        35                  40                  45

Gly Gly Ile Asn Pro Asn Asn Gly Gly Thr Ser Tyr Asn Gln Lys Phe
    50                  55                  60

Gln Gly Arg Val Thr Leu Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Tyr Tyr Gly Tyr Arg Glu Asp Tyr Phe Asp Tyr Trp
            100                 105                 110

Gly Gln Gly Thr Thr Leu Thr Val Ser Ser Gly Gly Gly Gly Ser Gly
        115                 120                 125

Gly Gly Gly Ser Gly Gly Gly Ser Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Arg Ala Ser Ser Ser Val
                165                 170                 175

Ser Tyr Met Tyr Trp Tyr Gln Gln Lys Pro Gly Gln Ala Pro Arg Pro
            180                 185                 190

Leu Ile Tyr Leu Thr Ser Asn Leu Ala Ser Gly Ile Pro Asp Arg Phe
        195                 200                 205

Ser Gly Ser Gly Ser Gly Thr Asp Tyr Thr Leu Thr Ile Ser Arg Leu
    210                 215                 220

Glu Pro Glu Asp Phe Ala Val Tyr Tyr Cys Gln Gln Trp Ser Ser Tyr
225                 230                 235                 240

Pro Pro Thr Phe Gly Gln Gly Thr Lys Val Glu Ile Lys
                245                 250

<210> SEQ ID NO 101
<211> LENGTH: 253
<212> TYPE: PRT
<213> ORGANISM: Artificial Sequence
<220> FEATURE:
<223> OTHER INFORMATION: single-chain variable fragment XVII

<400> SEQUENCE: 101

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Ser Arg His Gly Lys Ser Leu Glu Trp Ile
        35                  40                  45

Gly Gly Ile Asn Pro Asn Asn Gly Gly Thr Trp Tyr Asn Gln Lys Phe
    50                  55                  60
```

```
Lys Gly Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Phe Cys
                 85                  90                  95

Ala Arg Pro Tyr Tyr Tyr Gly Ser Arg Glu Asp Tyr Phe Asp Tyr Trp
            100                 105                 110

Gly Gln Gly Thr Thr Leu Thr Val Ser Ser Gly Gly Gly Gly Ser Gly
            115                 120                 125

Gly Gly Gly Ser Gly Gly Gly Ser Gly Gly Gly Ser Gly Gly
130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Ser Ala Ser Ser Ser Val
                165                 170                 175

Ser Tyr Met Tyr Trp Tyr Gln Gln Lys Pro Arg Ser Ser Pro Lys Pro
            180                 185                 190

Trp Ile Tyr Leu Thr Ser Asn Leu Ala Ser Gly Val Pro Ala Arg Phe
            195                 200                 205

Ser Gly Ser Gly Ser Gly Thr Ser Tyr Ser Leu Thr Ile Ser Ser Met
210                 215                 220

Glu Ala Glu Asp Ala Ala Thr Tyr Tyr Cys Gln Gln Trp Ser Ser Asn
225                 230                 235                 240

Pro Pro Thr Phe Gly Gly Gly Thr Lys Leu Glu Leu Lys
                245                 250

<210> SEQ ID NO 102
<211> LENGTH: 253
<212> TYPE: PRT
<213> ORGANISM: Artificial Sequence
<220> FEATURE:
<223> OTHER INFORMATION: single-chain variable fragment XVIII

<400> SEQUENCE: 102

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Arg His Gly Lys Ser Leu Glu Trp Ile
            35                  40                  45

Gly Gly Ile Asn Pro Asn Asn Gly Gly Thr Trp Tyr Asn Arg Lys Phe
        50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Phe Cys
                 85                  90                  95

Ala Arg Pro Tyr Tyr Tyr Gly Ser Arg Glu Asp Tyr Phe Asp Tyr Trp
            100                 105                 110

Gly Gln Gly Thr Thr Leu Thr Val Ser Ser Gly Gly Gly Gly Ser Gly
            115                 120                 125

Gly Gly Gly Ser Gly Gly Gly Ser Gly Gly Gly Ser Gly Gly
130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Ser Ala Ser Ser Ser Val
                165                 170                 175
```

Ser Tyr Met Tyr Trp Tyr Gln Gln Lys Pro Arg Ser Ser Pro Lys Pro
        180                 185                 190

Trp Ile Tyr Leu Thr Ser Asn Leu Ala Ser Gly Val Pro Ala Arg Phe
        195                 200                 205

Ser Gly Ser Gly Ser Gly Thr Ser Tyr Ser Leu Thr Ile Ser Ser Met
        210                 215                 220

Glu Ala Glu Asp Ala Ala Thr Tyr Tyr Cys Gln Gln Trp Ser Ser Asn
225                 230                 235                 240

Pro Pro Thr Phe Gly Gly Gly Thr Lys Leu Glu Leu Lys
                245                 250

<210> SEQ ID NO 103
<211> LENGTH: 253
<212> TYPE: PRT
<213> ORGANISM: Artificial Sequence
<220> FEATURE:
<223> OTHER INFORMATION: single-chain variable fragment XIX

<400> SEQUENCE: 103

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Arg His Gly Lys Ser Leu Glu Trp Ile
            35                  40                  45

Gly Gly Ile Asn Pro Asn Asn Gly Gly Thr Trp Tyr Asn Gln Lys Phe
        50                  55                  60

Lys Gly Lys Thr Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Tyr Tyr Tyr Gly Ser Arg Glu Asp Tyr Phe Asp Tyr Trp
            100                 105                 110

Gly Gln Gly Thr Thr Leu Thr Val Ser Ser Gly Gly Gly Gly Ser Gly
        115                 120                 125

Gly Gly Gly Ser Gly Gly Gly Gly Ser Gly Gly Gly Gly Ser Gly Gly
        130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Ser Ala Ser Ser Ser Val
                165                 170                 175

Ser Tyr Met Tyr Trp Tyr Gln Gln Lys Pro Arg Ser Ser Pro Lys Pro
            180                 185                 190

Trp Ile Tyr Leu Thr Ser Asn Leu Ala Ser Gly Val Pro Ala Arg Phe
        195                 200                 205

Ser Gly Ser Gly Ser Gly Thr Ser Tyr Ser Leu Thr Ile Ser Ser Met
        210                 215                 220

Glu Ala Glu Asp Ala Ala Thr Tyr Tyr Cys Gln Gln Trp Ser Ser Asn
225                 230                 235                 240

Pro Pro Thr Phe Gly Gly Gly Thr Lys Leu Glu Leu Lys
                245                 250

<210> SEQ ID NO 104
<211> LENGTH: 253
<212> TYPE: PRT
<213> ORGANISM: Artificial Sequence
<220> FEATURE:
<223> OTHER INFORMATION: single-chain variable fragment XX

<400> SEQUENCE: 104

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Arg His Gly Lys Ser Leu Glu Trp Ile
        35                  40                  45

Gly Gly Ile Asn Pro Asn Asn Gly Gly Thr Trp Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Tyr Tyr Tyr Gly Ser Arg Glu Asp Tyr Phe Asp Tyr Trp
            100                 105                 110

Gly Gln Gly Thr Thr Leu Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Gln Met Thr Gln Ser Pro Ser Ser Leu Ser Ala
145                 150                 155                 160

Ser Val Gly Asp Arg Val Thr Ile Thr Cys Ser Ala Ser Ser Ser Val
                165                 170                 175

Ser Tyr Met Tyr Trp Tyr Gln Gln Lys Pro Arg Ser Ser Pro Lys Pro
            180                 185                 190

Trp Ile Tyr Leu Thr Ser Asn Leu Ala Ser Gly Val Pro Ala Arg Phe
        195                 200                 205

Ser Gly Ser Gly Ser Gly Thr Ser Tyr Ser Leu Thr Ile Ser Ser Met
    210                 215                 220

Glu Ala Glu Asp Ala Ala Thr Tyr Tyr Cys Gln Gln Trp Ser Ser Asn
225                 230                 235                 240

Pro Pro Thr Phe Gly Gly Gly Thr Lys Leu Glu Ile Lys
                245                 250

<210> SEQ ID NO 105
<211> LENGTH: 233
<212> TYPE: PRT
<213> ORGANISM: Artificial Sequence
<220> FEATURE:
<223> OTHER INFORMATION: single-chain variable fragment XXI

<400> SEQUENCE: 105

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Arg His Gly Lys Ser Leu Glu Trp Ile
        35                  40                  45

Gly Gly Ile Asn Pro Asn Asn Gly Gly Thr Trp Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Phe Cys

```
                 85                  90                  95
Ala Arg Pro Tyr Tyr Gly Ser Arg Glu Asp Tyr Phe Asp Tyr Trp
            100                 105                 110

Gly Gln Gly Thr Thr Leu Thr Val Ser Ser Gly Gly Gly Ser Asp
            115                 120                 125

Ile Gln Met Thr Gln Ser Pro Ser Ser Leu Ser Ala Ser Val Gly Asp
        130                 135                 140

Arg Val Thr Ile Thr Cys Ser Ala Ser Ser Val Ser Tyr Met Tyr
145                 150                 155                 160

Trp Tyr Gln Gln Lys Pro Arg Ser Ser Pro Lys Pro Trp Ile Tyr Leu
                165                 170                 175

Thr Ser Asn Leu Ala Ser Gly Val Pro Ala Arg Phe Ser Gly Ser Gly
            180                 185                 190

Ser Gly Thr Ser Tyr Ser Leu Thr Ile Ser Ser Met Glu Ala Glu Asp
        195                 200                 205

Ala Ala Thr Tyr Tyr Cys Gln Gln Trp Ser Ser Asn Pro Pro Thr Phe
210                 215                 220

Gly Gly Gly Thr Lys Leu Glu Ile Lys
225                 230

<210> SEQ ID NO 106
<211> LENGTH: 233
<212> TYPE: PRT
<213> ORGANISM: Artificial Sequence
<220> FEATURE:
<223> OTHER INFORMATION: single-chain variable fragment XXII

<400> SEQUENCE: 106

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Arg His Gly Lys Ser Leu Glu Trp Ile
        35                  40                  45

Gly Gly Ile Asn Pro Asn Asn Gly Gly Thr Trp Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Tyr Tyr Gly Ser Arg Glu Asp Tyr Phe Asp Tyr Trp
            100                 105                 110

Gly Gln Gly Thr Thr Leu Thr Val Ser Ser Gly Gly Gly Ser Asp
            115                 120                 125

Ile Gln Met Thr Gln Ser Pro Ser Ser Leu Ser Ala Ser Val Gly Asp
        130                 135                 140

Arg Val Thr Ile Thr Cys Ser Ala Ser Ser Val Ser Tyr Met Tyr
145                 150                 155                 160

Trp Tyr Gln Gln Lys Pro Arg Ser Ser Pro Lys Pro Trp Ile Tyr Leu
                165                 170                 175

Thr Ser Asn Leu Ala Ser Gly Val Pro Ala Arg Phe Ser Gly Ser Gly
            180                 185                 190

Ser Gly Thr Ser Tyr Ser Leu Thr Ile Ser Ser Met Glu Ala Glu Asp
        195                 200                 205

Ala Ala Thr Tyr Tyr Cys Gln Gln Trp Ser Ser Asn Pro Pro Thr Phe
```

```
                    210                 215                 220

Gly Gly Gly Thr Lys Leu Glu Leu Lys
225                 230

<210> SEQ ID NO 107
<211> LENGTH: 238
<212> TYPE: PRT
<213> ORGANISM: Artificial Sequence
<220> FEATURE:
<223> OTHER INFORMATION: single-chain variable fragment XXIII

<400> SEQUENCE: 107

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Arg His Gly Lys Ser Leu Glu Trp Ile
        35                  40                  45

Gly Gly Ile Asn Pro Asn Asn Gly Gly Thr Trp Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Tyr Tyr Gly Ser Arg Glu Asp Tyr Phe Asp Tyr Trp
            100                 105                 110

Gly Gln Gly Thr Thr Leu Thr Val Ser Ser Gly Gly Gly Gly Ser Gly
        115                 120                 125

Gly Gly Gly Ser Asp Ile Gln Met Thr Gln Ser Pro Ser Ser Leu Ser
    130                 135                 140

Ala Ser Val Gly Asp Arg Val Thr Ile Thr Cys Ser Ala Ser Ser Ser
145                 150                 155                 160

Val Ser Tyr Met Tyr Trp Tyr Gln Gln Lys Pro Arg Ser Ser Pro Lys
                165                 170                 175

Pro Trp Ile Tyr Leu Thr Ser Asn Leu Ala Ser Gly Val Pro Ala Arg
            180                 185                 190

Phe Ser Gly Ser Gly Ser Gly Thr Ser Tyr Ser Leu Thr Ile Ser Ser
        195                 200                 205

Met Glu Ala Glu Asp Ala Ala Thr Tyr Tyr Cys Gln Gln Trp Ser Ser
    210                 215                 220

Asn Pro Pro Thr Phe Gly Gly Gly Thr Lys Leu Glu Leu Lys
225                 230                 235

<210> SEQ ID NO 108
<211> LENGTH: 510
<212> TYPE: PRT
<213> ORGANISM: Artificial Sequence
<220> FEATURE:
<223> OTHER INFORMATION: PD-L1 binding protein 115744

<400> SEQUENCE: 108

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Cys Gly Asp
        35                  40                  45
```

```
Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
 65                  70                  75                  80

Gly Phe Val Asn Arg Thr Asn Asn Val Phe Tyr Arg Phe Ala Asp Phe
                 85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
    195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Asp Ile Gln Met
            260                 265                 270

Thr Gln Ser Pro Ser Ser Leu Ser Ala Ser Val Gly Asp Arg Val Thr
            275                 280                 285

Ile Thr Cys Ser Ala Ser Ser Val Ser Tyr Met Tyr Trp Tyr Gln
    290                 295                 300

Gln Lys Pro Arg Ser Ser Pro Lys Pro Trp Ile Tyr Leu Thr Ser Asn
305                 310                 315                 320

Leu Ala Ser Gly Val Pro Ala Arg Phe Ser Gly Ser Gly Ser Gly Thr
                325                 330                 335

Ser Tyr Ser Leu Thr Ile Ser Ser Met Glu Ala Glu Asp Ala Ala Thr
            340                 345                 350

Tyr Tyr Cys Gln Gln Trp Ser Ser Asn Pro Pro Thr Phe Gly Gly Gly
            355                 360                 365

Thr Lys Leu Glu Ile Lys Gly Gly Gly Ser Glu Val His Leu Val
    370                 375                 380

Glu Ser Gly Pro Glu Leu Val Lys Pro Gly Ala Ser Val Lys Ile Ser
385                 390                 395                 400

Cys Lys Thr Ser Gly Tyr Thr Phe Thr Glu Tyr Thr Met His Trp Val
                405                 410                 415

Lys Gln Ser His Gly Lys Ser Leu Glu Trp Ile Gly Gly Ile Asp Pro
            420                 425                 430

Asn Asn Gly Gly Thr Trp Tyr Asn Gln Lys Phe Lys Gly Lys Ala Thr
            435                 440                 445

Leu Thr Val Asp Lys Ser Ser Thr Ala Tyr Met Glu Leu Arg Ser
450                 455                 460

Leu Thr Ser Glu Asp Ser Ala Val Tyr Phe Cys Ala Arg Pro Tyr Tyr
```

```
                465                 470                 475                 480
Tyr Gly Ser Arg Glu Asp Tyr Phe Asp Tyr Trp Gly Gln Gly Thr Thr
                    485                 490                 495
Leu Thr Val Ser Ser Asn Leu Val Pro Met Val Ala Thr Val
                    500                 505                 510

<210> SEQ ID NO 109
<211> LENGTH: 510
<212> TYPE: PRT
<213> ORGANISM: Artificial Sequence
<220> FEATURE:
<223> OTHER INFORMATION: PD-L1 binding protein 115745

<400> SEQUENCE: 109

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Cys Gly Asp
            35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
    195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Asp Ile Gln Met
            260                 265                 270

Thr Gln Ser Pro Ser Ser Leu Ser Ala Ser Val Gly Asp Arg Val Thr
    275                 280                 285

Ile Thr Cys Ser Ala Ser Ser Ser Val Ser Tyr Met Tyr Trp Tyr Gln
290                 295                 300

Gln Lys Pro Arg Ser Ser Pro Lys Pro Trp Ile Tyr Leu Thr Ser Asn
305                 310                 315                 320

Leu Ala Ser Gly Val Pro Ala Arg Phe Ser Gly Ser Gly Ser Gly Thr
```

```
            325                 330                 335
Ser Tyr Ser Leu Thr Ile Ser Ser Met Glu Ala Glu Asp Ala Ala Thr
        340                 345                 350

Tyr Tyr Cys Gln Gln Trp Ser Ser Asn Pro Pro Thr Phe Gly Gly Gly
        355                 360                 365

Thr Lys Leu Glu Leu Lys Gly Gly Gly Ser Glu Val Gln Leu Gln
        370                 375                 380

Gln Ser Gly Pro Glu Leu Val Lys Pro Gly Ala Ser Val Lys Ile Ser
385                 390                 395                 400

Cys Lys Thr Ser Gly Tyr Thr Phe Thr Glu Tyr Thr Met His Trp Val
                405                 410                 415

Lys Gln Arg His Gly Lys Ser Leu Glu Trp Ile Gly Gly Ile Asn Pro
                420                 425                 430

Asn Asn Gly Gly Thr Trp Tyr Asn Gln Lys Phe Lys Gly Lys Ala Thr
                435                 440                 445

Leu Thr Val Asp Lys Ser Ser Ser Thr Ala Tyr Met Glu Leu Arg Ser
        450                 455                 460

Leu Thr Ser Glu Asp Ser Ala Val Tyr Phe Cys Ala Arg Pro Tyr Tyr
465                 470                 475                 480

Tyr Gly Ser Arg Glu Asp Tyr Phe Asp Tyr Trp Gly Gln Gly Thr Thr
                485                 490                 495

Leu Thr Val Ser Ser Asn Leu Val Pro Met Val Ala Thr Val
                500                 505                 510

<210> SEQ ID NO 110
<211> LENGTH: 510
<212> TYPE: PRT
<213> ORGANISM: Artificial Sequence
<220> FEATURE:
<223> OTHER INFORMATION: PD-L1 binding protein 115746

<400> SEQUENCE: 110

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Cys Gly Asp
        35                  40                  45

Asn Leu Phe Ala Val Asp Ile Leu Gly Phe Asp Phe Thr Leu Gly Arg
        50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
```

```
            180                 185                 190
Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
            210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                    245                 250                 255

Pro Ser Thr Pro Pro Gly Ser Ser Gly Gly Ala Pro Asp Ile Gln Met
            260                 265                 270

Thr Gln Ser Pro Ser Ser Leu Ser Ala Ser Val Gly Asp Arg Val Thr
            275                 280                 285

Ile Thr Cys Ser Ala Ser Ser Val Ser Tyr Met Tyr Trp Tyr Gln
            290                 295                 300

Gln Lys Pro Arg Ser Ser Pro Lys Pro Trp Ile Tyr Leu Thr Ser Asn
305                 310                 315                 320

Leu Ala Ser Gly Val Pro Ala Arg Phe Ser Gly Ser Gly Ser Gly Thr
                    325                 330                 335

Ser Tyr Ser Leu Thr Ile Ser Ser Met Glu Ala Glu Asp Ala Ala Thr
            340                 345                 350

Tyr Tyr Cys Gln Gln Trp Ser Ser Asn Pro Pro Thr Phe Gly Gly Gly
            355                 360                 365

Thr Lys Leu Glu Ile Lys Gly Gly Gly Ser Glu Val Gln Leu Gln
370                 375                 380

Gln Ser Gly Pro Glu Leu Val Lys Pro Gly Ala Ser Val Lys Ile Ser
385                 390                 395                 400

Cys Lys Thr Ser Gly Tyr Thr Phe Thr Glu Tyr Thr Met His Trp Val
                    405                 410                 415

Lys Gln Ser His Gly Lys Ser Leu Glu Trp Ile Gly Gly Ile Asn Pro
            420                 425                 430

Asn Asn Gly Gly Thr Trp Tyr Asn Arg Lys Phe Lys Gly Lys Ala Ala
            435                 440                 445

Leu Thr Val Asp Lys Ser Ser Ser Thr Ala Tyr Met Glu Leu Arg Ser
450                 455                 460

Leu Thr Ser Glu Asp Ser Ala Val Tyr Phe Cys Ala Arg Pro Tyr Tyr
465                 470                 475                 480

Tyr Gly Ser Arg Glu Asp Tyr Phe Asp Tyr Trp Gly Gln Gly Thr Thr
                    485                 490                 495

Leu Thr Val Ser Ser Asn Leu Val Pro Met Val Ala Thr Val
            500                 505                 510

<210> SEQ ID NO 111
<211> LENGTH: 534
<212> TYPE: PRT
<213> ORGANISM: Artificial Sequence
<220> FEATURE:
<223> OTHER INFORMATION: PD-L1 binding protein 115747

<400> SEQUENCE: 111

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
```

-continued

```
                35                  40                  45
Asn Leu Phe Ala Val Asp Ile Leu Gly Phe Asp Phe Thr Leu Gly Arg
 50                  55                  60
Phe Asn Asn Leu Arg Leu Ile Val Glu Arg Asn Asn Leu Tyr Val Thr
 65                  70                  75                  80
Gly Phe Val Asn Arg Thr Asn Asn Val Phe Tyr Arg Phe Ala Asp Phe
                 85                  90                  95
Ser His Val Thr Phe Pro Gly Thr Thr Ala Val Thr Leu Ser Ala Asp
                100                 105                 110
Ser Ser Tyr Thr Thr Leu Gln Arg Val Ala Gly Ile Ser Arg Thr Gly
            115                 120                 125
Met Gln Ile Asn Arg His Ser Leu Thr Thr Ser Tyr Leu Asp Leu Met
        130                 135                 140
Ser His Ser Gly Thr Ser Leu Thr Gln Ser Val Ala Arg Ala Met Leu
145                 150                 155                 160
Arg Phe Val Thr Val Thr Ala Glu Ala Leu Arg Phe Arg Gln Ile Gln
                165                 170                 175
Arg Gly Phe Arg Thr Thr Leu Asp Asp Leu Ser Gly Ala Ser Tyr Val
            180                 185                 190
Met Thr Ala Glu Asp Val Asp Leu Thr Leu Asn Trp Gly Arg Leu Ser
        195                 200                 205
Ser Val Leu Pro Asp Tyr His Gly Gln Asp Ser Val Arg Val Gly Arg
210                 215                 220
Ile Ser Phe Gly Ser Ile Asn Ala Ile Leu Gly Ser Val Ala Leu Ile
225                 230                 235                 240
Leu Asn Ser His His His Ala Ser Ala Val Ala Ala Glu Phe Pro Lys
                245                 250                 255
Pro Ser Thr Pro Pro Gly Ser Ser Gly Ala Pro Glu Val Gln Leu
            260                 265                 270
Gln Glu Ser Gly Pro Glu Leu Val Lys Pro Gly Ala Ser Val Lys Ile
        275                 280                 285
Ser Cys Lys Thr Ser Gly Tyr Thr Phe Thr Glu Asn Ser Met His Trp
290                 295                 300
Val Lys Gln Ser His Gly Lys Ser Leu Glu Trp Ile Gly Gly Ile Asn
305                 310                 315                 320
Pro Asn Asn Gly Gly Thr Ser Tyr Asn Gln Lys Phe Lys Gly Lys Ala
                325                 330                 335
Thr Leu Thr Val Asp Lys Ser Ser Thr Ala Tyr Met Glu Phe Arg
            340                 345                 350
Ser Leu Thr Ser Glu Asp Ser Ala Val Tyr Tyr Cys Ala Arg Pro Tyr
        355                 360                 365
Tyr Tyr Gly Tyr Arg Glu Asp Tyr Phe Asp Tyr Trp Gly Gln Gly Thr
    370                 375                 380
Thr Leu Thr Val Ser Ser Gly Gly Gly Ser Gly Gly Gly Ser
385                 390                 395                 400
Gly Gly Gly Gly Ser Gly Gly Gly Ser Gly Gly Gly Ser Asp
                405                 410                 415
Ile Gln Met Thr Gln Ser Pro Ser Leu Ser Ala Ser Val Gly Asp
                420                 425                 430
Arg Val Thr Ile Thr Cys Ser Ala Ser Ser Val Ser Tyr Met Tyr
            435                 440                 445
Trp Tyr Gln Gln Lys Pro Arg Ser Ser Pro Lys Pro Trp Ile Tyr Leu
        450                 455                 460
```

```
Thr Ser Asn Leu Ala Ser Gly Val Pro Ala Arg Phe Ser Gly Ser Gly
465                 470                 475                 480

Ser Gly Thr Ser Tyr Ser Leu Thr Ile Ser Ser Met Glu Ala Glu Asp
            485                 490                 495

Ala Ala Thr Tyr Tyr Cys Gln Gln Trp Ser Ser Tyr Pro Pro Thr Phe
        500                 505                 510

Gly Gly Gly Thr Lys Leu Glu Ile Lys His His Ala Ala Asn Leu Val
        515                 520                 525

Pro Met Val Ala Thr Val
    530

<210> SEQ ID NO 112
<211> LENGTH: 534
<212> TYPE: PRT
<213> ORGANISM: Artificial Sequence
<220> FEATURE:
<223> OTHER INFORMATION: PD-L1 binding protein 115748

<400> SEQUENCE: 112

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val His Leu
            260                 265                 270

Val Glu Ser Gly Pro Glu Leu Val Lys Pro Gly Ala Ser Val Lys Ile
        275                 280                 285
```

Ser Cys Lys Thr Ser Gly Tyr Thr Phe Thr Glu Tyr Thr Met His Trp
290                 295                 300

Val Lys Gln Ser His Gly Lys Ser Leu Glu Trp Ile Gly Gly Ile Asp
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Thr Ala Tyr Met Glu Leu Arg
                340                 345                 350

Ser Leu Thr Ser Glu Asp Ser Ala Val Tyr Phe Cys Ala Arg Pro Tyr
                355                 360                 365

Tyr Tyr Gly Ser Arg Glu Asp Tyr Phe Asp Tyr Trp Gly Gln Gly Thr
                370                 375                 380

Thr Leu Thr Val Ser Ser Gly Gly Gly Ser Gly Gly Gly Ser
385                 390                 395                 400

Gly Gly Gly Gly Ser Gly Gly Gly Ser Gly Gly Gly Ser Asp
                405                 410                 415

Ile Gln Met Thr Gln Ser Pro Ser Ser Leu Ser Ala Ser Val Gly Asp
                420                 425                 430

Arg Val Thr Ile Thr Cys Ser Ala Ser Ser Ser Val Ser Tyr Met Tyr
                435                 440                 445

Trp Tyr Gln Gln Lys Pro Arg Ser Ser Pro Lys Pro Trp Ile Tyr Leu
450                 455                 460

Thr Ser Asn Leu Ala Ser Gly Val Pro Ala Arg Phe Ser Gly Ser Gly
465                 470                 475                 480

Ser Gly Thr Ser Tyr Ser Leu Thr Ile Ser Ser Met Glu Ala Glu Asp
                485                 490                 495

Ala Ala Thr Tyr Tyr Cys Gln Gln Trp Ser Ser Asn Pro Pro Thr Phe
                500                 505                 510

Gly Gly Gly Thr Lys Leu Glu Ile Lys His His Ala Ala Asn Leu Val
                515                 520                 525

Pro Met Val Ala Thr Val
                530

<210> SEQ ID NO 113
<211> LENGTH: 534
<212> TYPE: PRT
<213> ORGANISM: Artificial Sequence
<220> FEATURE:
<223> OTHER INFORMATION: PD-L1 binding protein 115749

<400> SEQUENCE: 113

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
                35                  40                  45

Asn Leu Phe Ala Val Asp Ile Leu Gly Phe Asp Phe Thr Leu Gly Arg
                50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

```
Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Thr Ala Tyr Met Glu Leu Arg
            340                 345                 350

Ser Leu Thr Ser Glu Asp Ser Ala Val Tyr Phe Cys Ala Arg Pro Tyr
        355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Gly Ser Gly Gly Gly Gly Ser
385                 390                 395                 400

Gly Gly Gly Gly Ser Gly Gly Gly Ser Gly Gly Gly Gly Ser Asp
                405                 410                 415

Ile Gln Met Thr Gln Ser Pro Ser Ser Leu Ser Ala Ser Val Gly Asp
            420                 425                 430

Arg Val Thr Ile Thr Cys Ser Ala Ser Ser Ser Val Ser Tyr Met Tyr
        435                 440                 445

Trp Tyr Gln Gln Lys Pro Arg Ser Ser Pro Lys Pro Trp Ile Tyr Leu
    450                 455                 460

Thr Ser Asn Leu Ala Ser Gly Val Pro Ala Arg Phe Ser Gly Ser Gly
465                 470                 475                 480

Ser Gly Thr Ser Tyr Ser Leu Thr Ile Ser Ser Met Glu Ala Glu Asp
                485                 490                 495

Ala Ala Thr Tyr Tyr Cys Gln Gln Trp Ser Ser Asn Pro Pro Thr Phe
            500                 505                 510

Gly Gly Gly Thr Lys Leu Glu Leu Lys His His Ala Ala Asn Leu Val
        515                 520                 525
```

```
Pro Met Val Ala Thr Val
        530

<210> SEQ ID NO 114
<211> LENGTH: 534
<212> TYPE: PRT
<213> ORGANISM: Artificial Sequence
<220> FEATURE:
<223> OTHER INFORMATION: PD-L1 binding protein 115750

<400> SEQUENCE: 114

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Ser His Gly Lys Ser Leu Glu Trp Ile Gly Gly Ile Asn
305                 310                 315                 320

Pro Asn Asn Gly Gly Thr Trp Tyr Asn Arg Lys Phe Lys Gly Lys Ala
                325                 330                 335

Ala Leu Thr Val Asp Lys Ser Ser Thr Ala Tyr Met Glu Leu Arg
            340                 345                 350
```

```
Ser Leu Thr Ser Glu Asp Ser Ala Val Tyr Phe Cys Ala Arg Pro Tyr
            355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Ser Gly Gly Gly Ser
385                 390                 395                 400

Gly Gly Gly Gly Ser Gly Gly Gly Ser Gly Gly Gly Ser Asp
                405                 410                 415

Ile Gln Met Thr Gln Ser Pro Ser Ser Leu Ser Ala Ser Val Gly Asp
            420                 425                 430

Arg Val Thr Ile Thr Cys Ser Ala Ser Ser Ser Val Ser Tyr Met Tyr
            435                 440                 445

Trp Tyr Gln Gln Lys Pro Arg Ser Ser Pro Lys Pro Trp Ile Tyr Leu
    450                 455                 460

Thr Ser Asn Leu Ala Ser Gly Val Pro Ala Arg Phe Ser Gly Ser Gly
465                 470                 475                 480

Ser Gly Thr Ser Tyr Ser Leu Thr Ile Ser Ser Met Glu Ala Glu Asp
                485                 490                 495

Ala Ala Thr Tyr Tyr Cys Gln Gln Trp Ser Ser Asn Pro Pro Thr Phe
            500                 505                 510

Gly Gly Gly Thr Lys Leu Glu Ile Lys His His Ala Ala Asn Leu Val
            515                 520                 525

Pro Met Val Ala Thr Val
    530

<210> SEQ ID NO 115
<211> LENGTH: 510
<212> TYPE: PRT
<213> ORGANISM: Artificial Sequence
<220> FEATURE:
<223> OTHER INFORMATION: PD-L1 binding protein 115751

<400> SEQUENCE: 115

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175
```

```
Arg Gly Phe Arg Thr Thr Leu Asp Asp Leu Ser Gly Ala Ser Tyr Val
            180                 185                 190
Met Thr Ala Glu Asp Val Asp Leu Thr Leu Asn Trp Gly Arg Leu Ser
            195                 200                 205
Ser Val Leu Pro Asp Tyr His Gly Gln Asp Ser Val Arg Val Gly Arg
            210                 215                 220
Ile Ser Phe Gly Ser Ile Asn Ala Ile Leu Gly Ser Val Ala Leu Ile
225                 230                 235                 240
Leu Asn Ser His His His Ala Ser Ala Val Ala Ala Ser Pro Ser Thr
            245                 250                 255
Pro Pro Thr Pro Ser Pro Ser Thr Pro Pro Ala Ser Asp Ile Gln Met
            260                 265                 270
Thr Gln Ser Pro Ser Ser Leu Ser Ala Ser Val Gly Asp Arg Val Thr
            275                 280                 285
Ile Thr Cys Arg Ala Ser Ser Ser Val Ser Tyr Met Tyr Trp Tyr Gln
            290                 295                 300
Gln Lys Pro Gly Gln Ala Pro Arg Pro Leu Ile Tyr Leu Thr Ser Asn
305                 310                 315                 320
Leu Ala Ser Gly Ile Pro Asp Arg Phe Ser Gly Ser Gly Ser Gly Thr
            325                 330                 335
Asp Tyr Thr Leu Thr Ile Ser Arg Leu Glu Pro Glu Asp Phe Ala Val
            340                 345                 350
Tyr Tyr Cys Gln Gln Trp Ser Ser Tyr Pro Pro Thr Phe Gly Gln Gly
            355                 360                 365
Thr Lys Val Glu Ile Lys Gly Gly Gly Ser Gln Val Gln Leu Val
            370                 375                 380
Gln Ser Gly Pro Glu Val Lys Lys Pro Gly Ala Ser Val Lys Val Ser
385                 390                 395                 400
Cys Lys Ala Ser Gly Tyr Thr Phe Thr Glu Asn Ser Met His Trp Val
            405                 410                 415
Arg Gln Ser His Gly Lys Ser Leu Glu Trp Met Gly Gly Ile Asn Pro
            420                 425                 430
Asn Asn Gly Gly Thr Ser Tyr Asn Gln Lys Phe Lys Gly Lys Val Thr
            435                 440                 445
Met Thr Thr Asp Lys Ser Thr Ser Thr Ala Tyr Met Glu Leu Arg Ser
450                 455                 460
Leu Thr Ser Asp Asp Thr Ala Val Tyr Tyr Cys Ala Arg Pro Tyr Tyr
465                 470                 475                 480
Tyr Gly Tyr Arg Glu Asp Tyr Phe Asp Tyr Trp Gly Gln Gly Thr Thr
            485                 490                 495
Leu Thr Val Ser Ser Asn Leu Val Pro Met Val Ala Thr Val
            500                 505                 510

<210> SEQ ID NO 116
<211> LENGTH: 510
<212> TYPE: PRT
<213> ORGANISM: Artificial Sequence
<220> FEATURE:
<223> OTHER INFORMATION: PD-L1 binding protein 115752

<400> SEQUENCE: 116

Met Lys Glu Phe Thr Leu Asp Phe Ser Thr Ala Lys Thr Tyr Val Asp
1               5                   10                  15
Ser Leu Asn Val Ile Arg Ser Ala Ile Gly Thr Pro Leu Gln Thr Ile
            20                  25                  30
```

```
Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
 50                  55                  60

Phe Asn Asn Leu Arg Leu Ile Val Glu Arg Asn Asn Leu Tyr Val Thr
 65                  70                  75                  80

Gly Phe Val Asn Arg Thr Asn Asn Val Phe Tyr Arg Phe Ala Asp Phe
                 85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
                115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
                180                 185                 190

Met Thr Ala Glu Asp Val Asp Leu Thr Leu Asn Trp Gly Arg Leu Ser
                195                 200                 205

Ser Val Leu Pro Asp Tyr His Gly Gln Asp Ser Val Arg Val Gly Arg
                210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Ser Pro Ser Thr
                245                 250                 255

Pro Pro Thr Pro Ser Pro Ser Thr Pro Pro Ala Ser Asp Ile Gln Met
                260                 265                 270

Thr Gln Ser Pro Ser Ser Leu Ser Ala Ser Val Gly Asp Arg Val Thr
                275                 280                 285

Ile Thr Cys Arg Ala Ser Ser Ser Val Ser Tyr Met Tyr Trp Tyr Gln
                290                 295                 300

Gln Lys Pro Gly Gln Ala Pro Arg Pro Leu Ile Tyr Leu Thr Ser Asn
305                 310                 315                 320

Leu Ala Ser Gly Ile Pro Asp Arg Phe Ser Gly Ser Gly Ser Gly Thr
                325                 330                 335

Asp Tyr Thr Leu Thr Ile Ser Arg Leu Glu Pro Glu Asp Phe Ala Val
                340                 345                 350

Tyr Tyr Cys Gln Gln Trp Ser Ser Tyr Pro Pro Thr Phe Gly Gln Gly
                355                 360                 365

Thr Lys Val Glu Ile Lys Gly Gly Gly Ser Gln Val Gln Leu Val
                370                 375                 380

Gln Ser Gly Ala Glu Val Lys Lys Pro Gly Ala Ser Val Lys Val Ser
385                 390                 395                 400

Cys Lys Ala Ser Gly Tyr Thr Phe Thr Glu Asn Ser Met His Trp Val
                405                 410                 415

Arg Gln Ala His Gly Gln Arg Leu Glu Trp Ile Gly Ile Asn Pro
                420                 425                 430

Asn Asn Gly Gly Thr Trp Tyr Asn Arg Lys Phe Lys Gly Lys Ala Ala
                435                 440                 445

Ile Thr Val Asp Thr Ser Ala Ser Thr Ala Tyr Met Glu Leu Ser Ser
```

```
                 450                 455                 460
Leu Arg Ser Glu Asp Thr Ala Val Tyr Cys Ala Arg Pro Tyr Tyr
465                 470                 475                 480

Tyr Gly Tyr Arg Glu Asp Tyr Phe Asp Tyr Trp Gly Gln Gly Thr Thr
                485                 490                 495

Leu Thr Val Ser Ser Asn Leu Val Pro Met Val Ala Thr Val
                500                 505                 510

<210> SEQ ID NO 117
<211> LENGTH: 510
<212> TYPE: PRT
<213> ORGANISM: Artificial Sequence
<220> FEATURE:
<223> OTHER INFORMATION: PD-L1 binding protein 115753

<400> SEQUENCE: 117

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
                180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Ser Pro Ser Thr
                245                 250                 255

Pro Pro Thr Pro Ser Pro Ser Thr Pro Pro Ala Ser Asp Ile Gln Met
            260                 265                 270

Thr Gln Ser Pro Ser Ser Leu Ser Ala Ser Val Gly Asp Arg Val Thr
                275                 280                 285

Ile Thr Cys Arg Ala Ser Ser Ser Val Ser Tyr Met Tyr Trp Tyr Gln
290                 295                 300

Gln Lys Pro Gly Gln Ala Pro Arg Pro Leu Ile Tyr Leu Thr Ser Asn
```

```
                305                 310                 315                 320
Leu Ala Ser Gly Ile Pro Asp Arg Phe Ser Gly Ser Gly Ser Gly Thr
                325                 330                 335
Asp Tyr Thr Leu Thr Ile Ser Arg Leu Glu Pro Glu Asp Phe Ala Val
                340                 345                 350
Tyr Tyr Cys Gln Gln Trp Ser Ser Tyr Pro Pro Thr Phe Gly Gln Gly
                355                 360                 365
Thr Lys Val Glu Ile Lys Gly Gly Gly Ser Gln Val Gln Leu Val
                370                 375             380
Gln Ser Gly Ala Glu Val Lys Lys Pro Gly Ala Ser Val Lys Val Ser
385                 390                 395                 400
Cys Lys Ala Ser Gly Tyr Thr Phe Thr Glu Asn Ser Met His Trp Val
                405                 410                 415
Arg Gln Ala His Gly Gln Arg Leu Glu Trp Ile Gly Gly Ile Asn Pro
                420                 425                 430
Asn Asn Gly Gly Thr Ser Tyr Asn Gln Lys Phe Lys Gly Lys Ala Thr
                435                 440                 445
Ile Thr Val Asp Thr Ser Ala Ser Thr Ala Tyr Met Glu Leu Ser Ser
                450                 455                 460
Leu Arg Ser Glu Asp Thr Ala Val Tyr Tyr Cys Ala Arg Pro Tyr Tyr
465                 470                 475                 480
Tyr Gly Tyr Arg Glu Asp Tyr Phe Asp Tyr Trp Gly Gln Gly Thr Thr
                485                 490                 495
Leu Thr Val Ser Ser Asn Leu Val Pro Met Val Ala Thr Val
                500                 505                 510

<210> SEQ ID NO 118
<211> LENGTH: 510
<212> TYPE: PRT
<213> ORGANISM: Artificial Sequence
<220> FEATURE:
<223> OTHER INFORMATION: PD-L1 binding protein 115754

<400> SEQUENCE: 118

Met Lys Glu Phe Thr Leu Asp Phe Ser Thr Ala Lys Thr Tyr Val Asp
1               5                   10                  15
Ser Leu Asn Val Ile Arg Ser Ala Ile Gly Thr Pro Leu Gln Thr Ile
                20                  25                  30
Ser Ser Gly Gly Thr Ser Leu Leu Met Ile Asp Ser Gly Ile Gly Asp
                35                  40                  45
Asn Leu Phe Ala Val Asp Ile Leu Gly Phe Asp Phe Thr Leu Gly Arg
                50                  55                  60
Phe Asn Asn Leu Arg Leu Ile Val Glu Arg Asn Asn Leu Tyr Val Thr
65                  70                  75                  80
Gly Phe Val Asn Arg Thr Asn Asn Val Phe Tyr Arg Phe Ala Asp Phe
                85                  90                  95
Ser His Val Thr Phe Pro Gly Thr Thr Ala Val Thr Leu Ser Ala Asp
                100                 105                 110
Ser Ser Tyr Thr Thr Leu Gln Arg Val Ala Gly Ile Ser Arg Thr Gly
                115                 120                 125
Met Gln Ile Asn Arg His Ser Leu Thr Thr Ser Tyr Leu Asp Leu Met
                130                 135                 140
Ser His Ser Gly Thr Ser Leu Thr Gln Ser Val Ala Arg Ala Met Leu
145                 150                 155                 160
Arg Phe Val Thr Val Thr Ala Glu Ala Leu Arg Phe Arg Gln Ile Gln
```

```
                165                 170                 175
Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
            210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Ser Pro Ser Thr
                245                 250                 255

Pro Pro Thr Pro Ser Pro Ser Thr Pro Pro Ala Ser Asp Ile Gln Met
            260                 265                 270

Thr Gln Ser Pro Ser Ser Leu Ser Ala Ser Val Gly Asp Arg Val Thr
            275                 280                 285

Ile Thr Cys Arg Ala Ser Ser Ser Val Ser Tyr Met Tyr Trp Tyr Gln
            290                 295                 300

Gln Lys Pro Gly Gln Ala Pro Arg Pro Leu Ile Tyr Leu Thr Ser Asn
305                 310                 315                 320

Leu Ala Ser Gly Ile Pro Asp Arg Phe Ser Gly Ser Gly Ser Gly Thr
                325                 330                 335

Asp Tyr Thr Leu Thr Ile Ser Arg Leu Glu Pro Glu Asp Phe Ala Val
            340                 345                 350

Tyr Tyr Cys Gln Gln Trp Ser Ser Tyr Pro Pro Thr Phe Gly Gln Gly
            355                 360                 365

Thr Lys Val Glu Ile Lys Gly Gly Gly Ser Gln Val Gln Leu Val
            370                 375                 380

Gln Ser Gly Ala Glu Val Lys Lys Pro Gly Ala Ser Val Lys Val Ser
385                 390                 395                 400

Cys Lys Thr Ser Gly Tyr Thr Phe Thr Glu Asn Ser Met His Trp Val
                405                 410                 415

Arg Gln Ala Pro Gly Gln Arg Leu Glu Trp Met Gly Gly Ile Asn Pro
            420                 425                 430

Asn Asn Gly Gly Thr Ser Tyr Asn Gln Lys Phe Gln Gly Arg Val Thr
            435                 440                 445

Leu Thr Val Asp Lys Ser Ser Thr Ala Tyr Met Glu Leu Ser Ser
            450                 455                 460

Leu Arg Ser Glu Asp Thr Ala Val Tyr Tyr Cys Ala Arg Pro Tyr Tyr
465                 470                 475                 480

Tyr Gly Tyr Arg Glu Asp Tyr Phe Asp Tyr Trp Gly Gln Gly Thr Thr
                485                 490                 495

Leu Thr Val Ser Ser Asn Leu Val Pro Met Val Ala Thr Val
            500                 505                 510

<210> SEQ ID NO 119
<211> LENGTH: 534
<212> TYPE: PRT
<213> ORGANISM: Artificial Sequence
<220> FEATURE:
<223> OTHER INFORMATION: PD-L1 binding protein 115755

<400> SEQUENCE: 119

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
```

```
                20                  25                  30
Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
        130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
        210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ser Pro Ser Thr
                245                 250                 255

Pro Pro Thr Pro Ser Pro Ser Thr Pro Pro Ala Ser Gln Val Gln Leu
            260                 265                 270

Val Gln Ser Gly Pro Glu Val Lys Lys Pro Gly Ala Ser Val Lys Val
        275                 280                 285

Ser Cys Lys Ala Ser Gly Tyr Thr Phe Thr Glu Asn Ser Met His Trp
    290                 295                 300

Val Arg Gln Ser His Gly Lys Ser Leu Glu Trp Met Gly Gly Ile Asn
305                 310                 315                 320

Pro Asn Asn Gly Gly Thr Ser Tyr Asn Gln Lys Phe Lys Gly Lys Val
                325                 330                 335

Thr Met Thr Thr Asp Lys Ser Thr Ser Thr Ala Tyr Met Glu Leu Arg
            340                 345                 350

Ser Leu Thr Ser Asp Asp Thr Ala Val Tyr Tyr Cys Ala Arg Pro Tyr
            355                 360                 365

Tyr Tyr Gly Tyr Arg Glu Asp Tyr Phe Asp Tyr Trp Gly Gln Gly Thr
        370                 375                 380

Thr Leu Thr Val Ser Ser Gly Gly Gly Gly Ser Gly Gly Gly Gly Ser
385                 390                 395                 400

Gly Gly Gly Gly Ser Gly Gly Gly Ser Gly Gly Gly Gly Ser Asp
                405                 410                 415

Ile Gln Met Thr Gln Ser Pro Ser Ser Leu Ser Ala Ser Val Gly Asp
            420                 425                 430

Arg Val Thr Ile Thr Cys Arg Ala Ser Ser Ser Val Ser Tyr Met Tyr
            435                 440                 445
```

```
Trp Tyr Gln Gln Lys Pro Gly Gln Ala Pro Arg Pro Leu Ile Tyr Leu
        450                 455                 460

Thr Ser Asn Leu Ala Ser Gly Ile Pro Asp Arg Phe Ser Gly Ser Gly
465                 470                 475                 480

Ser Gly Thr Asp Tyr Thr Leu Thr Ile Ser Arg Leu Glu Pro Glu Asp
                485                 490                 495

Phe Ala Val Tyr Tyr Cys Gln Gln Trp Ser Ser Tyr Pro Pro Thr Phe
                500                 505                 510

Gly Gln Gly Thr Lys Val Glu Ile Lys His His Ala Ala Asn Leu Val
            515                 520                 525

Pro Met Val Ala Thr Val
        530

<210> SEQ ID NO 120
<211> LENGTH: 534
<212> TYPE: PRT
<213> ORGANISM: Artificial Sequence
<220> FEATURE:
<223> OTHER INFORMATION: PD-L1 binding protein 115756

<400> SEQUENCE: 120

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Ser Pro Ser Thr
                245                 250                 255

Pro Pro Thr Pro Ser Pro Ser Thr Pro Pro Ala Ser Gln Val Gln Leu
            260                 265                 270
```

-continued

```
Val Gln Ser Gly Ala Glu Val Lys Lys Pro Gly Ala Ser Val Lys Val
            275                 280                 285

Ser Cys Lys Ala Ser Gly Tyr Thr Phe Thr Glu Asn Ser Met His Trp
290                 295                 300

Val Arg Gln Ala His Gly Gln Arg Leu Glu Trp Ile Gly Gly Ile Asn
305                 310                 315                 320

Pro Asn Asn Gly Gly Thr Trp Tyr Asn Arg Lys Phe Lys Gly Lys Ala
                325                 330                 335

Ala Ile Thr Val Asp Thr Ser Ala Ser Thr Ala Tyr Met Glu Leu Ser
            340                 345                 350

Ser Leu Arg Ser Glu Asp Thr Ala Val Tyr Tyr Cys Ala Arg Pro Tyr
            355                 360                 365

Tyr Tyr Gly Tyr Arg Glu Asp Tyr Phe Asp Tyr Trp Gly Gln Gly Thr
        370                 375                 380

Thr Leu Thr Val Ser Ser Gly Gly Gly Gly Ser Gly Gly Gly Gly Ser
385                 390                 395                 400

Gly Gly Gly Gly Ser Gly Gly Gly Ser Gly Gly Gly Gly Ser Asp
                405                 410                 415

Ile Gln Met Thr Gln Ser Pro Ser Ser Leu Ser Ala Ser Val Gly Asp
            420                 425                 430

Arg Val Thr Ile Thr Cys Arg Ala Ser Ser Ser Val Ser Tyr Met Tyr
            435                 440                 445

Trp Tyr Gln Gln Lys Pro Gly Gln Ala Pro Arg Pro Leu Ile Tyr Leu
        450                 455                 460

Thr Ser Asn Leu Ala Ser Gly Ile Pro Asp Arg Phe Ser Gly Ser Gly
465                 470                 475                 480

Ser Gly Thr Asp Tyr Thr Leu Thr Ile Ser Arg Leu Glu Pro Glu Asp
                485                 490                 495

Phe Ala Val Tyr Tyr Cys Gln Gln Trp Ser Ser Tyr Pro Pro Thr Phe
            500                 505                 510

Gly Gln Gly Thr Lys Val Glu Ile Lys His His Ala Ala Asn Leu Val
            515                 520                 525

Pro Met Val Ala Thr Val
    530
```

<210> SEQ ID NO 121
<211> LENGTH: 534
<212> TYPE: PRT
<213> ORGANISM: Artificial Sequence
<220> FEATURE:
<223> OTHER INFORMATION: PD-L1 binding protein 115757

<400> SEQUENCE: 121

```
Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95
```

```
Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Ser Pro Ser Thr
                245                 250                 255

Pro Pro Thr Pro Ser Pro Ser Thr Pro Pro Ala Ser Gln Val Gln Leu
            260                 265                 270

Val Gln Ser Gly Ala Glu Val Lys Lys Pro Gly Ala Ser Val Lys Val
        275                 280                 285

Ser Cys Lys Ala Ser Gly Tyr Thr Phe Thr Glu Asn Ser Met His Trp
    290                 295                 300

Val Arg Gln Ala His Gly Gln Arg Leu Glu Trp Ile Gly Gly Ile Asn
305                 310                 315                 320

Pro Asn Asn Gly Gly Thr Ser Tyr Asn Gln Lys Phe Lys Gly Lys Ala
                325                 330                 335

Thr Ile Thr Val Asp Thr Ser Ala Ser Thr Ala Tyr Met Glu Leu Ser
            340                 345                 350

Ser Leu Arg Ser Glu Asp Thr Ala Val Tyr Tyr Cys Ala Arg Pro Tyr
        355                 360                 365

Tyr Tyr Gly Tyr Arg Glu Asp Tyr Phe Asp Tyr Trp Gly Gln Gly Thr
    370                 375                 380

Thr Leu Thr Val Ser Ser Gly Gly Gly Ser Gly Gly Gly Gly Gly Ser
385                 390                 395                 400

Gly Gly Gly Gly Ser Gly Gly Gly Ser Gly Gly Gly Gly Ser Asp
                405                 410                 415

Ile Gln Met Thr Gln Ser Pro Ser Ser Leu Ser Ala Ser Val Gly Asp
            420                 425                 430

Arg Val Thr Ile Thr Cys Arg Ala Ser Ser Ser Val Ser Tyr Met Tyr
        435                 440                 445

Trp Tyr Gln Gln Lys Pro Gly Gln Ala Pro Arg Pro Leu Ile Tyr Leu
    450                 455                 460

Thr Ser Asn Leu Ala Ser Gly Ile Pro Asp Arg Phe Ser Gly Ser Gly
465                 470                 475                 480

Ser Gly Thr Asp Tyr Thr Leu Thr Ile Ser Arg Leu Glu Pro Glu Asp
                485                 490                 495

Phe Ala Val Tyr Tyr Cys Gln Gln Trp Ser Ser Tyr Pro Pro Thr Phe
            500                 505                 510
```

```
Gly Gln Gly Thr Lys Val Glu Ile Lys His His Ala Ala Asn Leu Val
        515                 520                 525
Pro Met Val Ala Thr Val
        530

<210> SEQ ID NO 122
<211> LENGTH: 534
<212> TYPE: PRT
<213> ORGANISM: Artificial Sequence
<220> FEATURE:
<223> OTHER INFORMATION: PD-L1 binding protein 115758

<400> SEQUENCE: 122

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Ser Pro Ser Thr
                245                 250                 255

Pro Pro Thr Pro Ser Pro Ser Thr Pro Pro Ala Ser Gln Val Gln Leu
            260                 265                 270

Val Gln Ser Gly Ala Glu Val Lys Lys Pro Gly Ala Ser Val Lys Val
        275                 280                 285

Ser Cys Lys Thr Ser Gly Tyr Thr Phe Thr Glu Asn Ser Met His Trp
    290                 295                 300

Val Arg Gln Ala Pro Gly Gln Arg Leu Glu Trp Met Gly Gly Ile Asn
305                 310                 315                 320

Pro Asn Asn Gly Gly Thr Ser Tyr Asn Gln Lys Phe Gln Gly Arg Val
                325                 330                 335
```

Thr Leu Thr Val Asp Lys Ser Ser Thr Ala Tyr Met Glu Leu Ser
            340                 345                 350

Ser Leu Arg Ser Glu Asp Thr Ala Val Tyr Tyr Cys Ala Arg Pro Tyr
        355                 360                 365

Tyr Tyr Gly Tyr Arg Glu Asp Tyr Phe Asp Tyr Trp Gly Gln Gly Thr
370                 375                 380

Thr Leu Thr Val Ser Ser Gly Gly Gly Gly Ser Gly Gly Gly Gly Ser
385                 390                 395                 400

Gly Gly Gly Ser Gly Gly Gly Ser Gly Gly Gly Ser Asp
            405                 410                 415

Ile Gln Met Thr Gln Ser Pro Ser Ser Leu Ser Ala Ser Val Gly Asp
            420                 425                 430

Arg Val Thr Ile Thr Cys Arg Ala Ser Ser Ser Val Ser Tyr Met Tyr
            435                 440                 445

Trp Tyr Gln Gln Lys Pro Gly Gln Ala Pro Arg Pro Leu Ile Tyr Leu
        450                 455                 460

Thr Ser Asn Leu Ala Ser Gly Ile Pro Asp Arg Phe Ser Gly Ser Gly
465                 470                 475                 480

Ser Gly Thr Asp Tyr Thr Leu Thr Ile Ser Arg Leu Glu Pro Glu Asp
            485                 490                 495

Phe Ala Val Tyr Tyr Cys Gln Gln Trp Ser Ser Tyr Pro Pro Thr Phe
            500                 505                 510

Gly Gln Gly Thr Lys Val Glu Ile Lys His His Ala Ala Asn Leu Val
            515                 520                 525

Pro Met Val Ala Thr Val
        530

<210> SEQ ID NO 123
<211> LENGTH: 521
<212> TYPE: PRT
<213> ORGANISM: Artificial Sequence
<220> FEATURE:
<223> OTHER INFORMATION: PD-L1 binding protein 115961

<400> SEQUENCE: 123

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
            85                  90                  95

Ser His Val Thr Phe Pro Gly Thr Thr Ala Val Thr Leu Ser Ala Asp
        100                 105                 110

Ser Ser Tyr Thr Thr Leu Gln Arg Val Ala Gly Ile Ser Arg Thr Gly
    115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
            165                 170                 175

Arg Gly Phe Arg Thr Thr Leu Asp Asp Leu Ser Gly Ala Ser Tyr Val
        180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Thr Ala Tyr Met Glu Leu Arg
            340                 345                 350

Ser Leu Thr Ser Glu Asp Ser Ala Val Tyr Phe Cys Ala Arg Pro Tyr
        355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Gly Ser Gly Gly Gly Gly Ser
385                 390                 395                 400

Gly Gly Gly Gly Ser Gly Gly Gly Gly Ser Gly Gly Gly Gly Ser Asp
                405                 410                 415

Ile Gln Met Thr Gln Ser Pro Ser Ser Leu Ser Ala Ser Val Gly Asp
            420                 425                 430

Arg Val Thr Ile Thr Cys Ser Ala Ser Ser Val Ser Tyr Met Tyr
        435                 440                 445

Trp Tyr Gln Gln Lys Pro Arg Ser Ser Pro Lys Pro Trp Ile Tyr Leu
    450                 455                 460

Thr Ser Asn Leu Ala Ser Gly Val Pro Ala Arg Phe Ser Gly Ser Gly
465                 470                 475                 480

Ser Gly Thr Ser Tyr Ser Leu Thr Ile Ser Ser Met Glu Ala Glu Asp
                485                 490                 495

Ala Ala Thr Tyr Tyr Cys Gln Gln Trp Ser Ser Asn Pro Pro Thr Phe
            500                 505                 510

Gly Gly Gly Thr Lys Leu Glu Leu Lys
        515                 520

<210> SEQ ID NO 124
<211> LENGTH: 521
<212> TYPE: PRT
<213> ORGANISM: Artificial Sequence
<220> FEATURE:
<223> OTHER INFORMATION: PD-L1 binding protein 115962

<400> SEQUENCE: 124

```
Met Lys Glu Phe Thr Leu Asp Phe Ser Thr Ala Lys Thr Tyr Val Asp
1               5                   10                  15
Ser Leu Asn Val Ile Arg Ser Ala Ile Gly Thr Pro Leu Gln Thr Ile
            20                  25                  30
Ser Ser Gly Gly Thr Ser Leu Leu Met Ile Asp Ser Gly Ile Gly Asp
        35                  40                  45
Asn Leu Phe Ala Val Asp Ile Leu Gly Phe Asp Phe Thr Leu Gly Arg
50                  55                  60
Phe Asn Asn Leu Arg Leu Ile Val Glu Arg Asn Asn Leu Tyr Val Thr
65                  70                  75                  80
Gly Phe Val Asn Arg Thr Asn Asn Val Phe Tyr Arg Phe Ala Asp Phe
                85                  90                  95
Ser His Val Thr Phe Pro Gly Thr Thr Ala Val Thr Leu Ser Ala Asp
                100                 105                 110
Ser Ser Tyr Thr Thr Leu Gln Arg Val Ala Gly Ile Ser Arg Thr Gly
            115                 120                 125
Met Gln Ile Asn Arg His Ser Leu Thr Thr Ser Tyr Leu Asp Leu Met
    130                 135                 140
Ser His Ser Gly Thr Ser Leu Thr Gln Ser Val Ala Arg Ala Met Leu
145                 150                 155                 160
Arg Phe Val Thr Val Thr Ala Glu Ala Leu Arg Phe Arg Gln Ile Gln
                165                 170                 175
Arg Gly Phe Arg Thr Thr Leu Asp Asp Leu Ser Gly Ala Ser Tyr Val
            180                 185                 190
Met Thr Ala Glu Asp Val Asp Leu Thr Leu Asn Trp Gly Arg Leu Ser
        195                 200                 205
Ser Val Leu Pro Asp Tyr His Gly Gln Asp Ser Val Arg Val Gly Arg
    210                 215                 220
Ile Ser Phe Gly Ser Ile Asn Ala Ile Leu Gly Ser Val Ala Leu Ile
225                 230                 235                 240
Leu Asn Ser His His His Ala Ser Ala Val Ala Glu Phe Pro Lys
                245                 250                 255
Pro Ser Thr Pro Pro Gly Ser Ser Gly Gly Ala Pro Glu Val Gln Leu
                260                 265                 270
Gln Gln Ser Gly Pro Glu Leu Val Lys Pro Gly Ala Ser Val Lys Ile
        275                 280                 285
Ser Cys Lys Thr Ser Gly Tyr Thr Phe Thr Glu Tyr Thr Met His Trp
    290                 295                 300
Val Lys Gln Ser His Gly Lys Ser Leu Glu Trp Ile Gly Gly Ile Asn
305                 310                 315                 320
Pro Asn Asn Gly Gly Thr Trp Tyr Asn Arg Lys Phe Lys Gly Lys Ala
                325                 330                 335
Ala Leu Thr Val Asp Lys Ser Ser Thr Ala Tyr Met Glu Leu Arg
                340                 345                 350
Ser Leu Thr Ser Glu Asp Ser Ala Val Tyr Phe Cys Ala Arg Pro Tyr
            355                 360                 365
Tyr Tyr Gly Ser Arg Glu Asp Tyr Phe Asp Tyr Trp Gly Gln Gly Thr
        370                 375                 380
Thr Leu Thr Val Ser Gly Gly Gly Gly Ser Gly Gly Gly Ser
385                 390                 395                 400
Gly Gly Gly Gly Ser Gly Gly Gly Ser Gly Gly Gly Ser Asp
                405                 410                 415
Ile Gln Met Thr Gln Ser Pro Ser Ser Leu Ser Ala Ser Val Gly Asp
```

```
                    420              425              430
Arg Val Thr Ile Thr Cys Ser Ala Ser Ser Val Ser Tyr Met Tyr
                435              440              445

Trp Tyr Gln Gln Lys Pro Arg Ser Ser Pro Lys Pro Trp Ile Tyr Leu
    450              455              460

Thr Ser Asn Leu Ala Ser Gly Val Pro Ala Arg Phe Ser Gly Ser Gly
465              470              475              480

Ser Gly Thr Ser Tyr Ser Leu Thr Ile Ser Ser Met Glu Ala Glu Asp
            485              490              495

Ala Ala Thr Tyr Tyr Cys Gln Gln Trp Ser Ser Asn Pro Pro Thr Phe
            500              505              510

Gly Gly Gly Thr Lys Leu Glu Ile Lys
            515              520

<210> SEQ ID NO 125
<211> LENGTH: 501
<212> TYPE: PRT
<213> ORGANISM: Artificial Sequence
<220> FEATURE:
<223> OTHER INFORMATION: PD-L1 binding protein 116187

<400> SEQUENCE: 125

Met Lys Glu Phe Thr Leu Asp Phe Ser Thr Ala Lys Thr Tyr Val Asp
1               5                  10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
        130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
                180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
        210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
```

```
            260                 265                 270
Gln Gln Ser Gly Pro Glu Leu Val Lys Pro Gly Ala Ser Val Lys Ile
        275                 280                 285
Ser Cys Lys Thr Ser Gly Tyr Thr Phe Thr Glu Tyr Thr Met His Trp
        290                 295                 300
Val Lys Gln Arg His Gly Lys Ser Leu Glu Trp Ile Gly Gly Ile Asn
305                 310                 315                 320
Pro Asn Asn Gly Gly Thr Trp Tyr Asn Gln Lys Phe Lys Gly Lys Ala
                325                 330                 335
Thr Leu Thr Val Asp Lys Ser Ser Thr Ala Tyr Met Glu Leu Arg
                340                 345                 350
Ser Leu Thr Ser Glu Asp Ser Ala Val Tyr Phe Cys Ala Arg Pro Tyr
        355                 360                 365
Tyr Tyr Gly Ser Arg Glu Asp Tyr Phe Asp Tyr Trp Gly Gln Gly Thr
        370                 375                 380
Thr Leu Thr Val Ser Ser Gly Gly Gly Ser Asp Ile Gln Met Thr
385                 390                 395                 400
Gln Ser Pro Ser Ser Leu Ser Ala Ser Val Gly Asp Arg Val Thr Ile
                405                 410                 415
Thr Cys Ser Ala Ser Ser Ser Val Ser Tyr Met Tyr Trp Tyr Gln Gln
                420                 425                 430
Lys Pro Arg Ser Ser Pro Lys Pro Trp Ile Tyr Leu Thr Ser Asn Leu
                435                 440                 445
Ala Ser Gly Val Pro Ala Arg Phe Ser Gly Ser Gly Ser Gly Thr Ser
        450                 455                 460
Tyr Ser Leu Thr Ile Ser Ser Met Glu Ala Glu Asp Ala Ala Thr Tyr
465                 470                 475                 480
Tyr Cys Gln Gln Trp Ser Ser Asn Pro Pro Thr Phe Gly Gly Gly Thr
                485                 490                 495
Lys Leu Glu Ile Lys
            500

<210> SEQ ID NO 126
<211> LENGTH: 514
<212> TYPE: PRT
<213> ORGANISM: Artificial Sequence
<220> FEATURE:
<223> OTHER INFORMATION: PD-L1 binding protein 116188

<400> SEQUENCE: 126

Met Lys Glu Phe Thr Leu Asp Phe Ser Thr Ala Lys Thr Tyr Val Asp
1               5                   10                  15
Ser Leu Asn Val Ile Arg Ser Ala Ile Gly Thr Pro Leu Gln Thr Ile
                20                  25                  30
Ser Ser Gly Gly Thr Ser Leu Leu Met Ile Asp Ser Gly Ile Gly Asp
        35                  40                  45
Asn Leu Phe Ala Val Asp Ile Leu Gly Phe Asp Phe Thr Leu Gly Arg
        50                  55                  60
Phe Asn Asn Leu Arg Leu Ile Val Glu Arg Asn Asn Leu Tyr Val Thr
65                  70                  75                  80
Gly Phe Val Asn Arg Thr Asn Asn Val Phe Tyr Arg Phe Ala Asp Phe
                85                  90                  95
Ser His Val Thr Phe Pro Gly Thr Thr Ala Val Thr Leu Ser Ala Asp
                100                 105                 110
Ser Ser Tyr Thr Thr Leu Gln Arg Val Ala Gly Ile Ser Arg Thr Gly
```

```
            115                 120                 125
Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
                180                 185                 190

Met Thr Ala Glu Asp Val Asp Leu Thr Leu Asn Trp Gly Arg Leu Ser
                195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
                260                 265                 270

Gln Gln Ser Gly Pro Glu Leu Val Lys Pro Gly Ala Ser Val Lys Ile
            275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Thr Ala Tyr Met Glu Leu Arg
                340                 345                 350

Ser Leu Thr Ser Glu Asp Ser Ala Val Tyr Phe Cys Ala Arg Pro Tyr
            355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Ser Ala Ser Ser Ser Val Ser Tyr Met Tyr Trp Tyr Gln Gln
                420                 425                 430

Lys Pro Arg Ser Ser Pro Lys Pro Trp Ile Tyr Leu Thr Ser Asn Leu
            435                 440                 445

Ala Ser Gly Val Pro Ala Arg Phe Ser Gly Ser Gly Ser Gly Thr Ser
    450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Pro Thr Phe Gly Gly Gly Thr
                485                 490                 495

Lys Leu Glu Ile Lys His His Ala Ala Asn Leu Val Pro Met Val Ala
            500                 505                 510

Thr Val

<210> SEQ ID NO 127
<211> LENGTH: 501
```

```
<212> TYPE: PRT
<213> ORGANISM: Artificial Sequence
<220> FEATURE:
<223> OTHER INFORMATION: PD-L1 binding protein 116296

<400> SEQUENCE: 127
```

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Ser Thr Ala Tyr Met Glu Leu Arg
            340                 345                 350

Ser Leu Thr Ser Glu Asp Ser Ala Val Tyr Phe Cys Ala Arg Pro Tyr
        355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Ser Asp Ile Gln Met Thr
385                 390                 395                 400

Gln Ser Pro Ser Ser Leu Ser Ala Ser Val Gly Asp Arg Val Thr Ile
            405                 410                 415

Thr Cys Ser Ala Ser Ser Val Ser Tyr Met Tyr Trp Tyr Gln Gln
            420                 425                 430

Lys Pro Arg Ser Ser Pro Lys Pro Trp Ile Tyr Leu Thr Ser Asn Leu
            435                 440                 445

Ala Ser Gly Val Pro Ala Arg Phe Ser Gly Ser Gly Ser Gly Thr Ser
        450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Pro Thr Phe Gly Gly Gly Thr
            485                 490                 495

Lys Leu Glu Leu Lys
        500

<210> SEQ ID NO 128
<211> LENGTH: 514
<212> TYPE: PRT
<213> ORGANISM: Artificial Sequence
<220> FEATURE:
<223> OTHER INFORMATION: PD-L1 binding protein 116297

<400> SEQUENCE: 128

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Thr Ala Tyr Met Glu Leu Arg
            340                 345                 350

Ser Leu Thr Ser Glu Asp Ser Ala Val Tyr Phe Cys Ala Arg Pro Tyr
        355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Ser Ala Ser Ser Ser Val Ser Tyr Met Tyr Trp Tyr Gln Gln
            420                 425                 430

Lys Pro Arg Ser Ser Pro Lys Pro Trp Ile Tyr Leu Thr Ser Asn Leu
        435                 440                 445

Ala Ser Gly Val Pro Ala Arg Phe Ser Gly Ser Gly Ser Gly Thr Ser
    450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Pro Thr Phe Gly Gly Gly Thr
                485                 490                 495

Lys Leu Glu Leu Lys His His Ala Ala Asn Leu Val Pro Met Val Ala
            500                 505                 510

Thr Val

<210> SEQ ID NO 129
<211> LENGTH: 519
<212> TYPE: PRT
<213> ORGANISM: Artificial Sequence
<220> FEATURE:
<223> OTHER INFORMATION: PD-L1 binding protein 116299

<400> SEQUENCE: 129

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
        50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe

```
                85                  90                  95
Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
        130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Thr Ala Tyr Met Glu Leu Arg
            340                 345                 350

Ser Leu Thr Ser Glu Asp Ser Ala Val Tyr Phe Cys Ala Arg Pro Tyr
        355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Ser Gly Gly Gly Ser
385                 390                 395                 400

Asp Ile Gln Met Thr Gln Ser Pro Ser Ser Leu Ser Ala Ser Val Gly
                405                 410                 415

Asp Arg Val Thr Ile Thr Cys Ser Ala Ser Ser Val Ser Tyr Met
            420                 425                 430

Tyr Trp Tyr Gln Gln Lys Pro Arg Ser Ser Pro Lys Pro Trp Ile Tyr
        435                 440                 445

Leu Thr Ser Asn Leu Ala Ser Gly Val Pro Ala Arg Phe Ser Gly Ser
    450                 455                 460

Gly Ser Gly Thr Ser Tyr Ser Leu Thr Ile Ser Ser Met Glu Ala Glu
465                 470                 475                 480

Asp Ala Ala Thr Tyr Tyr Cys Gln Gln Trp Ser Ser Asn Pro Pro Thr
                485                 490                 495

Phe Gly Gly Gly Thr Lys Leu Glu Leu Lys His His Ala Ala Asn Leu
            500                 505                 510
```

```
Val Pro Met Val Ala Thr Val
            515

<210> SEQ ID NO 130
<211> LENGTH: 534
<212> TYPE: PRT
<213> ORGANISM: Artificial Sequence
<220> FEATURE:
<223> OTHER INFORMATION: PD-L1 binding protein 116324

<400> SEQUENCE: 130

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Ser Thr Ala Tyr Met Glu Leu Arg
            340                 345                 350
```

Ser Leu Thr Ser Glu Asp Ser Ala Val Tyr Phe Cys Ala Arg Pro Tyr
          355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Gly Ser Gly Gly Gly Gly Ser
385                 390                 395                 400

Gly Gly Gly Gly Ser Gly Gly Gly Ser Gly Gly Gly Gly Ser Asp
            405                 410                 415

Ile Val Met Thr Gln Ser Pro Ala Ile Met Ser Ala Ser Pro Gly Glu
                420                 425                 430

Lys Val Thr Met Thr Cys Ser Ala Ser Ser Ser Val Ser Tyr Met Tyr
            435                 440                 445

Trp Tyr Gln Gln Lys Pro Arg Ser Ser Pro Lys Pro Trp Ile Tyr Leu
        450                 455                 460

Thr Ser Asn Leu Ala Ser Gly Val Pro Ala Arg Phe Ser Gly Ser Gly
465                 470                 475                 480

Ser Gly Thr Ser Tyr Ser Leu Thr Ile Ser Ser Met Glu Ala Glu Asp
            485                 490                 495

Ala Ala Thr Tyr Tyr Cys Gln Gln Trp Ser Ser Asn Pro Pro Thr Phe
                500                 505                 510

Gly Gly Gly Thr Lys Leu Glu Leu Lys His His Ala Ala Asn Leu Val
            515                 520                 525

Pro Met Val Ala Thr Val
        530

<210> SEQ ID NO 131
<211> LENGTH: 514
<212> TYPE: PRT
<213> ORGANISM: Artificial Sequence
<220> FEATURE:
<223> OTHER INFORMATION: PD-L1 binding protein 116325

<400> SEQUENCE: 131

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
            210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
            245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
            275                 280                 285

Ser Cys Lys Thr Ser Gly Tyr Thr Phe Thr Glu Tyr Thr Met His Trp
            290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
            325                 330                 335

Thr Leu Thr Val Asp Lys Ser Ser Thr Ala Tyr Met Glu Leu Arg
            340                 345                 350

Ser Leu Thr Ser Glu Asp Ser Ala Val Tyr Phe Cys Ala Arg Pro Tyr
            355                 360                 365

Tyr Tyr Gly Ser Arg Glu Asp Tyr Phe Asp Tyr Trp Gly Gln Gly Thr
            370                 375                 380

Thr Leu Thr Val Ser Ser Gly Gly Gly Ser Asp Ile Val Met Thr
385                 390                 395                 400

Gln Ser Pro Ala Ile Met Ser Ala Ser Pro Gly Glu Lys Val Thr Met
            405                 410                 415

Thr Cys Ser Ala Ser Ser Ser Val Ser Tyr Met Tyr Trp Tyr Gln Gln
            420                 425                 430

Lys Pro Arg Ser Ser Pro Lys Pro Trp Ile Tyr Leu Thr Ser Asn Leu
            435                 440                 445

Ala Ser Gly Val Pro Ala Arg Phe Ser Gly Ser Gly Ser Gly Thr Ser
            450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Pro Thr Phe Gly Gly Gly Thr
            485                 490                 495

Lys Leu Glu Leu Lys His His Ala Ala Asn Leu Val Pro Met Val Ala
            500                 505                 510

Thr Val

<210> SEQ ID NO 132
<211> LENGTH: 509
<212> TYPE: PRT
<213> ORGANISM: Artificial Sequence
<220> FEATURE:
<223> OTHER INFORMATION: PD-L1 binding protein #1

<400> SEQUENCE: 132

Lys Glu Phe Thr Leu Asp Phe Ser Thr Ala Lys Thr Tyr Val Asp Ser
1               5                   10                  15

```
Leu Asn Val Ile Arg Ser Ala Ile Gly Thr Pro Leu Gln Thr Ile Ser
             20                  25                  30

Ser Gly Gly Thr Ser Leu Leu Met Ile Asp Ser Gly Cys Gly Asp Asn
         35                  40                  45

Leu Phe Ala Val Asp Ile Leu Gly Phe Asp Phe Thr Leu Gly Arg Phe
     50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Gly Ala Pro Asp Ile Gln Met Thr
            260                 265                 270

Gln Ser Pro Ser Ser Leu Ser Ala Ser Val Gly Asp Arg Val Thr Ile
        275                 280                 285

Thr Cys Ser Ala Ser Ser Ser Val Ser Tyr Met Tyr Trp Tyr Gln Gln
    290                 295                 300

Lys Pro Arg Ser Ser Pro Lys Pro Trp Ile Tyr Leu Thr Ser Asn Leu
305                 310                 315                 320

Ala Ser Gly Val Pro Ala Arg Phe Ser Gly Ser Gly Ser Gly Thr Ser
                325                 330                 335

Tyr Ser Leu Thr Ile Ser Ser Met Glu Ala Glu Asp Ala Ala Thr Tyr
            340                 345                 350

Tyr Cys Gln Gln Trp Ser Ser Asn Pro Pro Thr Phe Gly Gly Gly Thr
        355                 360                 365

Lys Leu Glu Ile Lys Gly Gly Gly Ser Glu Val His Leu Val Glu
    370                 375                 380

Ser Gly Pro Glu Leu Val Lys Pro Gly Ala Ser Val Lys Ile Ser Cys
385                 390                 395                 400

Lys Thr Ser Gly Tyr Thr Phe Thr Glu Tyr Thr Met His Trp Val Lys
                405                 410                 415

Gln Ser His Gly Lys Ser Leu Glu Trp Ile Gly Gly Ile Asp Pro Asn
            420                 425                 430

Asn Gly Gly Thr Trp Tyr Asn Gln Lys Phe Lys Gly Lys Ala Thr Leu
```

|   |   |   | 435 |   |   |   | 440 |   |   |   | 445 |   |
|---|---|---|---|---|---|---|---|---|---|---|---|---|

Thr Val Asp Lys Ser Ser Thr Ala Tyr Met Glu Leu Arg Ser Leu
        450                 455                 460

Thr Ser Glu Asp Ser Ala Val Tyr Phe Cys Ala Arg Pro Tyr Tyr
465                 470                 475                 480

Gly Ser Arg Glu Asp Tyr Phe Asp Tyr Trp Gly Gln Gly Thr Thr Leu
                485                 490                 495

Thr Val Ser Ser Asn Leu Val Pro Met Val Ala Thr Val
        500                 505

<210> SEQ ID NO 133
<211> LENGTH: 509
<212> TYPE: PRT
<213> ORGANISM: Artificial Sequence
<220> FEATURE:
<223> OTHER INFORMATION: PD-L1 binding protein #2

<400> SEQUENCE: 133

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Cys Gly Asp Asn
        35                  40                  45

Leu Phe Ala Val Asp Ile Leu Gly Phe Asp Phe Thr Leu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Gly Ala Pro Asp Ile Gln Met Thr
            260                 265                 270

Gln Ser Pro Ser Ser Leu Ser Ala Ser Val Gly Asp Arg Val Thr Ile
        275                 280                 285

Thr Cys Ser Ala Ser Ser Ser Val Ser Tyr Met Tyr Trp Tyr Gln Gln

```
                290                 295                 300

Lys Pro Arg Ser Ser Pro Lys Pro Trp Ile Tyr Leu Thr Ser Asn Leu
305                 310                 315                 320

Ala Ser Gly Val Pro Ala Arg Phe Ser Gly Ser Gly Ser Gly Thr Ser
                325                 330                 335

Tyr Ser Leu Thr Ile Ser Ser Met Glu Ala Glu Asp Ala Ala Thr Tyr
                340                 345                 350

Tyr Cys Gln Gln Trp Ser Ser Asn Pro Pro Thr Phe Gly Gly Gly Thr
            355                 360                 365

Lys Leu Glu Leu Lys Gly Gly Gly Ser Glu Val Gln Leu Gln Gln
        370                 375                 380

Ser Gly Pro Glu Leu Val Lys Pro Gly Ala Ser Val Lys Ile Ser Cys
385                 390                 395                 400

Lys Thr Ser Gly Tyr Thr Phe Thr Glu Tyr Thr Met His Trp Val Lys
                405                 410                 415

Gln Arg His Gly Lys Ser Leu Glu Trp Ile Gly Gly Ile Asn Pro Asn
            420                 425                 430

Asn Gly Gly Thr Trp Tyr Asn Gln Lys Phe Lys Gly Lys Ala Thr Leu
        435                 440                 445

Thr Val Asp Lys Ser Ser Ser Thr Ala Tyr Met Glu Leu Arg Ser Leu
450                 455                 460

Thr Ser Glu Asp Ser Ala Val Tyr Phe Cys Ala Arg Pro Tyr Tyr
465                 470                 475                 480

Gly Ser Arg Glu Asp Tyr Phe Asp Tyr Trp Gly Gln Gly Thr Thr Leu
            485                 490                 495

Thr Val Ser Ser Asn Leu Val Pro Met Val Ala Thr Val
            500                 505

<210> SEQ ID NO 134
<211> LENGTH: 509
<212> TYPE: PRT
<213> ORGANISM: Artificial Sequence
<220> FEATURE:
<223> OTHER INFORMATION: PD-L1 binding protein #3

<400> SEQUENCE: 134

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Cys Gly Asp Asn
            35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
```

```
            145                 150                 155                 160
        Phe Val Thr Val Thr Ala Glu Ala Leu Arg Phe Arg Gln Ile Gln Arg
                        165                 170                 175
        Gly Phe Arg Thr Thr Leu Asp Asp Leu Ser Gly Ala Ser Tyr Val Met
                        180                 185                 190
        Thr Ala Glu Asp Val Asp Leu Thr Leu Asn Trp Gly Arg Leu Ser Ser
                        195                 200                 205
        Val Leu Pro Asp Tyr His Gly Gln Asp Ser Val Arg Val Gly Arg Ile
        210                 215                 220
        Ser Phe Gly Ser Ile Asn Ala Ile Leu Gly Ser Val Ala Leu Ile Leu
        225                 230                 235                 240
        Asn Ser His His His Ala Ser Ala Val Ala Ala Glu Phe Pro Lys Pro
                        245                 250                 255
        Ser Thr Pro Pro Gly Ser Ser Gly Gly Ala Pro Asp Ile Gln Met Thr
                        260                 265                 270
        Gln Ser Pro Ser Ser Leu Ser Ala Ser Val Gly Asp Arg Val Thr Ile
                        275                 280                 285
        Thr Cys Ser Ala Ser Ser Ser Val Ser Tyr Met Tyr Trp Tyr Gln Gln
                        290                 295                 300
        Lys Pro Arg Ser Ser Pro Lys Pro Trp Ile Tyr Leu Thr Ser Asn Leu
        305                 310                 315                 320
        Ala Ser Gly Val Pro Ala Arg Phe Ser Gly Ser Gly Ser Gly Thr Ser
                        325                 330                 335
        Tyr Ser Leu Thr Ile Ser Ser Met Glu Ala Glu Asp Ala Ala Thr Tyr
                        340                 345                 350
        Tyr Cys Gln Gln Trp Ser Ser Asn Pro Pro Thr Phe Gly Gly Gly Thr
                        355                 360                 365
        Lys Leu Glu Ile Lys Gly Gly Gly Ser Glu Val Gln Leu Gln Gln
                        370                 375                 380
        Ser Gly Pro Glu Leu Val Lys Pro Gly Ala Ser Val Lys Ile Ser Cys
        385                 390                 395                 400
        Lys Thr Ser Gly Tyr Thr Phe Thr Glu Tyr Thr Met His Trp Val Lys
                        405                 410                 415
        Gln Ser His Gly Lys Ser Leu Glu Trp Ile Gly Gly Ile Asn Pro Asn
                        420                 425                 430
        Asn Gly Gly Thr Trp Tyr Asn Arg Lys Phe Lys Gly Lys Ala Ala Leu
                        435                 440                 445
        Thr Val Asp Lys Ser Ser Thr Ala Tyr Met Glu Leu Arg Ser Leu
        450                 455                 460
        Thr Ser Glu Asp Ser Ala Val Tyr Phe Cys Ala Arg Pro Tyr Tyr Tyr
        465                 470                 475                 480
        Gly Ser Arg Glu Asp Tyr Phe Asp Tyr Trp Gly Gln Gly Thr Thr Leu
                        485                 490                 495
        Thr Val Ser Ser Asn Leu Val Pro Met Val Ala Thr Val
                        500                 505

<210> SEQ ID NO 135
<211> LENGTH: 533
<212> TYPE: PRT
<213> ORGANISM: Artificial Sequence
<220> FEATURE:
<223> OTHER INFORMATION: PD-L1 binding protein #4

<400> SEQUENCE: 135

Lys Glu Phe Thr Leu Asp Phe Ser Thr Ala Lys Thr Tyr Val Asp Ser
```

-continued

```
1               5                   10                  15
Leu Asn Val Ile Arg Ser Ala Ile Gly Thr Pro Leu Gln Thr Ile Ser
            20                  25                  30
Ser Gly Gly Thr Ser Leu Leu Met Ile Asp Ser Gly Ile Gly Asp Asn
            35                  40                  45
Leu Phe Ala Val Asp Ile Leu Gly Phe Asp Phe Thr Leu Gly Arg Phe
50                  55                  60
Asn Asn Leu Arg Leu Ile Val Glu Arg Asn Asn Leu Tyr Val Thr Gly
65                  70                  75                  80
Phe Val Asn Arg Thr Asn Asn Val Phe Tyr Arg Phe Ala Asp Phe Ser
            85                  90                  95
His Val Thr Phe Pro Gly Thr Thr Ala Val Thr Leu Ser Ala Asp Ser
            100                 105                 110
Ser Tyr Thr Thr Leu Gln Arg Val Ala Gly Ile Ser Arg Thr Gly Met
            115                 120                 125
Gln Ile Asn Arg His Ser Leu Thr Thr Ser Tyr Leu Asp Leu Met Ser
            130                 135                 140
His Ser Gly Thr Ser Leu Thr Gln Ser Val Ala Arg Ala Met Leu Arg
145                 150                 155                 160
Phe Val Thr Val Thr Ala Glu Ala Leu Arg Phe Arg Gln Ile Gln Arg
            165                 170                 175
Gly Phe Arg Thr Thr Leu Asp Asp Leu Ser Gly Ala Ser Tyr Val Met
            180                 185                 190
Thr Ala Glu Asp Val Asp Leu Thr Leu Asn Trp Gly Arg Leu Ser Ser
            195                 200                 205
Val Leu Pro Asp Tyr His Gly Gln Asp Ser Val Arg Val Gly Arg Ile
210                 215                 220
Ser Phe Gly Ser Ile Asn Ala Ile Leu Gly Ser Val Ala Leu Ile Leu
225                 230                 235                 240
Asn Ser His His His Ala Ser Ala Val Ala Ala Glu Phe Pro Lys Pro
            245                 250                 255
Ser Thr Pro Pro Gly Ser Ser Gly Gly Ala Pro Glu Val Gln Leu Gln
            260                 265                 270
Glu Ser Gly Pro Glu Leu Val Lys Pro Gly Ala Ser Val Lys Ile Ser
            275                 280                 285
Cys Lys Thr Ser Gly Tyr Thr Phe Thr Glu Asn Ser Met His Trp Val
            290                 295                 300
Lys Gln Ser His Gly Lys Ser Leu Glu Trp Ile Gly Gly Ile Asn Pro
305                 310                 315                 320
Asn Asn Gly Gly Thr Ser Tyr Asn Gln Lys Phe Lys Gly Lys Ala Thr
                325                 330                 335
Leu Thr Val Asp Lys Ser Ser Thr Ala Tyr Met Glu Phe Arg Ser
            340                 345                 350
Leu Thr Ser Glu Asp Ser Ala Val Tyr Tyr Cys Ala Arg Pro Tyr Tyr
            355                 360                 365
Tyr Gly Tyr Arg Glu Asp Tyr Phe Asp Tyr Trp Gly Gln Gly Thr Thr
            370                 375                 380
Leu Thr Val Ser Ser Gly Gly Gly Gly Gly Gly Gly Ser Gly
385                 390                 395                 400
Gly Gly Gly Ser Gly Gly Gly Gly Ser Gly Gly Gly Ser Asp Ile
                405                 410                 415
Gln Met Thr Gln Ser Pro Ser Ser Leu Ser Ala Ser Val Gly Asp Arg
            420                 425                 430
```

-continued

```
Val Thr Ile Thr Cys Ser Ala Ser Ser Val Ser Tyr Met Tyr Trp
            435                 440                 445

Tyr Gln Gln Lys Pro Arg Ser Ser Pro Lys Pro Trp Ile Tyr Leu Thr
    450                 455                 460

Ser Asn Leu Ala Ser Gly Val Pro Ala Arg Phe Ser Gly Ser Gly Ser
465                 470                 475                 480

Gly Thr Ser Tyr Ser Leu Thr Ile Ser Ser Met Glu Ala Glu Asp Ala
                485                 490                 495

Ala Thr Tyr Tyr Cys Gln Gln Trp Ser Ser Tyr Pro Pro Thr Phe Gly
                500                 505                 510

Gly Gly Thr Lys Leu Glu Ile Lys His His Ala Ala Asn Leu Val Pro
            515                 520                 525

Met Val Ala Thr Val
        530

<210> SEQ ID NO 136
<211> LENGTH: 533
<212> TYPE: PRT
<213> ORGANISM: Artificial Sequence
<220> FEATURE:
<223> OTHER INFORMATION: PD-L1 binding protein #5

<400> SEQUENCE: 136

Lys Glu Phe Thr Leu Asp Phe Ser Thr Ala Lys Thr Tyr Val Asp Ser
1               5                  10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255
```

```
Ser Thr Pro Pro Gly Ser Ser Gly Ala Pro Glu Val His Leu Val
            260                 265                 270

Glu Ser Gly Pro Glu Leu Val Lys Pro Gly Ala Ser Val Lys Ile Ser
            275                 280                 285

Cys Lys Thr Ser Gly Tyr Thr Phe Thr Glu Tyr Thr Met His Trp Val
            290                 295                 300

Lys Gln Ser His Gly Lys Ser Leu Glu Trp Ile Gly Gly Ile Asp Pro
305                 310                 315                 320

Asn Asn Gly Gly Thr Trp Tyr Asn Gln Lys Phe Lys Gly Lys Ala Thr
                325                 330                 335

Leu Thr Val Asp Lys Ser Ser Thr Ala Tyr Met Glu Leu Arg Ser
            340                 345                 350

Leu Thr Ser Glu Asp Ser Ala Val Tyr Phe Cys Ala Arg Pro Tyr Tyr
            355                 360                 365

Tyr Gly Ser Arg Glu Asp Tyr Phe Asp Tyr Trp Gly Gln Gly Thr Thr
            370                 375                 380

Leu Thr Val Ser Ser Gly Gly Gly Ser Gly Gly Gly Ser Gly
385                 390                 395                 400

Gly Gly Gly Ser Gly Gly Gly Ser Gly Gly Gly Ser Asp Ile
                405                 410                 415

Gln Met Thr Gln Ser Pro Ser Ser Leu Ser Ala Ser Val Gly Asp Arg
            420                 425                 430

Val Thr Ile Thr Cys Ser Ala Ser Ser Ser Val Ser Tyr Met Tyr Trp
            435                 440                 445

Tyr Gln Gln Lys Pro Arg Ser Ser Pro Lys Pro Trp Ile Tyr Leu Thr
            450                 455                 460

Ser Asn Leu Ala Ser Gly Val Pro Ala Arg Phe Ser Gly Ser Gly Ser
465                 470                 475                 480

Gly Thr Ser Tyr Ser Leu Thr Ile Ser Ser Met Glu Ala Glu Asp Ala
                485                 490                 495

Ala Thr Tyr Tyr Cys Gln Gln Trp Ser Ser Asn Pro Pro Thr Phe Gly
            500                 505                 510

Gly Gly Thr Lys Leu Glu Ile Lys His His Ala Ala Asn Leu Val Pro
            515                 520                 525

Met Val Ala Thr Val
        530

<210> SEQ ID NO 137
<211> LENGTH: 533
<212> TYPE: PRT
<213> ORGANISM: Artificial Sequence
<220> FEATURE:
<223> OTHER INFORMATION: PD-L1 binding protein #6

<400> SEQUENCE: 137

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80
```

```
Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
                210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Gly Ala Pro Glu Val Gln Leu Gln
                260                 265                 270

Gln Ser Gly Pro Glu Leu Val Lys Pro Gly Ala Ser Val Lys Ile Ser
                275                 280                 285

Cys Lys Thr Ser Gly Tyr Thr Phe Thr Glu Tyr Thr Met His Trp Val
                290                 295                 300

Lys Gln Arg His Gly Lys Ser Leu Glu Trp Ile Gly Gly Ile Asn Pro
305                 310                 315                 320

Asn Asn Gly Gly Thr Trp Tyr Asn Gln Lys Phe Lys Gly Lys Ala Thr
                325                 330                 335

Leu Thr Val Asp Lys Ser Ser Thr Ala Tyr Met Glu Leu Arg Ser
                340                 345                 350

Leu Thr Ser Glu Asp Ser Ala Val Tyr Phe Cys Ala Arg Pro Tyr Tyr
                355                 360                 365

Tyr Gly Ser Arg Glu Asp Tyr Phe Asp Tyr Trp Gly Gln Gly Thr Thr
370                 375                 380

Leu Thr Val Ser Ser Gly Gly Gly Gly Ser Gly Gly Gly Gly Ser Gly
385                 390                 395                 400

Gly Gly Gly Ser Gly Gly Gly Gly Ser Gly Gly Gly Gly Ser Asp Ile
                405                 410                 415

Gln Met Thr Gln Ser Pro Ser Ser Leu Ser Ala Ser Val Gly Asp Arg
                420                 425                 430

Val Thr Ile Thr Cys Ser Ala Ser Ser Ser Val Ser Tyr Met Tyr Trp
                435                 440                 445

Tyr Gln Gln Lys Pro Arg Ser Ser Pro Lys Pro Trp Ile Tyr Leu Thr
                450                 455                 460

Ser Asn Leu Ala Ser Gly Val Pro Ala Arg Phe Ser Gly Ser Gly Ser
465                 470                 475                 480

Gly Thr Ser Tyr Ser Leu Thr Ile Ser Ser Met Glu Ala Glu Asp Ala
                485                 490                 495
```

Ala Thr Tyr Tyr Cys Gln Gln Trp Ser Ser Asn Pro Pro Thr Phe Gly
            500                 505                 510

Gly Gly Thr Lys Leu Glu Leu Lys His His Ala Ala Asn Leu Val Pro
        515                 520                 525

Met Val Ala Thr Val
    530

<210> SEQ ID NO 138
<211> LENGTH: 533
<212> TYPE: PRT
<213> ORGANISM: Artificial Sequence
<220> FEATURE:
<223> OTHER INFORMATION: PD-L1 binding protein #7

<400> SEQUENCE: 138

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Gly Ala Pro Glu Val Gln Leu Gln
            260                 265                 270

Gln Ser Gly Pro Glu Leu Val Lys Pro Gly Ala Ser Val Lys Ile Ser
        275                 280                 285

Cys Lys Thr Ser Gly Tyr Thr Phe Thr Glu Tyr Thr Met His Trp Val
    290                 295                 300

Lys Gln Ser His Gly Lys Ser Leu Glu Trp Ile Gly Gly Ile Asn Pro
305                 310                 315                 320

-continued

```
Asn Asn Gly Gly Thr Trp Tyr Asn Arg Lys Phe Lys Gly Lys Ala Ala
            325                 330                 335

Leu Thr Val Asp Lys Ser Ser Thr Ala Tyr Met Glu Leu Arg Ser
            340                 345                 350

Leu Thr Ser Glu Asp Ser Ala Val Tyr Phe Cys Ala Arg Pro Tyr Tyr
            355                 360                 365

Tyr Gly Ser Arg Glu Asp Tyr Phe Asp Tyr Trp Gly Gln Gly Thr Thr
            370                 375                 380

Leu Thr Val Ser Ser Gly Gly Gly Ser Gly Gly Gly Ser Gly
385                 390                 395                 400

Gly Gly Gly Ser Gly Gly Gly Ser Gly Gly Gly Ser Asp Ile
            405                 410                 415

Gln Met Thr Gln Ser Pro Ser Ser Leu Ser Ala Ser Val Gly Asp Arg
            420                 425                 430

Val Thr Ile Thr Cys Ser Ala Ser Ser Val Ser Tyr Met Tyr Trp
            435                 440                 445

Tyr Gln Gln Lys Pro Arg Ser Ser Pro Lys Pro Trp Ile Tyr Leu Thr
            450                 455                 460

Ser Asn Leu Ala Ser Gly Val Pro Ala Arg Phe Ser Gly Ser Gly Ser
465                 470                 475                 480

Gly Thr Ser Tyr Ser Leu Thr Ile Ser Ser Met Glu Ala Glu Asp Ala
            485                 490                 495

Ala Thr Tyr Tyr Cys Gln Gln Trp Ser Ser Asn Pro Pro Thr Phe Gly
            500                 505                 510

Gly Gly Thr Lys Leu Glu Ile Lys His His Ala Ala Asn Leu Val Pro
            515                 520                 525

Met Val Ala Thr Val
    530

<210> SEQ ID NO 139
<211> LENGTH: 509
<212> TYPE: PRT
<213> ORGANISM: Artificial Sequence
<220> FEATURE:
<223> OTHER INFORMATION: PD-L1 binding protein #8

<400> SEQUENCE: 139

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
            35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
            85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140
```

```
His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
            165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Ser Pro Ser Thr Pro
            245                 250                 255

Pro Thr Pro Ser Pro Ser Thr Pro Pro Ala Ser Asp Ile Gln Met Thr
            260                 265                 270

Gln Ser Pro Ser Ser Leu Ser Ala Ser Val Gly Asp Arg Val Thr Ile
            275                 280                 285

Thr Cys Arg Ala Ser Ser Val Ser Tyr Met Tyr Trp Tyr Gln Gln
            290                 295                 300

Lys Pro Gly Gln Ala Pro Arg Pro Leu Ile Tyr Leu Thr Ser Asn Leu
305                 310                 315                 320

Ala Ser Gly Ile Pro Asp Arg Phe Ser Gly Ser Gly Ser Gly Thr Asp
            325                 330                 335

Tyr Thr Leu Thr Ile Ser Arg Leu Glu Pro Glu Asp Phe Ala Val Tyr
            340                 345                 350

Tyr Cys Gln Gln Trp Ser Ser Tyr Pro Pro Thr Phe Gly Gln Gly Thr
            355                 360                 365

Lys Val Glu Ile Lys Gly Gly Gly Ser Gln Val Gln Leu Val Gln
            370                 375                 380

Ser Gly Pro Glu Val Lys Lys Pro Gly Ala Ser Val Lys Val Ser Cys
385                 390                 395                 400

Lys Ala Ser Gly Tyr Thr Phe Thr Glu Asn Ser Met His Trp Val Arg
            405                 410                 415

Gln Ser His Gly Lys Ser Leu Glu Trp Met Gly Gly Ile Asn Pro Asn
            420                 425                 430

Asn Gly Gly Thr Ser Tyr Asn Gln Lys Phe Lys Gly Lys Val Thr Met
            435                 440                 445

Thr Thr Asp Lys Ser Thr Ser Thr Ala Tyr Met Glu Leu Arg Ser Leu
450                 455                 460

Thr Ser Asp Asp Thr Ala Val Tyr Tyr Cys Ala Arg Pro Tyr Tyr
465                 470                 475                 480

Gly Tyr Arg Glu Asp Tyr Phe Asp Tyr Trp Gly Gln Gly Thr Thr Leu
            485                 490                 495

Thr Val Ser Ser Asn Leu Val Pro Met Val Ala Thr Val
            500                 505

<210> SEQ ID NO 140
<211> LENGTH: 509
<212> TYPE: PRT
<213> ORGANISM: Artificial Sequence
<220> FEATURE:
<223> OTHER INFORMATION: PD-L1 binding protein #9

<400> SEQUENCE: 140
```

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ser Pro Ser Thr Pro
                245                 250                 255

Pro Thr Pro Ser Pro Ser Thr Pro Pro Ala Ser Asp Ile Gln Met Thr
            260                 265                 270

Gln Ser Pro Ser Ser Leu Ser Ala Ser Val Gly Asp Arg Val Thr Ile
            275                 280                 285

Thr Cys Arg Ala Ser Ser Ser Val Ser Tyr Met Tyr Trp Tyr Gln Gln
        290                 295                 300

Lys Pro Gly Gln Ala Pro Arg Pro Leu Ile Tyr Leu Thr Ser Asn Leu
305                 310                 315                 320

Ala Ser Gly Ile Pro Asp Arg Phe Ser Gly Ser Gly Ser Gly Thr Asp
                325                 330                 335

Tyr Thr Leu Thr Ile Ser Arg Leu Glu Pro Glu Asp Phe Ala Val Tyr
            340                 345                 350

Tyr Cys Gln Gln Trp Ser Ser Tyr Pro Pro Thr Phe Gly Gln Gly Thr
        355                 360                 365

Lys Val Glu Ile Lys Gly Gly Gly Ser Gln Val Gln Leu Val Gln
    370                 375                 380

Ser Gly Ala Glu Val Lys Lys Pro Gly Ala Val Lys Val Ser Cys
385                 390                 395                 400

Lys Ala Ser Gly Tyr Thr Phe Thr Glu Asn Ser Met His Trp Val Arg
                405                 410                 415

Gln Ala His Gly Gln Arg Leu Glu Trp Ile Gly Gly Ile Asn Pro Asn
```

```
                420             425             430
Asn Gly Gly Thr Trp Tyr Asn Arg Lys Phe Lys Gly Lys Ala Ala Ile
            435             440             445

Thr Val Asp Thr Ser Ala Ser Thr Ala Tyr Met Glu Leu Ser Ser Leu
        450             455             460

Arg Ser Glu Asp Thr Ala Val Tyr Tyr Cys Ala Arg Pro Tyr Tyr Tyr
465             470             475             480

Gly Tyr Arg Glu Asp Tyr Phe Asp Tyr Trp Gly Gln Gly Thr Thr Leu
            485             490             495

Thr Val Ser Ser Asn Leu Val Pro Met Val Ala Thr Val
        500             505

<210> SEQ ID NO 141
<211> LENGTH: 509
<212> TYPE: PRT
<213> ORGANISM: Artificial Sequence
<220> FEATURE:
<223> OTHER INFORMATION: PD-L1 binding protein #10

<400> SEQUENCE: 141

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Ser Pro Ser Thr Pro
                245                 250                 255

Pro Thr Pro Ser Pro Ser Thr Pro Pro Ala Ser Asp Ile Gln Met Thr
            260                 265                 270

Gln Ser Pro Ser Ser Leu Ser Ala Ser Val Gly Asp Arg Val Thr Ile
```

```
                    275                 280                 285
Thr Cys Arg Ala Ser Ser Val Ser Tyr Met Tyr Trp Tyr Gln Gln
290                 295                 300

Lys Pro Gly Gln Ala Pro Arg Pro Leu Ile Tyr Leu Thr Ser Asn Leu
305                 310                 315                 320

Ala Ser Gly Ile Pro Asp Arg Phe Ser Gly Ser Gly Ser Gly Thr Asp
                    325                 330                 335

Tyr Thr Leu Thr Ile Ser Arg Leu Glu Pro Glu Asp Phe Ala Val Tyr
                340                 345                 350

Tyr Cys Gln Gln Trp Ser Ser Tyr Pro Pro Thr Phe Gly Gln Gly Thr
                355                 360                 365

Lys Val Glu Ile Lys Gly Gly Gly Gly Ser Gln Val Gln Leu Val Gln
370                 375                 380

Ser Gly Ala Glu Val Lys Lys Pro Gly Ala Ser Val Lys Val Ser Cys
385                 390                 395                 400

Lys Ala Ser Gly Tyr Thr Phe Thr Glu Asn Ser Met His Trp Val Arg
                    405                 410                 415

Gln Ala His Gly Gln Arg Leu Glu Trp Ile Gly Gly Ile Asn Pro Asn
                420                 425                 430

Asn Gly Gly Thr Ser Tyr Asn Gln Lys Phe Lys Gly Lys Ala Thr Ile
                435                 440                 445

Thr Val Asp Thr Ser Ala Ser Thr Ala Tyr Met Glu Leu Ser Ser Leu
450                 455                 460

Arg Ser Glu Asp Thr Ala Val Tyr Tyr Cys Ala Arg Pro Tyr Tyr
465                 470                 475                 480

Gly Tyr Arg Glu Asp Tyr Phe Asp Tyr Trp Gly Gln Gly Thr Thr Leu
                    485                 490                 495

Thr Val Ser Ser Asn Leu Val Pro Met Val Ala Thr Val
                500                 505

<210> SEQ ID NO 142
<211> LENGTH: 509
<212> TYPE: PRT
<213> ORGANISM: Artificial Sequence
<220> FEATURE:
<223> OTHER INFORMATION: PD-L1 binding protein #11

<400> SEQUENCE: 142

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ile Gly Asp Asn
            35                  40                  45

Leu Phe Ala Val Asp Ile Leu Gly Phe Asp Phe Thr Leu Gly Arg Phe
        50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
```

```
            130                 135                 140
His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Ser Pro Ser Thr Pro
                245                 250                 255

Pro Thr Pro Ser Pro Ser Thr Pro Pro Ala Ser Asp Ile Gln Met Thr
                260                 265                 270

Gln Ser Pro Ser Ser Leu Ser Ala Ser Val Gly Asp Arg Val Thr Ile
                275                 280                 285

Thr Cys Arg Ala Ser Ser Ser Val Ser Tyr Met Tyr Trp Tyr Gln Gln
            290                 295                 300

Lys Pro Gly Gln Ala Pro Arg Pro Leu Ile Tyr Leu Thr Ser Asn Leu
305                 310                 315                 320

Ala Ser Gly Ile Pro Asp Arg Phe Ser Gly Ser Gly Ser Gly Thr Asp
                325                 330                 335

Tyr Thr Leu Thr Ile Ser Arg Leu Glu Pro Glu Asp Phe Ala Val Tyr
                340                 345                 350

Tyr Cys Gln Gln Trp Ser Ser Tyr Pro Pro Thr Phe Gly Gln Gly Thr
            355                 360                 365

Lys Val Glu Ile Lys Gly Gly Gly Ser Gln Val Gln Leu Val Gln
370                 375                 380

Ser Gly Ala Glu Val Lys Lys Pro Gly Ala Ser Val Lys Val Ser Cys
385                 390                 395                 400

Lys Thr Ser Gly Tyr Thr Phe Thr Glu Asn Ser Met His Trp Val Arg
                405                 410                 415

Gln Ala Pro Gly Gln Arg Leu Glu Trp Met Gly Gly Ile Asn Pro Asn
                420                 425                 430

Asn Gly Gly Thr Ser Tyr Asn Gln Lys Phe Gln Gly Arg Val Thr Leu
                435                 440                 445

Thr Val Asp Lys Ser Ser Ser Thr Ala Tyr Met Glu Leu Ser Ser Leu
            450                 455                 460

Arg Ser Glu Asp Thr Ala Val Tyr Tyr Cys Ala Arg Pro Tyr Tyr Tyr
465                 470                 475                 480

Gly Tyr Arg Glu Asp Tyr Phe Asp Tyr Trp Gly Gln Gly Thr Thr Leu
                485                 490                 495

Thr Val Ser Ser Asn Leu Val Pro Met Val Ala Thr Val
            500                 505

<210> SEQ ID NO 143
<211> LENGTH: 533
<212> TYPE: PRT
<213> ORGANISM: Artificial Sequence
<220> FEATURE:
<223> OTHER INFORMATION: PD-L1 binding protein #12
```

```
<400> SEQUENCE: 143

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Ser Pro Ser Thr Pro
                245                 250                 255

Pro Thr Pro Ser Pro Ser Thr Pro Pro Ala Ser Gln Val Gln Leu Val
            260                 265                 270

Gln Ser Gly Pro Glu Val Lys Lys Pro Gly Ala Ser Val Lys Val Ser
        275                 280                 285

Cys Lys Ala Ser Gly Tyr Thr Phe Thr Glu Asn Ser Met His Trp Val
    290                 295                 300

Arg Gln Ser His Gly Lys Ser Leu Glu Trp Met Gly Ile Asn Pro
305                 310                 315                 320

Asn Asn Gly Gly Thr Ser Tyr Asn Gln Lys Phe Lys Gly Lys Val Thr
                325                 330                 335

Met Thr Thr Asp Lys Ser Thr Ser Thr Ala Tyr Met Glu Leu Arg Ser
            340                 345                 350

Leu Thr Ser Asp Asp Thr Ala Val Tyr Tyr Cys Ala Arg Pro Tyr Tyr
        355                 360                 365

Tyr Gly Tyr Arg Glu Asp Tyr Phe Asp Tyr Trp Gly Gln Gly Thr Thr
    370                 375                 380

Leu Thr Val Ser Ser Gly Gly Gly Ser Gly Gly Gly Ser Gly
385                 390                 395                 400

Gly Gly Gly Ser Gly Gly Gly Ser Gly Gly Gly Ser Asp Ile
                405                 410                 415
```

```
Gln Met Thr Gln Ser Pro Ser Ser Leu Ser Ala Ser Val Gly Asp Arg
            420                 425                 430

Val Thr Ile Thr Cys Arg Ala Ser Ser Val Ser Tyr Met Tyr Trp
            435                 440                 445

Tyr Gln Gln Lys Pro Gly Gln Ala Pro Arg Pro Leu Ile Tyr Leu Thr
    450                 455                 460

Ser Asn Leu Ala Ser Gly Ile Pro Asp Arg Phe Ser Gly Ser Gly Ser
465                 470                 475                 480

Gly Thr Asp Tyr Thr Leu Thr Ile Ser Arg Leu Glu Pro Glu Asp Phe
                485                 490                 495

Ala Val Tyr Tyr Cys Gln Gln Trp Ser Ser Tyr Pro Pro Thr Phe Gly
            500                 505                 510

Gln Gly Thr Lys Val Glu Ile Lys His His Ala Ala Asn Leu Val Pro
            515                 520                 525

Met Val Ala Thr Val
            530

<210> SEQ ID NO 144
<211> LENGTH: 533
<212> TYPE: PRT
<213> ORGANISM: Artificial Sequence
<220> FEATURE:
<223> OTHER INFORMATION: PD-L1 binding protein #13

<400> SEQUENCE: 144

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ile Gly Asp Asn
            35                  40                  45

Leu Phe Ala Val Asp Ile Leu Gly Phe Asp Phe Thr Leu Gly Arg Phe
        50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240
```

```
Asn Ser His His His Ala Ser Ala Val Ala Ala Ser Pro Ser Thr Pro
                245                 250                 255

Pro Thr Pro Ser Pro Ser Thr Pro Pro Ala Ser Gln Val Gln Leu Val
            260                 265                 270

Gln Ser Gly Ala Glu Val Lys Lys Pro Gly Ala Ser Val Lys Val Ser
        275                 280                 285

Cys Lys Ala Ser Gly Tyr Thr Phe Thr Glu Asn Ser Met His Trp Val
    290                 295                 300

Arg Gln Ala His Gly Gln Arg Leu Glu Trp Ile Gly Ile Asn Pro
305                 310                 315                 320

Asn Asn Gly Gly Thr Trp Tyr Asn Arg Lys Phe Lys Gly Lys Ala Ala
                325                 330                 335

Ile Thr Val Asp Thr Ser Ala Ser Thr Ala Tyr Met Glu Leu Ser Ser
            340                 345                 350

Leu Arg Ser Glu Asp Thr Ala Val Tyr Tyr Cys Ala Arg Pro Tyr Tyr
        355                 360                 365

Tyr Gly Tyr Arg Glu Asp Tyr Phe Asp Tyr Trp Gly Gln Gly Thr Thr
    370                 375                 380

Leu Thr Val Ser Ser Gly Gly Gly Gly Ser Gly Gly Gly Gly Ser Gly
385                 390                 395                 400

Gly Gly Gly Ser Gly Gly Gly Gly Ser Gly Gly Gly Gly Ser Asp Ile
                405                 410                 415

Gln Met Thr Gln Ser Pro Ser Ser Leu Ser Ala Ser Val Gly Asp Arg
            420                 425                 430

Val Thr Ile Thr Cys Arg Ala Ser Ser Val Ser Tyr Met Tyr Trp
        435                 440                 445

Tyr Gln Gln Lys Pro Gly Gln Ala Pro Arg Pro Leu Ile Tyr Leu Thr
    450                 455                 460

Ser Asn Leu Ala Ser Gly Ile Pro Asp Arg Phe Ser Gly Ser Gly Ser
465                 470                 475                 480

Gly Thr Asp Tyr Thr Leu Thr Ile Ser Arg Leu Glu Pro Glu Asp Phe
                485                 490                 495

Ala Val Tyr Tyr Cys Gln Gln Trp Ser Ser Tyr Pro Pro Thr Phe Gly
            500                 505                 510

Gln Gly Thr Lys Val Glu Ile Lys His His Ala Ala Asn Leu Val Pro
        515                 520                 525

Met Val Ala Thr Val
        530

<210> SEQ ID NO 145
<211> LENGTH: 533
<212> TYPE: PRT
<213> ORGANISM: Artificial Sequence
<220> FEATURE:
<223> OTHER INFORMATION: PD-L1 binding protein #14

<400> SEQUENCE: 145

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60
```

```
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Ser Pro Ser Thr Pro
                245                 250                 255

Pro Thr Pro Ser Pro Ser Thr Pro Pro Ala Ser Gln Val Gln Leu Val
                260                 265                 270

Gln Ser Gly Ala Glu Val Lys Lys Pro Gly Ala Ser Val Lys Val Ser
                275                 280                 285

Cys Lys Ala Ser Gly Tyr Thr Phe Thr Glu Asn Ser Met His Trp Val
                290                 295                 300

Arg Gln Ala His Gly Gln Arg Leu Glu Trp Ile Gly Gly Ile Asn Pro
305                 310                 315                 320

Asn Asn Gly Gly Thr Ser Tyr Asn Gln Lys Phe Lys Gly Lys Ala Thr
                325                 330                 335

Ile Thr Val Asp Thr Ser Ala Ser Thr Ala Tyr Met Glu Leu Ser Ser
                340                 345                 350

Leu Arg Ser Glu Asp Thr Ala Val Tyr Tyr Cys Ala Arg Pro Tyr Tyr
                355                 360                 365

Tyr Gly Tyr Arg Glu Asp Tyr Phe Asp Tyr Trp Gly Gln Gly Thr Thr
                370                 375                 380

Leu Thr Val Ser Ser Gly Gly Gly Ser Gly Gly Gly Gly Ser Gly Gly
385                 390                 395                 400

Gly Gly Ser Gly Gly Gly Gly Ser Gly Gly Gly Ser Asp Ile
                405                 410                 415

Gln Met Thr Gln Ser Pro Ser Ser Leu Ser Ala Ser Val Gly Asp Arg
                420                 425                 430

Val Thr Ile Thr Cys Arg Ala Ser Ser Ser Val Ser Tyr Met Tyr Trp
                435                 440                 445

Tyr Gln Gln Lys Pro Gly Gln Ala Pro Arg Pro Leu Ile Tyr Leu Thr
                450                 455                 460

Ser Asn Leu Ala Ser Gly Ile Pro Asp Arg Phe Ser Gly Ser Gly Ser
465                 470                 475                 480
```

Gly Thr Asp Tyr Thr Leu Thr Ile Ser Arg Leu Glu Pro Glu Asp Phe
                    485                 490                 495

Ala Val Tyr Tyr Cys Gln Gln Trp Ser Ser Tyr Pro Pro Thr Phe Gly
            500                 505                 510

Gln Gly Thr Lys Val Glu Ile Lys His His Ala Ala Asn Leu Val Pro
        515                 520                 525

Met Val Ala Thr Val
    530

<210> SEQ ID NO 146
<211> LENGTH: 533
<212> TYPE: PRT
<213> ORGANISM: Artificial Sequence
<220> FEATURE:
<223> OTHER INFORMATION: PD-L1 binding protein #15

<400> SEQUENCE: 146

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Ser Pro Ser Thr Pro
                245                 250                 255

Pro Thr Pro Ser Pro Ser Thr Pro Pro Ala Ser Gln Val Gln Leu Val
            260                 265                 270

Gln Ser Gly Ala Glu Val Lys Lys Pro Gly Ala Ser Val Lys Val Ser
        275                 280                 285

Cys Lys Thr Ser Gly Tyr Thr Phe Thr Glu Asn Ser Met His Trp Val
290                 295                 300

Arg Gln Ala Pro Gly Gln Arg Leu Glu Trp Met Gly Gly Ile Asn Pro
305                 310                 315                 320

Asn Asn Gly Gly Thr Ser Tyr Asn Gln Lys Phe Gln Gly Arg Val Thr
            325                 330                 335

Leu Thr Val Asp Lys Ser Ser Ser Thr Ala Tyr Met Glu Leu Ser Ser
            340                 345                 350

Leu Arg Ser Glu Asp Thr Ala Val Tyr Tyr Cys Ala Arg Pro Tyr Tyr
            355                 360                 365

Tyr Gly Tyr Arg Glu Asp Tyr Phe Asp Tyr Trp Gly Gln Gly Thr Thr
        370                 375                 380

Leu Thr Val Ser Ser Gly Gly Gly Gly Ser Gly Gly Gly Gly Ser Gly
385                 390                 395                 400

Gly Gly Gly Ser Gly Gly Gly Gly Ser Gly Gly Gly Gly Ser Asp Ile
            405                 410                 415

Gln Met Thr Gln Ser Pro Ser Ser Leu Ser Ala Ser Val Gly Asp Arg
            420                 425                 430

Val Thr Ile Thr Cys Arg Ala Ser Ser Ser Val Ser Tyr Met Tyr Trp
            435                 440                 445

Tyr Gln Gln Lys Pro Gly Gln Ala Pro Arg Pro Leu Ile Tyr Leu Thr
        450                 455                 460

Ser Asn Leu Ala Ser Gly Ile Pro Asp Arg Phe Ser Gly Ser Gly Ser
465                 470                 475                 480

Gly Thr Asp Tyr Thr Leu Thr Ile Ser Arg Leu Glu Pro Glu Asp Phe
            485                 490                 495

Ala Val Tyr Tyr Cys Gln Gln Trp Ser Ser Tyr Pro Pro Thr Phe Gly
            500                 505                 510

Gln Gly Thr Lys Val Glu Ile Lys His His Ala Ala Asn Leu Val Pro
        515                 520                 525

Met Val Ala Thr Val
        530

<210> SEQ ID NO 147
<211> LENGTH: 520
<212> TYPE: PRT
<213> ORGANISM: Artificial Sequence
<220> FEATURE:
<223> OTHER INFORMATION: PD-L1 binding protein #16

<400> SEQUENCE: 147

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
            85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
            115                 120                 125

-continued

```
Gln Ile Asn Arg His Ser Leu Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Gly Ala Pro Glu Val Gln Leu Gln
                260                 265                 270

Gln Ser Gly Pro Glu Leu Val Lys Pro Gly Ala Ser Val Lys Ile Ser
            275                 280                 285

Cys Lys Thr Ser Gly Tyr Thr Phe Thr Glu Tyr Thr Met His Trp Val
290                 295                 300

Lys Gln Arg His Gly Lys Ser Leu Glu Trp Ile Gly Gly Ile Asn Pro
305                 310                 315                 320

Asn Asn Gly Gly Thr Trp Tyr Asn Gln Lys Phe Lys Gly Lys Ala Thr
                325                 330                 335

Leu Thr Val Asp Lys Ser Ser Thr Ala Tyr Met Glu Leu Arg Ser
                340                 345                 350

Leu Thr Ser Glu Asp Ser Ala Val Tyr Phe Cys Ala Arg Pro Tyr Tyr
            355                 360                 365

Tyr Gly Ser Arg Glu Asp Tyr Phe Asp Tyr Trp Gly Gln Gly Thr Thr
370                 375                 380

Leu Thr Val Ser Ser Gly Gly Gly Gly Ser Gly Gly Gly Gly Ser Gly
385                 390                 395                 400

Gly Gly Gly Ser Gly Gly Gly Gly Ser Gly Gly Gly Gly Ser Asp Ile
                405                 410                 415

Gln Met Thr Gln Ser Pro Ser Ser Leu Ser Ala Ser Val Gly Asp Arg
                420                 425                 430

Val Thr Ile Thr Cys Ser Ala Ser Ser Val Ser Tyr Met Tyr Trp
            435                 440                 445

Tyr Gln Gln Lys Pro Arg Ser Ser Pro Lys Pro Trp Ile Tyr Leu Thr
450                 455                 460

Ser Asn Leu Ala Ser Gly Val Pro Ala Arg Phe Ser Gly Ser Gly Ser
465                 470                 475                 480

Gly Thr Ser Tyr Ser Leu Thr Ile Ser Ser Met Glu Ala Glu Asp Ala
                485                 490                 495

Ala Thr Tyr Tyr Cys Gln Gln Trp Ser Ser Asn Pro Pro Thr Phe Gly
                500                 505                 510

Gly Gly Thr Lys Leu Glu Leu Lys
                515                 520
```

<210> SEQ ID NO 148
<211> LENGTH: 520
<212> TYPE: PRT

<213> ORGANISM: Artificial Sequence
<220> FEATURE:
<223> OTHER INFORMATION: PD-L1 binding protein #17

<400> SEQUENCE: 148

| | | | | | | | | | | | | | | |
|---|---|---|---|---|---|---|---|---|---|---|---|---|---|---|
| Lys | Glu | Phe | Thr | Leu | Asp | Phe | Ser | Thr | Ala | Lys | Thr | Tyr | Val | Asp | Ser |
| 1 | | | | 5 | | | | | 10 | | | | | 15 | |

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Tr

```
                385                 390                 395                 400
Gly Gly Gly Ser Gly Gly Gly Ser Gly Gly Gly Ser Asp Ile
            405                 410                 415

Gln Met Thr Gln Ser Pro Ser Leu Ser Ala Ser Val Gly Asp Arg
            420                 425                 430

Val Thr Ile Thr Cys Ser Ala Ser Ser Ser Val Ser Tyr Met Tyr Trp
            435                 440                 445

Tyr Gln Gln Lys Pro Arg Ser Ser Pro Lys Pro Trp Ile Tyr Leu Thr
        450                 455                 460

Ser Asn Leu Ala Ser Gly Val Pro Ala Arg Phe Ser Gly Ser Gly Ser
465                 470                 475                 480

Gly Thr Ser Tyr Ser Leu Thr Ile Ser Ser Met Glu Ala Glu Asp Ala
                485                 490                 495

Ala Thr Tyr Tyr Cys Gln Gln Trp Ser Ser Asn Pro Thr Phe Gly
            500                 505                 510

Gly Gly Thr Lys Leu Glu Ile Lys
            515                 520
```

<210> SEQ ID NO 149
<211> LENGTH: 500
<212> TYPE: PRT
<213> ORGANISM: Artificial Sequence
<220> FEATURE:
<223> OTHER INFORMATION: PD-L1 binding protein #18

<400> SEQUENCE: 149

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
```

```
                225                 230                 235                 240
Asn Ser His His His Ala Ser Ala Val Ala Ala Glu Phe Pro Lys Pro
                    245                 250                 255
Ser Thr Pro Pro Gly Ser Ser Gly Gly Ala Pro Glu Val Gln Leu Gln
                260                 265                 270
Gln Ser Gly Pro Glu Leu Val Lys Pro Gly Ala Ser Val Lys Ile Ser
                275                 280                 285
Cys Lys Thr Ser Gly Tyr Thr Phe Thr Glu Tyr Thr Met His Trp Val
                290                 295                 300
Lys Gln Arg His Gly Lys Ser Leu Glu Trp Ile Gly Gly Ile Asn Pro
305                 310                 315                 320
Asn Asn Gly Gly Thr Trp Tyr Asn Gln Lys Phe Lys Gly Lys Ala Thr
                    325                 330                 335
Leu Thr Val Asp Lys Ser Ser Thr Ala Tyr Met Glu Leu Arg Ser
                340                 345                 350
Leu Thr Ser Glu Asp Ser Ala Val Tyr Phe Cys Ala Arg Pro Tyr Tyr
                355                 360                 365
Tyr Gly Ser Arg Glu Asp Tyr Phe Asp Tyr Trp Gly Gln Gly Thr Thr
                370                 375                 380
Leu Thr Val Ser Ser Gly Gly Gly Ser Asp Ile Gln Met Thr Gln
385                 390                 395                 400
Ser Pro Ser Ser Leu Ser Ala Ser Val Gly Asp Arg Val Thr Ile Thr
                    405                 410                 415
Cys Ser Ala Ser Ser Ser Val Ser Tyr Met Tyr Trp Tyr Gln Gln Lys
                420                 425                 430
Pro Arg Ser Ser Pro Lys Pro Trp Ile Tyr Leu Thr Ser Asn Leu Ala
                435                 440                 445
Ser Gly Val Pro Ala Arg Phe Ser Gly Ser Gly Ser Gly Thr Ser Tyr
                450                 455                 460
Ser Leu Thr Ile Ser Ser Met Glu Ala Glu Asp Ala Ala Thr Tyr Tyr
465                 470                 475                 480
Cys Gln Gln Trp Ser Ser Asn Pro Pro Thr Phe Gly Gly Gly Thr Lys
                    485                 490                 495
Leu Glu Ile Lys
            500

<210> SEQ ID NO 150
<211> LENGTH: 513
<212> TYPE: PRT
<213> ORGANISM: Artificial Sequence
<220> FEATURE:
<223> OTHER INFORMATION: PD-L1 binding protein #19

<400> SEQUENCE: 150

Lys Glu Phe Thr Leu Asp Phe Ser Thr Ala Lys Thr Tyr Val Asp Ser
1               5                   10                  15
Leu Asn Val Ile Arg Ser Ala Ile Gly Thr Pro Leu Gln Thr Ile Ser
                20                  25                  30
Ser Gly Gly Thr Ser Leu Leu Met

-continued

```
                85                  90                  95
His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
            130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
                210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Gly Ala Pro Glu Val Gln Leu Gln
                260                 265                 270

Gln Ser Gly Pro Glu Leu Val Lys Pro Gly Ala Ser Val Lys Ile Ser
                275                 280                 285

Cys Lys Thr Ser Gly Tyr Thr Phe Thr Glu Tyr Thr Met His Trp Val
                290                 295                 300

Lys Gln Arg His Gly Lys Ser Leu Glu Trp Ile Gly Gly Ile Asn Pro
305                 310                 315                 320

Asn Asn Gly Gly Thr Trp Tyr Asn Gln Lys Phe Lys Gly Lys Ala Thr
                325                 330                 335

Leu Thr Val Asp Lys Ser Ser Thr Ala Tyr Met Glu Leu Arg Ser
                340                 345                 350

Leu Thr Ser Glu Asp Ser Ala Val Tyr Phe Cys Ala Arg Pro Tyr Tyr
                355                 360                 365

Tyr Gly Ser Arg Glu Asp Tyr Phe Asp Tyr Trp Gly Gln Gly Thr Thr
                370                 375                 380

Leu Thr Val Ser Ser Gly Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Val Ser Tyr Met Tyr Trp Tyr Gln Gln Lys
                420                 425                 430

Pro Arg Ser Ser Pro Lys Pro Trp Ile Tyr Leu Thr Ser Asn Leu Ala
                435                 440                 445

Ser Gly Val Pro Ala Arg Phe Ser Gly Ser Gly Ser Gly Thr Ser Tyr
                450                 455                 460

Ser Leu Thr Ile Ser Ser Met Glu Ala Glu Asp Ala Ala Thr Tyr Tyr
465                 470                 475                 480

Cys Gln Gln Trp Ser Ser Asn Pro Pro Thr Phe Gly Gly Gly Thr Lys
                485                 490                 495

Leu Glu Ile Lys His His Ala Ala Asn Leu Val Pro Met Val Ala Thr
                500                 505                 510
```

Val

<210> SEQ ID NO 151
<211> LENGTH: 500
<212> TYPE: PRT
<213> ORGANISM: Artificial Sequence
<220> FEATURE:
<223> OTHER INFORMATION: PD-L1 binding protein #20

<400> SEQUENCE: 151

```
Lys Glu Phe Thr Leu Asp Phe Ser Thr Ala Lys Thr Tyr Val Asp Ser
1               5                   10                  15
Leu Asn Val Ile Arg Ser Ala Ile Gly Thr Pro Leu Gln Thr Ile Ser
            20                  25                  30
Ser Gly Gly Thr Ser Leu Leu Met Ile Asp Ser Gly Ile Gly Asp Asn
        35                  40                  45
Leu Phe Ala Val Asp Ile Leu Gly Phe Asp Phe Thr Leu Gly Arg Phe
    50                  55                  60
Asn Asn Leu Arg Leu Ile Val Glu Arg Asn Asn Leu Tyr Val Thr Gly
65                  70                  75                  80
Phe Val Asn Arg Thr Asn Asn Val Phe Tyr Arg Phe Ala Asp Phe Ser
                85                  90                  95
His Val Thr Phe Pro Gly Thr Thr Ala Val Thr Leu Ser Ala Asp Ser
            100                 105                 110
Ser Tyr Thr Thr Leu Gln Arg Val Ala Gly Ile Ser Arg Thr Gly Met
        115                 120                 125
Gln Ile Asn Arg His Ser Leu Thr Thr Ser Tyr Leu Asp Leu Met Ser
    130                 135                 140
His Ser Gly Thr Ser Leu Thr Gln Ser Val Ala Arg Ala Met Leu Arg
145                 150                 155                 160
Phe Val Thr Val Thr Ala Glu Ala Leu Arg Phe Arg Gln Ile Gln Arg
                165                 170                 175
Gly Phe Arg Thr Thr Leu Asp Asp Leu Ser Gly Ala Ser Tyr Val Met
            180                 185                 190
Thr Ala Glu Asp Val Asp Leu Thr Leu Asn Trp Gly Arg Leu Ser Ser
        195                 200                 205
Val Leu Pro Asp Tyr His Gly Gln Asp Ser Val Arg Val Gly Arg Ile
    210                 215                 220
Ser Phe Gly Ser Ile Asn Ala Ile Leu Gly Ser Val Ala Leu Ile Leu
225                 230                 235                 240
Asn Ser His His His Ala Ser Ala Val Ala Ala Glu Phe Pro Lys Pro
                245                 250                 255
Ser Thr Pro Pro Gly Ser Ser Gly Gly Ala Pro Glu Val Gln Leu Gln
            260                 265                 270
Gln Ser Gly Pro Glu Leu Val Lys Pro Gly Ala Ser Val Lys Ile Ser
        275                 280                 285
Cys Lys Thr Ser Gly Tyr Thr Phe Thr Glu Tyr Thr Met His Trp Val
    290                 295                 300
Lys Gln Arg His Gly Lys Ser Leu Glu Trp Ile Gly Gly Ile Asn Pro
305                 310                 315                 320
Asn Asn Gly Gly Thr Trp Tyr Asn Gln Lys Phe Lys Gly Lys Ala Thr
                325                 330                 335
Leu Thr Val Asp Lys Ser Ser Thr Ala Tyr Met Glu Leu Arg Ser
            340                 345                 350
```

-continued

```
Leu Thr Ser Glu Asp Ser Ala Val Tyr Phe Cys Ala Arg Pro Tyr Tyr
            355                 360                 365

Tyr Gly Ser Arg Glu Asp Tyr Phe Asp Tyr Trp Gly Gln Gly Thr Thr
        370                 375                 380

Leu Thr Val Ser Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Val Ser Tyr Met Tyr Trp Tyr Gln Gln Lys
                420                 425                 430

Pro Arg Ser Ser Pro Lys Pro Trp Ile Tyr Leu Thr Ser Asn Leu Ala
            435                 440                 445

Ser Gly Val Pro Ala Arg Phe Ser Gly Ser Gly Ser Gly Thr Ser Tyr
        450                 455                 460

Ser Leu Thr Ile Ser Ser Met Glu Ala Glu Asp Ala Ala Thr Tyr Tyr
465                 470                 475                 480

Cys Gln Gln Trp Ser Ser Asn Pro Pro Thr Phe Gly Gly Gly Thr Lys
                485                 490                 495

Leu Glu Leu Lys
            500

<210> SEQ ID NO 152
<211> LENGTH: 513
<212> TYPE: PRT
<213> ORGANISM: Artificial Sequence
<220> FEATURE:
<223> OTHER INFORMATION: PD-L1 binding protein #21

<400> SEQUENCE: 152

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205
```

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Ala Pro Glu Val Gln Leu Gln
            260                 265                 270

Gln Ser Gly Pro Glu Leu Val Lys Pro Gly Ala Ser Val Lys Ile Ser
            275                 280                 285

Cys Lys Thr Ser Gly Tyr Thr Phe Thr Glu Tyr Thr Met His Trp Val
    290                 295                 300

Lys Gln Arg His Gly Lys Ser Leu Glu Trp Ile Gly Gly Ile Asn Pro
305                 310                 315                 320

Asn Asn Gly Gly Thr Trp Tyr Asn Gln Lys Phe Lys Gly Lys Ala Thr
                325                 330                 335

Leu Thr Val Asp Lys Ser Ser Thr Ala Tyr Met Glu Leu Arg Ser
            340                 345                 350

Leu Thr Ser Glu Asp Ser Ala Val Tyr Phe Cys Ala Arg Pro Tyr Tyr
            355                 360                 365

Tyr Gly Ser Arg Glu Asp Tyr Phe Asp Tyr Trp Gly Gln Gly Thr Thr
            370                 375                 380

Leu Thr Val Ser Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Ser Val Ser Tyr Met Tyr Trp Tyr Gln Gln Lys
            420                 425                 430

Pro Arg Ser Ser Pro Lys Pro Trp Ile Tyr Leu Thr Ser Asn Leu Ala
            435                 440                 445

Ser Gly Val Pro Ala Arg Phe Ser Gly Ser Gly Ser Gly Thr Ser Tyr
            450                 455                 460

Ser Leu Thr Ile Ser Ser Met Glu Ala Glu Asp Ala Ala Thr Tyr Tyr
465                 470                 475                 480

Cys Gln Gln Trp Ser Ser Asn Pro Pro Thr Phe Gly Gly Gly Thr Lys
            485                 490                 495

Leu Glu Leu Lys His His Ala Ala Asn Leu Val Pro Met Val Ala Thr
            500                 505                 510

Val

<210> SEQ ID NO 153
<211> LENGTH: 518
<212> TYPE: PRT
<213> ORGANISM: Artificial Sequence
<220> FEATURE:
<223> OTHER INFORMATION: PD-L1 binding protein #22

<400> SEQUENCE: 153

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe

```
            50                  55                  60
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                     85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
            130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                    165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                    245                 250                 255

Ser Thr Pro Pro Gly Ser Ser Gly Ala Pro Glu Val Gln Leu Gln
                260                 265                 270

Gln Ser Gly Pro Glu Leu Val Lys Pro Gly Ala Ser Val Lys Ile Ser
                275                 280                 285

Cys Lys Thr Ser Gly Tyr Thr Phe Thr Glu Tyr Thr Met His Trp Val
            290                 295                 300

Lys Gln Arg His Gly Lys Ser Leu Glu Trp Ile Gly Gly Ile Asn Pro
305                 310                 315                 320

Asn Asn Gly Gly Thr Trp Tyr Asn Gln Lys Phe Lys Gly Lys Ala Thr
                    325                 330                 335

Leu Thr Val Asp Lys Ser Ser Thr Ala Tyr Met Glu Leu Arg Ser
                340                 345                 350

Leu Thr Ser Glu Asp Ser Ala Val Tyr Phe Cys Ala Arg Pro Tyr Tyr
            355                 360                 365

Tyr Gly Ser Arg Glu Asp Tyr Phe Asp Tyr Trp Gly Gln Gly Thr Thr
370                 375                 380

Leu Thr Val Ser Ser Gly Gly Gly Ser Gly Gly Gly Ser Asp
385                 390                 395                 400

Ile Gln Met Thr Gln Ser Pro Ser Ser Leu Ser Ala Ser Val Gly Asp
                    405                 410                 415

Arg Val Thr Ile Thr Cys Ser Ala Ser Ser Val Ser Tyr Met Tyr
                420                 425                 430

Trp Tyr Gln Gln Lys Pro Arg Ser Ser Pro Lys Pro Trp Ile Tyr Leu
            435                 440                 445

Thr Ser Asn Leu Ala Ser Gly Val Pro Ala Arg Phe Ser Gly Ser Gly
            450                 455                 460

Ser Gly Thr Ser Tyr Ser Leu Thr Ile Ser Ser Met Glu Ala Glu Asp
465                 470                 475                 480
```

Ala Ala Thr Tyr Tyr Cys Gln Gln Trp Ser Ser Asn Pro Thr Phe
            485                 490                 495

Gly Gly Gly Thr Lys Leu Glu Leu Lys His His Ala Ala Asn Leu Val
            500                 505                 510

Pro Met Val Ala Thr Val
        515

<210> SEQ ID NO 154
<211> LENGTH: 533
<212> TYPE: PRT
<213> ORGANISM: Artificial Sequence
<220> FEATURE:
<223> OTHER INFORMATION: PD-L1 binding protein #23

<400> SEQUENCE: 154

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Gly Ala Pro Glu Val Gln Leu Gln
            260                 265                 270

Gln Ser Gly Pro Glu Leu Val Lys Pro Gly Ala Ser Val Lys Ile Ser
        275                 280                 285

Cys Lys Thr Ser Gly Tyr Thr Phe Thr Glu Tyr Thr Met His Trp Val
    290                 295                 300

Lys Gln Arg His Gly Lys Ser Leu Glu Trp Ile Gly Gly Ile Asn Pro
305                 310                 315                 320

```
Asn Asn Gly Gly Thr Trp Tyr Asn Gln Lys Phe Lys Gly Lys Ala Thr
                325                 330                 335

Leu Thr Val Asp Lys Ser Ser Ser Thr Ala Tyr Met Glu Leu Arg Ser
            340                 345                 350

Leu Thr Ser Glu Asp Ser Ala Val Tyr Phe Cys Ala Arg Pro Tyr Tyr
        355                 360                 365

Tyr Gly Ser Arg Glu Asp Tyr Phe Asp Tyr Trp Gly Gln Gly Thr Thr
    370                 375                 380

Leu Thr Val Ser Ser Gly Gly Gly Ser Gly Gly Gly Ser Gly
385                 390                 395                 400

Gly Gly Gly Ser Gly Gly Gly Ser Gly Gly Gly Ser Asp Ile
                405                 410                 415

Val Met Thr Gln Ser Pro Ala Ile Met Ser Ala Ser Pro Gly Glu Lys
            420                 425                 430

Val Thr Met Thr Cys Ser Ala Ser Ser Val Ser Tyr Met Tyr Trp
        435                 440                 445

Tyr Gln Gln Lys Pro Arg Ser Ser Pro Lys Pro Trp Ile Tyr Leu Thr
    450                 455                 460

Ser Asn Leu Ala Ser Gly Val Pro Ala Arg Phe Ser Gly Ser Gly Ser
465                 470                 475                 480

Gly Thr Ser Tyr Ser Leu Thr Ile Ser Ser Met Glu Ala Glu Asp Ala
                485                 490                 495

Ala Thr Tyr Tyr Cys Gln Gln Trp Ser Ser Asn Pro Pro Thr Phe Gly
            500                 505                 510

Gly Gly Thr Lys Leu Glu Leu Lys His His Ala Ala Asn Leu Val Pro
        515                 520                 525

Met Val Ala Thr Val
    530

<210> SEQ ID NO 155
<211> LENGTH: 513
<212> TYPE: PRT
<213> ORGANISM: Artificial Sequence
<220> FEATURE:
<223> OTHER INFORMATION: PD-L1 binding protein #24

<400> SEQUENCE: 155

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140
```

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Ala Pro Glu Val Gln Leu Gln
            260                 265                 270

Gln Ser Gly Pro Glu Leu Val Lys Pro Gly Ala Ser Val Lys Ile Ser
        275                 280                 285

Cys Lys Thr Ser Gly Tyr Thr Phe Thr Glu Tyr Thr Met His Trp Val
    290                 295                 300

Lys Gln Arg His Gly Lys Ser Leu Glu Trp Ile Gly Gly Ile Asn Pro
305                 310                 315                 320

Asn Asn Gly Gly Thr Trp Tyr Asn Gln Lys Phe Lys Gly Lys Ala Thr
                325                 330                 335

Leu Thr Val Asp Lys Ser Ser Thr Ala Tyr Met Glu Leu Arg Ser
            340                 345                 350

Leu Thr Ser Glu Asp Ser Ala Val Tyr Phe Cys Ala Arg Pro Tyr Tyr
        355                 360                 365

Tyr Gly Ser Arg Glu Asp Tyr Phe Asp Tyr Trp Gly Gln Gly Thr Thr
    370                 375                 380

Leu Thr Val Ser Ser Gly Gly Gly Ser Asp Ile Val Met Thr Gln
385                 390                 395                 400

Ser Pro Ala Ile Met Ser Ala Ser Pro Gly Glu Lys Val Thr Met Thr
                405                 410                 415

Cys Ser Ala Ser Ser Ser Val Ser Tyr Met Tyr Trp Tyr Gln Gln Lys
            420                 425                 430

Pro Arg Ser Ser Pro Lys Pro Trp Ile Tyr Leu Thr Ser Asn Leu Ala
        435                 440                 445

Ser Gly Val Pro Ala Arg Phe Ser Gly Ser Gly Ser Gly Thr Ser Tyr
    450                 455                 460

Ser Leu Thr Ile Ser Ser Met Glu Ala Glu Asp Ala Ala Thr Tyr Tyr
465                 470                 475                 480

Cys Gln Gln Trp Ser Ser Asn Pro Pro Thr Phe Gly Gly Gly Thr Lys
                485                 490                 495

Leu Glu Leu Lys His His Ala Ala Asn Leu Val Pro Met Val Ala Thr
            500                 505                 510

Val

<210> SEQ ID NO 156
<211> LENGTH: 253
<212> TYPE: PRT
<213> ORGANISM: Artificial Sequence
<220> FEATURE:
<223> OTHER INFORMATION: single-chain variable fragment XXIV

<400> SEQUENCE: 156

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Arg His Gly Lys Ser Leu Glu Trp Ile
        35                  40                  45

Gly Gly Ile Asn Pro Asn Asn Gly Gly Thr Trp Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Tyr Tyr Gly Ser Arg Glu Asp Tyr Phe Asp Tyr Trp
            100                 105                 110

Gly Gln Gly Thr Thr Leu Thr Val Ser Ser Gly Gly Gly Ser Gly
            115                 120                 125

Gly Gly Gly Ser Gly Gly Gly Ser Gly Gly Gly Ser Gly Gly
        130                 135                 140

Gly Gly Ser Asp Ile Val Met Thr Gln Ser Pro Ala Ile Met Ser Ala
145                 150                 155                 160

Ser Pro Gly Glu Lys Val Thr Met Thr Cys Ser Ala Ser Ser Ser Val
                165                 170                 175

Ser Tyr Met Tyr Trp Tyr Gln Gln Lys Pro Arg Ser Ser Pro Lys Pro
            180                 185                 190

Trp Ile Tyr Leu Thr Ser Asn Leu Ala Ser Gly Val Pro Ala Arg Phe
        195                 200                 205

Ser Gly Ser Gly Ser Gly Thr Ser Tyr Ser Leu Thr Ile Ser Ser Met
    210                 215                 220

Glu Ala Glu Asp Ala Ala Thr Tyr Tyr Cys Gln Gln Trp Ser Ser Asn
225                 230                 235                 240

Pro Pro Thr Phe Gly Gly Gly Thr Lys Leu Glu Leu Lys
                245                 250

<210> SEQ ID NO 157
<211> LENGTH: 233
<212> TYPE: PRT
<213> ORGANISM: Artificial Sequence
<220> FEATURE:
<223> OTHER INFORMATION: single-chain variable fragment XXV

<400> SEQUENCE: 157

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Arg His Gly Lys Ser Leu Glu Trp Ile
        35                  40                  45

Gly Gly Ile Asn Pro Asn Asn Gly Gly Thr Trp Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

```
Ala Arg Pro Tyr Tyr Gly Ser Arg Glu Asp Tyr Phe Asp Tyr Trp
            100                 105                 110

Gly Gln Gly Thr Thr Leu Thr Val Ser Ser Gly Gly Gly Ser Asp
        115                 120                 125

Ile Val Met Thr Gln Ser Pro Ala Ile Met Ser Ala Ser Pro Gly Glu
    130                 135                 140

Lys Val Thr Met Thr Cys Ser Ala Ser Ser Val Ser Tyr Met Tyr
145                 150                 155                 160

Trp Tyr Gln Gln Lys Pro Arg Ser Ser Pro Lys Pro Trp Ile Tyr Leu
                165                 170                 175

Thr Ser Asn Leu Ala Ser Gly Val Pro Ala Arg Phe Ser Gly Ser Gly
            180                 185                 190

Ser Gly Thr Ser Tyr Ser Leu Thr Ile Ser Ser Met Glu Ala Glu Asp
        195                 200                 205

Ala Ala Thr Tyr Tyr Cys Gln Gln Trp Ser Ser Asn Pro Pro Thr Phe
    210                 215                 220

Gly Gly Gly Thr Lys Leu Glu Leu Lys
225                 230
```

<210> SEQ ID NO 158
<211> LENGTH: 513
<212> TYPE: PRT
<213> ORGANISM: Artificial Sequence
<220> FEATURE:
<223> OTHER INFORMATION: PD-L1 binding protein #25

<400> SEQUENCE: 158

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Ser Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Asp Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220
```

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
            245                 250                 255

Ser Thr Pro Pro Gly Ser Ser Gly Gly Ala Pro Glu Val Gln Leu Gln
        260                 265                 270

Gln Ser Gly Pro Glu Leu Val Lys Pro Gly Ala Ser Val Lys Ile Ser
    275                 280                 285

Cys Lys Thr Ser Gly Tyr Thr Phe Thr Glu Tyr Thr Met His Trp Val
290                 295                 300

Lys Gln Arg His Gly Lys Ser Leu Glu Trp Ile Gly Gly Ile Asn Pro
305                 310                 315                 320

Asn Asn Gly Gly Thr Trp Tyr Asn Gln Lys Phe Lys Gly Lys Ala Thr
                325                 330                 335

Leu Thr Val Asp Lys Ser Ser Thr Ala Tyr Met Glu Leu Arg Ser
            340                 345                 350

Leu Thr Ser Glu Asp Ser Ala Val Tyr Phe Cys Ala Arg Pro Tyr Tyr
        355                 360                 365

Tyr Gly Ser Arg Glu Asp Tyr Phe Asp Tyr Trp Gly Gln Gly Thr Thr
370                 375                 380

Leu Thr Val Ser Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Ser Val Ser Tyr Met Tyr Trp Tyr Gln Gln Lys
            420                 425                 430

Pro Arg Ser Ser Pro Lys Pro Trp Ile Tyr Leu Thr Ser Asn Leu Ala
        435                 440                 445

Ser Gly Val Pro Ala Arg Phe Ser Gly Ser Gly Ser Gly Thr Ser Tyr
    450                 455                 460

Ser Leu Thr Ile Ser Ser Met Glu Ala Glu Asp Ala Ala Thr Tyr Tyr
465                 470                 475                 480

Cys Gln Gln Trp Ser Ser Asn Pro Pro Thr Phe Gly Gly Gly Thr Lys
                485                 490                 495

Leu Glu Leu Lys His His Ala Ala Asn Leu Val Pro Met Val Ala Thr
            500                 505                 510

Val

<210> SEQ ID NO 159
<211> LENGTH: 532
<212> TYPE: PRT
<213> ORGANISM: Artificial Sequence
<220> FEATURE:
<223> OTHER INFORMATION: PD-L1 binding protein #26

<400> SEQUENCE: 159

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser

-continued

```
                65                  70                  75                  80
        Phe Val Asn Arg Thr Asn Asn Val Phe Tyr Arg Phe Ala Asp Phe Ser
                        85                  90                  95
        His Val Thr Phe Pro Gly Thr Thr Ala Val Thr Leu Ser Ala Asp Ser
                        100                 105                 110
        Ser Tyr Thr Thr Leu Gln Arg Val Ala Gly Ile Ser Arg Thr Gly Met
                        115                 120                 125
        Gln Ile Asn Arg His Ser Leu Thr Thr Ser Tyr Leu Asp Leu Met Ser
                        130                 135                 140
        His Ser Gly Thr Ser Leu Thr Gln Ser Val Ala Arg Ala Met Leu Arg
        145                 150                 155                 160
        Phe Val Thr Val Thr Ala Glu Ala Leu Arg Phe Arg Gln Ile Gln Arg
                        165                 170                 175
        Gly Phe Arg Thr Thr Leu Asp Asp Leu Ser Gly Ala Ser Tyr Val Met
                        180                 185                 190
        Thr Ala Glu Asp Val Asp Leu Thr Leu Asn Trp Gly Arg Leu Ser Ser
                        195                 200                 205
        Val Leu Pro Asp Tyr His Gly Gln Asp Ser Val Arg Val Gly Arg Ile
                        210                 215                 220
        Ser Phe Gly Ser Ile Asn Ala Ile Leu Gly Ser Val Ala Leu Ile Leu
        225                 230                 235                 240
        Asn Ser His His His Ala Ser Ala Val Ala Ala Ser Pro Ser Thr Pro
                        245                 250                 255
        Pro Thr Pro Ser Pro Ser Thr Pro Pro Ala Ser Asp Ile Gln Met Thr
                        260                 265                 270
        Gln Ser Pro Ser Ser Leu Ser Ala Ser Val Gly Asp Arg Val Thr Ile
                        275                 280                 285
        Thr Cys Thr Gly Thr Ser Ser Asp Val Gly Ser Tyr Asn Arg Val Ser
                        290                 295                 300
        Trp Tyr Gln Gln Pro Pro Gly Thr Ala Pro Lys Leu Met Ile Tyr Glu
        305                 310                 315                 320
        Val Ser Asn Arg Pro Ser Gly Val Ser Asn Arg Phe Ser Gly Ser Lys
                        325                 330                 335
        Ser Gly Asn Thr Ala Ser Leu Thr Ile Ser Gly Leu Gln Ala Glu Asp
                        340                 345                 350
        Glu Ala Asp Tyr Tyr Cys Ser Ser His Thr Thr Ser Gly Thr Tyr Val
                        355                 360                 365
        Phe Gly Thr Gly Thr Lys Leu Thr Val Leu Gly Gly Gly Ser Glu
                        370                 375                 380
        Val Gln Leu Val Gln Ser Gly Ala Glu Val Lys Lys Pro Gly Ala Ser
        385                 390                 395                 400
        Val Lys Val Ser Cys Lys Ala Ser Gly Gly Thr Phe Ser Ser Tyr Ala
                        405                 410                 415
        Ile Ser Trp Val Arg Gln Ala Pro Gly Gln Gly Leu Glu Trp Met Gly
                        420                 425                 430
        Gly Ile Ile Pro Ile Phe Gly Thr Ala Asn Tyr Ala Gln Lys Phe Gln
                        435                 440                 445
        Gly Arg Val Thr Ile Thr Ala Asp Glu Ser Thr Ser Thr Ala Tyr Met
                        450                 455                 460
        Glu Leu Ser Ser Leu Arg Ser Glu Asp Thr Ala Val Tyr Tyr Cys Ala
        465                 470                 475                 480
        Arg Asp Gln Gly Tyr Ala His Ala Phe Asp Ile Trp Gly Arg Gly Thr
                        485                 490                 495
```

```
Thr Val Thr Val Ser Ser His His Ala Ala Asn Leu Pro Met Val
                500                 505                 510

Ala Thr Val Arg Arg Asn Leu Val Pro Met Val Ala Thr Val Arg Arg
        515                 520                 525

Asn Leu Val Pro
    530

<210> SEQ ID NO 160
<211> LENGTH: 514
<212> TYPE: PRT
<213> ORGANISM: Artificial Sequence
<220> FEATURE:
<223> OTHER INFORMATION: Binding Molecule 116555

<400> SEQUENCE: 160

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Ser Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Asp Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320
```

```
Pro Asn Asn Gly Gly Thr Trp Tyr Asn Gln Lys Phe Lys Gly Lys Ala
                325                 330                 335

Thr Leu Thr Val Asp Lys Ser Ser Thr Ala Tyr Met Glu Leu Arg
            340                 345                 350

Ser Leu Thr Ser Glu Asp Ser Ala Val Tyr Phe Cys Ala Arg Pro Tyr
            355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Ser Ala Ser Ser Ser Val Ser Tyr Met Tyr Trp Tyr Gln Gln
                420                 425                 430

Lys Pro Arg Ser Ser Pro Lys Pro Trp Ile Tyr Leu Thr Ser Asn Leu
                435                 440                 445

Ala Ser Gly Val Pro Ala Arg Phe Ser Gly Ser Gly Ser Gly Thr Ser
            450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Pro Thr Phe Gly Gly Gly Thr
                485                 490                 495

Lys Leu Glu Leu Lys His His Ala Ala Asn Leu Val Pro Met Val Ala
                500                 505                 510

Thr Val

<210> SEQ ID NO 161
<211> LENGTH: 533
<212> TYPE: PRT
<213> ORGANISM: Artificial Sequence
<220> FEATURE:
<223> OTHER INFORMATION: Binding Molecule 115765

<400> SEQUENCE: 161

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
        50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160
```

```
Arg Phe Val Thr Val Thr Ala Glu Ala Leu Arg Phe Arg Gln Ile Gln
            165                 170                 175

Arg Gly Phe Arg Thr Thr Leu Asp Asp Leu Ser Gly Ala Ser Tyr Val
        180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Ser Pro Ser Thr
                245                 250                 255

Pro Pro Thr Pro Ser Pro Ser Thr Pro Pro Ala Ser Asp Ile Gln Met
            260                 265                 270

Thr Gln Ser Pro Ser Ser Leu Ser Ala Ser Val Gly Asp Arg Val Thr
        275                 280                 285

Ile Thr Cys Thr Gly Thr Ser Ser Asp Val Gly Ser Tyr Asn Arg Val
        290                 295                 300

Ser Trp Tyr Gln Gln Pro Pro Gly Thr Ala Pro Lys Leu Met Ile Tyr
305                 310                 315                 320

Glu Val Ser Asn Arg Pro Ser Gly Val Ser Asn Arg Phe Ser Gly Ser
                325                 330                 335

Lys Ser Gly Asn Thr Ala Ser Leu Thr Ile Ser Gly Leu Gln Ala Glu
            340                 345                 350

Asp Glu Ala Asp Tyr Tyr Cys Ser Ser His Thr Thr Ser Gly Thr Tyr
        355                 360                 365

Val Phe Gly Thr Gly Thr Lys Leu Thr Val Leu Gly Gly Gly Gly Ser
    370                 375                 380

Glu Val Gln Leu Val Gln Ser Gly Ala Glu Val Lys Lys Pro Gly Ala
385                 390                 395                 400

Ser Val Lys Val Ser Cys Lys Ala Ser Gly Thr Phe Ser Ser Tyr
                405                 410                 415

Ala Ile Ser Trp Val Arg Gln Ala Pro Gly Gln Gly Leu Glu Trp Met
            420                 425                 430

Gly Gly Ile Ile Pro Ile Phe Gly Thr Ala Asn Tyr Ala Gln Lys Phe
        435                 440                 445

Gln Gly Arg Val Thr Ile Thr Ala Asp Glu Ser Thr Ser Thr Ala Tyr
    450                 455                 460

Met Glu Leu Ser Ser Leu Arg Ser Glu Asp Thr Ala Val Tyr Tyr Cys
465                 470                 475                 480

Ala Arg Asp Gln Gly Tyr Ala His Ala Phe Asp Ile Trp Gly Arg Gly
                485                 490                 495

Thr Thr Val Thr Val Ser Ser His His Ala Ala Asn Leu Val Pro Met
            500                 505                 510

Val Ala Thr Val Arg Arg Asn Leu Val Pro Met Val Ala Thr Val Arg
        515                 520                 525

Arg Asn Leu Val Pro
    530

<210> SEQ ID NO 162
<211> LENGTH: 503
<212> TYPE: PRT
<213> ORGANISM: Artificial Sequence
<220> FEATURE:
<223> OTHER INFORMATION: Binding Molecule 115695
```

<400> SEQUENCE: 162

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Ser Pro Ser Thr
                245                 250                 255

Pro Pro Thr Pro Ser Pro Ser Thr Pro Ala Ser Asp Ile Gln Met
            260                 265                 270

Thr Gln Ser Pro Ser Ser Leu Ser Ala Ser Val Gly Asp Arg Val Thr
        275                 280                 285

Ile Thr Cys Thr Gly Thr Ser Ser Asp Val Gly Ser Tyr Asn Arg Val
    290                 295                 300

Ser Trp Tyr Gln Gln Pro Pro Gly Thr Ala Pro Lys Leu Met Ile Tyr
305                 310                 315                 320

Glu Val Ser Asn Arg Pro Ser Gly Val Ser Asn Arg Phe Ser Gly Ser
                325                 330                 335

Lys Ser Gly Asn Thr Ala Ser Leu Thr Ile Ser Gly Leu Gln Ala Glu
            340                 345                 350

Asp Glu Ala Asp Tyr Tyr Cys Ser Ser His Thr Thr Ser Gly Thr Tyr
        355                 360                 365

Val Phe Gly Thr Gly Thr Lys Leu Thr Val Leu Gly Gly Gly Gly Ser
    370                 375                 380

Glu Val Gln Leu Val Gln Ser Gly Ala Glu Val Lys Lys Pro Gly Ala
385                 390                 395                 400

Ser Val Lys Val Ser Cys Lys Ala Ser Gly Gly Thr Phe Ser Ser Tyr

-continued

```
                405                 410                 415
Ala Ile Ser Trp Val Arg Gln Ala Pro Gly Gln Gly Leu Glu Trp Met
            420                 425                 430

Gly Gly Ile Ile Pro Ile Phe Gly Thr Ala Asn Tyr Ala Gln Lys Phe
        435                 440                 445

Gln Gly Arg Val Thr Ile Thr Ala Asp Glu Ser Thr Ser Thr Ala Tyr
    450                 455                 460

Met Glu Leu Ser Ser Leu Arg Ser Glu Asp Thr Ala Val Tyr Tyr Cys
465                 470                 475                 480

Ala Arg Asp Gln Gly Tyr Ala His Ala Phe Asp Ile Trp Gly Arg Gly
                485                 490                 495

Thr Thr Val Thr Val Ser Ser
                500

<210> SEQ ID NO 163
<211> LENGTH: 508
<212> TYPE: PRT
<213> ORGANISM: Artificial Sequence
<220> FEATURE:
<223> OTHER INFORMATION: Binding Molecule 114895

<400> SEQUENCE: 163

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Asp Ile Val Leu
```

```
            260                 265                 270
Thr Gln Ser Pro Ala Ser Leu Ala Val Ser Leu Gly Gln Arg Ala Thr
            275                 280                 285
Ile Ser Cys Arg Ala Thr Glu Ser Val Glu Tyr Tyr Gly Thr Ser Leu
            290                 295                 300
Val Gln Trp Tyr Gln Gln Lys Pro Gly Gln Pro Pro Lys Leu Leu Ile
305                 310                 315                 320
Tyr Ala Ala Ser Ser Val Asp Ser Gly Val Pro Ala Arg Phe Ser Gly
                325                 330                 335
Ser Gly Ser Gly Thr Asp Phe Ser Leu Thr Ile His Pro Val Glu Glu
            340                 345                 350
Asp Asp Ile Ala Met Tyr Phe Cys Gln Gln Ser Arg Arg Val Pro Tyr
            355                 360                 365
Thr Phe Gly Gly Gly Thr Lys Leu Glu Ile Lys Gly Gly Gly Gly Ser
    370                 375                 380
Glu Val Gln Leu Gln Gln Ser Gly Pro Glu Leu Val Lys Pro Gly Ala
385                 390                 395                 400
Ser Val Lys Met Ser Cys Lys Ala Ser Gly Tyr Thr Phe Thr Ser Tyr
                405                 410                 415
Val Met His Trp Val Lys Gln Lys Pro Gly Gln Gly Leu Glu Trp Ile
            420                 425                 430
Gly Tyr Val Asn Pro Phe Asn Asp Gly Thr Lys Tyr Asn Glu Met Phe
                435                 440                 445
Lys Gly Lys Ala Thr Leu Thr Ser Asp Lys Ser Ser Ser Thr Ala Tyr
    450                 455                 460
Met Glu Leu Ser Ser Leu Thr Ser Glu Asp Ser Ala Val Tyr Tyr Cys
465                 470                 475                 480
Ala Arg Gln Ala Trp Gly Tyr Pro Trp Gly Gln Gly Thr Leu Val Thr
                485                 490                 495
Val Ser Ala Asn Leu Val Pro Met Val Ala Thr Val
            500                 505
```

<210> SEQ ID NO 164
<211> LENGTH: 532
<212> TYPE: PRT
<213> ORGANISM: Artificial Sequence
<220> FEATURE:
<223> OTHER INFORMATION: Binding molecule V1

<400> SEQUENCE: 164

```
Met Lys Glu Phe Thr Leu Asp Phe Ser Thr Ala Lys Thr Tyr Val Asp
1               5                   10                  15
Ser Leu Asn Val Ile Arg Ser Ala Ile Gly Thr Pro Leu Gln Thr Ile
            20                  25                  30
Ser Ser Gly Gly Thr Ser Leu Leu Met Ile Asp Ser Gly Ile Gly Asp
        35                  40                  45
Asn Leu Phe Ala Val Asp Ile Leu Gly Phe Asp Phe Thr Leu Gly Arg
    50                  55                  60
Phe Asn Asn Leu Arg Leu Ile Val Glu Arg Asn Asn Leu Tyr Val Thr
65                  70                  75                  80
Gly Phe Val Asn Arg Thr Asn Asn Val Phe Tyr Arg Phe Ala Asp Phe
                85                  90                  95
Ser His Val Thr Phe Pro Gly Thr Thr Ala Val Thr Leu Ser Ala Asp
            100                 105                 110
Ser Ser Tyr Thr Thr Leu Gln Arg Val Ala Gly Ile Ser Arg Thr Gly
```

```
                115                 120                 125
Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
                180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
        210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
                260                 265                 270

Gln Gln Ser Gly Pro Glu Leu Val Lys Pro Gly Ala Ser Val Lys Ile
            275                 280                 285

Ser Cys Lys Thr Ser Gly Tyr Thr Phe Thr Glu Tyr Thr Met His Trp
        290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Thr Ala Tyr Met Glu Leu Arg
                340                 345                 350

Ser Leu Thr Ser Glu Asp Ser Ala Val Tyr Phe Cys Ala Arg Pro Tyr
            355                 360                 365

Tyr Tyr Gly Ser Arg Glu Asp Tyr Phe Asp Tyr Trp Gly Gln Gly Thr
        370                 375                 380

Thr Leu Thr Val Ser Ser Gly Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Ser Ala Ser Ser Ser Val Ser Tyr Met Tyr Trp Tyr Gln Gln
                420                 425                 430

Lys Pro Arg Ser Ser Pro Lys Pro Trp Ile Tyr Leu Thr Ser Asn Leu
            435                 440                 445

Ala Ser Gly Val Pro Ala Arg Phe Ser Gly Ser Gly Ser Gly Thr Ser
        450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Pro Thr Phe Gly Gly Gly Thr
                485                 490                 495

Lys Leu Glu Leu Lys Asn Leu Val Pro Met Val Ala Thr Val Arg Arg
                500                 505                 510

Asn Leu Val Pro Met Val Ala Thr Val Arg Arg Asn Leu Val Pro Met
            515                 520                 525

Val Ala Thr Val
            530
```

-continued

```
<210> SEQ ID NO 165
<211> LENGTH: 527
<212> TYPE: PRT
<213> ORGANISM: Artificial Sequence
<220> FEATURE:
<223> OTHER INFORMATION: Binding molecule V2

<400> SEQUENCE: 165

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
        50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Thr Ala Tyr Met Glu Leu Arg
            340                 345                 350

Ser Leu Thr Ser Glu Asp Ser Ala Val Tyr Phe Cys Ala Arg Pro Tyr
        355                 360                 365
```

```
Tyr Tyr Gly Ser Arg Glu Asp Tyr Phe Asp Tyr Trp Gly Gln Gly Thr
            370                 375                 380

Thr Leu Thr Val Ser Ser Gly Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Ser Ala Ser Ser Val Ser Tyr Met Tyr Trp Tyr Gln Gln
                420                 425                 430

Lys Pro Arg Ser Ser Pro Lys Pro Trp Ile Tyr Leu Thr Ser Asn Leu
            435                 440                 445

Ala Ser Gly Val Pro Ala Arg Phe Ser Gly Ser Gly Ser Gly Thr Ser
450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Pro Thr Phe Gly Gly Gly Thr
                485                 490                 495

Lys Leu Glu Leu Lys Asn Leu Val Pro Met Val Ala Thr Val Arg Arg
            500                 505                 510

Asn Leu Val Pro Met Val Ala Thr Val Arg Arg Asn Leu Val Pro
            515                 520                 525

<210> SEQ ID NO 166
<211> LENGTH: 502
<212> TYPE: PRT
<213> ORGANISM: Artificial Sequence
<220> FEATURE:
<223> OTHER INFORMATION: PD-L1 Binding protein #27

<400> SEQUENCE: 166

Lys Glu Phe Thr Leu Asp Phe Ser Thr Ala Lys Thr Tyr Val Asp Ser
1               5                  10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205
```

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Ser Pro Ser Thr Pro
                245                 250                 255

Pro Thr Pro Ser Pro Ser Thr Pro Pro Ala Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Thr Gly Thr Ser Ser Asp Val Gly Ser Tyr Asn Arg Val Ser
    290                 295                 300

Trp Tyr Gln Gln Pro Pro Gly Thr Ala Pro Lys Leu Met Ile Tyr Glu
305                 310                 315                 320

Val Ser Asn Arg Pro Ser Gly Val Ser Asn Arg Phe Ser Gly Ser Lys
                325                 330                 335

Ser Gly Asn Thr Ala Ser Leu Thr Ile Ser Gly Leu Gln Ala Glu Asp
            340                 345                 350

Glu Ala Asp Tyr Tyr Cys Ser Ser His Thr Thr Ser Gly Thr Tyr Val
        355                 360                 365

Phe Gly Thr Gly Thr Lys Leu Thr Val Leu Gly Gly Gly Gly Ser Glu
    370                 375                 380

Val Gln Leu Val Gln Ser Gly Ala Glu Val Lys Lys Pro Gly Ala Ser
385                 390                 395                 400

Val Lys Val Ser Cys Lys Ala Ser Gly Gly Thr Phe Ser Ser Tyr Ala
                405                 410                 415

Ile Ser Trp Val Arg Gln Ala Pro Gly Gln Gly Leu Glu Trp Met Gly
            420                 425                 430

Gly Ile Ile Pro Ile Phe Gly Thr Ala Asn Tyr Ala Gln Lys Phe Gln
        435                 440                 445

Gly Arg Val Thr Ile Thr Ala Asp Glu Ser Thr Ser Thr Ala Tyr Met
    450                 455                 460

Glu Leu Ser Ser Leu Arg Ser Glu Asp Thr Ala Val Tyr Tyr Cys Ala
465                 470                 475                 480

Arg Asp Gln Gly Tyr Ala His Ala Phe Asp Ile Trp Gly Arg Gly Thr
                485                 490                 495

Thr Val Thr Val Ser Ser
            500

<210> SEQ ID NO 167
<211> LENGTH: 507
<212> TYPE: PRT
<213> ORGANISM: Artificial Sequence
<220> FEATURE:
<223> OTHER INFORMATION: PD-L1 Binding Protein #28

<400> SEQUENCE: 167

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

-continued

```
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
            130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                    165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                    245                 250                 255

Ser Thr Pro Pro Gly Ser Ser Gly Gly Ala Pro Asp Ile Val Leu Thr
                260                 265                 270

Gln Ser Pro Ala Ser Leu Ala Val Ser Leu Gly Gln Arg Ala Thr Ile
            275                 280                 285

Ser Cys Arg Ala Thr Glu Ser Val Glu Tyr Tyr Gly Thr Ser Leu Val
290                 295                 300

Gln Trp Tyr Gln Gln Lys Pro Gly Gln Pro Pro Lys Leu Leu Ile Tyr
305                 310                 315                 320

Ala Ala Ser Ser Val Asp Ser Gly Val Pro Ala Arg Phe Ser Gly Ser
                325                 330                 335

Gly Ser Gly Thr Asp Phe Ser Leu Thr Ile His Pro Val Glu Glu Asp
                340                 345                 350

Asp Ile Ala Met Tyr Phe Cys Gln Gln Ser Arg Arg Val Pro Tyr Thr
            355                 360                 365

Phe Gly Gly Gly Thr Lys Leu Glu Ile Lys Gly Gly Gly Ser Glu
370                 375                 380

Val Gln Leu Gln Gln Ser Gly Pro Glu Leu Val Lys Pro Gly Ala Ser
385                 390                 395                 400

Val Lys Met Ser Cys Lys Ala Ser Gly Tyr Thr Phe Thr Ser Tyr Val
                405                 410                 415

Met His Trp Val Lys Gln Lys Pro Gly Gln Gly Leu Glu Trp Ile Gly
                420                 425                 430

Tyr Val Asn Pro Phe Asn Asp Gly Thr Lys Tyr Asn Glu Met Phe Lys
                435                 440                 445

Gly Lys Ala Thr Leu Thr Ser Asp Lys Ser Ser Thr Ala Tyr Met
            450                 455                 460

Glu Leu Ser Ser Leu Thr Ser Glu Asp Ser Ala Val Tyr Tyr Cys Ala
465                 470                 475                 480
```

```
Arg Gln Ala Trp Gly Tyr Pro Trp Gly Gln Gly Thr Leu Val Thr Val
                485                 490                 495

Ser Ala Asn Leu Val Pro Met Val Ala Thr Val
            500                 505

<210> SEQ ID NO 168
<211> LENGTH: 531
<212> TYPE: PRT
<213> ORGANISM: Artificial Sequence
<220> FEATURE:
<223> OTHER INFORMATION: Binding Molecule V3

<400> SEQUENCE: 168

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
        50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335
```

```
Thr Leu Thr Val Asp Lys Ser Ser Thr Ala Tyr Met Glu Leu Arg
                340                 345                 350

Ser Leu Thr Ser Glu Asp Ser Ala Val Tyr Phe Cys Ala Arg Pro Tyr
        355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Ser Ala Ser Ser Ser Val Ser Tyr Met Tyr Trp Tyr Gln Gln
            420                 425                 430

Lys Pro Arg Ser Ser Pro Lys Pro Trp Ile Tyr Leu Thr Ser Asn Leu
        435                 440                 445

Ala Ser Gly Val Pro Ala Arg Phe Ser Gly Ser Gly Ser Gly Thr Ser
    450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Pro Thr Phe Gly Gly Gly Thr
                485                 490                 495

Lys Leu Glu Leu Lys His His Ala Ala Asn Leu Val Pro Met Val Ala
            500                 505                 510

Thr Val Arg Arg Asn Leu Val Pro Met Val Ala Thr Val Arg Arg Asn
        515                 520                 525

Leu Val Pro
    530

<210> SEQ ID NO 169
<211> LENGTH: 251
<212> TYPE: PRT
<213> ORGANISM: Artificial Sequence
<220> FEATURE:
<223> OTHER INFORMATION: Shiga toxin effector polypeptide 30

<400> SEQUENCE: 169

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Ser Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160
```

-continued

```
Phe Val Thr Val Thr Ala Asp Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 170
<211> LENGTH: 251
<212> TYPE: PRT
<213> ORGANISM: Artificial Sequence
<220> FEATURE:
<223> OTHER INFORMATION: Shiga toxin effector polypeptide 31

<400> SEQUENCE: 170

Lys Glu Phe Thr Leu Asp Phe Ser Thr Ala Lys Thr Tyr Val Asp Ser
1               5                   10                  15

Le

<400> SEQUENCE: 171

000

<210> SEQ ID NO 172

<400> SEQUENCE: 172

000

<210> SEQ ID NO 173
<211> LENGTH: 251
<212> TYPE: PRT
<213> ORGANISM: Artificial Sequence
<220> FEATURE:
<223> OTHER INFORMATION: Shiga toxin effector polypeptide 30

<400> SEQUENCE: 173

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Asp Ala Leu Ser Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250
```

<210> SEQ ID NO 174
<211> LENGTH: 26
<212> TYPE: PRT
<213> ORGANISM: Artificial Sequence
<220> FEATURE:
<223> OTHER INFORMATION: Carboxy-terminal moiety

<400> SEQUENCE: 174

```
Asn Leu Val Pro Met Val Ala Thr Val Arg Arg Asn Leu Val Pro Met
1               5                   10                  15

Val Ala Thr Val Arg Arg Asn Leu Val Pro
            20                  25
```

<210> SEQ ID NO 175
<211> LENGTH: 31
<212> TYPE: PRT
<213> ORGANISM: Artificial Sequence
<220> FEATURE:
<223> OTHER INFORMATION: Carboxy-terminal moiety

<400> SEQUENCE: 175

```
Asn Leu Val Pro Met Val Ala Thr Val Arg Arg Asn Leu Val Pro Met
1               5                   10                  15

Val Ala Thr Val Arg Arg Asn Leu Val Pro Met Val Ala Thr Val
            20                  25                  30
```

<210> SEQ ID NO 176
<211> LENGTH: 13
<212> TYPE: PRT
<213> ORGANISM: Artificial Sequence
<220> FEATURE:
<223> OTHER INFORMATION: Carboxy-terminal moiety

<400> SEQUENCE: 176

```
His His Ala Ala Asn Leu Val Pro Met Val Ala Thr Val
1               5                   10
```

<210> SEQ ID NO 177
<211> LENGTH: 30
<212> TYPE: PRT
<213> ORGANISM: Artificial Sequence
<220> FEATURE:
<223> OTHER INFORMATION: Carboxy-terminal moiety

<400> SEQUENCE: 177

```
His His Ala Ala Asn Leu Val Pro Met Val Ala Thr Val Arg Arg Asn
1               5                   10                  15

Leu Val Pro Met Val Ala Thr Val Arg Arg Asn Leu Val Pro
            20                  25                  30
```

<210> SEQ ID NO 178
<211> LENGTH: 20
<212> TYPE: PRT
<213> ORGANISM: Unknown
<220> FEATURE:
<223> OTHER INFORMATION: Carboxy-terminal moiety

<400> SEQUENCE: 178

```
Asn Leu Val Pro Met Val Ala Thr Val Arg Arg Asn Leu Val Pro Met
1               5                   10                  15

Val Ala Thr Val
            20
```

<210> SEQ ID NO 179
<211> LENGTH: 22
<212> TYPE: PRT
<213> ORGANISM: Unknown
<220> FEATURE:
<223> OTHER INFORMATION: Carboxy-terminal moiety

<400> SEQUENCE: 179

```
Asn Leu Val Pro Met Val Ala Thr Val His His Ala Ala Asn Leu Val
1               5                   10                  15
```

```
Pro Met Val Ala Thr Val
        20

<210> SEQ ID NO 180
<211> LENGTH: 11
<212> TYPE: PRT
<213> ORGANISM: Unknown
<220> FEATURE:
<223> OTHER INFORMATION: Carboxy-terminal moiety

<400> SEQUENCE: 180

Arg Arg Asn Leu Val Pro Met Val Ala Thr Val
1               5                   10

<210> SEQ ID NO 181
<211> LENGTH: 28
<212> TYPE: PRT
<213> ORGANISM: Unknown
<220> FEATURE:
<223> OTHER INFORMATION: Carboxy-terminal moiety

<400> SEQUENCE: 181

Arg Arg Asn Leu Val Pro Met Val Ala Thr Val Arg Arg Asn Leu Val
1               5                   10                  15

Pro Met Val Ala Thr Val Arg Arg Asn Leu Val Pro
            20                  25

<210> SEQ ID NO 182
<211> LENGTH: 33
<212> TYPE: PRT
<213> ORGANISM: Unknown
<220> FEATURE:
<223> OTHER INFORMATION: Carboxy-terminal moiety

<400> SEQUENCE: 182

Asn Leu Val Pro Met Val Ala Thr Val Arg Arg Asn Leu Val Pro Met
1               5                   10                  15

Val Ala Thr Val His His Ala Ala Asn Leu Val Pro Met Val Ala Thr
            20                  25                  30

Val

<210> SEQ ID NO 183
<211> LENGTH: 30
<212> TYPE: PRT
<213> ORGANISM: Unknown
<220> FEATURE:
<223> OTHER INFORMATION: Carboxy-terminal moiety

<400> SEQUENCE: 183

Asn Leu Val Pro Met Val Ala Thr Val Arg Arg Ala Ala Asn Leu Val
1               5                   10                  15

Pro Met Val Ala Thr Val His His Ala Ala Asn Leu Val Pro
            20                  25                  30

<210> SEQ ID NO 184
<211> LENGTH: 33
<212> TYPE: PRT
<213> ORGANISM: Unknown
<220> FEATURE:
<223> OTHER INFORMATION: Carboxy-terminal moiety

<400> SEQUENCE: 184

Asn Leu Val Pro Met Val Ala Thr Val His His Ala Ala Asn Leu Val
1               5                   10                  15
```

-continued

```
Pro Met Val Ala Thr Val Arg Arg Asn Leu Val Pro Met Val Ala Thr
            20                  25                  30
Val

<210> SEQ ID NO 185
<211> LENGTH: 28
<212> TYPE: PRT
<213> ORGANISM: Unknown
<220> FEATURE:
<223> OTHER INFORMATION: Carboxy-terminal moiety

<400> SEQUENCE: 185

Asn Leu Val Pro Met Val Ala Thr Val His His Ala Ala Asn Leu Val
1               5                   10                  15

Pro Met Val Ala Thr Val Arg Arg Asn Leu Val Pro
            20                  25

<210> SEQ ID NO 186
<211> LENGTH: 35
<212> TYPE: PRT
<213> ORGANISM: Unknown
<220> FEATURE:
<223> OTHER INFORMATION: Carboxy-terminal moiety

<400> SEQUENCE: 186

Asn Leu Val Pro Met Val Ala Thr Val His His Ala Ala Asn Leu Val
1               5                   10                  15

Pro Met Val Ala Thr Val His His Ala Ala Asn Leu Val Pro Met Val
            20                  25                  30

Ala Thr Val
        35

<210> SEQ ID NO 187
<211> LENGTH: 30
<212> TYPE: PRT
<213> ORGANISM: Unknown
<220> FEATURE:
<223> OTHER INFORMATION: Carboxy-terminal moiety

<400> SEQUENCE: 187

Asn Leu Val Pro Met Val Ala Thr Val His His Ala Ala Asn Leu Val
1               5                   10                  15

Pro Met Val Ala Thr Val His His Ala Ala Asn Leu Val Pro
            20                  25                  30

<210> SEQ ID NO 188
<211> LENGTH: 12
<212> TYPE: PRT
<213> ORGANISM: Unknown
<220> FEATURE:
<223> OTHER INFORMATION: proteinaceous linker

<400> SEQUENCE: 188

Gly Lys Ser Ser Gly Ser Gly Ser Glu Ser Lys Ser
1               5                   10

<210> SEQ ID NO 189
<211> LENGTH: 14
<212> TYPE: PRT
<213> ORGANISM: Unknown
<220> FEATURE:
<223> OTHER INFORMATION: proteinaceous linker

<400> SEQUENCE: 189
```

```
Glu Gly Lys Ser Ser Gly Ser Gly Ser Glu Ser Lys Glu Phe
1               5                   10
```

<210> SEQ ID NO 190
<211> LENGTH: 14
<212> TYPE: PRT
<213> ORGANISM: Unknown
<220> FEATURE:
<223> OTHER INFORMATION: proteinaceous linker

<400> SEQUENCE: 190

```
Gly Ser Thr Ser Gly Ser Gly Lys Ser Ser Glu Gly Lys Gly
1               5                   10
```

<210> SEQ ID NO 191
<211> LENGTH: 18
<212> TYPE: PRT
<213> ORGANISM: Unknown
<220> FEATURE:
<223> OTHER INFORMATION: proteinaceous linker

<400> SEQUENCE: 191

```
Gly Ser Thr Ser Gly Ser Gly Lys Ser Ser Glu Gly Ser Gly Ser Thr
1               5                   10                  15

Lys Gly
```

<210> SEQ ID NO 192
<211> LENGTH: 18
<212> TYPE: PRT
<213> ORGANISM: Unknown
<220> FEATURE:
<223> OTHER INFORMATION: proteinaceous linker

<400> SEQUENCE: 192

```
Gly Ser Thr Ser Gly Ser Gly Lys Pro Gly Ser Gly Glu Gly Ser Thr
1               5                   10                  15

Lys Gly
```

<210> SEQ ID NO 193
<211> LENGTH: 5
<212> TYPE: PRT
<213> ORGANISM: Unknown
<220> FEATURE:
<223> OTHER INFORMATION: proteinaceous linker

<400> SEQUENCE: 193

```
Ser Arg Ser Ser Gly
1               5
```

<210> SEQ ID NO 194
<211> LENGTH: 5
<212> TYPE: PRT
<213> ORGANISM: Unknown
<220> FEATURE:
<223> OTHER INFORMATION: proteinaceous linker

<400> SEQUENCE: 194

```
Ser Gly Ser Ser Cys
1               5
```

<210> SEQ ID NO 195
<211> LENGTH: 28
<212> TYPE: PRT
<213> ORGANISM: Unknown
<220> FEATURE:

<223> OTHER INFORMATION: proteinaceous linker

<400> SEQUENCE: 195

Ala Met Gly Arg Ser Gly Gly Cys Ala Gly Asn Arg Val Gly Ser
1               5                   10                  15

Ser Leu Ser Cys Gly Gly Leu Asn Leu Gln Ala Met
            20                  25

<210> SEQ ID NO 196
<211> LENGTH: 4
<212> TYPE: PRT
<213> ORGANISM: Artificial Sequence
<220> FEATURE:
<223> OTHER INFORMATION: scFv linker

<400> SEQUENCE: 196

Gly Gly Gly Ser
1

<210> SEQ ID NO 197
<211> LENGTH: 8
<212> TYPE: PRT
<213> ORGANISM: Artificial Sequence
<220> FEATURE:
<223> OTHER INFORMATION: scFv linker

<400> SEQUENCE: 197

Gly Gly Gly Gly Ser Gly Gly Gly
1               5

<210> SEQ ID NO 198
<211> LENGTH: 7
<212> TYPE: PRT
<213> ORGANISM: Artificial Sequence
<220> FEATURE:
<223> OTHER INFORMATION: scFv linker

<400> SEQUENCE: 198

Gly Gly Ser Gly Gly Gly Gly
1               5

<210> SEQ ID NO 199
<211> LENGTH: 18
<212> TYPE: PRT
<213> ORGANISM: Artificial Sequence
<220> FEATURE:
<223> OTHER INFORMATION: scFv linker

<400> SEQUENCE: 199

Gly Ser Thr Ser Gly Gly Gly Ser Gly Gly Gly Ser Gly Gly Gly
1               5                   10                  15

Ser Ser

<210> SEQ ID NO 200
<211> LENGTH: 18
<212> TYPE: PRT
<213> ORGANISM: Artificial Sequence
<220> FEATURE:
<223> OTHER INFORMATION: scFv linker

<400> SEQUENCE: 200

Gly Ser Thr Ser Gly Ser Gly Lys Pro Gly Ser Ser Glu Gly Ser Thr
1               5                   10                  15

Lys Gly

```
<210> SEQ ID NO 201
<211> LENGTH: 10
<212> TYPE: PRT
<213> ORGANISM: Artificial Sequence
<220> FEATURE:
<223> OTHER INFORMATION: scFv linker
<220> FEATURE:
<221> NAME/KEY: VARIANT
<222> LOCATION: (3)..(4)
<223> OTHER INFORMATION: may be absent
<220> FEATURE:
<221> NAME/KEY: VARIANT
<222> LOCATION: (5)..(6)
<223> OTHER INFORMATION: may be absent
<220> FEATURE:
<221> NAME/KEY: VARIANT
<222> LOCATION: (7)..(8)
<223> OTHER INFORMATION: may be absent
<220> FEATURE:
<221> NAME/KEY: VARIANT
<222> LOCATION: (9)..(10)
<223> OTHER INFORMATION: may be absent

<400> SEQUENCE: 201

Gly Ser Gly Ser Gly Ser Gly Ser Gly Ser
1               5                   10

<210> SEQ ID NO 202
<211> LENGTH: 25
<212> TYPE: PRT
<213> ORGANISM: Artificial Sequence
<220> FEATURE:
<223> OTHER INFORMATION: scFv linker
<220> FEATURE:
<221> NAME/KEY: VARIANT
<222> LOCATION: (6)..(10)
<223> OTHER INFORMATION: may be absent
<220> FEATURE:
<221> NAME/KEY: VARIANT
<222> LOCATION: (11)..(15)
<223> OTHER INFORMATION: may be absent
<220> FEATURE:
<221> NAME/KEY: VARIANT
<222> LOCATION: (16)..(20)
<223> OTHER INFORMATION: may be absent
<220> FEATURE:
<221> NAME/KEY: VARIANT
<222> LOCATION: (21)..(25)
<223> OTHER INFORMATION: may be absent

<400> SEQUENCE: 202

Gly Ser Gly Gly Ser Gly Ser Gly Ser Gly Ser Gly Gly Ser Gly
1               5                   10                  15

Ser Gly Gly Ser Gly Ser Gly Gly Ser
            20                  25

<210> SEQ ID NO 203
<211> LENGTH: 25
<212> TYPE: PRT
<213> ORGANISM: Artificial Sequence
<220> FEATURE:
<223> OTHER INFORMATION: scFv linker
<220> FEATURE:
<221> NAME/KEY: VARIANT
<222> LOCATION: (6)..(10)
<223> OTHER INFORMATION: may be absent
<220> FEATURE:
<221> NAME/KEY: VARIANT
<222> LOCATION: (11)..(15)
<223> OTHER INFORMATION: may be absent
<220> FEATURE:
<221> NAME/KEY: VARIANT
<222> LOCATION: (16)..(20)
```

```
<223> OTHER INFORMATION: may be absent
<220> FEATURE:
<221> NAME/KEY: VARIANT
<222> LOCATION: (21)..(25)
<223> OTHER INFORMATION: may be absent

<400> SEQUENCE: 203

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 204
<211> LENGTH: 20
<212> TYPE: PRT
<213> ORGANISM: Artificial Sequence
<220> FEATURE:
<223> OTHER INFORMATION: scFv linker
<220> FEATURE:
<221> NAME/KEY: VARIANT
<222> LOCATION: (5)..(8)
<223> OTHER INFORMATION: may be absent
<220> FEATURE:
<221> NAME/KEY: VARIANT
<222> LOCATION: (9)..(12)
<223> OTHER INFORMATION: may be absent
<220> FEATURE:
<221> NAME/KEY: VARIANT
<222> LOCATION: (13)..(16)
<223> OTHER INFORMATION: may be absent
<220> FEATURE:
<221> NAME/KEY: VARIANT
<222> LOCATION: (17)..(20)
<223> OTHER INFORMATION: may be absent

<400> SEQUENCE: 204

Gly Gly Gly Ser Gly Gly Gly Ser Gly Gly Gly Ser Gly Gly Gly Ser
1               5                   10                  15

Gly Gly Gly Ser
            20

<210> SEQ ID NO 205
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 205

Lys Asp Glu Leu
1

<210> SEQ ID NO 206
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 206

His Asp Glu Phe
1

<210> SEQ ID NO 207
<211> LENGTH: 4
<212> TYPE: PRT
<213> ORGANISM: Artificial Sequence
```

```
<220> FEATURE:
<223> OTHER INFORMATION: endoplasmic reticulum retention/retrieval
      signal motif

<400> SEQUENCE: 207

His Asp Glu Leu
1

<210> SEQ ID NO 208
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 208

Arg Asp Glu Phe
1

<210> SEQ ID NO 209
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 209

Arg Asp Glu Leu
1

<210> SEQ ID NO 210
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 210

Trp Asp Glu Leu
1

<210> SEQ ID NO 211
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 211

Tyr Asp Glu Leu
1

<210> SEQ ID NO 212
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 212

His Glu Glu Phe
1
```

<210> SEQ ID NO 213
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 213

His Glu Glu Leu
1

<210> SEQ ID NO 214
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 214

Lys Glu Glu Leu
1

<210> SEQ ID NO 215
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 215

Arg Glu Glu Leu
1

<210> SEQ ID NO 216
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 216

Lys Ala Glu Leu
1

<210> SEQ ID NO 217
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 217

Lys Cys Glu Leu
1

<210> SEQ ID NO 218
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

```
<400> SEQUENCE: 218

Lys Phe Glu Leu
1

<210> SEQ ID NO 219
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 219

Lys Gly Glu Leu
1

<210> SEQ ID NO 220
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 220

Lys His Glu Leu
1

<210> SEQ ID NO 221
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 221

Lys Leu Glu Leu
1

<210> SEQ ID NO 222
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 222

Lys Asn Glu Leu
1

<210> SEQ ID NO 223
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 223

Lys Gln Glu Leu
1

<210> SEQ ID NO 224
<211> LENGTH: 4
<212> TYPE: PRT
```

```
<213> ORGANISM: Artificial Sequence
<220> FEATURE:
<223> OTHER INFORMATION: endoplasmic reticulum retention/retrieval
      signal motif

<400> SEQUENCE: 224

Lys Arg Glu Leu
1

<210> SEQ ID NO 225
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 225

Lys Ser Glu Leu
1

<210> SEQ ID NO 226
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 226

Lys Val Glu Leu
1

<210> SEQ ID NO 227
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 227

Lys Trp Glu Leu
1

<210> SEQ ID NO 228
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 228

Lys Tyr Glu Leu
1

<210> SEQ ID NO 229
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 229

Lys Glu Asp Leu
1
```

```
<210> SEQ ID NO 230
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 230

Lys Ile Glu Leu
1

<210> SEQ ID NO 231
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 231

Asp Lys Glu Leu
1

<210> SEQ ID NO 232
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 232

Phe Asp Glu Leu
1

<210> SEQ ID NO 233
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 233

Lys Asp Glu Phe
1

<210> SEQ ID NO 234
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 234

Lys Lys Glu Leu
1

<210> SEQ ID NO 235
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif
```

```
<400> SEQUENCE: 235

His Ala Asp Leu
1

<210> SEQ ID NO 236
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 236

His Ala Glu Leu
1

<210> SEQ ID NO 237
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 237

His Ile Glu Leu
1

<210> SEQ ID NO 238
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 238

His Asn Glu Leu
1

<210> SEQ ID NO 239
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 239

His Thr Glu Leu
1

<210> SEQ ID NO 240
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 240

Lys Thr Glu Leu
1

<210> SEQ ID NO 241
<211> LENGTH: 4
```

```
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 241

His Val Glu Leu
1

<210> SEQ ID NO 242
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 242

Asn Asp Glu Leu
1

<210> SEQ ID NO 243
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 243

Gln Asp Glu Leu
1

<210> SEQ ID NO 244
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 244

Arg Glu Asp Leu
1

<210> SEQ ID NO 245
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 245

Arg Asn Glu Leu
1

<210> SEQ ID NO 246
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 246

Arg Thr Asp Leu
```

```
<210> SEQ ID NO 247
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 247

Arg Thr Glu Leu
1

<210> SEQ ID NO 248
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 248

Ser Asp Glu Leu
1

<210> SEQ ID NO 249
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 249

Thr Asp Glu Leu
1

<210> SEQ ID NO 250
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 250

Ser Lys Glu Leu
1

<210> SEQ ID NO 251
<211> LENGTH: 4
<212> TYPE: PRT
<213> ORGANISM: Artificial Sequence
<220> FEATURE:
<223> OTHER INFORMATION: endoplasmic reticulum retention/retrieval
      signal motif

<400> SEQUENCE: 251

Ser Thr Glu Leu
1

<210> SEQ ID NO 252
<211> LENGTH: 4
<212> TYPE: PRT
<213> ORGANISM: Artificial Sequence
<220> FEATURE:
<223> OTHER INFORMATION: endoplasmic reticulum retention/retrieval
``` signal motif

<400> SEQUENCE: 252

Glu Asp Glu Leu
1

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259
<211> LENGTH: 498
<212> TYPE: PRT
<213> ORGANISM: Artificial Sequence
<220> FEATURE:
<223> OTHER INFORMATION: Binding Molecule 114962

<400> SEQUENCE: 259

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
        50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
       115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Val Glu Ser Gly Gly Gly Leu Val Gln Pro Gly Gly Ser Leu Arg Leu
        275                 280                 285

Ser Cys Ala Ala Ser Gly Phe Thr Phe Ser Asp Ser Trp Ile His Trp
    290                 295                 300

Val Arg Gln Ala Pro Gly Lys Gly Leu Glu Trp Val Ala Trp Ile Ser
305                 310                 315                 320

Pro Tyr Gly Gly Ser Thr Tyr Tyr Ala Asp Ser Val Lys Gly Arg Phe
                325                 330                 335

Thr Ile Ser Ala Asp Thr Ser Lys Asn Thr Ala Tyr Leu Gln Met Asn
            340                 345                 350

Ser Leu Arg Ala Glu Asp Thr Ala Val Tyr Tyr Cys Ala Arg Arg His
        355                 360                 365

Trp Pro Gly Gly Phe Asp Tyr Trp Gly Gln Gly Thr Leu Val Thr Val
    370                 375                 380

Ser Ser Gly Gly Gly Gly Ser Asp Ile Gln Met Thr Gln Ser Pro Ser
385                 390                 395                 400

Ser Leu Ser Ala Ser Val Gly Asp Arg Val Thr Ile Thr Cys Arg Ala
                405                 410                 415

Ser Gln Asp Val Ser Thr Ala Val Ala Trp Tyr Gln Gln Lys Pro Gly
            420                 425                 430

Lys Ala Pro Lys Leu Leu Ile Tyr Ser Ala Ser Phe Leu Tyr Ser Gly
        435                 440                 445

Val Pro Ser Arg Phe Ser Gly Ser Gly Ser Gly Thr Asp Phe Thr Leu
    450                 455                 460

Thr Ile Ser Ser Leu Gln Pro Glu Asp Phe Ala Thr Tyr Tyr Cys Gln
465                 470                 475                 480

Gln Tyr Leu Tyr His Pro Ala Thr Phe Gly Gln Gly Thr Lys Val Glu
                485                 490                 495

Ile Lys

<210> SEQ ID NO 260
<211> LENGTH: 498
<212> TYPE: PRT

<213> ORGANISM: Artificial Sequence
<220> FEATURE:
<223> OTHER INFORMATION: Binding Molecule 114963

<400> SEQUENCE: 260

```
Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Asp Ile Gln Met
            260                 265                 270

Thr Gln Ser Pro Ser Ser Leu Ser Ala Ser Val Gly Asp Arg Val Thr
        275                 280                 285

Ile Thr Cys Arg Ala Ser Gln Gly Ile Ser Ser Trp Leu Ala Trp Tyr
    290                 295                 300

Gln Gln Lys Pro Glu Lys Ala Pro Lys Ser Leu Ile Tyr Ala Ala Ser
305                 310                 315                 320

Ser Leu Gln Ser Gly Val Pro Ser Arg Phe Ser Gly Ser Gly Ser Gly
                325                 330                 335

Thr Asp Phe Thr Leu Thr Ile Ser Ser Leu Gln Pro Glu Asp Phe Ala
            340                 345                 350

Thr Tyr Tyr Cys Gln Gln Tyr Asn Ser Tyr Pro Tyr Thr Phe Gly Gln
        355                 360                 365

Gly Thr Lys Leu Glu Ile Lys Gly Gly Gly Gly Ser Gln Val Gln Leu
    370                 375                 380

Val Gln Ser Gly Ala Glu Val Lys Lys Pro Gly Ala Ser Val Lys Val
```

```
385                 390                 395                 400
Ser Cys Lys Ala Ser Gly Tyr Thr Phe Thr Ser Tyr Asp Val His Trp
                405                 410                 415

Val Arg Gln Ala Pro Gly Gln Arg Leu Glu Trp Met Gly Trp Leu His
            420                 425                 430

Ala Asp Thr Gly Ile Thr Lys Phe Ser Gln Lys Phe Gln Gly Arg Val
        435                 440                 445

Thr Ile Thr Arg Asp Thr Ser Ala Ser Thr Ala Tyr Met Glu Leu Ser
    450                 455                 460

Ser Leu Arg Ser Glu Asp Thr Ala Val Tyr Tyr Cys Ala Arg Glu Arg
465                 470                 475                 480

Ile Gln Leu Trp Phe Asp Tyr Trp Gly Gln Gly Thr Leu Val Thr Val
                485                 490                 495

Ser Ser

<210> SEQ ID NO 261
<211> LENGTH: 518
<212> TYPE: PRT
<213> ORGANISM: Artificial Sequence
<220> FEATURE:
<223> OTHER INFORMATION: Binding Molecule 114964

<400> SEQUENCE: 261

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255
```

```
Pro Ser Thr Pro Pro Gly Ser Ser Gly Gly Ala Pro Glu Val Gln Leu
            260                 265                 270

Val Glu Ser Gly Gly Gly Leu Val Gln Pro Gly Gly Ser Leu Arg Leu
        275                 280                 285

Ser Cys Ala Ala Ser Gly Phe Thr Phe Ser Asp Ser Trp Ile His Trp
    290                 295                 300

Val Arg Gln Ala Pro Gly Lys Gly Leu Glu Trp Val Ala Trp Ile Ser
305                 310                 315                 320

Pro Tyr Gly Gly Ser Thr Tyr Tyr Ala Asp Ser Val Lys Gly Arg Phe
                325                 330                 335

Thr Ile Ser Ala Asp Thr Ser Lys Asn Thr Ala Tyr Leu Gln Met Asn
            340                 345                 350

Ser Leu Arg Ala Glu Asp Thr Ala Val Tyr Tyr Cys Ala Arg Arg His
        355                 360                 365

Trp Pro Gly Gly Phe Asp Tyr Trp Gly Gln Gly Thr Leu Val Thr Val
    370                 375                 380

Ser Ser Gly Gly Gly Gly Ser Gly Gly Gly Gly Ser Gly Gly Gly Gly
385                 390                 395                 400

Ser Gly Gly Gly Gly Ser Gly Gly Gly Gly Ser Asp Ile Gln Met Thr
                405                 410                 415

Gln Ser Pro Ser Ser Leu Ser Ala Ser Val Gly Asp Arg Val Thr Ile
            420                 425                 430

Thr Cys Arg Ala Ser Gln Asp Val Ser Thr Ala Val Ala Trp Tyr Gln
        435                 440                 445

Gln Lys Pro Gly Lys Ala Pro Lys Leu Leu Ile Tyr Ser Ala Ser Phe
    450                 455                 460

Leu Tyr Ser Gly Val Pro Ser Arg Phe Ser Gly Ser Gly Ser Gly Thr
465                 470                 475                 480

Asp Phe Thr Leu Thr Ile Ser Ser Leu Gln Pro Glu Asp Phe Ala Thr
                485                 490                 495

Tyr Tyr Cys Gln Gln Tyr Leu Tyr His Pro Ala Thr Phe Gly Gln Gly
            500                 505                 510

Thr Lys Val Glu Ile Lys
        515

<210> SEQ ID NO 262
<211> LENGTH: 210
<212> TYPE: PRT
<213> ORGANISM: Artificial Sequence
<220> FEATURE:
<223> OTHER INFORMATION: linker
<220> FEATURE:
<221> NAME/KEY: VARIANT
<222> LOCATION: (2)..(6)
<223> OTHER INFORMATION: may be absent
<220> FEATURE:
<221> NAME/KEY: VARIANT
<222> LOCATION: (8)..(14)
<223> OTHER INFORMATION: may be absent
<220> FEATURE:
<221> NAME/KEY: VARIANT
<222> LOCATION: (9)..(14)
<223> OTHER INFORMATION: may be absent
<220> FEATURE:
<221> NAME/KEY: VARIANT
<222> LOCATION: (15)..(21)
<223> OTHER INFORMATION: may be absent
<220> FEATURE:
<221> NAME/KEY: VARIANT
<222> LOCATION: (16)..(20)
<223> OTHER INFORMATION: may be absent
```

```
<220> FEATURE:
<221> NAME/KEY: VARIANT
<222> LOCATION: (22)..(28)
<223> OTHER INFORMATION: may be absent
<220> FEATURE:
<221> NAME/KEY: VARIANT
<222> LOCATION: (23)..(27)
<223> OTHER INFORMATION: may be absent
<220> FEATURE:
<221> NAME/KEY: VARIANT
<222> LOCATION: (29)..(34)
<223> OTHER INFORMATION: may be absent
<220> FEATURE:
<221> NAME/KEY: VARIANT
<222> LOCATION: (30)..(33)
<223> OTHER INFORMATION: may be absent
<220> FEATURE:
<221> NAME/KEY: VARIANT
<222> LOCATION: (35)..(42)
<223> OTHER INFORMATION: may be absent
<220> FEATURE:
<221> NAME/KEY: VARIANT
<222> LOCATION: (36)..(41)
<223> OTHER INFORMATION: may be absent
<220> FEATURE:
<221> NAME/KEY: VARIANT
<222> LOCATION: (43)..(49)
<223> OTHER INFORMATION: may be absent
<220> FEATURE:
<221> NAME/KEY: VARIANT
<222> LOCATION: (44)..(48)
<223> OTHER INFORMATION: may be absent
<220> FEATURE:
<221> NAME/KEY: VARIANT
<222> LOCATION: (50)..(56)
<223> OTHER INFORMATION: may be absent
<220> FEATURE:
<221> NAME/KEY: VARIANT
<222> LOCATION: (51)..(55)
<223> OTHER INFORMATION: may be absent
<220> FEATURE:
<221> NAME/KEY: VARIANT
<222> LOCATION: (57)..(63)
<223> OTHER INFORMATION: may be absent
<220> FEATURE:
<221> NAME/KEY: VARIANT
<222> LOCATION: (58)..(62)
<223> OTHER INFORMATION: may be absent
<220> FEATURE:
<221> NAME/KEY: VARIANT
<222> LOCATION: (64)..(70)
<223> OTHER INFORMATION: may be absent
<220> FEATURE:
<221> NAME/KEY: VARIANT
<222> LOCATION: (65)..(69)
<223> OTHER INFORMATION: may be absent
<220> FEATURE:
<221> NAME/KEY: VARIANT
<222> LOCATION: (71)..(77)
<223> OTHER INFORMATION: may be absent
<220> FEATURE:
<221> NAME/KEY: VARIANT
<222> LOCATION: (72)..(76)
<223> OTHER INFORMATION: may be absent
<220> FEATURE:
<221> NAME/KEY: VARIANT
<222> LOCATION: (78)..(84)
<223> OTHER INFORMATION: may be absent
<220> FEATURE:
<221> NAME/KEY: VARIANT
<222> LOCATION: (79)..(83)
<223> OTHER INFORMATION: may be absent
<220> FEATURE:
<221> NAME/KEY: VARIANT
<222> LOCATION: (85)..(91)
<223> OTHER INFORMATION: may be absent
<220> FEATURE:
<221> NAME/KEY: VARIANT
<222> LOCATION: (86)..(90)
```

```
<223> OTHER INFORMATION: may be absent
<220> FEATURE:
<221> NAME/KEY: VARIANT
<222> LOCATION: (92)..(98)
<223> OTHER INFORMATION: may be absent
<220> FEATURE:
<221> NAME/KEY: VARIANT
<222> LOCATION: (93)..(97)
<223> OTHER INFORMATION: may be absent
<220> FEATURE:
<221> NAME/KEY: VARIANT
<222> LOCATION: (99)..(105)
<223> OTHER INFORMATION: may be absent
<220> FEATURE:
<221> NAME/KEY: VARIANT
<222> LOCATION: (100)..(104)
<223> OTHER INFORMATION: may be absent
<220> FEATURE:
<221> NAME/KEY: VARIANT
<222> LOCATION: (106)..(112)
<223> OTHER INFORMATION: may be absent
<220> FEATURE:
<221> NAME/KEY: VARIANT
<222> LOCATION: (107)..(111)
<223> OTHER INFORMATION: may be absent
<220> FEATURE:
<221> NAME/KEY: VARIANT
<222> LOCATION: (113)..(119)
<223> OTHER INFORMATION: may be absent
<220> FEATURE:
<221> NAME/KEY: VARIANT
<222> LOCATION: (114)..(118)
<223> OTHER INFORMATION: may be absent
<220> FEATURE:
<221> NAME/KEY: VARIANT
<222> LOCATION: (120)..(126)
<223> OTHER INFORMATION: may be absent
<220> FEATURE:
<221> NAME/KEY: VARIANT
<222> LOCATION: (121)..(125)
<223> OTHER INFORMATION: may be absent
<220> FEATURE:
<221> NAME/KEY: VARIANT
<222> LOCATION: (127)..(133)
<223> OTHER INFORMATION: may be absent
<220> FEATURE:
<221> NAME/KEY: VARIANT
<222> LOCATION: (128)..(132)
<223> OTHER INFORMATION: may be absent
<220> FEATURE:
<221> NAME/KEY: VARIANT
<222> LOCATION: (134)..(140)
<223> OTHER INFORMATION: may be absent
<220> FEATURE:
<221> NAME/KEY: VARIANT
<222> LOCATION: (135)..(139)
<223> OTHER INFORMATION: may be absent
<220> FEATURE:
<221> NAME/KEY: VARIANT
<222> LOCATION: (141)..(147)
<223> OTHER INFORMATION: may be absent
<220> FEATURE:
<221> NAME/KEY: VARIANT
<222> LOCATION: (142)..(146)
<223> OTHER INFORMATION: may be absent
<220> FEATURE:
<221> NAME/KEY: VARIANT
<222> LOCATION: (148)..(154)
<223> OTHER INFORMATION: may be absent
<220> FEATURE:
<221> NAME/KEY: VARIANT
<222> LOCATION: (149)..(153)
<223> OTHER INFORMATION: may be absent
<220> FEATURE:
<221> NAME/KEY: VARIANT
<222> LOCATION: (155)..(161)
<223> OTHER INFORMATION: may be absent
<220> FEATURE:
<221> NAME/KEY: VARIANT
```

```
<222> LOCATION: (156)..(160)
<223> OTHER INFORMATION: may be absent
<220> FEATURE:
<221> NAME/KEY: VARIANT
<222> LOCATION: (162)..(168)
<223> OTHER INFORMATION: may be absent
<220> FEATURE:
<221> NAME/KEY: VARIANT
<222> LOCATION: (163)..(167)
<223> OTHER INFORMATION: may be absent
<220> FEATURE:
<221> NAME/KEY: VARIANT
<222> LOCATION: (169)..(175)
<223> OTHER INFORMATION: may be absent
<220> FEATURE:
<221> NAME/KEY: VARIANT
<222> LOCATION: (170)..(174)
<223> OTHER INFORMATION: may be absent
<220> FEATURE:
<221> NAME/KEY: VARIANT
<222> LOCATION: (176)..(182)
<223> OTHER INFORMATION: may be absent
<220> FEATURE:
<221> NAME/KEY: VARIANT
<222> LOCATION: (177)..(181)
<223> OTHER INFORMATION: may be absent
<220> FEATURE:
<221> NAME/KEY: VARIANT
<222> LOCATION: (183)..(189)
<223> OTHER INFORMATION: may be absent
<220> FEATURE:
<221> NAME/KEY: VARIANT
<222> LOCATION: (184)..(188)
<223> OTHER INFORMATION: may be absent
<220> FEATURE:
<221> NAME/KEY: VARIANT
<222> LOCATION: (190)..(196)
<223> OTHER INFORMATION: may be absent
<220> FEATURE:
<221> NAME/KEY: VARIANT
<222> LOCATION: (191)..(195)
<223> OTHER INFORMATION: may be absent
<220> FEATURE:
<221> NAME/KEY: VARIANT
<222> LOCATION: (197)..(203)
<223> OTHER INFORMATION: may be absent
<220> FEATURE:
<221> NAME/KEY: VARIANT
<222> LOCATION: (198)..(202)
<223> OTHER INFORMATION: may be absent
<220> FEATURE:
<221> NAME/KEY: VARIANT
<222> LOCATION: (204)..(210)
<223> OTHER INFORMATION: may be absent
<220> FEATURE:
<221> NAME/KEY: VARIANT
<222> LOCATION: (205)..(209)
<223> OTHER INFORMATION: may be absent

<400> SEQUENCE: 262

Gly Gly Gly Gly Gly Ser Gly Gly Gly Gly Gly Ser Gly Gly
1               5                   10                  15

Gly Gly Gly Gly Ser Gly Gly Gly Gly Gly Ser Gly Gly Gly Gly
            20                  25                  30

Gly Gly Ser Gly Gly Gly Gly Gly Ser Gly Gly Gly Gly Gly
        35                  40                  45

Ser Gly Gly Gly Gly Gly Ser Gly Gly Gly Gly Gly Ser Gly
    50                  55                  60

Gly Gly Gly Gly Ser Gly Gly Gly Gly Gly Ser Gly Gly Gly
65                  70                  75                  80

Gly Gly Gly Ser Gly Gly Gly Gly Gly Ser Gly Gly Gly Gly
            85                  90                  95
```

Gly Ser Gly Gly Gly Gly Gly Ser Gly Gly Gly Gly Gly Ser
            100                 105                 110
Gly Gly Gly Gly Gly Ser Gly Gly Gly Gly Gly Ser Gly Gly
        115                 120                 125
Gly Gly Gly Gly Ser Gly Gly Gly Gly Gly Ser Gly Gly Gly
        130                 135                 140
Gly Gly Ser Gly Gly Gly Gly Gly Ser Gly Gly Gly Gly Gly
145                 150                 155                 160
Ser Gly Gly Gly Gly Gly Ser Gly Gly Gly Gly Gly Ser Gly
                165                 170                 175
Gly Gly Gly Gly Ser Gly Gly Gly Gly Gly Ser Gly Gly Gly
            180                 185                 190
Gly Gly Ser Gly Gly Gly Gly Gly Ser Gly Gly Gly Gly Gly
        195                 200                 205
Gly Ser
    210

<210> SEQ ID NO 263
<211> LENGTH: 210
<212> TYPE: PRT
<213> ORGANISM: Artificial Sequence
<220> FEATURE:
<223> OTHER INFORMATION: linker
<220> FEATURE:
<221> NAME/KEY: VARIANT
<222> LOCATION: (2)..(6)
<223> OTHER INFORMATION: may be absent
<220> FEATURE:
<221> NAME/KEY: VARIANT
<222> LOCATION: (8)..(14)
<223> OTHER INFORMATION: may be absent
<220> FEATURE:
<221> NAME/KEY: VARIANT
<222> LOCATION: (9)..(14)
<223> OTHER INFORMATION: may be absent
<220> FEATURE:
<221> NAME/KEY: VARIANT
<222> LOCATION: (15)..(21)
<223> OTHER INFORMATION: may be absent
<220> FEATURE:
<221> NAME/KEY: VARIANT
<222> LOCATION: (16)..(20)
<223> OTHER INFORMATION: may be absent
<220> FEATURE:
<221> NAME/KEY: VARIANT
<222> LOCATION: (22)..(28)
<223> OTHER INFORMATION: may be absent
<220> FEATURE:
<221> NAME/KEY: VARIANT
<222> LOCATION: (23)..(27)
<223> OTHER INFORMATION: may be absent
<220> FEATURE:
<221> NAME/KEY: VARIANT
<222> LOCATION: (29)..(34)
<223> OTHER INFORMATION: may be absent
<220> FEATURE:
<221> NAME/KEY: VARIANT
<222> LOCATION: (30)..(33)
<223> OTHER INFORMATION: may be absent
<220> FEATURE:
<221> NAME/KEY: VARIANT
<222> LOCATION: (35)..(42)
<223> OTHER INFORMATION: may be absent
<220> FEATURE:
<221> NAME/KEY: VARIANT
<222> LOCATION: (36)..(41)
<223> OTHER INFORMATION: may be absent
<220> FEATURE:
<221> NAME/KEY: VARIANT
<222> LOCATION: (43)..(49)
<223> OTHER INFORMATION: may be absent -continued

```
<220> FEATURE:
<221> NAME/KEY: VARIANT
<222> LOCATION: (44)..(48)
<223> OTHER INFORMATION: may be absent
<220> FEATURE:
<221> NAME/KEY: VARIANT
<222> LOCATION: (50)..(56)
<223> OTHER INFORMATION: may be absent
<220> FEATURE:
<221> NAME/KEY: VARIANT
<222> LOCATION: (51)..(55)
<223> OTHER INFORMATION: may be absent
<220> FEATURE:
<221> NAME/KEY: VARIANT
<222> LOCATION: (57)..(63)
<223> OTHER INFORMATION: may be absent
<220> FEATURE:
<221> NAME/KEY: VARIANT
<222> LOCATION: (58)..(62)
<223> OTHER INFORMATION: may be absent
<220> FEATURE:
<221> NAME/KEY: VARIANT
<222> LOCATION: (64)..(70)
<223> OTHER INFORMATION: may be absent
<220> FEATURE:
<221> NAME/KEY: VARIANT
<222> LOCATION: (65)..(69)
<223> OTHER INFORMATION: may be absent
<220> FEATURE:
<221> NAME/KEY: VARIANT
<222> LOCATION: (71)..(77)
<223> OTHER INFORMATION: may be absent
<220> FEATURE:
<221> NAME/KEY: VARIANT
<222> LOCATION: (72)..(76)
<223> OTHER INFORMATION: may be absent
<220> FEATURE:
<221> NAME/KEY: VARIANT
<222> LOCATION: (78)..(84)
<223> OTHER INFORMATION: may be absent
<220> FEATURE:
<221> NAME/KEY: VARIANT
<222> LOCATION: (79)..(83)
<223> OTHER INFORMATION: may be absent
<220> FEATURE:
<221> NAME/KEY: VARIANT
<222> LOCATION: (85)..(91)
<223> OTHER INFORMATION: may be absent
<220> FEATURE:
<221> NAME/KEY: VARIANT
<222> LOCATION: (86)..(90)
<223> OTHER INFORMATION: may be absent
<220> FEATURE:
<221> NAME/KEY: VARIANT
<222> LOCATION: (92)..(98)
<223> OTHER INFORMATION: may be absent
<220> FEATURE:
<221> NAME/KEY: VARIANT
<222> LOCATION: (93)..(97)
<223> OTHER INFORMATION: may be absent
<220> FEATURE:
<221> NAME/KEY: VARIANT
<222> LOCATION: (99)..(105)
<223> OTHER INFORMATION: may be absent
<220> FEATURE:
<221> NAME/KEY: VARIANT
<222> LOCATION: (100)..(104)
<223> OTHER INFORMATION: may be absent
<220> FEATURE:
<221> NAME/KEY: VARIANT
<222> LOCATION: (106)..(112)
<223> OTHER INFORMATION: may be absent
<220> FEATURE:
<221> NAME/KEY: VARIANT
<222> LOCATION: (107)..(111)
<223> OTHER INFORMATION: may be absent
<220> FEATURE:
<221> NAME/KEY: VARIANT
<222> LOCATION: (113)..(119)
```

```
<223> OTHER INFORMATION: may be absent
<220> FEATURE:
<221> NAME/KEY: VARIANT
<222> LOCATION: (114)..(118)
<223> OTHER INFORMATION: may be absent
<220> FEATURE:
<221> NAME/KEY: VARIANT
<222> LOCATION: (120)..(126)
<223> OTHER INFORMATION: may be absent
<220> FEATURE:
<221> NAME/KEY: VARIANT
<222> LOCATION: (121)..(125)
<223> OTHER INFORMATION: may be absent
<220> FEATURE:
<221> NAME/KEY: VARIANT
<222> LOCATION: (127)..(133)
<223> OTHER INFORMATION: may be absent
<220> FEATURE:
<221> NAME/KEY: VARIANT
<222> LOCATION: (128)..(132)
<223> OTHER INFORMATION: may be absent
<220> FEATURE:
<221> NAME/KEY: VARIANT
<222> LOCATION: (134)..(140)
<223> OTHER INFORMATION: may be absent
<220> FEATURE:
<221> NAME/KEY: VARIANT
<222> LOCATION: (135)..(139)
<223> OTHER INFORMATION: may be absent
<220> FEATURE:
<221> NAME/KEY: VARIANT
<222> LOCATION: (141)..(147)
<223> OTHER INFORMATION: may be absent
<220> FEATURE:
<221> NAME/KEY: VARIANT
<222> LOCATION: (142)..(146)
<223> OTHER INFORMATION: may be absent
<220> FEATURE:
<221> NAME/KEY: VARIANT
<222> LOCATION: (148)..(154)
<223> OTHER INFORMATION: may be absent
<220> FEATURE:
<221> NAME/KEY: VARIANT
<222> LOCATION: (149)..(153)
<223> OTHER INFORMATION: may be absent
<220> FEATURE:
<221> NAME/KEY: VARIANT
<222> LOCATION: (155)..(161)
<223> OTHER INFORMATION: may be absent
<220> FEATURE:
<221> NAME/KEY: VARIANT
<222> LOCATION: (156)..(160)
<223> OTHER INFORMATION: may be absent
<220> FEATURE:
<221> NAME/KEY: VARIANT
<222> LOCATION: (162)..(168)
<223> OTHER INFORMATION: may be absent
<220> FEATURE:
<221> NAME/KEY: VARIANT
<222> LOCATION: (163)..(167)
<223> OTHER INFORMATION: may be absent
<220> FEATURE:
<221> NAME/KEY: VARIANT
<222> LOCATION: (169)..(175)
<223> OTHER INFORMATION: may be absent
<220> FEATURE:
<221> NAME/KEY: VARIANT
<222> LOCATION: (170)..(174)
<223> OTHER INFORMATION: may be absent
<220> FEATURE:
<221> NAME/KEY: VARIANT
<222> LOCATION: (176)..(182)
<223> OTHER INFORMATION: may be absent
<220> FEATURE:
<221> NAME/KEY: VARIANT
<222> LOCATION: (177)..(181)
<223> OTHER INFORMATION: may be absent
<220> FEATURE:
<221> NAME/KEY: VARIANT
```

```
<222> LOCATION: (183)..(189)
<223> OTHER INFORMATION: may be absent
<220> FEATURE:
<221> NAME/KEY: VARIANT
<222> LOCATION: (184)..(188)
<223> OTHER INFORMATION: may be absent
<220> FEATURE:
<221> NAME/KEY: VARIANT
<222> LOCATION: (190)..(196)
<223> OTHER INFORMATION: may be absent
<220> FEATURE:
<221> NAME/KEY: VARIANT
<222> LOCATION: (191)..(195)
<223> OTHER INFORMATION: may be absent
<220> FEATURE:
<221> NAME/KEY: VARIANT
<222> LOCATION: (197)..(203)
<223> OTHER INFORMATION: may be absent
<220> FEATURE:
<221> NAME/KEY: VARIANT
<222> LOCATION: (198)..(202)
<223> OTHER INFORMATION: may be absent
<220> FEATURE:
<221> NAME/KEY: VARIANT
<222> LOCATION: (204)..(210)
<223> OTHER INFORMATION: may be absent
<220> FEATURE:
<221> NAME/KEY: VARIANT
<222> LOCATION: (205)..(209)
<223> OTHER INFORMATION: may be absent

<400> SEQUENCE: 263

Ser Ser Ser Ser Ser Gly Ser Ser Ser Ser Gly Ser Ser
1               5                   10                  15

Ser Ser Ser Ser Gly Ser Ser Ser Ser Ser Gly Ser Ser Ser Ser
                20                  25                  30

Ser Ser Gly Ser Ser Ser Ser Ser Gly Ser Ser Ser Ser Ser
            35                  40                  45

Gly Ser Ser Ser Ser Ser Gly Ser Ser Ser Ser Ser Gly Ser
50                  55                  60

Ser Ser Ser Ser Gly Ser Ser Ser Ser Ser Gly Ser Ser Ser
65                  70                  75                  80

Ser Ser Ser Gly Ser Ser Ser Ser Ser Gly Ser Ser Ser Ser
            85                  90                  95

Ser Gly Ser Ser Ser Ser Ser Gly Ser Ser Ser Ser Ser Gly
            100                 105                 110

Ser Ser Ser Ser Ser Gly Ser Ser Ser Ser Ser Gly Ser Ser
            115                 120                 125

Ser Ser Ser Gly Ser Ser Ser Ser Ser Gly Ser Ser Ser Ser
            130                 135                 140

Ser Ser Gly Ser Ser Ser Ser Ser Gly Ser Ser Ser Ser Ser
145                 150                 155                 160

Gly Ser Ser Ser Ser Ser Gly Ser Ser Ser Ser Ser Gly Ser
                165                 170                 175

Ser Ser Ser Ser Gly Ser Ser Ser Ser Ser Gly Ser Ser Ser
            180                 185                 190

Ser Ser Ser Gly Ser Ser Ser Ser Ser Gly Ser Ser Ser Ser
        195                 200                 205

Ser Gly
    210

<210> SEQ ID NO 264
<211> LENGTH: 30
<212> TYPE: PRT
```

```
<213> ORGANISM: Artificial Sequence
<220> FEATURE:
<223> OTHER INFORMATION: linker
<220> FEATURE:
<221> NAME/KEY: VARIANT
<222> LOCATION: (2)..(30)
<223> OTHER INFORMATION: each residue individually may be absent or
      present

<400> SEQUENCE: 264

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
                20                  25                  30

<210> SEQ ID NO 265
<211> LENGTH: 4
<212> TYPE: PRT
<213> ORGANISM: Artificial Sequence
<220> FEATURE:
<223> OTHER INFORMATION: cleavable spacer

<400> SEQUENCE: 265

His His Ala Ala
1

<210> SEQ ID NO 266
<211> LENGTH: 150
<212> TYPE: PRT
<213> ORGANISM: Artificial Sequence
<220> FEATURE:
<223> OTHER INFORMATION: linker
<220> FEATURE:
<221> NAME/KEY: VARIANT
<222> LOCATION: (6)..(10)
<223> OTHER INFORMATION: may be absent
<220> FEATURE:
<221> NAME/KEY: VARIANT
<222> LOCATION: (11)..(15)
<223> OTHER INFORMATION: may be absent
<220> FEATURE:
<221> NAME/KEY: VARIANT
<222> LOCATION: (16)..(20)
<223> OTHER INFORMATION: may be absent
<220> FEATURE:
<221> NAME/KEY: VARIANT
<222> LOCATION: (21)..(25)
<223> OTHER INFORMATION: may be absent
<220> FEATURE:
<221> NAME/KEY: VARIANT
<222> LOCATION: (26)..(30)
<223> OTHER INFORMATION: may be absent
<220> FEATURE:
<221> NAME/KEY: VARIANT
<222> LOCATION: (31)..(35)
<223> OTHER INFORMATION: may be absent
<220> FEATURE:
<221> NAME/KEY: VARIANT
<222> LOCATION: (36)..(40)
<223> OTHER INFORMATION: may be absent
<220> FEATURE:
<221> NAME/KEY: VARIANT
<222> LOCATION: (41)..(45)
<223> OTHER INFORMATION: may be absent
<220> FEATURE:
<221> NAME/KEY: VARIANT
<222> LOCATION: (46)..(50)
<223> OTHER INFORMATION: may be absent
<220> FEATURE:
<221> NAME/KEY: VARIANT
<222> LOCATION: (51)..(55)
<223> OTHER INFORMATION: may be absent
<220> FEATURE:
<221> NAME/KEY: VARIANT
```

```
<222> LOCATION: (56)..(60)
<223> OTHER INFORMATION: may be absent
<220> FEATURE:
<221> NAME/KEY: VARIANT
<222> LOCATION: (61)..(65)
<223> OTHER INFORMATION: may be absent
<220> FEATURE:
<221> NAME/KEY: VARIANT
<222> LOCATION: (66)..(70)
<223> OTHER INFORMATION: may be absent
<220> FEATURE:
<221> NAME/KEY: VARIANT
<222> LOCATION: (71)..(75)
<223> OTHER INFORMATION: may be absent
<220> FEATURE:
<221> NAME/KEY: VARIANT
<222> LOCATION: (76)..(80)
<223> OTHER INFORMATION: may be absent
<220> FEATURE:
<221> NAME/KEY: VARIANT
<222> LOCATION: (81)..(85)
<223> OTHER INFORMATION: may be absent
<220> FEATURE:
<221> NAME/KEY: VARIANT
<222> LOCATION: (86)..(90)
<223> OTHER INFORMATION: may be absent
<220> FEATURE:
<221> NAME/KEY: VARIANT
<222> LOCATION: (91)..(95)
<223> OTHER INFORMATION: may be absent
<220> FEATURE:
<221> NAME/KEY: VARIANT
<222> LOCATION: (96)..(100)
<223> OTHER INFORMATION: may be absent
<220> FEATURE:
<221> NAME/KEY: VARIANT
<222> LOCATION: (106)..(110)
<223> OTHER INFORMATION: may be absent
<220> FEATURE:
<221> NAME/KEY: VARIANT
<222> LOCATION: (111)..(115)
<223> OTHER INFORMATION: may be absent
<220> FEATURE:
<221> NAME/KEY: VARIANT
<222> LOCATION: (116)..(120)
<223> OTHER INFORMATION: may be absent
<220> FEATURE:
<221> NAME/KEY: VARIANT
<222> LOCATION: (121)..(125)
<223> OTHER INFORMATION: may be absent
<220> FEATURE:
<221> NAME/KEY: VARIANT
<222> LOCATION: (126)..(130)
<223> OTHER INFORMATION: may be absent
<220> FEATURE:
<221> NAME/KEY: VARIANT
<222> LOCATION: (131)..(135)
<223> OTHER INFORMATION: may be absent
<220> FEATURE:
<221> NAME/KEY: VARIANT
<222> LOCATION: (136)..(140)
<223> OTHER INFORMATION: may be absent
<220> FEATURE:
<221> NAME/KEY: VARIANT
<222> LOCATION: (141)..(145)
<223> OTHER INFORMATION: may be absent
<220> FEATURE:
<221> NAME/KEY: VARIANT
<222> LOCATION: (146)..(150)
<223> OTHER INFORMATION: may be absent

<400> SEQUENCE: 266

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30
```

Gly Gly Ser Gly Gly Gly Gly Ser Gly Gly Gly Gly Ser Gly Gly Gly
                35                  40                  45
Gly Ser Gly Gly Gly Gly Ser Gly Gly Gly Gly Ser Gly Gly Gly Gly
    50                  55                  60
Ser Gly Gly Gly Gly Ser Gly Gly Gly Gly Ser Gly Gly Gly Gly Ser
65                  70                  75                  80
Gly Gly Gly Gly Ser Gly Gly Gly Gly Ser Gly Gly Gly Gly Ser Gly
                85                  90                  95
Gly Gly Gly Ser Gly Gly Gly Gly Ser Gly Gly Gly Gly Ser Gly Gly
            100                 105                 110
Gly Gly Ser Gly Gly Gly Gly Ser Gly Gly Gly Gly Ser Gly Gly Gly
        115                 120                 125
Gly Ser Gly Gly Gly Gly Ser Gly Gly Gly Gly Ser Gly Gly Gly Gly
    130                 135                 140
Ser Gly Gly Gly Gly Ser
145                 150

<210> SEQ ID NO 267
<211> LENGTH: 6
<212> TYPE: PRT
<213> ORGANISM: Artificial Sequence
<220> FEATURE:
<223> OTHER INFORMATION: linker

<400> SEQUENCE: 267

Ala Ser Gly Gly Pro Glu
1               5

<210> SEQ ID NO 268
<211> LENGTH: 54
<212> TYPE: PRT
<213> ORGANISM: Artificial Sequence
<220> FEATURE:
<223> OTHER INFORMATION: linker
<220> FEATURE:
<221> NAME/KEY: VARIANT
<222> LOCATION: (1)..(54)
<223> OTHER INFORMATION: up to 2 G residues in each iteration of the
      (G2-4S)1-10 can be deleted
<220> FEATURE:
<221> NAME/KEY: REPEAT
<222> LOCATION: (3)..(7)
<223> OTHER INFORMATION: single repeat of (GnS)x where n= 2-4 and x=
      1-10
<220> FEATURE:
<221> NAME/KEY: VARIANT
<222> LOCATION: (3)..(52)
<223> OTHER INFORMATION: up to 9 copies of (G2-4S)1-10 can be deleted

<400> SEQUENCE: 268

Ala Met Gly Gly Gly Gly Ser Gly Gly Gly Gly Ser Gly Gly Gly Gly
1               5                   10                  15
Ser Gly Gly Gly Gly Ser Gly Gly Gly Gly Ser Gly Gly Gly Gly Ser
            20                  25                  30
Gly Gly Gly Gly Ser Gly Gly Gly Gly Ser Gly Gly Gly Gly Ser Gly
        35                  40                  45
Gly Gly Gly Ser Ala Met
    50

<210> SEQ ID NO 269
<211> LENGTH: 15
<212> TYPE: PRT
<213> ORGANISM: Artificial Sequence
<220> FEATURE:

```
<223> OTHER INFORMATION: linker

<400> SEQUENCE: 269

Gly Gly Gly Gly Ser Gly Gly Gly Gly Ser Gly Gly Gly Gly Ser
1               5                   10                  15
```